United States Patent
Falb et al.

(10) Patent No.: US 9,688,967 B2
(45) Date of Patent: *Jun. 27, 2017

(54) BACTERIA ENGINEERED TO TREAT DISEASES ASSOCIATED WITH HYPERAMMONEMIA

(71) Applicant: Synlogic, Inc., Cambridge, MA (US)

(72) Inventors: Dean Falb, Sherborn, MA (US); Vincent M. Isabella, Cambridge, MA (US); Jonathan W. Kotula, Somerville, MA (US); Paul F. Miller, Salem, CT (US); Suman Machinani, Cambridge, MA (US)

(73) Assignee: Synlogic, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/164,828

(22) Filed: May 25, 2016

(65) Prior Publication Data

US 2016/0333326 A1 Nov. 17, 2016
US 2017/0137789 A9 May 18, 2017

Related U.S. Application Data

(63) Continuation-in-part of application No. PCT/US2016/020530, filed on Mar. 2, 2016, and a continuation-in-part of application No. 14/960,333, filed on Dec. 4, 2015, now Pat. No. 9,487,764.

(60) Provisional application No. 62/291,468, filed on Feb. 4, 2016, provisional application No. 62/256,048, filed on Nov. 16, 2015, provisional application No. 62/248,805, filed on Oct. 30, 2015, provisional application No. 62/184,770, filed on Jun. 25, 2015, provisional application No. 62/263,329, filed on Dec. 4, 2015, provisional application No. 62/256,039, filed on Nov. 16, 2015, provisional application No. 62/256,041, filed on Nov. 16, 2015, provisional application No. 62/184,811, filed on Jun. 25, 2015, provisional application No. 62/183,935, filed on Jun. 24, 2015, provisional application No. 62/173,706, filed on Jun. 10, 2015, provisional application No. 62/173,710, filed on Jun. 10, 2015, provisional application No. 62/150,508, filed on Apr. 21, 2015, provisional application No. 62/103,513, filed on Jan. 14, 2015, provisional application No. 62/087,854, filed on Dec. 5, 2014, provisional application No. 62/293,749, filed on Feb. 10, 2016, provisional application No. 62/277,654, filed on Jan. 12, 2016.

(51) Int. Cl.
| | |
|---|---|
| A01N 63/00 | (2006.01) |
| C12N 1/20 | (2006.01) |
| C12N 9/10 | (2006.01) |
| A61K 35/74 | (2015.01) |
| C12R 1/19 | (2006.01) |
| A61K 35/741 | (2015.01) |
| C07K 14/245 | (2006.01) |
| C12N 15/52 | (2006.01) |
| C12N 15/70 | (2006.01) |
| C12P 7/52 | (2006.01) |

(52) U.S. Cl.
CPC ............ *C12N 9/1029* (2013.01); *A61K 35/74* (2013.01); *A61K 35/741* (2013.01); *C07K 14/245* (2013.01); *C12N 15/52* (2013.01); *C12N 15/70* (2013.01); *C12R 1/19* (2013.01); *C12Y 203/01001* (2013.01); *C12P 7/52* (2013.01)

(58) Field of Classification Search
None
See application file for complete search history.

(56) References Cited

U.S. PATENT DOCUMENTS

| | | | |
|---|---|---|---|
| 5,589,168 A | 12/1996 | Allen et al. | |
| 5,989,463 A | 11/1999 | Tracy et al. | |
| 6,203,797 B1 | 3/2001 | Perry | |
| 6,835,376 B1 | 12/2004 | Neeser et al. | |
| 7,731,976 B2 | 6/2010 | Cobb et al. | |
| 2003/0166191 A1 | 9/2003 | Gardner et al. | |
| 2014/0079701 A1 | 3/2014 | Miller et al. | |
| 2015/0238545 A1 | 8/2015 | Borody | |
| 2015/0359894 A1 | 12/2015 | Weinrich et al. | |
| 2016/0333326 A1* | 11/2016 | Falb ..................... | C12N 9/1029 |

FOREIGN PATENT DOCUMENTS

| | | |
|---|---|---|
| EP | 1 170 361 A2 | 1/2002 |
| WO | WO 2014/138324 A1 | 9/2014 |

OTHER PUBLICATIONS

Aboulnaga, E-H. et al. (2013) "Effect of an Oxygen-Tolerant Bifurcating Butyryl Coenzyme A Dehydrogenase/Electron-Transferring Flavoprotein Complex from *Clostridium difficile* on Butyrate Production in *Escherichia coli*" *J Bacteriol*, 195(16):3704-3713.

Ahboucha, S. and R.F. Butterworth (Dec. 2004) "Pathophysiology of hepatic encephalopathy: a new look at GABA from the molecular standpoint" *Metab Brain Dis*, 19(3-4):331-343.

Albiniak, A.M. et al. (2013) "High-level secretion of a recombinant protein to the culture medium with a *Bacillus subtilis* twin-arginine translocation system in *Escherichia coli*" *FEBS J*, 280:3810-3821.

Alifano et al. (Mar. 1996) "Histidine biosynthetic pathway and genes: structure, regulation, and evolution" *Microbiol Rev*, 60(1):44-69.

Altenhoefer et al. (Apr. 9, 2004) "The probiotic *Escherichia coli* strain Nissle 1917 interferes with invasion of human intestinal epithelial cells by different enteroinvasive bacterial pathogens" *FEMS Immunol Med Microbiol*, 40(3):223-229.

(Continued)

*Primary Examiner* — Michael Burkhart

(74) *Attorney, Agent, or Firm* — Finnegan, Henderson, Farabow, Garrett & Dunner, LLP

(57) ABSTRACT

Genetically engineered bacteria, pharmaceutical compositions thereof, and methods of modulating and treating disorders associated with hyperammonemia are disclosed.

20 Claims, 113 Drawing Sheets

(56) References Cited

OTHER PUBLICATIONS

Andersen, P.S. et al. (Apr. 1995) "Uracil uptake in *Escherichia coli* K-12: isolation of uraA mutants and cloning of the gene" *J Bacteriol*, 177(8):2008-2013.

Aoyagi et al. (Dec. 1966) "Gastrointestinal urease in man. Activity of mucosal urease" *Gut*, 7(6):631-635.

Arai et al. (Aug. 28, 1995) "Expression of the nir and nor genes for denitrification of Pseudomonas aeruginosa requires a novel CRP/FNR-related transcriptional regulator, DNR, in addition to ANR" *FEBS Lett*, 371(1):73-76.

Argos, P. (1989) "A possible homology between immunodeficiency virus p24 core protein and picornaviral VP2 coat protein: prediction of HIV p24 antigenic sites" *EMBO J*, 8(3):779-785.

Arthur et al. (Oct. 5, 2012) "Intestinal inflammation targets cancer-inducing activity of the microbiota" *Science*, 338(6103):120-123. NIH Public Access Author Manuscript; available in PMC May 6, 2013 (11 pages).

Aschner et al. (Apr.-Jun. 1999) "Manganese uptake and distribution in the central nervous system (CNS)" *Neurotoxicology*, 20(2-3):173-180.

Azorin et al. (Sep. 1999) "A simple animal model of hyperammonemia" *Hepatology*, 10(3):311-314.

Bansky et al. (1985) "Reversal of hepatic coma by benzodiazepene antagonists (Ro15-1788)" *Lancet*, 1:1324-1325.

Basile, A.S. et al. (Jul. 1990) "Brain concentrations of benzodiazepines are elevated in an animal model of hepatic encephalopathy" *Proc Natl Acad Sci USA*, 87(14):5263-5267.

Bass, N.M. et al. (Mar. 2010) "Rifaximin Treatment in Hepatic Encephalopathy" *N Engl J Med*, 362(12):1071-1081.

Bearden, S.W. and R.D. Perry (1999) "The Yfe system of *Yersinia pestis* transports iron and manganese and is required for full virulence of plague" *Mol Microbiol*, 32(2):403-414.

Berk, D.P. and T. Chalmers (Sep. 1970) "Deafness complicating antibiotic therapy of hepatic encephalopathy" *Ann Intern Med*, 73(3):393-396.

Blanc, P. et al. (Feb. 1992) "Lactitol or lactulose in the treatment of chronic hepatic encephalopathy: Results of a meta-analysis" *Hepatology*, 15(2):222-228.

Boysen, A. et al. (2010 Apr) "Translational Regulation of Gene Expression by an Anaerobically Induced Small Non-coding RNA in *Escherichia coli*" *J Biol Chem*, 285(14):10690-10702.

Bussmann, M. et al. (Sep. 2010) "RosR (Cg1324), a Hydrogen Peroxide-sensitive MarR-type Transcriptional Regulator of *Corynebacterium glutamicum*" *J Biol Chem*, 285(38):29305-29318.

Caldara et al. (Mar. 7, 2008) "Arginine biosynthesis in *Escherichia coli*: experimental perturbation and mathematical modeling" *J Biol Chem*, 283(10):6347-6358.

Caldara et al. (Nov. 2009) "The arginine regulon of *Escherichia coli*: whole-system transcriptome analysis discovers new genes and provides an integrated view of arginine regulation" *Microbiology*, 152(Pt 11):3343-3354.

Caldovic et al. (2010) "N-acetylglutamate synthase: structure, function and defects" *Mol Genet Metab*, 100 Suppl 1:S13-S19. NIH Public Access Author Manuscript; available in PMC Feb. 26, 2011 (16 pages).

Callura et al. (Sep. 7, 2010) "Tracking, tuning, and terminating microbial physiology using synthetic riboregulators" *Proc Natl Acad Sci USA*, 107(36):15898-15903.

Cash, W.J. et al. (2010) "Current concepts in the assessment and treatment of Hepatic Encephalopathy" *Q J Med*, 103(1):9-16.

Castiglione et al. (Sep. 2009) "The transcription factor DNR from *Pseudomonas aeruginosa* specifically requires nitric oxide and haem for the activation of a target promoter in *Escherichia coli*" *Microbiology*, 155(Pt 9):2838-2844.

Cellier, M. et al. (Jun. 1996) "Resistance to intracellular infections: comparative genomic analysis of Nramp" *Trends Genet*, 12(6):201-204.

Charlier et al. (Jul. 20, 1992) "Arginine regulon of *Escherichia coli* K-12. A study of repressor-operator interactions and of in vitro binding affinities versus in vivo repression" *J Mol Biol*, 226(2):367-386.

Chassaing, B. et al. (Feb. 4, 2014) "Dextran sulfate sodium (DSS)-induced colitis in mice" *Curr Protoc Immunol*, 104:Unit 15.25. NIH Public Access Author Manuscript; available in PMC Feb. 4, 2015 (16 pages).

Chen, C-M. et al. (2015) "High Protein Diet and Huntington's Disease" *PLoS ONE*, 10(5):e0127654 (9 pages).

Chiang, M-C. et al. (2007) "Dysregulation of C/EBPα by mutant Huntingtin causes the urea cycle deficiency in Huntington's disease" *Hum Mol Genet*, 16(5):483-498.

Clarkson et al. (1971) "Diaminopimelic Acid and Lysine Auxotrophs of *Pseudomonas aeruginosa* 8602" *J Gen Microbiol*, 66:161-169.

Collinson, I. et al. (2015) "Channel crossing: how are proteins shipped across the bacterial plasma membrane?" *Philos Trans R Soc B*, 370:20150025 [online]. Retrieved from: http://rstb.royalsocietypublishing.org/, on Jun. 16, 2016 (13 pages).

Cordoba, J. and B. Minguez (2008) "Hepatic Encephalopathy" *Semin Liver Dis*, 28(1):70-80.

Costa, T.R.D. et al. (May 2015) "Secretion systems in Gram-negative bacteria: structural and mechanistic insights" *Nat Rev Microbiol*, 13(6):343-359.

Crabeel et al. (Dec. 1, 1997) "Characterization of the *Saccharomyces cerevisiae* ARG7 gene encoding ornithine acetyltransferase, an enzyme also endowed with acetylglutamate synthase activity" *Eur J Biochem*, 250(2):232-241.

Cuevas-Ramos et al. (Jun. 22, 2010) "*Escherichia coli* induces DNA damage in vivo and triggers genomic instability in mammalian cells" *Proc Natl Aced Sci USA*, 107(25):11537-11542.

Cunin et al. (Sep. 1986) "Biosynthesis and metabolism of arginine in bacteria" *Microbiol Rev*, 50(3):314-352. Erratum in: Microbiol Rev, Mar. 1987; 51(1):178.

Cunin et al. (Aug. 11, 1983) "Molecular basis for modulated regulation of gene expression in the arginine regulon of *Escherichia coli* K-12" *Nucleic Acids Res*, 11(15):5007-5019.

Danino, T. et al. (May 2015) "Programmable probiotics for detection of cancer in urine" *Sci Transl Med*,7(289):289ra84 [online]. Retrieved from: www.sciencetranslational medicine.org, on Jul. 30, 2015 (11 pages).

Deignan et al. (Jan. 2008) "Contrasting features of urea cycle disorders in human patients" *Mol Genet Metab*,93(1):7-14. NIH Public Access Author Manuscript; available in PMC Jun. 8, 2009 (13 pages).

Deutscher (Apr. 2008) "The mechanisms of carbon catabolite repression in bacteria" *Curr Opin Microbiol*, 11(2):87-93.

Diaz et al. (Jun. 2013) "Ammonia control and neurocognitive outcome among urea cycle disorder patients treated with glycerol phenylbutyrate" *Hepatology*, 57(6):2171-2179.

Dinleyici et al. (Nov. 2014) "*Saccharomyces boulardii* CNCM I-745 in different clinical conditions" *Expert Opin Biol Ther*, 14(11):1593-1609.

Dogovski et al. "Enzymology of Bacterial Lysine Biosynthesis" Chapter 9 in *Biochemistry*. Prof. Deniz Ekinci (Ed.), InTech, Mar. 2012; pp. 225-262. ISBN: 978-953-51-0076-8. [online] Retrieved from: http://www.intechopen.com/books/biochemistry/enzymology-of-bacterial-lysine-biosynthesis (39 pages).

Doolittle et al. (May-Jun. 1974) "A new allele of the sparse fur gene in the mouse" *J Hered*, 65(3):194-195.

Dover, S. and Y.S. Halpern (1972 Feb) "Utilization of γ-Aminobutyric Acid as the Sole Carbon and Nitrogen Source by *Escherichia coli* K-12 Mutants" *J Bacteriol*, 109(2):835-843.

Duarte, V. and J-M. Latour (2010) "PerR vs OhrR: selective peroxide sensing in *Bacillus subtilis*" *Mol BioSyst*, 6:316-323.

Dubbs, J.M. and S. Mongkolsuk (Oct. 2012) "Peroxide-Sensing Transcriptional Regulators in Bacteria" *J Bacteriol*, 194(20):5495-5503.

Dunn, A.K. et al. (Jul. 2010) "The alternative oxidase (AOX) gene in *Vibrio fischeri* is controlled by NsrR and upregulated in response to nitric oxide" *Mol Microbiol*, 77(1):44-55. NIH Public Access Author Manuscript; available in PMC Jun. 14, 2013 (24 pages).

(56) References Cited

OTHER PUBLICATIONS

Durand, S. and G. Storz (Mar. 2010) "Reprogramming of Anaerobic Metabolism by the FnrS Small RNA" *Mol Microbiol*, 75(5):1215-1231. NIH Public Access Author Manuscript; available in PMC Sep. 17, 2010 (28 pages).
Eckhardt and Leisinger (Jun. 19, 1975) "Isolation and characterization of mutants with a feedback resistant N-acetylglutamate synthase in *Escherichia coli* K 12" *Mol Gen Genet*, 138(3):225-232.
Eiglmeier et al. (Jul. 1989) "Molecular genetic analysis of FNR-dependent promoters" *Mol Microbiol*, 3(7):869-878.
Feng et al. (Oct. 1992) "Role of phosphorylated metabolic intermediates in the regulation of glutamine synthetase synthesis in *Escherichia coli*" *J Bacteriol*, 174(19):6061-6070.
Fraga et al. "Real-Time PCR" in *Current Protocols Essential Laboratory Techniques*. John Wiley & Sons, Inc., 2008; Unit 10.3, pp. 1-33.
Galimand et al. (Mar. 1991) "Positive FNR-like control of anaerobic arginine degradation and nitrate respiration in *Pseudomonas aeruginosa*" *J Bacteriol*, 173(5):1598-1606.
Gamper et al. (Aug. 1991) "Anaerobic regulation of transcription initiation in the arcDABC operon of *Pseudomonas aeruginosa*" *J Bacteriol*, 173(15):4742-4750.
Gardner et al. (2000) "Construction of a genetic toggle switch in *Escherichia coli*" *Nature*, 403:339-342.
Gerdes et al. (Oct. 2006) "Essential genes on metabolic maps" *Curr Opin Biotechnol*, 17(5):448-456.
Gerlach, R.G. and M. Hensel (2007) "Protein secretion systems and adhesins: The molecular armory of Gram-negative pathogens" *Int J Med Microbiol*, 297:401-415.
Giardina, G. et al. (2008) "NO sensing in *Pseudomonas aeruginosa*: Structure of the Transcriptional Regulator DNR" *J Mol Biol*, 378:1002-1015.
Goldstein, B.P. (Sep. 2014) "Resistance to rifampicin: a review" *J Antibiot*, 67(9):625-630.
Görke and Stülke. (Aug. 2008) "Carbon catabolite repression in bacteria: many ways to make the most out of nutrients" *Nat Rev Microbiol*, 6(8):613-624.
Häberle et al. (May 29, 2012) "Suggested guidelines for the diagnosis and management of urea cycle disorders" *Orphanet J Rare Dis*, 7:32 (30 pages).
Häberle, J. (Aug. 15, 2013) "Clinical and biochemical aspects of primary and secondary hyperammonemic disorders" *Arch Biochem Biophys*, 536(2):101-108.
Hasegawa et al. (Sep. 15, 1998) "Activation of a consensus FNR-dependent promoter by DNR of *Pseudomonas aeruginosa* in response to nitrite" *FEMS Microbiol Lett*, 166(2):213-217.
Hazell, A.S and M.D. Norenberg (Jun. 1998) "Ammonia and manganese increase arginine uptake in cultured astrocytes" *Neurochem Res*, 23(6):869-873.
Hazell, A.S. et al. (2006) "Alzheimer type II astrocytic changes following sub-acute exposure to manganese and its prevention by antioxidant treatment" *Neurosci Lett*, 396:167-171.
Hetzel, M. et al. (2003) "Acryloyl-CoA reductase from *Clostridium propionicum*. An enzyme complex of propionyl-CoA dehydrogenase and electron-transferring flavoprotein" *Eur J Biochem*, 270:902-910.
Higgins, C.F. (1992) "ABC Transporters: From Microorganisms to Man" *Annu Rev Cell Biol*, 8:67-113.
Hodges et al. (Jun. 1989) "The spf$^{ash}$ mouse: A missense mutation in the ornithine transcarbamylase gene also causes aberrant mRNA splicing" *Proc Natl Acad Sci USA*, 86(11):4142-4126.
Hoeren et al. (Nov. 15, 1993) "Sequence and expression of the gene encoding the respiratory nitrous-oxide reductase from *Paracoccus denitrificans*" *Eur J Biochem*, 218(1):49-57.
Hoffmann and Kölker (2013) "Defects in amino acid catabolism and the urea cycle" *Handbk Clin Neurol*, 113:1755-1773.
Horsburgh, M. et al. (2002) "MntR modulates expression of the PerR regulon and superoxide resistance in *Staphylococcus aureus* through control of manganese uptake" *Mol Microbiol*, 44(5):1269-1286.
Hosseini et al. (May 2011) "Propionate as a health-promoting microbial metabolite in the human gut" *Nutr Rev*, 69(5):245-258.
Hu, L.A. and S.C. King (1998) "Membrane topology of the *Escherichia coli* γ-aminobutyrate transporter: implications on the topography and mechanism of prokaryotic and eukaryotic transporters from the APC superfamily" *Biochem J*, 336:69-76.
Hu, L.A. and S.C. King (1998) "Functional sensitivity of polar surfaces on transmembrane helix 8 and cytoplasmic loop 8-9 of the *Escherichia coli* GABA (4-aminobutyrate) transporter encoded by gabP: mutagenic analysis of a consensus amphipathic region found in transporters from bacteria to mammals" *Biochem J*, 330:771-776.
International Patent Application No. PCT/US2015/064140, filed Dec. 4, 2015, by Synlogic, Inc.: International Search Report and Written Opinion, mailed Apr. 22, 2016.
Isabella, V.M. et al. (2009; online Nov. 6, 2008) "Functional analysis of NsrR, a nitric oxide-sensing Rrf2 repressor in *Neisseria gonorrhoeae*" *Mol Microbiol*, 71(1):227-239.
Isabella et al. (Jan. 20, 2011) "Deep sequencing-based analysis of the anaerobic stimulon in *Neisseria gonorrhoeae*" *BMC Genomics*, 12:51 (24 pages).
Ivanovska, V. et al. (2014) "Pediatric Drug Formulations: A Review of Challenges and Progress" *Pediatrics*, 134:361-372.
Jack, D.L. (2000) "The amino acid/polyamine/organocation (APC) superfamily of transporters specific for amino acids, polyamines and organocations" *Microbiol*, 146:1797-1814.
Jayakumar et al. (Nov. 2004) "Combined effects of ammonia and manganese on astrocytes in culture" *Neurochem Res*, 29(11):2051-2056.
Jensen, A.N. and L.T. Jensen (2014) "Manganese Transport, Trafficking and Function in Invertebrates" Chapter 1 in *Manganese in Health and Disease*. RSC Publishing, p. 1-33 [online]. Retrieved from: http://pubs.rsc.org/en/content/chapterhtml/2014/bk9781849739436-00001?isbn=978-1-84973-943-6 (30 pages).
Jones, E.A. and A.S. Basile (1997) "The involvement of ammonia with the mechanisms that enhance GABA-ergic neurotransmission in hepatic failure" *Adv Exp Med Biol*, 420:75-83.
Jones-Davis, D.M. and R.L. Macdonald (Feb. 2002) "GABA(A) receptor function and pharmacology in epilepsy and status epilepticus" *Curr Opin Pharmacol*, 3(1):12-18.
Karlinsey, J. et al. (Sep. 2012) "The NsrR Regulon in Nitrosative Stress Resistance of *Salmonella enterica* serovar Typhimurium" *Mol Microbiol*, 85(6):1179-1193. NIH Public Access Author Manuscript; available in PMC Sep. 1, 2013 (24 pages).
Kehres, D.G. et al. (Jun. 2002) "SitABCD is the alkaline $Mn^{2+}$ transporter of *Salmonella enterica* serovar Typhimurium" *J Bacteriol*, 184(12):3159-3166.
Kondrup, J. and M.J. Muller (Jul. 1997) "Energy and protein requirements of patients with chronic liver disease" *J Hepatol*, 27(1):239-247.
Konieczna et al. (Dec. 2012) "Bacterial urease and its role in long-lasting human diseases" *Curr Protein Pept Sci*, 13(8):789-806.
Koo, M-S. et al. (2003) "A reducing system of the superoxide sensor SoxR in *Escherichia coli*" *EMBO J*, 22(11):2614-2622.
Krogsgaard-Larsen (Feb. 1992) "GABA and glutamate receptors as therapeutic targets in neurodegenerative disorders" *Pharmacol Toxicol*, 70(2):95-104.
Lazier et al. (Oct. 2014) "Hyperammonemic encephalopathy in an adenocarcinoma patient managed with carglumic acid" *Curr Oncol*, 21(5):e736-e739.
Leonard, "Disorders of the urea cycle and related enzymes" in *Inborn Metabolic Diseases*, 4th ed. Heidelberg: Springer Medizin Verlag, 2006; pp. 263-272.
Li, X-D. et al. (Apr. 2001) "Monomeric state and ligand binding of recombinant GABA transporter from *Escherichia coli*" *FEBS Lett*, 494(3):165-169.
Lim et al. (Oct. 1987) "Nucleotide sequence of the argR gene of *Escherichia coli* K-12 and isolation of its product, the arginine repressor" *Proc Natl Aced Sci USA*, 84(19):6697-6701.
Liu et al. (Jul. 2010) "Methanococci use the diaminopimelate aminotransferase (DapL) pathway for lysine biosynthesis" *J Bacteriol*, 192(13):3304-3310.

(56) References Cited

OTHER PUBLICATIONS

Lodeiro et al. (Apr. 2008) "Robustness in *Escherichia coli* glutamate and glutamine synthesis studied by a kinetic model" *J Biol Phys*, 34(1-2):91-106.

Lopez and Anderson (Dec. 2015) "Synthetic Auxotrophs with Ligand-Dependent Essential Genes for a BL21(DE3) Biosafety Strain" *ACS Synthetic Biology*, 4(12):1279-1286.

Low et al. (Sep. 2013) "Chitin-Binding Domains of *Escherichia coli* chiA Mediate Interactions with Intestinal Epithelial Cells in Mice with Colitis" *Gastroenterol*, 145(3):602-612. NIH Public Access Author Manuscript; available in PMC Sep. 1, 2014 (18 pages).

Maas et al. (Mar. 1964) "Studies on the mechanism of repression of arginine biosynthesis in *Escherichia coli*. II. Dominance of repressibility in diploids" *J Mol Biol*, 8:365-370.

Maas, W.K. (Dec. 1994) "The arginine repressor of *Escherichia coli*" *Microbiol Rev*, 58(4):631-640.

Makarova et al. (2001) "Conservation of the binding site for the arginine repressor in all bacterial lineages" *Genome Biol*,2(4):research0013.1-0013.8.

Marinho, H.S. et al. (2014) "Hydrogen peroxide sensing, signaling and regulation of transcription factors" *Redox Biol*, 2:535-562.

McAllister, L.J. et al. (Aug. 2004) "Molecular analysis of the psa permease complex of *Streptococcus pneumoniae*" *Mol Microbiol*, 53(3):889-901.

Meadow et al. (Jun. 1957) "Interrelationships between lysine and alpha epsilon-diaminopimelic acid and their derivatives and analogues in mutants of *Escherichia coli*" *Biochem J*, 66(2):270-282.

Meng et al. (Apr. 1992) "Nucleotide sequence of the *Escherichia coli cad* operon: a system for neutralization of low extracellular pH" *J Bacteriol*, 174(8):2659-2669.

Moore et al. (Nov. 3, 2006) "Regulation of FNR dimerization by subunit charge repulsion" *J Biol Chem*, 281(44):33268-33275.

Mountain et al. (1984) "Cloning of a *Bacillus subtilis* restriction fragment complementing auxotrophic mutants of eight *Escherichia coli* genes of arginine biosynthesis" *Mol Gen Genet*, 197(1):82-89.

Nagamani et al. (Sep. 2012) "Optimizing therapy for argininosuccinic aciduria" *Mol Genet Metab.*, 107(1-2):10-14. NIH Public Access Author Manuscript; available in PMC Sep. 1, 2013 (12 pages).

Nguyen, D.L. and T. Morgan (Sep. 1, 2014) "Protein restriction in hepatic encephalopathy is appropriate for selected patients: a point of view" *Hepatol Int*, 8(2):447-451. NIH Public Access Author Manuscript; available in PMC Dec. 16, 2014 (8 pages).

Nhung, T.H. et al. (2014) "Establishment of a standardized mouse model of hepatic fibrosis for biomedical research" *Biomedical Research and Therapy*, 1(2):43-49.

Nicaise et al. (Oct. 2008) "Control of acute, chronic, and constitutive hyperammonemia by wild-type and genetically engineered *Lactobacillus plantarum* in rodents" *Hepatology*, 48(4):1184-1192.

Nicoloff et al. (Sep. 2004) "Two arginine repressors regulate arginine biosynthesis in *Lactobacillus plantarum*" *J Bacteriol*, 186(18):6059-6069.

Nougayrede et al. (Aug. 11, 2006) "*Escherichia coli* induces DNA double-strand breaks in eukaryotic cells" *Science*, 313(5788):848-851.

Olier et al. (Nov.-Dec. 2012) "Genotoxicity of *Escherichia coli* Nissle 1917 strain cannot be dissociated from its probiotic activity" *Gut Microbes*, 3(6):501-509.

Pham et al. (Oct. 2013) "Multiple myeloma-induced hyperammonemic encephalopathy: An entity associated with high in-patient mortality" *Leuk Res*, 37(10):1229-1232.

Porcheron, G. et al. (Dec. 5, 2013) "Iron, copper, zinc, and manganese transport and regulation in pathogenic Enterobacteria: correlations between strains, site of infection and the relative importance of the different metal transport systems for virulence" *Front Cell Infect Microbiol*, 3:90 (24 pages).

Pugsley, A.P. (Mar. 1993) "The complete general secretory pathway in gram-negative bacteria" *Microbiol Rev*, 57(1):50-108.

Purcell et al. Rule-Based Design of Synthetic Transcription Factors in Eukaryotes. *ACS Synthetic Biology*. 2014;3(10):737-744; online publication date Dec. 12, 2013.

Que, Q. and J.D. Helmann (Mar. 2000) "Manganese homeostasis in *Bacillus subtilis* is regulated by MntR, a bifunctional regulator related to the diphtheria toxin repressor family of proteins" *Mol Microbiol*, 35(6):1454-1468.

Ragsdale, S.W. (Mar. 2008) "Enzymology of the Wood-Ljungdahl Pathway of Acetogenesis" *Ann NY Acad Sci*, 1125:129-136. NIH Public Access Author Manuscript; available in PMC Feb. 16, 2011 (15 pages).

Rajagopal et al. (May 1998) "Use of inducible feedback-resistant N-acetylglutamate synthetase (argA) genes for enhanced arginine biosynthesis by genetically engineered *Escherichia coli* K-12 strains" *Appl Environ Microbiol*, 64(5):1805-1811.

Rao, R. et al. (Jul. 2007) "Manganese induces cell swelling in cultured astrocytes" *Neurotoxicology*, 28(4):807-812.

Ray et al. (Nov. 15, 1997) "The effects of mutation of the anr gene on the aerobic respiratory chain of *Pseudomonas aeruginosa*" *FEMS Microbiol Lett*, 156(2):227-232.

Reboul et al. (2012) Structural and dynamic requirements for optimal activity of the essential bacterial enzyme dihydrodipicolinate synthase. *PLoS Comput Biol*, 8(6):e1002537 [online]. DOI: 10.1371/journal.pcbi.1002537 (11 pages).

Rees, D.C. et al. (Mar. 2009) "ABC transporters: The power to change" *Nat Rev Mol Cell Biol*, 10(3):218-227. NIH Public Access Author Manuscript; available in PMC Mar. 2, 2010 (21 pages).

Reeves, A.Z. et al. (Apr. 2015) "Engineering *E. coli* into a protein delivery system for mammalian cells" *ACS Synth Biol*, Just Accepted Manuscript, DOI: 10.1021/acssynbio.5b00002 [online]. Retrieved from: http://pubs.acs.org, on Apr. 20, 2015 (26 pages). Final publication in vol. 5, pp. 644-654.

Reister et al. (Oct. 10, 2014) "Complete genome sequence of the Gram-negative probiotic *Escherichia coli* strain Nissle 1917" *J Biotechnol*, 187:106-107.

Rembacken et al. (Aug. 21, 1999) "Non-pathogenic *Escherichia coli* versus mesalazine for the treatment of ulcerative colitis: a randomised trial" *Lancet*, 354(9179):635-639.

Rigel, N.W. and Braunstein (2008) "A new twist on an old pathway—accessory secretion systems" *Mol Microbiol*, 69(2):291-302.

Rivera-Mancia et al. (May 2012) "Manganese and ammonia interactions in the brain of cirrhotic rats: effects on brain ammonia metabolism" *Neurochem Res*, 37(5):1074-1084.

Rodriguez-Verdugo, A. (Feb. 22, 2013) "Evolution of *Escherichia coli* rifampicin resistance in an antibiotic-free environment during thermal stress" *BMC Evol Biol*, 13:50 (11 pages).

Saier Jr., M.H. (2006) "Protein Secretion and Membrane Insertion Systems in Gram-Negative Bacteria" *J Membrane Biol*, 214:75-90.

Saier Jr., M.H. (2006) "Protein Secretion Systems in Gram-Negative Bacteria. Gram-negative bacteria possess many protein secretion-membrane insertion systems that apparently evolved independently" *Microbe*, 1(9):414-419.

Saint-Girons et al. (Nov. 25, 1984) "Structure and autoregulation of the metJ regulatory gene in *Escherichia coli*"*J Biol Chem*, 259(22):14282-14285.

Salmon et al. (Aug. 8, 2003) "Global gene expression profiling in *Escherichia coli* K12. The effects of oxygen availability and FNR" *J Biol Chem*, 278(32):29837-29855.

Sat et al. (Mar. 2003) "The *Escherichia coli* mazEF suicide module mediates thymineless death" *J Bacteriol*, 185(6):1803-1807.

Sawers (Jun. 1991) "Identification and molecular characterization of a transcriptional regulator from *Pseudomonas aeruginosa* PAO1 exhibiting structural and functional similarity to the FNR protein of *Escherichia coli*" *Mol Microbiol*, 5(6):1469-1481.

Schiel-Bengelsdorf, B. and P. Dürre (2012) "Pathway engineering and synthetic biology using acetogens" *FEBS Letters*, 586:2191-2198.

Schneider et al. (Aug. 1998) "Arginine catabolism and the arginine succinyltransferase pathway in *Escherichia coli*" *J Bacteriol*, 180(16):4278-4286.

Schultz (Jul. 2008) "Clinical use of *E. coli* Nissle 1917 in inflammatory bowel disease" *Inflamm Bowel Dis*, 14(7):1012-1018.

(56) References Cited

OTHER PUBLICATIONS

Scollo-Lavizzari, G. and E. Steinmann (Jun. 8, 1985) "Reversal of hepatic coma by benzodiazepine antagonist (Ro 15-1788)" *Lancet*, 1(8441):1324-1325.
Selmer, T. et al. (2002) "Propionate CoA-transferase from *Clostridium propionicum*. Cloning of the gene and identification of gluatamate 324 at the active site" *Eur J Biochem*, 269:372-380.
Shannon, K.M. and A. Fraint (Sep. 15, 2015) "Therapeutic advances in Huntington's Disease" *Mov Disord*, 30(11):1539-1546.
Shoeman et al. (Jun. 1985) "Regulation of methionine synthesis in *Escherichia coli*: Effect of metJ gene product and S-adenosylmethionine on the expression of the metF gene" *Proc Natl Acad Sci USA*, 82(11):3601-3605.
Silhavy, T.J. et al. (2010) "The bacterial cell envelope" *Cold Spring Herb Perspect Biol*, 2, a000414 (17 pages).
Sonnenborn and Schulze (2009) "The non-pathogenic *Escherichia coli* strain Nissle 1917—features of a versatile probiotic" *Microbial Ecology in Health and Disease*, 21:122-158.
Spiro, S. (2006) "Nitric oxide-sensing mechanisms in *Escherichia coli*" *Biochem Soc Trans*, 34(1):200-202.
Stanley, S.A. et al. (Oct. 2003) "Acute infection and macrophage subversion by *Mycobacterium tuberculosis* require a specialized secretion system" *PNAS*, 100(22):13001-13006.
Steppan, J. et al. (Sep. 17, 2013) "Development of Novel Arginase Inhibitors for Therapy of Endothelial Dysfunction" *Front Immunol*, 4:278 (6 pages).
Suiter et al. (Oct. 28, 2003) "Fitness consequences of a regulatory polymorphism in a seasonal environment" *Proc Natl Acad Sci USA*, 100(22):12782-12786.
Summerskill (Nov. 1966) "On the origin and transfer of ammonia in the human gastrointestinal tract" *Medicine*, 45(6):491-496.
Szwajkajzer et al. ( Oct. 5, 2001) "Quantitative analysis of DNA binding by the *Escherichia coli* arginine repressor" *J Mol Biol*, 312(5):949-962.
Tag, C.G. et al. (Feb. 2015) "Bile Duct Ligation in Mice: Induction of Inflammatory Liver Injury and Fibrosis by Obstructive Cholestasis" *J Vis Exp*, 96:e52438 (11 pages).
Tian et al. (Jul. 20, 1992) "Binding of the arginine repressor of *Escherichia coli* K12 to its operator sites" *J Mol Biol*, 226(2):387-397.
Tian et al. (Jan. 7, 1994) "Explanation for different types of regulation of arginine biosynthesis in *Escherichia coli* B and *Escherichia coli* K12 caused by a difference between their arginine repressors" *J Mol Biol.*, 235(1):221-230.
Tian et al. (Aug. 1, 1994) "Mutational analysis of the arginine repressor of *Escherichia coli*" *Mol. Microbiol.*, 13(4):599-608.
Torres-Vega et al. (Oct. 23, 2014) "Delivery of glutamine synthetase gene by baculovirus vectors: a proof of concept for the treatment of acute hyperammonemia" *Gene Ther*, 22(1):58-64.
Trunk et al. (Jun. 2010) "Anaerobic adaptation in *Pseudomonas aeruginosa*: definition of the Anr and Dnr regulons" *Environ Microbiol*, 12(6):1719-1733.
Tseng, H-C. and K.L.J. Prather (Oct. 2012) "Controlled biosynthesis of odd-chain fuels and chemicals via engineered modular metabolic pathways" *PNAS*, 109(44):17925-17930.

Tuchman et al. (Jan. 1997) "Enhanced production of arginine and urea by genetically engineered *Escherichia coli* K-12 strains" *Appl Environ Microbiol*, 63(1):33-38.
Ukena et al. (Dec. 12, 2007) "Probiotic *Escherichia coli* Nissle 1917 inhibits leaky gut by enhancing mucosal integrity" *PLoS One*, 2(12):e1308. [online] DOI: 10.1371/journal.pone.0001308 (11 pages).
Unden et al. (Jul. 4, 1997) "Alternative respiratory pathways of *Escherichia coli*: energetics and transcriptional regulation in response to electron acceptors" *Biochim Biophys Acta*, 1320(3):217-234.
Vaquero et al. (Aug. 2003) "Pathogenesis of hepatic encephalopathy in acute liver failure" *Semin Liver Dis*, 23(3):259-269.
Van Heeswijk et al. (Dec. 2013) "Nitrogen assimilation in *Escherichia coli*: putting molecular data into a systems perspective" *Microbiol Mol Biol Rev*, 77(4):628-695.
Vander Wauven et al. (Dec. 1984) "*Pseudomonas aeruginosa* mutants affected in anaerobic growth on arginine: evidence for a four-gene cluster encoding the arginine deiminase pathway" *J Bacteriol*, 160(3):928-934.
Vine, C.E. and J.A. Cole (2011) "Unresolved sources, sinks, and pathways for the recovery of enteric bacteria from nitrosative stress" *FEMS Microbiol Lett*, 325:99-107.
Walker (May 2012) "Severe hyperammonaemia in adults not explained by liver disease" *Ann Clin Biochem*, 49(Pt 3):214-228.
Wallace, M.C. et al. (Apr. 2015) "Standard operating procedures in experimental liver research: thioacetamide model in mice and rats" *Lab Anim*, 49(1 Suppl):21-29.
Williams, R. (2006) "Review article: bacterial flora and pathogenesis in hepatic encephalopathy" *Aliment Pharmacol Ther*, 25(Suppl 1):17-22.
Winteler et al. (Mar. 1996) "The homologous regulators ANR of *Pseudomonas aeruginosa* and FNR of *Escherichia coli* have overlapping but distinct specificities for anaerobically inducible promoters" *Microbiology*, 142(Pt 3):685-693.
Wright et al. (Mar. 20, 2015) "GeneGuard: A modular plasmid system designed for biosafety" *ACS Synth Biol*, 4(3):307-316.
Wu et al. (Oct. 7, 2015) "Direct regulation of the natural competence regulator gene tfoX by cyclic AMP (cAMP) and cAMP receptor protein in *Vibrios*" *Sci Rep*, 5:14921 (15 pages).
Zhang and Lin (2009) "DEG 5.0, a database of essential genes in both prokaryotes and eukaryotes" *Nucl Acids Res*, 37(suppl. 1):D455-D458.
Zheng, M. et al. (Aug. 2001) "DNA Microarray-Mediated Transcriptional Profiling of the *Escherichia coli* Response to Hydrogen Peroxide" *J Bacteriol*, 183(15):4562-4570.
Zhou, D. et al. (Apr. 1999) "*Salmonella typhimurium* Encodes a Putative Iron Transport System within the Centisome 63 Pathogenicity Island" *Infect Immun*, 67(4):1974-1981.
Zimmermann et al. (Jun. 1991) "Anaerobic growth and cyanide synthesis of *Pseudomonas aeruginosa* depend on anr, a regulatory gene homologous with fnr of *Escherichia coli*" *Mol Microbiol*, 5(6):1483-1490.
U.S. Appl. No. 62/183,935, filed Jun. 24, 2015, by Kotula et al.
U.S. Appl. No. 62/184,811, filed Jun. 25, 2015, by Falb et al.
U.S. Appl. No. 62/263,329, filed Dec. 4, 2015, by Kotula et al.

* cited by examiner

Brightness of constitutive RFP integrated in three locations:
1. AraB/C
2. MalE/K
3. MetY/ArgG
4. Nissle (non-fluorescent)

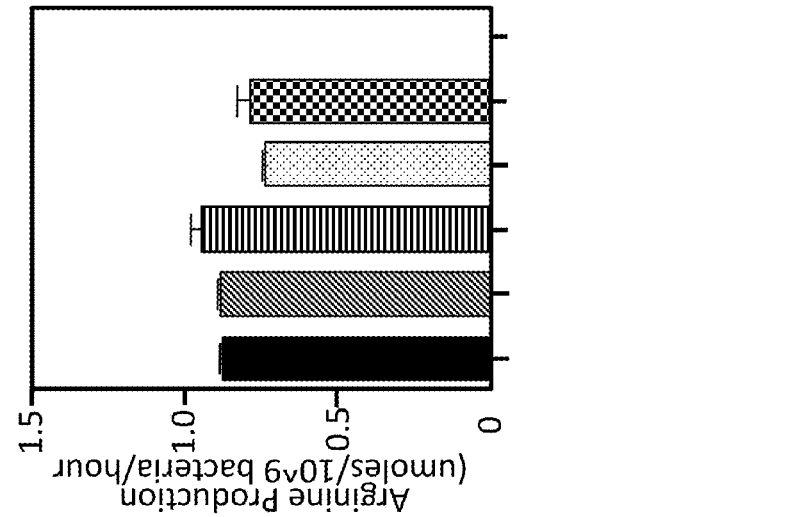
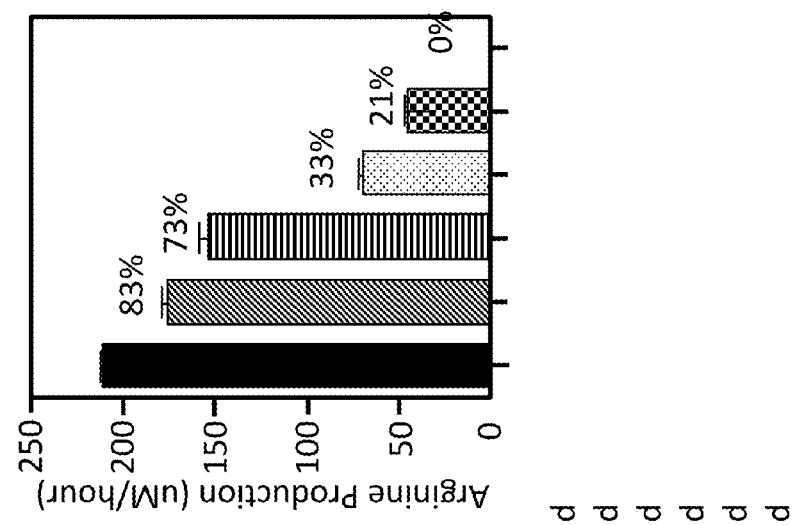
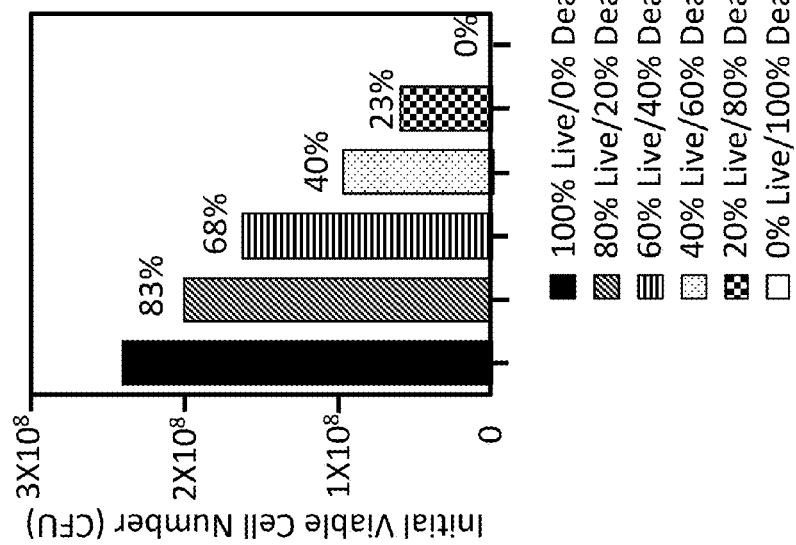

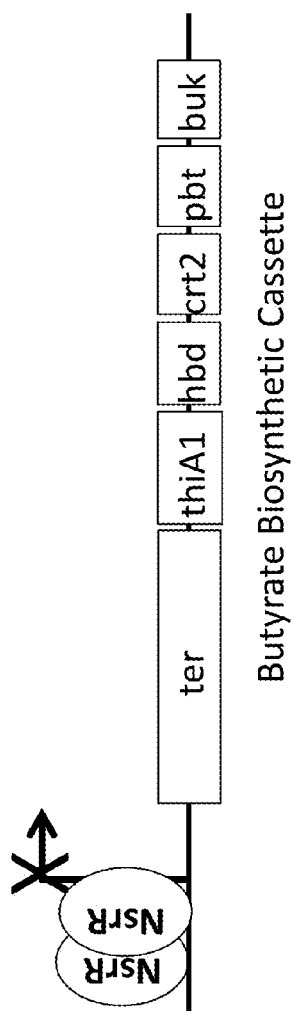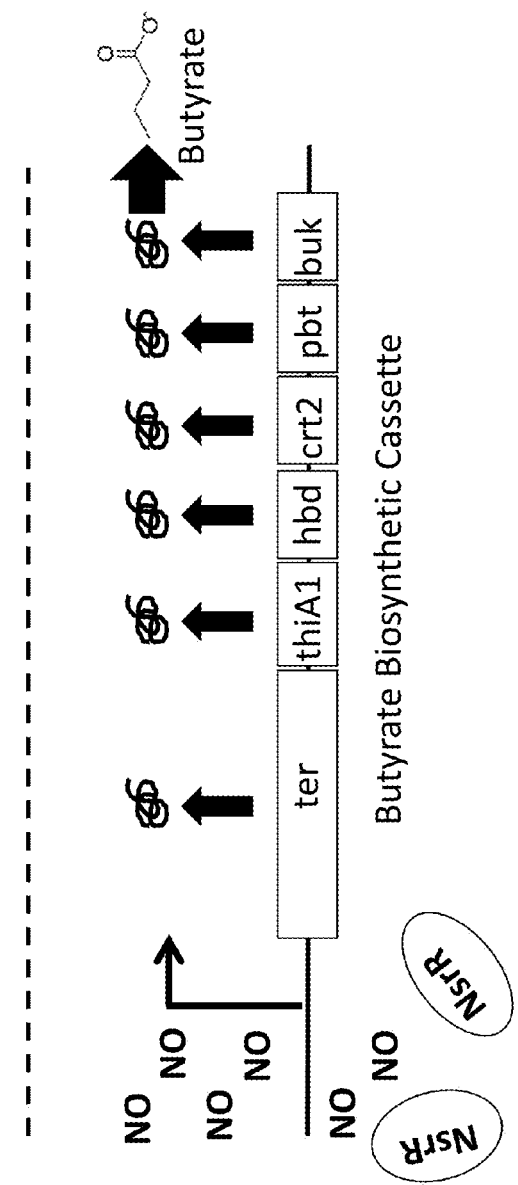
FIG. 50C
FIG. 50D

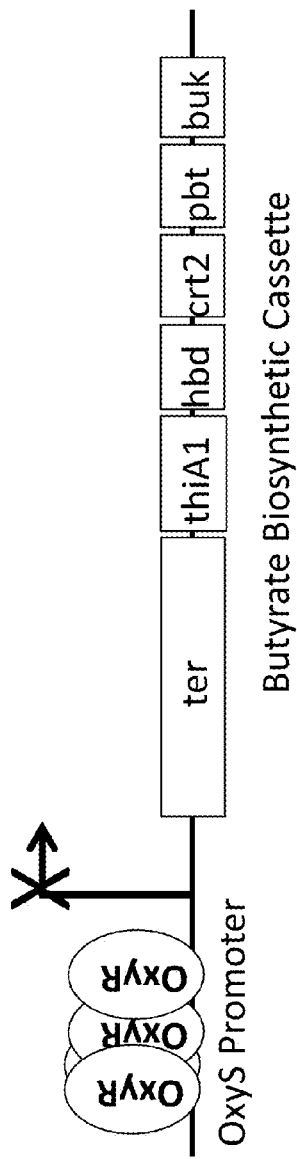
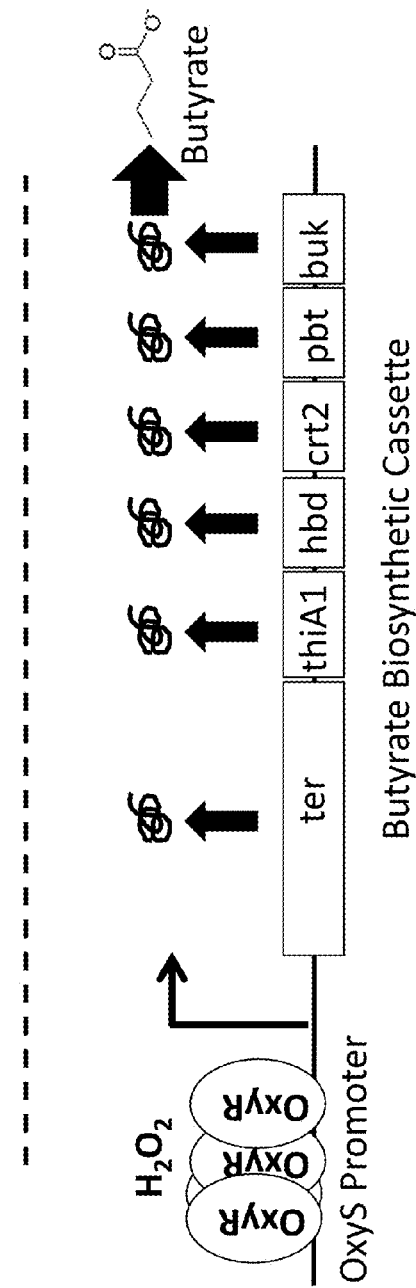
FIG. 50E
FIG. 50F

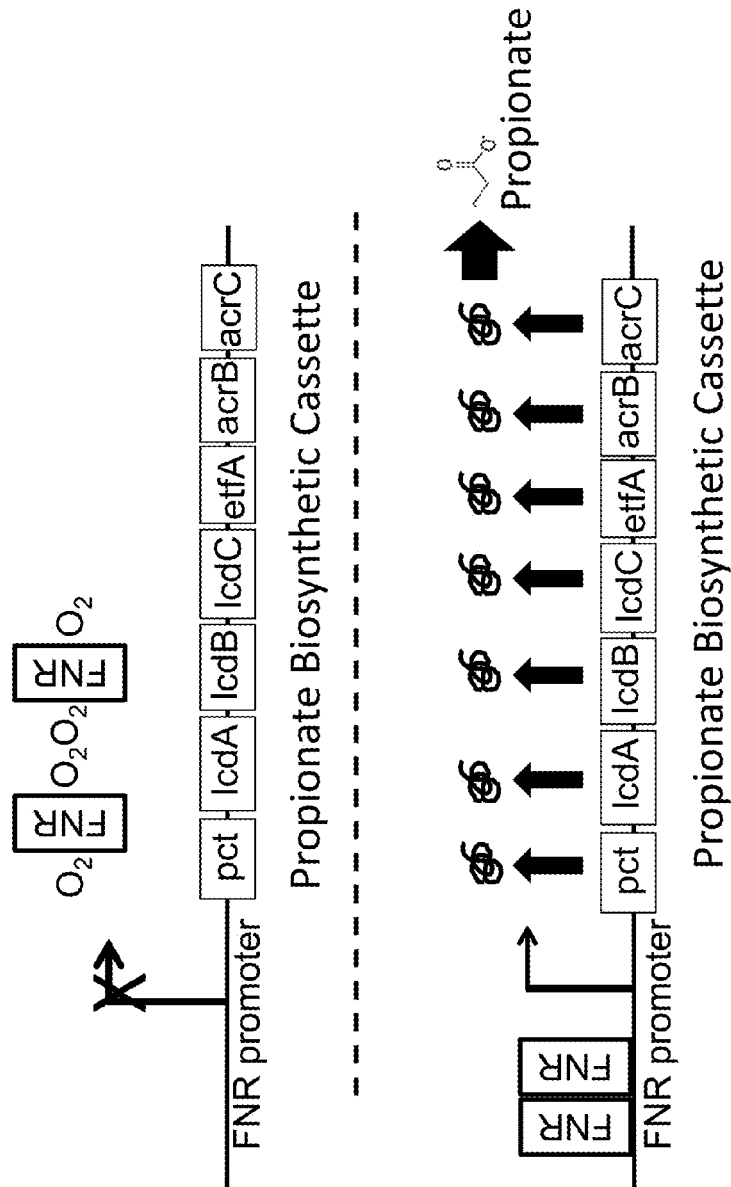

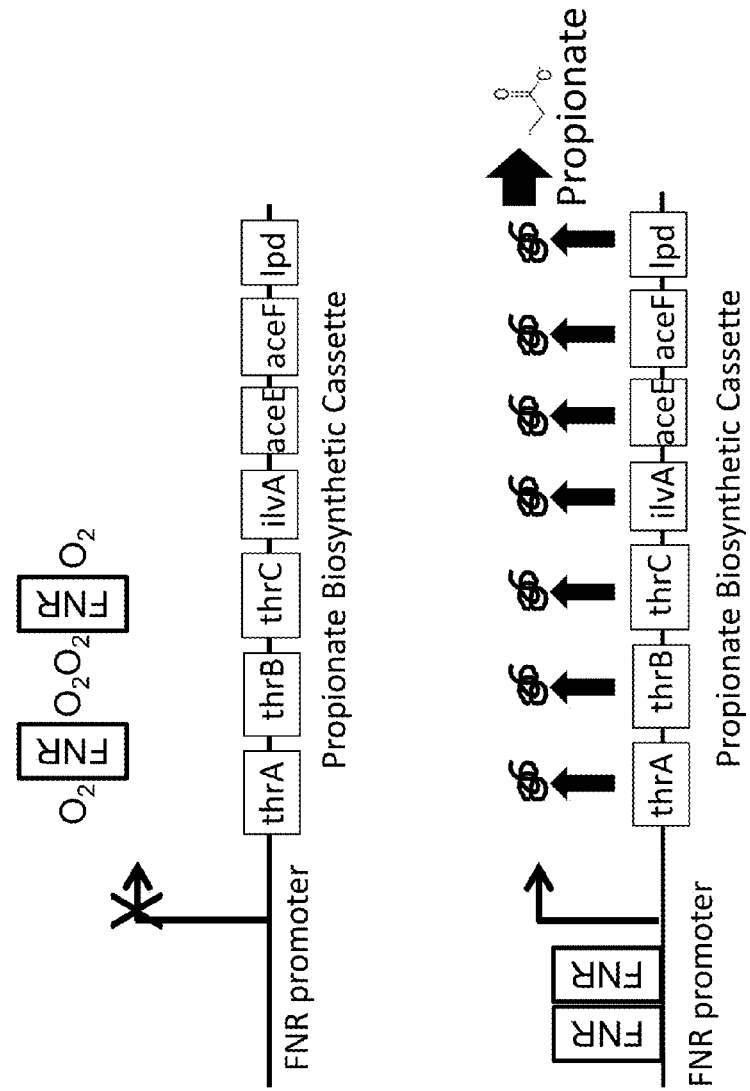

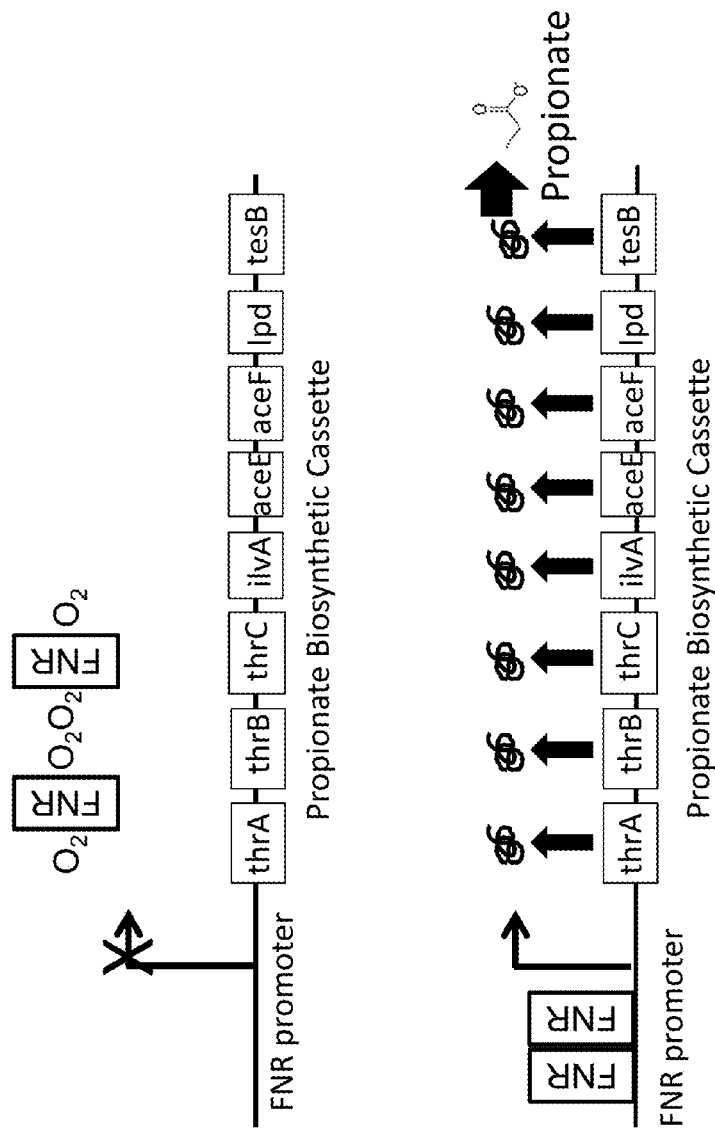

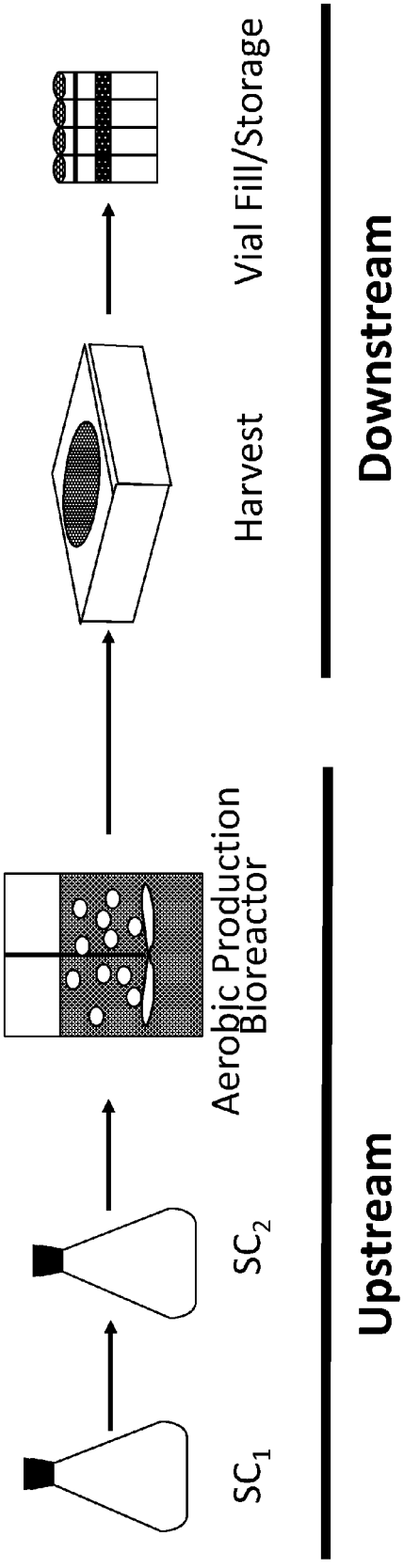

BACTERIA ENGINEERED TO TREAT DISEASES ASSOCIATED WITH HYPERAMMONEMIA

BACKGROUND

This application is a continuation-in-part of U.S. application Ser. No. 14/960,333, filed Dec. 4, 2015; a continuation-in-part of PCT Application No. PCT/US2016/020530, filed Mar. 2, 2016; and claims the benefit of U.S. Provisional Application No. 62/173,710, filed Jun. 10, 2015; U.S. Provisional Application No. 62/173,706, filed Jun. 10, 2015; U.S. Provisional Application No. 62/183,935, filed Jun. 24, 2015; U.S. Provisional Application No. 62/184,811, filed Jun. 25, 2015; U.S. Provisional Application No. 62/184,770, filed Jun. 25, 2015; U.S. Provisional Application No. 62/248,805, filed Oct. 30, 2015; U.S. Provisional Application No. 62/256,041, filed Nov. 16, 2015; U.S. Provisional Application No. 62/256,039, filed Nov. 16, 2015; U.S. Provisional Application No. 62/256,048, filed Nov. 16, 2015; U.S. Provisional Application No. 62/263,329, filed Dec. 4, 2015; U.S. Provisional Application No. 62/291,468, filed Feb. 4, 2016; U.S. Provisional Application No. 62/277,654, filed Jan. 12, 2016; U.S. Provisional Application No. 62/150,508, filed Apr. 21, 2015; U.S. Provisional Application No. 62/103,513, filed Jan. 14, 2015; U.S. Provisional Application No. 62/087,854, filed Dec. 5, 2014; and U.S. Provisional Application No. 62/293,749, filed Feb. 10, 2016; which are incorporated herein by reference in their entirety to provide continuity of disclosure.

SEQUENCE LISTING

The instant application contains a Sequence Listing which has been submitted electronically in ASCII format and is hereby incorporated by reference in its entirety. Said ASCII copy, created on Jun. 23, 2016, is named 12671_0006-01000_SL.txt and is 252,583 bytes in size.

Ammonia is highly toxic and generated during metabolism in all organs (Walker, 2012). In mammals, the healthy liver protects the body from ammonia by converting ammonia to non-toxic molecules, e.g., urea or glutamine, and preventing excess amounts of ammonia from entering the systemic circulation. Hyperammonemia is characterized by the decreased detoxification and/or increased production of ammonia. In mammals, the urea cycle detoxifies ammonia by enzymatically converting ammonia into urea, which is then removed in the urine. Decreased ammonia detoxification may be caused by urea cycle disorders (UCDs) in which urea cycle enzymes are defective, such as argininosuccinic aciduria, arginase deficiency, carbamoylphosphate synthetase deficiency, citrullinemia, N-acetylglutamate synthetase deficiency, and ornithine transcarbamylase deficiency (Häberle et al., 2012). The National Urea Cycle Disorders Foundation estimates that the prevalence of UCDs is 1 in 8,500 births. In addition, several non-UCD disorders, such as hepatic encephalopathy, portosystemic shunting, and organic acid disorders, can also cause hyperammonemia. Hyperammonemia can produce neurological manifestations, e.g., seizures, ataxia, stroke-like lesions, coma, psychosis, vision loss, acute encephalopathy, cerebral edema, as well as vomiting, respiratory alkalosis, hypothermia, or death (Häberle et al., 2012; Häberle et al., 2013).

Ammonia is also a source of nitrogen for amino acids, which are synthesized by various biosynthesis pathways. For example, arginine biosynthesis converts glutamate, which comprises one nitrogen atom, to arginine, which comprises four nitrogen atoms. Intermediate metabolites formed in the arginine biosynthesis pathway, such as citrulline, also incorporate nitrogen. Thus, enhancement of arginine biosynthesis may be used to incorporate excess nitrogen in the body into non-toxic molecules in order to modulate or treat conditions associated with hyperammonemia. Likewise, histidine biosynthesis, methionine biosynthesis, lysine biosynthesis, asparagine biosynthesis, glutamine biosynthesis, and tryptophan biosynthesis are also capable of incorporating excess nitrogen, and enhancement of those pathways may be used to modulate or treat conditions associated with hyperammonemia.

Current therapies for hyperammonemia and UCDs aim to reduce ammonia excess, but are widely regarded as suboptimal (Nagamani et al., 2012; Hoffmann et al., 2013; Torres-Vega et al., 2014). Most UCD patients require substantially modified diets consisting of protein restriction. However, a low-protein diet must be carefully monitored; when protein intake is too restrictive, the body breaks down muscle and consequently produces ammonia. In addition, many patients require supplementation with ammonia scavenging drugs, such as sodium phenylbutyrate, sodium benzoate, and glycerol phenylbutyrate, and one or more of these drugs must be administered three to four times per day (Leonard, 2006; Diaz et al., 2013). Side effects of these drugs include nausea, vomiting, irritability, anorexia, and menstrual disturbance in females (Leonard, 2006). In children, the delivery of food and medication may require a gastrostomy tube surgically implanted in the stomach or a nasogastric tube manually inserted through the nose into the stomach. When these treatment options fail, a liver transplant may be required (National Urea Cycle Disorders Foundation). Thus, there is significant unmet need for effective, reliable, and/or long-term treatment for disorders associated with hyperammonemia, including urea cycle disorders.

The liver plays a central role in amino acid metabolism and protein synthesis and breakdown, as well as in several detoxification processes, notably those of end-products of intestinal metabolism, like ammonia. Liver dysfunction, resulting in hyperammonemia, may cause hepatic encephalopathy (HE), which disorder encompasses a spectrum of potentially reversible neuropsychiatric abnormalities observed in patients with liver dysfunction (after exclusion of unrelated neurologic and/or metabolic abnormalities). In HE, severe liver failure (e.g., cirrhosis) and/or portosystemic shunting of blood around the liver permit elevated arterial levels of ammonia to permeate the blood-brain barrier (Williams, 2006), resulting in altered brain function.

Ammonia accumulation in the brain leads to cognitive and motor disturbances, reduced cerebral perfusion, as well as oxidative stress-mediated injury to astrocytes, the brain cells capable of metabolizing ammonia. There is evidence to suggest that excess ammonia in the brain disrupts neurotransmission by altering levels of the predominant inhibitory neurotransmitter, γ-aminobutyric acid (GABA) (Ahboucha and Butterworth, 2004). Elevated cerebral manganese concentrations and manganese deposition have also been reported in the basal ganglia of cirrhosis patients, and are suspected to contribute to the clinical presentation of HE (Cash et al., 2010; Rivera-Mancía et al., 2012). General neurological manifestations of hyperammonemia include seizures, ataxia, stroke-like lesions, Parkinsonian symptoms (such as tremors), coma, psychosis, vision loss, acute encephalopathy, cerebral edema, as well as vomiting, respiratory alkalosis, hypothermia, or death (Häberle et al., 2012; Häberle et al., 2013).

Ammonia dysmetabolism cannot solely explain all the neurological changes that are seen in patients with HE. Sepsis is a well-known precipitating factor for HE. The systemic inflammatory response syndrome (SIRS) results from the release and circulation of proinflammatory cytokines and mediators. In patients with cirrhosis, SIRS may exacerbate the symptoms of HE, both in patients with minimal and overt HE in a process likely mediated by tumor necrosis factor (TNF) and interleukin-6 (IL6). Notably, enhanced production of reactive nitrogen species (RNS) and reactive oxygen species (ROS) occurs in cultured astrocytes that are exposed to ammonia, inflammatory cytokines, hyponatremia or benzodiazepines.

Hyperammonemia is also a prominent feature of Huntington's disease, an autosomal dominant disorder characterized by intranuclear/cytoplasmic aggregates and cell death in the brain (Chen et al., 2015; Chiang et al., 2007). In fact, hyperammonemia is a feature of several other disorders, as discussed herein, all of which can be treated by reducing the levels of ammonia.

Current therapies for hepatic encephalopathy, Huntington's disease, and other diseases and disorders associated with excess ammonia levels, are insufficient (Cash et al., 2010; Cordoba and Minguez, 2008; Shannon and Fraint, 2015). In Huntington's disease, the side effects of antipsychotic drugs (e.g., haloperidol, risperidone, quetiapine) and drugs administered to suppress involuntary movements (e.g., tetrabenazine, amantadine, levetiracetam, clonazepam) may worsen muscle rigidity and cognitive decline in patients (Mayo Clinic). Antibiotics directed to urease-producing bacteria were shown to have severe secondary effects, such as nephrotoxicity, especially if administered for long periods (Blanc et al., 1992; Berk and Chalmers, 1970). Protein restriction is also no longer a mainstay therapy, as it can favor protein degradation and poor nutritional status, and has been associated with increased mortality (Kondrup and Müller, 1997; Vaqero et al., 2003). Protein restriction is only appropriate for one third of cirrhotic patients with HE (Nguyen and Morgan, 2014). Thus, there is significant unmet need for effective, reliable, and/or long-term treatment for hepatic encephalopathy and Huntington's disease.

SUMMARY

The disclosure provides genetically engineered bacteria that are capable of reducing excess ammonia and converting ammonia and/or nitrogen into alternate byproducts. In certain embodiments, the genetically engineered bacteria reduce excess ammonia and convert ammonia and/or nitrogen into alternate byproducts. In certain embodiments, the genetically engineered bacteria are non-pathogenic and may be introduced into the gut in order to reduce toxic ammonia. As much as 70% of excess ammonia in a hyperammonemic patient accumulates in the gastrointestinal tract. Another aspect of the invention provides methods for selecting or targeting genetically engineered bacteria based on increased levels of ammonia and/or nitrogen consumption, or production of a non-toxic byproduct, e.g., arginine or citrulline. The invention also provides pharmaceutical compositions comprising the genetically engineered bacteria, and methods of modulating and treating disorders associated with hyperammonemia, e.g., urea cycle disorders and hepatic encephalopathy.

The disclosure also provides genetically engineered bacteria that are capable of reducing excess ammonia and other deleterious molecules, e.g., GABA, manganese. In certain embodiments, the genetically engineered bacteria reduce excess ammonia and convert ammonia and/or nitrogen into alternate byproducts. In certain embodiments, the genetically engineered bacteria are non-pathogenic and may be introduced into the gut in order to reduce toxic ammonia. In certain embodiments, the genetically engineered bacteria are capable of reducing excess ammonia and other deleterious molecules, e.g., GABA, manganese, and are also capable of producing one or more gut barrier enhancer molecules, e.g., one or more short chain fatty acid(s), such as butyrate. Another aspect of the disclosure provides methods for selecting or targeting genetically engineered bacteria based on increased levels of ammonia and/or nitrogen consumption, or production of a non-toxic byproduct, e.g., arginine or citrulline. The invention also provides pharmaceutical compositions comprising the genetically engineered bacteria, and methods of modulating and treating disorders associated with excess ammonia, including, for example, hepatic encephalopathy and Huntington's disease.

In some embodiments, the genetically engineered bacteria comprise one or more gene(s) or gene cassette(s) or circuit(s), containing one or more native or non-native component(s), which mediate one or more mechanisms of action. Additionally, one or more endogenous genes or regulatory regions within the bacterial chromosome may be mutated or deleted. The genetically engineered bacteria harbor these genes or gene cassettes or circuits on a plasmid or, alternatively, the genes/gene cassettes have been inserted into the chromosome at certain regions, where they do not interfere with essential gene expression.

These gene(s)/gene cassette(s) may be under the control of constitutive or inducible promoters. Exemplary inducible promoters described herein include oxygen level-dependent promoters (e.g., FNR-inducible promoter), promoters induced by HE-specific molecules or metabolites indicative of liver damage (e.g., bilirubin), promoters induced by inflammation or an inflammatory response (RNS, ROS promoters), and promoters induced by a metabolite that may or may not be naturally present (e.g., can be exogenously added) in the gut, e.g., arabinose and tetracycline.

In addition, the engineered bacteria may further comprise one or more of more of the following: (1) one or more auxotrophies, such as any auxotrophies known in the art and provided herein, e.g., thyA auxotrophy, (2) one or more kill switch circuits, such as any of the kill-switches described herein or otherwise known in the art, (3) one or more antibiotic resistance circuits, (4) one or more transporters for importing biological molecules or substrates, such any of the transporters described herein or otherwise known in the art, (5) one or more secretion circuits, such as any of the secretion circuits described herein and otherwise known in the art, and (6) combinations of one or more of such additional circuits.

BRIEF DESCRIPTION OF THE FIGURES

FIG. 1A depicts relatively low arginine production under aerobic conditions due to arginine ("Arg" in oval) interacting with ArgA (squiggle ✱) to inhibit (indicated by "X") ArgA activity, while oxygen ($O_2$) prevents (indicated by "X") FNR (dotted boxed FNR) from dimerizing and activating the FNR promoter (grey FNR box) and the argA$^{fbr}$ gene under its control. FIG. 1B depicts up-regulated arginine production under anaerobic conditions due to FNR dimerizing (two dotted boxed FNRs) and inducing FNR promoter (grey FNR box)-mediated expression of ArgA$^{fbr}$ (squiggle above argA$^{fbr}$), which is resistant to inhibition by arginine. This overcomes (curved arrow) the inhibition of the wild-type ArgA caused by arginine ("Arg" in oval) interacting with ArgA (squiggle above box depicting argA). Each gene in the arginine regulon is depicted by a rectangle containing the name of the gene. Each arrow adjacent to one or a cluster of rectangles depict the promoter responsible for driving transcription, in the direction of the arrow, of such gene(s). Heavier lines adjacent one or a series of rectangles depict ArgR binding sites, which are not utilized because of the ArgR deletion in this bacterium. Arrows above each rectangle depict the expression product of each gene.

FIG. 2A depicts the embodiment under aerobic conditions where, in the presence of oxygen, the FNR proteins (FNR boxes) remain as monomers and are unable to bind to and activate the FNR promoter ("FNR") which drives expression of the arginine feedback resistant argA$^{fbr}$ gene. The wild-type ArgA protein is functional, but is susceptible to negative feedback inhibition by binding to arginine, thus keeping arginine levels at or below normal. All of the arginine repressor (ArgR) binding sites in the promoter regions of each arginine biosynthesis gene (argA, argE, argC, argB, argH, argD, argI, argG, carA, and carB) have been mutated (black bars; black "X") to reduce or eliminate binding to ArgR. FIG. 2B depicts the same embodiment under anaerobic conditions where, in the absence of oxygen the FNR protein (FNR boxes) dimerizes and binds to and activates the FNR promoter ("FNR"). This drives expression of the arginine feedback resistant argA$^{fbr}$ gene (black squiggle ( )=argA$^{fbr}$ gene expression product), which is resistant to feedback inhibition by arginine ("Arg" in ovals). All of the arginine repressor (ArgR) binding sites in the promoter regions of each arginine biosynthetic gene (argA, argE, argC, argB, argH, argD, argI, argG, carA, and carB) have been mutated (black bars) to reduce or eliminate binding to ArgR (black "X"), thus preventing inhibition by an arginine-ArgR complex. This allows high level production of arginine.

FIG. 9A depicts a map of the FNR-CRP promoter region, with restriction sites shown in bold. FIG. 9B depicts a schematic diagram of the argA$^{fbr}$ gene under the control of an exemplary FNR promoter (nirB promoter), fused to both a CRP binding site and a ribosome binding site. Other regulatory elements may also be present.

FIG. 10A depicts a map of the FNR-CRP promoter region, with restriction shown in bold. FIG. 10B depicts a schematic diagram of the argA$^{fbr}$ gene under the control of an exemplary FNR promoter (fnrS promoter), fused to both a CRP binding site and a ribosome binding site.

FIG. 28A depicts a bar graph of ammonia levels in hyperammonemic mice treated with unmodified control Nissle or SYN-UCD202, a genetically engineered strain in which the Arg repressor gene is deleted and the argA$^{fbr}$ gene is under the control of a tetracycline-inducible promoter on a high-copy plasmid. A total of 96 mice were tested, and the error bars represent standard error. Blood ammonia (BA) levels in mice treated with SYN-UCD202 are lower than ammonia levels in mice treated with unmodified control Nissle at day 4 and day 5 (Nissle, BA=220 mM; SYN-UCD202, BA=105 mM; BA$_{Nissle}$−BA$_{SYN-UCD202}$=115 mM; average blood volume=1.5 mL. FIG. 28B depicts a bar graph showing in vivo efficacy (ammonia consumption) of SYN-UCD204 in the TAA mouse model, relative to streptomycin-resistant control Nissle (SYN-UCD103) and vehicle-only controls. FIG. 28C depicts a bar graph of the percent change in blood ammonia concentration between 24-48 hours post-TAA treatment.

As seen in FIG. 30, at 48 hours after switch to high protein chow ammonia levels were reduced to a similar extent in both SYN-UCD205 and SYN-UCD206, indicating that ThyA auxotrophy does not have a significant effect on efficacy.

FIG. 31A depicts a bar graph of the levels of arginine production of SYN-UCD205, SYN-UCD206, and SYN-UCD301 measured at 0, 30, 60, and 120 minutes. FIG. 31B depicts a bar graph of the levels of arginine production of SYN-UCD204 (comprising ΔArgR, PfnrS-ArgAfbr on a low-copy plasmid and wild type ThyA), SYN-UCD301, SYN-UCD302, and SYN-UCD303 (all three of which comprise an integrated FNR-ArgAfbr construct; SYN UCD301 comprises ΔArgR, and wtThyA; SYN 303 comprises ΔArgR, and ΔThyA). Results indicate that chromosomal integration of FNR ArgA fbr results in similar levels of arginine production as seen with the low copy plasmid strains expressing the same construct.

FIG. 32A depicts a bar graph of ammonia levels in hyperammonemic spf$^{ash}$ mice on a normal (NC) or high protein (HP) diet. Ammonia levels of spf-ash mice in a high protein diet were reduced in the SYN-UCD301 and SYN-UCD303 groups as compared to the H2O high protein diet control group. The observed reduction in ammonia levels was similar in both SYN-UCD301 and SYN-UCD303, indicating that ThyA auxotrophy does not have a significant effect on efficacy of SYN-UCD303. FIG. 32B depicts a survival curve of hyperammonemic spf$^{ash}$ mice on a normal (NC) or high protein (HP) diet and shows that SYN-UCD301 and SYN-UCD303 displayed prolonged survival as compared to controls.

FIG. 35A depicts a bar graph of residence over time for SYN-UCD103 (streptomycin resistant Nissle). FIG. 35B depicts a bar graph residence over time for SYN-UCD106, comprising ΔArgR and ΔThyA and no ArgAfbr. FIG. 35C depicts a bar graph showing residence over time for SYN-UCD303, comprising ΔArgR, PfnrS-ArgAfbr integrated into the chromosome at the malEK locus, and ΔThyA.

FIGS. 36A, 36B, and 36C depict bar graphs of viable bacterial cells and arginine production. Cells were either incubated with 70% isopropanol or phosphate buffered saline (PBS) as a control for 1 hour with shaking. After treatment, the cells were mixed at specific ratios in M9 media supplemented with 0.5% glucose and 3 mM thymidine and incubated with shaking at 37 C for 2 hours. As seen in FIGS. 36A and 36B, a greater ratio of isopropanol treated cells to untreated in a culture results in fewer CFUs as determined by plating, and lower levels of arginine production. Arginine production relative to amount of bacteria present remained constant across the various cultures (FIG. 36C). These results indicate that only viable bacteria are contributing to arginine production.

In FIG. 41A, upon entry into the cell, GABA is converted to succinyl semialdehyde by GABA α-ketoglutarate transaminase (GSST). Succinate-semialdehyde dehydrogenase (SSDH) then catalyzes the second and only other specific step in GABA catabolism, the oxidation of succinyl semialdehyde to succinate. Ultimately, succinate becomes a substrate for the citric acid (TCA) cycle. GOT (glutamate oxaloacetate transaminase) converts alpha-ketoglutarate to glutamate. In certain embodiments, the genetically engineered bacteria of the disclosure comprise a GABA consuming circuit including, but not limited to, one or more of GSST, SSDH, and GOT. FIG. 41B depicts a schematic representation of the GABA utilization pathway in E. coli Nissle.

In FIG. 46A, an ammonia conversion circuit, a butyrate production circuit, and a GABA transport and/or GABA metabolic circuit are inserted at three different chromosomal insertion sites. In FIG. 46B, an ammonia conversion circuit, a GABA transport and/or GABA metabolic circuit, and a manganese transport circuit are inserted at three or more different chromosomal insertion sites.

In FIG. 47A, an ammonia conversion circuit, and a manganese transport circuit are inserted at two different chromosomal insertion sites. In FIG. 47B, an ammonia conversion circuit, and a GABA transport and/or GABA metabolic circuit are inserted at two or more different chromosomal insertion sites.

FIGS. 49A and 49B depict the gene organization of an exemplary recombinant bacterium of the invention and its induction under low-oxygen conditions. FIG. 49A depicts relatively low butyrate production under aerobic conditions in which oxygen (02) prevents (indicated by "X") FNR (grey boxed "FNR") from dimerizing and activating the FNR-responsive promoter ("FNR promoter"). Therefore, none of the butyrate biosynthesis enzymes (bcd2, etfB3, etfA3, thiA1, hbd, crt2, pbt, and buk; black boxes) is expressed. FIG. 49B depicts increased butyrate production under low-oxygen conditions due to FNR dimerizing (two grey boxed "FNR" s), binding to the FNR-responsive promoter, and inducing expression of the butyrate biosynthesis enzymes, which leads to the production of butyrate. FIGS. 49C and 49D depict the gene organization of an exemplary recombinant bacterium of the invention and its derepression in the presence of nitric oxide (NO). In FIG. 49C, in the absence of NO, the NsrR transcription factor (gray circle, "NsrR") binds to and represses a corresponding regulatory region. Therefore, none of the butyrate biosynthesis enzymes (bcd2, etfB3, etfA3, thiA1, hbd, crt2, pbt, buk; black boxes) is expressed. In FIG. 49D, in the presence of NO, the NsrR transcription factor interacts with NO, and no longer binds to or represses the regulatory sequence. This leads to expression of the butyrate biosynthesis enzymes (indicated by gray arrows and black squiggles) and ultimately to the production of butyrate. FIGS. 49E and F depict the gene organization of an exemplary recombinant bacterium of the invention and its induction in the presence of H2O2. In FIG. 49E, in the absence of H2O2, the OxyR transcription factor (gray circle, "OxyR") binds to, but does not induce, the oxyS promoter. Therefore, none of the butyrate biosynthesis enzymes (bcd2, etfB3, etfA3, thiA1, hbd, crt2, pbt, buk; black boxes) is expressed. In FIG. 49F, in the presence of H2O2, the OxyR transcription factor interacts with H2O2 and is then capable of inducing the oxyS promoter. This leads to expression of the butyrate biosynthesis enzymes (indicated by gray arrows and black squiggles) and ultimately to the production of butyrate.

FIGS. 50A-F depict the gene organization of exemplary recombinant bacteria of the disclosure and their induction under anaerobic or inflammatory conditions for the production of butyrate. FIGS. 50A and 50B depict the gene organization of an exemplary recombinant bacterium of the invention and its induction under low-oxygen conditions. FIG. 50A depicts relatively low butyrate production under aerobic conditions in which oxygen ($O_2$) prevents (indicated by "X") FNR (grey boxed "FNR") from dimerizing and activating the FNR-responsive promoter ("FNR promoter"). Therefore, none of the butyrate biosynthesis enzymes (ter, thiA1, hbd, crt2, pbt, and buk; black boxes) is expressed. FIG. 50B depicts increased butyrate production under low-oxygen conditions due to FNR dimerizing (two grey boxed "FNR" s), binding to the FNR-responsive promoter, and inducing expression of the butyrate biosynthesis enzymes, which leads to the production of butyrate. FIGS. 50C and 50D depict the gene organization of another exemplary recombinant bacterium of the invention and its derepression in the presence of NO. In FIG. 50C, in the absence of NO, the NsrR transcription factor (gray circle, "NsrR") binds to and represses a corresponding regulatory region. Therefore, none of the butyrate biosynthesis enzymes (ter, thiA1, hbd, crt2, pbt, buk; black boxes) is expressed. In FIG. 50D, in the presence of NO, the NsrR transcription factor interacts with NO, and no longer binds to or represses the regulatory sequence. This leads to expression of the butyrate biosynthesis enzymes (indicated by gray arrows and black squiggles) and ultimately to the production of butyrate. FIGS. 50E and 50F depict the gene organization of another exemplary recombinant bacterium of the invention and its induction in the presence of $H_2O_2$. In FIG. 50E, in the absence of $H_2O_2$, the OxyR transcription factor (gray circle, "OxyR") binds to, but does not induce, the oxyS promoter. Therefore, none of the butyrate biosynthesis enzymes (ter, thiA1, hbd, crt2, pbt, buk; black boxes) is expressed. In FIG. 50F, in the presence of $H_2O_2$, the OxyR transcription factor interacts with $H_2O_2$ and is then capable of inducing the oxyS promoter. This leads to expression of the butyrate biosynthesis enzymes (indicated by gray arrows and black squiggles) and ultimately to the production of butyrate.

As seen in FIG. 51A, similar amounts of butyrate were produced for each construct under aerobic vs anaerobic conditions. The ter strain produces more butyrate overall. SYN-UCD503 comprises pLogic031 (bdc2 butyrate cassette under control of tet promoter on a plasmid) and SYN-UCD504 comprises pLogic046 (ter butyrate cassette under control of tet promoter on a plasmid). FIG. 51B depicts butyrate production of SYN-UCD504 (pLogic046 (ter butyrate cassette under control of tet promoter on a plasmid)) and SYN-UCD505 (a Nissle strain comprising plasmid pLOGIC046-delta pbt.buk/tesB+, an ATC-inducible ter-comprising butyrate construct with a deletion in the pbt-buk genes and their replacement with the tesB gene). The tesB construct results in greater butyrate production.

FIGS. 55A and 55B depict the gene organization of an exemplary engineered bacterium of the invention and its induction under low-oxygen conditions for the production of propionate. FIG. 55A depicts relatively low propionate production under aerobic conditions in which oxygen ($O_2$) prevents (indicated by "X") FNR (grey boxed "FNR") from dimerizing and activating the FNR-responsive promoter ("FNR promoter"). Therefore, none of the propionate biosynthesis enzymes (pct, lcdA, lcdB, lcdC, etfA, acre, acrC; black boxes) are expressed. FIG. 55B depicts increased propionate production under low-oxygen conditions due to FNR dimerizing (two grey boxed "FNR" s), binding to the FNR-responsive promoter, and inducing expression of the propionate biosynthesis enzymes, which leads to the production of propionate.

FIGS. 57A, 57B and 57C depict the gene organization of an exemplary engineered bacterium and its induction under low-oxygen conditions for the production of propionate. FIG. 57A depicts relatively low propionate production under aerobic conditions in which oxygen ($O_2$) prevents (indicated by "X") FNR (grey boxed "FNR") from dimerizing and activating the FNR-responsive promoter ("FNR promoter"). Therefore, none of the propionate biosynthesis enzymes (thrA, thrB, thrC, ilvA, aceE, aceF, lpd; black boxes) are expressed. FIG. 57B depicts increased propionate production under low-oxygen conditions due to FNR dimerizing (two grey boxed "FNR" s), binding to the FNR-responsive promoter, and inducing expression of the propionate biosynthesis enzymes, which leads to the production of propionate. FIG. 57C depicts an exemplary propionate biosynthesis gene cassette.

FIGS. 58A and 58B depict the gene organization of an exemplary engineered bacterium of the invention and its induction under low-oxygen conditions for the production of propionate. FIG. 58A depicts relatively low propionate production under aerobic conditions in which oxygen ($O_2$) prevents (indicated by "X") FNR (grey boxed "FNR") from dimerizing and activating the FNR-responsive promoter ("FNR promoter"). Therefore, none of the propionate biosynthesis enzymes (thrA, thrB, thrC, ilvA, aceE, aceF, lpd, tesB; black boxes) are expressed. FIG. 58B depicts increased propionate production under low-oxygen conditions due to FNR dimerizing (two grey boxed "FNR" s), binding to the FNR-responsive promoter, and inducing expression of the propionate biosynthesis enzymes, which leads to the production of propionate.

FIG. 60A depicts a map of the astC promoter driving expression of thyA. FIG. 60B depicts a schematic diagram of the thyA gene under the control of an astC promoter. The regulatory region comprises binding sites for CRP, ArgR, and RNA polymerase (RNAP), and may also comprise additional regulatory elements.

Hyperammonemia can also contribute to other pathologies. FIG. 66A also depicts another non-limiting embodiment of the disclosure, wherein the expression of an essential gene not found in the recombinant bacteria is activated by an exogenous environmental signal. In the absence of arabinose, the AraC transcription factor adopts a conformation that represses transcription of the essential gene under the control of the araBAD promoter and the bacterial cell cannot survive. In the presence of arabinose, the AraC transcription factor undergoes a conformational change that allows it to bind to and activate the araBAD promoter, which induces expression of the essential gene and maintains viability of the bacterial cell.

FIGS. 81A, B, C, D, and E depict a schematic of non-limiting manufacturing processes for upstream and downstream production of the genetically engineered bacteria of the present disclosure. FIG. 81A depicts the parameters for starter culture 1 (SC1): loop full—glycerol stock, duration overnight, temperature 37° C., shaking at 250 rpm. FIG. 81B depicts the parameters for starter culture 2 (SC2): 1/100 dilution from SC1, duration 1.5 hours, temperature 37° C., shaking at 250 rpm. FIG. 81C depicts the parameters for the production bioreactor: inoculum—SC2, temperature 37° C., pH set point 7.00, pH dead band 0.05, dissolved oxygen set point 50%, dissolved oxygen cascade agitation/gas FLO, agitation limits 300-1200 rpm, gas FLO limits 0.5-20 standard liters per minute, duration 24 hours. FIG. 81D depicts the parameters for harvest: centrifugation at speed 4000 rpm and duration 30 minutes, wash 1×10% glycerol/PBS, centrifugation, re-suspension 10% glycerol/PBS. FIG. 81E depicts the parameters for vial fill/storage: 1-2 mL aliquots, −80° C.

FIG. 82C depicts a schematic of the constructs.

DESCRIPTION OF EMBODIMENTS

Figure 1A:
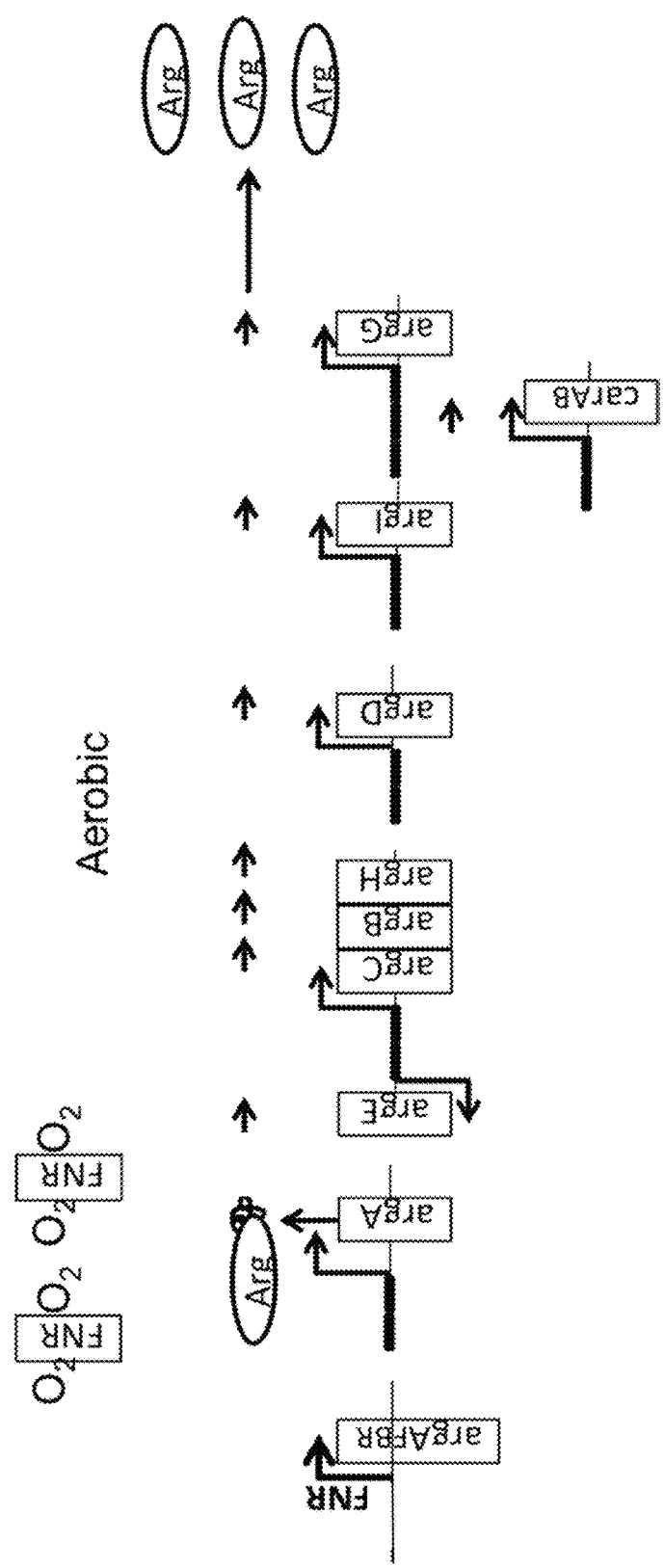
FIGS. 1A and 1B depict the state of the arginine regulon in one embodiment of an ArgR deletion bacterium of the invention under non-inducing (FIG. 1A) and inducing (FIG. 1B) conditions.
Figure 1B:
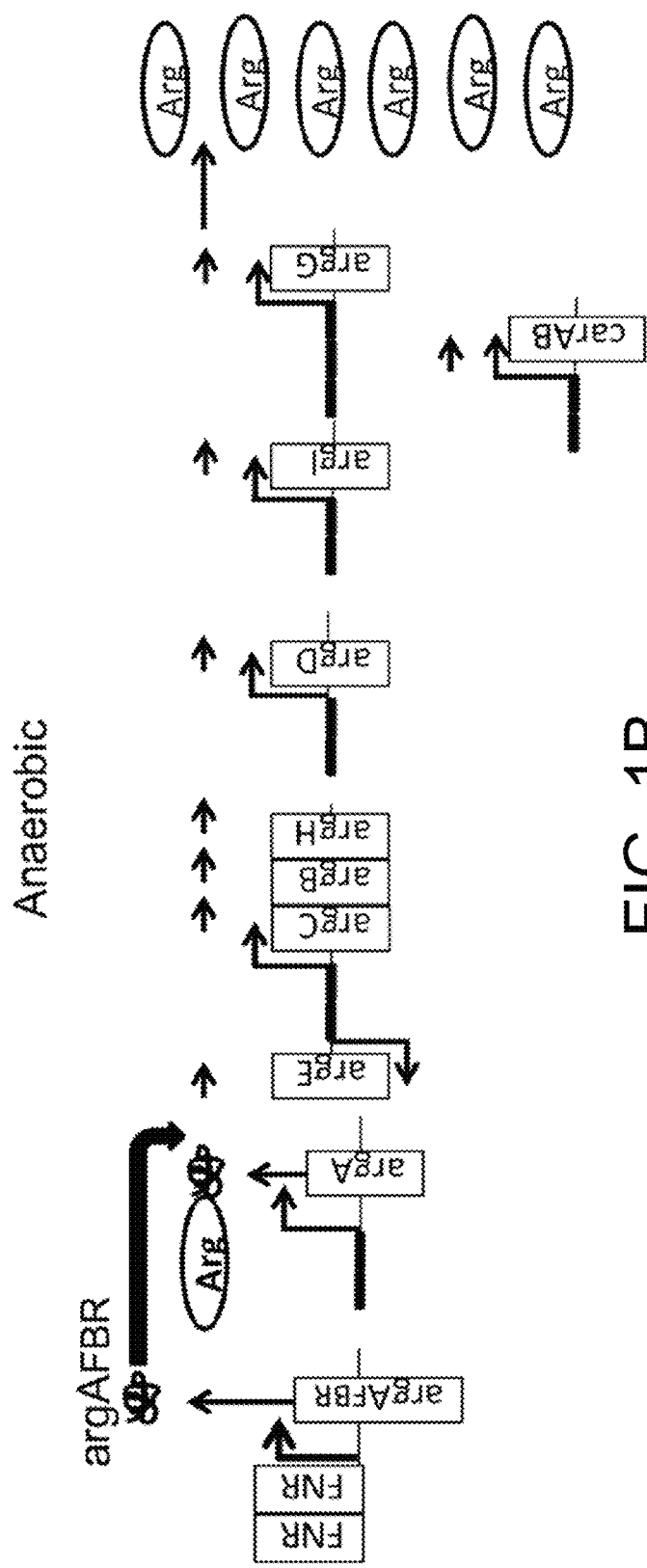
Figure 2A:
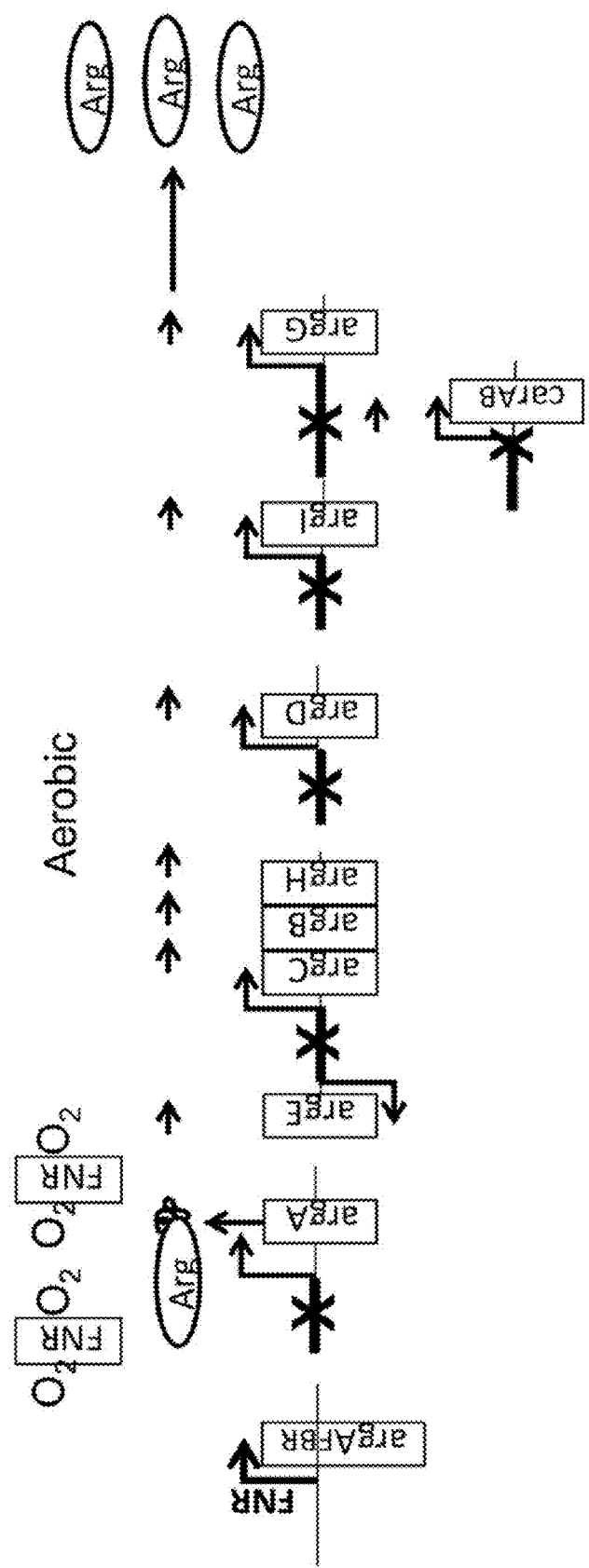
FIGS. 2A and 2B depict an alternate exemplary embodiment of the present invention.
Figure 2B:
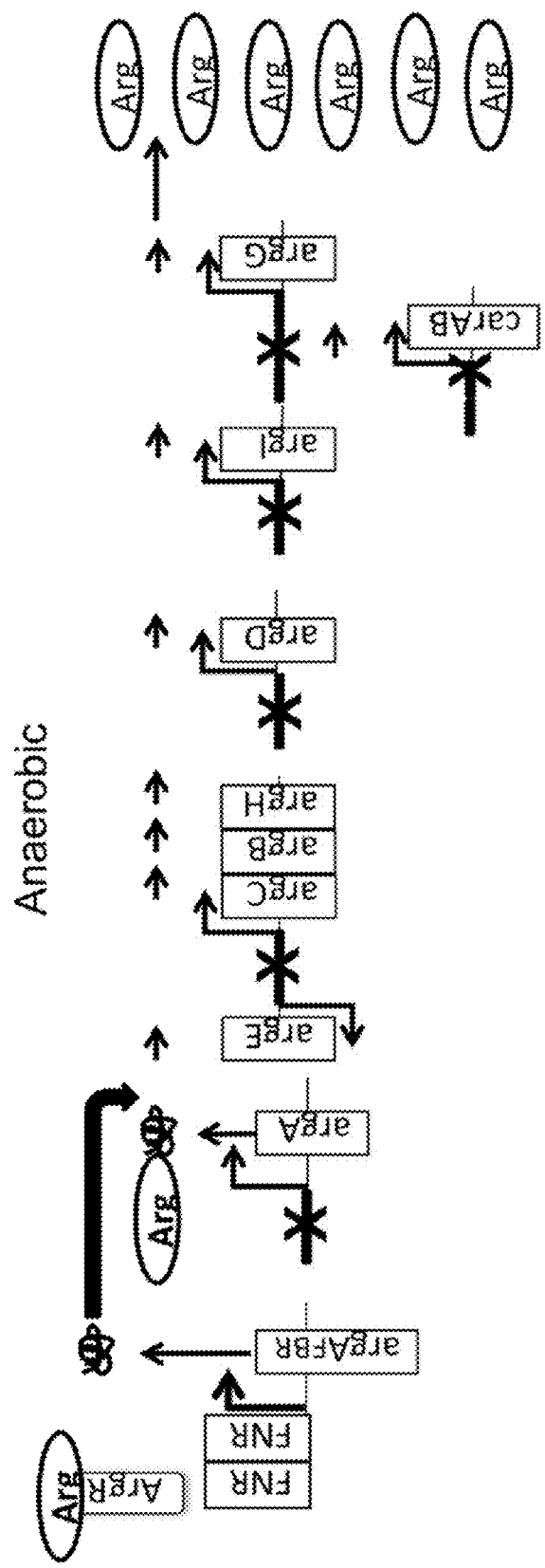
Figure 3:
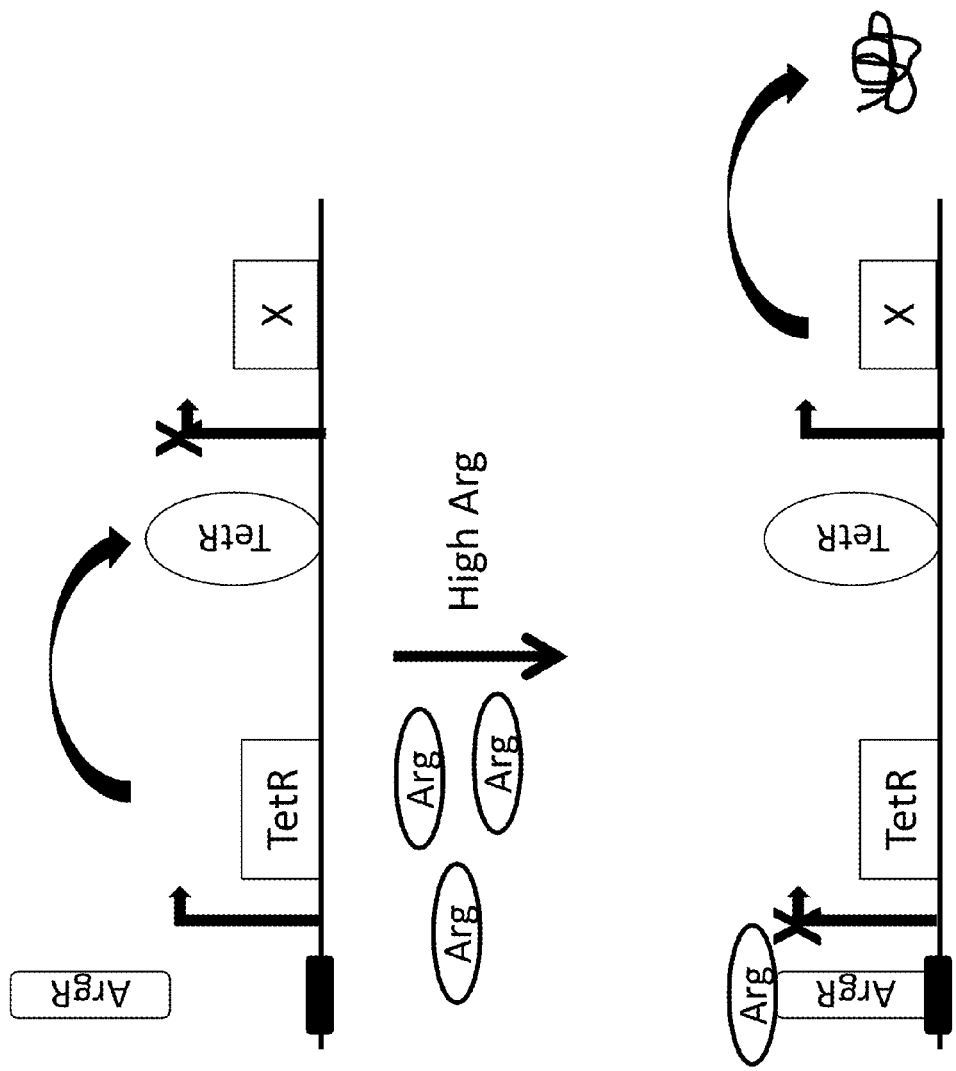
FIG. 3 depicts another embodiment of the invention. In this embodiment, a construct comprising an ArgR binding site (black bar) in a promoter driving expression of the Tet repressor (TetR) from the tetR gene is linked to a second promoter comprising a TetR binding site (black bar between TetR and X) that drives expression of gene X. Under low arginine concentrations, TetR is expressed and inhibits the expression of gene X. At high arginine concentrations, ArgR associates with arginine and binds to the ArgR binding site, thereby inhibiting expression of TetR from the tetR gene. This, in turn, removes the inhibition by TetR allowing gene X expression (black squiggle ( )).
Figure 4:
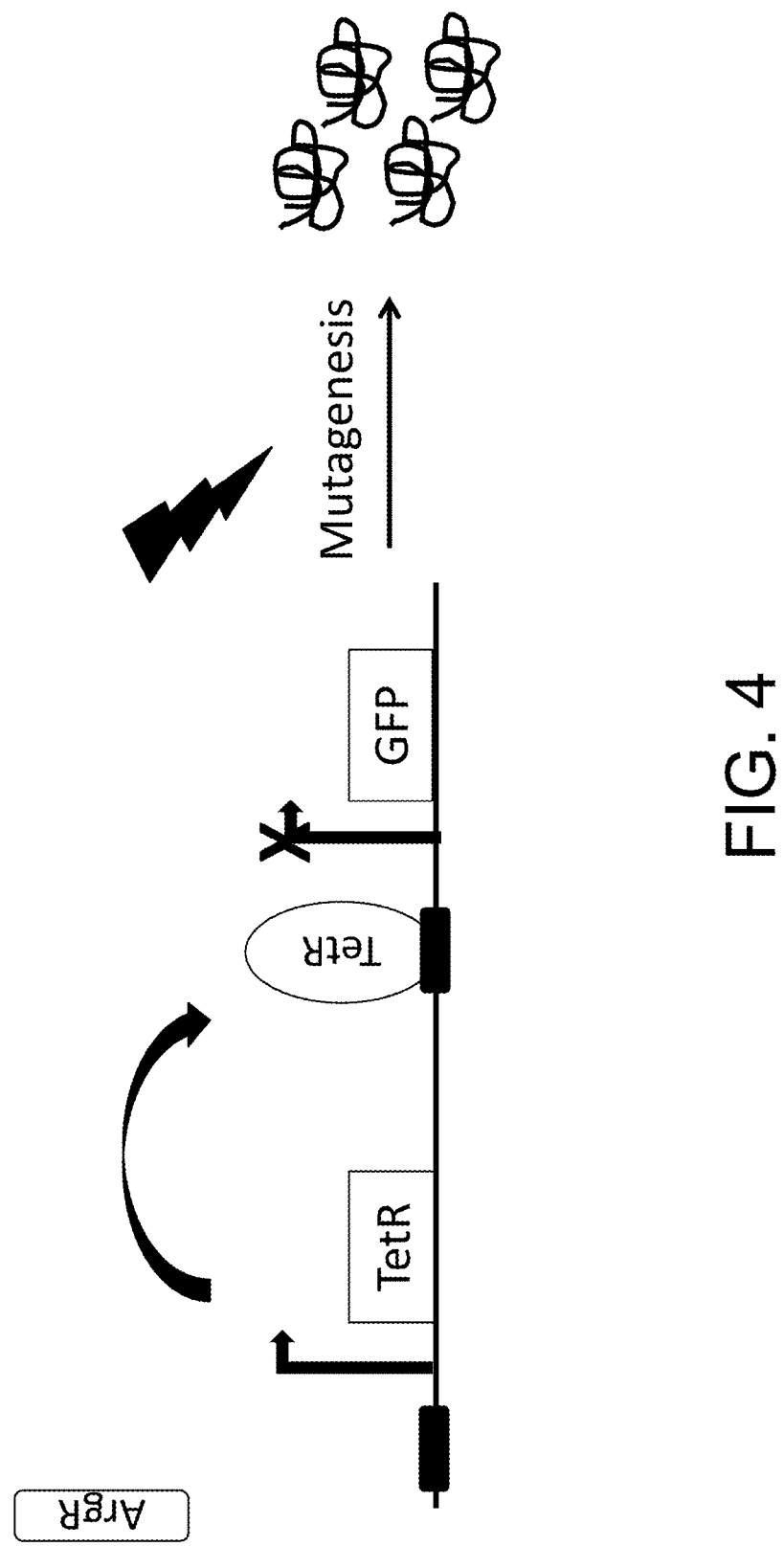
FIG. 4 depicts another embodiment of the invention. In this embodiment, a construct comprising an ArgR binding site (black bar) in a promoter driving expression of the Tet repressor (TetR) from the tetR gene is linked to a second promoter comprising a TetR binding site (black bar bound to TetR oval) that drives expression of green fluorescent protein ("GFP"). Under low arginine concentrations, TetR is expressed and inhibits the expression of GFP. At high arginine concentrations, ArgR associates with arginine and binds to the ArgR binding site, thereby inhibiting expression of TetR from the tetR gene. This, in turn, removes the inhibition by TetR allowing GFP expression. By mutating a host containing this construct, high arginine producers can be selected on the basis of GFP expression using fluorescence-activated cell sorting ("FACS").
Figure 5:
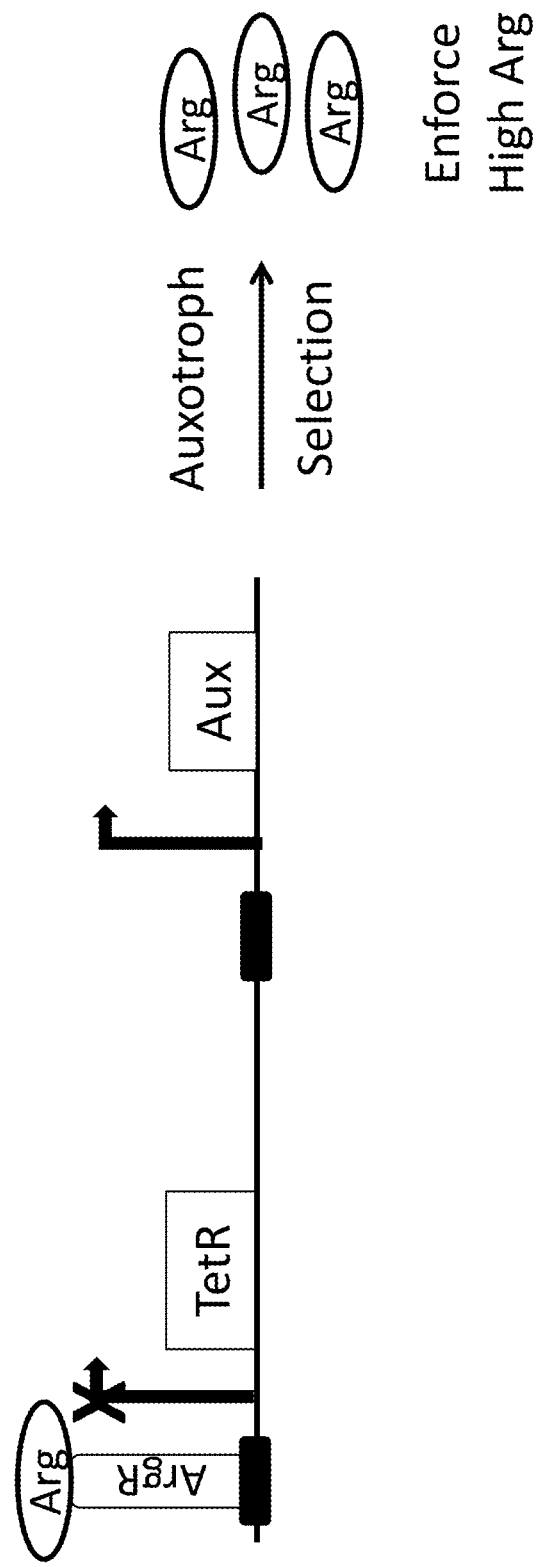
FIG. 5 depicts another embodiment of the invention. In this embodiment, a construct comprising an ArgR binding site (black bar bound by the ArgR-Arg complex) in a promoter driving expression of the Tet repressor (not shown) from the tetR gene is linked to a second promoter comprising a TetR binding site (black bar) that drives expression of an auxotrophic protein necessary for host survival ("AUX"). Under high arginine concentrations, the ArgR-arginine complex binds to the ArgR binding site, thereby inhibiting expression of TetR from the tetR gene. This, in turn, allows expression of AUX, allowing the host to survive. Under low arginine concentrations, TetR is expressed from the tetR gene and inhibits the expression of AUX, thus killing the host. The construct in FIG. 5 enforces high arginine ("Arg") production by making it necessary for host cell survival through its control of AUX expression.
Figure 6:
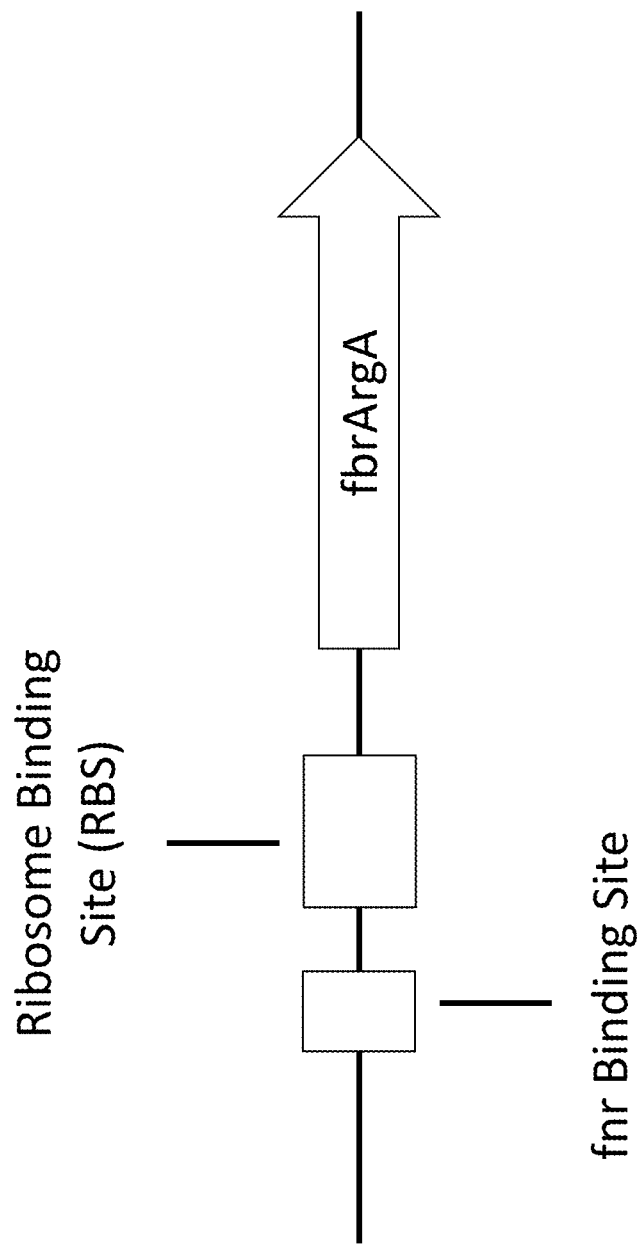
FIG. 6 depicts a schematic diagram of the argA$^{fbr}$ gene under the control of an exemplary FNR promoter (fnrS) fused to a strong ribosome binding site.
Figure 7:
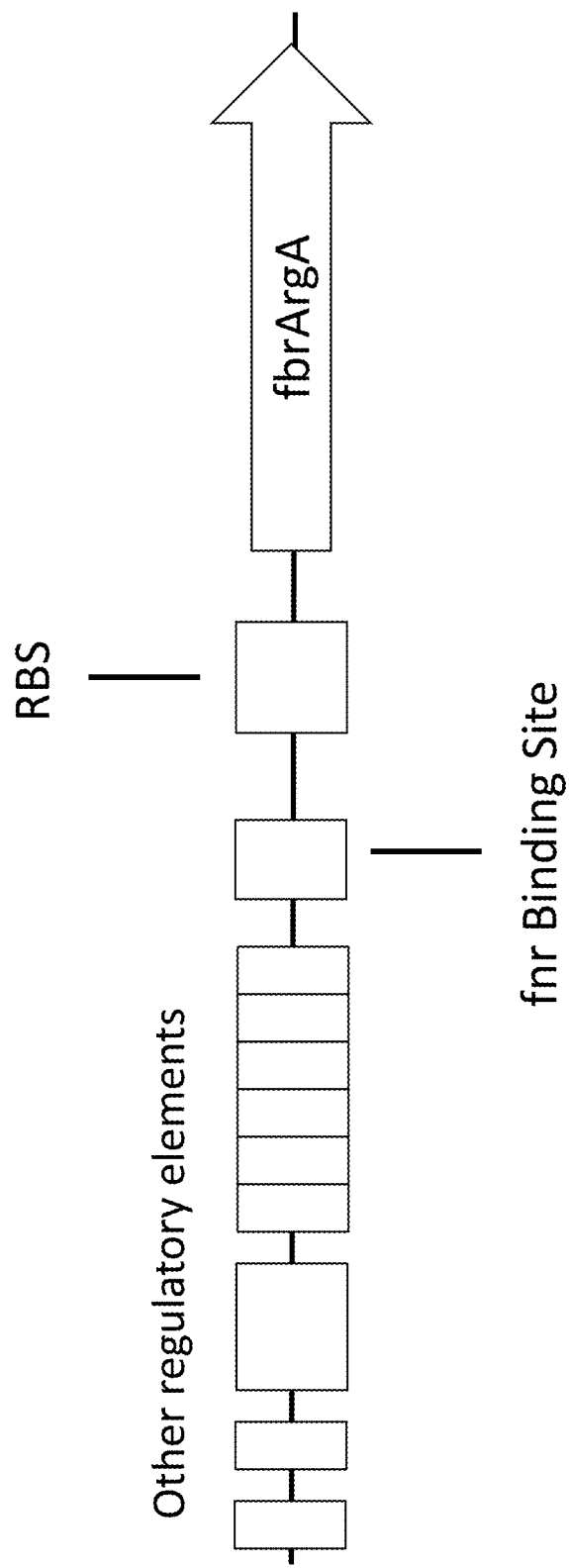
FIG. 7 depicts another schematic diagram of the argA$^{fbr}$ gene under the control of an exemplary FNR promoter (nirB) fused to a strong ribosome binding site. Other regulatory elements may also be present.
Figure 8:
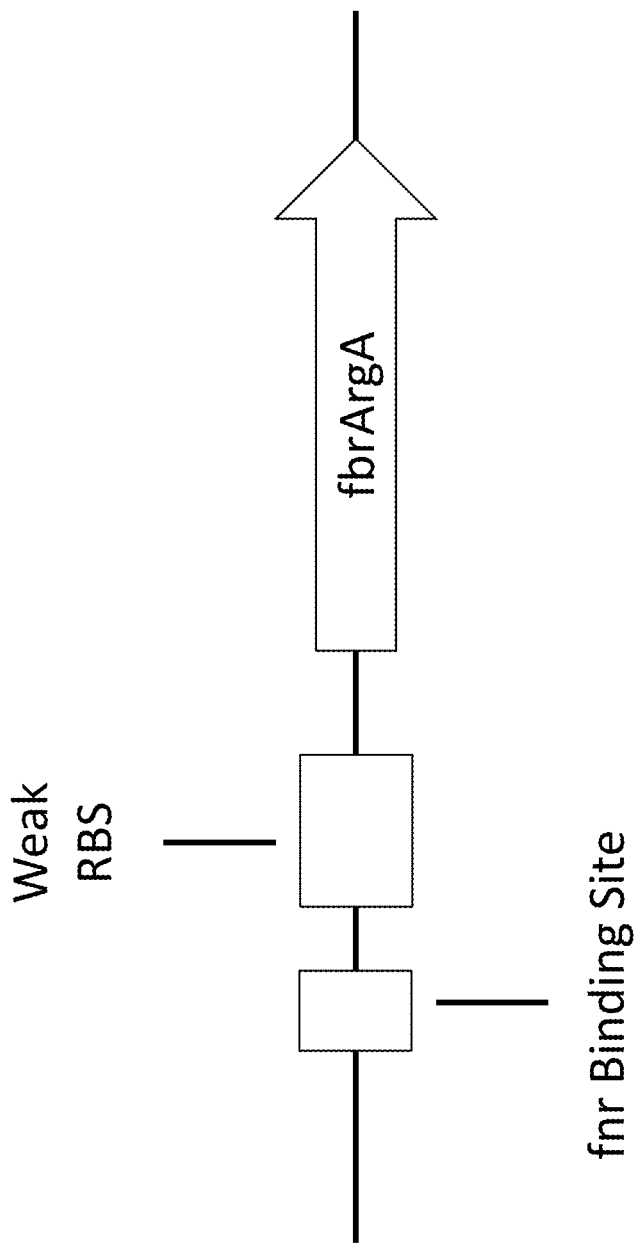
FIG. 8 depicts a schematic diagram of the argA$^{fbr}$ gene under the control of an exemplary FNR promoter (nirB) fused to a weak ribosome binding site.
Figure 9A:
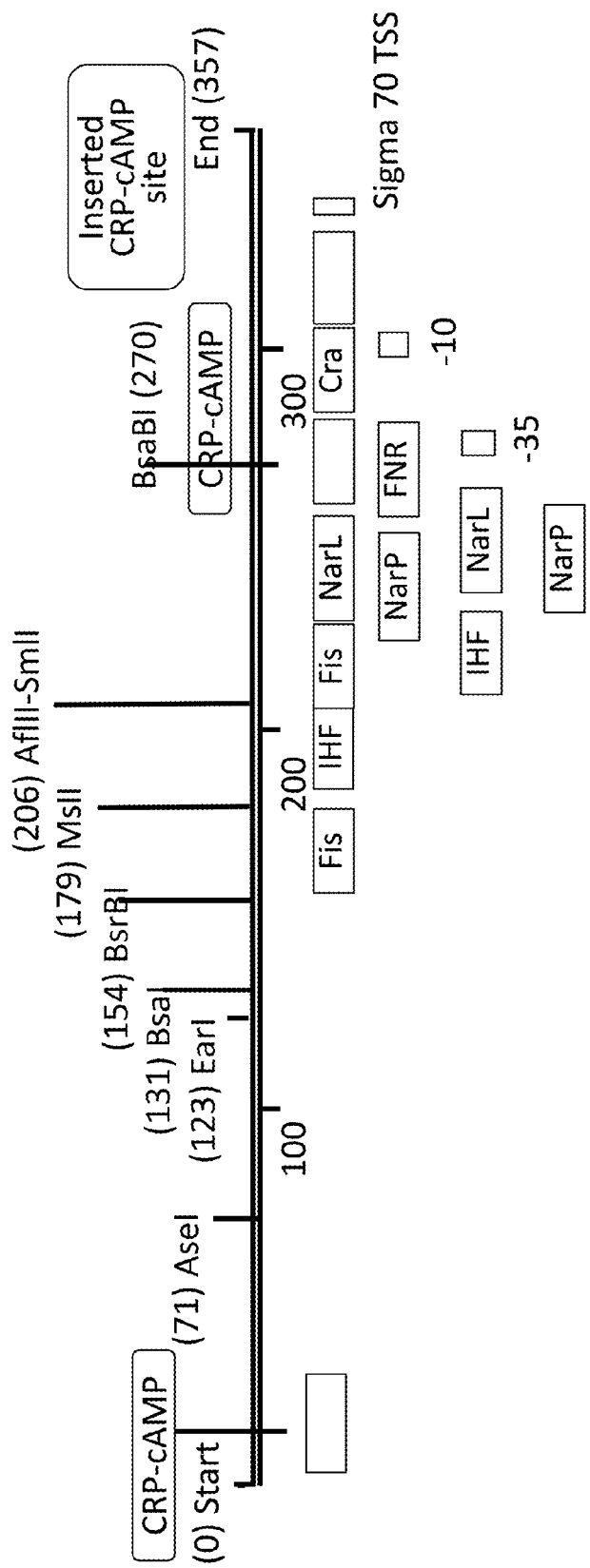
FIGS. 9A and 9B depict exemplary embodiments of a FNR-responsive promoter fused to a CRP binding site.
Figure 9B:
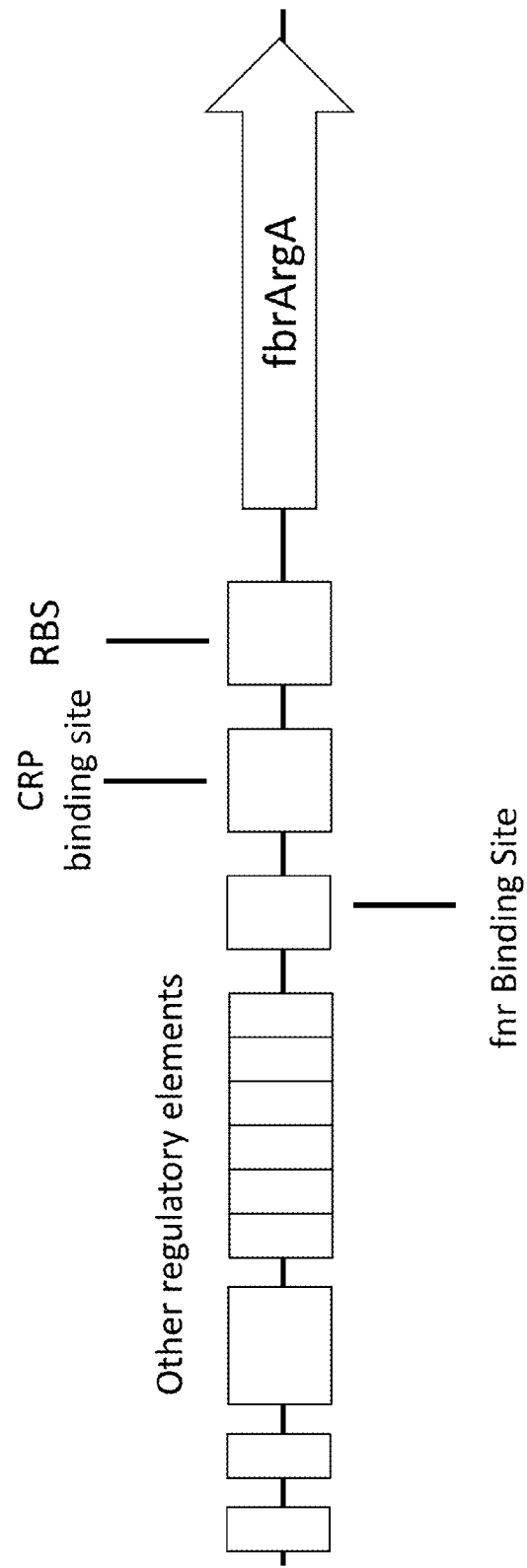
Figure 10A:
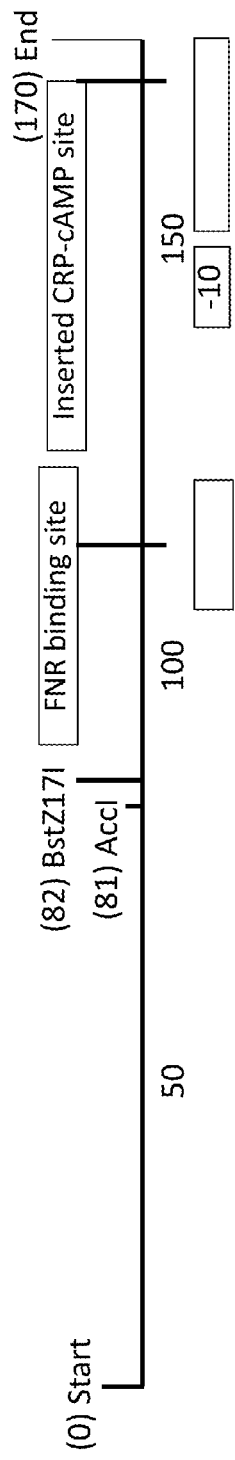
FIGS. 10A and 10B depict alternate exemplary embodiments of a FNR-responsive promoter fused to a CRP binding site.
Figure 10B:
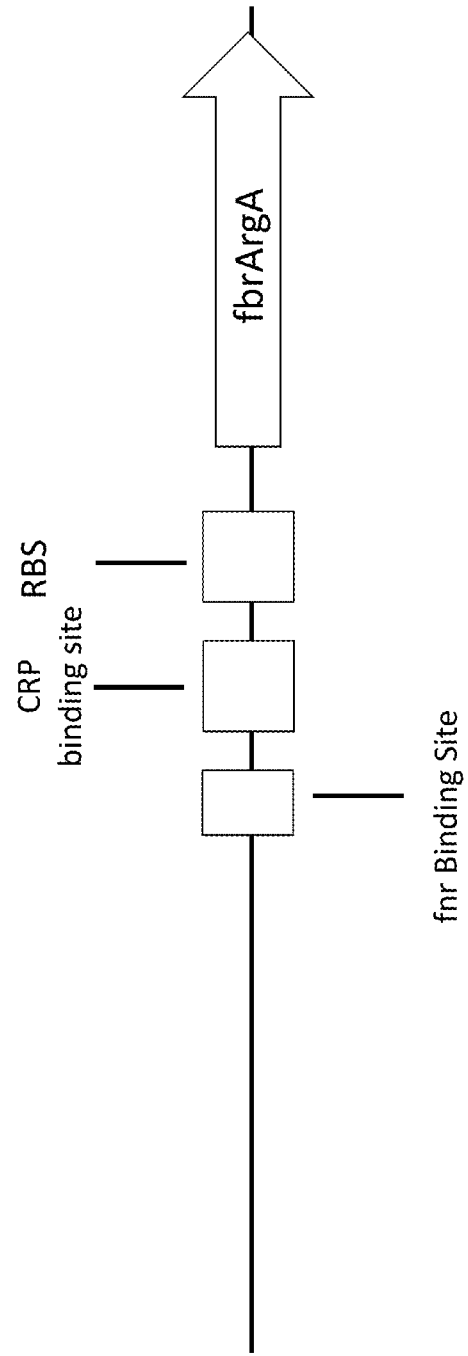
Figure 11:
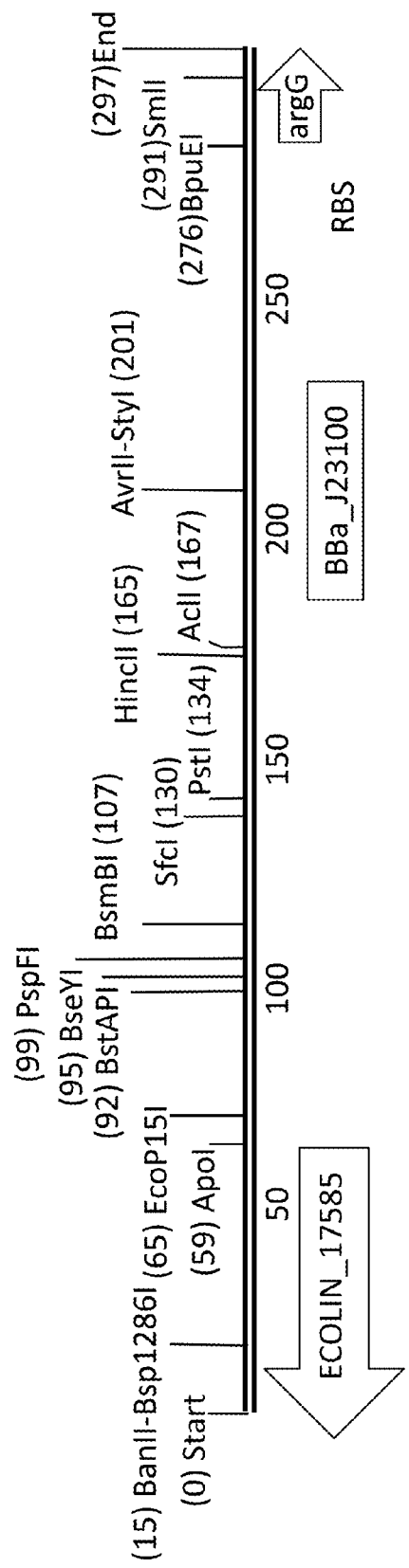
FIG. 11 depicts an exemplary embodiment of a constitutively expressed argG construct in E. coli Nissle. The constitutive promoter is BBa_J23100, boxed in gray. Restriction sites for use in cloning are in bold.

The invention includes genetically engineered bacteria, pharmaceutical compositions thereof, and methods of modulating or treating disorders associated with hyperammonemia, e.g., urea cycle disorders, hepatic encephalopathy and other disorders associated with excess ammonia or elevated ammonia levels. The genetically engineered bacteria are capable of reducing excess ammonia, particularly under certain environmental conditions, such as those in the mammalian gut. In some embodiments, the genetically engineered bacteria reduce excess ammonia by incorporating excess nitrogen in the body into non-toxic molecules, e.g., arginine, citrulline, methionine, histidine, lysine, asparagine, glutamine, or tryptophan. In some embodiments, the genetically engineered bacteria reduce excess ammonia and also reduce one or more other toxic substances, e.g., GABA and/or manganese. In some embodiments, the genetically engineered bacteria reduce excess ammonia and also reduce GABA levels, e.g., by importing GABA and/or by metabolizing GABA. In some embodiments, the genetically engineered bacteria reduce excess ammonia and also reduce manganese levels, e.g., by importing manganese. The genetically engineered bacteria may additionally produce one or molecules that improve gut barrier function or otherwise alleviate a symptom of a disorder associated with elevated ammonia (e.g., UCDs, HE, etc). Thus, in any of the described embodiments, the genetically engineered bacteria may also produce one or molecules that improve gut barrier function or otherwise alleviate a symptom of a disorder associated with elevated ammonia. In some embodiments, the genetically engineered bacteria produce a short chain fatty acid, e.g., butyrate, propionate, and/or acetate. In some embodiments, the engineered bacteria reduce excess ammonia and produce one or molecules that improve gut barrier function or otherwise alleviate a symptom of a disorder associated with elevated ammonia, e.g., produce a short chain fatty acid, such as butyrate, propionate, and/or acetate. In some embodiments, the engineered bacteria reduce excess ammonia, reduce one or more other toxic substances, e.g., GABA and/or manganese, and produce one or molecules that improve gut barrier function or alleviate a symptom of a disorder associated with elevated ammonia, e.g., produce a short chain fatty acid, such as butyrate, propionate, and/or acetate. In some embodiments, the genetically engineered bacteria reduce excess ammonia, reduce GABA levels, e.g., by importing GABA and/or by metabolizing GABA, and produce one or molecules that improve gut barrier function or alleviate a symptom of a disorder associated with elevated ammonia, e.g., produce a short chain fatty acid, such as butyrate, propionate, and/or acetate. In some embodiments, the genetically engineered bacteria reduce excess ammonia, reduce manganese levels, e.g., by importing manganese, and produce one or molecules that improve gut barrier function or alleviate a symptom of a disorder associated with elevated ammonia, e.g., produce a short chain fatty acid, such as butyrate, propionate, and/or acetate.

In any of the described embodiments, the engineered bacteria may further comprise one or more of more of the following: (1) one or more auxotrophies, such as any auxotrophies known in the art and provided herein, e.g., thyA auxotrophy, (2) one or more kill switch circuits, such as any of the kill-switches described herein or otherwise known in the art, (3) one or more antibiotic resistance circuits, (4) one or more transporters for importing biological molecules or substrates, such any of the transporters described herein or otherwise known in the art, (5) one or more secretion circuits, such as any of the secretion circuits described herein and otherwise known in the art, and (6) combinations of one or more of such additional circuits.

In some embodiments, any one or more of the payload or therapeutic circuits (e.g., ammonia consuming, GABA reducing, manganese reducing, short chain fatty acid producing circuits) and/or any one or more of the additional circuits (e.g., auxotrophies, kill switch circuits, antibiotic resistance circuits, transporters, and secretion circuits) may be regulated by a constitutive promoter. In some embodiments, any one or more of the payload or therapeutic circuits (e.g., ammonia consuming, GABA reducing, manganese reducing, short chain fatty acid producing circuits) and/or any one or more of the additional circuits (e.g., auxotrophies, kill switch circuits, antibiotic resistance circuits, transporters, and secretion circuits) may be regulated by a tissue-specific promoter. In some embodiments, any one or more of the payload or therapeutic circuits (e.g., ammonia consuming, GABA reducing, manganese reducing, short chain fatty acid producing circuits) and/or any one or more of the additional circuits (e.g., auxotrophies, kill switch circuits, antibiotic resistance circuits, transporters, and secretion circuits) may be regulated by an inducible promoter. In some embodiments, any one or more of the payload or therapeutic circuits (e.g., ammonia consuming, GABA reducing, manganese reducing, short chain fatty acid producing circuits) and/or any one or more of the additional circuits (e.g., auxotrophies, kill switch circuits, antibiotic resistance circuits, transporters, and secretion circuits) may be regulated by an inducible promoter that is responsive to environmental conditions, factors, or cues, e.g., environmental conditions, factors, or cues found in the mammalian gut. Exemplary inducible promoters include oxygen level-dependent promoters (e.g., FNR-inducible promoter), promoters induced by HE-specific molecules or metabolites indicative of liver damage (e.g., bilirubin), promoters induced by inflammation or an inflammatory response (RNS, ROS promoters), and promoters induced by a metabolite that may or may not be naturally present (e.g., can be exogenously added) in the gut, e.g., arabinose and tetracycline.

In some embodiments, any one or more of the payload or therapeutic circuits (e.g., ammonia consuming, GABA reducing, manganese reducing, short chain fatty acid producing circuits) and/or any one or more of the additional circuits (e.g., auxotrophies, kill switch circuits, antibiotic resistance circuits, transporters, and secretion circuits) may be present on one or more low copy or high copy plasmids. In some embodiments, any one or more of the payload or therapeutic circuits (e.g., ammonia consuming, GABA reducing, manganese reducing, short chain fatty acid producing circuits) and/or any one or more of the additional circuits (e.g., auxotrophies, kill switch circuits, antibiotic resistance circuits, transporters, and secretion circuits) may be integrated into the bacterial chromosome. In order that the disclosure may be more readily understood, certain terms are first defined. These definitions should be read in light of the remainder of the disclosure and as understood by a person of ordinary skill in the art. Unless defined otherwise, all technical and scientific terms used herein have the same meaning as commonly understood by a person of ordinary skill in the art. Additional definitions are set forth throughout the detailed description.

"Hyperammonemia," "hyperammonemic," or "excess ammonia" is used to refer to increased concentrations of ammonia in the body. Hyperammonemia is caused by decreased detoxification and/or increased production of ammonia. Decreased detoxification may result from urea cycle disorders (UCDs), such as argininosuccinic aciduria, arginase deficiency, carbamoylphosphate synthetase deficiency, citrullinemia, N-acetylglutamate synthetase deficiency, and ornithine transcarbamylase deficiency; or from bypass of the liver, e.g., open ductus hepaticus; and/or deficiencies in glutamine synthetase (Hoffman et al., 2013; Häberle et al., 2013). Decreased detoxification may also result from liver disorders such as hepatic encephalopathy, acute liver failure, or chronic liver failure; and neurodegenerative disorders such as Huntington's disease (Chen et al., 2015; Chiang et al., 2007). Increased production of ammonia may result from infections, drugs, neurogenic bladder, and intestinal bacterial overgrowth (Häberle et al., 2013). Other disorders and conditions associated with hyperammonemia include, but are not limited to, liver disorders such as hepatic encephalopathy, acute liver failure, or chronic liver failure; organic acid disorders; isovaleric aciduria; 3-methylcrotonylglycinuria; methylmalonic acidemia; propionic aciduria; fatty acid oxidation defects; carnitine cycle defects; carnitine deficiency; β-oxidation deficiency; lysinuric protein intolerance; pyrroline-5-carboxylate synthetase deficiency; pyruvate carboxylase deficiency; ornithine aminotransferase deficiency; carbonic anhydrase deficiency; hyperinsulinism-hyperammonemia syndrome; mitochondrial disorders; valproate therapy; asparaginase therapy; total parenteral nutrition; cystoscopy with glycine-containing solutions; post-lung/bone marrow transplantation; portosystemic shunting; urinary tract infections; ureter dilation; multiple myeloma; and chemotherapy (Hoffman et al., 2013; Häberle et al., 2013; Pham et al., 2013; Lazier et al., 2014). In healthy subjects, plasma ammonia concentrations are typically less than about 50 μmol/L (Leonard, 2006). In some embodiments, a diagnostic signal of hyperammonemia is a plasma ammonia concentration of at least about 50 μmol/L, at least about 80 μmol/L, at least about 150 μmol/L, at least about 180 μmol/L, or at least about 200 μmol/L (Leonard, 2006; Hoffman et al., 2013; Häberle et al., 2013).

"Ammonia" is used to refer to gaseous ammonia ($NH_3$), ionic ammonia ($NH_4^+$), or a mixture thereof. In bodily fluids, gaseous ammonia and ionic ammonium exist in equilibrium:

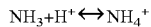

Some clinical laboratory tests analyze total ammonia ($NH_3+NH_4^+$) (Walker, 2012). In any embodiment of the invention, unless otherwise indicated, "ammonia" may refer to gaseous ammonia, ionic ammonia, and/or total ammonia.

"Detoxification" of ammonia is used to refer to the process or processes, natural or synthetic, by which toxic ammonia is removed and/or converted into one or more non-toxic molecules, including but not limited to: arginine, citrulline, methionine, histidine, lysine, asparagine, glutamine, tryptophan, or urea. The urea cycle, for example, enzymatically converts ammonia into urea for removal from the body in the urine. Because ammonia is a source of nitrogen for many amino acids, which are synthesized via numerous biochemical pathways, enhancement of one or more of those amino acid biosynthesis pathways may be used to incorporate excess nitrogen into non-toxic molecules. For example, arginine biosynthesis converts glutamate, which comprises one nitrogen atom, to arginine, which comprises four nitrogen atoms, thereby incorporating excess nitrogen into non-toxic molecules. In humans, arginine is not reabsorbed from the large intestine, and as a result, excess arginine in the large intestine is not considered to be harmful. Likewise, citrulline is not reabsorbed from the large intestine, and as a result, excess citrulline in the large intestine is not considered to be harmful. Arginine biosynthesis may also be modified to produce citrulline as an end product; citrulline comprises three nitrogen atoms and thus the modified pathway is also capable of incorporating excess nitrogen into non-toxic molecules.

"Arginine regulon," "arginine biosynthesis regulon," and "arg regulon" are used interchangeably to refer to the collection of operons in a given bacterial species that comprise the genes encoding the enzymes responsible for converting glutamate to arginine and/or intermediate metabolites, e.g., citrulline, in the arginine biosynthesis pathway. The arginine regulon also comprises operators, promoters, ARG boxes, and/or regulatory regions associated with those operons. The arginine regulon includes, but is not limited to, the operons encoding the arginine biosynthesis enzymes N-acetylglutamate synthetase, N-acetylglutamate kinase, N-acetylglutamylphosphate reductase, acetylornithine am inotransferase, N-acetylornithinase, ornithine transcarbamylase, argininosuccinate synthase, argininosuccinate lyase, carbamoylphosphate synthase, operators thereof, promoters thereof, ARG boxes thereof, and/or regulatory regions thereof. In some embodiments, the arginine regulon comprises an operon encoding ornithine acetyltransferase and associated operators, promoters, ARG boxes, and/or regulatory regions, either in addition to or in lieu of N-acetylglutamate synthetase and/or N-acetylornithinase. In some embodiments, one or more operons or genes of the arginine regulon may be present on a plasmid in the bacterium. In some embodiments, a bacterium may comprise multiple copies of any gene or operon in the arginine regulon, wherein one or more copies may be mutated or otherwise altered as described herein.

One gene may encode one enzyme, e.g., N-acetylglutamate synthetase (argA). Two or more genes may encode distinct subunits of one enzyme, e.g., subunit A and subunit B of carbamoylphosphate synthase (carA and carB). In some bacteria, two or more genes may each independently encode the same enzyme, e.g., ornithine transcarbamylase (argF and argI). In some bacteria, the arginine regulon includes, but is not limited to, argA, encoding N-acetylglutamate synthetase; argB, encoding N-acetylglutamate kinase; argC, encoding N-acetylglutamylphosphate reductase; argD, encoding acetylornithine aminotransferase; argE, encoding N-acetylornithinase; argG, encoding argininosuccinate synthase; argH, encoding argininosuccinate lyase; one or both of argF and argI, each of which independently encodes ornithine transcarbamylase; carA, encoding the small subunit of carbamoylphosphate synthase; carB, encoding the large subunit of carbamoylphosphate synthase; operons thereof; operators thereof; promoters thereof; ARG boxes thereof; and/or regulatory regions thereof. In some embodiments, the arginine regulon comprises argJ, encoding ornithine acetyltransferase (either in addition to or in lieu of N-acetylglutamate synthetase and/or N-acetylornithinase), operons thereof, operators thereof, promoters thereof, ARG boxes thereof, and/or regulatory regions thereof.

"Arginine operon," "arginine biosynthesis operon," and "arg operon" are used interchangeably to refer to a cluster of one or more of the genes encoding arginine biosynthesis enzymes under the control of a shared regulatory region comprising at least one promoter and at least one ARG box. In some embodiments, the one or more genes are co-transcribed and/or co-translated. Any combination of the genes encoding the enzymes responsible for arginine biosynthesis may be organized, naturally or synthetically, into an operon. For example, in B. subtilis, the genes encoding N-acetylglutamylphosphate reductase, N-acetylglutamate kinase, N-acetylornithinase, N-acetylglutamate kinase, acetylornithine am inotransferase, carbamoylphosphate synthase, and ornithine transcarbamylase are organized in a single operon, argCAEBD-carAB-argF (see, e.g., Table 2), under the control of a shared regulatory region comprising a promoter and ARG boxes. In *E. coli* K12 and Nissle, the genes encoding N-acetylornithinase, N-acetylglutamylphosphate reductase, N-acetylglutamate kinase, and argininosuccinate lyase are organized in two bipolar operons, argECBH. The operons encoding the enzymes responsible for arginine biosynthesis may be distributed at different loci across the chromosome. In unmodified bacteria, each operon may be repressed by arginine via ArgR. In some embodiments, arginine and/or intermediate byproduct production may be altered in the genetically engineered bacteria of the invention by modifying the expression of the enzymes encoded by the arginine biosynthesis operons as provided herein. Each arginine operon may be present on a plasmid or bacterial chromosome. In addition, multiple copies of any arginine operon, or a gene or regulatory region within an arginine operon, may be present in the bacterium, wherein one or more copies of the operon or gene or regulatory region may be mutated or otherwise altered as described herein. In some embodiments, the genetically engineered bacteria are engineered to comprise multiple copies of the same product (e.g., operon or gene or regulatory region) to enhance copy number or to comprise multiple different components of an operon performing multiple different functions.

"ARG box consensus sequence" refers to an ARG box nucleic acid sequence, the nucleic acids of which are known to occur with high frequency in one or more of the regulatory regions of argR, argA, argB, argC, argD, argE, argF, argG, argH, argI, argJ, carA, and/or carB. As described above, each arg operon comprises a regulatory region comprising at least one 18-nucleotide imperfect palindromic sequence, called an ARG box, that overlaps with the promoter and to which the repressor protein binds (Tian et al., 1992). The nucleotide sequences of the ARG boxes may vary for each operon, and the consensus ARG box sequence is A/T nTGAAT A/T A/T T/A T/A ATTCAn T/A (SEQ ID NO: 120) (Maas, 1994). The arginine repressor binds to one or more ARG boxes to actively inhibit the transcription of the arginine biosynthesis enzyme(s) that are operably linked to that one or more ARG boxes.

"Mutant arginine regulon" or "mutated arginine regulon" is used to refer to an arginine regulon comprising one or more nucleic acid mutations that reduce or eliminate arginine-mediated repression of each of the operons that encode the enzymes responsible for converting glutamate to arginine and/or an intermediate byproduct, e.g., citrulline, in the arginine biosynthesis pathway, such that the mutant arginine regulon produces more arginine and/or intermediate byproduct than an unmodified regulon from the same bacterial subtype under the same conditions. In some embodiments, the genetically engineered bacteria comprise an arginine feedback resistant N-acetylglutamate synthase mutant, e.g., argA$^{fbr}$, and a mutant arginine regulon comprising one or more nucleic acid mutations in at least one ARG box for one or more of the operons that encode the arginine biosynthesis enzymes N-acetylglutamate kinase, N-acetylglutamylphosphate reductase, acetylornithine aminotransferase, N-acetylornithinase, ornithine transcarbamylase, argininosuccinate synthase, argininosuccinate lyase, and carbamoylphosphate synthase, thereby derepressing the regulon and enhancing arginine and/or intermediate byproduct biosynthesis. In some embodiments, the genetically engineered bacteria comprise a mutant arginine repressor comprising one or more nucleic acid mutations such that arginine repressor function is decreased or inactive, or the genetically engineered bacteria do not have an arginine repressor (e.g., the arginine repressor gene has been deleted), resulting in derepression of the regulon and enhancement of arginine and/or intermediate byproduct biosynthesis. In some embodiments, the genetically engineered bacteria comprise an arginine feedback resistant N-acetylglutamate synthase mutant, e.g., argA$^{fbr}$, a mutant arginine regulon comprising one or more nucleic acid mutations in at least one ARG box for each of the operons that encode the arginine biosynthesis enzymes, and/or a mutant or deleted arginine repressor. In some embodiments, the genetically engineered bacteria comprise an arginine feedback resistant N-acetylglutamate synthase mutant, e.g., argA$^{fbr}$ and a mutant arginine regulon comprising one or more nucleic acid mutations in at least one ARG box for each of the operons that encode the arginine biosynthesis enzymes. In some embodiments, the genetically engineered bacteria comprise an arginine feedback resistant N-acetylglutamate synthase mutant, e.g., argA$^{fbr}$ and a mutant or deleted arginine repressor. In some embodiments, the mutant arginine regulon comprises an operon encoding wild-type N-acetylglutamate synthetase and one or more nucleic acid mutations in at least one ARG box for said operon. In some embodiments, the mutant arginine regulon comprises an operon encoding wild-type N-acetylglutamate synthetase and mutant or deleted arginine repressor. In some embodiments, the mutant arginine regulon comprises an operon encoding ornithine acetyltransferase (either in addition to or in lieu of N-acetylglutamate synthetase and/or N-acetylornithinase) and one or more nucleic acid mutations in at least one ARG box for said operon.

The ARG boxes overlap with the promoter in the regulatory region of each arginine biosynthesis operon. In the mutant arginine regulon, the regulatory region of one or more arginine biosynthesis operons is sufficiently mutated to disrupt the palindromic ARG box sequence and reduce ArgR binding, but still comprises sufficiently high homology to the promoter of the non-mutant regulatory region to be recognized as the native operon-specific promoter. The operon comprises at least one nucleic acid mutation in at least one ARG box such that ArgR binding to the ARG box and to the regulatory region of the operon is reduced or eliminated. In some embodiments, bases that are protected from DNA methylation and bases that are protected from hydroxyl radical attack during ArgR binding are the primary targets for mutations to disrupt ArgR binding (see, e.g., Table 3). The promoter of the mutated regulatory region retains sufficiently high homology to the promoter of the non-mutant regulatory region such that RNA polymerase binds to it with sufficient affinity to promote transcription of the operably linked arginine biosynthesis enzyme(s). In some embodiments, the G/C:A/T ratio of the promoter of the mutant differs by no more than 10% from the G/C:A/T ratio of the wild-type promoter.

In some embodiments, more than one ARG box may be present in a single operon. In one aspect of these embodiments, at least one of the ARG boxes in an operon is altered to produce the requisite reduced ArgR binding to the regulatory region of the operon. In an alternate aspect of these embodiments, each of the ARG boxes in an operon is altered to produce the requisite reduced ArgR binding to the regulatory region of the operon.

"Reduced" ArgR binding is used to refer to a reduction in repressor binding to an ARG box in an operon or a reduction in the total repressor binding to the regulatory region of said operon, as compared to repressor binding to an unmodified ARG box and regulatory region in bacteria of the same subtype under the same conditions. In some embodiments, ArgR binding to a mutant ARG box and regulatory region of an operon is at least about 50% lower, at least about 60% lower, at least about 70% lower, at least about 80% lower, at least about 90% lower, or at least about 95% lower than ArgR binding to an unmodified ARG box and regulatory region in bacteria of the same subtype under the same conditions. In some embodiments, reduced ArgR binding to a mutant ARG box and regulatory region results in at least about 1.5-fold, at least about 2-fold, at least about 10-fold, at least about 15-fold, at least about 20-fold, at least about 30-fold, at least about 50-fold, at least about 100-fold, at least about 200-fold, at least about 300-fold, at least about 400-fold, at least about 500-fold, at least about 600-fold, at least about 700-fold, at least about 800-fold, at least about 900-fold, at least about 1,000-fold, or at least about 1,500-fold increased mRNA expression of the one or more genes in the operon.

"ArgR" or "arginine repressor" is used to refer to a protein that is capable of suppressing arginine biosynthesis by regulating the transcription of arginine biosynthesis genes in the arginine regulon. When expression of the gene that encodes for the arginine repressor protein ("argR") is increased in a wild-type bacterium, arginine biosynthesis is decreased. When expression of argR is decreased in a wild-type bacterium, or if argR is deleted or mutated to inactivate arginine repressor function, arginine biosynthesis is increased.

Bacteria that "lack any functional ArgR" and "ArgR deletion bacteria" are used to refer to bacteria in which each arginine repressor has significantly reduced or eliminated activity as compared to unmodified arginine repressor from bacteria of the same subtype under the same conditions. Reduced or eliminated arginine repressor activity can result in, for example, increased transcription of the arginine biosynthesis genes and/or increased concentrations of arginine and/or intermediate byproducts, e.g., citrulline. Bacteria in which arginine repressor activity is reduced or eliminated can be generated by modifying the bacterial argR gene or by modifying the transcription of the argR gene. For example, the chromosomal argR gene can be deleted, can be mutated, or the argR gene can be replaced with an argR gene that does not exhibit wild-type repressor activity.

"Operably linked" refers a nucleic acid sequence, e.g., a gene encoding feedback resistant ArgA, that is joined to a regulatory region sequence in a manner which allows expression of the nucleic acid sequence, e.g., acts in cis. A regulatory region is a nucleic acid that can direct transcription of a gene of interest and may comprise promoter sequences, enhancer sequences, response elements, protein recognition sites, inducible elements, promoter control elements, protein binding sequences, 5' and 3' untranslated regions, transcriptional start sites, termination sequences, polyadenylation sequences, and introns.

An "inducible promoter" refers to a regulatory region that is operably linked to one or more genes, wherein expression of the gene(s) is increased in the presence of an inducer of said regulatory region. In some embodiments, the genetically engineered bacteria of the invention comprise an oxygen level-dependent promoter induced by low-oxygen, microaerobic, or anaerobic conditions. In some embodiments, the genetically engineered bacteria comprise a promoter induced by a molecule or metabolite, for example, a tissue-specific molecule or metabolite or a molecule or metabolite indicative of liver damage. In some embodiments, the metabolites may be gut specific. In some embodiments, the metabolite may be associated with hepatic encephalopathy, e.g., bilirubin. Non-limiting examples of molecules or metabolites include, e.g., bilirubin, aspartate aminotransferase, alanine aminotransferase, blood coagulation factors II, VII, IX, and X, alkaline phosphatase, gamma glutamyl transferase, hepatitis antigens and antibodies, alpha fetoprotein, anti-mitochondrial, smooth muscle, and anti-nuclear antibodies, iron, transferrin, ferritin, copper, ceruloplasmin, ammonia, and manganese in their blood and intestines. Promoters that respond to one of these molecules or their metabolites may be used in the genetically engineered bacteria provided herein. In some embodiments, the genetically engineered bacteria comprise a promoter induced by inflammation or an inflammatory response, e.g., RNS or ROS promoter. In some embodiments, the genetically engineered bacteria comprise a promoter induced by a metabolite that may or may not be naturally present (e.g., can be exogenously added) in the gut, e.g., arabinose and tetracycline.

"Exogenous environmental condition(s)" refer to setting(s) or circumstance(s) under which the promoter described herein is induced. The phrase "exogenous environmental conditions" is meant to refer to the environmental conditions external to the engineered microorganism, but endogenous or native to the host subject environment. Thus, "exogenous" and "endogenous" may be used interchangeably to refer to environmental conditions in which the environmental conditions are endogenous to a mammalian body, but external or exogenous to an intact microorganism cell. In some embodiments, the exogenous environmental conditions are specific to the gut of a mammal. In some embodiments, the exogenous environmental conditions are specific to the upper gastrointestinal tract of a mammal. In some embodiments, the exogenous environmental conditions are specific to the lower gastrointestinal tract of a mammal. In some embodiments, the exogenous environmental conditions are specific to the small intestine of a mammal. In some embodiments, exogenous environmental conditions refer to the presence of molecules or metabolites that are specific to the mammalian gut in a healthy or disease state (e.g., HE). In some embodiments, the exogenous environmental conditions are low-oxygen, microaerobic, or anaerobic conditions, such as the environment of the mammalian gut. In some embodiments, exogenous environmental conditions are molecules or metabolites that are specific to the mammalian gut, e.g., propionate. In some embodiments, the exogenous environmental condition is a tissue-specific or disease-specific metabolite or molecule(s). In some embodiments, the exogenous environmental condition is a low-pH environment. In some embodiments, the genetically engineered microorganism of the disclosure comprises a pH-dependent promoter. In some embodiments, the genetically engineered microorganism of the diclosure comprise an oxygen level-dependent promoter. In some aspects, bacteria have evolved transcription factors that are capable of sensing oxygen levels. Different signaling pathways may be triggered by different oxygen levels and occur with different kinetics.

An "oxygen level-dependent promoter" or "oxygen level-dependent regulatory region" refers to a nucleic acid sequence to which one or more oxygen level-sensing transcription factors is capable of binding, wherein the binding and/or activation of the corresponding transcription factor activates downstream gene expression.

Examples of oxygen level-dependent transcription factors include, but are not limited to, FNR, ANR, and DNR. Corresponding FNR-responsive promoters, ANR-responsive promoters, and DNR-responsive promoters are known in the art (see, e.g., Castiglione et al., 2009; Eiglmeier et al., 1989; Galimand et al., 1991; Hasegawa et al., 1998; Hoeren et al., 1993; Salmon et al., 2003), and non-limiting examples are shown in Table 1.

In a non-limiting example, a promoter (PfnrS) was derived from the *E. coli* Nissle fumarate and nitrate reductase gene S (fnrS) that is known to be highly expressed under conditions of low or no environmental oxygen (Durand and Storz, 2010; Boysen et al, 2010). The PfnrS promoter is activated under anaerobic conditions by the global transcriptional regulator FNR that is naturally found in Nissle. Under anaerobic conditions, FNR forms a dimer and binds to specific sequences in the promoters of specific genes under its control, thereby activating their expression. However, under aerobic conditions, oxygen reacts with iron-sulfur clusters in FNR dimers and converts them to an inactive form. In this way, the PfnrS inducible promoter is adopted to modulate the expression of proteins or RNA. PfnrS is used interchangeably in this application as FNRS, fnrs, FNR, P-FNRS promoter and other such related designations to indicate the promoter PfnrS.

TABLE 1

Examples of transcription factors and responsive genes and regulatory regions

| Transcription Factor | Exemplary responsive genes, promoters, and/or regulatory regions: |
|---|---|
| FNR | nirB, ydfZ, pdhR, focA, ndH, hlyE, narK, narX, narG, yfiD, tdcD |
| ANR | arcDABC |
| DNR | norb, norC |

"Gut barrier function enhancer molecules" include, but are not limited to, short-chain fatty acids, butyrate, propionate, acetate, GLP-2, IL-10, IL-27, TGF-β1, TGF-β2, N-acylphosphatidylethanolamines (NAPEs), elafin (also called peptidase inhibitor 3 and SKALP), trefoil factor, melatonin, PGD2, kynurenic acid, and kynurenine. A gut barrier function enhancer molecule may be encoded by a single gene, e.g., elafin is encoded by the PI3 gene. Alternatively, a gut barrier function enhancer molecule may be synthesized by a biosynthetic pathway requiring multiple genes, e.g., butyrate. These molecules may also be referred to as therapeutic molecules.

As used herein, a "gene cassette" or "operon" encoding a biosynthetic pathway refers to the two or more genes that are required to produce a gut barrier function enhancer molecule, e.g., butyrate, propionate. In addition to encoding a set of genes capable of producing said molecule, the gene cassette or operon may also comprise additional transcription and translation elements, e.g., a ribosome binding site.

A "butyrogenic gene cassette," "butyrate biosynthesis gene cassette," and "butyrate operon" are used interchangeably to refer to a set of genes capable of producing butyrate in a biosynthetic pathway. Unmodified bacteria that are capable of producing butyrate via an endogenous butyrate biosynthesis pathway include, but are not limited to, *Clostridium, Peptoclostridium, Fusobacterium, Butyrivibrio, Eubacterium*, and *Treponema*, and these endogenous butyrate biosynthesis pathways may be a source of genes for the genetically engineered bacteria of the invention. The genetically engineered bacteria of the invention may comprise butyrate biosynthesis genes from a different species, strain, or substrain of bacteria, or a combination of butyrate biosynthesis genes from different species, strains, and/or substrains of bacteria. A butyrogenic gene cassette may comprise, for example, the eight genes of the butyrate production pathway from Peptoclostridium *difficile* (also called *Clostridium difficile*): bcd2, etfB3, etfA3, thiA1, hbd, crt2, pbt, and buk, which encode butyryl-CoA dehydrogenase subunit, electron transfer flavoprotein subunit beta, electron transfer flavoprotein subunit alpha, acetyl-CoA C-acetyltransferase, 3-hydroxybutyryl-CoA dehydrogenase, crotonase, phosphate butyryltransferase, and butyrate kinase, respectively (Aboulnaga et al., 2013). One or more of the butyrate biosynthesis genes may be functionally replaced or modified. *Peptoclostridium difficile* strain 630 and strain 1296 are both capable of producing butyrate, but comprise different nucleic acid sequences for etfA3, thiA1, hbd, crt2, pbt, and buk. A butyrogenic gene cassette may comprise bcd2, etfB3, etfA3, and thiA1 from *Peptoclostridium difficile* strain 630, and hbd, crt2, pbt, and buk from *Peptoclostridium difficile* strain 1296. Alternatively, a single gene from *Treponema denticola* (ter, encoding trans-2-enoynl-CoA reductase) is capable of functionally replacing all three of the bcd2, etfB3, and etfA3 genes from *Peptoclostridium difficile*. Thus, a butyrogenic gene cassette may comprise thiA1, hbd, crt2, pbt, and buk from *Peptoclostridium difficile* and ter from *Treponema denticola*. The butyrogenic gene cassette may comprise genes for the aerobic biosynthesis of butyrate and/or genes for the anaerobic or microaerobic biosynthesis of butyrate.

Likewise, a "propionate gene cassette" or "propionate operon" refers to a set of genes capable of producing propionate in a biosynthetic pathway. Unmodified bacteria that are capable of producing propionate via an endogenous propionate biosynthesis pathway include, but are not limited to, *Clostridium propionicum, Megasphaera elsdenii*, and *Prevotella ruminicola*, and these endogenous propionate biosynthesis pathways may be a source of genes for the genetically engineered bacteria of the invention. The genetically engineered bacteria of the invention may comprise propionate biosynthesis genes from a different species, strain, or substrain of bacteria, or a combination of propionate biosynthesis genes from different species, strains, and/or substrains of bacteria. In some embodiments, the propionate gene cassette comprises acrylate pathway propionate biosynthesis genes, e.g., pct, lcdA, lcdB, lcdC, etfA, acre, and acrC, which encode propionate CoA-transferase, lactoyl-CoA dehydratase A, lactoyl-CoA dehydratase B, lactoyl-CoA dehydratase C, electron transfer flavoprotein subunit A, acryloyl-CoA reductase B, and acryloyl-CoA reductase C, respectively (Hetzel et al., 2003, Selmer et al., 2002). In alternate embodiments, the propionate gene cassette comprises pyruvate pathway propionate biosynthesis genes (see, e.g., Tseng and Prather, 2012), e.g., thrA$^{fbr}$, thrB, thrC, ilvA$^{fbr}$, aceE, aceF, and lpd, which encode homoserine dehydrogenase 1, homoserine kinase, L-threonine synthase, L-threonine dehydratase, pyruvate dehydrogenase, dihydrolipoamide acetyltransferase, and dihydrolipoyl dehydrogenase, respectively. In some embodiments, the propionate gene cassette further comprises tesB, which encodes acyl-CoA thioesterase. The propionate gene cassette may comprise genes for the aerobic biosynthesis of propionate and/or genes for the anaerobic or microaerobic biosynthesis of propionate. One or more of the propionate biosynthesis genes may be functionally replaced or modified, e.g., codon optimized.

An "acetate gene cassette" or "acetate operon" refers to a set of genes capable of producing acetate in a biosynthetic pathway. Bacteria "synthesize acetate from a number of carbon and energy sources," including a variety of substrates such as cellulose, lignin, and inorganic gases, and utilize different biosynthetic mechanisms and genes, which are known in the art (Ragsdale et al., 2008). Unmodified bacteria that are capable of producing acetate via an endogenous acetate biosynthesis pathway may be a source of acetate biosynthesis genes for the genetically engineered bacteria of the invention. The genetically engineered bacteria of the invention may comprise acetate biosynthesis genes from a different species, strain, or substrain of bacteria, or a combination of acetate biosynthesis genes from different species, strains, and/or substrains of bacteria. *Escherichia coli* are capable of consuming glucose and oxygen to produce acetate and carbon dioxide during aerobic growth (Kleman et al., 1994). Several bacteria, such as *Acetitomaculum, Acetoanaerobium, Acetohalobium, Acetonema, Balutia, Butyribacterium, Clostridium, Moorella, Oxobacter, Sporomusa*, and *Thermoacetogenium*, are acetogenic anaerobes that are capable of converting CO or $CO_2+H_2$ into acetate, e.g., using the Wood-Ljungdahl pathway (Schiel-Bengelsdorf et al., 2012). Genes in the Wood-Ljungdahl pathway for various bacterial species are known in the art. The acetate gene cassette may comprise genes for the aerobic biosynthesis of acetate and/or genes for the anaerobic or microaerobic biosynthesis of acetate. One or more of the acetate biosynthesis genes may be functionally replaced or modified.

"GABA" and "γ-aminobutyric acid" are used to refer to the predominant inhibitory neurotransmitter ($C_4H_9NO_2$) in the mammalian central nervous system. In humans, GABA is also directly responsible for regulating muscle tone. GABA is capable of activating the $GABA_A$ receptor, which is part of a ligand-gated ion channel complex, as well as the $GABA_B$ metabotropic G protein-coupled receptor. Neurons that produce GABA are known as "GABAergic" neurons, and activation of GABA receptors is described as GABAergic tone (i.e., increased activation of GABA receptors refers to increased GABAergic tone).

"GABA transporter" and "GabP" are used to refer to a membrane transport protein that is capable of transporting GABA into bacterial cells (see, e.g., Li et al., 2001). In *Escherichia coli*, the gabP gene encodes a high-affinity GABA permease responsible for GABA transport (Li et al., 2001). In some embodiments, the GABA transporter is encoded by a gabP gene derived from a bacterial species, including but not limited to, *Bacillus subtilis* and *Escherichia coli*. These endogenous GABA transporter genes may be a source of genes for the genetically engineered bacteria of the invention. Any suitable gene(s) encoding a GABA transporter may be used.

"Manganese" refers to a chemical element with the symbol "Mn" and atomic number 25. In biological systems, manganese is an essential trace metal and plays an important role in enzyme-mediated catalysis, but can also have deleterious effects. Cells maintain manganese under tight homeostatic control in order to avoid toxicity. Some disorders associated with hyperammonemia may also be characterized by elevated levels of manganese; manganese may contribute to disease pathogenesis (e.g., hepatic encephalopathy) (Rivera-Mancía et al., 2012).

"Manganese transporter" and "MntH" refer to a membrane transport protein that is capable of transporting manganese into bacterial cells (see, e.g., Jensen and Jensen, 2014). In *Escherichia coli*, the mntH gene encodes a proton-stimulated, divalent metal cation uptake system involved in manganese transport (Porcheron et al., 2013). In some embodiments, the manganese transporter is encoded by a mntH gene derived from a bacterial species, including but not limited to, *Salmonella typhimurium, Shigella flexneri, Yersinia pestis*, and *Escherichia coli*. These endogenous manganese transporter genes may be a source of genes for the genetically engineered bacteria of the invention. Any suitable gene(s) encoding a manganese transporter may be used.

As used herein, a "non-native" nucleic acid sequence refers to a nucleic acid sequence not normally present in a bacterium, e.g., an extra copy of an endogenous sequence, or a heterologous sequence such as a sequence from a different species, strain, or substrain of bacteria, or a sequence that is modified and/or mutated as compared to the unmodified sequence from bacteria of the same subtype. In some embodiments, the non-native nucleic acid sequence is a synthetic, non-naturally occurring sequence (see, e.g., Purcell et al., 2013). The non-native nucleic acid sequence may be a regulatory region, a promoter, a gene, and/or one or more genes in gene cassette. In some embodiments, "non-native" refers to two or more nucleic acid sequences that are not found in the same relationship to each other in nature. The non-native nucleic acid sequence, e.g., gene or gene cassette, may be present on a plasmid or bacterial chromosome. In some embodiments, the genetically engineered bacteria of the invention comprise a gene cassette that is operably linked to a directly or indirectly inducible promoter that is not associated with said gene cassette in nature, e.g., a FNR-responsive promoter operably linked to a butyrogenic gene cassette, or an arginine production cassette. In addition, multiple copies of the gene, gene cassette, or regulatory region may be present in the bacterium, wherein one or more copies may be mutated or otherwise altered as described herein. In some embodiments, the genetically engineered bacteria are engineered to comprise multiple copies of the same non-native nucleic acid sequence, e.g., gene, gene cassette, or regulatory region, in order to enhance copy number or to comprise multiple different components of a gene cassette performing multiple different functions.

"Constitutive promoter" refers to a promoter that is capable of facilitating continuous transcription of a coding sequence or gene under its control and/or to which it is operably linked. Constitutive promoters and variants are well known in the art and include, but are not limited to, BBa_J23100, a constitutive *Escherichia coli* $\sigma^S$ promoter (e.g., an osmY promoter (International Genetically Engineered Machine (iGEM) Registry of Standard Biological Parts Name BBa_J45992; BBa_J45993)), a constitutive *Escherichia coli* $\sigma^{32}$ promoter (e.g., htpG heat shock promoter (BBa_J45504)), a constitutive *Escherichia coli* $\sigma^{70}$ promoter (e.g., lacq promoter (BBa_J54200; BBa_J56015), *E. coli* CreABCD phosphate sensing operon promoter (BBa_J64951), GlnRS promoter (BBa_K088007), lacZ promoter (BBa_K119000; BBa_K119001); M13K07 gene I promoter (BBa_M13101); M13K07 gene II promoter (BBa_M13102), M13K07 gene III promoter (BBa_M13103), M13K07 gene IV promoter (BBa_M13104), M13K07 gene V promoter (BBa_M13105), M13K07 gene VI promoter (BBa_M13106), M13K07 gene VIII promoter (BBa_M13108), M13110 (BBa_M13110)), a constitutive *Bacillus subtilis* $\sigma^A$ promoter (e.g., promoter veg (BBa_K143013), promoter 43 (BBa_K143013), $P_{liaG}$ (BBa_K823000), $P_{lepA}$ (BBa_K823002), $P_{veg}$ (BBa_K823003)), a constitutive *Bacillus subtilis* $\sigma^B$ promoter (e.g., promoter ctc (BBa_K143010), promoter gsiB (BBa_K143011)), a *Salmonella* promoter (e.g., Pspv2 from *Salmonella* (BBa_K112706), Pspv from *Salmonella* (BBa_K112707)), a bacteriophage T7 promoter (e.g., T7 promoter (BBa_I712074; BBa_I719005; BBa_J34814;

BBa_J64997; BBa_K113010; BBa_K113011; BBa_K113012; BBa_R0085; BBa_R0180; BBa_R0181; BBa_R0182; BBa_R0183; BBa_Z0251; BBa_Z0252; BBa_Z0253)), a bacteriophage SP6 promoter (e.g., SP6 promoter (BBa_J64998), and functional fragments thereof.

As used herein, genetically engineered bacteria that "overproduce" arginine or an intermediate byproduct, e.g., citrulline, refer to bacteria that comprise a mutant arginine regulon. For example, the engineered bacteria may comprise a feedback resistant form of ArgA, and when the arginine feedback resistant ArgA is expressed, are capable of producing more arginine and/or intermediate byproduct than unmodified bacteria of the same subtype under the same conditions. The genetically engineered bacteria may alternatively or further comprise a mutant arginine regulon comprising one or more nucleic acid mutations in at least one ARG box for each of the operons that encode the arginine biosynthesis enzymes. The genetically engineered bacteria may alternatively or further comprise a mutant or deleted arginine repressor. In some embodiments, the genetically engineered bacteria produce at least about 1.5-fold, at least about 2-fold, at least about 10-fold, at least about 15-fold, at least about 20-fold, at least about 30-fold, at least about 50-fold, at least about 100-fold, at least about 200-fold, at least about 300-fold, at least about 400-fold, at least about 500-fold, at least about 600-fold, at least about 700-fold, at least about 800-fold, at least about 900-fold, at least about 1,000-fold, or at least about 1,500-fold more arginine than unmodified bacteria of the same subtype under the same conditions. In some embodiments, the genetically engineered bacteria produce at least about 1.5-fold, at least about 2-fold, at least about 10-fold, at least about 15-fold, at least about 20-fold, at least about 30-fold, at least about 50-fold, at least about 100-fold, at least about 200-fold, at least about 300-fold, at least about 400-fold, at least about 500-fold, at least about 600-fold, at least about 700-fold, at least about 800-fold, at least about 900-fold, at least about 1,000-fold, or at least about 1,500-fold more citrulline or other intermediate byproduct than unmodified bacteria of the same subtype under the same conditions. In some embodiments, the mRNA transcript levels of one or more of the arginine biosynthesis genes in the genetically engineered bacteria are at least about 1.5-fold, at least about 2-fold, at least about 10-fold, at least about 15-fold, at least about 20-fold, at least about 30-fold, at least about 50-fold, at least about 100-fold, at least about 200-fold, at least about 300-fold, at least about 400-fold, at least about 500-fold, at least about 600-fold, at least about 700-fold, at least about 800-fold, at least about 900-fold, at least about 1,000-fold, or at least about 1,500-fold higher than the mRNA transcript levels in unmodified bacteria of the same subtype under the same conditions. In certain embodiments, the unmodified bacteria will not have detectable levels of arginine, intermediate byproduct, and/or transcription of the gene(s) in such operons. However, protein and/or transcription levels of arginine and/or intermediate byproduct will be detectable in the corresponding genetically engineered bacterium having the mutant arginine regulon. Transcription levels may be detected by directly measuring mRNA levels of the genes. Methods of measuring arginine and/or intermediate byproduct levels, as well as the levels of transcript expressed from the arginine biosynthesis genes, are known in the art. Arginine and citrulline, for example, may be measured by mass spectrometry.

"Gut" refers to the organs, glands, tracts, and systems that are responsible for the transfer and digestion of food, absorption of nutrients, and excretion of waste. In humans, the gut comprises the gastrointestinal tract, which starts at the mouth and ends at the anus, and additionally comprises the esophagus, stomach, small intestine, and large intestine. The gut also comprises accessory organs and glands, such as the spleen, liver, gallbladder, and pancreas. The upper gastrointestinal tract comprises the esophagus, stomach, and duodenum of the small intestine. The lower gastrointestinal tract comprises the remainder of the small intestine, i.e., the jejunum and ileum, and all of the large intestine, i.e., the cecum, colon, rectum, and anal canal. Bacteria can be found throughout the gut, e.g., in the gastrointestinal tract, and particularly in the intestines.

As used herein, the term "gene sequence" is meant to refer to a genetic sequence, e.g., a nucleic acid sequence. The gene sequence or genetic sequence is meant to include a complete gene sequence or a partial gene sequence. The gene sequence or genetic sequence is meant to include sequence that encodes a protein or polypeptide and is also menat to include genetic sequence that does not encode a protein or polypeptide, e.g., a regulatory sequence, leader sequence, signal sequence, or other non-protein coding sequence.

"Microorganism" refers to an organism or microbe of microscopic, submicroscopic, or ultramicroscopic size that typically consists of a single cell. Examples of microorganisms include bacteria, viruses, parasites, fungi, certain algae, and protozoa. In some aspects, the microorganism is engineered ("engineered microorganism") to produce one or more therapeutic molecules. In certain aspects, the microorganism is engineered to import and/or catabolize certain toxic metabolites, substrates, or other compounds from its environment, e.g., the gut. In certain aspects, the microorganism is engineered to synthesize certain beneficial metabolites, molecules, or other compounds (synthetic or naturally occurring) and release them into its environment. In certain embodiments, the engineered microorganism is an engineered bacterium. In certain embodiments, the engineered microorganism is an engineered virus.

"Non-pathogenic bacteria" refer to bacteria that are not capable of causing disease or harmful responses in a host. In some embodiments, non-pathogenic bacteria are commensal bacteria. Examples of non-pathogenic bacteria include, but are not limited to *Bacillus, Bacteroides, Bifidobacterium, Brevibacteria, Clostridium, Enterococcus, Escherichia coli, Lactobacillus, Lactococcus, Saccharomyces*, and *Staphylococcus*, e.g., *Bacillus coagulans, Bacillus subtilis, Bacteroides fragilis, Bacteroides subtilis, Bacteroides thetaiotaomicron, Bifidobacterium bifidum, Bifidobacterium infantis, Bifidobacterium lactis, Bifidobacterium longum, Clostridium butyricum, Enterococcus faecium, Lactobacillus acidophilus, Lactobacillus bulgaricus, Lactobacillus casei, Lactobacillus johnsonii, Lactobacillus paracasei, Lactobacillus plantarum, Lactobacillus reuteri, Lactobacillus rhamnosus, Lactococcus lactis*, and *Saccharomyces boulardii* (Sonnenborn et al., 2009; Dinleyici et al., 2014; U.S. Pat. No. 6,835,376; U.S. Pat. No. 6,203,797; U.S. Pat. No. 5,589,168; U.S. Pat. No. 7,731,976). Naturally pathogenic bacteria may be genetically engineered to provide reduce or eliminate pathogenicity.

As used herein, "payload" refers to one or more polynucleotides and/or polypeptides of interest to be produced by a genetically engineered microorganism, such as a bacteria or a virus. In some embodiments, the payload is encoded by a gene or multiple genes or an operon. In some embodiments, the one or more genes and/or operon(s) comprising the payload are endogenous to the microorganism. In some embodiments, the one or more elements of the payload is derived from a different microorganism and/or organism. In some embodiments, the payload is a therapeutic payload. In some embodiments, the payload is encoded by genes for the biosynthesis of a molecule. In some embodiments, the payload is encoded by genes for the metabolism, catabolism, or degradation of a molecule. In some embodiments, the payload is encoded by genes for the importation of a molecule. In some embodiments, the payload is encoded by genes for the exportation of a molecule. In some embodiments, the payload is a regulatory molecule(s), e.g., a transcriptional regulator such as FNR. In some embodiments, the payload comprises a regulatory element, such as a promoter or a repressor. In some embodiments, the payload comprises an inducible promoter, such as from FNRS. In some embodiments the payload comprises a repressor element, such as a kill switch. In alternate embodiments, the payload is produced by a biosynthetic or biochemical pathway, wherein the biosynthetic or biochemical pathway may optionally be endogenous to the microorganism. In some embodiments, the genetically engineered microorganism comprises two or more payloads. Non-limiting examples of payload(s) include one or more of the following: (1) ArgAfbr, (2) mutated Arg Boxes, (3) mutated ArgR, (4) mutated ArgG, (5) butyrate biosynthetic cassette, (6) proprionate biosynthetic cassette, (7) acetate biosynthetic cassette; (8) GABA-metabolizing cassette, (9) GABA-transporter, (10) Mn-transporter. Other exemplary payloads include GLP-2, IL-10, IL-27, TGF-β1, TGF-β2, elafin (also known as peptidase inhibitor 3 or SKALP), trefoil factor, melatonin, $PGD_2$, kynurenic acid, and kynurenine. Other exemplary payloads include mutated sequence(s) that result in an auxotrophy, e.g., thyA auxotrophy, kill switch circuit, antibiotic resistance circuits, transporter sequence for importing biological molecules or substrates, secretion circuit.

"Probiotic" is used to refer to live, non-pathogenic microorganisms, e.g., bacteria, which can confer health benefits to a host organism that contains an appropriate amount of the microorganism. In some embodiments, the host organism is a mammal. In some embodiments, the host organism is a human. Some species, strains, and/or subtypes of non-pathogenic bacteria are currently recognized as probiotic bacteria. Examples of probiotic bacteria include, but are not limited to, Bifidobacteria, Escherichia coli, Lactobacillus, and Saccharomyces, e.g., Bifidobacterium bifidum, Enterococcus faecium, Escherichia coli strain Nissle, Lactobacillus acidophilus, Lactobacillus bulgaricus, Lactobacillus paracasei, Lactobacillus plantarum, and Saccharomyces boulardii (Dinleyici et al., 2014; U.S. Pat. Nos. 5,589,168; 6,203,797; 6,835,376). The probiotic may be a variant or a mutant strain of bacterium (Arthur et al., 2012; Cuevas-Ramos et al., 2010; Olier et al., 2012; Nougayrede et al., 2006). Non-pathogenic bacteria may be genetically engineered to enhance or improve desired biological properties, e.g., survivability. Non-pathogenic bacteria may be genetically engineered to provide probiotic properties. Probiotic bacteria may be genetically engineered to enhance or improve probiotic properties.

As used herein, "stably maintained" or "stable" bacterium is used to refer to a bacterial host cell carrying non-native genetic material, e.g., a feedback resistant argA gene, mutant arginine repressor, and/or other mutant arginine regulon that is incorporated into the host genome or propagated on a self-replicating extra-chromosomal plasmid, such that the non-native genetic material is retained, expressed, and propagated. The stable bacterium is capable of survival and/or growth in vitro, e.g., in medium, and/or in vivo, e.g., in the gut. For example, the stable bacterium may be a genetically engineered bacterium comprising an $argA^{fbr}$ gene, in which the plasmid or chromosome carrying the $argA^{fbr}$ gene is stably maintained in the bacterium, such that $argA^{fbr}$ can be expressed in the bacterium, and the bacterium is capable of survival and/or growth in vitro and/or in vivo.

As used herein, the terms "modulate" and "treat" and their cognates refer to an amelioration of a disease, disorder, and/or condition, or at least one discernible symptom thereof. In another embodiment, "modulate" and "treat" refer to an amelioration of at least one measurable physical parameter, not necessarily discernible by the patient. In another embodiment, "modulate" and "treat" refer to inhibiting the progression of a disease, disorder, and/or condition, either physically (e.g., stabilization of a discernible symptom), physiologically (e.g., stabilization of a physical parameter), or both. In another embodiment, "modulate" and "treat" refer to slowing the progression or reversing the progression of a disease, disorder, and/or condition. As used herein, "prevent" and its cognates refer to delaying the onset or reducing the risk of acquiring a given disease, disorder and/or condition or a symptom associated with such disease, disorder, and/or condition.

Those in need of treatment may include individuals already having a particular medical disorder, as well as those at risk of having, or who may ultimately acquire the disorder. The need for treatment is assessed, for example, by the presence of one or more risk factors associated with the development of a disorder, the presence or progression of a disorder, or likely receptiveness to treatment of a subject having the disorder. Primary hyperammonemia is caused by UCDs, which are autosomal recessive or X-linked inborn errors of metabolism for which there are no known cures. Hyperammonemia can also be secondary to other disruptions of the urea cycle, e.g., toxic metabolites, infections, and/or substrate deficiencies. Hyperammonemia can also contribute to other pathologies. For example, Huntington's disease is an autosomal dominant disorder for which there are no known cures. Urea cycle abnormalities characterized by hyperammonemia, high blood citrulline, and suppression of urea cycle enzymes may contribute to the pathology of Huntington's disease, an autosomal dominant disorder for which there are no known cures. Treating hyperammonemia may encompass reducing or eliminating excess ammonia and/or associated symptoms, and does not necessarily encompass the elimination of the underlying hyperammonemia-associated disorder.

As used herein a "pharmaceutical composition" refers to a preparation of genetically engineered bacteria of the invention with other components such as a physiologically suitable carrier and/or excipient.

The phrases "physiologically acceptable carrier" and "pharmaceutically acceptable carrier" which may be used interchangeably refer to a carrier or a diluent that does not cause significant irritation to an organism and does not abrogate the biological activity and properties of the administered bacterial compound. An adjuvant is included under these phrases.

The term "excipient" refers to an inert substance added to a pharmaceutical composition to further facilitate administration of an active ingredient. Examples include, but are not limited to, calcium bicarbonate, calcium phosphate, various sugars and types of starch, cellulose derivatives, gelatin, vegetable oils, polyethylene glycols, and surfactants, including, for example, polysorbate 20.

The terms "therapeutically effective dose" and "therapeutically effective amount" are used to refer to an amount of a compound that results in prevention, delay of onset of symptoms, or amelioration of symptoms of a condition, e.g., hyperammonemia. A therapeutically effective amount may, for example, be sufficient to treat, prevent, reduce the severity, delay the onset, and/or reduce the risk of occurrence of one or more symptoms of a disorder associated with elevated ammonia concentrations. A therapeutically effective amount, as well as a therapeutically effective frequency of administration, can be determined by methods known in the art and discussed below.

As used herein, the term "polypeptide" includes "polypeptide" as well as "polypeptides," and refers to a molecule composed of amino acid monomers linearly linked by amide bonds (i.e., peptide bonds). The term "polypeptide" refers to any chain or chains of two or more amino acids, and does not refer to a specific length of the product. Thus, "peptides," "dipeptides," "tripeptides, "oligopeptides," "protein," "amino acid chain," or any other term used to refer to a chain or chains of two or more amino acids, are included within the definition of "polypeptide," and the term "polypeptide" may be used instead of, or interchangeably with any of these terms. The term "polypeptide" is also intended to refer to the products of post-expression modifications of the polypeptide, including but not limited to glycosylation, acetylation, phosphorylation, amidation, derivatization, proteolytic cleavage, or modification by non-naturally occurring amino acids. A polypeptide may be derived from a natural biological source or produced by recombinant technology. In other embodiments, the polypeptide is produced by the genetically engineered bacteria or virus of the current invention. A polypeptide of the invention may be of a size of about 3 or more, 5 or more, 10 or more, 20 or more, 25 or more, 50 or more, 75 or more, 100 or more, 200 or more, 500 or more, 1,000 or more, or 2,000 or more amino acids. Polypeptides may have a defined three-dimensional structure, although they do not necessarily have such structure. Polypeptides with a defined three-dimensional structure are referred to as folded, and polypeptides, which do not possess a defined three-dimensional structure, but rather can adopt a large number of different conformations, are referred to as unfolded. The term "peptide" or "polypeptide" may refer to an amino acid sequence that corresponds to a protein or a portion of a protein or may refer to an amino acid sequence that corresponds with non-protein sequence, e.g., a sequence selected from a regulatory peptide sequence, leader peptide sequence, signal peptide sequence, linker peptide sequence, and other peptide sequence.

An "isolated" polypeptide or a fragment, variant, or derivative thereof refers to a polypeptide that is not in its natural milieu. No particular level of purification is required. Recombinantly produced polypeptides and proteins expressed in host cells, including but not limited to bacterial or mammalian cells, are considered isolated for purposed of the invention, as are native or recombinant polypeptides which have been separated, fractionated, or partially or substantially purified by any suitable technique. Recombinant peptides, polypeptides or proteins refer to peptides, polypeptides or proteins produced by recombinant DNA techniques, i.e. produced from cells, microbial or mammalian, transformed by an exogenous recombinant DNA expression construct encoding the polypeptide. Proteins or peptides expressed in most bacterial cultures will typically be free of glycan. Fragments, derivatives, analogs or variants of the foregoing polypeptides, and any combination thereof are also included as polypeptides. The terms "fragment," "variant," "derivative" and "analog" include polypeptides having an amino acid sequence sufficiently similar to the amino acid sequence of the original peptide and include any polypeptides, which retain at least one or more properties of the corresponding original polypeptide. Fragments of polypeptides of the present invention include proteolytic fragments, as well as deletion fragments. Fragments also include specific antibody or bioactive fragments or immunologically active fragments derived from any polypeptides described herein. Variants may occur naturally or be non-naturally occurring. Non-naturally occurring variants may be produced using mutagenesis methods known in the art. Variant polypeptides may comprise conservative or non-conservative amino acid substitutions, deletions or additions.

Polypeptides also include fusion proteins. As used herein, the term "variant" includes a fusion protein, which comprises a sequence of the original peptide or sufficiently similar to the original peptide. As used herein, the term "fusion protein" refers to a chimeric protein comprising amino acid sequences of two or more different proteins. Typically, fusion proteins result from well known in vitro recombination techniques. Fusion proteins may have a similar structural function (but not necessarily to the same extent), and/or similar regulatory function (but not necessarily to the same extent), and/or similar biochemical function (but not necessarily to the same extent) and/or immunological activity (but not necessarily to the same extent) as the individual original proteins which are the components of the fusion proteins. "Derivatives" include but are not limited to peptides, which contain one or more naturally occurring amino acid derivatives of the twenty standard amino acids. "Similarity" between two peptides is determined by comparing the amino acid sequence of one peptide to the sequence of a second peptide. An amino acid of one peptide is similar to the corresponding amino acid of a second peptide if it is identical or a conservative amino acid substitution. Conservative substitutions include those described in Dayhoff, M. O., ed., The Atlas of Protein Sequence and Structure 5, National Biomedical Research Foundation, Washington, D.C. (1978), and in Argos, EMBO J. 8 (1989), 779-785. For example, amino acids belonging to one of the following groups represent conservative changes or substitutions: –Ala, Pro, Gly, Gln, Asn, Ser, Thr; –Cys, Ser, Tyr, Thr; –Val, Ile, Leu, Met, Ala, Phe; –Lys, Arg, His; –Phe, Tyr, Trp, His; and –Asp, Glu.

As used herein, the term "sufficiently similar" means a first amino acid sequence that contains a sufficient or minimum number of identical or equivalent amino acid residues relative to a second amino acid sequence such that the first and second amino acid sequences have a common structural domain and/or common functional activity. For example, amino acid sequences that comprise a common structural domain that is at least about 45%, at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or at least about 100%, identical are defined herein as sufficiently similar. Preferably, variants will be sufficiently similar to the amino acid sequence of the peptides of the invention. Such variants generally retain the functional activity of the peptides of the present invention. Variants include peptides that differ in amino acid sequence from the native and wt peptide, respectively, by way of one or more amino acid deletion(s), addition(s), and/or substitution(s). These may be naturally occurring variants as well as artificially designed ones.

As used herein the term "linker", "linker peptide" or "peptide linkers" or "linker" refers to synthetic or non-native or non-naturally-occurring amino acid sequences that connect or link two polypeptide sequences, e.g., that link two polypeptide domains. As used herein the term "synthetic" refers to amino acid sequences that are not naturally occurring. Exemplary linkers are described herein. Additional exemplary linkers are provided in US 20140079701, the contents of which are herein incorporated by reference in its entirety.

As used herein the term "codon-optimized sequence" refers to a sequence, which was modified from an existing coding sequence, or designed, for example, to improve translation in an expression host cell or organism of a transcript RNA molecule transcribed from the coding sequence, or to improve transcription of a coding sequence. Codon optimization includes, but is not limited to, processes including selecting codons for the coding sequence to suit the codon preference of the expression host organism.

Many organisms display a bias or preference for use of particular codons to code for insertion of a particular amino acid in a growing polypeptide chain. Codon preference or codon bias, differences in codon usage between organisms, is allowed by the degeneracy of the genetic code, and is well documented among many organisms. Codon bias often correlates with the efficiency of translation of messenger RNA (mRNA), which is in turn believed to be dependent on, inter alia, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization.

As used herein, the terms "secretion system" or "secretion protein" refers to a native or non-native secretion mechanism capable of secreting or exporting the protein of interest or therapeutic protein from the microbial, e.g., bacterial cytoplasm. The secretion system may comprise a single protein or may comprise two or more proteins assembled in a complex e.g. HlyBD. Non-limiting examples of secretion systems for gram negative bacteria include the modified type III flagellar, type I (e.g., hemolysin secretion system), type II, type IV, type V, type VI, and type VII secretion systems, resistance-nodulation-division (RN D) multi-drug efflux pumps, various single membrane secretion systems. Non-liming examples of secretion systems for gram positive bacteria include Sec and TAT secretion systems. In some embodiments, the the protein(s) of interest or therapeutic protein(s) include a "secretion tag" of either RNA or peptide origin to direct the protein(s) of interest or therapeutic protein(s) to specific secretion systems. In some embodiments, the secretion system is able to remove this tag before secreting the protein(s) of interest or therapeutic protein(s) from the engineered bacteria. For example, in Type V auto-secretion-mediated secretion the N-terminal peptide secretion tag is removed upon translocation of the "passenger" peptide from the cytoplasm into the periplasmic compartment by the native Sec system. Further, once the auto-secretor is translocated across the outer membrane the C-terminal secretion tag can be removed by either an autocatalytic or protease-catalyzed e.g., OmpT cleavage thereby releasing the protein(s) of interest or therapeutic protein(s) into the extracellular milieu.

As used herein, the term "transporter" is meant to refer to a mechanism, e.g., protein or proteins, for importing a molecule, e.g., amino acid, toxin, metabolite, substrate, etc. into the microorganism from the extracellular milieu.

The articles "a" and "an," as used herein, should be understood to mean "at least one," unless clearly indicated to the contrary.

The phrase "and/or," when used between elements in a list, is intended to mean either (1) that only a single listed element is present, or (2) that more than one element of the list is present. For example, "A, B, and/or C" indicates that the selection may be A alone; B alone; C alone; A and B; A and C; B and C; or A, B, and C. The phrase "and/or" may be used interchangeably with "at least one of" or "one or more of" the elements in a list.

Bacteria

The genetically engineered bacteria disclosed herein are capable of reducing excess ammonia and converting ammonia and/or nitrogen into alternate byproducts. In some embodiments, the genetically engineered bacteria are naturally non-pathogenic bacteria. In some embodiments, the genetically engineered bacteria are commensal bacteria. In some embodiments, the genetically engineered bacteria are probiotic bacteria. In some embodiments, the genetically engineered bacteria are naturally pathogenic bacteria that are modified or mutated to reduce or eliminate pathogenicity. Exemplary bacteria include, but are not limited to *Bacillus, Bacteroides, Bifidobacterium, Brevibacteria, Clostridium, Enterococcus, Escherichia coli, Lactobacillus, Lactococcus, Saccharomyces*, and *Staphylococcus*, e.g., *Bacillus coagulans, Bacillus subtilis, Bacteroides fragilis, Bacteroides subtilis, Bacteroides thetaiotaomicron, Bifidobacterium bifidum, Bifidobacterium infantis, Bifidobacterium lactis, Bifidobacterium longum, Clostridium butyricum, Enterococcus faecium, Lactobacillus acidophilus, Lactobacillus bulgaricus, Lactobacillus casei, Lactobacillus johnsonii, Lactobacillus paracasei, Lactobacillus plantarum, Lactobacillus reuteri, Lactobacillus rhamnosus, Lactococcus lactis*, and *Saccharomyces boulardii*. In certain embodiments, the genetically engineered bacteria are selected from the group consisting of *Bacteroides fragilis, Bacteroides thetaiotaomicron, Bacteroides subtilis, Bifidobacterium bifidum, Bifidobacterium infantis, Bifidobacterium lactis, Clostridium butyricum, Escherichia coli* Nissle, *Lactobacillus acidophilus, Lactobacillus plantarum, Lactobacillus reuteri*, and *Lactococcus lactis*.

In some embodiments, the genetically engineered bacteria are *Escherichia coli* strain Nissle 1917 (*E. coli* Nissle), a Gram-negative bacterium of the Enterobacteriaceae family that has evolved into one of the best characterized probiotics (Ukena et al., 2007). The strain is characterized by its complete harmlessness (Schultz, 2008), and has GRAS (generally recognized as safe) status (Reister et al., 2014, emphasis added). Genomic sequencing confirmed that *E. coli* Nissle lacks prominent virulence factors (e.g., *E. coli* α-hemolysin, P-fimbrial adhesins) (Schultz, 2008). In addition, it has been shown that *E. coli* Nissle does not carry pathogenic adhesion factors, does not produce any enterotoxins or cytotoxins, is not invasive, and not uropathogenic (Sonnenborn et al., 2009). As early as in 1917, *E. coli* Nissle was packaged into medicinal capsules, called Mutaflor, for therapeutic use. *E. coli* Nissle has since been used to treat ulcerative colitis in humans in vivo (Rembacken et al., 1999), to treat inflammatory bowel disease, Crohn's disease, and pouchitis in humans in vivo (Schultz, 2008), and to inhibit enteroinvasive *Salmonella, Legionella, Yersinia*, and *Shigella* in vitro (Altenhoefer et al., 2004). It is commonly accepted that *E. coli* Nissle's therapeutic efficacy and safety have convincingly been proven (Ukena et al., 2007).

One of ordinary skill in the art would appreciate that the genetic modifications disclosed herein may be modified and adapted for other species, strains, and subtypes of bacteria. It is known, for example, that arginine-mediated regulation is remarkably well conserved in very divergent bacteria, i.e., Gram-negative bacteria, such as *E. coli, Salmonella enterica* serovar *Typhimurium, Thermotoga*, and *Moritella profunda*, and Gram-positive bacteria, such as *B. subtilis, Geobacillus stearothermophilus*, and *Streptomyces clavuligerus*, as well as other bacteria (Nicoloff et al., 2004). Furthermore, the arginine repressor is universally conserved in bacterial genomes and that its recognition signal (the ARG box), a weak palindrome, is also conserved between genomes (Makarova et al., 2001).

Unmodified *E. coli* Nissle and the genetically engineered bacteria of the invention may be destroyed, e.g., by defense factors in the gut or blood serum (Sonnenborn et al., 2009). The residence time of bacteria in vivo can be determined using the methods described herein. In some embodiments, the residence time is calculated for a human subject. A non-limiting example using a streptomycin-resistant *E. coli* Nissle comprising a wild-type ArgR and a wild-type arginine regulon is provided herein. In some embodiments, residence time in vivo is calculated for the genetically engineered bacteria of the invention.

Reduction of Excess Ammonia

Arginine Biosynthesis Pathway

In bacteria such as *Escherichia coli* (*E. coli*), the arginine biosynthesis pathway is capable of converting glutamate to arginine in an eight-step enzymatic process involving the enzymes N-acetylglutamate synthetase, N-acetylglutamate kinase, N-acetylglutamate phosphate reductase, acetylornithine aminotransferase, N-acetylornithinase, carbamoylphosphate synthase, ornithine transcarbamylase, argininosuccinate synthase, and argininosuccinate lyase (Cunin et al., 1986). The first five steps involve N-acetylation to generate an ornithine precursor. In the sixth step, ornithine transcarbamylase (also known as ornithine carbamoyltransferase) catalyzes the formation of citrulline. The final two steps involve carbamoylphosphate utilization to generate arginine from citrulline.

In some bacteria, e.g., *Bacillus stearothermophilus* and *Neisseria gonorrhoeae*, the first and fifth steps in arginine biosynthesis may be catalyzed by the bifunctional enzyme ornithine acetyltransferase. This bifunctionality was initially identified when ornithine acetyltransferase (argJ) was shown to complement both N-acetylglutamate synthetase (argA) and N-acetylornithinase (argE) auxotrophic gene mutations in *E. coli* (Mountain et al., 1984; Crabeel et al., 1997).

ArgA encodes N-acetylglutamate synthetase, argB encodes N-acetylglutamate kinase, argC encodes N-acetylglutamylphosphate reductase, argD encodes acetylornithine aminotransferase, argE encodes N-acetylornithinase, argF encodes ornithine transcarbamylase, argI also encodes ornithine transcarbamylase, argG encodes argininosuccinate synthase, argH encodes argininosuccinate lyase, and argJ encodes ornithine acetyltransferase. CarA encodes the small A subunit of carbamoylphosphate synthase having glutaminase activity, and carB encodes the large B subunit of carbamoylphosphate synthase that catalyzes carbamoylphosphate synthesis from ammonia. Different combinations of one or more of these arginine biosynthesis genes (i.e., argA, argB, argC, argD, argE, argF, argG, argH, argI, argJ, carA, and carc) may be organized, naturally or synthetically, into one or more operons, and such organization may vary between bacterial species, strains, and subtypes (see, e.g., Table 2). The regulatory region of each operon contains at least one ARG box, and the number of ARG boxes per regulatory region may vary between operons and bacteria.

All of the genes encoding these enzymes are subject to repression by arginine via its interaction with ArgR to form a complex that binds to the regulatory region of each gene and inhibits transcription. N-acetylglutamate synthetase is also subject to allosteric feedback inhibition at the protein level by arginine alone (Tuchman et al., 1997; Caldara et al., 2006; Caldara et al., 2008; Caldovic et al., 2010).

The genes that regulate arginine biosynthesis in bacteria are scattered across the chromosome and organized into multiple operons that are controlled by a single repressor, which Maas and Clark (1964) termed a "regulon." Each operon is regulated by a regulatory region comprising at least one 18-nucleotide imperfect palindromic sequence, called an ARG box, that overlaps with the promoter and to which the repressor protein binds (Tian et al., 1992; Tian et al., 1994). The argR gene encodes the repressor protein, which binds to one or more ARG boxes (Lim et al., 1987). Arginine functions as a corepressor that activates the arginine repressor. The ARG boxes that regulate each operon may be non-identical, and the consensus ARG box sequence is A/T nTGAAT A/T A/T T/A T/A ATTCAn T/A (SEQ ID NO: 120) (Maas, 1994). In addition, the regulatory region of argR contains two promoters, one of which overlaps with two ARG boxes and is autoregulated.

In some embodiments, the genetically engineered bacteria comprise a mutant arginine regulon and produce more arginine and/or an intermediate byproduct, e.g., citrulline, than unmodified bacteria of the same subtype under the same conditions. The mutant arginine regulon comprises one or more nucleic acid mutations that reduce or prevent arginine-mediated repression—via ArgR binding to ARG boxes and/or arginine binding to N-acetylglutamate synthetase—of one or more of the operons that encode the enzymes responsible for converting glutamate to arginine in the arginine biosynthesis pathway, thereby enhancing arginine and/or intermediate byproduct biosynthesis.

In alternate embodiments, the bacteria are genetically engineered to consume excess ammonia via another metabolic pathway, e.g., a histidine biosynthesis pathway, a methionine biosynthesis pathway, a lysine biosynthesis pathway, an asparagine biosynthesis pathway, a glutamine biosynthesis pathway, and a tryptophan biosynthesis pathway. As used herein, "an ammonia conversion circuit" refers to a metabolic pathway by which excess ammonia may be consumed and/or reduced.

Histidine Biosynthesis Pathway

Histidine biosynthesis, for example, is carried out by eight genes located within a single operon in *E. coli*. Three of the eight genes of the operon (hisD, hisB, and hisI) encode bifunctional enzymes, and two (hisH and hisF) encode polypeptide chains which together form one enzyme to catalyze a single step, for a total of 10 enzymatic reactions (Alifano et al., 1996). The product of the hisG gene, ATP phosphoribosyltransferase, is inhibited at the protein level by histidine. In some embodiments, the genetically engineered bacteria of the invention comprise a feedback-resistant hisG. Bacteria may be mutagenized and/or screened for feedback-resistant hisG mutants using techniques known in the art. Bacteria engineered to comprise a feedback-resistant hisG would have elevated levels of histidine production, thus increasing ammonia consumption and reducing hyperammonemia. Alternatively, one or more genes required for histidine biosynthesis could be placed under the control of an inducible promoter, such as a FNR-inducible promoter, and allow for increased production of rate-limiting enzymes.

Any other suitable modification(s) to the histidine biosynthesis pathway may be used to increase ammonia consumption.

Methionine Biosynthesis Pathway

The bacterial methionine regulon controls the three-step synthesis of methionine from homoserine (i.e., acylation, sulfurylation, and methylation). The metJ gene encodes a regulatory protein that, when combined with methionine or a derivative thereof, causes repression of genes within the methionine regulon at the transcriptional level (Saint-Girons et al., 1984; Shoeman et al., 1985). In some embodiments, the genetically engineered bacteria of the invention comprise deleted, disrupted, or mutated metJ. Bacteria engineered to delete, disrupt, or mutate metJ would have elevated levels of methionine production, thus increasing ammonia consumption and reducing hyperammonemia. Any other suitable modification(s) to the methionine biosynthesis pathway may be used to increase ammonia consumption.

Lysine Biosynthesis Pathway

Microorganisms synthesize lysine by one of two pathways. The diaminopimelate (DAP) pathway is used to synthesize lysine from aspartate and pyruvate (Dogovski et al., 2012), and the aminoadipic acid pathway is used to synthesize lysine from alpha-ketoglutarate and acetyl coenzyme A. The dihydrodipicolinate synthase (DHDPS) enzyme catalyzes the first step of the DAP pathway, and is subject to feedback inhibition by lysine (Liu et al., 2010; Reboul et al., 2012). In some embodiments, the genetically engineered bacteria of the invention comprise a feedback-resistant DHDPS. Bacteria engineered to comprise a feedback-resistant DHDPS would have elevated levels of histidine production, thus increasing ammonia consumption and reducing hyperammonemia. Alternatively, lysine production could be optimized by placing one or more genes required for lysine biosynthesis under the control of an inducible promoter, such as a FNR-inducible promoter. Any other suitable modification(s) to the lysine biosynthesis pathway may be used to increase ammonia consumption.

Asparagine Biosynthesis Pathway

Asparagine is synthesized directly from oxaloacetate and aspartic acid via the oxaloacetate transaminase and asparagine synthetase enzymes, respectively. In the second step of this pathway, either L-glutamine or ammonia serves as the amino group donor. In some embodiments, the genetically engineered bacteria of the invention overproduce asparagine as compared to unmodified bacteria of the same subtype under the same conditions, thereby consuming excess ammonia and reducing hyperammonemia. Alternatively, asparagine synthesis may be optimized by placing one or both of these genes under the control of an inducible promoter, such as a FNR-inducible promoter. Any other suitable modification(s) to the asparagine biosynthesis pathway may be used to increase ammonia consumption.

Glutamine Biosynthesis Pathway

The synthesis of glutamine and glutamate from ammonia and oxoglutarate is tightly regulated by three enzymes. Glutamate dehydrogenase catalyzes the reductive amination of oxoglutarate to yield glutamate in a single step. Glutamine synthetase catalyzes the ATP-dependent condensation of glutamate and ammonia to form glutamine (Lodeiro et al., 2008). Glutamine synthetase also acts with glutamine-oxoglutarate amino transferase (also known as glutamate synthase) in a cyclic reaction to produce glutamate from glutamine and oxoglutarate. In some embodiments, the genetically engineered bacteria of the invention express glutamine synthetase at elevated levels as compared to unmodified bacteria of the same subtype under the same conditions. Bacteria engineered to have increased expression of glutamine synthetase would have elevated levels of glutamine production, thus increasing ammonia consumption and reducing hyperammonemia. Alternatively, expression of glutamate dehydrogenase and/or glutamine-oxoglutarate amino transferase could be modified to favor the consumption of ammonia. Since the production of glutamine synthetase is regulated at the transcriptional level by nitrogen (Feng et al., 1992; van Heeswijk et al., 2013), placing the glutamine synthetase gene under the control of different inducible promoter, such as a FNR-inducible promoter, may also be used to improve glutamine production. Any other suitable modification(s) to the glutamine and glutamate biosynthesis pathway may be used to increase ammonia consumption.

Tryptophan Biosynthesis Pathway

In most bacteria, the genes required for the synthesis of tryptophan from a chorismate precursor are organized as a single transcriptional unit, the trp operon. The trp operon is under the control of a single promoter that is inhibited by the tryptophan repressor (TrpR) when high levels of tryptophan are present. Transcription of the trp operon may also be terminated in the presence of high levels of charged tryptophan tRNA. In some embodiments, the genetically engineered bacteria of the invention comprise a deleted, disrupted, or mutated trpR gene. The deletion, disruption, or mutation of the trpR gene, and consequent inactivation of TrpR function, would result in elevated levels of both tryptophan production and ammonia consumption. Alternatively, one or more enzymes required for tryptophan biosynthesis could be placed under the control of an inducible promoter, such as a FNR-inducible promoter. Any other suitable modification(s) to the tryptophan biosynthesis pathway may be used to increase ammonia consumption.

Engineered Bacteria Comprising a Mutant Arginine Regulon

In some embodiments, the genetically engineered bacteria comprise an arginine biosynthesis pathway and are capable of reducing excess ammonia. In a more specific aspect, the genetically engineered bacteria comprise a mutant arginine regulon in which one or more operons encoding arginine biosynthesis enzyme(s) is derepressed to produce more arginine or an intermediate byproduct, e.g., citrulline, than unmodified bacteria of the same subtype under the same conditions. In some embodiments, the genetically engineered bacteria overproduce arginine. In some embodiments, the genetically engineered bacteria overproduce citrulline; this may be additionally beneficial, because citrulline is currently used as a therapeutic for particular urea cycle disorders (National Urea Cycle Disorders Foundation). In some embodiments, the genetically engineered bacteria overproduce an alternate intermediate byproduct in the arginine biosynthesis pathway, such as any of the intermediates described herein. In some embodiments, the genetically engineered bacterium consumes excess ammonia by producing more arginine, citrulline, and/or other intermediate byproduct than an unmodified bacterium of the same bacterial subtype under the same conditions. Enhancement of arginine and/or intermediate byproduct biosynthesis may be used to incorporate excess nitrogen in the body into non-toxic molecules in order to treat conditions associated with hyperammonemia, including urea cycle disorders and hepatic encephalopathy.

One of skill in the art would appreciate that the organization of arginine biosynthesis genes within an operon varies across species, strains, and subtypes of bacteria, e.g., bipolar argECBH in *E. coli* K12, argCAEBD-carAB-argF in B. subtilis, and bipolar carAB-argCJBDF in L. plantarum. Non-limiting examples of operon organization from different bacteria are shown in Table 2 (in some instances, the genes are putative and/or identified by sequence homology to known sequences in Escherichia coli; in some instances, not all of the genes in the arginine regulon are known and/or shown below). In certain instances, the arginine biosynthesis enzymes vary across species, strains, and subtypes of bacteria.

TABLE 2

Examples of arg operon organization

| Bacteria | Operon organization | | | | |
|---|---|---|---|---|---|
| Escherichia coli Nissle | argA | bipolar argECBH | argD | argI | argG carAB |
| Bacteroides | argRGCD | argF | argB | argE | carAB |
| Clostridium | argR | | argGH | | argI |
| Bacillus subtilis | argGH | | argCAEBD-carAB-argF | | |
| Bacillus subtilis | argGH | | argCJBD-carAB-argF | | |
| Lactobacillus plantarum | argGH | | bipolar carAB-argCJBDF | | |
| Lactococcus | argE | carA carB | argGH | | argFBDJC |

Each operon is regulated by a regulatory region comprising at least one promoter and at least one ARG box, which control repression and expression of the arginine biosynthesis genes in said operon.

In some embodiments, the genetically engineered bacteria of the invention comprise an arginine regulon comprising one or more nucleic acid mutations that reduce or eliminate arginine-mediated repression of one or more of the operons that encode the enzymes responsible for converting glutamate to arginine and/or an intermediate byproduct in the arginine biosynthesis pathway. Reducing or eliminating arginine-mediated repression may be achieved by reducing or eliminating ArgR repressor binding (e.g., by mutating or deleting the arginine repressor or by mutating at least one ARG box for each of the operons that encode the arginine biosynthesis enzymes) and/or arginine binding to N-acetylglutamate synthetase (e.g., by mutating the N-acetylglutamate synthetase to produce an arginine feedback resistant N-acetylglutamate synthase mutant, e.g., argA$^{fbr}$).

ARG Box

In some embodiments, the genetically engineered bacteria comprise a mutant arginine regulon comprising one or more nucleic acid mutations in at least one ARG box for one or more of the operons that encode the arginine biosynthesis enzymes N-acetylglutamate kinase, N-acetylglutamylphosphate reductase, acetylornithine aminotransferase, N-acetylornithinase, ornithine transcarbamylase, argininosuccinate synthase, argininosuccinate lyase, and carbamoylphosphate synthase, thereby derepressing the regulon and enhancing arginine and/or intermediate byproduct biosynthesis. In some embodiments, the genetically engineered bacteria comprise a mutant arginine repressor comprising one or more nucleic acid mutations such that arginine repressor function is decreased or inactive, or the genetically engineered bacteria do not have an arginine repressor (e.g., the arginine repressor gene has been deleted), resulting in derepression of the regulon and enhancement of arginine and/or intermediate byproduct biosynthesis. In either of these embodiments, the genetically engineered bacteria may further comprise an arginine feedback resistant N-acetylglutamate synthase mutant, e.g., argA$^{fbr}$. Thus, in some embodiments, the genetically engineered bacteria comprise a mutant arginine regulon comprising one or more nucleic acid mutations in at least one ARG box for one or more of the operons that encode the arginine biosynthesis enzymes and an arginine feedback resistant N-acetylglutamate synthase mutant, e.g., argA$^{fbr}$. In some embodiments, the genetically engineered bacteria comprise a mutant or deleted arginine repressor and an arginine feedback resistant N-acetylglutamate synthase mutant, e.g., argA$^{fbr}$. In some embodiments, the genetically engineered bacteria comprise an arginine feedback resistant N-acetylglutamate synthase mutant, e.g., argA$^{fbr}$, a mutant arginine regulon comprising one or more nucleic acid mutations in at least one ARG box for each of the operons that encode the arginine biosynthesis enzymes, and/or a mutant or deleted arginine repressor.

In some embodiments, the genetically engineered bacteria encode an arginine feedback resistant N-acetylglutamate synthase and further comprise a mutant arginine regulon comprising one or more nucleic acid mutations in each ARG box for one or more of the operons that encode N-acetylglutamate kinase, N-acetylglutamylphosphate reductase, acetylornithine aminotransferase, N-acetylornithinase, ornithine transcarbamylase, argininosuccinate synthase, argininosuccinate lyase, carbamoylphosphate synthase, and wild-type N-acetylglutamate synthetase, such that ArgR binding is reduced or eliminated, thereby derepressing the regulon and enhancing arginine and/or intermediate byproduct biosynthesis.

In some embodiments, the ARG boxes for the operon encoding argininosuccinate synthase (argG) maintain the ability to bind to ArgR, thereby driving citrulline biosynthesis. For example, the regulatory region of the operon encoding argininosuccinate synthase (argG) may be a constitutive, thereby driving arginine biosynthesis. In alternate embodiments, the regulatory region of one or more alternate operons may be constitutive. In certain bacteria, however, genes encoding multiple enzymes may be organized in bipolar operons or under the control of a shared regulatory region; in these instances, the regulatory regions may need to be deconvoluted in order to engineer constitutively active regulatory regions. For example, in E. coli K12 and Nissle, argE and argCBH are organized in two bipolar operons, argECBH, and those regulatory regions may be deconvoluted in order to generate constitutive versions of argE and/or argCBH.

In some embodiments, all ARG boxes in one or more operons that comprise an arginine biosynthesis gene are mutated to reduce or eliminate ArgR binding. In some embodiments, all ARG boxes in one or more operons that encode an arginine biosynthesis enzyme are mutated to reduce or eliminate ArgR binding. In some embodiments, all ARG boxes in each operon that comprises an arginine biosynthesis gene are mutated to reduce or eliminate ArgR binding. In some embodiments, all ARG boxes in each operon that encodes an arginine biosynthesis enzyme are mutated to reduce or eliminate ArgR binding.

In some embodiments, the genetically engineered bacteria encode an arginine feedback resistant N-acetylglutamate synthase, argininosuccinate synthase driven by a ArgR-repressible regulatory region, and further comprise a mutant arginine regulon comprising one or more nucleic acid mutations in each ARG box for each of the operons that encode N-acetylglutamate kinase, N-acetylglutamylphosphate reductase, acetylornithine am inotransferase, N-acetylornithinase, ornithine transcarbamylase, argininosuccinate synthase, argininosuccinate lyase, carbamoylphosphate synthase, and optionally, wild-type N-acetylglutamate synthetase, such that ArgR binding is reduced or eliminated, thereby derepressing the regulon and enhancing citrulline biosynthesis. In some embodiments, the genetically engineered bacteria capable of producing citrulline is particularly advantageous, because citrulline further serves as a therapeutically effective supplement for the treatment of certain urea cycle disorders (National Urea Cycle Disorders Foundation).

In some embodiments, the genetically engineered bacteria encode an arginine feedback resistant N-acetylglutamate synthase, argininosuccinate synthase driven by a constitutive promoter, and further comprise a mutant arginine regulon comprising one or more nucleic acid mutations in each ARG box for each of the operons that encode N-acetylglutamate kinase, N-acetylglutamylphosphate reductase, acetylornithine am inotransferase, N-acetylornithinase, ornithine transcarbamylase, argininosuccinate lyase, carbamoylphosphate synthase, and optionally, wild-type N-acetylglutamate synthetase, such that ArgR binding is reduced or eliminated, thereby derepressing the regulon and enhancing arginine biosynthesis.

In some embodiments, the genetically engineered bacteria comprise a mutant arginine regulon and a feedback resistant ArgA, and when the arginine feedback resistant ArgA is expressed, are capable of producing more arginine and/or an intermediate byproduct than unmodified bacteria of the same subtype under the same conditions. In any of these embodiments, the mutant arginine regulon and/or a feedback resistant ArgA may be integrated into the bacterial chromosome at one or more integration sites or may be present on one or more plasmids.

Arginine Repressor Binding Sites (ARG Boxes)

In some embodiments, the genetically engineered bacteria additionally comprise a mutant arginine regulon comprising one or more nucleic acid mutations in at least one ARG box for one or more of the operons that encode the arginine biosynthesis enzymes N-acetylglutamate kinase, N-acetylglutamylphosphate reductase, acetylornithine am inotransferase, N-acetylornithinase, ornithine transcarbamylase, argininosuccinate synthase, argininosuccinate lyase, and carbamoylphosphate synthase, such that the arginine regulon is derepressed and biosynthesis of arginine and/or an intermediate byproduct, e.g., citrulline, is enhanced.

In some embodiments, the mutant arginine regulon comprises an operon encoding ornithine acetyltransferase and one or more nucleic acid mutations in at least one ARG box for said operon. The one or more nucleic acid mutations results in the disruption of the palindromic ARG box sequence, such that ArgR binding to that ARG box and to the regulatory region of the operon is reduced or eliminated, as compared to ArgR binding to an unmodified ARG box and regulatory region in bacteria of the same subtype under the same conditions. In some embodiments, nucleic acids that are protected from DNA methylation and hydroxyl radical attack during ArgR binding are the primary targets for mutations to disrupt ArgR binding. In some embodiments, the mutant arginine regulon comprises at least three nucleic acid mutations in one or more ARG boxes for each of the operons that encode the arginine biosynthesis enzymes described above. The ARG box overlaps with the promoter, and in the mutant arginine regulon, the G/C:A/T ratio of the mutant promoter region differs by no more than 10% from the G/C:A/T ratio of the wild-type promoter region (Table 3). The promoter retains sufficiently high homology to the non-mutant promoter such that RNA polymerase binds with sufficient affinity to promote transcription.

The wild-type genomic sequences comprising ARG boxes and mutants thereof for each arginine biosynthesis operon in *E. coli* Nissle are shown in Table 3. For exemplary wild-type sequences, the ARG boxes are indicated in italics, and the start codon of each gene is boxed. The RNA polymerase binding sites are underlined (Cunin, 1983; Maas, 1994). In some embodiments, the underlined sequences are not altered. Bases that are protected from DNA methylation during ArgR binding are highlighted, and bases that are protected from hydroxyl radical attack during ArgR binding are bolded (Charlier et al., 1992). The highlighted and bolded bases are the primary targets for mutations to disrupt ArgR binding.

TABLE 3

| Regulatory region | Sequence |
| --- | --- |
| argA WT (SEQ ID NO: 1) | GCAAAAAAACA*G*AATAAAAAT*A*CAATAATT*TC*G*AATAA*TCAT*G*CAAAGAGGTGTACC GTG |
| argA mutant (SEQ ID NO: 2) | gcaaaaaaacactttaaaaacttaataatt tcctttaatcacttaaagaggtgtaccgtg |
| argI WT SEQ ID NO: 3) | AGACTTGCAAAT*G*AATAA*T*CATC*G*ATATAG ATT*G*AATTTTAATT*G*ATTAAGGCGTTAGCC ACAGGAGGGATCT ATG |
| argI mutant (SEQ ID NO: 4) | agacttgcaaacttatacttatccatatag attttgttttaatttgttaaggcgttagcc acaggagggatctatg |
| argCBH WT (SEQ ID NO: 5) | TCATTGTTGACACACCTCTGGTCATGATAG TATCAATA*T*T*CAT*G*G*AGTATTAT*G*AATA*A* AAATA*G*ACTAACGTTGAGCGTAATAAAACC CACCAGCCGTAAGGTGAATGTTTTACGTTT AACCTGGCAACCAGACATAAGAAGGTGAAT AGCCCCG ATG |
| argCBH mutant (SEQ ID NO: 6) | tcattgttgacacacctctggtcatgatag tatcaaacttcatgggatatttatctttaa aaatacttgaacgttgagcgtaataaaacc caccagccgtaaggtgaatgttttacgttt aacctggcaaccagacataagaaggtgaat agccccgatg |
| argE WT | CATCGGGGCTATTCACCTTCTTATGTCTGG TTGCCAGGTTAAACGTAAAACATTCACCTT ACGGCTGGTGGGTTTTATTACGCTCAACGT TAGT*G*TATTTTTATT*G*ATAAATACTG*G*ATG AATATTGATACTATCATGACCAGAGGTGTG TCAACA ATG A |
| argE mutant (SEQ ID NO: 8) | catcggggctattcaccttcttatgtctgg ttgccaggttaaacgtaaaacattcacctt acggctggtgggttttattacgctcaacgt tcaagtatttttaaagataaatatcccatg aagtttgatactatcatgaccagaggtgtg tcaacaatga |

TABLE 3-continued

| Regulatory region | Sequence |
|---|---|
| carAB WT (SEQ ID NO: 9) | AGCAGATTTGCATTGATTTACGTCATCAT*T GT☒AATTAATAT☒☒AAATAAAGT☒AGTGAA TATT☒TCTGGAGGGTGTT`TTG` |
| carAB mutant (SEQ ID NO: 10) | agcagatttgcattgatttacgtcatcatt gtcttttaatatcttaataactggagtgac gtttctctggagggtgttttg |
| argD WT (SEQ ID NO: 11) | TTTCTGATTGCCATTCAGT☒ATTTTTTAT☒ ☒ATATTTTGT☒ATTATAATTT☒ATATTTAT TTATGCGTAACAGGGTGATCATGAGATG |
| argD mutant (SEQ ID NO: 12) | tttctgattgccattcagtctttttttact tatattttgtctttataatcttatatttat ttatgcgtaacagggtgatcatgagatg |
| argG WT (SEQ ID NO: 13) | CTAATCA*CGT☒AATGAATAT☒☒AGTTCACT TTCATTTGTTGAATACTTTTACCTTCTCCT GCTTTCCCTTAAGCGCATTATTTTACAAAA AACACACTAAACTCTTCCTGTCTCCGATAA AAGATGATTAAATGAAAACT☒ATTTATTTT ☒☒ATAAAAATT☒AGTGAAAGCAGAAATCCA GGCTCATCATCAGTTAATTAAGCAGGGTGT TATTTT`ATG` |
| argG mutant (SEQ ID NO: 14) | ctaatcaccttaatgaatcttcagttcact ttcatttgttgaatacttttaccttctcct gctttcccttaagcgcattattttacaaaa aacacactaaactcttcctgtctccgataa aagatgatcttatgaaaacttttttatttc ttataaaaatcttgtgaaagcagaaatcca ggctcatcatcagttaattaagcagggtgt tattttatg |
| argG mutant (SEQ ID NO: 15) | cctgaaacgtggcaaattctactcgttttg ggtaaaaaatgcaaatactgctgggatttg gtgtaccgagacgggacgtaaaatctgcag gcattatagtgatccacgccacattttgtc aacgtttattgctaatcattgacggctagc tcagtcctaggtacagtgctagcACCCGTT TTTTTGGGCTAGAAATAATTTTGTTTAACT TTAAGAAGGAGATATACATACCC |

In some embodiments, more than one ARG box may be present in a single operon. In one aspect of these embodiments, at least one of the ARG boxes in an operon is mutated to produce the requisite reduced ArgR binding to the regulatory region of the operon. In an alternate aspect of these embodiments, each of the ARG boxes in an operon is mutated to produce the requisite reduced ArgR binding to the regulatory region of the operon. One of skill in the art would appreciate that the number of ARG boxes per regulatory region may vary across bacteria, and the nucleotide sequences of the ARG boxes may vary for each operon. For example, the carAB operon in *E. coli* Nissle comprises two ARG boxes, and one or both ARG box sequences may be mutated. The argG operon in *E. coli* Nissle comprises three ARG boxes, and one, two, or three ARG box sequences may be mutated, disrupted, or deleted. In some embodiments, all three ARG box sequences are mutated, disrupted, or deleted, and a constitutive promoter, e.g., BBa_J23100, is inserted in the regulatory region of the argG operon. One of skill in the art would appreciate that the number of ARG boxes per regulatory region may vary across bacteria, and the nucleotide sequences of the ARG boxes may vary for each operon.

Figure 12:
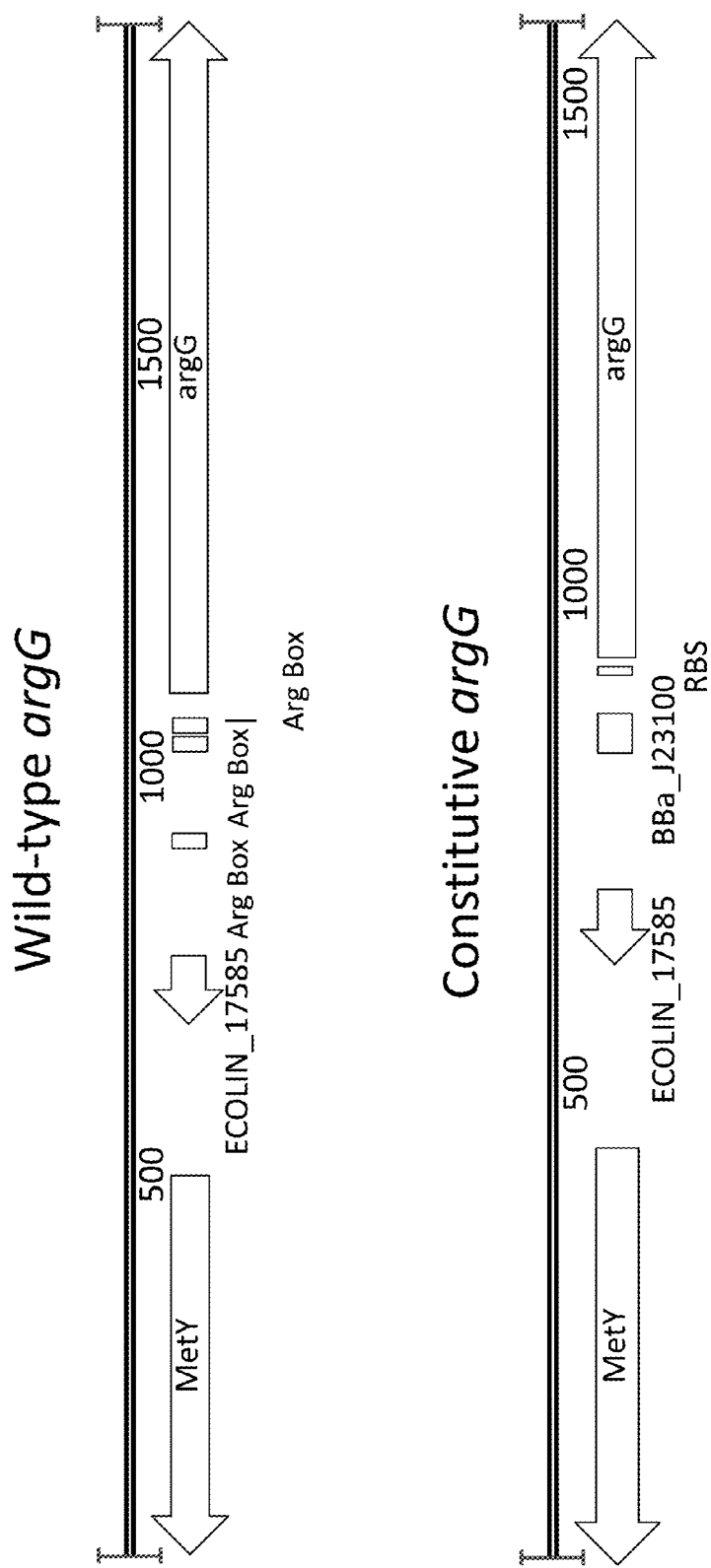
FIG. 12 depicts a map of the wild-type argG operon E. coli Nissle, and a constitutively expressing mutant thereof. ARG boxes are present in the wild-type operon, but absent from the mutant. ArgG is constitutively expressed under the control of the BBa_J23100 promoter.

An exemplary embodiment of a constitutively expressed argG construct in *E. coli* Nissle is depicted in Table 4. Table 4 depicts the wild-type genomic sequence of the regulatory region and 5' portion of the argG gene in *E. coli* Nissle, and a constitutive mutant thereof. The promoter region of each sequence is underlined, and a 5' portion of the argG gene is `boxed`. In the wild-type sequence, ArgR binding sites are in uppercase and underlined. In the mutant sequence, the 5' untranslated region is in uppercase and underlined. Bacteria expressing argG under the control of the constitutive promoter are capable of producing arginine. Bacteria expressing argG under the control of the wild-type, ArgR-repressible promoter are capable of producing citrulline. A map of the wild-type argG operon *E. coli* Nissle and a constitutively expressing mutant thereof is shown in FIG. 12.

TABLE 4

| Wild-type argG (SEQ ID NO: 16) | gtgatccacgccacattttgtcaacgtttattgctaatcaCGTG AATGAATATCCAGTtcactttcatttgttgaatacttttaccttt ctcctgctttcccttaagcgcattattttacaaaaaacacacta aactcttcctgtctccgataaaagatgATTAAATGAAAACTCAT TtatTTTGCATAAAAATTCAGTgaaagcagaaatccaggctcat<br><br>catcagttaattaagcagggtgttattttt`atgacgacgattct`<br><br>`caagcatctcccggtaggtcaacgtattggtatcgcttttttcc`<br><br>`ggcggtctggacaccagtgccgcactgctgtggatgcgacaaa`<br><br>`agggagcggttccttatgcatatactgcaaacctgggccagcc`<br><br>`agacgaagaggattatgatgcgatccctcgtcgtgccatggaa`<br><br>`tacggcgcggagaacgcacgtctgatcgactgccgcaaacaac`<br><br>`tggtggccgaaggtattgccgctattcagtgtggcgcatttca`<br><br>`taacaccactggtggactgacctatttcaacacgacgccgctg` |

TABLE 4-continued

```
                    ggccgcgccgtgaccggcaccatgctggttgctgctatgaaag aagatggcgtgaatatctggggtgacggcagcacctataaagg aaacgatatcgaacgtttctaccgttacggtctgctgaccaat gctgaactgcagatttacaaaccgtggcttgatactgacttta ttgatgaactgggtggccgtcatgagatgtctgaatttatgat tgcctgcggtttcgactacaaaatgtctgtcgaaaaagcttac tccacggactccaacatgcttggtgcaacgcatgaagcgaagg atctggaatacctcaactccagcgtcaaaatcgtcaacccaat tatgggcgtgaagttttgggatgagagcgtgaaaatcccggca gaagaagtcacagtacgctttgagcaaggtcatccggtggcgc tgaacggtaaaacctttagcgacgacgtagaaatgatgctgga agctaaccgcatcggc Constitutive        ttgacggctagctcagtcctaggtacagtgctagcACCCGTTTT
argG                TTTGGGCTAGAAATAATTTTGTTTAACTTTAAGAAGGAGATATA
(SEQ ID NO: 17)     CATACCatgacgacgattctcaagcatctcccggtaggtcaa cgtattggtatcgcttttccggcggtctggacaccagtgccg cactgctgtggatgcgacaaaagggagcggttccttatgcata tactgcaaacctgggccagccagacgaagaggattatgatgcg atccctcgtcgtgccatggaatacggcgcggagaacgcacgtc tgatcgactgccgcaaacaactggtggccgaaggtattgccgc tattcagtgtggcgcatttcataacaccactggtggactgacc tatttcaacacgacgccgctgggccgcgccgtgaccggcacca tgctggttgctgctatgaaagaagatggcgtgaatatctgggg tgacggcagcacctataaaggaaacgatatcgaacgtttctac cgttacggtctgctgaccaatgctgaactgcagatttacaaac cgtggcttgatactgactttattgatgaactgggtggccgtca tgagatgtctgaatttatgattgcctgcggtttcgactacaaa
```

TABLE 4-continued

```
atgtctgtcgaaaaagcttactccacggactccaacatgcttg
```

```
gtgcaacgcatgaagcgaaggatctggaatacctcaactccag
```

```
c
```

In some embodiments, the ArgR binding affinity to a mutant ARG box or regulatory region of an operon is at least about 50% lower, at least about 60% lower, at least about 70% lower, at least about 80% lower, at least about 90% lower, or at least about 95% lower than the ArgR binding affinity to an unmodified ARG box and regulatory region in bacteria of the same subtype under the same conditions. In some embodiments, the reduced ArgR binding to a mutant ARG box and regulatory region increases mRNA expression of the gene(s) in the associated operon by at least about 1.5-fold, at least about 2-fold, at least about 10-fold, at least about 15-fold, at least about 20-fold, at least about 30-fold, at least about 50-fold, at least about 100-fold, at least about 200-fold, at least about 300-fold, at least about 400-fold, at least about 500-fold, at least about 600-fold, at least about 700-fold, at least about 800-fold, at least about 900-fold, at least about 1,000-fold, or at least about 1,500-fold.

In some embodiments, quantitative PCR (qPCR) is used to amplify, detect, and/or quantify mRNA expression levels of the arginine biosynthesis genes. Primers specific for arginine biosynthesis genes, e.g., argA, argB, argC, argD, argE, argF, argG, argH, argI, argJ, carA, and care, may be designed and used to detect mRNA in a sample according to methods known in the art (Fraga et al., 2008). In some embodiments, a fluorophore is added to a sample reaction mixture that may contain arg mRNA, and a thermal cycler is used to illuminate the sample reaction mixture with a specific wavelength of light and detect the subsequent emission by the fluorophore. The reaction mixture is heated and cooled to predetermined temperatures for predetermined time periods. In certain embodiments, the heating and cooling is repeated for a predetermined number of cycles. In some embodiments, the reaction mixture is heated and cooled to 90-100° C., 60-70° C., and 30-50° C. for a predetermined number of cycles. In a certain embodiment, the reaction mixture is heated and cooled to 93-97° C., 55-65° C., and 35-45° C. for a predetermined number of cycles. In some embodiments, the accumulating amplicon is quantified after each cycle of the qPCR. The number of cycles at which fluorescence exceeds the threshold is the threshold cycle ($C_T$). At least one $C_T$ result for each sample is generated, and the $C_T$ result(s) may be used to determine mRNA expression levels of the arginine biosynthesis genes.

In some embodiments, the genetically engineered bacteria comprising one or more nucleic acid mutations in at least one ARG box for one or more of the operons that encode the arginine biosynthesis enzymes N-acetylglutamate kinase, N-acetylglutamylphosphate reductase, acetylornithine aminotransferase, N-acetylornithinase, ornithine transcarbamylase, argininosuccinate synthase, argininosuccinate lyase, and carbamoylphosphate synthase additionally comprise an arginine feedback resistant N-acetylglutamate synthase mutant, e.g., argA$^{fbr}$.

In some embodiments, the genetically engineered bacteria comprise a feedback resistant form of ArgA, as well as one or more nucleic acid mutations in each ARG box of one or more of the operons that encode the arginine biosynthesis enzymes N-acetylglutamate kinase, N-acetylglutamylphosphate reductase, acetylornithine aminotransferase, N-acetylornithinase, ornithine transcarbamylase, argininosuccinate synthase, argininosuccinate lyase, ornithine acetyltransferase, and carbamoylphosphate synthase.

In some embodiments, the genetically engineered bacteria comprise a feedback resistant form of ArgA, argininosuccinate synthase driven by a ArgR-repressible regulatory region, as well as one or more nucleic acid mutations in each ARG box of each of the operons that encode the arginine biosynthesis enzymes N-acetylglutamate kinase, N-acetylglutamylphosphate reductase, acetylornithine aminotransferase, N-acetylornithinase, ornithine transcarbamylase, argininosuccinate lyase, ornithine acetyltransferase, and carbamoylphosphate synthase. In these embodiments, the bacteria are capable of producing citrulline.

In some embodiments, the genetically engineered bacteria comprise a feedback resistant form of ArgA, argininosuccinate synthase expressed from a constitutive promoter, as well as one or more nucleic acid mutations in each ARG box of each of the operons that encode the arginine biosynthesis enzymes N-acetylglutamate kinase, N-acetylglutamylphosphate reductase, acetylornithine aminotransferase, N-acetylornithinase, ornithine transcarbamylase, argininosuccinate synthase, argininosuccinate lyase, ornithine acetyltransferase, and carbamoylphosphate synthase. In these embodiments, the bacteria are capable of producing arginine.

Table 3 shows examples of mutant constructs in which one or more nucleic acid mutations reduce or eliminate arginine-mediated repression of each of the arginine operons. The mutant constructs comprise feedback resistant form of ArgA driven by an oxygen level-dependent promoter, e.g., a FNR promoter. Each mutant arginine regulon comprises one or more nucleic acid mutations in at least one ARG box for one or more of the operons that encode N-acetylglutamate kinase, N-acetylglutamylphosphate reductase, acetylornithine aminotransferase, N-acetylornithinase, ornithine transcarbamylase, argininosuccinate synthase, argininosuccinate lyase, carbamoylphosphate synthase, and wild-type N-acetylglutamate synthetase, such that ArgR binding is reduced or eliminated, thereby enhancing arginine and/or intermediate byproduct biosynthesis. Non-limiting examples of mutant arginine regulon constructs are shown in Table 5.

TABLE 5

Examples of ARG Box mutant constructs

| Mutant construct comprises: | | Exemplary constructs (* indicates constitutive): | | | | | |
|---|---|---|---|---|---|---|---|
| | | Construct 1 | Construct 2 | Construct 3 | Construct 4 | Construct 5 | Construct 6 |
| Arginine feedback resistant N-acetylglutamate synthetase driven by an oxygen level-dependent promoter | | ✓ | ✓ | ✓ | ✓ | ✓ | ✓ |
| Wild-type N-acetylglutamate synthetase | | ✓ | ✓ | | ✓ | ✓ | |
| Mutation(s) in at least one ARG box for the operon encoding: | Wild-type N-acetylglutamate synthetase | ✓ | | ✓ | ✓ | | ✓ |
| | N-acetylglutamate kinase | ✓ | ✓ | ✓ | ✓ | ✓ | ✓ |
| | N-acetylglutamylphosphate reductase | ✓ | ✓ | ✓ | ✓ | ✓ | ✓ |
| | acetylornithine aminotransferase | ✓ | ✓ | ✓ | ✓ | ✓ | ✓ |
| | N-acetylornithinase | ✓ | ✓ | ✓ | ✓ | ✓ | ✓ |
| | ornithine transcarbamylase | ✓ | ✓ | ✓ | ✓ | ✓ | ✓ |
| | argininosuccinate synthase | ✓ | ✓ | ✓ | ✓* | ✓* | ✓* |
| | argininosuccinate lyase | ✓ | ✓ | ✓ | ✓ | ✓ | ✓ |
| | ornithine acetyltransferase | ✓ | ✓ | ✓ | ✓ | ✓ | ✓ |
| | carbamoylphosphate synthase | ✓ | ✓ | ✓ | ✓ | ✓ | ✓ |

The mutations may be present on a plasmid or chromosome. In some embodiments, the arginine regulon is regulated by a single repressor protein. In particular species, strains, and/or subtypes of bacteria, it has been proposed that the arginine regulon may be regulated by two putative repressors (Nicoloff et al., 2004). Thus, in certain embodiments, the arginine regulon of the invention is regulated by more than one repressor protein.

In certain embodiments, the mutant arginine regulon is expressed in one species, strain, or subtype of genetically engineered bacteria. In alternate embodiments, the mutant arginine regulon is expressed in two or more species, strains, and/or subtypes of genetically engineered bacteria.

Arginine Repressor (ArgR)

The genetically engineered bacteria of the invention comprise an arginine regulon comprising one or more nucleic acid mutations that reduce or eliminate arginine-mediated repression of one or more of the operons that encode the enzymes responsible for converting glutamate to arginine and/or an intermediate byproduct in the arginine biosynthesis pathway. In some embodiments, the reduction or elimination of arginine-mediated repression may be achieved by reducing or eliminating ArgR repressor binding, e.g., by mutating at least one ARG box for one or more of the operons that encode the arginine biosynthesis enzymes (as discussed above) or by mutating or deleting the arginine repressor (discussed here) and/or by reducing or eliminating arginine binding to N-acetylglutamate synthetase (e.g., by mutating the N-acetylglutamate synthetase to produce an arginine feedback resistant N-acetylglutamate synthase mutant, e.g., argA$^{fbr}$).

Thus, in some embodiments, the genetically engineered bacteria lack a functional ArgR repressor and therefore ArgR repressor-mediated transcriptional repression of each of the arginine biosynthesis operons is reduced or eliminated. In some embodiments, the engineered bacteria comprise a mutant arginine repressor comprising one or more nucleic acid mutations such that arginine repressor function is decreased or inactive. In some embodiments, the genetically engineered bacteria do not have an arginine repressor (e.g., the arginine repressor gene has been deleted), resulting in derepression of the regulon and enhancement of arginine and/or intermediate byproduct biosynthesis. In some embodiments, each copy of a functional argR gene normally present in a corresponding wild-type bacterium is independently deleted or rendered inactive by one or more nucleotide deletions, insertions, or substitutions. In some embodiments, each copy of the functional argR gene normally present in a corresponding wild-type bacterium is deleted.

In some embodiments, the arginine regulon is regulated by a single repressor protein. In particular species, strains, and/or subtypes of bacteria, it has been proposed that the arginine regulon may be regulated by two distinct putative repressors (Nicoloff et al., 2004). Thus, in certain embodiments, two distinct ArgR proteins each comprising a different amino acid sequence are mutated or deleted in the genetically engineered bacteria.

In some embodiments, the genetically modified bacteria comprising a mutant or deleted arginine repressor additionally comprise an arginine feedback resistant N-acetylglutamate synthase mutant, e.g., argA$^{fbr}$. In some embodiments, the genetically engineered bacteria comprise a feedback resistant form of ArgA, lack any functional arginine repressor, and are capable of producing arginine. In certain embodiments, the genetically engineered bacteria further lack functional ArgG and are capable of producing citrulline. In some embodiments, the argR gene is deleted in the genetically engineered bacteria. In some embodiments, the argR gene is mutated to inactivate ArgR function. In some embodiments, the argG gene is deleted in the genetically engineered bacteria. In some embodiments, the argG gene is mutated to inactivate ArgR function. In some embodiments, the genetically engineered bacteria comprise argA$^{fbr}$ and deleted ArgR. In some embodiments, the genetically engineered bacteria comprise argA$^{fbr}$, deleted ArgR, and deleted argG. In some embodiments, the deleted ArgR and/or the deleted argG is deleted from the bacterial genome and the argA$^{fbr}$ is present in a plasmid. In some embodiments, the deleted ArgR and/or the deleted argG is deleted from the bacterial genome and the argA$^{fbr}$ is chromosomally integrated. In one specific embodiment, the genetically modified bacteria comprise chromosomally integrated argA$^{fbr}$, deleted genomic ArgR, and deleted genomic argG. In another specific embodiment, the genetically modified bacteria comprise argA$^{fbr}$ present on a plasmid, deleted genomic ArgR, and deleted genomic argG. In any of the embodiments in which argG is deleted, citrulline rather than arginine is produced In some embodiments, under conditions where a feedback resistant form of ArgA is expressed, the genetically engineered bacteria of the invention produce at least about 1.5-fold, at least about 2-fold, at least about 10-fold, at least about 15-fold, at least about 20-fold, at least about 30-fold, at least about 50-fold, at least about 100-fold, at least about 200-fold, at least about 300-fold, at least about 400-fold, at least about 500-fold, at least about 600-fold, at least about 700-fold, at least about 800-fold, at least about 900-fold, at least about 1,000-fold, or at least about 1,500-fold more arginine, citrulline, other intermediate byproduct, and/or transcript of the gene(s) in the operon as compared to unmodified bacteria of the same subtype under the same conditions.

In some embodiments, quantitative PCR (qPCR) is used to amplify, detect, and/or quantify mRNA expression levels of the arginine biosynthesis genes. Primers specific for arginine biosynthesis genes, e.g., argA, argB, argC, argD, argE, argF, argG, argH, argI, argJ, carA, and care, may be designed and used to detect mRNA in a sample according to methods known in the art (Fraga et al., 2008). In some embodiments, a fluorophore is added to a sample reaction mixture that may contain arg mRNA, and a thermal cycler is used to illuminate the sample reaction mixture with a specific wavelength of light and detect the subsequent emission by the fluorophore. The reaction mixture is heated and cooled to predetermined temperatures for predetermined time periods. In certain embodiments, the heating and cooling is repeated for a predetermined number of cycles. In some embodiments, the reaction mixture is heated and cooled to 90-100° C., 60-70° C., and 30-50° C. for a predetermined number of cycles. In a certain embodiment, the reaction mixture is heated and cooled to 93-97° C., 55-65° C., and 35-45° C. for a predetermined number of cycles. In some embodiments, the accumulating amplicon is quantified after each cycle of the qPCR. The number of cycles at which fluorescence exceeds the threshold is the threshold cycle ($C_T$). At least one $C_T$ result for each sample is generated, and the $C_T$ result(s) may be used to determine mRNA expression levels of the arginine biosynthesis genes.

In any of these embodiments in which the ArgR is mutated, the mutant ArgR and/or a feedback resistant ArgA may be integrated into the bacterial chromosome at one or more integration sites or may be present on one or more plasmids.

Feedback Resistant N-Acetylglutamate Synthetase

In some embodiments, the genetically engineered bacteria comprise an arginine feedback resistant N-acetylglutamate synthase mutant, e.g., argA$^{fbr}$. In some embodiments, the genetically engineered bacteria comprise a mutant arginine regulon comprising an arginine feedback resistant ArgA, and when the arginine feedback resistant ArgA is expressed, are capable of producing more arginine and/or an intermediate byproduct than unmodified bacteria of the same subtype under the same conditions. The arginine feedback resistant N-acetylglutamate synthetase protein (argA$^{fbr}$) is significantly less sensitive to L-arginine than the enzyme from the feedback sensitive parent strain (see, e.g., Eckhardt et al., 1975; Rajagopal et al., 1998). The feedback resistant argA gene can be present on a plasmid or chromosome. In some embodiments, expression from the plasmid may be useful for increasing argA$^{fbr}$ expression. In some embodiments, expression from the chromosome may be useful for increasing stability of argA$^{fbr}$ expression.

In some embodiments, any of the described mutant sequences involved in the arginine biosynthetic pathway (e.g., ArgR, argA$^{fbr}$, Arg Box sequence) are integrated into the bacterial chromosome at one or more integration sites. For example, one or more copies of the sequence encoding the arginine feedback resistant N-acetylglutamate synthase may be integrated into the bacterial chromosome. Having multiple copies of the arginine feedback resistant N-acetylglutamate synthase integrated into the chromosome allows for greater production of the N-acetylglutamate synthase and also permits fine-tuning of the level of expression. Alternatively, different circuits described herein, such as any of the transporter or kill-switch circuits, in addition to the arginine feedback resistant N-acetylglutamate synthase could be integrated into the bacterial chromosome at one or more different integration sites to perform multiple different functions. Multiple distinct feedback resistant N-acetylglutamate synthetase proteins are known in the art and may be combined in the genetically engineered bacteria. In some embodiments, the argA$^{fbr}$ gene is expressed under the control of a constitutive promoter. In some embodiments, the argA$^{fbr}$ gene is expressed under the control of a promoter that is induced by exogenous environmental conditions. In some embodiments, the exogenous environmental conditions are specific to the gut of a mammal. In some embodiments, exogenous environmental conditions are molecules or metabolites that are specific to the mammalian gut in a healthy or disease state, e.g., propionate. In some embodiments, the exogenous environmental conditions are low-oxygen or anaerobic conditions, such as the environment of the mammalian gut.

Bacteria have evolved transcription factors that are capable of sensing oxygen levels. Different signaling pathways may be triggered by different oxygen levels and occur with different kinetics. An oxygen level-dependent promoter is a nucleic acid sequence to which one or more oxygen level-sensing transcription factors is capable of binding, wherein the binding and/or activation of the corresponding transcription factor activates downstream gene expression. In one embodiment, the argA$^{fbr}$ gene is under control of an oxygen level-dependent promoter. In a more specific aspect, the argA$^{fbr}$ gene is under control of an oxygen level-dependent promoter that is activated under low-oxygen or anaerobic environments, such as the environment of the mammalian gut.

In certain embodiments, the genetically engineered bacteria comprise argA$^{fbr}$ expressed under the control of the fumarate and nitrate reductase regulator (FNR) promoter. In E. coli, FNR is a major transcriptional activator that controls the switch from aerobic to anaerobic metabolism (Unden et al., 1997). In the anaerobic state, FNR dimerizes into an active DNA binding protein that activates hundreds of genes responsible for adapting to anaerobic growth. In the aerobic state, FNR is prevented from dimerizing by oxygen and is inactive. In alternate embodiments, the genetically engineered bacteria comprise argA$^{fbr}$ expressed under the control of an alternate oxygen level-dependent promoter, e.g., an anaerobic regulation of arginine deiminiase and nitrate reduction ANR promoter (Ray et al., 1997), a dissimilatory nitrate respiration regulator DNR promoter (Trunk et al., 2010). In these embodiments, the arginine biosynthesis pathway is particularly activated in a low-oxygen or anaerobic environment, such as in the gut.

In *P. aeruginosa*, the anaerobic regulation of arginine deiminiase and nitrate reduction (ANR) transcriptional regulator is "required for the expression of physiological functions which are inducible under oxygen-limiting or anaerobic conditions" (Winteler et al., 1996; Sawers 1991). *P. aeruginosa* ANR is homologous with *E. coli* FNR, and "the consensus FNR site (TTGAT----ATCAA) (SEQ ID NO: 121) was recognized efficiently by ANR and FNR" (Winteler et al., 1996). Like FNR, in the anaerobic state, ANR activates numerous genes responsible for adapting to anaerobic growth. In the aerobic state, ANR is inactive. *Pseudomonas fluorescens, Pseudomonas putida, Pseudomonas syringae*, and *Pseudomonas mendocina* all have functional analogs of ANR (Zimmermann et al., 1991). Promoters that are regulated by ANR are known in the art, e.g., the promoter of the arcDABC operon (see, e.g., Hasegawa et al., 1998).

The FNR family also includes the dissimilatory nitrate respiration regulator (DNR) (Arai et al., 1995), a transcriptional regulator that is required in conjunction with ANR for "anaerobic nitrate respiration of *Pseudomonas aeruginosa*" (Hasegawa et al., 1998). For certain genes, the FNR-binding motifs "are probably recognized only by DNR" (Hasegawa et al., 1998). Any suitable transcriptional regulator that is controlled by exogenous environmental conditions and corresponding regulatory region may be used. Non-limiting examples include ArcA/B, ResD/E, NreA/B/C, and AirSR, and others are known in the art.

FNR promoter sequences are known in the art, and any suitable FNR promoter sequence(s) may be used in the genetically engineered bacteria of the invention. Any suitable FNR promoter(s) may be combined with any suitable argA$^{fbr}$ (e.g., the exemplary argA$^{fbr}$ sequence shown in Table 7). Non-limiting FNR promoter sequences are provided in Table 6. Table 6 depicts the nucleic acid sequences of exemplary regulatory region sequences comprising a FNR-responsive promoter sequence. Underlined sequences are predicted ribosome binding sites, and bolded sequences are restriction sites used for cloning. In some embodiments, the genetically engineered bacteria of the invention comprise one or more of: SEQ ID NO: 18, SEQ ID NO: 19, nirB1 promoter (SEQ ID NO: 20), nirB2 promoter (SEQ ID NO: 21), nirB3 promoter (SEQ ID NO: 22), ydfZ promoter (SEQ ID NO: 23), nirB promoter fused to a strong ribosome binding site (SEQ ID NO: 24), ydfZ promoter fused to a strong ribosome binding site (SEQ ID NO: 25), fnrS, an anaerobically induced small RNA gene (fnrS1 promoter SEQ ID NO: 26 or fnrS2 promoter SEQ ID NO: 27), nirB promoter fused to a crp binding site (SEQ ID NO: 28), and fnrS fused to a crp binding site (SEQ ID NO: 29).

In some embodiments, genetically engineered bacteria comprise a nucleic acid sequence that is at least about 80%, at least about 85%, at least about 90%, at least about 95%, or at least about 99% homologous to the DNA sequence of SEQ ID NO: 18, 19, 20, 21, 22, 23, 24, 25, 26, 27, 28, or 29, or a functional fragment thereof.

TABLE 6

| FNR-responsive regulatory region | 12345678901234567890123456789012345678901234567890 |
|---|---|
| SEQ ID NO: 18 | ATCCCCATCACTCTTGATGGAGATCAATTCCCCAAGCTGCTAGAGCGTTA<br>CCTTGCCCTTAAACATTAGCAATGTCGATTTATCAGAGGGCCGACAGGCT<br>CCCACAGGAGAAAACCG |
| SEQ ID NO: 19 | CTCTTGATCGTTATCAATTCCCACGCTGTTTCAGAGCGTTACCTTGCCCT<br>TAAACATTAGCAATGTCGATTTATCAGAGGGCCGACAGGCTCCCACAGGA<br>GAAAACCG |
| nirB1<br>SEQ ID NO: 20 | GTCAGCATAACACCCTGACCTCTCATTAATTGTTCATGCCGGGCGGCACT<br>ATCGTCGTCCGGCCTTTTCCTCTCTTACTCTGCTACGTACATCTATTTCT<br>ATAAATCCGTTCAATTTGTCTGTTTTTTGCACAAACATGAAATATCAGAC<br>AATTCCGTGACTTAAGAAAATTTATACAAATCAGCAATATACCCCTTAAG<br>GAGTATATAAAGGTGAATTTGATTTACATCAATAAGCGGGGTTGCTGAAT<br>CGTTAAGGTAGGCGGTAATAGAAAAG<u>AAATCGAGGCAAAA</u> |
| nirB2<br>SEQ ID NO: 21 | CGGCCCGATCGTTGAACATAGCGGTCCGCAGGCGGCACTGCTTACAGCAA<br>ACGGTCTGTACGCTGTCGTCTTTGTGATGTGCTTCCTGTTAGGTTTCGTC<br>AGCCGTCACCGTCAGCATAACACCCTGACCTCTCATTAATTGCTCATGCC<br>GGACGGCACTATCGTCGTCCGGCCTTTTCCTCTCTTCCCCCGCTACGTGC<br>ATCTATTTCTATAAACCCGCTCATTTTGTCTATTTTTTGCACAAACATGA<br>AATATCAGACAATTCCGTGACTTAAGAAAATTTATACAAATCAGCAATAT<br>ACCCATTAAGGAGTATATAAAGGTGAATTTGATTTACATCAATAAGCGGG<br>GTTGCTGAATCGTTAAGGTAGGCGGTAATAGAAAAGAAATCGAGGCAAAA<br>atgtttgtttaactttaagaaggagatatacat |
| nirB3<br>SEQ ID NO: 22 | GTCAGCATAACACCCTGACCTCTCATTAATTGCTCATGCCGGACGGCACT<br>ATCGTCGTCCGGCCTTTTCCTCTCTTCCCCCGCTACGTGCATCTATTTCT<br>ATAAACCCGCTCATTTTGTCTATTTTTTGCACAAACATGAAATATCAGAC<br>AATTCCGTGACTTAAGAAAATTTATACAAATCAGCAATATACCCATTAAG<br>GAGTATATAAAGGTGAATTTGATTTACATCAATAAGCGGGGTTGCTGAAT<br>CGTTAAGGTAGGCGGTAATAGAAAAGAAATCGAGGCAAAA |
| ydfZ<br>SEQ ID NO: 23 | ATTTCCTCTCATCCCATCCGGGGTGAGAGTCTTTTCCCCCGACTTATGGC<br>TCATGCATGCATCAAAAAAGATGTGAGCTTGATCAAAAACAAAAAATATT<br>TCACTCGACAGGAGTATTTATATTGCGCCCGTTACGTGGGCTTCGACTGT<br>AAATC<u>AGAAAGGAGAAAACACCT</u> |

TABLE 6-continued

| FNR-responsive regulatory region | 123456789012345678901234567890123456789012345678 90 |
|---|---|
| nirB + RBS SEQ ID NO: 24 | GTCAGCATAACACCCTGACCTCTCATTAATTGTTCATGCCGGGCGGCACT ATCGTCGTCCGGCCTTTTCCTCTCTTACTCTGCTACGTACATCTATTTCT ATAAATCCGTTCAATTTGTCTGTTTTTTGCACAAACATGAAATATCAGAC AATTCCGTGACTTAAGAAAATTTATACAAATCAGCAATATACCCCTTAAG GAGTATATAAAGGTGAATTTGATTTACATCAATAAGCGGGGTTGCTGAAT CGTTAAGGATCCCTCTAGAAATAATTTTGTTTAACTTTAAGAAGGAGATA TACAT |
| ydfZ + RBS SEQ ID NO: 25 | CATTTCCTCTCATCCCATCCGGGGTGAGAGTCTTTTCCCCCGACTTATGG CTCATGCATGCATCAAAAAAGATGTGAGCTTGATCAAAAACAAAAAATAT TTCACTCGACAGGAGTATTTATATTGCGCCCGGATCCCTCTAGAAATAAT TTTGTTTAACTTTAAGAAGGAGATATACAT |
| fnrS1 SEQ ID NO: 26 | AGTTGTTCTTATTGGTGGTGTTGCTTTATGGTTGCATCGTAGTAAATGGT TGTAACAAAAGCAATTTTTCCGGCTGTCTGTATACAAAAACGCCGTAAAG TTTGAGCGAAGTCAATAAACTCTCTACCCATTCAGGGCAATATCTCTCTT GGATCCCTCTAGAAATAATTTTGTTTAACTTTAAGAAGGAGATATACAT |
| fnrS2 SEQ ID NO: 27 | AGTTGTTCTTATTGGTGGTGTTGCTTTATGGTTGCATCGTAGTAAATGGT TGTAACAAAAGCAATTTTTCCGGCTGTCTGTATACAAAAACGCCGCAAAG TTTGAGCGAAGTCAATAAACTCTCTACCCATTCAGGGCAATATCTCTCTT GGATCCAAAGTGAACTCTAGAAATAATTTTGTTTAACTTTAAGAAGGAGA TATACAT |
| nirB + crp SEQ ID NO: 28 | TCGTCTTTGTGATGTGCTTCCTGTTAGGTTTCGTCAGCCGTCACCGTCAG CATAACACCCTGACCTCTCATTAATTGCTCATGCCGGACGGCACTATCGT CGTCCGGCCTTTTCCTCTCTTCCCCCGCTACGTGCATCTATTTCTATAAA CCCGCTCATTTTGTCTATTTTTTGCACAAACATGAAATATCAGACAATTC CGTGACTTAAGAAAATTTATACAAATCAGCAATATACCCATTAAGGAGTA TATAAAGGTGAATTTGATTTACATCAATAAGCGGGGTTGCTGAATCGTTA AGGTAGaaatgtgatctagttcacatttGCGGTAATAGAAAAGAAATCGA GGCAAAAatgtttgtttaactttaagaaggagatatacat |
| fnrS + crp SEQ ID NO: 29 | AGTTGTTCTTATTGGTGGTGTTGCTTTATGGTTGCATCGTAGTAAATGGT TGTAACAAAAGCAATTTTTCCGGCTGTCTGTATACAAAAACGCCGCAAAG TTTGAGCGAAGTCAATAAACTCTCTACCCATTCAGGGCAATATCTCTCaa atgtgatctagttcacattttttgtttaactttaagaaggagatatacat |

In other embodiments, argA$^{fbr}$ is expressed under the control of an oxygen level-dependent promoter fused to a binding site for a transcriptional activator, e.g., CRP. CRP (cyclic AMP receptor protein or catabolite activator protein or CAP) plays a major regulatory role in bacteria by repressing genes responsible for the uptake, metabolism and assimilation of less favorable carbon sources when rapidly metabolizable carbohydrates, such as glucose, are present (Wu et al., 2015). This preference for glucose has been termed glucose repression, as well as carbon catabolite repression (Deutscher, 2008; Görke and Stülke, 2008). In some embodiments, argA$^{fbr}$ expression is controlled by an oxygen level-dependent promoter fused to a CRP binding site. In some embodiments, argA$^{fbr}$ expression is controlled by a FNR promoter fused to a CRP binding site. In these embodiments, cyclic AMP binds to CRP when no glucose is present in the environment. This binding causes a conformational change in CRP, and allows CRP to bind tightly to its binding site. CRP binding then activates transcription of the argA$^{fbr}$ gene by recruiting RNA polymerase to the FNR promoter via direct protein-protein interactions. In the presence of glucose, cyclic AMP does not bind to CRP and argA$^{fbr}$ gene transcription is repressed. In some embodiments, an oxygen level-dependent promoter (e.g., a FNR promoter) fused to a binding site for a transcriptional activator is used to ensure that argA$^{fbr}$ is not expressed under anaerobic conditions when sufficient amounts of glucose are present, e.g., by adding glucose to growth media in vitro.

In some embodiments, argA$^{fbr}$ is expressed under the control of an inducible promoter that is responsive to specific molecules or metabolites in the environment, e.g., the mammalian gut. For example, the short-chain fatty acid propionate is a major microbial fermentation metabolite localized to the gut (Hosseini et al., 2011). In one embodiment, argA$^{fbr}$ gene expression is under the control of a propionate-inducible promoter. In a more specific embodiment, argA$^{fbr}$ gene expression is under the control of a propionate-inducible promoter that is activated by the presence of propionate in the mammalian gut. Any molecule or metabolite found in the mammalian gut, in a healthy and/or disease state, may be used to induce argA$^{fbr}$ expression. Non-limiting examples include propionate, bilirubin, aspartate aminotransferase, alanine aminotransferase, blood coagulation factors II, VII, IX, and X, alkaline phosphatase, gamma glutamyl transferase, hepatitis antigens and antibodies, alpha fetoprotein, anti-mitochondrial, smooth muscle, and anti-nuclear antibodies, iron, transferrin, ferritin, copper, ceruloplasmin, ammonia, and manganese. In alternate embodiments, argA$^{fbr}$ gene expression is under the control of a P araBAD promoter, which is activated in the presence of the sugar arabinose (see, e.g., FIG. 13).

Subjects with hepatic encephalopathy (HE) and other liver disease or disorders have chronic liver damage that results in high ammonia levels in their blood and intestines. In addition to ammonia, these patients also have elevated levels of bilirubin, aspartate aminotransferase, alanine aminotransferase, blood coagulation factors II, VII, IX, and X, alkaline phosphatase, gamma glutamyl transferase, hepatitis antigens and antibodies, alpha fetoprotein, anti-mitochondrial, smooth muscle, and anti-nuclear antibodies, iron, transferrin, ferritin, copper, ceruloplasmin, ammonia, and manganese in their blood and intestines. Promoters that respond to one of these HE-related molecules or their metabolites may be used in the genetically engineered bacteria to induce expression of argA$^{fbr}$ in the gut. These promoters would not be expected to be induced in non-HE patients.

In some embodiments, the argA$^{fbr}$ gene is expressed under the control of a promoter that is induced by exposure to tetracycline. In some embodiments, the argA$^{fbr}$ gene is expressed under the control of a promoter that is induced by exposure to inflammation or an imflammatory response (e.g., RNS or ROS promoters). In some embodiments, the argA$^{fbr}$ gene is expressed under the control of a promoter that is induced by exposure to a metabolite such as arabinose (e.g., AraBAD promoter).

In some embodiments, gene expression is further optimized by methods known in the art, e.g., by optimizing ribosomal binding sites, manipulating transcriptional regulators, and/or increasing mRNA stability. The nucleic acid sequence of an exemplary argA$^{fbr}$ sequence is shown in Table 7. The polypeptide sequence of an exemplary argA$^{fbr}$ sequence is shown in Table 8.

TABLE 7

Nucleotide sequence of exemplary argA$^{fbr}$ sequence
(SEQ ID NO: 30)

ATGGTAAAGGAACGTAAAACCGAGTTGGTCGAGGGATTCCGCCATTCGGT
TCCCTGTATCAATACCCACCGGGGAAAAACGTTTGTCATCATGCTCGGCG
GTGAAGCCATTGAGCATGAGAATTTCTCCAGTATCGTTAATGATATCGGG
TTGTTGCACAGCCTCGGCATCCGTCTGGTGGTGGTCTATGGCGCACGTCC
GCAGATCGACGCAAATCTGGCTGCGCATCACCACGAACCGCTGTATCACA
AGAATATACGTGTGACCGACGCCAAAACACTGGAACTGGTGAAGCAGGCT
GCGGGAACATTGCAACTGGATATTACTGCTCGCCTGTCGATGAGTCTCAA
TAACACGCCGCTGCAGGGCGCGCATATCAACGTCGTCAGTGGCAATTTTA
TTATTGCCCAGCCGCTGGGCGTCGATGACGGCGTGGATTACTGCCATAGC
GGGCGTATCCGGCGGATTGATGAAGACGCGATCCATCGTCAACTGGACAG
CGGTGCAATAGTGCTAATGGGGCCGGTCGCTGTTTCAGTCACTGGCGAGA
GCTTTAACCTGACCTCGGAAGAGATTGCCACTCAACTGGCCATCAAACTG
AAAGCTGAAAAGATGATTGGTTTTTGCTCTTCCCAGGGCGTCACTAATGA
CGACGGTGATATTGTCTCCGAACTTTTCCCTAACGAAGCGCAAGCGCGGG
TAGAAGCCCAGGAAGAGAAAGGCGATTACAACTCCGGTACGGTGCGCTTT
TTGCGTGGCGCAGTGAAAGCCTGCCGCAGCGGCGTGCGTCGCTGTCATTT
AATCAGTTATCAGGAAGATGGCCGCTGTTGCAAGAGTTGTTCTCACGCG
ACGGTATCGGTACGCAGATTGTGATGGAAAGCGCCGAGCAGATTCGTCGC
GCAACAATCAACGATATTGGCGGTATTCTGGAGTTGATTCGCCCACTGGA
GCAGCAAGGTATTCTGGTACGCCGTTCTCGCGAGCAGCTGGAGATGGAAA
TCGACAAATTCACCATTATTCAGCGCGATAACACGACTATTGCCTGCGCC
GCGCTCTATCCGTTCCCGGAAGAGAAGATTGGGGAAATGGCCTGTGTGGC
AGTTCACCCGGATTACCGCAGTTCATCAAGGGGTGAAGTTCTGCTGGAAC
GCATTGCCGCTCAGGCTAAGCAGAGCGGCTTAAGCAAATTGTTTGTGCTG
ACCACGCGCAGTATTCACTGGTTCCAGGAACGTGGATTTACCCCAGTGGA
TATTGATTTACTGCCCGAGAGCAAAAAGCAGTTGTACAACTACCAGCGTA
AATCCAAAGTGTTGATGGCGGATTTAGGGTAA

TABLE 8

Polypeptide sequence of exemplary argA$^{fbr}$ sequence
(SEQ ID NO: 31)

MVKERKTELVEGFRHSVPCINTHRGKTFVIMLGGEAIEHENFSSIVNDIG
LLHSLGIRLVVVYGARPQIDANLAAHHHEPLYHKNIRVTDAKTLELVKQA
AGTLQLDITARLSMSLNNTPLQGAHINVVSGNFIIAQPLGVDDGVDYCHS
GRIRRIDEDAIHRQLDSGAIVLMGPVAVSVTGESFNLTSEEIATQLAIKL
KAEKMIGFCSSQGVTNDDGDIVSELFPNEAQARVEAQEEKGDYNSGTVRF

TABLE 8-continued

Polypeptide sequence of exemplary argA$^{fbr}$ sequence
(SEQ ID NO: 31)

LRGAVKACRSGVRRCHLISYQEDGALLQELFSRDGIGTQIVMESAEQIRR
ATINDIGGILELIRPLEQQGILVRRSREQLEMEIDKFTIIQRDNTTIACA
ALYPFPEEKIGEMACVAVHPDYRSSSRGEVLLERIAAQAKQSGLSKLFVL
TTRSIHWFQERGFTPVDIDLLPESKKQLYNYQRKSKVLMADLG

Bold underline: mutated amino acid resulting feedback resistance. (mutation is Y19C)

In some embodiments, the genetically engineered bacteria comprise the nucleic acid sequence of SEQ ID NO: 30 or a functional fragment thereof. In some embodiments, the genetically engineered bacteria comprise a nucleic acid sequence that, but for the redundancy of the genetic code, encodes the same polypeptide as SEQ ID NO: 30 or a functional fragment thereof. In some embodiments, genetically engineered bacteria comprise a nucleic acid sequence that is at least about 80%, at least about 85%, at least about 90%, at least about 95%, or at least about 99% homologous to the DNA sequence of SEQ ID NO: 30 or a functional fragment thereof, or a nucleic acid sequence that, but for the redundancy of the genetic code, encodes the same polypeptide as SEQ ID NO: 30 or a functional fragment thereof.

In some embodiments, the genetically engineered bacteria encode a polypeptide sequence of SEQ ID NO: 31 or a functional fragment thereof. In some embodiments, the genetically engineered bacteria encode a polypeptide sequence encodes a polypeptide, which contains one or more conservative amino acid substutions relative to SEQ ID NO: 31 or a functional fragment thereof. In some embodiments, genetically engineered bacteria encode a polypeptide sequence that is at least about 80%, at least about 85%, at least about 90%, at least about 95%, or at least about 99% homologous to the DNA sequence of SEQ ID NO: 31 or a functional fragment thereof.

In some embodiments, arginine feedback inhibition of N-acetylglutamate synthetase is reduced by at least about 50%, at least about 60%, at least about 70%, at least about 80%, at least about 90%, or at least about 95% in the genetically engineered bacteria when the arginine feedback resistant N-acetylglutamate synthetase is active, as compared to a wild-type N-acetylglutamate synthetase from bacteria of the same subtype under the same conditions.

In some embodiments, the genetically engineered bacteria comprise a stably maintained plasmid or chromosome carrying the argA$^{fbr}$ gene, such that argA$^{fbr}$ can be expressed in the host cell, and the host cell is capable of survival and/or growth in vitro, e.g., in medium, and/or in vivo, e.g., in the gut. In some embodiments, a bacterium may comprise multiple copies of the feedback resistant argA gene. In some embodiments, the feedback resistant argA gene is expressed on a low-copy plasmid. In some embodiments, the low-copy plasmid may be useful for increasing stability of expression. In some embodiments, the low-copy plasmid may be useful for decreasing leaky expression under non-inducing conditions. In some embodiments, the feedback resistant argA gene is expressed on a high-copy plasmid. In some embodiments, the high-copy plasmid may be useful for increasing argA$^{fbr}$ expression. In some embodiments, the feedback resistant argA gene is expressed on a chromosome.

Figure 18:
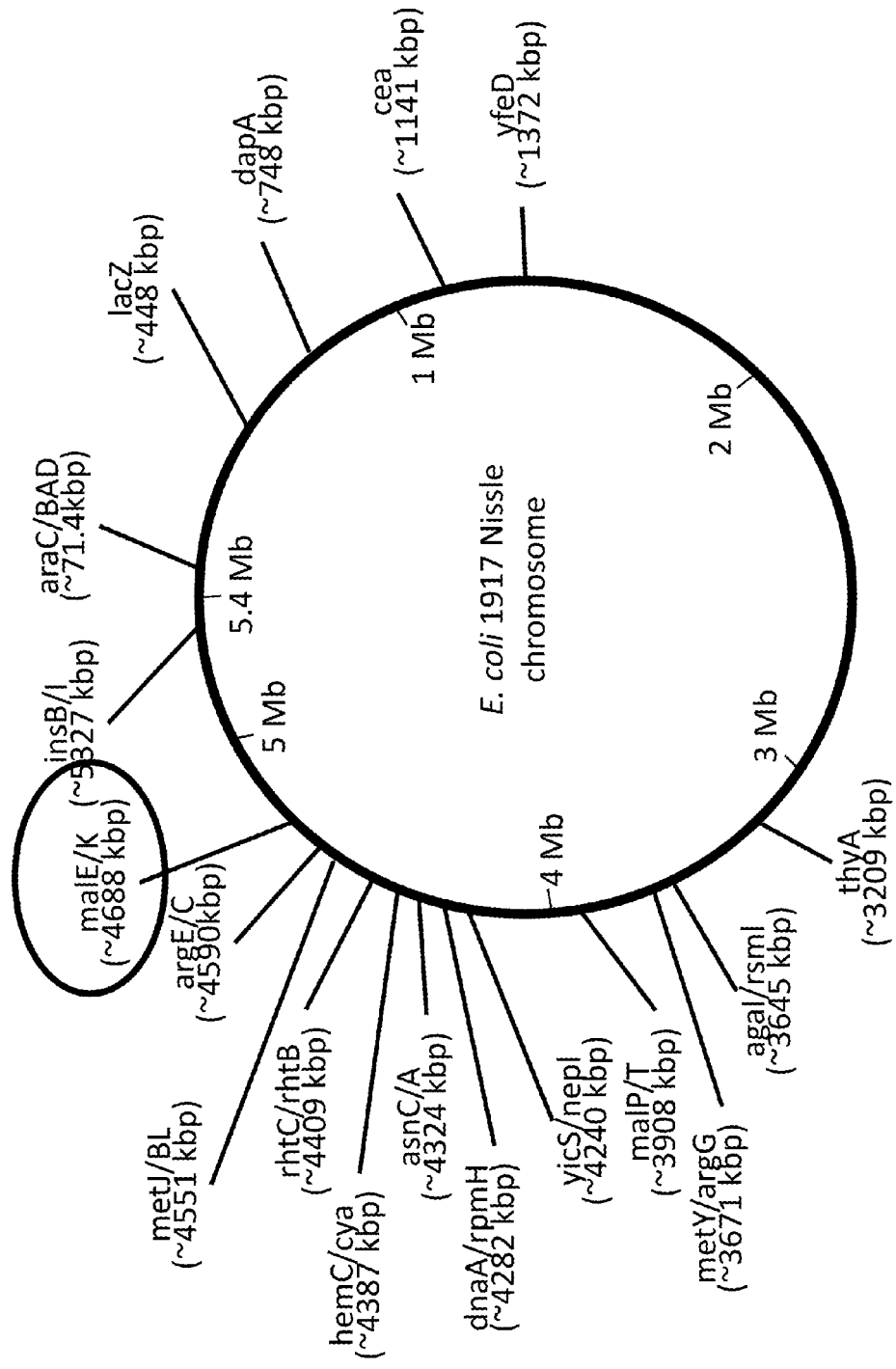
FIG. 18 depicts a map of exemplary integration sites within the *E. coli* 1917 Nissle chromosome. These sites indicate regions where circuit components may be inserted into the chromosome without interfering with essential gene expression. Backslashes (/) are used to show that the insertion will occur between divergently or convergently expressed genes. Insertions within biosynthetic genes, such as thyA, can be useful for creating nutrient auxotrophies. In some embodiments, an individual circuit component is inserted into more than one of the indicated sites. The malE/K site is circled. In some embodiments of the disclosure, FNR-ArgAfbr is inserted at the malEK locus.
Figure 19:
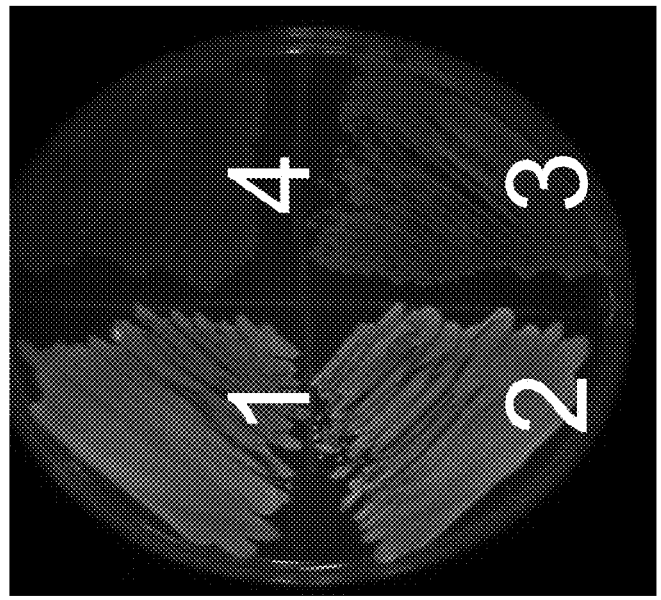
FIG. 19 depicts three bacterial strains which constitutively express red fluorescent protein (RFP). In strains 1-3, the rfp gene has been inserted into different sites within the bacterial chromosome, and results in varying degrees of brightness under fluorescent light. Unmodified *E. coli* Nissle (strain 4) is non-fluorescent.

In some embodiments, the bacteria are genetically engineered to include multiple mechanisms of action (MOAs), e.g., circuits producing multiple copies of the same product or circuits performing multiple different functions. Examples of insertion sites include, but are not limited to, malE/K, insB/I, araC/BAD, lacZ, dapA, cea, and other shown in FIG. 18. For example, the genetically engineered bacteria may include four copies of argA$^{fbr}$ inserted at four different insertion sites, e.g., malE/K, insB/I, araC/BAD, and lacZ. Alternatively, the genetically engineered bacteria may include three copies of argA$^{fbr}$ inserted at three different insertion sites, e.g., malE/K, insB/I, and lacZ, and three mutant arginine regulons, e.g., two producing citrulline and one producing arginine, inserted at three different insertion sites dapA, cea, and araC/BAD.

In some embodiments, the plasmid or chromosome also comprises wild-type ArgR binding sites, e.g., ARG boxes. In some instances, the presence and/or build-up of functional ArgR may result in off-target binding at sites other than the ARG boxes, which may cause off-target changes in gene expression. A plasmid or chromosome that further comprises functional ARG boxes may be used to reduce or eliminate off-target ArgR binding, i.e., by acting as an ArgR sink. In some embodiments, the plasmid or chromosome does not comprise functional ArgR binding sites, e.g., the plasmid or chromosome comprises modified ARG boxes or does not comprise ARG boxes.

In some embodiments, the feedback resistant argA gene is present on a plasmid and operably linked to a promoter that is induced under low-oxygen or anaerobic conditions. In some embodiments, the feedback resistant argA gene is present in the chromosome and operably linked to a promoter that is induced under low-oxygen or anaerobic conditions. In some embodiments, the feedback resistant argA gene is present on a plasmid and operably linked to a promoter that is induced by molecules or metabolites that are specific to the mammalian gut. In some embodiments, the feedback resistant argA gene is present on a chromosome and operably linked to a promoter that is induced by molecules or metabolites that are specific to the mammalian gut. In some embodiments, the feedback resistant argA gene is present on a chromosome and operably linked to a promoter that is induced by exposure to tetracycline. In some embodiments, the feedback resistant argA gene is present on a plasmid and operably linked to a promoter that is induced by exposure to tetracycline.

In some embodiments, the genetically engineered bacteria comprise a variant or mutated oxygen level-dependent transcriptional regulator, e.g., FNR, ANR, or DNR, in addition to the corresponding oxygen level-dependent promoter. The variant or mutated oxygen level-dependent transcriptional regulator increases the transcription of operably linked genes in a low-oxygen or anaerobic environment. In some embodiments, the corresponding wild-type transcriptional regulator retains wild-type activity. In alternate embodiments, the corresponding wild-type transcriptional regulator is deleted or mutated to reduce or eliminate wild-type activity. In certain embodiments, the mutant oxygen level-dependent transcriptional regulator is a FNR protein comprising amino acid substitutions that enhance dimerization and FNR activity (see, e.g., Moore et al., 2006).

In some embodiments, the genetically engineered bacteria comprise an oxygen level-dependent transcriptional regulator from a different bacterial species that reduces and/or consumes ammonia in low-oxygen or anaerobic environments. In certain embodiments, the mutant oxygen level-dependent transcriptional regulator is a FNR protein from N. gonorrhoeae (see, e.g., Isabella et al., 2011). In some embodiments, the corresponding wild-type transcriptional regulator is left intact and retains wild-type activity. In alternate embodiments, the corresponding wild-type transcriptional regulator is deleted or mutated to reduce or eliminate wild-type activity.

In some embodiments, the genetically engineered bacteria comprise argA$^{fbr}$ expressed under the control of an oxygen level-dependent promoter, e.g., a FNR promoter, as well as wild-type argA expressed under the control of a mutant regulatory region comprising one or more ARG box mutations as discussed above. In certain embodiments, the genetically engineered bacteria comprise argA$^{fbr}$ expressed under the control of an oxygen level-dependent promoter, e.g., a FNR promoter and do not comprise wild-type argA. In still other embodiments, the mutant arginine regulon comprises argA$^{fbr}$ expressed under the control of an oxygen level-dependent promoter, e.g., a FNR promoter, and further comprises wild-type argA without any ARG box mutations.

In some embodiments, the genetically engineered bacteria express argA$^{fbr}$ from a plasmid and/or chromosome. In some embodiments, the argA$^{fbr}$ gene is expressed under the control of a constitutive promoter. In some embodiments, the argA$^{fbr}$ gene is expressed under the control of an inducible promoter. In one embodiment, argA$^{fbr}$ is expressed under the control of an oxygen level-dependent promoter that is activated under low-oxygen or anaerobic environments, e.g., a FNR promoter. The nucleic acid sequence of an exemplary FNR promoter-driven argA$^{fbr}$ sequence is shown in Table 9. The FNR promoter sequence is bolded and the argA$^{fbr}$ sequence is boxed. The nucleic acid sequence of a FNR promoter-driven argA$^{fbr}$ plasmid is shown in Table 10, with the FNR promoter sequence bolded and argA$^{fbr}$ sequence boxed. Table 11 shows the nucleic acid sequence of an exemplary pSC101 plasmid. Any suitable FNR promoter(s) may be combined with any suitable feedback-resistant ArgA. Non-limiting FNR promoter sequences are provided in Table 6. In some embodiments, the genetically engineered bacteria of the invention comprise one or more of: SEQ ID NO: 16, SEQ ID NO: 17, nirB1 promoter (SEQ ID NO: 18), nirB2 promoter (SEQ ID NO: 19), nirB3 promoter (SEQ ID NO: 20), ydfZ promoter (SEQ ID NO: 21), nirB promoter fused to a strong ribosome binding site (SEQ ID NO: 22), ydfZ promoter fused to a strong ribosome binding site (SEQ ID NO: 23), fnrS, an anaerobically induced small RNA gene (fnrS1 promoter SEQ ID NO: 24 or fnrS2 promoter SEQ ID NO: 25), nirB promoter fused to a crp binding site (SEQ ID NO: 26), and fnrS fused to a crp binding site (SEQ ID NO: 27). Table 12 depicts the nucleic acid sequence of an exemplary fnrS promoter-driven argA$^{fbr}$ sequence. The FNR promoter sequence is bolded, the ribosome binding site is highlighted, and the argA$^{fbr}$ sequence is boxed.

In some embodiments, the genetically engineered bacteria comprise the nucleic acid sequence of SEQ ID NO: 32 or a functional fragment thereof. In some embodiments, the genetically engineered bacteria comprise a nucleic acid sequence that, but for the redundancy of the genetic code, encodes the same polypeptide as SEQ ID NO: 32. In some embodiments, genetically engineered bacteria comprise a nucleic acid sequence that is at least about 80%, at least about 85%, at least about 90%, at least about 95%, or at least about 99% homologous to the DNA sequence of SEQ ID NO: 32, or a nucleic acid sequence that, but for the redundancy of the genetic code, encodes the same polypeptide as SEQ ID NO: 32.

In some embodiments, the genetically engineered bacteria comprise the nucleic acid sequence of SEQ ID NO: 33 or a functional fragment thereof. In some embodiments, the genetically engineered bacteria comprise a nucleic acid sequence that, but for the redundancy of the genetic code, encodes the same polypeptide as SEQ ID NO: 33. In some embodiments, genetically engineered bacteria comprise a nucleic acid sequence that is at least about 80%, at least about 85%, at least about 90%, at least about 95%, or at least about 99% homologous to the DNA sequence of SEQ ID NO: 33, or a nucleic acid sequence that, but for the redundancy of the genetic code, encodes the same polypeptide as SEQ ID NO: 33.

In some embodiments, the genetically engineered bacteria comprise the nucleic acid sequence of SEQ ID NO: 35 or a functional fragment thereof. In some embodiments, the genetically engineered bacteria comprise a nucleic acid sequence that, but for the redundancy of the genetic code, encodes the same polypeptide as SEQ ID NO: 35. In some embodiments, genetically engineered bacteria comprise a nucleic acid sequence that is at least about 80%, at least about 85%, at least about 90%, at least about 95%, or at least about 99% homologous to the DNA sequence of SEQ ID NO: 35, or a nucleic acid sequence that, but for the redundancy of the genetic code, encodes the same polypeptide as SEQ ID NO: 35.

TABLE 9

Exemplary FNR promoter-driven argA$^{fbr}$ sequence (SEQ ID NO: 32)

AGTTGTTCTTATTGGTGGTGTTGCTTTATGGTTGCATCGTAGTAAATGGTTGTAACAA
AAGCAATTTTTCCGGCTGTCTGTATACAAAAACGCCGCAAAGTTTGAGCGAAGTCAAT
AAACTCTCTACCCATTCAGGGCAATATCTCTCTTggatccaaagtgaactctagaaat aattttgtttaactttaagaaggagatatacatATGGTAAAGGAACGTAAAACCGAG

TTGGTCGAGGGATTCCGCCATTCGGTTCCCTGTATCAATACCCACCGGGGAAAAACG

TTTGTCATCATGCTCGGCGGTGAAGCCATTGAGCATGAGAATTTCTCCAGTATCGTT

AATGATATCGGGTTGTTGCACAGCCTCGGCATCCGTCTGGTGGTGGTCTATGGCGCA

CGTCCGCAGATCGACGCAAATCTGGCTGCGCATCACCACGAACCGCTGTATCACAAG

AATATACGTGTGACCGACGCCAAAACACTGGAACTGGTGAAGCAGGCTGCGGGAACA

TTGCAACTGGATATTACTGCTCGCCTGTCGATGAGTCTCAATAACACGCCGCTGCAG

GGCGCGCATATCAACGTCGTCAGTGGCAATTTTATTATTGCCCAGCCGCTGGGCGTC

GATGACGGCGTGGATTACTGCCATAGCGGGCGTATCCGGCGGATTGATGAAGACGCG

ATCCATCGTCAACTGGACAGCGGTGCAATAGTGCTAATGGGGCCGGTCGCTGTTTCA

GTCACTGGCGAGAGCTTTAACCTGACCTCGGAAGAGATTGCCACTCAACTGGCCATC

AAACTGAAAGCTGAAAAGATGATTGGTTTTTGCTCTTCCCAGGGCGTCACTAATGAC

GACGGTGATATTGTCTCCGAACTTTTCCCTAACGAAGCGCAAGCGCGGGTAGAAGCC

CAGGAAGAGAAAGGCGATTACAACTCCGGTACGGTGCGCTTTTTGCGTGGCGCAGTG

AAAGCCTGCCGCAGCGGCGTGCGTCGCTGTCATTTAATCAGTTATCAGGAAGATGGC

GCGCTGTTGCAAGAGTTGTTCTCACGCGACGGTATCGGTACGCAGATTGTGATGGAA

AGCGCCGAGCAGATTCGTCGCGCAACAATCAACGATATTGGCGGTATTCTGGAGTTG

ATTCGCCCACTGGAGCAGCAAGGTATTCTGGTACGCCGTTCTCGCGAGCAGCTGGAG

ATGGAAATCGACAAATTCACCATTATTCAGCGCGATAACACGACTATTGCCTGCGCC

GCGCTCTATCCGTTCCCGGAAGAGAAGATTGGGGAAATGGCCTGTGTGGCAGTTCAC

CCGGATTACCGCAGTTCATCAAGGGGTGAAGTTCTGCTGGAACGCATTGCCGCTCAG

TABLE 9-continued

Exemplary FNR promoter-driven argA^fbr sequence
(SEQ ID NO: 32)

GCTAAGCAGAGCGGCTTAAGCAAATTGTTTGTGCTGACCACGCGCAGTATTCACTGG

TTCCAGGAACGTGGATTTACCCCAGTGGATATTGATTTACTGCCCGAGAGCAAAAG

CAGTTGTACAACTACCAGCGTAAATCCAAAGTGTTGATGGCGGATTTAGGGTAA

TABLE 10

Exemplary sequence of FNR promoter-driven argA^fbr plasmid
(SEQ ID NO: 33)

GTAAAACGACGGCCAGTGAATTCGAGCTCGGTACC**ATCCCCATCACTCTTGATGGAGATCAA
TTCCCCAAGCTGCTAGAGCGTTACCTTGCCCTTAAACATTAGCAATGTCGATTTATCAGAGG
GCCGACAGGCTCCCACAGGAGAAAACCG**ATGGTAAAGGAACGTAAAACCGAGTTGGTCGAGG

GATTCCGCCATTCGGTTCCCTGTATCAATACCCACCGGGGAAAAACGTTTGTCATCATGCTC

GGCGGTGAAGCCATTGAGCATGAGAATTTCTCCAGTATCGTTAATGATATCGGGTTGTTGCA

CAGCCTCGGCATCCGTCTGGTGGTGGTCTATGGCGCACGTCCGCAGATCGACGCAAATCTGG

CTGCGCATCACCACGAACCGCTGTATCACAAGAATATACGTGTGACCGACGCCAAAACACTG

GAACTGGTGAAGCAGGCTGCGGGAACATTGCAACTGGATATTACTGCTCGCCTGTCGATGAG

TCTCAATAACACGCCGCTGCAGGGCGCGCATATCAACGTCGTCAGTGGCAATTTTATTATTG

CCCAGCCGCTGGGCGTCGATGACGGCGTGGATTACTGCCATAGCGGGCGTATCCGGCGGATT

GATGAAGACGCGATCCATCGTCAACTGGACAGCGGTGCAATAGTGCTAATGGGGCCGGTCGC

TGTTTCAGTCACTGGCGAGAGCTTTAACCTGACCTCGGAAGAGATTGCCACTCAACTGGCCA

TCAAACTGAAAGCTGAAAAGATGATTGGTTTTTGCTCTTCCCAGGGCGTCACTAATGACGAC

GGTGATATTGTCTCCGAACTTTTCCCTAACGAAGCGCAAGCGCGGGTAGAAGCCCAGGAAGA

GAAAGGCGATTACAACTCCGGTACGGTGCGCTTTTTGCGTGGCGCAGTGAAAGCCTGCCGCA

GCGGCGTGCGTCGCTGTCATTTAATCAGTTATCAGGAAGATGGCGCGCTGTTGCAAGAGTTG

TTCTCACGCGACGGTATCGGTACGCAGATTGTGATGGAAAGCGCCGAGCAGATTCGTCGCGC

AACAATCAACGATATTGGCGGTATTCTGGAGTTGATTCGCCCACTGGAGCAGCAAGGTATTC

TGGTACGCCGTTCTCGCGAGCAGCTGGAGATGGAAATCGACAAATTCACCATTATTCAGCGC

GATAACACGACTATTGCCTGCGCCGCGCTCTATCCGTTCCCGGAAGAGAAGATTGGGGAAAT

GGCCTGTGTGGCAGTTCACCCGGATTACCGCAGTTCATCAAGGGGTGAAGTTCTGCTGGAAC

GCATTGCCGCTCAGGCTAAGCAGAGCGGCTTAAGCAAATTGTTTGTGCTGACCACGCGCAGT

TABLE 10-continued

Exemplary sequence of FNR promoter-driven argA^fbr plasmid
(SEQ ID NO: 33)

```
ATTCACTGGTTCCAGGAACGTGGATTTACCCCAGTGGATATTGATTTACTGCCCGAGAGCAA
```

```
AAAGCAGTTGTACAACTACCAGCGTAAATCCAAAGTGTTGATGGCGGATTTAGGGTAAACAG
```

AATAAAAATACAATAATTTCGAATAATCATGCAAAGCTTGGCGTAATCATGGTCATAGCTGT
TTCCTGTGTGAAATTGTTATCCGCTCACAATTCCACACAACATACGAGCCGGAAGCATGTAC
GGGTTTTGCTGCCCGCAAACGGGCTGTTCTGGTGTTGCTAGTTTGTTATCAGAATCGCAGAT
CCGGCTTCAGGTTTGCCGGCTGAAAGCGCTATTTCTTCCAGAATTGCCATGATTTTTTCCCC
ACGGGAGGCGTCACTGGCTCCCGTGTTGTCGGCAGCTTTGATTCGATAAGCAGCATCGCCTG
TTTCAGGCTGTCTATGTGTGACTGTTGAGCTGTAACAAGTTGTCTCAGGTGTTCAATTTCAT
GTTCTAGTTGCTTTGTTTTACTGGTTTCACCTGTTCTATTAGGTGTTACATGCTGTTCATCT
GTTACATTGTCGATCTGTTCATGGTGAACAGCTTTAAATGCACCAAAAACTCGTAAAAGCTC
TGATGTATCTATCTTTTTTACACCGTTTTCATCTGTGCATATGGACAGTTTTCCCTTTGATA
TCTAACGGTGAACAGTTGTTCTACTTTTGTTTGTTAGTCTTGATGCTTCACTGATAGATACA
AGAGCCATAAGAACCTCAGATCCTTCCGTATTTAGCCAGTATGTTCTCTAGTGTGGTTCGTT
GTTTTTGCGTGAGCCATGAGAACGAACCATTGAGATCATGCTTACTTTGCATGTCACTCAAA
AATTTTGCCTCAAAACTGGTGAGCTGAATTTTTGCAGTTAAAGCATCGTGTAGTGTTTTCT
TAGTCCGTTACGTAGGTAGGAATCTGATGTAATGGTTGTTGGTATTTTGTCACCATTCATTT
TTATCTGGTTGTTCTCAAGTTCGGTTACGAGATCCATTTGTCTATCTAGTTCAACTTGGAAA
ATCAACGTATCAGTCGGGCGGCCTCGCTTATCAACCACCAATTTCATATTGCTGTAAGTGTT
TAAATCTTTACTTATTGGTTTCAAAACCCATTGGTTAAGCCTTTTAAACTCATGGTAGTTAT
TTTCAAGCATTAACATGAACTTAAATTCATCAAGGCTAATCTCTATATTTGCCTTGTGAGTT
TTCTTTTGTGTTAGTTCTTTTAATAACCACTCATAAATCCTCATAGAGTATTTGTTTTCAAA
AGACTTAACATGTTCCAGATTATATTTTATGAATTTTTTTAACTGGAAAAGATAAGGCAATA
TCTCTTCACTAAAAACTAATTCTAATTTTTCGCTTGAGAACTTGGCATAGTTTGTCCACTGG
AAAATCTCAAAGCCTTTAACCAAAGGATTCCTGATTTCCACAGTTCTCGTCATCAGCTCTCT
GGTTGCTTTAGCTAATACACCATAAGCATTTTCCCTACTGATGTTCATCATCTGAGCGTATT
GGTTATAAGTGAACGATACCGTCCGTTCTTTCCTTGTAGGGTTTTCAATCGTGGGGTTGAGT
AGTGCCACACAGCATAAAATTAGCTTGGTTTCATGCTCCGTTAAGTCATAGCGACTAATCGC
TAGTTCATTTGCTTTGAAAACAACTAATTCAGACATACATCTCAATTGGTCTAGGTGATTTT
AATCACTATACCAATTGAGATGGGCTAGTCAATGATAATTACTAGTCCTTTTCCTTTGAGTT
GTGGGTATCTGTAAATTCTGCTAGACCTTTGCTGGAAAACTTGTAAATTCTGCTAGACCCTC
TGTAAATTCCGCTAGACCTTTGTGTGTTTTTTTGTTTATATTCAAGTGGTTATAATTTATA
GAATAAAGAAAGAATAAAAAAAGATAAAAAGAATAGATCCCAGCCCTGTGTATAACTCACTA
CTTTAGTCAGTTCCGCAGTATTACAAAAGGATGTCGCAAACGCTGTTTGCTCCTCTACAAAA
CAGACCTTAAAACCCTAAAGGCTTAAGTAGCACCCTCGCAAGCTCGGGCAAATCGCTGAATA
TTCCTTTTGTCTCCGACCATCAGGCACCTGAGTCGCTGTCTTTTTCGTGACATTCAGTTCGC
TGCGCTCACGGCTCTGGCAGTGAATGGGGGTAAATGGCACTACAGGCGCCTTTTATGGATTC
ATGCAAGGAAACTACCCATAATACAAGAAAAGCCCGTCACGGGCTTCTCAGGGCGTTTTATG
GCGGGTCTGCTATGTGGTGCTATCTGACTTTTTGCTGTTCAGCAGTTCCTGCCCTCTGATTT
TCCAGTCTGACCACTTCGGATTATCCCGTGACAGGTCATTCAGACTGGCTAATGCACCCAGT
AAGGCAGCGGTATCATCAACAGGCTTACCCGTCTTACTGTCTTTTCTACGGGGTCTGACGCT
CAGTGGAACGAAAACTCACGTTAAGGGATTTTGGTCATGAGATTATCAAAAGGATCTTCAC
CTAGATCCTTTTAAATTAAAAATGAAGTTTTAAATCAATCTAAAGTATATATGAGTAAACTT
GGTCTGACAGTTACCAATGCTTAATCAGTGAGGCACCTATCTCAGCGATCTGTCTATTTCGT
TCATCCATAGTTGCCTGACTCCCCGTCGTGTAGATAACTACGATACGGGAGGGCTTACCATC
TGGCCCCAGTGCTGCAATGATACCGCGAGACCCACGCTCACCGGCTCCAGATTTATCAGCAA
TAAACCAGCCAGCCGGAAGGGCCGAGCGCAGAAGTGGTCCTGCAACTTTATCCGCCTCCATC
CAGTCTATTAATTGTTGCCGGGAAGCTAGAGTAAGTAGTTCGCCAGTTAATAGTTTGCGCAA
CGTTGTTGCCATTGCTACAGGCATCGTGGTGTCACGCTCGTCGTTTGGTATGGCTTCATTCA
GCTCCGGTTCCCAACGATCAAGGCGAGTTACATGATCCCCCATGTTGTGCAAAAAAGCGGTT
AGCTCCTTCGGTCCTCCGATCGTTGTCAGAAGTAAGTTGGCCGCAGTGTTATCACTCATGGT
TATGGCAGCACTGCATAATTCTCTTACTGTCATGCCATCCGTAAGATGCTTTTCTGTGACTG
GTGAGTACTCAACCAAGTCATTCTGAGAATAGTGTATGCGGCGACCGAGTTGCTCTTGCCCG
GCGTCAATACGGGATAATACCGCGCCACATAGCAGAACTTTAAAAGTGCTCATCATTGGAAA
ACGTTCTTCGGGGCGAAAACTCTCAAGGATCTTACCGCTGTTGAGATCCAGTTCGATGTAAC
CCACTCGTGCACCCAACTGATCTTCAGCATCTTTTACTTTCACCAGCGTTTCTGGGTGAGCA
AAAACAGGAAGGCAAAATGCCGCAAAAAAGGGAATAAGGGCGACACGGAAATGTTGAATACT
CATACTCTTCCTTTTTCAATATTATTGAAGCATTTATCAGGGTTATTGTCTCATGAGCGGAT
ACATATTTGAATGTATTTAGAAAAATAAACAAATAGGGGTTCCGCGCACATTTCCCCGAAAA
GTGCCACCTGACGTCTAAGAAACCATTATTATCATGACATTAACCTATAAAAATAGGCGTAT
CACGAGGCCCTTTCGTCTCGCGCGTTTCGGTGATGACGGTGAAAACCTCTGACACATGCAGC
TCCCGGAGACGGTCACAGCTTGTCTGTAAGCGGATGCCGGGAGCAGACAAGCCCGTCAGGGC
GCGTCAGCGGGTGTTGGCGGGTGTCGGGGCTGGCTTAACTATGCGGCATCAGAGCAGATTGT
ACTGAGAGTGCACCATATGCGGTGTGAAATACCGCACAGATGCGTAAGGAGAAAATACCGCA
TCAGGCGCCATTCGCCATTCAGGCTGCGCAACTGTTGGGAAGGGCGATCGGTGCGGGCCTCT
TCGCTATTACGCCAGCTGGCGAAAGGGGGATGTGCTGCAAGGCGATTAAGTTGGGTAACGCC
AGGGTTTTCCCAGTCACGACGTT

TABLE 11

Nucleic acid sequence of pSC101 plasmid (SEQ ID NO: 34)

ATTAAGTTGGGTAACGCCAGGGTTTTCCCAGTCACGACGTTATTGCGTTG
CGCTCACTGCCCGCTTTCCAGTCGGGAAACCTGTCGTGCCAGCTGCATTA
ATGAATCGGCCAACGCGCGGGGAGAGGCGGTTTGCGTATTGGGCGCTCTT
CCGCTTCCTCGCTCACTGACTCGCTGCGCTCGGTCGTTCGGCTGCGGCGA
GCGGTATCAGCTCACTCAAAGGCGGTAGTACGGGTTTTGCTGCCCGCAAA
CGGGCTGTTCTGGTGTTGCTAGTTTGTTATCAGAATCGCAGATCCGGCTT
CAGGTTTGCCGGCTGAAAGCGCTATTTCTTCCAGAATTGCCATGATTTTT
TCCCCACGGGAGGCGTCACTGGCTCCCGTGTTGTCGGCAGCTTTGATTCG
ATAAGCAGCATCGCCTGTTTCAGGCTGTCTATGTGTGACTGTTGAGCTGT
AACAAGTTGTCTCAGGTGTTCAATTTCATGTTCTAGTTGCTTTGTTTTAC
TGGTTTCACCTGTTCTATTAGGTGTTACATGCTGTTCATCTGTTACATTG
TCGATCTGTTCATGGTGAACAGCTTTAAATGCACCAAAAACTCGTAAAAG
CTCTGATGTATCTATCTTTTTTACACCGTTTTCATCTGTGCATATGGACA
GTTTTCCCTTTGATATCTAACGGTGAACAGTTGTTCTACTTTTGTTTGTT
AGTCTTGATGCTTCACTGATAGATACAAGAGCCATAAGAACCTCAGATCC
TTCCGTATTTAGCCAGTATGTTCTCTAGTGTGGTTCGTTGTTTTTGCGTG
AGCCATGAGAACGAACCATTGAGATCATGCTTACTTTGCATGTCACTCAA
AAATTTTGCCTCAAAACTGGTGAGCTGAATTTTTGCAGTTAAAGCATCGT
GTAGTGTTTTCTTAGTCCGTTACGTAGGTAGGAATCTGATGTAATGGTT
GTTGGTATTTTGTCACCATTCATTTTTATCTGGTTGTTCTCAAGTTCGGT
TACGAGATCCATTTGTCTATCTAGTTCAACTTGGAAAATCAACGTATCAG
TCGGGCGGCCTCGCTTATCAACCACCAATTTCATATTGCTGTAAGTGTTT
AAATCTTTACTTATTGGTTTCAAAACCCATTGGTTAAGCCTTTTAAACTC
ATGGTAGTTATTTTCAAGCATTAACATGAACTTAAATTCATCAAGGCTAA
TCTCTATATTTGCCTTGTGAGTTTTCTTTTGTGTTAGTTCTTTTAATAAC
CACTCATAAATCCTCATAGAGTATTTGTTTTCAAAAGACTTAACATGTTC
CAGATTATATTTTATGAATTTTTTTAACTGGAAAAGATAAGGCAATATCT
CTTCACTAAAAACTAATTCTAATTTTTCGCTTGAGAACTTGGCATAGTTT
GTCCACTGGAAAATCTCAAAGCCTTTAACCAAAGGATTCCTGATTTCCAC
AGTTCTCGTCATCAGCTCTCTGGTTGCTTTAGCTAATACACCATAAGCAT
TTTCCCTACTGATGTTCATCATCTGAGCGTATTGGTTATAAGTGAACGAT
ACCGTCCGTTCTTTCCTTGTAGGGTTTTCAATCGTGGGGTTGAGTAGTGC
CACACAGCATAAAATTAGCTTGGTTTCATGCTCCGTTAAGTCATAGCGAC
TAATCGCTAGTTCATTTGCTTTGAAAACAACTAATTCAGACATACATCTC
AATTGGTCTAGGTGATTTTAATCACTATACCAATTGAGATGGGCTAGTCA
ATGATAATTACTAGTCCTTTTCCTTTGAGTTGTGGGTATCTGTAAATTCT
GCTAGACCTTTGCTGGAAAACTTGTAAATTCTGCTAGACCCTCTGTAAAT
TCCGCTAGACCTTTGTGTGTTTTTTTGTTTATATTCAAGTGGTTATAAT
TTATAGAATAAAGAAAGAATAAAAAAAGATAAAAAGAATAGATCCCAGCC
CTGTGTATAACTCACTACTTTAGTCAGTTCCGCAGTATTACAAAAGGATG
TCGCAAACGCTGTTTGCTCCTCTACAAAACAGACCTTAAAACCCTAAAGG

TABLE 11-continued

Nucleic acid sequence of pSC101 plasmid (SEQ ID NO: 34)

CTTAAGTAGCACCCTCGCAAGCTCGGGCAAATCGCTGAATATTCCTTTTG
TCTCCGACCATCAGGCACCTGAGTCGCTGTCTTTTTCGTGACATTCAGTT
CGCTGCGCTCACGGCTCTGGCAGTGAATGGGGGTAAATGGCACTACAGGC
GCCTTTTATGGATTCATGCAAGGAAACTACCCATAATACAAGAAAAGCCC
GTCACGGGCTTCTCAGGGCGTTTTATGGCGGGTCTGCTATGTGGTGCTAT
CTGACTTTTTGCTGTTCAGCAGTTCCTGCCCTCTGATTTTCCAGTCTGAC
CACTTCGGATTATCCCGTGACAGGTCATTCAGACTGGCTAATGCACCCAG
TAAGGCAGCGGTATCATCAACAGGCTTACCCGTCTTACTGTCTTTTCTAC
GGGGTCTGACGCTCAGTGGAACGAAAACTCACGTTAAGGGATTTTGGTCA
TGAGATTATCAAAAAGGATCTTCACCTAGATCCTTTTAAATTAAAAATGA
AGTTTTAAATCAATCTAAAGTATATATGAGTAAACTTGGTCTGACAGTTA
CCAATGCTTAATCAGTGAGGCACCTATCTCAGCGATCTGTCTATTTCGTT
CATCCATAGTTGCCTGACTCCCCGTCGTGTAGATAACTACGATACGGGAG
GGCTTACCATCTGGCCCCAGTGCTGCAATGATACCGCGAGACCCACGCTC
ACCGGCTCCAGATTTATCAGCAATAAACCAGCCAGCCGGAAGGGCCGAGC
GCAGAAGTGGTCCTGCAACTTTATCCGCCTCCATCCAGTCTATTAATTGT
TGCCGGGAAGCTAGAGTAAGTAGTTCGCCAGTTAATAGTTTGCGCAACGT
TGTTGCCATTGCTACAGGCATCGTGGTGTCACGCTCGTCGTTTGGTATGG
CTTCATTCAGCTCCGGTTCCCAACGATCAAGGCGAGTTACATGATCCCCC
ATGTTGTGCAAAAAAGCGGTTAGCTCCTTCGGTCCTCCGATCGTTGTCAG
AAGTAAGTTGGCCGCAGTGTTATCACTCATGGTTATGGCAGCACTGCATA
ATTCTCTTACTGTCATGCCATCCGTAAGATGCTTTTCTGTGACTGGTGAG
TACTCAACCAAGTCATTCTGAGAATAGTGTATGCGGCGACCGAGTTGCTC
TTGCCCGGCGTCAATACGGGATAATACCGCGCCACATAGCAGAACTTTAA
AAGTGCTCATCATTGGAAAACGTTCTTCGGGGCGAAAACTCTCAAGGATC
TTACCGCTGTTGAGATCCAGTTCGATGTAACCCACTCGTGCACCCAACTG
ATCTTCAGCATCTTTTACTTTCACCAGCGTTTCTGGGTGAGCAAAAACAG
GAAGGCAAAATGCCGCAAAAAAGGGAATAAGGGCGACACGGAAATGTTGA
ATACTCATACTCTTCCTTTTTCAATATTATTGAAGCATTTATCAGGGTTA
TTGTCTCATGAGCGGATACATATTTGAATGTATTTAGAAAAATAAACAAA
TAGGGGTTCCGCGCACATTTCCCCGAAAAGTGCCACCTGACGTCTAAGAA
ACCATTATTATCATGACATTAACCTATAAAAATAGGCGTATCACGAGGCC
CTTTCGTCTCGCGCGTTTCGGTGATGACGGTGAAAACCTCTGACACATGC
AGCTCCCGGAGACGGTCACAGCTTGTCTGTAAGCGGATGCCGGGAGCAGA
CAAGCCCGTCAGGGCGCGTCAGCGGGTGTTGGCGGGTGTCGGGGCTGGCT
TAACTATGCGGCATCAGAGCAGATTGTACTGAGAGTGCACCATATGCGGT
GTGAAATACCGCACAGATGCGTAAGGAGAAAATACCGCATCAGGCGCCAT
TCGCCATTCAGGCTGCGCAACTGTTGGGAAGGGCGATCGGTGCGGGCCTC
TTCGCTATTACGCCAGCTGGCGAAAGGGGGATGTGCTGCAAGGCG

Table 12

Nucleotide sequence of exemplary fnrS promoter-driven argA$^{fbr}$ pSC101 plasmid (SEQ ID NO: 35)

ggtacc*AGTTGTTCTTATTGGTGGTGTTGCTTTATGGTTGCATCGTAGTAAATGGTTGTAACAA*

*AAGCAATTTTTCCGGCTGTCTGTATACAAAAACGCCGCAAAGTTTGAGCGAAGTCAATAAACTC*

*TCTACCCATTCAGGGCAATATCTCTCTT*ggatccaaagtgaactctagaaataa<mark>ttttgtttaa</mark>

<mark>ctttaagaaggagatatacat</mark>ATGGTAAAGGAACGTAAAACCGAGTTGGTCGAGGGATTCCGCC

ATTCGGTTCCCTGTATCAATACCCACCGGGGAAAAACGTTTGTCATCATGCTCGGCGGTGAAGC

CATTGAGCATGAGAATTTCTCCAGTATCGTTAATGATATCGGGTTGTTGCACAGCCTCGGCATC

CGTCTGGTGGTGGTCTATGGCGCACGTCCGCAGATCGACGCAAATCTGGCTGCGCATCACCACG

AACCGCTGTATCACAAGAATATACGTGTGACCGACGCCAAAACACTGGAACTGGTGAAGCAGGC

TGCGGGAACATTGCAACTGGATATTACTGCTCGCCTGTCGATGAGTCTCAATAACACGCCGCTG

CAGGGCGCGCATATCAACGTCGTCAGTGGCAATTTTATTATTGCCCAGCCGCTGGGCGTCGATG

Table 12-continued

Nucleotide sequence of exemplary fnrS promoter-driven argA^fbr pSC101 plasmid (SEQ ID NO: 35)

ACGGCGTGGATTACTGCCATAGCGGGCGTATCCGGCGGATTGATGAAGACGCGATCCATCGTCA

ACTGGACAGCGGTGCAATAGTGCTAATGGGGCCGGTCGCTGTTTCAGTCACTGGCGAGAGCTTT

AACCTGACCTCGGAAGAGATTGCCACTCAACTGGCCATCAAACTGAAAGCTGAAAAGATGATTG

GTTTTTGCTCTTCCCAGGGCGTCACTAATGACGACGGTGATATTGTCTCCGAACTTTTCCCTAA

CGAAGCGCAAGCGCGGGTAGAAGCCCAGGAAGAGAAAGGCGATTACAACTCCGGTACGGTGCGC

TTTTTGCGTGGCGCAGTGAAAGCCTGCCGCAGCGGCGTGCGTCGCTGTCATTTAATCAGTTATC

AGGAAGATGGCGCGCTGTTGCAAGAGTTGTTCTCACGCGACGGTATCGGTACGCAGATTGTGAT

GGAAAGCGCCGAGCAGATTCGTCGCGCAACAATCAACGATATTGGCGGTATTCTGGAGTTGATT

CGCCCACTGGAGCAGCAAGGTATTCTGGTACGCCGTTCTCGCGAGCAGCTGGAGATGGAAATCG

ACAAATTCACCATTATTCAGCGCGATAACACGACTATTGCCTGCGCCGCGCTCTATCCGTTCCC

GGAAGAGAAGATTGGGGAAATGGCCTGTGTGGCAGTTCACCCGGATTACCGCAGTTCATCAAGS

GGTGAAGTTCTGCTGGAACGCATTGCCGCTCAGGCTAAGCAGAGCGGCTTAAGCAAATTGTTTG

TGCTGACCACGCGCAGTATTCACTGGTTCCAGGAACGTGGATTTACCCCAGTGGATATTGATTT

ACTGCCCGAGAGCAAAAAGCAGTTGTACAACTACCAGCGTAAATCCAAAGTGTTGATGGCGGAT

TTAGGGTAAGGAAGTTTGTCTAGATCTCAGGCGTGGATGGCTTGGCGTAATCATGGTCATAGCT
GTTTCCTGTGTGAAATTGTTATCCGCTCACAATTCCACACAACATACGAGCCGGAAGCATAAAG
TGTAAAGCCTGGGGTGCCTAATGAGTGAGCTAACTCACATTAATTGCGTTGCGCTCACTGCCCG
CTTTCCAGTCGGGAAACCTGTCGTGCCAGCTGCATTAATGAATCGGCCAACGCGCGGGGAGAGG
CGGTTTGCGTATTGGGCGCTCTTCCGCTTCCTCGCTCACTGACTCGCTGCGCTCGGTCGTTCGG
CTGCGGCGAGCGGTATCAGCTCACTCAAAGGCGGTAGTACGGGTTTTGCTGCCCGCAAACGGGC
TGTTCTGGTGTTGCTAGTTTGTTATCAGAATCGCAGATCCGGCTTCAGGTTTGCCGGCTGAAAG
CGCTATTTCTTCCAGAATTGCCATGATTTTTTCCCCACGGGAGGCGTCACTGGCTCCCGTGTTG
TCGGCAGCTTTGATTCGATAAGCAGCATCGCCTGTTTCAGGCTGTCTATGTGTGACTGTTGAGC
TGTAACAAGTTGTCTCAGGTGTTCAATTTCATGTTCTAGTTGCTTTGTTTTACTGGTTTCACCT
GTTCTATTAGGTGTTACATGCTGTTCATCTGTTACATTGTCGATCTGTTCATGGTGAACAGCTT
TAAATGCACCAAAAACTCGTAAAAGCTCTGATGTATCTATCTTTTTTACACCGTTTTCATCTGT
GCATATGGACAGTTTTCCCTTTGATATCTAACGGTGAACAGTTGTTCTACTTTTGTTTGTTAGT
CTTGATGCTTCACTGATAGATACAAGAGCCATAAGAACCTCAGATCCTTCCGTATTTAGCCAGT
ATGTTCTCTAGTGTGGTTCGTTGTTTTTGCGTGAGCCATGAGAACGAACCATTGAGATCATGCT
TACTTTGCATGTCACTCAAAAATTTTGCCTCAAAACTGGTGAGCTGAATTTTTGCAGTTAAAGC
ATCGTGTAGTGTTTTTCTTAGTCCGTTACGTAGGTAGGAATCTGATGTAATGGTTGTTGGTATT
TTGTCACCATTCATTTTTATCTGGTTGTTCTCAAGTTCGGTTACGAGATCCATTTGTCTATCTA
GTTCAACTTGGAAAATCAACGTATCAGTCGGGCGGCTCGCTTATCAACCACCAATTTCATATT
GCTGTAAGTGTTTAAATCTTTACTTATTGGTTTCAAAACCCATTGGTTAAGCCTTTTAAACTCA
TGGTAGTTATTTTCAAGCATTAACATGAACTTAAATTCATCAAGGCTAATCTCTATATTTGCCT
TGTGAGTTTTCTTTTGTGTTAGTTCTTTTAATAACCACTCATAAATCCTCATAGAGTATTTGTT
TTCAAAAGACTTAACATGTTCCAGATTATATTTTATGAATTTTTTTAACTGGAAAAGATAAGGC
AATATCTCTTCACTAAAAACTAATTCTAATTTTTCGCTTGAGAACTTGGCATAGTTTGTCCACT
GGAAAATCTCAAAGCCTTTAACCAAAGGATTCCTGATTTCTCACAGTTCTCGTCATCAGCTCTCT
GGTTGCTTTAGCTAATACACCATAAGCATTTTCCCTACTGATGTTCATCATCTGAGCGTATTGG
TTATAAGTGAACGATACCGTCCGTTCTTTCCTTGTAGGGTTTTCAATCGTGGGGTTGAGTAGTG
CCACACAGCATAAAATTAGCTTGGTTTCATGCTCCGTTAAGTCATAGCGACTAATCGCTAGTTC
ATTTGCTTTGAAAACAACTAATTCAGACATACATCTCAATTGGTCTAGGTGATTTTAATCACTA
TACCAATTGAGATGGGCTAGTCAATGATAATTACTAGTCCTTTTCCTTTGAGTTGTGGGTATCT
GTAAATTCTGCTAGACCTTTGCTGGAAAACTTGTAAATTCTGCTAGACCCTCTGTAAATTCCGC
TAGACCTTTGTGTGTTTTTTTGTTTATATTCAAGTGGTTATAATTTATAGAATAAAGAAAGAA
TAAAAAAAGATAAAAAGAATAGATCCCAGCCCTGTGTATAACTCACTACTTTAGTCAGTTCCGC
AGTATTACAAAAGGATGTCGCAAACGCTGTTTGCTCCTCTACAAAACAGACCTTAAAACCCTAA
AGGCTTAAGTAGCACCCTCGCAAGCTCGGGCAAATCGCTGAATATTCCTTTTGTCTCCGACCAT

Table 12-continued

Nucleotide sequence of exemplary fnrS promoter-driven
argA$^{fbr}$ pSC101 plasmid (SEQ ID NO: 35)

```
CAGGCACCTGAGTCGCTGTCTTTTTCGTGACATTCAGTTCGCTGCGCTCACGGCTCTGGCAGTG
AATGGGGGTAAATGGCACTACAGGCGCCTTTTATGGATTCATGCAAGGAAACTACCCATAATAC
AAGAAAAGCCCGTCACGGGCTTCTCAGGGCGTTTTATGGCGGGTCTGCTATGTGGTGCTATCTG
ACTTTTTGCTGTTCAGCAGTTCCTGCCCTCTGATTTTCCAGTCTGACCACTTCGGATTATCCCG
TGACAGGTCATTCAGACTGGCTAATGCACCCAGTAAGGCAGCGGTATCATCAACAGGCTTACCC
GTCTTACTGTCTTTTCTACGGGGTCTGACGCTCAGTGGAACGAAAACTCACGTTAAGGGATTTT
GGTCATGAGATTATCAAAAAGGATCTTCACCTAGATCCTTTTAAATTAAAAATGAAGTTTTAAA
TCAATCTAAAGTATATATGAGTAAACTTGGTCTGACAGTTACCAATGCTTAATCAGTGAGGCAC
CTATCTCAGCGATCTGTCTATTTCGTTCATCCATAGTTGCCTGACTCCCCGTCGTGTAGATAAC
TACGATACGGGAGGGCTTACCATCTGGCCCCAGTGCTGCAATGATACCGCGAGACCCACGCTCA
CCGGCTCCAGATTTATCAGCAATAAACCAGCCAGCCGGAAGGGCCGAGCGCAGAAGTGGTCCTG
CAACTTTATCCGCCTCCATCCAGTCTATTAATTGTTGCCGGGAAGCTAGAGTAAGTAGTTCGCC
AGTTAATAGTTTGCGCAACGTTGTTGCCATTGCTACAGGCATCGTGGTGTCACGCTCGTCGTTT
GGTATGGCTTCATTCAGCTCCGGTTCCCAACGATCAAGGCGAGTTACATGATCCCCCATGTTGT
GCAAAAAAGCGGTTAGCTCCTTCGGTCCTCCGATCGTTGTCAGAAGTAAGTTGGCCGCAGTGTT
ATCACTCATGGTTATGGCAGCACTGCATAATTCTCTTACTGTCATGCCATCCGTAAGATGCTTT
TCTGTGACTGGTGAGTACTCAACCAAGTCATTCTGAGAATAGTGTATGCGGCGACCGAGTTGCT
CTTGCCCGGCGTCAATACGGGATAATACCGCGCCACATAGCAGAACTTTAAAAGTGCTCATCAT
TGGAAAACGTTCTTCGGGGCGAAAACTCTCAAGGATCTTACCGCTGTTGAGATCCAGTTCGATG
TAACCCACTCGTGCACCCAACTGATCTTCAGCATCTTTTACTTTCACCAGCGTTTCTGGGTGAG
CAAAAACAGGAAGGCAAAATGCCGCAAAAAAGGGAATAAGGGCGACACGGAAATGTTGAATACT
CATACTCTTCCTTTTTCAATATTATTGAAGCATTTATCAGGGTTATTGTCTCATGAGCGGATAC
ATATTTGAATGTATTTAGAAAAATAAACAAATAGGGGTTCCGCGCACATTTCCCCGAAAAGTGC
CACCTGACGTCTAAGAAACCATTATTATCATGACATTAACCTATAAAAATAGGCGTATCACGAG
GCCCTTTCGTCTCGCGCGTTTCGGTGATGACGGTGAAAACCTCTGACACATGCAGCTCCCGGAG
ACGGTCACAGCTTGTCTGTAAGCGGATGCCGGGAGCAGACAAGCCCGTCAGGGCGCGTCAGCGG
GTGTTGGCGGGTGTCGGGGCTGGCTTAACTATGCGGCATCAGAGCAGATTGTACTGAGAGTGCA
CCATATGCGGTGTGAAATACCGCACAGATGCGTAAGGAGAAAATACCGCATCAGGCGCCATTCG
CCATTCAGGCTGCGCAACTGTTGGGAAGGGCGATCGGTGCGGGCCTCTTCGCTATTACGCCAGC
TGGCGAAAGGGGGATGTGCTGCAAGGCG
```

In some embodiments, the genetically engineered bacteria comprise argA$^{fbr}$ integrated into the chromosome. In some embodiments, the integrated fbrArgA is under the control of the fnrS promoter. In some embodiments, an antibiotic resistance cassette is also present at the same site. In some embodiments, no antibiotic resistance cassette is present. In some embodiments, the antibiotic resistance is chloramphenicol. In some embodiments, the antibiotic resistance is kanamycin. In some embodiments, the genetically engineered bacteria comprising argA$^{fbr}$ integrated into the chromosome is a thyA auxotroph. In some embodiments, the genetically engineered bacteria comprise argA$^{fbr}$ integrated into the chromosome and also comprise an ArgR mutation or have ArgR deleted. In one specific embodiment, the genetically engineered bacteria comprise argA$^{fbr}$ under the control of the fnrS promoter and integrated into the chromosome, comprise an ArgR mutation or have ArgR deleted, and comprise a thyA auxotrophy. In another specific embodiment, the genetically engineered bacteria comprise argA$^{fbr}$ under the control of the fnrS promoter and integrated into the chromosome, comprise an ArgR mutation or have ArgR deleted, comprise a thyA auxotrophy, and comprise an antibiotic resistance cassette. In another specific embodiment, the genetically engineered bacteria comprise argAfbr under the control of the fnrS promoter and integrated into the chromosome, comprise an ArgR mutation or have ArgR deleted, comprise a thyA auxotrophy, and comprise a kanamycin resistance cassette. In one specific embodiment, the genetically engineered bacteria is SYN-UCD305. In another specific embodiment, the genetically engineered bacteria is SYN_UCD303.

Table 13 shows non-limiting examples of FNRS-fbrArgA constructs which are integrated into the chromosome.

SEQ ID NO: 36 comprises FNRS-fbrArgA and chloramphenicol resistance, e.g., as comprised in SYN-UCD301, SYN-UCD302. SEQ ID NO: 37 comprises FNRS-fbrArgA and kanamycin resistance, e.g., as comprised in SYN-UCD303, SYN-UCD306, SYN-UCD307, and SYN-UCD309. SEQ ID NO: 38 FNRS-fbrArgA and no antibiotic resistance, e.g., as comprised in SYN-UCD305 SYN-UCD304, SYN-UCD308, SYNUCD310.

TABLE 13 of Integrated argA$^{fbr}$ sequences

Figure 20:
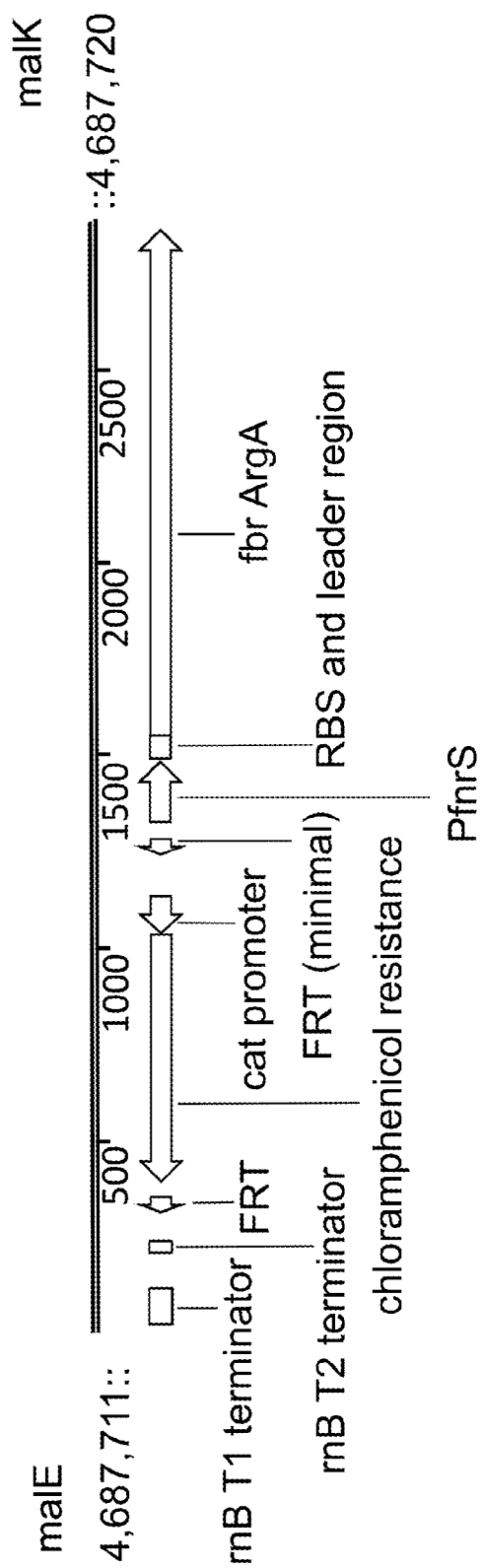
FIG. 20 depicts the gene organization of exemplary contructs of the disclosure. Non-limiting examples of strains comprising such a construct include SYN-UCD301 and SYN-UCD302. SYN-UCD301 comprises ΔArgR, PfnrS-ArgAfbr integrated into the chromosome at the malEK locus, Wild type ThyA, and Chloramphenicol resistance.

| Description | Sequence | SEQ ID NO |
|---|---|---|
| FNRS-fbrArgA and chloramphenicol resistance, e.g., SYN-UCD301, SYN-UCD302; a schematic of the construct is depicted in FIG. 20; UPPERCASE | ctacgccccatcgttgctttgtgtgatctctgttacaga attggcggtaatgtggagatgcgcacataaaatcgccat gatttttgcaagcaacatcacgaaattccttacatgacc tcggtttagttcacaggacgtcccatggctcgagCATGC GAGAGTAGGGAACTGCCAGGCATCAAATAAAAtGAAAGG CTCAGTCGAAAGACTGGGCCTTTCGTTTTATCTGTTGTT TGTCGGTGAACGCTCTCCTGAGTAGGACAAATCCGCGG GAGCGGATTTGAACGTTGCGAAGCAACGGCCCGGAGGGT GGCGGGCAGGACGCCCGCCATAAACTGCCAGGCATCAAA TTAAGCAGAAGGCCATCCTGACGGATGGCCTTTTTGCGT | SEQ ID NO: 36 |

TABLE 13-continued of Integrated argA^fbr sequences

| Description | Sequence | SEQ ID NO |
|---|---|---|
| underlined: CmR gene; UPPERCASE italics: CmR promoter; UPPERCASE italic and underlined: fnrS promoter; UPPERCASE bold: ArgAfbr; UPPERCASE bold underline: terminator sequence; *UPPERCASE italic bold:* frt sites | GGCCAGTGCCAAGCTTGCATGCAGATTGCAGCATTACAC<br>GTCTTGAGCGATTGTGTAGGCTGGAGCTGCTTC*GAAGTT*<br>*CCTATACTTTCTAGAGAATAGGAACTTCGGAATAGGAAC*<br>*TTC*ATTTAAATGGCGCGCCTTACGCCCCGCCCTGCCAC<u>T</u><br><u>CATCGCAGTACTGTTGTATTCATTAAGCATCTGCCGACA</u><br><u>TGGAAGCCATCACAAACGGCATGATGAACCTGAATCGCC</u><br><u>AGCGGCATCAGCACCTTGTCGCCTTGCGTATAATATTTG</u><br><u>CCCATGGTGAAAACGGGGGCGAAGAAGTTGTCCATATTG</u><br><u>GCCACGTTTAAATCAAAACTGGTGAAACTCACCCAGGGA</u><br><u>TTGGCTGAGACGAAAAACATATTCTCAATAAACCCTTTA</u><br><u>GGGAAATAGGCCAGGTTTTCACCGTAACACGCCACATCT</u><br><u>TGCGAATATATGTGTAGAAACTGCCGGAAATCGTCGTGG</u><br><u>TATTCACTCCAGAGCGATGAAAACGTTTCAGTTTGCTCA</u><br><u>TGGAAAACGGTGTAACAAGGGTGAACACTATCCCATATC</u><br><u>ACCAGCTCACCGTCTTTCATTGCCATACGTAATTCCGGA</u><br><u>TGAGCATTCATCAGGCGGGCAAGAATGTGAATAAAGGCC</u><br><u>GGATAAAACTTGTGCTTATTTTTCTTTACGGTCTTTAAA</u><br><u>AAGGCCGTAATATCCAGCTGAACGGTCTGGTTATAGGTA</u><br><u>CATTGAGCAACTGACTGAAATGCCTCAAAATGTTCTTTA</u><br><u>CGATGCCATTGGGATATATCAACGGTGGTATATCCAGTG</u><br><u>ATTTTTTTCTCCATTTTAGCTTCCTTAGCTCCTGAAAAT</u><br><u>CTCGACAACTCAAAAAATACGCCCGGTAGTGATCTTATT</u><br><u>TCATTATGGTGAAAGTTGGAACCTCTTACGTGCCGATCA</u><br><u>ACGTCTCATTTTCGCCAAAAGTTGGCCCAGGGCTTCCCG</u><br><u>GTATCAACAGGGACACCAGGATTTATTTATTCTGCGAAG</u><br>TGATCTTCCGTCACAGGTAGGCGCGCC*GAAGTTCCTATA*<br>*CTTTCTAGAGAATAGGAACTTCGGAATAGGAACTA*AGGA<br>GGATATTCATATGGACCATGGCTAATTCCCAG<u>GTACCAG</u><br><u>TTGTTCTTATTGGTGGTGTTGCTTTATGGTTGCATCGTA</u><br><u>GTAAATGGTTGTAACAAAAGCAATTTTTCCGGCTGTCTG</u><br><u>TATACAAAAACGCCGTAAAGTTTGAGCGAAGTCAATAAA</u><br><u>CTCTCTACCCATTCAGGGCAATATCTCTCTTGGATCC</u>aa<br>agtgaactctagaaataattttgtttaactttaagaagg<br>agatatacatATGGTAAAGGAACGTAAAACCGAGTTGGT<br>CGAGGGATTCCGCCATTCGGTTCCCTGTATCAATACCCA<br>CCGGGGAAAAACGTTTGTCATCATGCTCGGCGGTGAAGC<br>CATTGAGCATGAGAATTTCTCCAGTATCGTTAATGATAT<br>CGGGTTGTTGCACAGCCTCGGCATCCGTCTGGTGGTGGT<br>CTATGGCGCACGTCCGCAGATCGACGCAAATCTGGCTGC<br>GCATCACCACGAACCGCTGTATCACAAGAATATACGTGT<br>GACCGACGCCAAAACACTGGAACTGGTGAAGCAGGCTGC<br>GGGAACATTGCAACTGGATATTACTGCTCGCCTGTCGAT<br>GAGTCTCAATAACACGCCGCTGCAGGGCGCGCATATCAA<br>CGTCGTCAGTGGCAATTTTATTATTGCCCAGCCGCTGGG<br>CGTCGATGACGGCGTGGATTACTGCCATAGCGGGCGTAT<br>CCGGCGGATTGATGAAGACGCGATCCATCGTCAACTGGA<br>CAGCGGTGCAATAGTGCTAATGGGGCCGGTCGCTGTTTC<br>AGTCACTGGCGAGAGCTTTAACCTGACCTCGGAAGAGAT<br>TGCCACTCAACTGGCCATCAAACTGAAAGCTGAAAAGAT<br>GATTGGTTTTTGCTCTTCCCAGGGCGTCACTAATGACGA<br>CGGTGATATTGTCTCCGAACTTTTCCCTAACGAAGCGCA<br>AGCGCGGGTAGAAGCCCAGGAAGAGAAAGGCGATTACAA<br>CTCCGGTACGGTGCGCTTTTTGCGTGGCGCAGTGAAAGC<br>CTGCCGCAGCGGCGTGCGTCGCTGTCATTTAATCAGTTA<br>TCAGGAAGATGGCGCGTGTTGCAAGAGTTGTTCTCACG<br>CGACGGTATCGGTACGCAGATTGTGATGGAAAGCGCCGA<br>GCAGATTCGTCGCGCAACAATCAACGATATTGGCGGTAT<br>TCTGGAGTTGATTCGCCCACTGGAGCAGCAAGGTATTCT<br>GGTACGCCGTTCTCGCGAGCAGCTGGAGATGGAAATCGA<br>CAAATTCACCATTATTCAGCGCGATAACACGACTATTGC<br>CTGCGCCGCGCTCTATCCGTTCCCGGAAGAGAAGATTGG<br>GGAAATGGCCTGTGTGGCAGTTCACCCGGATTACCGCAG<br>TTCATCAAGGGGTGAAGTTCTGCTGGAACGCATTGCCGC<br>TCAGGCTAAGCAGAGCGGCTTAAGCAAATTGTTTGTGCT<br>GACCACGCGCAGTATTCACTGGTTCCAGGAACGTGGATT<br>TACCCCAGTGGATATTGATTTACTGCCCGAGAGCAAAAA<br>GCAGTTGTACAACTACCAGCGTAAATCCAAAGTGTTGAT<br>GGCGGATTTAGGGTAAgtcgacgcatgcatcgataagcc<br>gcgttctcatcctcccgcctcctcccccataaaaaagcc<br>agggggtggaggatttaagccatctcctgatgac | |

TABLE 13-continued of Integrated argA^fbr sequences

Figure 21:
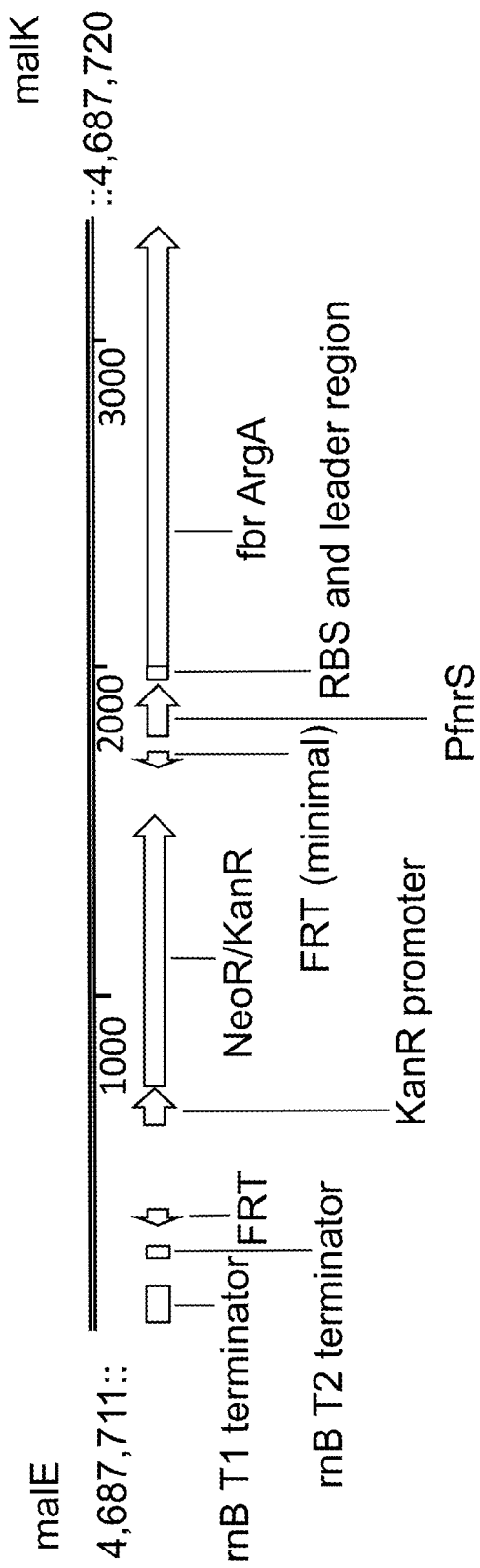
FIG. 21 depicts the gene organization of an exemplary construct of the disclosure. Non-limiting examples of strains comprising such a construct include SYN-UCD303, SYN-UCD306, SYN-UCD307, and SYN-UCD309. For example, SYN-UCD303 comprises ΔArgR, PfnrS-ArgAfbr integrated into the chromosome at the malEK locus, ΔThyA, and kanamycin resistance.

| Description | Sequence | SEQ ID NO |
|---|---|---|
| FNRS-fbrArgA and kanamycin resistance, e.g., SYN-UCD303, SYN-UCD306, SYN-UCD307, and SYN-UCD309; a schematic of the construct is depicted in FIG. 21 Lowercase underlined: KanR promoter; *lowercase italic*: KanR gene; UPPERCASE underlined: fnrS promoter; UPPERCASE bold: ArgAfbr UPPERCASE bold underline: terminator sequence; *UPPERCASE italic bold:* frt sites | ctacgccccatcgttgctttgtgtgatctctgttacaga attggcggtaatgtggagatgcgcacataaaatcgccat gatttttgcaagcaacatcacgaaattccttacatgacc tcggtttagttcacaggacgtcccatggctcgagCATGC GAGAGTAGGGAACTGCCAGGCATCAAATAAAATGAAAGG CTCAGTCGAAAGACTGGGCCTTTCGTTTTATCTGTTGTT TGTCGGTGAACGCTCTCCTGAGTAGGACAAATCCGCCGG GAGCGGATTTGAACGTTGCGAAGCAACGGCCCGGAGGGT GGCGGGCAGGACGCCCGCCATAAACTGCCAGGCATCAAA TTAAGC<u>AGAAGGCCATCCTGACGGATGGCCTTTT</u>TGCGT GGCCAGTGCCAAGCTTGCATGCAGATTGCAGCATTACAC GTCTTGAGCGATTGTGTAGGCTGGAGCTGCTTC*GAAGTT CCTATACTTTCTAGAGAATAGGAACTTCGGAATAGGAAC TTC*aagatccctcacgctgccgcaagcactcagggcgc aagggctgctaaaggaagcggaacacgtagaaagccagt ccgcagaaacggtgctgacccccggatgaatgtcagctac tgggctatctggacaagggaaaacgcaagcgcaaagaga aagcaggtagcttgcagtgggcttacatggcgatagcta gactgggcggttttatggacagcaagcgaaccggaattg ccagctggggcgccctctggtaa<u>ggttgggaagccctgc aaagtaaactggatggctttcttgccgccaaggatctga tggcgcagggatcaagatctgatcaagagacaggatga ggatcgtttcgcatgattgaacaagatggattgcacgca ggttctccggccgcttgggtggagaggctattcggctat gactgggcacaacagacaatcggctgctctgatgccgcc gtgttccggctgtcagcgcaggggcgcccggttcttttt gtcaagaccgacctgtccggtgccctgaatgaactgcag gacgaggcagcgcggctatcgtggctggccacgacgggc gttccttgcgcagctgtgctcgacgttgtcactgaagcg ggaagggactggctgctattgggcgaagtgccggggcag gatctcctgtcatctcaccttgctcctgccgagaaagta tccatcatggctgatgcaatgcggcggctgcatacgctt gatccggctacctgcccattcgaccaccaagcgaaacat cgcatcgagcgagcacgtactcggatggaagccggtctt gtcgatcaggatgatctggacgaagagcatcaggggctc gcgccagccgaactgttcgccaggctcaaggcgcgcatg cccgacgcgaggatctcgtcgtgacccatggcgatgcc tgcttgccgaatatcatggtggaaaatggccgcttttct ggattcatcgactgtggccggctgggtgtggcggaccgc tatcaggacatagcgttggctacccgtgatattgctgaa gagcttggcggcgaatgggctgaccgcttcctcgtgctt tacggtatcgccgctcccgattcgcagcgcatcgccttc tatcgccttcttgacgagttcttctgagcgggactctgg ggttcgaaatgaccgaccaagcgacgcccaacctgccat cacgagatttcgattccaccgccgccttctatgaaaggt tgggcttcggaatcgttttccgggacgccggctggatga tcctccagcgcggggatctcatgctggagttcttcgccc accccagcttcaaaagcgctct*GAAGTTCCTATACTTTC TAGAGAATAGGAACTTCGGAATAGGAACTA*AGGAGGATA TTCATATGGACCATGGCTAATTCCCAGATATG<u>GTACCAG TTGTTCTTATTGGTGGTGTTGCTTTATGGTTGCATCGTA GTAAATGGTTGTAACAAAAGCAATTTTTCCGGCTGTCTG TATACAAAAACGCCGTAAAGTTTGAGCGAAGTCAATAAA CTCTCTACCCATTCAGGGCAATATCTCTCTTGGATCC</u>aa agtgaactctagaaataattttgtttaactttaagaagg agatatacatATGGTAAAGGAACGTAAAACCGAGTTGGT CGAGGGATTCCGCCATTCGGTTCCCTGTATCAATACCCA CCGGGGAAAAACGTTTGTCATCATGCTCGGCGGTGAAGC CATTGAGCATGAGAATTTCTCCAGTATCGTTAATGATAT CGGGTTGTTGCACAGCCTCGGCATCCGTCGGTGGTGGT CTATGGCGCACGTCCGCAGATCGACGCAAATCTGGCTGC GCATCACCACGAACCGCTGTATCACAAGAATATACGTGT GACCGACGCCAAAACACTGGAACTGGTGAAGCAGGCTGC GGGAACATTGCAACTGGATATTACTGCTCGCCTGTCGAT GAGTCTCAATAACACGCCGCTGCAGGGCGCGCATATCAA CGTCGTCAGTGGCAATTTTATTATTGCCCAGCCGCTGGG CGTCGATGACGGCGTGGATTACTGCCATAGCGGGCGTAT CCGGCGGATTGATGAAGACGCGATCCATCGTCAACTGGA CAGCGGTGCAATAGTGCTAATGGGGCCGGTCGCTGTTTC AGTCACTGGCGAGAGCTTTAACCTGACCTCGGAAGAGAT TGCCACTCAACTGGCCATCAAACTGAAAGCTGAAAAGAT GATTGGTTTTTGCTCTTCCCAGGGCGTCACTAATGACGA CGGTGATATTGTCTCCGAACTTTTCCCTAACGAAGCGCA AGCGCGGGTAGAAGCCCAGGAAGAGAAAGGCGATTACAA CTCCGGTACGGTGCGCTTTTTGCGTGGCGCAGTGAAAGC | SEQ ID NO: 37 |

TABLE 13-continued of Integrated argA^fbr sequences

Figure 22:
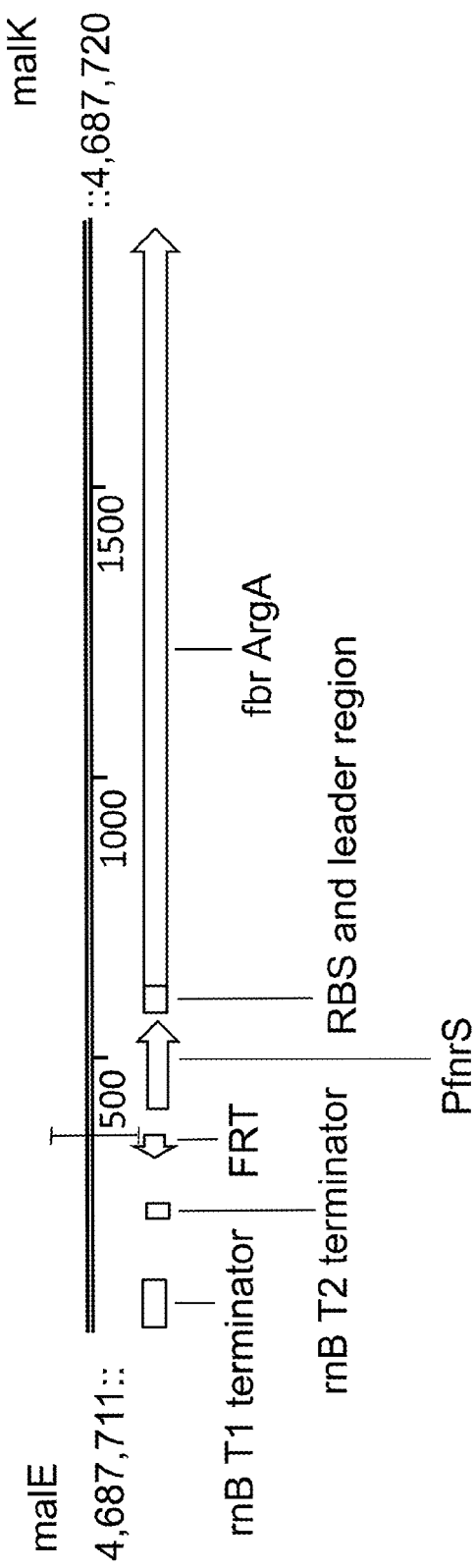
FIG. 22 depicts the gene organization of exemplary constructs of the disclosure. Non-limiting examples of strains comprising such a construct include SYN-UCD304, SYN-UCD305, SYN-UCD308, and SYN-UCD310. For example, SYN-UCD304 comprises ΔArgR, PfnrS-ArgAfbr integrated into the chromosome at the malEK locus, wild type ThyA, and no antibiotic resistance. SYN-UCD305 comprises ΔArgR, PfnrS-ArgAfbr integrated into the chromosome at the malEK locus, ΔThyA, and no antibiotic resistance.
Figure 23:
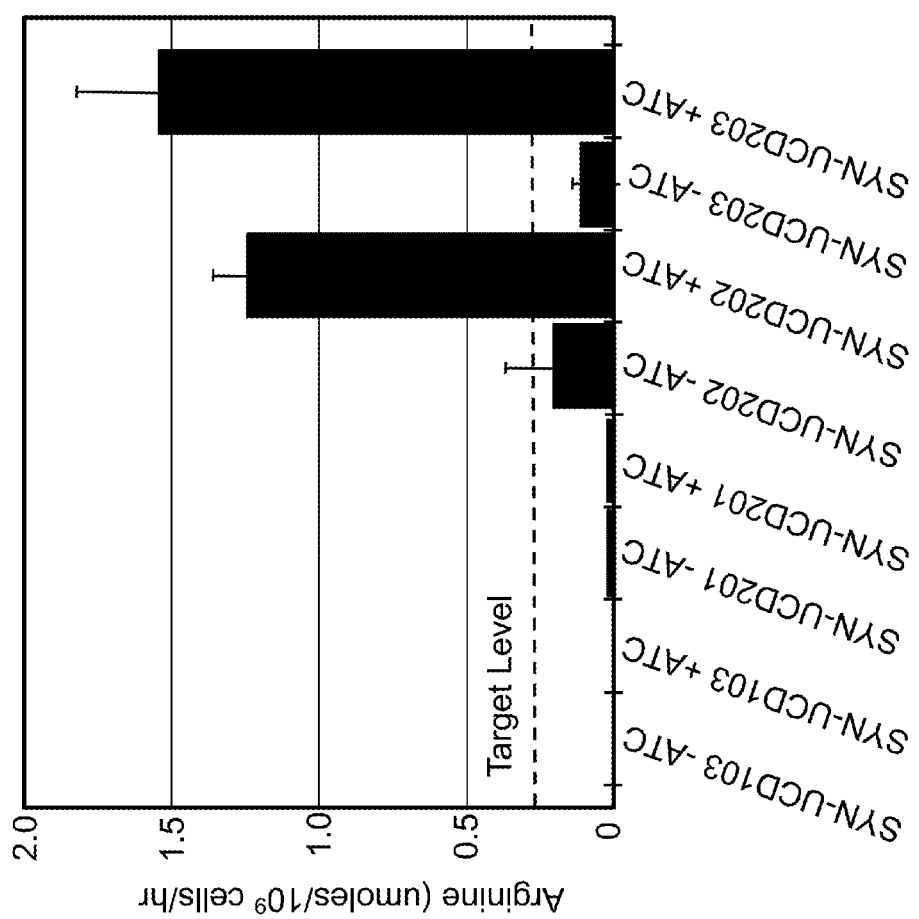
FIG. 23 depicts a bar graph of in vitro arginine levels produced by streptomycin-resistant control Nissle (SYN-UCD103), SYN-UCD201, SYN-UCD202, and SYN-UCD203 under inducing (+ATC) and non-inducing (−ATC) conditions. SYN-UCD201 comprises ΔArgR and no argA$^{fbr}$. SYN-UCD202 comprises ΔArgR and tetracycline-inducible argA$^{fbr}$ on a high-copy plasmid. SYN-UCD203 comprises ΔArgR and tetracycline-driven argA$^{fbr}$ on a low-copy plasmid.
Figure 24:
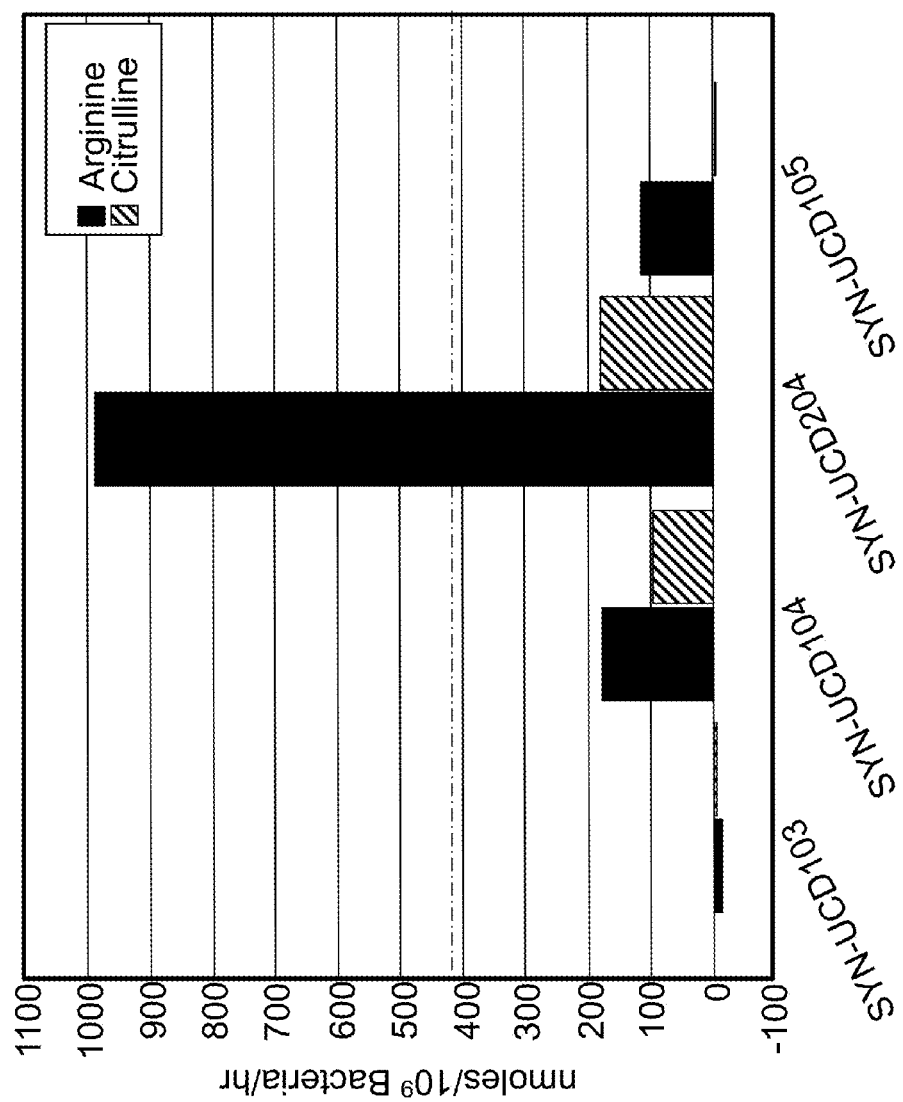
FIG. 24 depicts a bar graph of in vitro levels of arginine and citrulline produced by streptomycin-resistant control Nissle (SYN-UCD103), SYN-UCD104, SYN-UCD204, and SYN-UCD105 under inducing conditions. SYN-UCD104 comprises wild-type ArgR, tetracycline-inducible argA$^{fbr}$ on a low-copy plasmid, tetracycline-inducible argG, and mutations in each ARG box for each arginine biosynthesis operon except for argG. SYN-UCD204 comprises ΔArgR and argA$^{fbr}$ expressed under the control of a tetracycline-inducible promoter on a low-copy plasmid. SYN-UCD105 comprises wild-type ArgR, tetracycline-inducible argA$^{fbr}$ on a low-copy plasmid, constitutively expressed argG (BBa_J23100 constitutive promoter), and mutations in each ARG box for each arginine biosynthesis operon except for argG.

| Description | Sequence | SEQ ID NO |
|---|---|---|
| | CTGCCGCAGCGGCGTGCGTCGCTGTCATTTAATCAGTTA<br>TCAGGAAGATGGCGCGCTGTTGCAAGAGTTGTTCTCACG<br>CGACGGTATCGGTACGCAGATTGTGATGGAAAGCGCCGA<br>GCAGATTCGTCGCGCAACAATCAACGATATTGGCGGTAT<br>TCTGGAGTTGATTCGCCCACTGGAGCAGCAAGGTATTCT<br>GGTACGCCGTTCTCGCGAGCAGCTGGAGATGGAAATCGA<br>CAAATTCACCATTATTCAGCGCGATAACACGACTATTGC<br>CTGCGCCGCGCTCTATCCGTTCCCGGAAGAGAAGATTGG<br>GGAAATGGCCTGTGTGGCAGTTCACCCGGATTACCGCAG<br>TTCATCAAGGGGTGAAGTTCTGCTGGAACGCATTGCCGC<br>TCAGGCTAAGCAGAGCGGCTTAAGCAAATTGTTTGTGCT<br>GACCACGCGCAGTATTCACTGGTTCCAGGAACGTGGATT<br>TACCCCAGTGGATATTGATTTACTGCCCGAGAGCAAAAA<br>GCAGTTGTACAACTACCAGCGTAAATCCAAAGTGTTGAT<br>GGCGGATTTAGGGTAAgtcgacgcatgcatcgataagcc<br>gcgttctcatcctcccgcctcctcccccataaaaaagcc<br>aggggg tggaggatttaagccatctcctgatgac | |
| FNRS-fbrArgA and no antibiotic resistance, e.g., SYN-UCD305 SYN-UCD304, SYN-UCD308, SYNUCD310; a schematic of the construct is depicted in FIG. 22; UPPERCASE underline: fnrS promoter; UPPERCASE bold: ArgAfbr; UPPERCASE bold underline: terminator sequence; *UPPERCASE italic bold:* frt sites | ctacgcccca tcgttgctttgtgtgatctctgttacaga<br>attggcggtaatgtggagatgcgcacataaaatcgccat<br>gatttttgcaagcaacatcacgaaattccttacatgacc<br>tcggtttagttcacaggacgtcccatggctcgagCATGC<br>GAGAGTAGGGAACTGCCAGGCAT<u>CAAATAAAATGAAAGG</u><br><u>CTCAGTCGAAAGACTGGGCCTTTCGTTTTATCT</u>G<br>TTGTTTGTCGGTGAACGCTCTCCTGAGTAGGACAAATC<br>CGCCGGGAGCGGATTTGAACGTTGCGAAGCAACGGCCCG<br>GAGGGTGGCGGGCAGGACGCCCGCCATAAACTGCCAGGC<br>TCAAATTAAGCAGAAGGCCATCCTGACGGATGGCCTTT<br>TTGCGTGGCCAGTGCCAAGCTTGCATGCAGATTGCAGCA<br>TTACACGTCTTGAGCGATTGTGTAGGCTGGAGCTGCTTC<br>*GAAGTTCCTATACTTTCTAGAGAATAGGAACTTCGGAAT*<br>*AGGAACTA*AGGAGGATATTCATATGGACCATGGCTAATT<br>CCCAGGTACCAGTTGTTCTTATTGGTGGTGTTGCTTTAT<br>GGTTGCATCGTAGTAAATGGTTGTAACAAAAGCAATTTT<br>TCCGGCTGTCTGTATACAAAAACGCCGTAAAGTTTGAGC<br>GAAGTCAATAAACTCTCTACCCATTCAGGGCAATATCTC<br>TCTT<u>GGATCC</u>aaagtgaactctagaaataattttgttta<br>actttaagaaggagatatacatATGGTAAAGGAACGTAA<br>AACCGAGTTGGTCGAGGGATTCCGCCATTCGGTTCCCTG<br>TATCAATACCCACCGGGGAAAAACGTTTGTCATCATGCT<br>CGGCGGTGAAGCCATTGAGCATGAGAATTTCTCCAGTAT<br>CGTTAATGATATCGGGTTGTTGCACAGCCTCGGCATCCG<br>TCTGGTGGTGGTCTATGGCGCACGTCCGCAGATCGACGC<br>AAATCTGGCTGCGCATCACCACGAACCGCTGTATCACAA<br>GAATATACGTGTGACCGACGCCAAAACACTGGAACTGGT<br>GAAGCAGGCTGCGGGAACATTGCAACTGGATATTACTGC<br>TCGCCTGTCGATGAGTCTCAATAACACGCCGCTGCAGGG<br>CGCGCATATCAACGTCGTCAGTGGCAATTTTATTATTGC<br>CCAGCCGCTGGGCGTCGATGACGGCGTGGATTACTGCCA<br>TAGCGGGCGTATCCGGCGGATTGATGAAGACGCGATCCA<br>TCGTCAACTGGACAGCGGTGCAATAGTGCTAATGGGGCC<br>GGTCGCTGTTTCAGTCACTGGCGAGAGCTTTAACCTGAC<br>CTCGGAAGAGATTGCCACTCAACTGGCCATCAAACTGAA<br>AGCTGAAAAGATGATTGGTTTTTGCTCTTCCCAGGGCGT<br>CACTAATGACGACGGTGATATTGTCTCCGAACTTTTCCC<br>TAACGAAGCGCAAGCGCGGGTAGAAGCCCAGGAAGAGAA<br>AGGCGATTACAACTCCGGTACGGTGCGCTTTTTGCGTGG<br>CGCAGTGAAAGCCTGCCGCAGCGGCGTGCGTCGCTGTCA<br>TTTAATCAGTTATCAGGAAGATGGCGCGCTGTTGCAAGA<br>GTTGTTCTCACGCGACGGTATCGGTACGCAGATTGTGAT<br>GGAAAGCGCCGAGCAGATTCGTCGCGCAACAATCAACGA<br>TATTGGCGGTATTCTGGAGTTGATTCGCCCACTGGAGCA<br>GCAAGGTATTCTGGTACGCCGTTCTCGCGAGCAGCTGGA<br>GATGGAAATCGACAAATTCACCATTATTCAGCGCGATAA<br>CACGACTATTGCCTGCGCCGCGCTCTATCCGTTCCCGGA<br>AGAGAAGATTGGGGAAATGGCCTGTGTGGCAGTTCACCC<br>GGATTACCGCAGTTCATCAAGGGGTGAAGTTCTGCTGGA | SEQ ID NO: 38 |

TABLE 13-continued of Integrated argA^fbr sequences

| Description | Sequence | SEQ ID NO |
|---|---|---|
| | ACGCATTGCCGCTCAGGCTAAGCAGAGCGGCTTAAGCAA<br>ATTGTTTGTGCTGACCACGCGCAGTATTCACTGGTTCCA<br>GGAACGTGGATTTACCCCAGTGGATATTGATTTACTGCC<br>CGAGAGCAAAAAGCAGTTGTACAACTACCAGCGTAAATC<br>CAAAGTGTTGATGGCGGATTTAGGGTAAgtcgacgcatg<br>catcgataagccgcgttctcatcctccgcctcctccc<br>cataaaaaagccagggggtggaggatttaagccatctcc<br>tgatgac | |

In some embodiments, the genetically engineered bacteria comprise the nucleic acid sequence of SEQ ID NO: 36 or a functional fragment thereof. In some embodiments, the genetically engineered bacteria comprise a nucleic acid sequence that, but for the redundancy of the genetic code, encodes the same polypeptide as SEQ ID NO: 36 or a functional fragment thereof. In some embodiments, genetically engineered bacteria comprise a nucleic acid sequence that is at least about 80%, at least about 85%, at least about 90%, at least about 95%, or at least about 99% homologous to the DNA sequence of SEQ ID NO: 36 or a functional fragment thereof, or a nucleic acid sequence that, but for the redundancy of the genetic code, encodes the same polypeptide as SEQ ID NO: 37 or a functional fragment thereof.

In some embodiments, the genetically engineered bacteria comprise the nucleic acid sequence of SEQ ID NO: 37 or a functional fragment thereof. In some embodiments, the genetically engineered bacteria comprise a nucleic acid sequence that, but for the redundancy of the genetic code, encodes the same polypeptide as SEQ ID NO: 37 or a functional fragment thereof. In some embodiments, genetically engineered bacteria comprise a nucleic acid sequence that is at least about 80%, at least about 85%, at least about 90%, at least about 95%, or at least about 99% homologous to the DNA sequence of SEQ ID NO: 37 or a functional fragment thereof, or a nucleic acid sequence that, but for the redundancy of the genetic code, encodes the same polypeptide as SEQ ID NO: 37 or a functional fragment thereof.

In some embodiments, the genetically engineered bacteria comprise the nucleic acid sequence of SEQ ID NO: 38 or a functional fragment thereof. In some embodiments, the genetically engineered bacteria comprise a nucleic acid sequence that, but for the redundancy of the genetic code, encodes the same polypeptide as SEQ ID NO: 38 or a functional fragment thereof. In some embodiments, genetically engineered bacteria comprise a nucleic acid sequence that is at least about 80%, at least about 85%, at least about 90%, at least about 95%, or at least about 99% homologous to the DNA sequence of SEQ ID NO: 38 or a functional fragment thereof, or a nucleic acid sequence that, but for the redundancy of the genetic code, encodes the same polypeptide as SEQ ID NO: 38 or a functional fragment thereof.

Arginine Catabolism

An important consideration in practicing the invention is to ensure that ammonia is not overproduced as a byproduct of arginine and/or citrulline catabolism. In the final enzymatic step of the urea cycle, arginase catalyzes the hydrolytic cleavage of arginine into ornithine and urea (Cunin et al., 1986). Urease, which may be produced by gut bacteria, catalyzes the cleavage of urea into carbon dioxide and ammonia (Summerskill, 1966; Aoyagi et al., 1966; Cunin et al., 1986). Thus, urease activity may generate ammonia that can be toxic for human tissue (Konieczna et al., 2012). In some bacteria, including *E. coli* Nissle, the gene arcD encodes an arginine/ornithine antiporter, which may also liberate ammonia (Vander Wauven et al., 1984; Gamper et al., 1991; Meng et al., 1992).

AstA is an enzyme involved in the conversion of arginine to succinate, which liberates ammonia. SpeA is an enzyme involved in the conversion of arginine to agmatine, which can be further catabolized to produce ammonia. Thus, in some instances, it may be advantageous to prevent the breakdown of arginine. In some embodiments, the genetically engineered bacteria comprising a mutant arginine regulon additionally includes mutations that reduce or eliminate arginine catabolism, thereby reducing or eliminating further ammonia production. In some embodiments, the genetically engineered bacteria also comprise mutations that reduce or eliminate ArcD activity. In certain embodiments, ArcD is deleted. In some embodiments, the genetically engineered bacteria also comprise mutations that reduce or eliminate AstA activity. In certain embodiments, AstA is deleted. In some embodiments, the genetically engineered bacteria also comprise mutations that reduce or eliminate SpeA activity. In certain embodiments, SpeA is deleted. In some embodiments, the genetically engineered bacteria also comprise mutations that reduce or eliminate arginase activity. In certain embodiments, arginase is deleted. In some embodiments, the genetically engineered bacteria also comprise mutations that reduce or eliminate urease activity. In certain embodiments, urease is deleted. In some embodiments, one or more other genes involved in arginine catabolism are mutated or deleted.

Other Hyperammonemia Disorders

Hepatic encephalopathy (HE) is characterized by neurocognitive changes in patients and biochemical derangements have been implicated in pathogenesis. Specifically, elevated ammonia levels are suspected to partly contribute to disease pathophysiology. In addition to hyperammonemia, elevated levels of cerebral GABA and manganese levels have been noted and suspected to contribute to clinical presentation.

In some embodiments, the disclosure provides genetically engineered microorganisms, e.g., bacteria and virus, pharmaceutical compositions thereof, and methods of modulating or treating diseases or disorders associated with hyperammonemia, e.g., hepatic encephalopathy and Huntington's disease. The genetically engineered bacteria are capable of reducing excess ammonia in a mammal. In some embodiments, the genetically engineered bacteria reduce excess ammonia by incorporating excess nitrogen in the body into non-toxic molecules, e.g., arginine, citrulline, methionine, histidine, lysine, asparagine, glutamine, or tryptophan. In some embodiments, the genetically engineered bacteria further comprise one or more circuits (genetic sequence) to reduce the levels of other toxic or deleterious molecule(s), e.g., GABA, manganese. In some embodiments, the genetically engineered bacteria further comprise one or more circuits to produce a gut barrier enhancer molecule, e.g., a short chain fatty acid such as butyrate, propionate, and acetate. This disclosure also provides compositions and therapeutic methods for reducing excess ammonia and other deleterious molecules, e.g., GABA and manganese. In certain aspects, the disclosure provides genetically engineered bacteria that are capable of reducing excess ammonia and other deleterious molecules. In certain embodiments, the disclosure provides genetically engineered bacteria that are capable of reducing excess ammonia and other deleterious molecules and further producing one or more therapeutic molecules, such as a gut barrier function enhancer molecule, e.g., butyrate. In some embodiments, the disclosure provides genetically engineered bacteria comprising one or more circuits for reducing excess ammonia in which the circuits are under the control of an inducible promoter. In some embodiments, the disclosure provides genetically engineered bacteria comprising one or more circuits for reducing excess ammonia and one or more circuits for reducing other deleterious molecules in which one or more of the circuits are under the control of an inducible promoter. In some embodiments, the disclosure provides genetically engineered bacteria comprising one or more circuits for reducing excess ammonia and one or more circuits for reducing other deleterious molecules and further producing one or more therapeutic molecules, such as a gut barrier function enhancer molecule, e.g., butyrate in which one or more of the circuits and/or therapeutic molecule(s) are under the control of an inducible promoter. In certain aspects, the compositions and methods disclosed herein may be used for treating a disease or disorder associated with excess ammonia, for example, hepatic encephalopathy or Huntington's disease, and/or one or more symptoms associated with disease or disorder associated with excess ammonia, such as hepatic encephalopathy or Huntington's disease.

GABA Transport and Metabolism

γ-Aminobutyric acid (GABA) is the predominant inhibitory neurotransmitter in the mammalian central nervous system. In humans, GABA activates the post-synaptic $GABA_A$ receptor, which is part of a ligand-gated chloride-specific ion channel complex. Activation of this complex on a post-synaptic neuron allows chloride ions to enter the neuron and exert an inhibitory effect. Alterations of such GABAergic neurotransmission have been implicated in the pathophysiology of several neurological disorders, including epilepsy (Jones-Davis and MacDonald, 2003), Huntington's disease (Krogsgaard-Larsen, 1992), and hepatic encephalopathy (Jones and Basile, 1997).

Neurons in the brain that are modulated by GABA are said to be under inhibitory GABAergic tone. This inhibitory tone prevents neuronal firing until a sufficiently potent stimulatory stimulus is received, or until the inhibitory tone is otherwise released. Increased GABAergic tone in hepatic encephalopathy was initially described in the early 1980s, based on a report of similar visual response patterns in rabbits with galactosamine-induced liver failure and rabbits treated with allosteric modulators of the $GABA_A$ receptor (e.g., pentobarbital, diazepam) (Jones and Basile, 1997). Clinical improvements in HE patients treated with a highly selective benzodiazapene antagonist at the $GABA_A$ receptor, flumazenil, further confirmed these observations (Banksy et al., 1985; Scollo-Lavizzari and Steinmann, 1985). Increased GABAergic tone in HE has since been proposed as a consequence of one or more of the following: (1) increased GABA concentrations in the brain, (2) altered integrity of the $GABA_A$ receptor, and/or (3) increased concentrations of endogenous modulators of the $GABA_A$ receptor (Ahboucha and Butterworth, 2004).

GABA uptake in *E. coli* is driven by membrane potential and facilitated by the membrane transport protein, GabP (Li et al., 2001). GabP is a member of the amino acid/polymaine/organocation (APC) transporter superfamily, one of the two largest families of secondary active transporters (Jack et al., 2000). GabP protein, encoded by the gabP gene, consists of 466 amino acids and 12 transmembrane alpha-helices, wherein both N- and C-termini face the cytosol (Hu and King, 1998a). The GabP residue sequence also includes a consensus amphipathic region (CAR), which is conserved between members of the APC family from bacteria to mammals (Hu and King, 1998b). Upon entry into the cell, GABA is converted to succinyl semialdehyde (SSA) by GABA α-ketoglutarate transaminase (GSST). Succinate-semialdehyde dehydrogenase (SSDH) then catalyzes the second and only other specific step in GABA catabolism, the oxidation of succinyl semialdehyde to succinate (Dover and Halpern, 1972). Ultimately, succinate becomes a substrate for the citric acid (TCA) cycle.

Figure 41A:
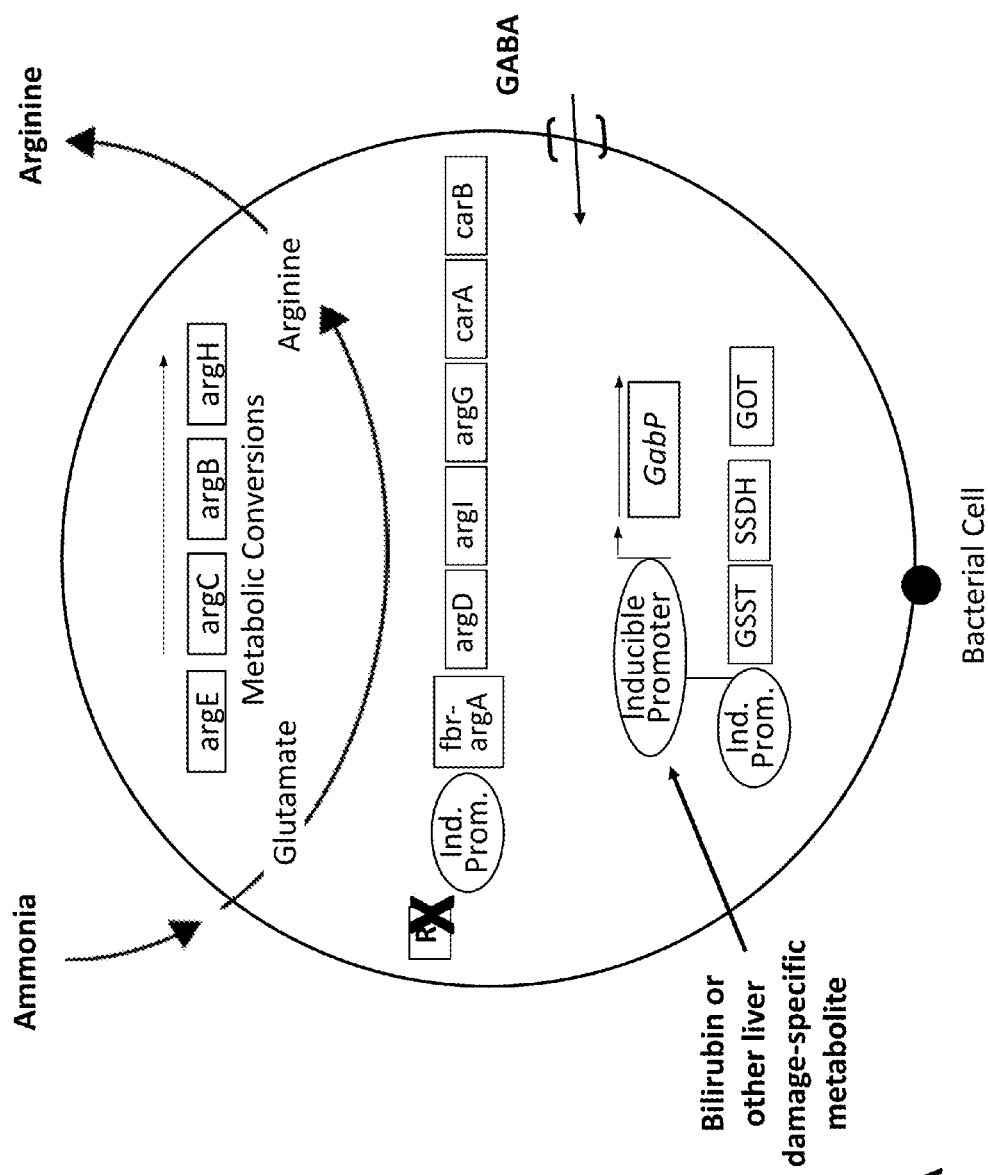
FIGS. 41A and 41B depict the catabolism of GABA following uptake into genetically engineered bacteria comprising synthetic genetic circuits.
Figure 41B:
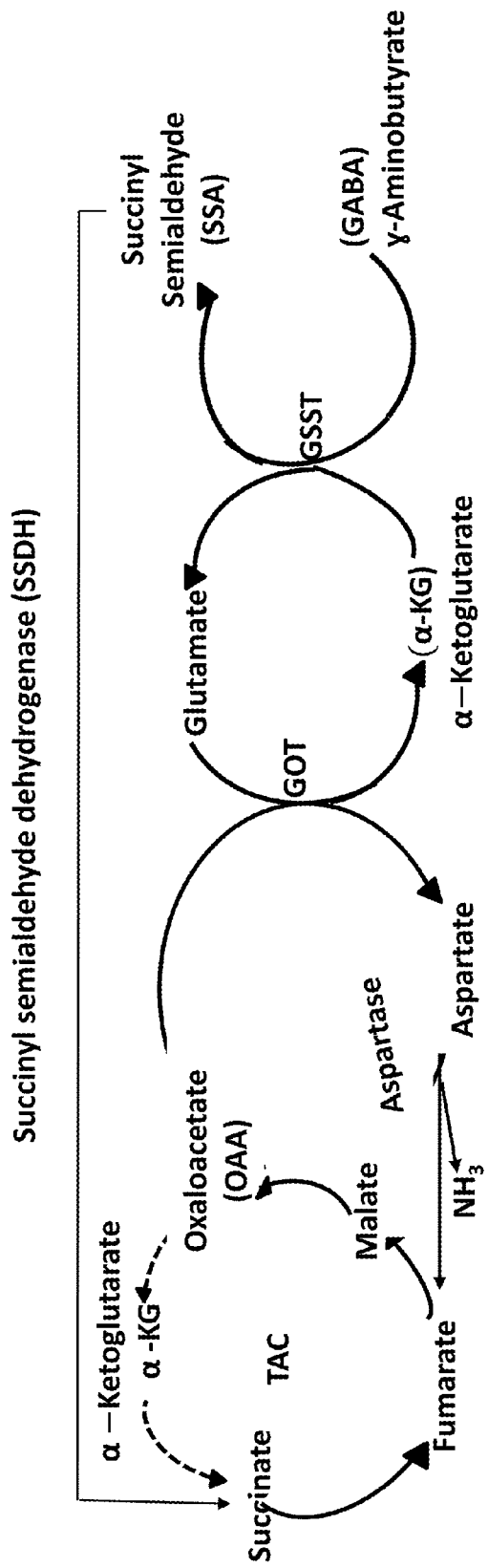

In some embodiments, the bacteria are genetically engineered to consume excess ammonia via a metabolic pathway, e.g., an arginine biosynthesis pathway, a histidine biosynthesis pathway, a methionine biosynthesis pathway, a lysine biosynthesis pathway, an asparagine biosynthesis pathway, a glutamine biosynthesis pathway, or a tryptophan biosynthesis pathway as described herein (an "ammonia conversion circuit"). In some embodiments, the genetically engineered bacteria comprise an arginine biosynthesis pathway and are capable of reducing excess ammonia. In some embodiments, the ammonia conversion circuit is under the control of an inducible promoter. In some embodiments, the ammonia conversion circuit is under the control of an oxygen level-dependent promoter, e.g., an FNR-inducible promoter. In some embodiments, the ammonia conversion circuit is under the control of a promoter induced by a molecule or metabolite associated with hepatic encephalopathy, e.g., bilirubin, aspartate aminotransferase, alanine aminotransferase, transferase, hepatitis antigens and antibodies, alpha fetoprotein, anti-mitochondrial, smooth muscle, and anti-nuclear antibodies, iron, transferrin, ferritin, copper, ceruloplasm in, ammonia, or manganese In some embodiments, the genetically engineered bacteria comprising an ammonia conversion circuit further comprise one or more circuits for producing one or more GABA membrane transport protein(s), e.g., GabP, and are capable of transporting GABA into the cell (a "GABA transport circuit") (FIG. 41).

In some embodiments, the genetically engineered bacteria comprising an ammonia conversion circuit further comprise one or more circuits for producing one or more GABA catabolism enzyme(s), e.g., GSST, SSDH, and/or COT (a "GABA metabolic circuit") (FIG. 49). In some embodiments, the genetically engineered bacteria comprising an ammonia conversion circuit further comprise one or more circuits for producing one or more GABA membrane transport protein(s), e.g., GabP, and one or more circuits for producing one or more GABA catabolism enzyme(s), e.g., GSST, SSDH, and/or COT (a "GABA metabolic circuit") (FIG. 41).

In a more specific aspect, the genetically engineered bacteria comprise an ammonia conversion circuit, a GABA transport circuit, and a GABA metabolic circuit. In some embodiments, the ammonia conversion circuit, GABA transport circuit, and GABA metabolic circuit are under the control of the same promoter. In alternate embodiments, the ammonia conversion circuit, GABA transport circuit, and GABA metabolic circuit are under the control of different promoters. Exemplary promoters include any of the promoters disclosed herein. For example, in some embodiments, the genetically engineered bacteria of the invention comprise an oxygen level-dependent promoter induced by low-oxygen, microaerobic, or anaerobic conditions. In some embodiments, the genetically engineered bacteria comprise a promoter induced by a molecule or metabolite, for example, a tissue-specific molecule or metabolite or a molecule or metabolite indicative of liver damage. Non-limiting examples of molecules or metabolites include, e.g., bilirubin, aspartate aminotransferase, alanine aminotransferase, blood coagulation factors II, VII, IX, and X, alkaline phosphatase, gamma glutamyl transferase, hepatitis antigens and antibodies, alpha fetoprotein, anti-mitochondrial, smooth muscle, and anti-nuclear antibodies, iron, transferrin, ferritin, copper, ceruloplasmin, ammonia, and manganese in their blood and intestines. In some embodiments, the genetically engineered bacteria comprise a promoter induced by inflammation or an inflammatory response, e.g., RNS or ROS promoter. In some embodiments, the genetically engineered bacteria comprise a promoter induced by a metabolite that may or may not be naturally present (e.g., can be exogenously added) in the gut, e.g., arabinose and tetracycline.

The amino acid sequence of an exemplary GabP transporter is shown in Table 42. In some embodiments, the genetically engineered bacteria comprise the amino acid sequence of SEQ ID NO: 105 or a functional fragment thereof. In some embodiments, the genetically engineered bacteria comprise a nucleic acid sequence that, but for the redundancy of the genetic code, encodes the same polypeptide as SEQ ID NO: 105 or a functional fragment thereof. In some embodiments, genetically engineered bacteria comprise an amino acid sequence that is at least about 80%, at least about 85%, at least about 90%, at least about 95%, or at least about 99% homologous to the amino acid sequence of SEQ ID NO: 105 or a functional fragment thereof, or a nucleic acid sequence that, but for the redundancy of the genetic code, encodes the same polypeptide as SEQ ID NO: 105 or a functional fragment thereof.

A non-limiting example of a polynucleotide sequence is shown in Table 43 (SEQ ID NO: 106).

Manganese Transport

Manganese is a biologically important trace metal and is required for the survival of most living organisms. In mammals, manganese is excreted in the bile, but its disposal is affected by the impaired flow of bile from the liver to the duodenum (i.e., cholestasis) that accompanies liver failure. Similar to ammonia, elevated concentrations of manganese play a role in the development of hepatic encephalopathy (Rivera-Mancía et al., 2012). Astrocytes in the brain which detoxify ammonia in a reaction catalyzed by glutamine synthetase, require manganese as a cofactor and thus have a tendency to accumulate this metal (Aschner et al., 1999). In vitro studies have demonstrated that manganese can result in the inhibition of glutamate transport (Hazell and Norenberg, 1996), abnormalities in astrocyte morphology (Hazell et al., 2006), and increased cell volume (Rama Rao et al., 2007). Manganese and ammonia have also been shown to act synergistically in the pathogenesis of hepatic encephalopathy (Jayakumar et al., 2004).

Metal ion homeostasis in prokaryotic cells, which lack internal compartmentalization, is maintained by the tight regulation of metal ion flux across in cytoplasmic membrane (Jensen and Jensen, 2014). Manganese uptake in bacteria predominantly involves two major types of transporters: proton-dependent Nramp-related transporters, and/or ATP-dependent ABC transporters. The Nramp (Natural resistance-associated macrophage protein) transporter family was first described in plants, animals, and yeasts (Cellier et al., 1996), but MntH has since been characterized in several bacterial species (Porcheron et al., 2013). Selectivity of the Nramp1 transporter for manganese has been shown in metal accumulation studies, wherein overexpression of *Staphylococcus aureus* mntH resulted in increased levels of cell-associated manganese, but no accumulation of calcium, copper, iron, magnesium, or zinc (Horsburgh et al., 2002). Additionally, *Bacillus subtilis* strains comprising a mutation in the mntH gene exhibited impaired growth in metal-free medium that was rescued by the addition of manganese (Que and Helmann, 2000). The amino acid sequence of an exemplary MntH transporter is shown in Table 44. In some embodiments, the genetically engineered bacteria comprise the amino acid sequence of SEQ ID NO: 107 or a functional fragment thereof. In some embodiments, the genetically engineered bacteria comprise a nucleic acid sequence that, but for the redundancy of the genetic code, encodes the same polypeptide as SEQ ID NO: 36 or a functional fragment thereof. In some embodiments, genetically engineered bacteria comprise an amino acid sequence that is at least about 80%, at least about 85%, at least about 90%, at least about 95%, or at least about 99% homologous to the amino acid sequence of SEQ ID NO: 107 or a functional fragment thereof, or a nucleic acid sequence that, but for the redundancy of the genetic code, encodes the same polypeptide as SEQ ID NO: 107 or a functional fragment thereof. A non-limiting example of a polynucleotide sequence is shown in Table 45 (SEQ ID NO: 108).

High-affinity manganese uptake may also be mediated by ABC (ATP-binding cassette) transporters. Members of this transporter superfamily utilize the hydrolysis of ATP to fuel the import or export of diverse substrates, ranging from ions to macromolecules, and are well characterized for their role in multi-drug resistance in both prokaryotic and eukaryotic cells. Non-limiting examples of bacterial ABC transporters involved in manganese import include MntABCD (*Bacillus subtilis, Staphylococcus aureus*), SitABCD (*Salmonella typhimurium, Shigella flexneri*), PsaABCD (*Streptococcus pneumoniae*), and YfeABCD (*Yersinia pestis*) (Bearden and Perry, 1999; Kehres et al., 2002; McAllister et al., 2004; Zhou et al., 1999). The MntABCD transporter complex consists of three subunits, wherein MntC and MntD are integral membrane proteins that comprise the permease subunit mediate cation transport, MntB is the ATPase, and MntA binds and delivers manganese to the permease submit. Other ABC transporter operons, such as sitABCD, psaABCD, and yfeABCD, exhibit similar subunit organization and function (Higgins, 1992; Rees et al., 2009).

Figure 42:
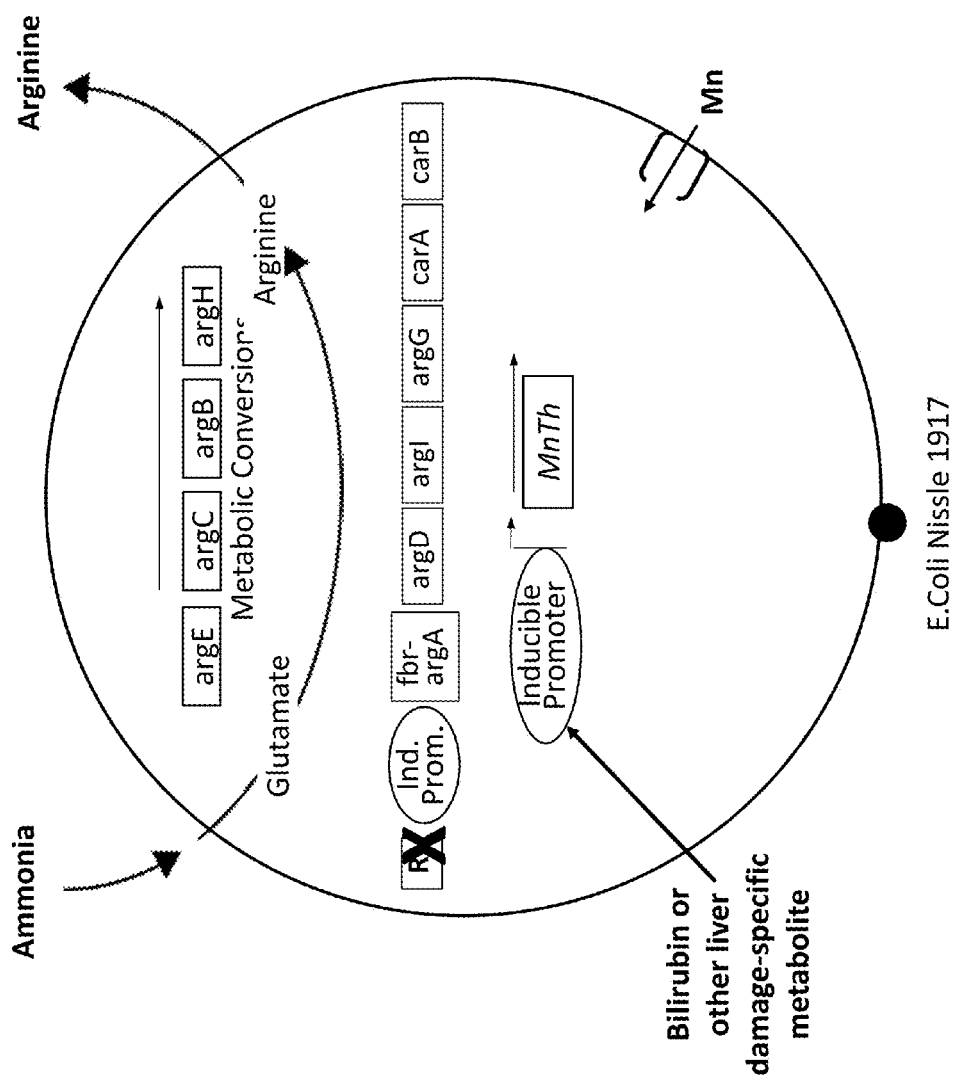
FIG. 42 depicts one embodiment of the invention. In this embodiment, the genetically engineered bacteria comprise two exemplary circuits for the treatment of hepatic encephalopathy. In one circuit, ammonia is taken up by the bacterium, converted to glutamate, and glutamate is subsequently metabolized to arginine. Arginine ultimately exits the bacterial cell. In a second circuit, the bacterial manganese transport protein (MntH) is expressed by the mntH gene, and facilitates manganese transport into the cell. In some embodiments, both circuits are under the control of the same inducible promoter. In other embodiments, the two circuits may each be under the control of different inducible promoter. Exemplary inducible promoters include oxygen level-dependent promoters (e.g., FNR-inducible promoter), promoters induced by HE-specific molecules or metabolites indicative of liver damage (e.g., bilirubin), promoters induced by inflammation or an inflammatory response, and promoters induced by a metabolite that may or may not be naturally present (e.g., can be exogenously added) in the gut, e.g., arabinose.

In some embodiments, the genetically engineered bacteria comprising an ammonia conversion circuit further comprise one or more circuits for producing a manganese membrane transport protein, e.g., MntH, and are capable of transporting manganese ions into the cell (a "manganese transport circuit") (FIG. 42).

In some embodiments, the genetically engineered bacteria comprise an ammonia conversion circuit, a manganese transport circuit, and a GABA metabolic circuit. In some embodiments, the genetically engineered bacteria comprise an ammonia conversion circuit, a manganese transport circuit, and a GABA transport circuit. In some embodiments, the genetically engineered bacteria comprise an ammonia conversion circuit, a manganese transport circuit, a GABA transport circuit, and a GABA metabolic circuit. In some embodiments, the circuits are under the control of the same promoter. In alternate embodiments, the circuits are under the control of different promoters. In some embodiments, the genetically engineered bacteria of the invention comprise an oxygen level-dependent promoter induced by low-oxygen, microaerobic, or anaerobic conditions. In some embodiments, the genetically engineered bacteria comprise a promoter induced by a molecule or metabolite, for example, a tissue-specific molecule or metabolite or a molecule or metabolite indicative of liver damage. Non-limiting examples of molecules or metabolites include, e.g., bilirubin, aspartate aminotransferase, alanine aminotransferase, blood coagulation factors II, VII, IX, and X, alkaline phosphatase, gamma glutamyl transferase, hepatitis antigens and antibodies, alpha fetoprotein, anti-mitochondrial, smooth muscle, and anti-nuclear antibodies, iron, transferrin, ferritin, copper, ceruloplasmin, ammonia, and manganese in their blood and intestines. In some embodiments, the genetically engineered bacteria comprise a promoter induced by inflammation or an inflammatory response, e.g., RNS or ROS promoter. In some embodiments, the genetically engineered bacteria comprise a promoter induced by a metabolite that may or may not be naturally present (e.g., can be exogenously added) in the gut, e.g., arabinose and tetracycline.

Production of Butyrate and Other Gut Barrier Function Enhancer Molecules

In some embodiments, the genetically engineered bacteria of the invention further comprise a gene encoding a gut barrier function enhancer molecule, or a gene cassette encoding a biosynthetic pathway capable of producing a gut barrier function enhancer molecule. In some embodiments, the molecule is selected from the group consisting of a short-chain fatty acid, butyrate, propionate, acetate, GLP-2, IL-10, IL-27, TGF-β1, TGF-β2, elafin (also known as peptidase inhibitor 3 or SKALP), trefoil factor, melatonin, PGD$_2$, kynurenic acid, and kynurenine.

In some embodiments, the genetically engineered bacteria of the invention express a gut barrier function enhancer molecule that is encoded by a single gene, e.g., the molecule is elafin and encoded by the PI3 gene. In alternate embodiments, the genetically engineered bacteria of the invention encode a gut barrier function enhancer molecule, e.g., butyrate or propionate, that is synthesized by a biosynthetic pathway requiring multiple genes.

The gene or gene cassette may be expressed on a high-copy plasmid, a low-copy plasmid, or a chromosome. In some embodiments, expression from the plasmid may be useful for increasing expression of the gut barrier function enhancer molecule. In some embodiments, expression from the chromosome may be useful for increasing stability of expression of the gut barrier function enhancer molecule. In some embodiments, the gene or gene cassette for producing the gut barrier function enhancer molecule is integrated into the bacterial chromosome at one or more integration sites in the genetically engineered bacteria. For example, one or more copies of the butyrate biosynthesis gene cassette may be integrated into the bacterial chromosome. In some embodiments, the gene or gene cassette for producing the gut barrier function enhancer molecule is expressed from a plasmid in the genetically engineered bacteria. In some embodiments, the gene or gene cassette for producing the gut barrier function enhancer molecule is inserted into the bacterial genome at one or more of the following insertion sites in *E. coli* Nissle: malE/K, araC/BAD, lacZ, thyA, malP/T. Any suitable insertion site may be used (see, e.g., FIG. 18). The insertion site may be anywhere in the genome, e.g., in a gene required for survival and/or growth, such as thyA (to create an auxotroph); in an active area of the genome, such as near the site of genome replication; and/or in between divergent promoters in order to reduce the risk of unintended transcription, such as between AraB and AraC of the arabinose operon.

In some embodiments, the genetically engineered bacteria of the invention comprise a butyrogenic gene cassette and are capable of producing butyrate. The genetically engineered bacteria may include any suitable set of butyrogenic genes (see, e.g., Table 14). Unmodified bacteria comprising butyrate biosynthesis genes are known and include, but are not limited to, *Peptoclostridium, Clostridium, Fusobacterium, Butyrivibrio, Eubacterium*, and *Treponema*, and these endogenous butyrate biosynthesis pathways may be a source of genes for the genetically engineered bacteria of the invention. In some embodiments, the genetically engineered bacteria of the invention comprise butyrate biosynthesis genes from a different species, strain, or substrain of bacteria. In some embodiments, the genetically engineered bacteria comprise the eight genes of the butyrate biosynthesis pathway from *Peptoclostridium difficile*, e.g., *Peptoclostridium difficile* strain 630: bcd2, etfB3, etfA3, thiA1, hbd, crt2, pbt, and buk (Aboulnaga et al., 2013), and are capable of producing butyrate in low-oxygen conditions, in the presence of HE-specific molecules or metabolites, in the presence of molecules or metabolites associated with liver damage, inflammation or an inflammatory response, or in the presence of some other metabolite such as arabinose. *Peptoclostridium difficile* strain 630 and strain 1296 are both capable of producing butyrate, but comprise different nucleic acid sequences for etfA3, thiA1, hbd, crt2, pbt, and buk. In some embodiments, the genetically engineered bacteria comprise a combination of butyrogenic genes from different species, strains, and/or substrains of bacteria, and are capable of producing butyrate in low-oxygen conditions or in the presence of HE-specific molecules or metabolites. For example, in some embodiments, the genetically engineered bacteria comprise bcd2, etfB3, etfA3, and thiA1 from *Peptoclostridium difficile* strain 630, and hbd, crt2, pbt, and buk from *Peptoclostridium difficile* strain 1296. In some embodiments, the genetically engineered bacteria are capable of expressing the butyrate biosynthesis cassette and producing butyrate in low-oxygen conditions or in the presence of HE-specific molecules or metabolites. The genes may be codon-optimized, and translational and transcriptional elements may be added. Table 14 depicts the nucleic acid sequences of exemplary genes in butyrate biosynthesis gene cassettes. In some embodiments, genetically engineered bacteria comprise a nucleic acid sequence that is at least about 80%, at least about 85%, at least about 90%, at least about 95%, or at least about 99% homologous to the DNA sequence of SEQ ID NO: 39, 40, 41, 42, 43, 44, 45, 46, 47, or 48 a functional fragment thereof. In some embodiments, genetically engineered bacteria comprise the nucleic acid sequence of SEQ ID NO: 39, 40, 41, 42, 43, 44, 45, 46, 47, or 48, or a functional fragment thereof.

TABLE 14

| Description | Sequence |
| --- | --- |
| bcd2 (SEQ ID NO: 39) | ATGGATTTAAATTCTAAAAAATATCAGATGCTTAAAGA GCTATATGTAAGCTTCGCTGAAAATGAAGTTAAACCTT TAGCAACAGAACTTGATGAAGAAGAAAGATTTCCTTAT GAAACAGTGGAAAAATGGCAAAAGCAGGAATGATGGG TATACCATATCCAAAAGAATATGGTGGAGAAGGTGGAG ACACTGTAGGATATATAATGGCAGTTGAAGAATTGTCT AGAGTTTGTGGTACTACAGGAGTTATATTATCAGCTCA TACATCTCTTGGCTCATGGCCTATATATCAATATGGTA ATGAAGAACAAAAACAAAAATTCTTAAGACCACTAGCA AGTGGAGAAAAATTAGGAGCATTTGGTCTTTACTGAGCC TAATGCTGGTACAGATGCGTCTGGCCAACAAACAACTG CTGTTTTAGACGGGGATGAATACATACTTAATGGCTCA AAAATATTTATAACAAACGCAATAGCTGGTGACATATA TGTAGTAATGGCAATGACTGATAAATCTAAGGGGAACA AAGGAATACAGCATTTATAGTTGAAAAAGGAACTCCT GGGTTTAGCTTTGGAGTTAAAGAAAAGAAAATGGGTAT AAGAGGTTCAGCTACGAGTGAATTAATATTTGAGGATT GCAGAATACCTAAAGAAAATTTACTTGGAAAAGAAGGT CAAGGATTTAAGATAGCAATGTCTACTCTTGATGGTGG TAGAATTGGTATAGCTGCACAAGCTTTAGGTTTAGCAC AAGGTGCTCTTGATGAAACTGTTAAATATGTAAAAGAA AGAGTACAATTTGGTAGACCATTATCAAAATTCCAAAA TACACAATTCCAATTAGCTGATAGAGAATGGTTAAGGTAC AAGCGGCTAGACACCTTGTATATCAAGCAGCTATAAAT AAAGACTTAGGAAAACCTTATGGAGTAGAAGCAGCAAT GGCAAAATTATTTGCAGCTGAAACAGCTATGGAAGTTA CTACAAAAGCTGTACAACTTCATGGAGGATATGGATAC ACTCGTGACTATCCAGTAGAAAGAATGATGAGAGATGC TAAGATAACTGAAATATATGAAGGAACTAGTGAAGTTC AAAGAATGGTTATTTCAGGAAAACTATTAAAATAG |
| etfB3 (SEQ ID NO: 40) | ATGAATATAGTCGTTTGTATAAAACAAGTTCCAGATAC AACGAAGTTAAACTAGATCCTAATACAGGTACTTTAA TTAGAGATGGAGTACCAAGTATAATAAACCCTGATGAT AAAGCAGGGTTTAGAAGAAGCTATAAAATTAAAAGAAGA AATGGGTGCTCATGTAACTGTTATAACAATGGGACCTC CTCAAGCAGATATGGCTTTAAAAGAAGCTTTAGCAATG GGTGCAGATAGAGGTATATATTATTAACAGATAGAGCATT TGCGGGTGCTGATACTTGGGCAACTTCATCAGCATTAG CAGGAGCATTAAAAAATATAGATTTTGATATTATAATA GCTGGAAGACAGGCGATAGATGGAGATACTGCACAAGT TGGACCTCAAATAGCTGAACATTTAAATCTTCCATCAA TAACATATGCTGAAGAATAAAAACTGAAGGTGAATAT GTATTAGTAAAAGACAATTTGAAGATTGTTGCCATGA CTTAAAAGTTAAAATGCCATGCCTTATAACAACTCTTA AAGATATGAACACACCAAGATACATGAAAGTTGGAAGA ATATATGATGCTTTCGAAAATGATGTAGTAGAAACATG GACTGTAAAGATATAGAAGTTGACCCTTCTAATTTAG GTCTTAAAGGTTCTCCAACTAGTGTATTTAAATCATTT ACAAAATCAGTTAAACCAGCTGGTACAATATACAATGA AGATGCGAAAACATCAGCTGGAATTATCATAGATAAAT TAAAAGAGAAGTATATCATATAA |
| etfA3 (SEQ ID NO: 41) | ATGGGTAACGTTTTAGTAGTAATAGAACAAAGAGAAAA TGTAATTCAAACTGTTTCTTTAGAATTACTAGGAAAGG CTACAGAAATAGCAAAAGATTATGATACAAAAGTTTCT GCATTACTTTTAGGTAGTAAGGTAGAAGGTTTAATAGA TACATTAGCACACTATGGTGCAGATGAGGTAATAGTAG TAGATGATGAAGCTTTAGCAGTGTATACAACTGAACCA TATACAAAAGCAGCTTATGAAGCAATAAAAGCAGCTGA CCCTATAGTTGTATTATTTGGTCAACTTCAATAGGTA GAGATTTAGCGCCTAGAGTTTCTGCTAGAATACATACA GGTCTTACTGCTGACTGTACAGGTCTTGCAGTAGCTGA AGATACAAAATTATTAATGACAAGACCTGCCTTTG GTGAAATATAATGGCAACAATAGTTTGTAAAGATTTC AGACCTCAAATGTCTACAGTTAGACCAGGGGTTATGAA GAAAAATGAACCTGATGAAACTAAAGAAGCTGTAATTA ACCGTTTCAAGGTAGAATTTAATGATGCTGATAAATTA GTTCAAGTTGTACAAGTAATAAAAGAGCTAAAAACA AGTTAAAATAGAAGATGCTAAGATATTAGTTTCTGCTG GACGTGGAATGGGTGGAAAAGAAAACTTAGACATACTT TATGAATTAGCTGAAATTAGGTGGAGAAGTTTCTGG TTCTCGTGCCACTATAGATGCAGGTTGGTTAGATAAAG CAAGACAAGTTGGTCAAACTGGTAAAACTGTAAGACCA GACCTTTATATAGCATGTGGTATATCTGGAGCAATACA ACATATAGCTGGTATGGAAGATGCTGAGTTTATAGTTG CTATAAATAAAATCCAGAAGCTCCAATATTTAAATAT GCTGATGTTGGTATAGTTGGAGATGTTCATAAAGTGCT TCCAGAACTTATCAGTCAGTTAAGTGTTGCAAAAGAAA AAGGTGAAGTTTTAGCTAACTAA |
| thiA1 (SEQ ID NO: 42) | ATGAGAGAAGTAGTAATTGCCAGTGCAGCTAGAACAGC AGTAGGAAGTTTTGGAGGAGCATTTAAATCAGTTTCAG CGGTAGAGTTAGGGGTAACAGCAGCTAAAGAAGCTATA AAAAGAGCTAACATAACTCCAGATATGATAGATGAATC TCTTTTAGGGGGAGTACTTACAGCAGGTCTTGGACAAA ATATAGCAAGACAAATAGCATTAGGAGCAGGAATACCA GTAGAAAAACCAGCTATGACTATAAATATAGTTTGTGG TTCTGGATTAAGATCTGTTTCAATGGCATCTCAACTTA TAGCATTAGGTGATGCTGATATAATGTTAGTTGGTGGA GCTGAAACATGAGTATGTCTCCTTATTTAGTACCAAG TGCAGATATGGTGCAAGAATGGGTGATGCTGCTTTTG TTGATTCAATGATAAAAGATGGATTATCAGACATATTT AATACTATCACATGGGTATTACTGCTGAAAACATAGC AGAGCAATGGAATATAACTAGAGAAGAACAAGATGAAT TAGCTCTTCAAGTCAAAATAAAGCTGAAAAAGCTCAA GCTGAAGGAAAATTTGATGAAGAAATAGTTCCTGTTGT TATAAAAGGAAGAAAAGGTGACACTGTAGTAGATAAAG ATGAATATATTAAGCCTGGCACTACAATGGAGAAACTT GCTAAGTTAAGACCTGCATTTAAAAAAGATGGAACAGT TACTGCTGGTAATGCATCAGGAATAAATGATGGTGCTG CTATGTTAGTAGTAATGGCTAAAGAAAAAGCTGAAGAA CTAGGAATAGAGCCTCTTGCAACTATAGTTTCTTATGG AACAGCTGGTGTTGACCCTAAAATAATGGGATATGGAC CAGTTCCAGCAACTAAAAAAGCTTTAGAAGCTGCTAAT ATGACTATTGAAGATATAGATTTAGTTGAAGCTAATGA GGCATTTGCTGCCCAATCTGTAGCTGTAATAAGAGACT TAAATATAGATATGAATAAAGTTAATGTTAATGGTGGA GCAATAGCTATAGGACATCCAATAGGATGCTCAGGAGC AAGAATACTTACTACACTTTTATATGAAATGAAGAGAA GAGATGCTAAAACTGGTCTTGCTACACTTTGTATAGGC GGTGGAATGGGAACTACTTTAATAGTTAAGAGATAG |
| hbd (SEQ ID NO: 43) | ATGAAATTAGCTGTAATAGGTAGTGGAACTATGGGAAG TGGTATTGTACAAACTTTTGCAAGTTGTGGACATGATG TATGTTTAAAGAGTAGAACTCAAGGTGCTATAGATAAA TGTTTAGCTTTATTAGATAAAAATTTAACTAAGTTAGT TACTAAGGGAAAAATGGATGAAGCTACAAAAGCAGAAA TATTAAGTCATGTTAGTTCAACTACTAATTATGAAGAT TTAAAAGATATGGATTTAATAATAGAAGCATCTGTAGA AGACATGAATATAAAGAAAGATGTTTTCAAGTTACTAG ATGAATTATGTAAGAAGATACTATCTTGGCAACAAAT ACTTCATCATTATCTATAACAGAAATAGCTTCTTCTAC TAAGCGCCCAGATAAAGTTATAGGAATGCATTTCTTTA ATCCAGTTCCTATGATGAAATTAGTTGAAGTTATAAGT GGTCAGTTAACATCAAAAGTTACTTTTGATACAGTATT TGAATTATCTAAGAGTATCAATAAAGTACCAGTAGATG TATCTGAATCTCCTGGATTTGTAGTAAATAGAATACTT ATACCTATGATAAATGAAGCTGTTGGTATATATGCAGA TGGTGTTGCAAGTAAAGAAGAAATAGATGAAGCTATGA AATTAGGAGCAAACCATCCAATGGGACCACTAGCATTA GGTGATTTAATCGGATTAGATGTTGTTTTAGCTATAAT GAACGTTTTATATACTGAATTTGGAGATACTAAATATA GACCTCATCCACTTTTAGCTAAAATGGTTAGAGCTAAT CAATTAGGAAGAAAAACTAAGATAGGATTCTATGATTA TAATAAATAA |
| crt2 (SEQ ID NO: 44) | ATGAGTACAAGTGATGTTAAAGTTTATGAGAATGTAGC TGTTGAAGTAGATGGAAATATATGTAGAGTGAAAATGA ATAGACCTAAAGCCCTTAATGCAATAAATTCAAAGACT TTAGAAGAACTTTATGAAGTATTTGTAGATATTAATAA TGATGAAACATTGATGTTGTAATATTGACAGGGGAAG GAAAGGCATTTGTAGCTGGAGCAGATATTGCATACATG AAAGATTTAGATGCTGGCTGCTAAAGATTTTAGTAT CTTAGGAGCAAAAGCTTTTGGAGAAATAGAAAATAGTA AAAAGTAGTGATAGCTGCTGTAAACGGATTTGCTTTA GGTGGAGGATGTGAACTTGCAATGGCATGTGATATAAG AATTGCATCTGCTAAAGCTAAATTTGGTCAGCCAGAAG TAACTCTTGGAATAACTCCAGGATATGGAGGAACTCAA AGGCTTACAAGATTGTTGGAATGGCAAAGCAAAAGA ATTAATCTTTACAGGTCAAGTTATAAAAGCTGATGAAG CTGAAAAAATAGGGCTAGTAAATAGAGTCGTTGAGCCA GACATTTTAATAGAAGAAGTTGAGAAATTAGCTAAGAT |

TABLE 14-continued

| Description | Sequence |
|---|---|
| | AATAGCTAAAAATGCTCAGCTTGCAGTTAGATACTCTA AAGAAGCAATACAACTTGGTGCTCAAACTGATATAAAT ACTGGAATAGATATAGAATCTAATTTATTTGGTCTTTG TTTTTCAACTAAAGACCAAAAAGAAGGAATGTCAGCTT TCGTTGAAAAGAGAGAAGCTAACTTTATAAAAGGGTAA |
| pbt (SEQ ID NO: 45) | ATGAGAAGTTTTGAAGAAGTAATTAAGTTTGCAAAAGA AAGAGGACCTAAAACTATATCAGTAGCATGTTGCCAAG ATAAAGAAGTTTTAATGGCAGTTGAAATGGCTAGAAAA GAAAAAATAGCAAATGCCATTTTAGTAGGAGATATAGA AAAGACTAAAGAAATTGCAAAAAGCATAGACATGGATA TCGAAAATTATGAACTGATAGATATAAAAGATTTAGCA GAAGCATCTCTAAAATCTGTTGAATTAGTTTCACAAGG AAAAGCCGACATGGTAATGAAAGGCTTAGTAGACACAT CAATAATACTAAAAGCAGTTTTAAATAAAGAAGTAGGT CTTAGAACTGGAAATGTATTAAGTCACGTAGCAGTATT TGATGTAGAGGGATATGATAGATTATTTTTCGTAACTG ACGCAGCTATGAACTTAGCTCCTGATACAAATACTAAA AAGCAAATCATAGAAAATGCTTGCACAGTAGCACATTC ATTAGATATAAGTGAACCAAAAGTTGCTGCAATATGCG CAAAAGAAAAAGTAAATCCAAAAATGAAAGATACAGTT GAAGCTAAAGAACTAGAAGAAATGTATGAAAGAGGAGA AATCAAAGGTTGTATGGTTGGTGGGCCTTTTGCAATTG ATAATGCAGTATCTTTAGAAGCAGCTAAACATAAAGGT ATAAATCATCCTGTAGCAGGACGAGCTGATATATTATT AGCCCCAGATATTGAAGGTGGTAACATATTATATAAAG CTTTGGTATTCTTCTCAAAATCAAAAATGCAGGAGTT ATAGTTGGGGCTAAAGCACCAATAATATTAACTTCTAG AGCAGACAGTGAAGAAACTAAACTAAACTCAATAGCTT TAGGTGTTTTAATGGCAGCAAAGGCATAA |
| buk (SEQ ID NO: 46) | ATGAGCAAAATATTTAAAATCTTAACAATAAATCCTGG TTCGACATCAACTAAAATAGCTGTATTTGATAATGAGG ATTTAGTATTTGAAAAAACTTTAAGACATTCTTCAGAA GAAATAGGAAAATATGAGAAGGTGTCTGACCAATTTGA ATTTCGTAAACAAGTAATAGAAGAAGCTCTAAAAGAAG GTGGAGTAAAAACATCTGAATTAGATGCTGTAGTAGGT AGAGGAGGACTTCTTAAACCTATAAAAGGTGGTACTTA TTCAGTAAGTGCTGCTATGATTGAAGATTTAAAAGTGG GAGTTTTAGGAGAACACGCTTCAAACCTAGGTGGAATA ATAGCAAAACAAATAGGTGAAGAAGTAAATGTTCCTTC ATACATAGTAGACCCTGTTGTTAGATGAATTAGAAG ATGTTGCTAGAATTTCTGGTATGCCTGAAATAAGTAGA GCAAGTGTAGTACATGCTTTAAATCAAAAGGCAATAGC AAGAAGATATGCTAGAGAAATAAACAAGAAATATGAAG ATATAAATCTTATAGTTGCACACATGGGTGGAGGAGTT TCTGTTGGAGCTCATAAAAATGGTAAAATAGTAGATGT TGCAAACGCATTAGATGGAGAAGGACCTTTCTCTCCAG AAAGAAGTGGTGGACTACCAGTAGGTGCATTAGTAAAA ATGTGCTTTAGTGGAAAATATACTCAAGATGAAATTAA AAAGAAAATAAAAGGTAATGGCGGACTAGTTGCATACT TAAACACTAATGATGCTAGAGAAGTTGAAGAAAGAATT GAAGCTGGTGATGAAAAAGCTAAATTAGTATATGAAGC TATGGCATATCAAATCTCTAAAGAAATAGGAGCTAGTG CTGCAGTTCTTAAGGGAGATGTAAAAGCAATATTATTA ACTGGTGGAATCGCATATTCAAAAATGTTTACAGAAAT GATTGCAGATAGAGTTAAATTTATAGCAGATGTAAAAG TTTATCCAGGTGAAGATGAAATGATTGCATTAGCTCAA GGTGGACTTAGAGTTTTAACTGGTGAAGAAGAGGCTCA AGTTTATGATAACTAA |
| ter (SEQ ID NO: 47) | ATGATCGTAAAACCTATGGTACGCAACAATATCTGCCT GAACGCCCATCCTCAGGGCTGCAAGAAGGGAGTGGAAG ATCAGATTGAATATACCAAGAAACGCATTACCGCAGAA GTCAAAGCTGGCGCAAAAGCTCCAAAAAACGTTCTGGT GCTTGGCTGCTCAAATGGTTACGGCCTGGCGAGCCGCA TTACTGCTGCGTTCGGATACGGGGCTGCGACCATCGGC GTGTCCTTTGAAAAAGCGGGTTCAGAAACCAAATATGG TACACCGGGATGGTACAATAATTTGGCATTTGATGAAG CGGCAAAACGCGAGGGTCTTTATAGCGTGACGATCGAC GGCGATGCGTTTTCAGACGAGATCAAGGCCCAGGTAAT TGAGGAAGCCAAAAAAAAAGGTATCAAATTTGATCTGA TCGTATACAGCTTGGCCAGCCCAGTACGTACTGATCCT GATACAGGTATCATGCACAAAAGCGTTTTGAAACCCTT TGGAAAAACGTTCACAGGCAAAACAGTAGATCCGTTTA CTGGCGAGCTGAAGGAAATCTCCGCGGAACCAGCAAAT GACGAGGAAGCAGCCGCCACTGTTAAAGTTATGGGGGG TGAAGATTGGGAACGTTGGATTAAGCAGCTGTCGAAGG |

TABLE 14-continued

| Description | Sequence |
|---|---|
| | AAGGCCTCTTAGAAGAAGGCTGTATTACCTTGGCCTAT AGTTATATTGGCCCTGAAGCTACCCAAGCTTTGTACCG TAAAGGCACAATCGGCAAGGCCAAAGAACACCTGGAGG CCACAGCACACCGTCTCAACAAAGAGAACCCGTCAATC CGTGCCTTCGTGAGCGTGAATAAAGGCCTGGTAACCCG CGCAAGCGCCGTAATCCCGGTAATCCCTCTGTATCTCG CCAGCTTGTTCAAAGTAATGAAAGAGAAGGGCAATCAT GAAGGTTGTATTGAACAGATCACGCGTCTGTACGCCGA GCGCCTGTACCGTAAAGATGGTACAATTCCAGTTGATG AGGAAAATCGCATTCGCATTGATGATTGGGAGTTAGAA GAAGACGTCCAGAAAGCGGTATCCGCGTTGATGGAGAA AGTCACGGGTGAAAACGCAGAATCTCTCACTGACTTAG CGGGGTACCGCCATGATTTCTTAGCTAGTAACGGCTTT GATGTAGAAGGTATTAATTATGAAGCGGAAGTTGAACG CTTCGACCGTATCTGA |
| tesB SEQ ID NO: 48 | ATGAGTCAGGCGCTAAAAAATTTACTGACATTGTTAAA TCTGGAAAAAATTGAGGAAGGACTCTTTCGCGGCCAGA GTGAAGATTTAGGTTTACGCCAGGTGTTTGGCGGCCAG GTCGTGGGTCAGGCCTTGTATGCTGCAAAAGAGACCGT CCCTGAAGAGCGGCTGGTACATTCGTTTCACAGCTACT TTCTTCGCCCTGGCGATAGTAAGAAGCCGATTATTTAT GATGTCGAAACGCTGCGTGACGGTAACAGCTTCAGCGC CCGCCGGGTTGCTGCTATTCAAAACGGCAAACCGATTT TTTATATGACTGCCTCTTTCCAGGCACCAGAAGCGGGT TTCGAACATCAAAAAACAATGCCGTCCGCGCCAGCGCC TGATGGCCTCCCTTCGGAAACGCAAATCGCCCAATCGC TGGCGCACCTGCTGCCGCCAGTGCTGAAAGATAAATTC ATCTGCGATCGTCCGCTGGAAGTCCGTCCGGTGGAGTT TCATAACCCACTGAAAGGTCACGTCGCAGAACCACATC GTCAGGTGTGGATCCGCGCAAATGGTAGCGTGCCGGAT GACCTGCGCGTTCATCAGTATCTGCTCGGTTACGCTTC TGATCTTAACTTCCTGCCGGTAGCTCTACAGCCGCACG GCATCGGTTTTCTCGAACCGGGGATTCAGATTGCCACC ATTGACCATTCCATGTGGTTCCATCGCCCGTTTAATTT GAATGAATGGCTGCTGTATAGCGTGGAGAGCACCTCGG CGTCCAGCGCACGTGGCTTTGTGCGCGGTGAGTTTTAT ACCCAAGACGGCGTACTGGTTGCCTCGACCGTTCAGGA AGGGGTGATGCGTAATCACAATTAA |

The gene products of the bcd2, etfA3, and etfB3 genes in *Clostridium difficile* form a complex that converts crotonyl-CoA to butyryl-CoA, which may function as an oxygen-dependent co-oxidant. In some embodiments, because the genetically engineered bacteria of the invention are designed to produce butyrate in a microaerobic or oxygen-limited environment, e.g., the mammalian gut, oxygen-dependence could have a negative effect on butyrate production in the gut. It has been shown that a single gene from *Treponema denticola* (ter, encoding trans-2-enoynl-CoA reductase) can functionally replace this three-gene complex in an oxygen-independent manner. In some embodiments, the genetically engineered bacteria comprise a ter gene, e.g., from *Treponema denticola*, which can functionally replace all three of the bcd2, etfB3, and etfA3 genes, e.g., from *Peptoclostridium difficile*. In this embodiment, the genetically engineered bacteria comprise thiA1, hbd, crt2, pbt, and buk, e.g., from *Peptoclostridium difficile*, and ter, e.g., from *Treponema denticola*, and produce butyrate in low-oxygen conditions, in the presence of HE-specific molecules or metabolites, in the presence of molecules or metabolites associated with liver damage, inflammation or an inflammatory response, or in the presence of some other metabolite that may or may not be present in the gut, such as arabinose. In some embodiments, the genetically engineered bacteria comprise genes for aerobic butyrate biosynthesis and/or genes for anaerobic or microaerobic butyrate biosynthesis. In some embodiments, the genetically engineered bacteria of the invention comprise thiA1, hbd, crt2, pbt, and buk, e.g., from *Peptoclostridium difficile*; ter, e.g., from *Treponema*

*denticola*; one or more of bcd2, etfB3, and etfA3, e.g., from *Peptoclostridium difficile*; and produce butyrate in low-oxygen conditions or in the presence of HE-specific molecules or metabolites. In some embodiments, one or more of the butyrate biosynthesis genes is functionally replaced, modified, and/or mutated in order to enhance stability and/or increase butyrate production in low-oxygen conditions or in the presence of HE-specific molecules or metabolites, or molecules or metabolites associated with liver damage, or other condition(s) such as inflammation or an inflammatory response, or in the presence of some other metabolite that may or may not be present in the gut, such as arabinose. In some embodiments, the local production of butyrate induces the differentiation of regulatory T cells in the gut and/or promotes the barrier function of colonic epithelial cells.

The gene products of pbt and buk convert butyrylCoA to Butyrate. In some embodiments, the pbt and buk genes can be replaced by a tesB gene. tesB can be used to cleave off the CoA from butyryl-coA. In one embodiment, the genetically engineered bacteria comprise bcd2, etfB3, etfA3, thiA1, hbd, and crt2, e.g., from *Peptoclostridium difficile*, and tesB from *E. Coli* and produce butyrate in low-oxygen conditions, in the presence of HE-specific molecules or metabolites, in the presence of molecules or metabolites associated with liver damage, inflammation or an inflammatory response, or in the presence of some other metabolite that may or may not be present in the gut, such as arabinose. In one embodiment, the genetically engineered bacteria comprise ter gene (encoding trans-2-enoynl-CoA reductase) e.g., from *Treponema denticola*, thiA1, hbd, crt2, pbt, and buk, e.g., from *Peptoclostridium difficile*, and tesB from *E. Coli*, and produce butyrate in low-oxygen conditions, in the presence of HE-specific molecules or metabolites, in the presence of molecules or metabolites associated with liver damage, inflammation or an inflammatory response, or in the presence of some other metabolite that may or may not be present in the gut, such as arabinose. In some embodiments, one or more of the butyrate biosynthesis genes is functionally replaced, modified, and/or mutated in order to enhance stability and/or increase butyrate production in low-oxygen conditions or in the presence of HE-specific molecules or metabolites, or molecules or metabolites associated with liver damage, or other condition(s) such as inflammation or an inflammatory response, or in the presence of some other metabolite that may or may not be present in the gut, such as arabinose. In some embodiments, the local production of butyrate induces the differentiation of regulatory T cells in the gut and/or promotes the barrier function of colonic epithelial cells.

In some embodiments, the genetically engineered bacteria of the invention comprise a propionate gene cassette and are capable of producing propionate in low-oxygen conditions or in the presence of HE-specific molecules or metabolites. The genetically engineered bacteria may express any suitable set of propionate biosynthesis genes (see, e.g., Table 15). Unmodified bacteria that are capable of producing propionate via an endogenous propionate biosynthesis pathway include, but are not limited to, *Clostridium propionicum*, *Megasphaera elsdenii*, and *Prevotella ruminicola*, and these endogenous propionate biosynthesis pathways may be a source of genes for the genetically engineered bacteria of the invention. In some embodiments, the genetically engineered bacteria of the invention comprise propionate biosynthesis genes from a different species, strain, or substrain of bacteria. In some embodiments, the genetically engineered bacteria comprise the genes pct, lcd, and acr from *Clostridium propionicum*. In some embodiments, the genetically engineered bacteria comprise acrylate pathway genes for propionate biosynthesis, e.g., pct, lcdA, lcdB, lcdC, etfA, acre, and acrC. In alternate embodiments, the genetically engineered bacteria comprise pyruvate pathway genes for propionate biosynthesis, e.g., thrA$^{fbr}$, thrB, thrC, ilvA$^{fbr}$, aceE, aceF, and lpd, and optionally further comprise tesB. The genes may be codon-optimized, and translational and transcriptional elements may be added. Table 15 depicts the nucleic acid sequences of exemplary genes in the propionate biosynthesis gene cassette. In some embodiments, genetically engineered bacteria comprise a nucleic acid sequence that is at least about 80%, at least about 85%, at least about 90%, at least about 95%, or at least about 99% homologous to the DNA sequence of SEQ ID NO: 48, 49, 50, 51, 52, 53, 54, 55, 56, 57, 58, 59, 60, 61 or 62 a functional fragment thereof. In some embodiments, genetically engineered bacteria comprise the nucleic acid sequence of SEQ ID NO: 48, 49, 50, 51, 52, 53, 54, 55, 56, 57, 58, 59, 60, 61 or 62, or a functional fragment thereof.

TABLE 15

| Description | Sequence |
|---|---|
| pct SEQ ID NO: 49 | ATGCGCAAAGTGCCGATTATCACGGCTGACGAGGCCGC<br>AAAACTGATCAAGGACGGCGACACCGTGACAACTAGCG<br>GCTTTGTGGGTAACGCGATCCCTGAGGCCCTTGACCGT<br>GCAGTCGAAAAGCGTTTCCTGGAAACGGGCGAACCGAA<br>GAACATTACTTATGTATATTGCGGCAGTCAGGGCAATC<br>GCGACGGTCGTGGCGCAGAACATTTCGCGCATGAAGGC<br>CTGCTGAAACGTTATATCGCTGGCCATTGGGCGACCGT<br>CCCGGCGTTAGGGAAAATGGCCATGGAGAATAAAATGG<br>AGGCCTACAATGTCTCTCAGGGCGCCTTGTGTCATCTC<br>TTTCGCGATATTGCGAGCCATAAACCGGGTGTGTTCAC<br>GAAAGTAGGAATCGGCACCTTCATTGATCCACGTAACG<br>GTGGTGGGAAGGTCAACGATATTACCAAGGAAGATATC<br>GTAGAACTGGTGGAAATTAAAGGGCAGGAATACCTGTT<br>TTATCCGGCGTTCCCGATCCATGTCGCGCTGATTCGTG<br>GCACCTATGCGGACGAGAGTGGTAACATCACCTTTGAA<br>AAAGAGGTAGCGCCTTTGGAAGGGACTTCTGTCTGTCA<br>AGCGGTGAAGAACTCGGGTGGCATTGTCGTGGTTCAGG<br>TTGAGCGTGTCGTCAAAGCAGGCACGCTGGATCCGCGC<br>CATGTGAAAGTTCCGGGTATCTATGTAGATTACGTAGT<br>CGTCGCGGATCCGGAGGACCATCAACAGTCCCTTGACT<br>GCGAATATGATCCTGCCCTTAGTGGAGAGCACCGTCGT<br>CCGGAGGTGGTGGGTGAACCACTGCCTTTATCCGCGAA<br>GAAAGTCATCGGCCGCCGTGGCGCGATTGAGCTCGAGA<br>AAGACGTTGCAGTGAACCTTGGGGTAGGTGCACCTGAG<br>TATGTGGCCTCCGTGGCCGATGAAGAAGGCATTGTGGA<br>TTTTATGACTCTCACAGCGGAGTCCGGCGCTATCGGTG<br>GCGTTCCAGCCGGCGGTGTTCGCTTTGGGGCGAGCTAC<br>AATGCTGACGCCTTGATCGACCAGGGCTACCAATTTGA<br>TTATTACGACGGTGGGGGTCTGGATCTTTGTTACCTGG<br>GTTTAGCTGAATGCGACGAAAAGGGTAATATCAATGTT<br>AGCCGCTTCGGTCCTCGTATCGCTGGGTGCGGCGGATT<br>CATTAACATTACCCAAAACACGCCGAAAGTCTTCTTTT<br>GTGGGACCTTTACAGCCGGGGGCTGAAAGTGAAAATT<br>GAAGATGGTAAGGTGATTATCGTTCAGGAAGGGAAACA<br>GAAGAAATTCCTTAAGGCAGTGGAGCAAATCACCTTTA<br>ATGGAGACGTGGCCTTAGCGAACAAGCAACAAGTTACC<br>TACATCACGGAGCGTTGCGTCTTCCTCCTCAAAGAAGA<br>CGGTTTACACCTTTCGGAAATCGCGCCAGGCATCGATC<br>TGCAGACCCAGATTTTGGATGTTATGGACTTTGCCCCG<br>ATCATTGATCGTGACGCAAACGGGCAGATTAAACTGAT<br>GGACGCGGCGTTATTCGCAGAAGGGCTGATGGGCTTGA<br>AAGAAATGAAGTCTTAA |
| lcdA SEQ ID NO: 50 | ATGAGCTTAACCCAAGGCATGAAAGCTAAACAACTGTT<br>AGCATACTTTCAGGGTAAAGCCGATCAGGATGCACGTG<br>AAGCGAAAGCCCGCGGTGAGCTGGTCTGCTGGTCGGCG<br>TCAGTCGCGCCGCCGGAATTTTGCGTAACAATGGGCAT<br>TGCCATGATCTACCCGGAGACTCATGCAGCGGGCATCG<br>GTGCCCGCAAAGGTGCGATGGACATGCTGGAAGTTGCG<br>GACCGCAAAGGCTACAACGTGGATTGTTGTTCCTACGG<br>CCGTGTAAATATGGGTTACATGGAATGTTTAAAAGAAG<br>CCGCCATCACGGGCGTCAAGCCGGAAGTTTTGGTTAAT<br>TCCCCTGCTGCTGACGTTCCGCTTCCCGATTTGGTGAT |

TABLE 15-continued

| Description | Sequence |
|---|---|
| | TACGTGTAATAATATCTGTAACACGCTGCTGAAATGGT ACGAAAACTTAGCAGCAGAACTCGATATTCCTTGCATC GTGATCGACGTACCGTTTAATCATACCATGCCGATTCC GGAATATGCCAAGGCCTACATCGCGGACCAGTTCCGCA ATGCAATTTCTCAGCTGGAAGTTATTTGTGGCCGTCCG TTCGATTGGAAGAAATTTAAGGAGGTCAAAGATCAGAC CAGCGTAGCGTATACCACTGGAACCGCATTGCCGAGA TGGCGAAATACAAGCCTAGCCCGCTGAACGGCTTCGAT CTGTTCAATTACATGGCGTTAATCGTGGCGTGCCGCAG CCTGGATTATGCAGAAATTACCTTTAAAGCGTTCGTGG ACGAATTAGAAGAGAATTTGAAGGCGGGTATCTACGCC TTTAAAGGTGCGGAAAAAACGCGCTTTCAATGGGAAGG TATCGCGGTGTGGCCACATTTAGGTCACACGTTTAAAT CTATGAAGAATCTGAATTCGATTATGACCGGTACGGCA TACCCCGCCCTTTGGGACCTGCACTATGACGCTAACGA CGAATCTATGCACTCTATGGCTGAAGCGTACACCCGTA TTTATATTAATACTTGTCTGCAGAACAAAGTAGAGGTC CTGCTTGGGATCATGGAAAAAGGCCAGGTGGATGGTAC CGTATATCATCTGAATCGCAGCTGCAAACTGATGAGTT TCCTGAACGTGGAAACGGCTGAAATTATTAAAGAGAAG AACGGTCTTCCTTACGTCTCCATTGATGGCGATCAGAC CGATCCTCGCGTTTTTCTCCGGCCCAGTTTGATACCC GTGTTCAGGCCCTGGTTGAGATGATGGAGGCCAATATG GCGGCAGCGGAATAA |
| lcdB SEQ ID NO: 51 | ATGTCACGCGTGGAGGCAATCCTGTCGCAGCTGAAAGA TGTCGCCGCGAATCCGAAAAAAGCCATGGATGACTATA AAGCTGAAACAGGTAAGGCGCGGTTGGTATCATGCCG ATCTACAGCCCCGAAGAAATGGTACACGCCGCTGGCTA TTTGCCGATGGGAATCTGGGGCGCCCAGGGCAAAACGA TTAGTAAAGCGCGCACCTATCTGCCTGCTTTTGCCTGC AGCGTAATGCAGCAGGTTATGCAATTACAGTGCGAGGG CGCGTATGATGACCTGTCCGCAGTTATTTTAGCGTAC CGTGCGACACTCTCAAATGTCTTAGCCAGAAATGGAAA GGTACGTCCCAGTGATTGTATTTACGCATCCGCAGAA CCGCGATTAGAAGCGGCGAACAATTCTTGGTTACCG AGTATGAACTGGTAAAAGCACAACTGGATCAGTTCTG GGTGTGAAAATTTCAAACGCCGCCCTGGAAAATTCGAT TGCAATTTATAACGAGAATCGTGCCGTGATGCGTGAGT TCGTGAAAGTGGCAGCGGACTATCCTCAAGTCATTGAC GCAGTGAGCCGCCACGCGGTTTTTAAAGCGCGCCAGTT TATGCTTAAGGAAAAACATACCGCACTTGTGAAAGAAC TGATCGCTGAGATTAAAGCAACGCCAGTCCAGCCGTGG GACGGAAAAAGGTTGTAGTGCAGCATTCTGTTGGA ACCGAATGAGTTATTAGATATCTTTAATGAGTTTAAGA TCGCGATTGTTGATGATGATTTAGCGCAGGAAAGCCGT CAGATCCGTGTTGACGTTCTGGACGGAGAAGGCGGACC GCTCTACCGTATGGCTAAAGCGTGACGCAAATGTATG GCTGCTCGCTGGCAACCGACACCAAGAAGGGTCGCGGC CGTATGTTAATTAACAAAACGATTCAGACCGGTGCGGA CGCTATCGTAGTTGCAATGATGAAGTTTGCGACCCAG AAGAATGGGATTATCCGGTAATGTACCGTGAATTTGAA GAAAAAGGGGTCAAATCACTTATGATTGAGGTGGATCA GGAAGTATCGTCTTTCGAACAGATTAAAACCCGTCTGC AGTCATTCGTCGAAATGCTTTAA |
| lcdC SEQ ID NO: 52 | ATGTATACCTTGGGGATTGATGTCGGTTCTGCCTCTAG TAAAGCGGTGATTCTGAAAGATGGAAAAGATATTGTCG CTGCCGAGGTTGTCCAAGTCGGTACCGGCTCCTCGGGT CCCCAACGCGCACTGGACAAAGCCTTTGAAGTCTCTGG CTTAAAAAAGGAAGACATCAGCTACACAGTAGCTACGG GCTATGGCGCTTCAATTTTAGCGACGCGGATAAACAG ATTTCGGAAATTAGCTGTCATGCCAAAGGCATTTATTT CTTAGTACCAACTGCGCGCACTATTATTGACATTGGCG GCCAAGATGCGAAAGCCATCCGCCTGGACGACAAGGGG GTATTAAGCAATTCTTCATGAATGATAAATGCGCGGC GGGCACGGGGCGTTTCCTGGAAGTCATGCTCGCGTAC TTGAAACCACCCTGGATGAAATGGCTGAACTGGATGAA CAGGCGACTGACACCGCTCCCATTTCAAGCACCTGCAC GGTTTTCGCCGAAAGCGAAGTAATTAGCCAATTGAGCA ATGGTGTCTCACGCAACAACATCATTAAAGGTGTCCAT CTGAGCGTTGCGTCACGTGCGTGTGCTGGCGTATCG CGGCGGTTTGGAGAAAGATGTTGTTATGCAGGTGGCG TGGCAAAAATGCAGGGGTGGTGCGCGCGGTGGCGGGC GTTCTGAAGACCGATGTTATCGTTGCTCCGAATCCTCA GACGACCGGTGCACTGGGGGCAGCGCTGTATGCTTATG AGGCCGCCCAGAAGAAGTA |
| etfA SEQ ID NO: 53 | ATGGCCTTCAATAGCGCAGATATTAATTCTTTCCGCGA TATTTGGGTGTTTTGTGAACAGCGTGAGGGCAAACTGA TTAACACCGATTTCGAATTAATTAGCGAAGGTCGTAAA CTGGCTGACGAACGCGGAAGCAAACTGGTTGGAATTTT GCTGGGGCACGAAGTTGAAGAAATCGCAAAAGAATTAG GCGGCTATGGTGCGACAAAGGTAATTGTGTGCGATCAT CCGGAACTTAAATTTTACACTACGGATGCTTATGCCAA AGTTTTATGTGACGTCGTGATGGAAGAGAAACCGGAGG TAATTTTGATCGGTGCCACCAACATTGGCCGTGATCTC GGACCGCGTTGTGCTGCACGCTTGCACACGGGGCTGAC GGCTGATTGCACGCACCTGGATATTGATATGAATAAT ATGTGGACTTTCTTAGCACCAGTAGCACCTTGGATATC TCGTCGATGACTTTCCCTATGGAAGATACAAACCTTAA AATGACGCGCCCTGCATTTGGCGGACATCTGATGGCAA CGATCATTTGTCCACGCTTCCGTCCCTGTATGAGCACA GTGCGCCCCGGAGTGATGAAGAAAGCGGAGTTCTCGCA GGAGATGGCGCAAGCATGTCAAGTAGTGACCCGTCACG TAAATTTGTCGGATGAAGACCTTAAAACTAAAGTAATT AATATCGTGAAGGAAACGAAAAAGATTGTGGATCTGAT CGGCGCAGAAATTATTGTGTCAGTTGGTCGTGGTATCT CGAAAGATGTCCAAGGTGGAATTGCACTGGCTGAAAAA CTTGCGGACGCATTTGGTAACGGTGTCGTGGGCGGCTC GCGCGCAGTGATTGATTCCGGCTGGTTACCTGCGGATC ATCAGGTTGGACAAACCGGTAAGACCGTGCACCCGAAA GTCTACGTGGCGCTGGGTATTAGTGGGCTATCCAGCA TAAGGCTGGGATGCAAGACTCTGAACTGATCATTGCCG TCAACAAAGACGAAACGGCGCCTATCTTCGACTGCGCC GATTATGGCATCACCGGTGATTTATTTAAAATCGTACC GATGATGATCGACGCGATCAAAGAGGGTAAAAACGCAT GA |
| acrB SEQ ID NO: 54 | ATGCGCATCTATGTGTGTGTGAAACAAGTCCCAGATAC GAGCGGCAAGGTGGCCGTTAACCCTGATGGGACCCTTA ACCGTGCCTCAATGGCAGCGATTATTAACCCGGACGAT ATGTCCGCGATCGAACAGGCATTAAAACTGAAAGATGA AACCGATGCCAGGTTACGGCGCTTACGATGGGTCCTC CTCCTGCCGAGGGCATGTGCGCGAAATTATTGCAATG GGGGCCGACGATGGTGTGCTGATTTCGGCCCGTGAATT TGGGGGGTCCGATACCTTCGCAACCAGTCAAATTATTA GCGCGGCAATCCATAAATTAGGCTTAAGCAATGAAGAC ATGATCTTTTGCGGTCGTCAGGCCATTGACGGTGATAC GGCCCAAGTCGGCCCTCAAATTGCCGAAAAACTGAGCA TCCCACAGGTAACCTATGGCGCAGGAATCAAAAAATCT GGTGATTTAGTCTGGTGAAGCGTATGTTGAGGATGG TTATATGATGATCGAAGTCGAAACTCCATGTCTGATTA CCTGCATTCAGGATAAAGCGGTAAAACCACGTTACATG ACTCTCAACGGTATTATGGAATGCTACTCCAAGCCGCT CCTCGTTCTCCAAGTTGATACCGGACGACTGAAAGATGAACCGC TGATCGAACTTGATACCATTGGGCTTAAAGGCTCCCCG ACGAATATCTTTAAATCGTTTACGCCGCCTCAGAAAGG CGTTGGTGTCATGCTCCAAGGCACCGATAAGGAAAAAG TCGAGGATCTGGTGGATAAGCTGATGCAGAAACATGTC ATCTAA |
| acrC SEQ ID NO: 55 | ATGTTCTTACTGAAGATTAAAAAAGAACGTATGAAACG CATGGACTTTAGTTTAACGCGTGAACAGGAGATGTTAA AAAAACTGGCGCGTCAGTTTGCTGAGATCGAGCTGGAA CCGGTGGCCGAAGAGATTGATCGTGAGCACGTTTTTCC TGCAGAAAACTTTAAGGAAGATGGCGGAAATTGGCTTAA CCGGGCATTGGTATCCCGAAAGAATTTGGTGGCTCCGGT GGAGGCCACCCTGGAAGAGTTCATTGCCGTGTCAGAATT CGGCAAAAAGTGTATGGCCTCAGCTTCCCATTTAAGCA TTCATCTTATCGCCCGCAGGCAATCTACAAATATGGG ACCAAAGAACAGAAAGAGACGTACCTGCCGCGTCTTAC CAAAGGTGGTGAACTGGGCGCCTTTGCGCTGACAGAAC CAAACGCCGGAAGCGATGCCGGCGCGGTAAAAACGACC GCGATTCTGGACAGCCAGACAAACGAGTACGTGCTGAA TGGCACCAAATGCTTTATCAGCGGGGCGGGCGCGCGG GTGTTCTTGTAATTTTTGCGCTTACTGAACCGAAAAAA GGTCTGAAAGGGATGAGCGCGATTATCGTGGAGAAAGG GACCCCGGGCTTCAGCATCGGCAAGGTGGAGAGCAAGA TGGGGATCGCAGGTTCGGAAACCGCGGAACTTATCTTC GAAGATTGTCCGCTTCCAACCTTTAGGTAA AGAAGGCAAAGGCTTTAAAATTGCTATGGAAGCCCTGG ATGGCGCCCGTATTGGCGTGGGCGCTCAAGCAATCGGA ATTGCCGAGGGGCGATCGACCTGAGTGTGAAGTACGT TCACGAGCGCATTCAATTTGGTAAACCGATCGCGAATC TGCAGGGAATTCAATGGTATATCGCGGATATGGCGACC |

TABLE 15-continued

| Description | Sequence |
|---|---|
| | AAAACCGCCGCGGCACGCGCACTTGTTGAGTTTGCAGC<br>GTATCTTGAAGACGCGGGTAAACCGTTCACAAAGGAAT<br>CTGCTATGTGCAAGCTGAACGCCTCCGAAAACGCGCGT<br>TTTGTGACAAATTTAGCTCTGCAGATTCACGGGGGTTA<br>CGGTTATATGAAAGATTATCCGTTAGAGCGTATGTATC<br>GCGATGCTAAGATTACGGAAATTTACGAGGGGACATCA<br>GAAATCCATAAGGTGGTGATTGCGCGTGAAGTAATGAA<br>ACGCTAA |
| thrA$^{fbr}$<br>SEQ ID NO:<br>56 | ATGCGAGTGTTGAAGTTCGGCGGTACATCAGTGGCAAA<br>TGCAGAACGTTTTCTGCGTGTTGCCGATATTCTGGAAA<br>GCAATGCCAGGCAGGGGCAGGTGGCCACCGTCCTCTCT<br>GCCCCCGCCAAAATCACCAACCACCTGGTGGCGATGAT<br>TGAAAAAACCATTAGCGGCCAGGATGCTTTACCCAATA<br>TCAAGCGATGCCGAACGTATTTTTGCCGAACTTTTGACG<br>GGACTCGCCGCCGCCCAGCCGGGGTTCCCGCTGGCGCA<br>ATTGAAAACTTTCGTCGATCAGGAATTTGCCCAAATAA<br>AACATGTCCTGCATGGCATTAGTTTGTTGGGGCAGTGC<br>CCGGATAGCATCAACGCTGCGTCGATTTGCCGTGGCGA<br>GAAAATGTCGATCGCCATTATGGCCGGCGTATTAGAAG<br>CGCGCGGTCACAACGTTACTGTTATCGATCCGGTCGAA<br>AAACTGCTGGCAGTGGGGCATTACCTCGAATCTACCGT<br>CGATATTGCTGAGTCCACCCGCCGTATTGCGGCAGGCG<br>GCATTCCGGCTGATCACATGGTGCTGATGGCAGGTTTC<br>ACCGCCGGTAATGAAAAAGGCGAACTGGTGGTGCTTGG<br>ACGCAACGGTTCCGACTACTCTGCTGCGGTGCTGGCTG<br>CCTGTTTACGCGCCGATTGTTGCGAGATTTGGACGGAC<br>GTTGACGGGGTCTATACCTGCGACCCGCGTCAGGTGCC<br>CGATGCGAGGTTGTTGAAGTCGATGTCCTACCAGGAAG<br>CGATGGAGCTTTCCTACTTCGGCGCTAAAGTTCTTCAC<br>CCCCGCACCATTACCCCCATCGCCCAGTTCCAGATCCC<br>TTGCCTGATTAAAAATACCGGAAATCCTCAAGCACCAG<br>GTACGCTCATTGGTGCCAGCCGTGATGAAGACGACTGG<br>CCGGTCAAGGGCATTTCCAATCTGAATAACATGGCAAT<br>GTTCAGCGTTTCTGGTCCGGGGATGAAAGGGATGGTCG<br>GCATGGCGGCGCGTCTTTGCAGCGATGTCACGCGCC<br>CGTATTTCCGTGGTGCTGATTACGCAATCATCTTCCGA<br>ATACAGCATCAGTTTCTGCGTTCCACAAAGCGACTGTG<br>TGCGAGCTGAACGGGCAATGCAGGAAGAGTTCTACCTG<br>GAACTGAAAGAAGGCTTACTGGAGCCGCTGGCAGTGAC<br>GGAACGGCTGGCCATTATCTCGGTGGTAGGTGATGGTA<br>TGCGCACCTTGCGTGGGATCTCGGCGAAATTCTTTGCC<br>GCACTGGCCCGCCGCCAATATCAACATTGTCGCCATTGC<br>TCAGAGATCTTCTGAACGCTCAATCTCTGTCGTGGTAA<br>ATAACGATGATGCGACCACTGGCGTGCGCGTTACTCAT<br>CAGATGCTGTTCAATACCGATCAGGTTATCGAAGTGTT<br>TGTGATTGGCGTCGGTGGCGTTGGCGGTGCGCTGCTGG<br>AGCAACTGAAGCGTCAGCAAAGCTGGCTGAAGAATAAA<br>CATATCGACTTACGTGTCTGCGGTGTTGCCAACTCGAA<br>GGCTCTGCTCACCAATGTACATGGCCTTAATCTGGAAA<br>ACTGGCAGGAAGAACTGGCGCAAGCCAAAGAGCCGTTT<br>AATCTCGGGCGCTTAATTCGCCTCGTGAAAGAATATCA<br>TCTGCTGAACCCGGTCATTGTTGACTGCACTTCCAGCC<br>AGGCAGTGGCGGATCAATATGCCGATTCCTGCGCAAGG<br>GGTTTCCACGTTGTCACGCCGAACAAAAAGGCCAACAC<br>CTCGTCGATGGATTACTACCATCAGTTGCGTTATGCGG<br>CGGAAAAATCGCGGCGTAAATTCCTCTATGACACCAAC<br>GTTGGGGCTGGATTACCGGTTATTGAGAACCTGCAAAA<br>TCTGCTCAATGCAGGTGATGAATTGATGAAGTTGTCCG<br>GCATTCTTTCTGGTTCGCTTTCTTATATCTTCGGCAAG<br>TTAGACGAAGGCATGAGTTTCTCCGAGGCGACCACGCT<br>GGCGCGGGAAATGGGTTATACCGAACCGGACCCCGCGAG<br>ATGATCTTTCTGGTATGGATGTGGCGCGTAAACTATTG<br>ATTCTCGCTCGTCGAAACGGACGTGAACTGGAGCTGGC<br>GGATATTGAAATTGAACCTGTCTGCCCGCAGAGTTTAA<br>ACGCCGAGGGTGATGTTGCCGCTTTTATGGCGAATCTG<br>TCACAACTCGACGATCTCTTTGCCGCGCGCGTGGCGAA<br>GGCCCGTGATGAAGGAAAAGTTTTGCGCTATGTTGGCA<br>ATATTGATGAAGATGGCGTCTGCCGCGTGAAGATTGCA<br>GAAGTGGATGGTAATGATCCGCTGTTCAAAGTGAAAAA<br>TGGCGAAAACGCCCTGGCCTTCTATAGCCACTATTATC<br>AGCCGCTGCCGTTGGTACTGCGCGGATATGGTGCGGGC<br>AATGACGTTACAGCTGCCGGTGTCTTTGCTGATCTGCT<br>ACGTACCCTCTCATGGAAGTTAGGAGTCTGA |
| thrB<br>SEQ ID NO:<br>57 | ATGGTTAAAGTTTATGCCCCGGCTTCCAGTGCCAATAT<br>GAGCGTCGGGTTTGATGTGCTCGGGGCGGCCGGTGACAC<br>CTGTTGATGGTGCATTGCTCGGAGATGTAGTCACGGTT<br>GAGGCGGCAGAGACATTCAGTCTCAACAACCTCGGACG<br>CTTTGCCGATAAGCTGCCGTCAGAACCACGGGAAAATA<br>TCGTTTATCGTGCTGGGGAGCGTTTTTGCCAGGAACTG<br>GGTAAGCAAATTCCAGTGGCGATGACCCTGGAAAAGAA<br>TATGCCGATCGGTTCGGGCTTAGGCTCCAGTGCCTGTT<br>CGGTGGTCGCGGCGCTGATGGCGATGAATGAACACTGC<br>GGCAAGCCGCTTAATGACACTCGTTTGCTGGCTTTGAT<br>GGGCGAGCTGGAAGGCCGTATCTCCGGCAGCATTCATT<br>ACGACAACGTGGCACCGTGTTTTCTCGGTGGTATGCAG<br>TTGATGATCGAAGAAACGACATCATCAGCCAGCAAGT<br>GCCAGGGTTTGATGAGTGGCTGTGGGTGCTGGCGTATC<br>CGGGGATTAAAGTCTCGACGGCAGAAGCCAGGGCTATT<br>TTACCGGCCGCAGTATCGCCGCCAGGATTGCATTGCGCA<br>CGGGCGACATCTGGCAGGCTTCATTCACGCCTGCTATT<br>CCCGTCAGCCTGAGCTTGCCGCGAAGCTGATGAAAGAT<br>GTTATCGCTGAACCCTACCGTGAACGGTTACTGCCAGG<br>CTTCCGGCAGGCGCGGCAGGCGGTCGCGGAAATCGGCG<br>CGGTAGCGAGCGGTATCTCCGGCTCCGGCCCGACCTTG<br>TTCGCTCTGTGTGACAAGCCGGAAACCGCCCAGCGCGT<br>TGCCGACTGGTTGGGTAAGAACTACCTGCAAAATCAGG<br>AAGGTTTTGTTCATATTTGCCGGCTGGATACGGCGGGC<br>GCACGAGTACTGGAAAACTAA |
| thrC<br>SEQ ID NO:<br>58 | ATGAAACTCTACAATCTGAAAGATCACAACGAGCAGGT<br>CAGCTTTGCGCAAGCCGTAACCCAGGGGTTGGGCAAAA<br>ATCAGGGGCTGTTTTTTCCGCACGACCTGCCGGAATTC<br>AGCCTGACTGAAATTGATGAGATGCTGAAGCTGGATTT<br>TGTCACCCGCAGTGCCGAAGATCCTCTCGGCGTTTATTG<br>GTGATGAAATCCCACAGGAAATCCTGGAAGAGCGCGTG<br>CGCGCGGCCGTTTGCCTTCCCGGCTCCGGTCGCCAATGT<br>TGAAAGCGATGTCGGTTGTCTGGAATTGTTCCACGGGC<br>CAACGCTGGCATTTAAAGATTTCGGCGGTCGCTTTATG<br>GCACAAATGCTGACCCATATTGCGGGTGATAAGCCAGT<br>GACCATTCTGACCGCGACCTCCGGTGATACCGGAGCGG<br>CAGTGGCTCATGCTTTCTACGGTTTACCGAATGTGAAA<br>GTGGTTATCCTCTATCCACGAGGCAAATCAGTCCACT<br>GCAAGAAAACTGTTCTGTACATTGGGCGGCAATATCG<br>AAACTGTTGCCATCGACGGCGATTTCGATGCCTGTCAG<br>GCGCTGGTGAAGCAGGCGTTTGATGATGAAGAACTGAA<br>AGTGGCGCTAGGGTTAAACTCGGCTAACTCGATTAACA<br>TCAGCCGTTTGCTGGCGCAGATTTGCTACTACTTTGAA<br>GCTGTTGCGCAGCTGCCGCAGGAGACGCGCAACCAGCT<br>GGTTGTCTCGGTGCCAAGCGAAACTTCGGCGATTTGA<br>CGGCGGGTCTGCTGGCGAAGTCACTCGGTCTGCCGGTG<br>AAACGTTTTATTGCTGCGACCAACGTGAACGATACCGT<br>GCCACGTTTCCTGCACGACGGTCAGTGGTCACCCAAAG<br>CGACTCAGGCGACGTTATCCAACGCGATGGACGTGAGT<br>CAGCCGAACAACTGGCCGCGTGTGGAAGAGTTGTTCCG<br>CCGCAAAATCTGCAACTGAAAGAGCTGGGTTATGCAG<br>CCGTGGATGATGAAACCACGCAACAGAACAATGCGTGAG<br>TTAAAAGAACTGGGCTACACTTCGGAGCCGCACGCTGC<br>CGTAGCTTATCGTGCGCTGCGTGATCAGTTGAATCCAG<br>GCGAATATGCTTGTTCCTCGGCACCGCGCATCCGGCG<br>AAATTTAAAGAGAGCGTGGAAGCGATTCTCGGTGAAAC<br>GTTGGATCTGCCAAAAGAGCTGGCAGAACGTGCTGATT<br>TACCCTTGCTTTCACATAATCTGCCCGCCGATTTTGCT<br>GCGTTGCGTAAATTGATGATGAATCATCAGTAA |
| ilvA$^{fbr}$<br>SEQ ID NO:<br>59 | ATGAGTGAAACATACGTGTCTGAGAAAAGTCCAGGAGT<br>GATGGCTAGCGGAGCGGAGCTGATTCGTGCCGCCGACA<br>TTCAAACGGCGCAGGCACGAATTTCCTCCGTCATTGCA<br>CCAACTCCATTGCAGTATTGCCCCTCGTCTTTCTGAGGA<br>AACCGGAGCGGAAATCTACCTTAAGCGTGAGGGATCTGC<br>AGGATGTTCGTTCCTACAAGATCCGGGTGCGCTGAAC<br>TCTGGAGCGCAGCTCACCCAAGAGCAGCGCGATGCAGG<br>TATCGTTGCCGCATCTGCAGGTAACATGCCCAGGGCG<br>TGGCCTATGTGTGCAAGTCCTTGGGCGTTCAGGGACGC<br>ATCTATGTTCCTGTGCAGACTCCAAAGCAAAAGCGTGA<br>CCGCATCATGGTTCACGGCGGAGAGTTTGTCTCCTTGG<br>TGGTCACTGGCAATAACTTCGACGAAGCATCCGCTGCA<br>GCGCATGAAGATGCAGAGCGCACCGGCGCAACGCTGAT<br>CGAGCCTTTCGATGCTCGCAACACCGTCATCGGTCAGG<br>GCACCGTGGCTGCTGAGATCTTGTCGCAGCTGACTTCC<br>ATGGGCAAGAGTGCAGATACACGTGATGGTTCCAGTCGG<br>CGGTGGCGGACTTCTTGCAGGTGTGGTCAGCTACATGG |

TABLE 15-continued

| Description | Sequence |
|---|---|
| | CTGATATGGCACCTCGCACTGCGATCGTTGGTATCGAA<br>CCAGCGGGAGCAGCATCCATGCAGGCTGCATTGCACAA<br>TGGTGGACCAATCACTTTGGAGACTGTTGATCCCTTTG<br>TGGACGGCGCAGCAGTCAAACGTGTCGGAGATCTCAAC<br>TACACCATCGTGGAGAAGAACCAGGGTCGCGTGCACAT<br>GATGAGCGCGACCGAGGGCGCTGTGTGTACTGAGATGC<br>TCGATCTTTACCAAAACGAAGGCATCATCGCGGAGCCT<br>GCTGGCGCGCTGTCTATCGCTGGGTTGAAGGAAATGTC<br>CTTTGCACCTGGTTCTGCAGTGGTGTGCATCATCTCTG<br>GTGGCAACAACGATGTGCTGCGTTATGCGGAAATCGCT<br>GAGCGCTCCTTGGTGCACCGCGGTTTGAAGCACTACTT<br>CTTGGTGAACTTCCCGCAAAAGCCTGGTCAGTTGCGTC<br>ACTTCCTGGAAGATATCCTGGGACCGGATGATGACATC<br>ACGCTGTTTGAGTACCTCAAGCGCAACAACCGTGAGAC<br>CGGTACTGCGTTGGTGGGTATTCACTTGAGTGAAGCAT<br>CAGGATTGGATTCTTTGCTGGAACGTATGGAGGAATCG<br>GCAATTGATTCCCGTCGCCTCGAGCCGGGCACCCCTGA<br>GTACGAATACTTGACCTAA |
| aceE<br>SEQ ID NO:<br>60 | ATGTCAGAACGTTTCCCAAATGACGTGGATCCGATCGA<br>AACTCGCGACTGGCTCCAGGCGATCGAATCGGTCATCC<br>GTGAAGAAGGTGTTGAGCGTGCTCAGTATCTGATCGAC<br>CAACTGCTTGCTGAAGCCCGCAAAGGCGGTGTAAACGT<br>AGCCGCAGGCACAGGTATCAGCAACTACATCAACACCA<br>TCCCCGTTGAAGAACAACCGGAGTATCCGGGTAATCTG<br>GAACTGGAACGCCGTATTCGTTCAGCTATCCGCTGGAA<br>CGCCATCATGACGGTGCTGCGTGCGTCGAAAAAAGACG<br>TCGAACTGGGCGGCCATATGGCGTCCTTCCAGTCTTCC<br>GCAACCATTTATGATGTGCTTTAACCACTTCTTCCG<br>TGCACGCAACGAGCAGGATGGCGGCGACCTGGTTTACT<br>TCCAGGGCCACATCTCCCCGGGCGTGTACGCTCGTGCT<br>TTCCTGGAAGGTCGTCTGACTCAGGAGCAGCTGGATAA<br>CTTCCGTCAGGAAGTTCACGGCAATGGCCTCTCTTCCT<br>ATCCGCACCCGAAACTGATGCCGAATTCTGGCAGTTC<br>CCGACCGTATCTATGGGTCTGGGTCCGATTGGTGCTAT<br>TTACCAGGCTAAATTCCTGAAATATCTGGAACACCGTG<br>GCCTGAAAGATACCCTAAACAAACCGTTTACGCGTTC<br>CTCGGTGACGGTGAAATGGACGAACCGGAATCCAAAGG<br>TGCGATCACCATCGCTACCCGTGAAAAACTGGATAACC<br>TGGTCTTCGTTATCAACTGTAACCTGCAGCGTCTTGAC<br>GGCCCGGTCACCGGTAACGGCAAGATCATCAACGAACT<br>GGAAGGCATCTTCGAAGGTGCTGGCTGGAACGTGATCA<br>AAGTGATGTGGGGTAGCCGTTGGGATGAACTGCTGCGT<br>AAGGATACCAGCGGTAAACTGATCCAGCTGATGAACGA<br>AACCGTTGACGGCGACTACCAGACCTTCAAATCGAAAG<br>ATGGTGCGTACGTTCGTGAACACTTCTTCGGTAAATAT<br>CCTGAAACCGCAGCACTGGTTGCAGACTGGACTGACGA<br>GCAGATCTGGGCACTGAACCGTGGCGGTCACGATCCGA<br>AGAAAATCTACGCTGCATTCAAGAAGCGCAGGAAACC<br>AAAGGCAAAGCGACAGTAATCCTTGCTCATACCATTAA<br>AGGTTACGGCATGGGCGACGCGGCTGAAGGTAAAAACA<br>TCGCGCACCAGGTTAAGAAAATGAACATGGACGGTGTG<br>CGTCATATCCGCGACCGTTTCAATGTGCCGGTGTCTGA<br>TGCAGATATCGAAAAACTGCCGTACATCACCTTCCCGG<br>AAGGTTCTGAAGAGCATACCTATCTGCACGCTCAGCGT<br>CAGAAGCTGCACGGTTATCTGCCAAGCCGTCAGCCGAA<br>CTTCACCGAGAAGCTTGAGCTGCCGAGCCTGCAAGACT<br>TCGGCGCGCTGTTGGAAGAGCAGAGCAAAGAGATCTCT<br>ACCACTATCGCTTTCGTTCGTGCTCTGAACGTGATGCT<br>GAAGAACAAGTCGATCAAAGATCGTCTGGTACCGATCA<br>TCGCCGACGAAGCGCGTACTTTCGGTATGGAAGGTCTG<br>TTCCGTCAGATTGGTATTTACAGCCGGAACGGTCAGCA<br>GTACACCCCGCAGGACCGCGAGCAGGTTGCTTACTATA<br>AGGAAGACGAGAAAGGTCAGATTCTGCAGGAAGGGATC<br>AACGAGCTGGGCGCAGGTTGTTCCTGGCTGGCAGCGGC<br>GACCTCTTACAGCACCAACAATCTGCCGATGATCCCGT<br>TCTACATCTATTACTCGATGTTCGGCTTCCAGCTATT<br>GGCGATCTGTGCTGGGCGGCTGGCGACCAGCAAGCGCG<br>TGGCTTCCTGATCGGCGCAACTTCCGGTCGTACCACCG<br>TGAACGGCGAAGGTCTGCAGCACGGAGATGGTCACAGC<br>CACATTCAGTCGCTGACTATCCCGAACTGTATCTCTTA<br>CGACCCGGCTTACGCTTACGAAGTTGCTGTCATCATGC<br>ATGACGGTCTGGAGCGTATGTACGGTGAAAAACGAAG<br>AACGTTACTACTACATCACTACGCTGAACGAAAACTA<br>CCACATGCCGGCAATGCCGGAAGGTGCTGAGGAAGGTA<br>TCCGTAAAGGTATCTACAAACTCGAAACTATTGAAGGT<br>AGCAAAGGTAAAGTTCAGCTGCTCGGCTCCGGTTCTAT<br>CCTGCGTCACGTCCGTGAAGCAGCTGAGATCCTGGCGA |
| aceF<br>SEQ ID NO:<br>61 | AAGATTACGGCGTAGGTTCTGACGTTTATAGCGTGACC<br>TCCTTCACCGAGCTGGCGCGTGATGGTCAGGATTGTGA<br>ACGCTGGAACATGCTGCACCCGCTGGAAACTCCGCGCG<br>TTCCGTATATCGCTCAGGTGATGAACGACGCTCCGGCA<br>GTGGCATCTACCGACTATATGAAACTGTTCGCTGAGCA<br>GGTCCGTACTTACGTACCGGCTGACGACTACCGCGTAC<br>TGGGTACTGATGGCTTCGGTCGTTCCGACAGCCGTGAG<br>AACCTGCGTCACCACTTCGAAGTTGATGCTTCTTATGT<br>CGTGGTTGCGGCGCTGGGCGAACTGGCTAAACGTGGCG<br>AAATCGATAAGAAAGTGGTTGCTGACGCAATCGCCAAA<br>TTCAACATCGATGCAGATAAAGTTAACCCGCGTCTGGC<br>GTAA<br>ATGGCTATCGAAATCAAAGTACCGGACATCGGGGCTGA<br>TGAAGTTGAAATCACCGAGATCCTGGTCAAAGTGGGCG<br>ACAAAGTTGAAGCCGAACAGTCGCTGATCACCGTAGAA<br>GGCGACAAAGCCTCTATGGAAGTTCCGTCTCCGCAGGC<br>GGGTATCGTTAAAGAGATCAAAGTCTCTGTTGGCGATA<br>AACCCAGACCGGCGCACTGATTATGTTTTCGATTCC<br>GCCGACGGTGCAGCAGACGCTGCACCTGCTCAGGCAGA<br>AGAGAAGAAAGAAGCAGCTCCGGCAGCAGCACCAGCGG<br>CTGCGGCGGCAAAAGACGTTAACGTTCCGGATATCGGC<br>AGCGACGAAGTTGAAGTGACCGAAATCCTGGTGAAAGT<br>TGGCGATAAAGTTGAAGCTGAACAGTCGCTGATCACCG<br>TAGAAGGCGACAAGGCTTCTATGGAAGTTCCGGCTCCG<br>TTTGCTGGCACCGTGAAAGAGATCAAAGTGAACGTGGG<br>TGACAAAGTGTCTACCGGCTCGCTGATTATGGTCTTCG<br>AAGTCGCGGGTGAAGCAGGCGCGGCAGCTCCGGCCGCT<br>AAACAGGAAGCAGCTCCGGCAGCGGCCCCTGCACCAGC<br>GGCTGGCGTGAAAGAAGTTAACGTTCCGGATATCGGCG<br>GTGACGAAGTTGAAGTGACTGAAGTGATGGTGAAAGTG<br>GGCGACAAAGTTGCCGCTGAACAGTCACTGATCACCGT<br>AGAAGGCGACAAAGCTTCTATGGAAGTTCCGGCGCCGT<br>TTGCAGGCGTCGTGAAGGAACTGAAAGTCAACGTTGGC<br>GATAAAGTGAAAACTGGCTCGCTGATTATGATCTTCGA<br>AGTTGAAGGCGCAGCGCCTGCGGCAACCGGCAGCAAAG<br>AGGAAGCGGCAGCCGGCACCGGCAGCAAAGCTGAA<br>GCCCCGGCAGCAGCACCAGCTGCAAAGCGGAAGGCAA<br>ATCTGAATTTGCTGAAAACGACGCTTATGTTCACGCGA<br>CTCCGCTGATCCGCCGTCTGGCACGCGAGTTTGGTGTT<br>AACCTTGCGAAAGTGAAGGGCACTGGCCGTAAAGGTCG<br>TATCCTGCGCGAAGACGTTCAGGCTTACGTGAAAGAAG<br>CTATCAAACGTGCAGAAGCAGCTCCGGCAGCGACTGGC<br>GGTGGTATCCCTGGCATGCTGCCGTGGCCGAAGGTGGA<br>CTTCAGCAAGTTTGGTGAAATCGAAGAAGTGGAACTGG<br>GCCGCATCCAGAAAATCTCTGGTGCGAACCTGAGCCGT<br>AACTGGGTAATGATCCCGCATGTTACTCACTTCGACAA<br>AACCGATATCACCGAGTTGGAAGCGTTCCGTAAACAGC<br>AGAACGAAGAAGCGGCGAAAGTAAGCTGGATGTGAAG<br>ATCACCCCGGTTGTCTTCATCATGAAAGCCGTTGCTGC<br>AGCTCTTGAGCAGATGCCTCGCTTCAATAGTTCGCTGT<br>CGGAAGACGGTCGTCTGACCCTGAAGAAATACATC<br>AACATCGGTGTGGCGGTGATACCCCGAACGGTCTGGT<br>TGTTCCGGTATTCAAAGACGTCAACAAGAAAGGCATCA<br>TCGAGCTGTCTCGCGAGCTGATGACTATTTCTAAGAAA<br>GCGCGTGACGGTAAGCTGACTGCGGGCGAAATGCAGGG<br>CGGTTGCTTCACCATCTCCAGCATCGGCGGCCTGGGTA<br>CTACCCACTTCGCGCCGATTGTGAACGCGCCGGAAGTG<br>GCTATCCTCGGCGTTTCCAAGTCCGCGATGGAGCCGGT<br>GTGGAATGGTAAAGAGTTCGTGCCGCGTCTGATGCTGC<br>CGATTTCTCTCCTTCGACCACCGCGTGATCGACGGT<br>GCTGATGGTGCCCGTTTCATTACCATCATTAACAACAC<br>GCTGTCTGACATTCGCCGTCTGGTGATGTAA |
| lpd<br>SEQ ID NO:<br>62 | ATGAGTACTGAAATCAAAACTCAGGTCGTGGTACTTGG<br>GGCAGGCCCCGCAGGTTACTCCGCTGCCTTCCGTTGCG<br>CTGATTAGGTCTGGAAACCGTAATCGTAGAACGTTAC<br>AACACCCTTGGCGGTGTTTGCCTGAACGTCGGCTGTAT<br>CCCTTCTAAAGCACTGCTGCACAGTAGCAAAAGTTATCG<br>AAGAAGCCAAAGCCTGGCTGAACACGGTATCGTCTTC<br>GGCGAACCGAAAACCGATATCGACAAGATTCGTACCTG<br>GAAAGAGAAGTGATCAATCAGCTGACCGGTGGTCTGG<br>CTGGTATGGCGAAAGGCCGCAAAGTCAAAGTGGTCAAC<br>GGTCTGGGTAAATTCACCGGGCTAACACCCTGGAAGT<br>TGAAGGTGAGAACGGCAAACCGTGATCAACTTCGACA<br>ACGCGATCATTGCAGCGGGTTCTCGCCCGATCCAACTG<br>CCGTTTATTCCGCATGAAGATCCGCGTATCTGGGACTC<br>CACTGACGCGCTGGAACTGAAAGAAGTACCAGAACGCC |

TABLE 15-continued

| Description | Sequence |
|---|---|
|  | TGCTGGTAATGGGTGGCGGTATCATCGGTCTGGAAATG GGCACCGTTTACCACGCGCTGGGTTCACAGATTGACGT GGTTGAAATGTTCGACCAGGTTATCCCGGCAGCTGACA AAGACATCGTTAAAGTCTTCACCAAGCGTATCAGCAAG AAATTCAACCTGATGCTGGAAACCAAAGTTACCGCCGT TGAAGCGAAAGAAGACGGCATTTATGTGACGATGGAAG GCAAAAAAGCACCCGCTGAACCGCAGCGTTACGACGCC GTGCTGGTAGCGATTGGTCGTGTGCCGAACGGTAAAAA CCTCGACGCAGGCAAAGCAGGCGTGGAAGTTGACGACC GTGGTTTCATCCGCGTTGACAAACAGCTGCGTACCAAC GTACCGCACATCTTTGCTATCGGCGATATCGTCGGTCA ACCGATGCTGGCACACAAAGGTGTTCACGAAGGTCACG TTGCCGCTGAAGTTATCGCCGGTAAGAAACACTACTTC GATCCGAAAGTTATCCCGTCCATCGCCTATACCAAACC AGAAGTTGCATGGGTGGGTCTGACTGAGAAAGAAGCGA AAGAGAAAGGCATCAGCTATGAAACCGCCACCTTCCCG TGGGCTGCTTCTGGTCGTGCTATCGCTTCCGACTGCGC AGACGGTATGACCAAGCTGATTTTCGACAAAGAATCTC ACCGTGTGATCGGTGGTGCGATTGTCGGTACTAACGGC GGCGAGCTGCTGGGTGAAATCGGCCTGGCAATCGAAAT GGGTTGTGATGCTGAAGCATCGCACTGACCATCCACG CGCACCCGACTCTGCACGAGTCTGTGGGCCTGGCGGCA GAAGTGTTCGAAGGTAGCATTACCGACCTGCCGAACCC GAAAGCGAAGAAGAAGTAA |
| tesB SEQ ID NO: 48 | ATGAGTCAGGCGCTAAAAAATTTACTGACATTGTTAAA TCTGGAAAAAATTGAGGAAGGACTCTTTCGCGGCCAGA GTGAAGATTTAGGTTTACGCCAGGTGTTTGGCGGCCAG GTCGTGGGTCAGGCCTTGTATGCTGCAAAAGAGACCGT CCCTGAAGAGCGGCTGGTACATTCGTTTCACAGCTACT TTCTTCGCCCTGGCGATAGTAAGAAGCCGATTATTTAT GATGTCGAAACGCTGCGTGACGGTAACAGCTTCAGCGC CCGCCGGGTTGCTGCTATTCAAAACGGCAAACCGATTT TTTATATGACTGCCTCTTTCCAGGCACCAGAAGCGGGT TTCGAACATCAAAAAACAATGCCGTCCGCGCCAGCGCC TGATGGCCTCCCTTCGGAAACGCAAATCGCCCAATCGC TGGCGCACCTGCTGCCGCCAGTGCTGAAAGATAAATTC ATCTGCGATCGTCCGCTGGAAGTCCGTCCGGTGGAGTT TCATAACCCACTGAAAGGTCACGTCGCAGAACCACATC GTCAGGTGTGGATCCGCGCAAATGGTAGCGTGCCGGAT GACCTGCGCGTTCATCAGTATCTGCTCGGTTACGCTTC TGATCTTAACTTCCTGCCGGTAGCTCTACAGCCGCACG GCATCGGTTTTCTCGAACCGGGGATTCAGATTGCCACC ATTGACCATTCCATGTGGTTCCATCGCCCGTTTAATTT GAATGAATGGCTGCTGTATAGCGTGGAGAGCACCTCGG CGTCCAGCGCACGTGGCTTTGTGCGCGGTGAGTTTTAT ACCCAAGACGGCGTACTGGTTGCCTCGACCGTTCAGGA AGGGGTGATGCGTAATCACAATTAA |

In some embodiments, one or more of the propionate biosynthesis genes is a synthetic propionate biosynthesis gene. In some embodiments, one or more of the propionate biosynthesis genes is an *E. coli* propionate biosynthesis gene. In some embodiments, one or more of the propionate biosynthesis genes is a *C. glutamicum* propionate biosynthesis gene. In some embodiments, one or more of the propionate biosynthesis genes is a *C. propionicum* propionate biosynthesis gene. The propionate gene cassette may comprise genes for the aerobic biosynthesis of propionate and/or genes for the anaerobic or microaerobic biosynthesis of propionate. One or more of the propionate biosynthesis genes may be functionally replaced or modified, e.g., codon optimized. In some embodiments, the genetically engineered bacteria comprise a combination of propionate biosynthesis genes from different species, strains, and/or substrains of bacteria, and are capable of producing propionate in low-oxygen conditions, in the presence of HE-specific molecules or metabolites, in the presence of molecules or metabolites associated with liver damage, inflammation or an inflammatory response, or in the presence of some other metabolite that may or may not be present in the gut, such as arabinose. In some embodiments, one or more of the propionate biosynthesis genes is functionally replaced, modified, and/or mutated in order to enhance stability and/or increase propionate production in low-oxygen conditions, in the presence of HE-specific molecules or metabolites, in the presence of molecules or metabolites associated with liver damage, inflammation or an inflammatory response, or in the presence of some other metabolite that may or may not be present in the gut, such as arabinose. In some embodiments, the genetically engineered bacteria are capable of expressing the propionate biosynthesis cassette and producing propionate in low-oxygen conditions, in the presence of HE-specific molecules or metabolites, in the presence of molecules or metabolites associated with liver damage, inflammation or an inflammatory response, or in the presence of some other metabolite that may or may not be present in the gut, such as arabinose.

In some embodiments, the genetically engineered bacteria of the invention comprise an acetate gene cassette and produce acetate. The genetically engineered bacteria may include any suitable set of acetate biosynthesis genes. Unmodified bacteria comprising endogenous acetate biosynthesis genes are known in the art and are capable of consuming various substrates to produce acetate under aerobic and/or anaerobic conditions (see, e.g., Ragsdale et al., 2008). These endogenous acetate biosynthesis genes may be a source of genes for the genetically engineered bacteria of the invention. In some embodiments, the genetically engineered bacteria of the invention comprise acetate biosynthesis genes from a different species, strain, or substrain of bacteria. In some embodiments, the native acetate biosynthesis genes in the genetically engineered bacteria are enhanced. In some embodiments, the genetically engineered bacteria comprise aerobic acetate biosynthesis genes, e.g., from *Escherichia coli*. In some embodiments, the genetically engineered bacteria comprise anaerobic acetate biosynthesis genes, e.g., from *Acetitomaculum, Acetoanaerobium, Acetohalobium, Acetonema, Balutia, Butyribacterium, Clostridium, Moorella, Oxobacter, Sporomusa*, and/or *Thermoacetogenium*. The genetically engineered bacteria may comprise genes for aerobic acetate biosynthesis or genes for anaerobic or microaerobic acetate biosynthesis. In some embodiments, the genetically engineered bacteria comprise both aerobic and anaerobic or microaerobic acetate biosynthesis genes. In some embodiments, the genetically engineered bacteria comprise a combination of acetate biosynthesis genes from different species, strains, and/or substrains of bacteria, and are capable of producing acetate. In some embodiments, one or more of the acetate biosynthesis genes is functionally replaced, modified, and/or mutated in order to enhance stability and/or acetate production. In some embodiments, the genetically engineered bacteria are capable of expressing the acetate biosynthesis cassette and producing acetate in low-oxygen conditions or in the presence of HE-specific molecules or metabolites. In some embodiments, the genetically engineered bacteria are capable of producing an alternate short-chain fatty acid.

One of skill in the art would appreciate that additional genes and gene cassettes capable of producing gut barrier function enhancer molecules are known in the art and may be expressed by the genetically engineered bacteria of the invention. In some embodiments, the gene or gene cassette for producing a therapeutic molecule also comprises additional transcription and translation elements, e.g., a ribosome binding site, to enhance expression of the therapeutic molecule.

In some embodiments, the genetically engineered bacteria produce two or more gut barrier function enhancer molecules. In certain embodiments, the two or more molecules behave synergistically to enhance gut barrier function. In certain embodiments, the genetically engineered bacteria express butyrate and propionate.

Figure 43:
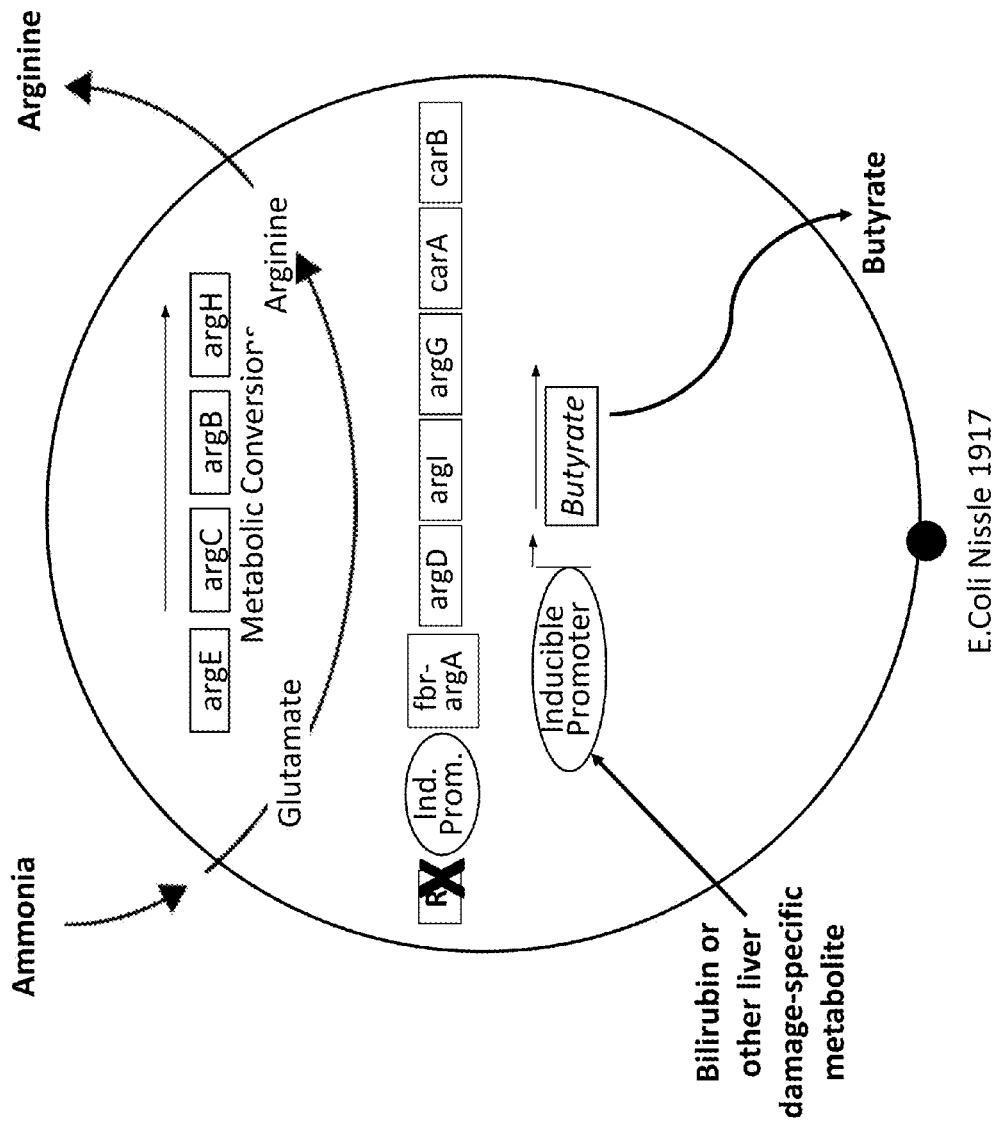
FIG. 43 depicts one embodiment of the invention. In this embodiment, the genetically engineered bacteria comprise two exemplary circuits for the treatment of hepatic encephalopathy. In one circuit, ammonia is taken up by the bacterium, converted to glutamate, and glutamate is subsequently metabolized to arginine. Arginine ultimately exits the bacterial cell. In a second circuit, expression of a butyrate gene cassette results in the production of butyrate, and release of this gut barrier enhancer molecule outside of the cell. In some embodiments, both circuits are under the control of the same inducible promoter. In other embodiments, the two circuits may each be under the control of different inducible promoter. Exemplary inducible promoters include oxygen level-dependent promoters (e.g., FNR-inducible promoter), promoters induced by HE-specific molecules or metabolites indicative of liver damage (e.g., bilirubin), promoters induced by inflammation or an inflammatory response, and promoters induced by a metabolite that may or may not be naturally present (e.g., can be exogenously added) in the gut, e.g., arabinose. One or more of the butyrate cassettes described herein may be expressed by the genetically engineered bacteria comprising an arginine (and/or citrulline) producing circuit.
Figure 44:
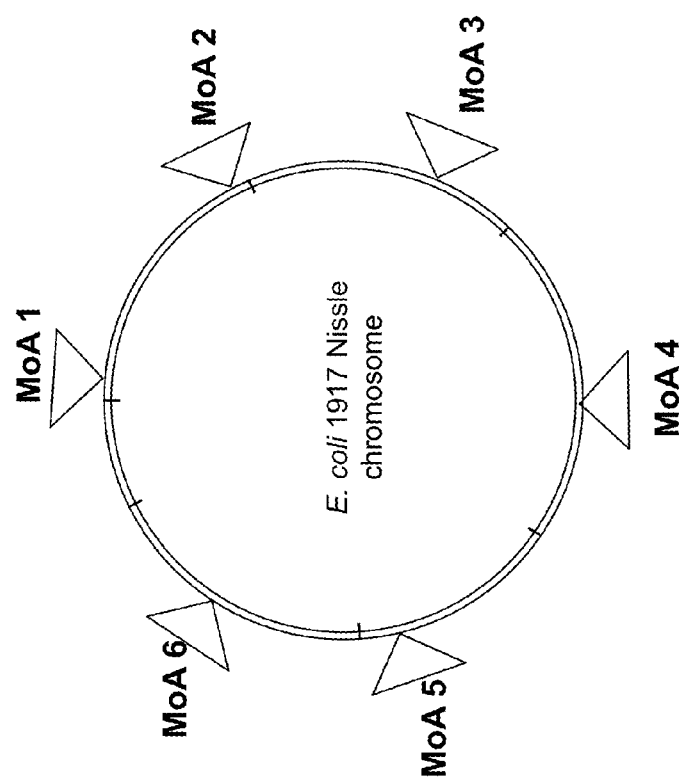
FIG. 44 depicts an exemplary schematic of the E. coli 1917 Nissle chromosome comprising multiple mechanisms of action (MoAs).

In some embodiments, the genetically engineered bacteria comprising an ammonia conversion circuit further comprise one or more circuits for producing a gut barrier enhancer molecule, e.g., butyrate (FIG. 43).

In some embodiments, the genetically engineered bacteria comprise an ammonia conversion circuit, a GABA metabolic circuit, and one or more circuits for producing a gut barrier enhancer molecule, e.g., butyrate. In some embodiments, the genetically engineered bacteria comprise an ammonia conversion circuit, a GABA transport circuit, and one or more circuits for producing a gut barrier enhancer molecule, e.g., butyrate. In some embodiments, the genetically engineered bacteria comprise an ammonia conversion circuit, a GABA transport circuit, a GABA metabolic circuit, and one or more circuits for producing a gut barrier enhancer molecule, e.g., butyrate. In some embodiments, the genetically engineered bacteria comprise an ammonia conversion circuit, a manganese transport circuit, a GABA metabolic circuit, and one or more circuits for producing a gut barrier enhancer molecule, e.g., butyrate. In some embodiments, the genetically engineered bacteria comprise an ammonia conversion circuit, a manganese transport circuit, a GABA transport circuit, and one or more circuits for producing a gut barrier enhancer molecule, e.g., butyrate. In some embodiments, the genetically engineered bacteria comprise an ammonia conversion circuit, a manganese transport circuit, a GABA transport circuit, a GABA metabolic circuit, and one or more circuits for producing a gut barrier enhancer molecule, e.g., butyrate. In some embodiments, the circuits are under the control of the same promoter. In alternate embodiments, the circuits are under the control of different promoters.

In some embodiments, the genetically engineered bacteria are capable of expressing any one or more of the described circuits in low-oxygen conditions, in the presence of HE-specific molecules or metabolites, in the presence of molecules or metabolites associated with liver damage, inflammation or an inflammatory response, or in the presence of some other metabolite that may or may not be present in the gut, such as arabinose. In some embodiments, any one or more of the described circuits are present on one or more plasmids (e.g., high copy or low copy) or are integrated into one or more sites in the bacterial chromosome. Also, in some embodiments, the genetically engineered bacteria are further capable of expressing any one or more of the described circuits and further comprise one or more of the following: (1) one or more auxotrophies, such as any auxotrophies known in the art and provided herein, e.g., thyA auxotrophy, (2) one or more kill switch circuits, such as any of the kill-switches described herein or otherwise known in the art, (3) one or more antibiotic resistance circuits, (4) one or more transporters for importing biological molecules or substrates, such any of the transporters described herein or otherwise known in the art, (5) one or more secretion circuits, such as any of the secretion circuits described herein and otherwise known in the art, and (6) combinations of one or more of such additional circuits.

In any of the embodiments described herein, the genetically engineered bacteria may further comprise a resistance to rifaximin. Resistance to rifaximin is caused primarily by mutations in the rpoB gene. In some embodiments, the genetically engineered bacteria comprise a known rifaximin resistance mutation, e.g., in the rpoB gene. In other embodiments, a screen can be employed, exposing the genetically engineered bacteria to increasing amounts of rifaximin, to identify a useful mutation which confers rifaximin resistance.

Inducible Promoters

In some embodiments, the bacterial cell comprises a stably maintained plasmid or chromosome carrying the gene(s) encoding the payload (s), such that the payload(s) can be expressed in the host cell, and the host cell is capable of survival and/or growth in vitro, e.g., in medium, and/or in vivo, e.g., in the gut. In some embodiments, bacterial cell comprises two or more distinct payloads or operons, e.g., two or more payload genes. In some embodiments, bacterial cell comprises three or more distinct transporters or operons, e.g., three or more payload genes. In some embodiments, bacterial cell comprises 4, 5, 6, 7, 8, 9, 10, or more distinct payloads or operons, e.g., 4, 5, 6, 7, 8, 9, 10, or more payload genes.

In some embodiments, the genetically engineered bacteria comprise multiple copies of the same payload gene(s). In some embodiments, the gene encoding the payload is present on a plasmid and operably linked to a directly or indirectly inducible promoter. In some embodiments, the gene encoding the payload is present on a plasmid and operably linked to a promoter that is induced under low-oxygen or anaerobic conditions. In some embodiments, the gene encoding the payload is present on a chromosome and operably linked to a directly or indirectly inducible promoter. In some embodiments, the gene encoding the payload is present in the chromosome and operably linked to a promoter that is induced under low-oxygen or anaerobic conditions. In some embodiments, the gene encoding the payload is present on a plasmid and operably linked to a promoter that is induced by exposure to tetracycline or arabinose.

In some embodiments, the promoter that is operably linked to the gene encoding the payload is directly induced by exogenous environmental conditions. In some embodiments, the promoter that is operably linked to the gene encoding the payload is indirectly induced by exogenous environmental conditions. In some embodiments, the promoter is directly or indirectly induced by exogenous environmental conditions specific to the gut of a mammal. In some embodiments, the promoter is directly or indirectly induced by exogenous environmental conditions specific to the small intestine of a mammal. In some embodiments, the promoter is directly or indirectly induced by low-oxygen or anaerobic conditions such as the environment of the mammalian gut. In some embodiments, the promoter is directly or indirectly induced by molecules or metabolites that are specific to the gut of a mammal. In some embodiments, the promoter is directly or indirectly induced by a molecule that is co-administered with the bacterial cell.

In certain embodiments, the bacterial cell comprises a gene encoding a payload expressed under the control of a fumarate and nitrate reductase regulator (FNR) responsive promoter. In E. coli, FNR is a major transcriptional activator that controls the switch from aerobic to anaerobic metabolism (Unden et al., 1997). In the anaerobic state, FNR dimerizes into an active DNA binding protein that activates hundreds of genes responsible for adapting to anaerobic growth. In the aerobic state, FNR is prevented from dimerizing by oxygen and is inactive. FNR responsive promoters include, but are not limited to, the FNR responsive promoters listed in the chart, below. Underlined sequences are predicted ribosome binding sites, and bolded sequences are restriction sites used for cloning.

FNR promoter sequences are known in the art, and any suitable FNR promoter sequence(s) may be used in the genetically engineered bacteria of the invention. Any suitable FNR promoter(s) may be combined with any suitable payload (e.g., the exemplary argA$^{fbr}$ sequence shown in Table 7). Non-limiting FNR promoter sequences are provided in Table 6. Table 6 depicts the nucleic acid sequences of exemplary regulatory region sequences comprising a FNR-responsive promoter sequence. Underlined sequences are predicted ribosome binding sites, and bolded sequences are restriction sites used for cloning. In some embodiments, the genetically engineered bacteria of the invention comprise one or more of: SEQ ID NO: 18, SEQ ID NO: 19, nirB1 promoter (SEQ ID NO: 20), nirB2 promoter (SEQ ID NO: 21), nirB3 promoter (SEQ ID NO: 22), ydfZ promoter (SEQ ID NO: 23), nirB promoter fused to a strong ribosome binding site (SEQ ID NO: 24), ydfZ promoter fused to a strong ribosome binding site (SEQ ID NO: 25), fnrS, an anaerobically induced small RNA gene (fnrS1 promoter SEQ ID NO: 26 or fnrS2 promoter SEQ ID NO: 27), nirB promoter fused to a crp binding site (SEQ ID NO: 28), and fnrS fused to a crp binding site (SEQ ID NO: 29).

In some embodiments, genetically engineered bacteria comprise a nucleic acid sequence that is at least about 80%, at least about 85%, at least about 90%, at least about 95%, or at least about 99% homologous to the DNA sequence of SEQ ID NO: 18, 19, 20, 21, 22, 23, 24, 25, 26, 27, 28, or 29, or a functional fragment thereof.

In one embodiment, the FNR responsive promoter comprises SEQ ID NO:1. In another embodiment, the FNR responsive promoter comprises SEQ ID NO:2. In another embodiment, the FNR responsive promoter comprises SEQ ID NO:3. In another embodiment, the FNR responsive promoter comprises SEQ ID NO:4. In yet another embodiment, the FNR responsive promoter comprises SEQ ID NO:5.

In some embodiments, multiple distinct FNR nucleic acid sequences are inserted in the genetically engineered bacteria. In alternate embodiments, the genetically engineered bacteria comprise a gene encoding a payload expressed under the control of an alternate oxygen level-dependent promoter, e.g., DNR (Trunk et al., 2010) or ANR (Ray et al., 1997). In these embodiments, expression of the payload gene is particularly activated in a low-oxygen or anaerobic environment, such as in the gut. In some embodiments, gene expression is further optimized by methods known in the art, e.g., by optimizing ribosomal binding sites and/or increasing mRNA stability. In one embodiment, the mammalian gut is a human mammalian gut.

In some embodiments, the bacterial cell comprises an oxygen-level dependent transcriptional regulator, e.g., FNR, ANR, or DNR, and corresponding promoter from a different bacterial species. The heterologous oxygen-level dependent transcriptional regulator and promoter increase the transcription of genes operably linked to said promoter, e.g., the gene encoding the payload, in a low-oxygen or anaerobic environment, as compared to the native gene(s) and promoter in the bacteria under the same conditions. In certain embodiments, the non-native oxygen-level dependent transcriptional regulator is an FNR protein from *N. gonorrhoeae* (see, e.g., Isabella et al., 2011). In some embodiments, the corresponding wild-type transcriptional regulator is left intact and retains wild-type activity. In alternate embodiments, the corresponding wild-type transcriptional regulator is deleted or mutated to reduce or eliminate wild-type activity.

In some embodiments, the genetically engineered bacteria comprise a wild-type oxygen-level dependent transcriptional regulator, e.g., FNR, ANR, or DNR, and corresponding promoter that is mutated relative to the wild-type promoter from bacteria of the same subtype. The mutated promoter enhances binding to the wild-type transcriptional regulator and increases the transcription of genes operably linked to said promoter, e.g., the gene encoding the payload, in a low-oxygen or anaerobic environment, as compared to the wild-type promoter under the same conditions. In some embodiments, the genetically engineered bacteria comprise a wild-type oxygen-level dependent promoter, e.g., FNR, ANR, or DNR promoter, and corresponding transcriptional regulator that is mutated relative to the wild-type transcriptional regulator from bacteria of the same subtype. The mutated transcriptional regulator enhances binding to the wild-type promoter and increases the transcription of genes operably linked to said promoter, e.g., the gene encoding the payload, in a low-oxygen or anaerobic environment, as compared to the wild-type transcriptional regulator under the same conditions. In certain embodiments, the mutant oxygen-level dependent transcriptional regulator is an FNR protein comprising amino acid substitutions that enhance dimerization and FNR activity (see, e.g., Moore et al., (2006).

In some embodiments, the bacterial cells comprise multiple copies of the endogenous gene encoding the oxygen level-sensing transcriptional regulator, e.g., the FNR gene. In some embodiments, the gene encoding the oxygen level-sensing transcriptional regulator is present on a plasmid. In some embodiments, the gene encoding the oxygen level-sensing transcriptional regulator and the gene encoding the payload are present on different plasmids. In some embodiments, the gene encoding the oxygen level-sensing transcriptional regulator and the gene encoding the payload are present on the same plasmid. In some embodiments, the gene encoding the oxygen level-sensing transcriptional regulator is present on a chromosome. In some embodiments, the gene encoding the oxygen level-sensing transcriptional regulator and the gene encoding the payload are present on different chromosomes. In some embodiments, the gene encoding the oxygen level-sensing transcriptional regulator and the gene encoding the payload are present on the same chromosome. In some instances, it may be advantageous to express the oxygen level-sensing transcriptional regulator under the control of an inducible promoter in order to enhance expression stability. In some embodiments, expression of the transcriptional regulator is controlled by a different promoter than the promoter that controls expression of the gene encoding the payload. In some embodiments, expression of the transcriptional regulator is controlled by the same promoter that controls expression of the payload. In some embodiments, the transcriptional regulator and the payload are divergently transcribed from a promoter region.

RNS-Dependent Regulation

In some embodiments, the genetically engineered bacteria or genetically engineered virus comprise a gene encoding a payload that is expressed under the control of an inducible promoter. In some embodiments, the genetically engineered bacterium or genetically engineered virus that expresses a payload under the control of a promoter that is activated by inflammatory conditions. In one embodiment, the gene for producing the payload is expressed under the control of an inflammatory-dependent promoter that is activated in inflammatory environments, e.g., a reactive nitrogen species or RNS promoter.

As used herein, "reactive nitrogen species" and "RNS" are used interchangeably to refer to highly active molecules, ions, and/or radicals derived from molecular nitrogen. RNS can cause deleterious cellular effects such as nitrosative stress. RNS includes, but is not limited to, nitric oxide (NO.), peroxynitrite or peroxynitrite anion (ONOO—), nitrogen dioxide (.NO2), dinitrogen trioxide (N2O3), peroxynitrous acid (ONOOH), and nitroperoxycarbonate (ONOOCO2-) (unpaired electrons denoted by .). Bacteria have evolved transcription factors that are capable of sensing RNS levels. Different RNS signaling pathways are triggered by different RNS levels and occur with different kinetics.

As used herein, "RNS-inducible regulatory region" refers to a nucleic acid sequence to which one or more RNS-sensing transcription factors is capable of binding, wherein the binding and/or activation of the corresponding transcription factor activates downstream gene expression; in the presence of RNS, the transcription factor binds to and/or activates the regulatory region. In some embodiments, the RNS-inducible regulatory region comprises a promoter sequence. In some embodiments, the transcription factor senses RNS and subsequently binds to the RNS-inducible regulatory region, thereby activating downstream gene expression. In alternate embodiments, the transcription factor is bound to the RNS-inducible regulatory region in the absence of RNS; in the presence of RNS, the transcription factor undergoes a conformational change, thereby activating downstream gene expression. The RNS-inducible regulatory region may be operatively linked to a gene or genes, e.g., a payload gene sequence(s), e.g., any of the payloads described herein. For example, in the presence of RNS, a transcription factor senses RNS and activates a corresponding RNS-inducible regulatory region, thereby driving expression of an operatively linked gene sequence. Thus, RNS induces expression of the gene or gene sequences.

As used herein, "RNS-derepressible regulatory region" refers to a nucleic acid sequence to which one or more RNS-sensing transcription factors is capable of binding, wherein the binding of the corresponding transcription factor represses downstream gene expression; in the presence of RNS, the transcription factor does not bind to and does not repress the regulatory region. In some embodiments, the RNS-derepressible regulatory region comprises a promoter sequence. The RNS-derepressible regulatory region may be operatively linked to a gene or genes, e.g., a payload gene sequence(s). For example, in the presence of RNS, a transcription factor senses RNS and no longer binds to and/or represses the regulatory region, thereby derepressing an operatively linked gene sequence or gene cassette. Thus, RNS derepresses expression of the gene or genes.

As used herein, "RNS-repressible regulatory region" refers to a nucleic acid sequence to which one or more RNS-sensing transcription factors is capable of binding, wherein the binding of the corresponding transcription factor represses downstream gene expression; in the presence of RNS, the transcription factor binds to and represses the regulatory region. In some embodiments, the RNS-repressible regulatory region comprises a promoter sequence. In some embodiments, the transcription factor that senses RNS is capable of binding to a regulatory region that overlaps with part of the promoter sequence. In alternate embodiments, the transcription factor that senses RNS is capable of binding to a regulatory region that is upstream or downstream of the promoter sequence. The RNS-repressible regulatory region may be operatively linked to a gene sequence or gene cassette. For example, in the presence of RNS, a transcription factor senses RNS and binds to a corresponding RNS-repressible regulatory region, thereby blocking expression of an operatively linked gene sequence or gene sequences. Thus, RNS represses expression of the gene or gene sequences.

As used herein, a "RNS-responsive regulatory region" refers to a RNS-inducible regulatory region, a RNS-repressible regulatory region, and/or a RNS-derepressible regulatory region. In some embodiments, the RNS-responsive regulatory region comprises a promoter sequence. Each regulatory region is capable of binding at least one corresponding RNS-sensing transcription factor. Examples of transcription factors that sense RNS and their corresponding RNS-responsive genes, promoters, and/or regulatory regions include, but are not limited to, those shown in Table A.

TABLE A

Examples of RNS-sensing transcription factors and RNS-responsive genes

| RNS-sensing transcription factor: | Primarily capable of sensing: | Examples of responsive genes, promoters, and/or regulatory regions: |
| --- | --- | --- |
| NsrR | NO | norB, aniA, nsrR, hmpA, ytfE, ygbA, hcp, hcr, nrfA, aox |
| NorR | NO | norVW, norR |
| DNR | NO | norCB, nir, nor, nos |

In some embodiments, the genetically engineered bacteria of the invention comprise a tunable regulatory region that is directly or indirectly controlled by a transcription factor that is capable of sensing at least one reactive nitrogen species. The tunable regulatory region is operatively linked to a gene or genes capable of directly or indirectly driving the expression of a payload, thus controlling expression of the payload relative to RNS levels. For example, the tunable regulatory region is a RNS-inducible regulatory region, and the payload is a payload, such as any of the payloads provided herein; when RNS is present, e.g., in an inflamed tissue, a RNS-sensing transcription factor binds to and/or activates the regulatory region and drives expression of the payload gene or genes. Subsequently, when inflammation is ameliorated, RNS levels are reduced, and production of the payload is decreased or eliminated.

In some embodiments, the tunable regulatory region is a RNS-inducible regulatory region; in the presence of RNS, a transcription factor senses RNS and activates the RNS-inducible regulatory region, thereby driving expression of an operatively linked gene or genes. In some embodiments, the transcription factor senses RNS and subsequently binds to the RNS-inducible regulatory region, thereby activating downstream gene expression. In alternate embodiments, the transcription factor is bound to the RNS-inducible regulatory region in the absence of RNS; when the transcription factor senses RNS, it undergoes a conformational change, thereby inducing downstream gene expression.

In some embodiments, the tunable regulatory region is a RNS-inducible regulatory region, and the transcription factor that senses RNS is NorR. NorR "is an NO-responsive transcriptional activator that regulates expression of the norVW genes encoding flavorubredoxin and an associated flavoprotein, which reduce NO to nitrous oxide" (Spiro 2006). The genetically engineered bacteria of the invention may comprise any suitable RNS-responsive regulatory region from a gene that is activated by NorR. Genes that are capable of being activated by NorR are known in the art (see, e.g., Spiro 2006; Vine et al., 2011; Karlinsey et al., 2012). In certain embodiments, the genetically engineered bacteria of the invention comprise a RNS-inducible regulatory region from norVW that is operatively linked to a gene or genes, e.g., one or more payload gene sequence(s). In the presence of RNS, a NorR transcription factor senses RNS and activates to the norVW regulatory region, thereby driving expression of the operatively linked gene(s) and producing the payload.

In some embodiments, the tunable regulatory region is a RNS-inducible regulatory region, and the transcription factor that senses RNS is DNR. DNR (dissimilatory nitrate respiration regulator) "promotes the expression of the nir, the nor and the nos genes" in the presence of nitric oxide (Castiglione et al., 2009). The genetically engineered bacteria of the invention may comprise any suitable RNS-responsive regulatory region from a gene that is activated by DNR. Genes that are capable of being activated by DNR are known in the art (see, e.g., Castiglione et al., 2009; Giardina et al., 2008). In certain embodiments, the genetically engineered bacteria of the invention comprise a RNS-inducible regulatory region from norCB that is operatively linked to a gene or gene cassette, e.g., a butyrogenic gene cassette. In the presence of RNS, a DNR transcription factor senses RNS and activates to the norCB regulatory region, thereby driving expression of the operatively linked gene or genes and producing one or more payloads. In some embodiments, the DNR is *Pseudomonas aeruginosa* DNR.

In some embodiments, the tunable regulatory region is a RNS-derepressible regulatory region, and binding of a corresponding transcription factor represses downstream gene expression; in the presence of RNS, the transcription factor no longer binds to the regulatory region, thereby derepressing the operatively linked gene or gene cassette.

In some embodiments, the tunable regulatory region is a RNS-derepressible regulatory region, and the transcription factor that senses RNS is NsrR. NsrR is "an Rrf2-type transcriptional repressor [that] can sense NO and control the expression of genes responsible for NO metabolism" (Isabella et al., 2009). The genetically engineered bacteria of the invention may comprise any suitable RNS-responsive regulatory region from a gene that is repressed by NsrR. In some embodiments, the NsrR is *Neisseria gonorrhoeae* NsrR. Genes that are capable of being repressed by NsrR are known in the art (see, e.g., Isabella et al., 2009; Dunn et al., 2010). In certain embodiments, the genetically engineered bacteria of the invention comprise a RNS-derepressible regulatory region from norB that is operatively linked to a gene or genes, e.g., a payload gene or genes. In the presence of RNS, an NsrR transcription factor senses RNS and no longer binds to the norB regulatory region, thereby derepressing the operatively linked a payload gene or genes and producing the encoding a payload(s).

In some embodiments, it is advantageous for the genetically engineered bacteria to express a RNS-sensing transcription factor that does not regulate the expression of a significant number of native genes in the bacteria. In some embodiments, the genetically engineered bacterium of the invention expresses a RNS-sensing transcription factor from a different species, strain, or substrain of bacteria, wherein the transcription factor does not bind to regulatory sequences in the genetically engineered bacterium of the invention. In some embodiments, the genetically engineered bacterium of the invention is *Escherichia coli*, and the RNS-sensing transcription factor is NsrR, e.g., from is *Neisseria gonorrhoeae*, wherein the *Escherichia coli* does not comprise binding sites for said NsrR. In some embodiments, the heterologous transcription factor minimizes or eliminates off-target effects on endogenous regulatory regions and genes in the genetically engineered bacteria.

In some embodiments, the tunable regulatory region is a RNS-repressible regulatory region, and binding of a corresponding transcription factor represses downstream gene expression; in the presence of RNS, the transcription factor senses RNS and binds to the RNS-repressible regulatory region, thereby repressing expression of the operatively linked gene or gene cassette. In some embodiments, the RNS-sensing transcription factor is capable of binding to a regulatory region that overlaps with part of the promoter sequence. In alternate embodiments, the RNS-sensing transcription factor is capable of binding to a regulatory region that is upstream or downstream of the promoter sequence.

In these embodiments, the genetically engineered bacteria may comprise a two repressor activation regulatory circuit, which is used to express a payload. The two repressor activation regulatory circuit comprises a first RNS-sensing repressor and a second repressor, which is operatively linked to a gene or gene cassette, e.g., encoding a payload. In one aspect of these embodiments, the RNS-sensing repressor inhibits transcription of the second repressor, which inhibits the transcription of the gene or gene cassette. Examples of second repressors useful in these embodiments include, but are not limited to, TetR, C1, and LexA. In the absence of binding by the first repressor (which occurs in the absence of RNS), the second repressor is transcribed, which represses expression of the gene or genes. In the presence of binding by the first repressor (which occurs in the presence of RNS), expression of the second repressor is repressed, and the gene or genes, e.g., a payload gene or genes is expressed.

A RNS-responsive transcription factor may induce, derepress, or repress gene expression depending upon the regulatory region sequence used in the genetically engineered bacteria. One or more types of RNS-sensing transcription factors and corresponding regulatory region sequences may be present in genetically engineered bacteria. In some embodiments, the genetically engineered bacteria comprise one type of RNS-sensing transcription factor, e.g., NsrR, and one corresponding regulatory region sequence, e.g., from norB. In some embodiments, the genetically engineered bacteria comprise one type of RNS-sensing transcription factor, e.g., NsrR, and two or more different corresponding regulatory region sequences, e.g., from norB and aniA. In some embodiments, the genetically engineered bacteria comprise two or more types of RNS-sensing transcription factors, e.g., NsrR and NorR, and two or more corresponding regulatory region sequences, e.g., from norB and norR, respectively. One RNS-responsive regulatory region may be capable of binding more than one transcription factor. In some embodiments, the genetically engineered bacteria comprise two or more types of RNS-sensing transcription factors and one corresponding regulatory region sequence. Nucleic acid sequences of several RNS-regulated regulatory regions are known in the art (see, e.g., Spiro 2006; Isabella et al., 2009; Dunn et al., 2010; Vine et al., 2011; Karlinsey et al., 2012).

In some embodiments, the genetically engineered bacteria of the invention comprise a gene encoding a RNS-sensing transcription factor, e.g., the nsrR gene, that is controlled by its native promoter, an inducible promoter, a promoter that is stronger than the native promoter, e.g., the GlnRS promoter or the P(Bla) promoter, or a constitutive promoter. In some instances, it may be advantageous to express the RNS-sensing transcription factor under the control of an inducible promoter in order to enhance expression stability. In some embodiments, expression of the RNS-sensing transcription factor is controlled by a different promoter than the promoter that controls expression of the therapeutic molecule. In some embodiments, expression of the RNS-sensing transcription factor is controlled by the same promoter that controls expression of the therapeutic molecule. In some embodiments, the RNS-sensing transcription factor and therapeutic molecule are divergently transcribed from a promoter region.

In some embodiments, the genetically engineered bacteria of the invention comprise a gene for a RNS-sensing transcription factor from a different species, strain, or substrain of bacteria. In some embodiments, the genetically engineered bacteria comprise a RNS-responsive regulatory region from a different species, strain, or substrain of bacteria. In some embodiments, the genetically engineered bacteria comprise a RNS-sensing transcription factor and corresponding RNS-responsive regulatory region from a different species, strain, or substrain of bacteria. The heterologous RNS-sensing transcription factor and regulatory region may increase the transcription of genes operatively linked to said regulatory region in the presence of RNS, as compared to the native transcription factor and regulatory region from bacteria of the same subtype under the same conditions.

In some embodiments, the genetically engineered bacteria comprise a RNS-sensing transcription factor, NsrR, and corresponding regulatory region, nsrR, from *Neisseria gonorrhoeae*. In some embodiments, the native RNS-sensing transcription factor, e.g., NsrR, is left intact and retains wild-type activity. In alternate embodiments, the native RNS-sensing transcription factor, e.g., NsrR, is deleted or mutated to reduce or eliminate wild-type activity.

In some embodiments, the genetically engineered bacteria of the invention comprise multiple copies of the endogenous gene encoding the RNS-sensing transcription factor, e.g., the nsrR gene. In some embodiments, the gene encoding the RNS-sensing transcription factor is present on a plasmid. In some embodiments, the gene encoding the RNS-sensing transcription factor and the gene or gene cassette for producing the therapeutic molecule are present on different plasmids. In some embodiments, the gene encoding the RNS-sensing transcription factor and the gene or gene cassette for producing the therapeutic molecule are present on the same plasmid. In some embodiments, the gene encoding the RNS-sensing transcription factor is present on a chromosome. In some embodiments, the gene encoding the RNS-sensing transcription factor and the gene or gene cassette for producing the therapeutic molecule are present on different chromosomes. In some embodiments, the gene encoding the RNS-sensing transcription factor and the gene or gene cassette for producing the therapeutic molecule are present on the same chromosome.

In some embodiments, the genetically engineered bacteria comprise a wild-type gene encoding a RNS-sensing transcription factor, e.g., the NsrR gene, and a corresponding regulatory region, e.g., a norB regulatory region, that is mutated relative to the wild-type regulatory region from bacteria of the same subtype. The mutated regulatory region increases the expression of the payload in the presence of RNS, as compared to the wild-type regulatory region under the same conditions. In some embodiments, the genetically engineered bacteria comprise a wild-type RNS-responsive regulatory region, e.g., the norB regulatory region, and a corresponding transcription factor, e.g., NsrR, that is mutated relative to the wild-type transcription factor from bacteria of the same subtype. The mutant transcription factor increases the expression of the payload in the presence of RNS, as compared to the wild-type transcription factor under the same conditions. In some embodiments, both the RNS-sensing transcription factor and corresponding regulatory region are mutated relative to the wild-type sequences from bacteria of the same subtype in order to increase expression of the payload in the presence of RNS.

In some embodiments, the gene or gene cassette for producing the anti-inflammation and/or gut barrier function enhancer molecule is present on a plasmid and operably linked to a promoter that is induced by RNS. In some embodiments, expression is further optimized by methods known in the art, e.g., by optimizing ribosomal binding sites, manipulating transcriptional regulators, and/or increasing mRNA stability.

In some embodiments, any of the gene(s) of the present disclosure may be integrated into the bacterial chromosome at one or more integration sites. For example, one or more copies of one or more encoding a payload gene(s) may be integrated into the bacterial chromosome. Having multiple copies of the gene or gen(s) integrated into the chromosome allows for greater production of the payload(s) and also permits fine-tuning of the level of expression. Alternatively, different circuits described herein, such as any of the secretion or exporter circuits, in addition to the therapeutic gene(s) or gene cassette(s) could be integrated into the bacterial chromosome at one or more different integration sites to perform multiple different functions.

ROS-Dependent Regulation

In some embodiments, the genetically engineered bacteria or genetically engineered virus comprise a gene for producing a payload that is expressed under the control of an inducible promoter. In some embodiments, the genetically engineered bacterium or genetically engineered virus that expresses a payload under the control of a promoter that is activated by conditions of cellular damage. In one embodiment, the gene for producing the payload is expressed under the control of an cellular damaged-dependent promoter that is activated in environments in which there is cellular or tissue damage, e.g., a reactive oxygen species or ROS promoter.

As used herein, "reactive oxygen species" and "ROS" are used interchangeably to refer to highly active molecules, ions, and/or radicals derived from molecular oxygen. ROS can be produced as byproducts of aerobic respiration or metal-catalyzed oxidation and may cause deleterious cellular effects such as oxidative damage. ROS includes, but is not limited to, hydrogen peroxide ($H_2O_2$), organic peroxide (ROOH), hydroxyl ion (OH—), hydroxyl radical (.OH), superoxide or superoxide anion (.$O_2$-), singlet oxygen ($1O_2$), ozone ($O_3$), carbonate radical, peroxide or peroxyl radical (.$O_2$-2), hypochlorous acid (HOCl), hypochlorite ion (OCl—), sodium hypochlorite (NaOCl), nitric oxide (NO.), and peroxynitrite or peroxynitrite anion (ONOO—) (unpaired electrons denoted by .). Bacteria have evolved transcription factors that are capable of sensing ROS levels. Different ROS signaling pathways are triggered by different ROS levels and occur with different kinetics (Marinho et al., 2014).

As used herein, "ROS-inducible regulatory region" refers to a nucleic acid sequence to which one or more ROS-sensing transcription factors is capable of binding, wherein the binding and/or activation of the corresponding transcription factor activates downstream gene expression; in the presence of ROS, the transcription factor binds to and/or activates the regulatory region. In some embodiments, the ROS-inducible regulatory region comprises a promoter sequence. In some embodiments, the transcription factor senses ROS and subsequently binds to the ROS-inducible regulatory region, thereby activating downstream gene expression. In alternate embodiments, the transcription factor is bound to the ROS-inducible regulatory region in the absence of ROS; in the presence of ROS, the transcription factor undergoes a conformational change, thereby activating downstream gene expression. The ROS-inducible regulatory region may be operatively linked to a gene sequence or gene sequence, e.g., a sequence or sequences encoding one or more payload(s). For example, in the presence of ROS, a transcription factor, e.g., OxyR, senses ROS and activates a corresponding ROS-inducible regulatory region, thereby driving expression of an operatively linked gene sequence or gene sequences. Thus, ROS induces expression of the gene or genes.

As used herein, "ROS-derepressible regulatory region" refers to a nucleic acid sequence to which one or more ROS-sensing transcription factors is capable of binding, wherein the binding of the corresponding transcription factor represses downstream gene expression; in the presence of ROS, the transcription factor does not bind to and does not repress the regulatory region. In some embodiments, the ROS-derepressible regulatory region comprises a promoter sequence. The ROS-derepressible regulatory region may be operatively linked to a gene or genes, e.g., one or more genes encoding one or more payload(s). For example, in the presence of ROS, a transcription factor, e.g., OhrR, senses ROS and no longer binds to and/or represses the regulatory region, thereby derepressing an operatively linked gene sequence or gene cassette. Thus, ROS derepresses expression of the gene or gene cassette.

As used herein, "ROS-repressible regulatory region" refers to a nucleic acid sequence to which one or more ROS-sensing transcription factors is capable of binding, wherein the binding of the corresponding transcription factor represses downstream gene expression; in the presence of ROS, the transcription factor binds to and represses the regulatory region. In some embodiments, the ROS-repressible regulatory region comprises a promoter sequence. In some embodiments, the transcription factor that senses ROS is capable of binding to a regulatory region that overlaps with part of the promoter sequence. In alternate embodiments, the transcription factor that senses ROS is capable of binding to a regulatory region that is upstream or downstream of the promoter sequence. The ROS-repressible regulatory region may be operatively linked to a gene sequence or gene sequences. For example, in the presence of ROS, a transcription factor, e.g., PerR, senses ROS and binds to a corresponding ROS-repressible regulatory region, thereby blocking expression of an operatively linked gene sequence or gene sequences. Thus, ROS represses expression of the gene or genes.

As used herein, a "ROS-responsive regulatory region" refers to a ROS-inducible regulatory region, a ROS-repressible regulatory region, and/or a ROS-derepressible regulatory region. In some embodiments, the ROS-responsive regulatory region comprises a promoter sequence. Each regulatory region is capable of binding at least one corresponding ROS-sensing transcription factor. Examples of transcription factors that sense ROS and their corresponding ROS-responsive genes, promoters, and/or regulatory regions include, but are not limited to, those shown in Table B.

TABLE B

Examples of ROS-sensing transcription factors and ROS-responsive genes

| ROS-sensing transcription factor: | Primarily capable of sensing: | Examples of responsive genes, promoters, and/or regulatory regions: |
|---|---|---|
| OxyR | $H_2O_2$ | ahpC; ahpF; dps; dsbG; fhuF; flu; fur; gor; grxA; hemH; katG; oxyS; sufA; sufB; sufC; sufD; sufE; sufS; trxC; uxuA; yaaA; yaeH; yaiA; ybjM; ydcH; ydeN; ygaQ; yljA; ytfK |
| PerR | $H_2O_2$ | katA; ahpCF; mrgA; zoaA; fur; hemAXCDBL; srfA |
| OhrR | Organic peroxides NaOCl | ohrA |
| SoxR | •$O_2^-$ NO• (also capable of sensing $H_2O_2$) | soxS |
| RosR | $H_2O_2$ | rbtT; tnp16a; rluC1; tnp5a; mscL; tnp2d; phoD; tnp15b; pstA; tnp5b; xylC; gabD1; rluC2; cgtS9; azlC; narKGHJI; rosR |

In some embodiments, the genetically engineered bacteria comprise a tunable regulatory region that is directly or indirectly controlled by a transcription factor that is capable of sensing at least one reactive oxygen species. The tunable regulatory region is operatively linked to a gene or gene cassette capable of directly or indirectly driving the expression of a payload, thus controlling expression of the payload relative to ROS levels. For example, the tunable regulatory region is a ROS-inducible regulatory region, and the molecule is a payload; when ROS is present, e.g., in an inflamed tissue, a ROS-sensing transcription factor binds to and/or activates the regulatory region and drives expression of the gene sequence for the payload, thereby producing the payload. Subsequently, when inflammation is ameliorated, ROS levels are reduced, and production of the payload is decreased or eliminated.

In some embodiments, the tunable regulatory region is a ROS-inducible regulatory region; in the presence of ROS, a transcription factor senses ROS and activates the ROS-inducible regulatory region, thereby driving expression of an operatively linked gene or gene cassette. In some embodiments, the transcription factor senses ROS and subsequently binds to the ROS-inducible regulatory region, thereby activating downstream gene expression. In alternate embodiments, the transcription factor is bound to the ROS-inducible regulatory region in the absence of ROS; when the transcription factor senses ROS, it undergoes a conformational change, thereby inducing downstream gene expression.

In some embodiments, the tunable regulatory region is a ROS-inducible regulatory region, and the transcription factor that senses ROS is OxyR. OxyR "functions primarily as a global regulator of the peroxide stress response" and is capable of regulating dozens of genes, e.g., "genes involved in H2O2 detoxification (katE, ahpCF), heme biosynthesis (hem H), reductant supply (grxA, gor, trxC), thiol-disulfide isomerization (dsbG), Fe—S center repair (sufA-E, sufS), iron binding (yaaA), repression of iron import systems (fur)" and "OxyS, a small regulatory RNA" (Dubbs et al., 2012). The genetically engineered bacteria may comprise any suitable ROS-responsive regulatory region from a gene that is activated by OxyR. Genes that are capable of being activated by OxyR are known in the art (see, e.g., Zheng et al., 2001;

Dubbs et al., 2012). In certain embodiments, the genetically engineered bacteria of the invention comprise a ROS-inducible regulatory region from oxyS that is operatively linked to a gene, e.g., a payload gene. In the presence of ROS, e.g., H2O2, an OxyR transcription factor senses ROS and activates to the oxyS regulatory region, thereby driving expression of the operatively linked payload gene and producing the payload. In some embodiments, OxyR is encoded by an *E. coli* oxyR gene. In some embodiments, the oxyS regulatory region is an *E. coli* oxyS regulatory region. In some embodiments, the ROS-inducible regulatory region is selected from the regulatory region of katG, dps, and ahpC.

In alternate embodiments, the tunable regulatory region is a ROS-inducible regulatory region, and the corresponding transcription factor that senses ROS is SoxR. When SoxR is "activated by oxidation of its [2Fe-2S] cluster, it increases the synthesis of SoxS, which then activates its target gene expression" (Koo et al., 2003). "SoxR is known to respond primarily to superoxide and nitric oxide" (Koo et al., 2003), and is also capable of responding to H2O2. The genetically engineered bacteria of the invention may comprise any suitable ROS-responsive regulatory region from a gene that is activated by SoxR. Genes that are capable of being activated by SoxR are known in the art (see, e.g., Koo et al., 2003). In certain embodiments, the genetically engineered bacteria of the invention comprise a ROS-inducible regulatory region from soxS that is operatively linked to a gene, e.g., a payload. In the presence of ROS, the SoxR transcription factor senses ROS and activates the soxS regulatory region, thereby driving expression of the operatively linked a payload gene and producing the a payload.

In some embodiments, the tunable regulatory region is a ROS-derepressible regulatory region, and binding of a corresponding transcription factor represses downstream gene expression; in the presence of ROS, the transcription factor no longer binds to the regulatory region, thereby derepressing the operatively linked gene or gene cassette.

In some embodiments, the tunable regulatory region is a ROS-derepressible regulatory region, and the transcription factor that senses ROS is OhrR. OhrR "binds to a pair of inverted repeat DNA sequences overlapping the ohrA promoter site and thereby represses the transcription event," but oxidized OhrR is "unable to bind its DNA target" (Duarte et al., 2010). OhrR is a "transcriptional repressor [that] . . . senses both organic peroxides and NaOCl" (Dubbs et al., 2012) and is "weakly activated by H2O2 but it shows much higher reactivity for organic hydroperoxides" (Duarte et al., 2010). The genetically engineered bacteria of the invention may comprise any suitable ROS-responsive regulatory region from a gene that is repressed by OhrR. Genes that are capable of being repressed by OhrR are known in the art (see, e.g., Dubbs et al., 2012). In certain embodiments, the genetically engineered bacteria of the invention comprise a ROS-derepressible regulatory region from ohrA that is operatively linked to a gene or gene cassette, e.g., a payload gene. In the presence of ROS, e.g., NaOCl, an OhrR transcription factor senses ROS and no longer binds to the ohrA regulatory region, thereby derepressing the operatively linked payload gene and producing the payload.

OhrR is a member of the MarR family of ROS-responsive regulators. "Most members of the MarR family are transcriptional repressors and often bind to the −10 or −35 region in the promoter causing a steric inhibition of RNA polymerase binding" (Bussmann et al., 2010). Other members of this family are known in the art and include, but are not limited to, OspR, MgrA, RosR, and SarZ. In some embodiments, the transcription factor that senses ROS is OspR, MgRA, RosR, and/or SarZ, and the genetically engineered bacteria of the invention comprises one or more corresponding regulatory region sequences from a gene that is repressed by OspR, MgRA, RosR, and/or SarZ. Genes that are capable of being repressed by OspR, MgRA, RosR, and/or SarZ are known in the art (see, e.g., Dubbs et al., 2012).

In some embodiments, the tunable regulatory region is a ROS-derepressible regulatory region, and the corresponding transcription factor that senses ROS is RosR. RosR is "a MarR-type transcriptional regulator" that binds to an "18-bp inverted repeat with the consensus sequence TTGTTGAY-RYRTCAACWA" (SEQ ID NO: 122) and is "reversibly inhibited by the oxidant H2O2" (Bussmann et al., 2010). RosR is capable of repressing numerous genes and putative genes, including but not limited to "a putative polyisoprenoid-binding protein (cg1322, gene upstream of and divergent from rosR), a sensory histidine kinase (cgtS9), a putative transcriptional regulator of the Crp/FNR family (cg3291), a protein of the glutathione S-transferase family (cg1426), two putative FMN reductases (cg1150 and cg1850), and four putative monooxygenases (cg0823, cg1848, cg2329, and cg3084)" (Bussmann et al., 2010). The genetically engineered bacteria of the invention may comprise any suitable ROS-responsive regulatory region from a gene that is repressed by RosR. Genes that are capable of being repressed by RosR are known in the art (see, e.g., Bussmann et al., 2010). In certain embodiments, the genetically engineered bacteria of the invention comprise a ROS-derepressible regulatory region from cgtS9 that is operatively linked to a gene or gene cassette, e.g., a payload. In the presence of ROS, e.g., H2O2, a RosR transcription factor senses ROS and no longer binds to the cgtS9 regulatory region, thereby derepressing the operatively linked payload gene and producing the payload.

In some embodiments, it is advantageous for the genetically engineered bacteria to express a ROS-sensing transcription factor that does not regulate the expression of a significant number of native genes in the bacteria. In some embodiments, the genetically engineered bacterium of the invention expresses a ROS-sensing transcription factor from a different species, strain, or substrain of bacteria, wherein the transcription factor does not bind to regulatory sequences in the genetically engineered bacterium of the invention. In some embodiments, the genetically engineered bacterium of the invention is *Escherichia coli*, and the ROS-sensing transcription factor is RosR, e.g., from *Corynebacterium glutamicum*, wherein the *Escherichia coli* does not comprise binding sites for said RosR. In some embodiments, the heterologous transcription factor minimizes or eliminates off-target effects on endogenous regulatory regions and genes in the genetically engineered bacteria.

In some embodiments, the tunable regulatory region is a ROS-repressible regulatory region, and binding of a corresponding transcription factor represses downstream gene expression; in the presence of ROS, the transcription factor senses ROS and binds to the ROS-repressible regulatory region, thereby repressing expression of the operatively linked gene or gene cassette. In some embodiments, the ROS-sensing transcription factor is capable of binding to a regulatory region that overlaps with part of the promoter sequence. In alternate embodiments, the ROS-sensing transcription factor is capable of binding to a regulatory region that is upstream or downstream of the promoter sequence.

In some embodiments, the tunable regulatory region is a ROS-repressible regulatory region, and the transcription factor that senses ROS is PerR. In *Bacillus subtilis*, PerR "when bound to DNA, represses the genes coding for proteins involved in the oxidative stress response (katA, ahpC, and mrgA), metal homeostasis (hemAXCDBL, fur, and zoaA) and its own synthesis (perR)" (Marinho et al., 2014). PerR is a "global regulator that responds primarily to H2O2" (Dubbs et al., 2012) and "interacts with DNA at the per box, a specific palindromic consensus sequence (TTATAATNATTATAA) (SEQ ID NO: 123) residing within and near the promoter sequences of PerR-controlled genes" (Marinho et al., 2014). PerR is capable of binding a regulatory region that "overlaps part of the promoter or is immediately downstream from it" (Dubbs et al., 2012). The genetically engineered bacteria of the invention may comprise any suitable ROS-responsive regulatory region from a gene that is repressed by PerR. Genes that are capable of being repressed by PerR are known in the art (see, e.g., Dubbs et al., 2012).

In these embodiments, the genetically engineered bacteria may comprise a two repressor activation regulatory circuit, which is used to express a payload. The two repressor activation regulatory circuit comprises a first ROS-sensing repressor, e.g., PerR, and a second repressor, e.g., TetR, which is operatively linked to a gene or gene cassette, e.g., a payload. In one aspect of these embodiments, the ROS-sensing repressor inhibits transcription of the second repressor, which inhibits the transcription of the gene or gene cassette. Examples of second repressors useful in these embodiments include, but are not limited to, TetR, C1, and LexA. In some embodiments, the ROS-sensing repressor is PerR. In some embodiments, the second repressor is TetR. In this embodiment, a PerR-repressible regulatory region drives expression of TetR, and a TetR-repressible regulatory region drives expression of the gene or gene cassette, e.g., a payload. In the absence of PerR binding (which occurs in the absence of ROS), tetR is transcribed, and TetR represses expression of the gene or gene cassette, e.g., a payload. In the presence of PerR binding (which occurs in the presence of ROS), tetR expression is repressed, and the gene or gene cassette, e.g., a payload, is expressed.

A ROS-responsive transcription factor may induce, derepress, or repress gene expression depending upon the regulatory region sequence used in the genetically engineered bacteria. For example, although "OxyR is primarily thought of as a transcriptional activator under oxidizing conditions . . . OxyR can function as either a repressor or activator under both oxidizing and reducing conditions" (Dubbs et al., 2012), and OxyR "has been shown to be a repressor of its own expression as well as that of fhuF (encoding a ferric ion reductase) and flu (encoding the antigen 43 outer membrane protein)" (Zheng et al., 2001). The genetically engineered bacteria of the invention may comprise any suitable ROS-responsive regulatory region from a gene that is repressed by OxyR. In some embodiments, OxyR is used in a two repressor activation regulatory circuit, as described above. Genes that are capable of being repressed by OxyR are known in the art (see, e.g., Zheng et al., 2001). Or, for example, although RosR is capable of repressing a number of genes, it is also capable of activating certain genes, e.g., the narKGHJI operon. In some embodiments, the genetically engineered bacteria comprise any suitable ROS-responsive regulatory region from a gene that is activated by RosR. In addition, "PerR-mediated positive regulation has also been observed . . . and appears to involve PerR binding to distant upstream sites" (Dubbs et al., 2012). In some embodiments, the genetically engineered bacteria comprise any suitable ROS-responsive regulatory region from a gene that is activated by PerR.

One or more types of ROS-sensing transcription factors and corresponding regulatory region sequences may be present in genetically engineered bacteria. For example, "OhrR is found in both Gram-positive and Gram-negative bacteria and can coreside with either OxyR or PerR or both" (Dubbs et al., 2012). In some embodiments, the genetically engineered bacteria comprise one type of ROS-sensing transcription factor, e.g., OxyR, and one corresponding regulatory region sequence, e.g., from oxyS. In some embodiments, the genetically engineered bacteria comprise one type of ROS-sensing transcription factor, e.g., OxyR, and two or more different corresponding regulatory region sequences, e.g., from oxyS and katG. In some embodiments, the genetically engineered bacteria comprise two or more types of ROS-sensing transcription factors, e.g., OxyR and PerR, and two or more corresponding regulatory region sequences, e.g., from oxyS and katA, respectively. One ROS-responsive regulatory region may be capable of binding more than one transcription factor. In some embodiments, the genetically engineered bacteria comprise two or more types of ROS-sensing transcription factors and one corresponding regulatory region sequence.

Nucleic acid sequences of several exemplary OxyR-regulated regulatory regions are shown in Table C. OxyR binding sites are underlined and bolded. In some embodiments, genetically engineered bacteria comprise a nucleic acid sequence that is at least about 80%, at least about 85%, at least about 90%, at least about 95%, or at least about 99% homologous to the DNA sequence of SEQ ID NO: 63, 64, 65, or 66, or a functional fragment thereof.

TABLE C

Nucleotide sequences of exemplary OxyR-regulated regulatory regions

| Regulatory sequence | Sequence |
|---|---|
| katG (SEQ ID NO: 63) | TGTGGCTTTTATGAAAATCACACAGTGATCACAAAT TTTAAACAGAGCACAAAATGCTGCCTCGAAATGAGG GCGGGAAAATAAGGTTATCAGCCTTGTTTTCTCCCT CATTACTTGAAGGATATGAAGCTAAAACCCTTTTTT ATAAAGCATTTGTCCGAATTCGGACATAATCAAAAA AGCTTAATTAAGATCAATTTGATCTACATCTCTTTA ACCAACAATATGTAAGATCTCAACTATCGCATCCGT GGATTAATTCAATTATAACTTCTCTCTAACGCTGTG TATCGTAACGGTAACACTGTAGAGGGGAGCACATTG ATGCGAATTCATTAAAGAGGAGAAAGGTACC |
| dps (SEQ ID NO: 64) | TTCCGAAAATTCCTGGCGAGCAGATAAATAAGAATT GTTCTTATCAATATATCTAACTCATTGAATCTTTAT TAGTTTTGTTTTTCACGCTTGTTACCACTATTAGTG TGATAGGAACAGCCAGAATAGCGGAACACATAGCCG GTGCTATACTTAATCTCGTTAATTACTGGGACATAA CATCAAGAGGATATGAAATTCGAATTCATTAAAGAG GAGAAAGGTACC |
| ahpC (SEQ ID NO: 65) | GCTTAGATCAGGTGATTGCCCTTTGTTTATGAGGGT GTTGTAATCCATGTCGTTGTTGCATTTGTAAGGGCA ACACCTCAGCCTGCAGGCAGGCACTGAAGATACCAA AGGGTAGTTCAGATTACACGGTCACCTGGAAAGGGG GCCATTTTACTTTTTATCGCCGCTGGCGGTGCAAAG TTCACAAAGTTGTCTTACGAAGGTTGTAAGGTAAAA CTTATCGATTTGATAATGGAAACGCATTAGCCGAAT CGGCAAAAATTGGTTACCTTACATCTCATCGAAAAC ACGGAGGAAGTATAGATGCGAATTCATTAAAGAGGA GAAAGGTACC |

TABLE C-continued

Nucleotide sequences of exemplary
OxyR-regulated regulatory regions

| Regulatory sequence | Sequence |
|---|---|
| oxyS (SEQ ID NO: 66) | CTCGAGTTCATTATCCATCCTCCATCGCCACGATAG TTCATGCGATAGGTAGAATAGCAATGAACGATTAT CCCTATCAAGCATTCTGACTGATAATTGCTCACACG AATTCATTAAAGAGGAGAAAGGTACC |

In some embodiments, the genetically engineered bacteria of the invention comprise a gene encoding a ROS-sensing transcription factor, e.g., the oxyR gene, that is controlled by its native promoter, an inducible promoter, a promoter that is stronger than the native promoter, e.g., the GlnRS promoter or the P(Bla) promoter, or a constitutive promoter. In some instances, it may be advantageous to express the ROS-sensing transcription factor under the control of an inducible promoter in order to enhance expression stability. In some embodiments, expression of the ROS-sensing transcription factor is controlled by a different promoter than the promoter that controls expression of the therapeutic molecule. In some embodiments, expression of the ROS-sensing transcription factor is controlled by the same promoter that controls expression of the therapeutic molecule. In some embodiments, the ROS-sensing transcription factor and therapeutic molecule are divergently transcribed from a promoter region.

In some embodiments, the genetically engineered bacteria of the invention comprise a gene for a ROS-sensing transcription factor from a different species, strain, or substrain of bacteria. In some embodiments, the genetically engineered bacteria comprise a ROS-responsive regulatory region from a different species, strain, or substrain of bacteria. In some embodiments, the genetically engineered bacteria comprise a ROS-sensing transcription factor and corresponding ROS-responsive regulatory region from a different species, strain, or substrain of bacteria. The heterologous ROS-sensing transcription factor and regulatory region may increase the transcription of genes operatively linked to said regulatory region in the presence of ROS, as compared to the native transcription factor and regulatory region from bacteria of the same subtype under the same conditions.

In some embodiments, the genetically engineered bacteria comprise a ROS-sensing transcription factor, OxyR, and corresponding regulatory region, oxyS, from *Escherichia coli*. In some embodiments, the native ROS-sensing transcription factor, e.g., OxyR, is left intact and retains wild-type activity. In alternate embodiments, the native ROS-sensing transcription factor, e.g., OxyR, is deleted or mutated to reduce or eliminate wild-type activity.

In some embodiments, the genetically engineered bacteria of the invention comprise multiple copies of the endogenous gene encoding the ROS-sensing transcription factor, e.g., the oxyR gene. In some embodiments, the gene encoding the ROS-sensing transcription factor is present on a plasmid. In some embodiments, the gene encoding the ROS-sensing transcription factor and the gene or gene cassette for producing the therapeutic molecule are present on different plasmids. In some embodiments, the gene encoding the ROS-sensing transcription factor and the gene or gene cassette for producing the therapeutic molecule are present on the same. In some embodiments, the gene encoding the ROS-sensing transcription factor is present on a chromosome. In some embodiments, the gene encoding the ROS-sensing transcription factor and the gene or gene cassette for producing the therapeutic molecule are present on different chromosomes. In some embodiments, the gene encoding the ROS-sensing transcription factor and the gene or gene cassette for producing the therapeutic molecule are present on the same chromosome.

In some embodiments, the genetically engineered bacteria comprise a wild-type gene encoding a ROS-sensing transcription factor, e.g., the soxR gene, and a corresponding regulatory region, e.g., a soxS regulatory region, that is mutated relative to the wild-type regulatory region from bacteria of the same subtype. The mutated regulatory region increases the expression of the payload in the presence of ROS, as compared to the wild-type regulatory region under the same conditions. In some embodiments, the genetically engineered bacteria comprise a wild-type ROS-responsive regulatory region, e.g., the oxyS regulatory region, and a corresponding transcription factor, e.g., OxyR, that is mutated relative to the wild-type transcription factor from bacteria of the same subtype. The mutant transcription factor increases the expression of the payload in the presence of ROS, as compared to the wild-type transcription factor under the same conditions. In some embodiments, both the ROS-sensing transcription factor and corresponding regulatory region are mutated relative to the wild-type sequences from bacteria of the same subtype in order to increase expression of the payload in the presence of ROS.

In some embodiments, the gene or gene cassette for producing the payload is present on a plasmid and operably linked to a promoter that is induced by ROS. In some embodiments, the gene or gene cassette for producing the payload is present in the chromosome and operably linked to a promoter that is induced by ROS. In some embodiments, the gene or gene cassette for producing the payload is present on a chromosome and operably linked to a promoter that is induced by exposure to tetracycline. In some embodiments, the gene or gene cassette for producing the payload is present on a plasmid and operably linked to a promoter that is induced by exposure to tetracycline. In some embodiments, expression is further optimized by methods known in the art, e.g., by optimizing ribosomal binding sites, manipulating transcriptional regulators, and/or increasing mRNA stability.

In some embodiments, the genetically engineered bacteria may comprise multiple copies of the gene(s) capable of producing a payload(s). In some embodiments, the gene(s) capable of producing a payload(s) is present on a plasmid and operatively linked to a ROS-responsive regulatory region. In some embodiments, the gene(s) capable of producing a payload is present in a chromosome and operatively linked to a ROS-responsive regulatory region.

Thus, in some embodiments, the genetically engineered bacteria or genetically engineered virus produce one or more payloads under the control of an oxygen level-dependent promoter, a reactive oxygen species (ROS)-dependent promoter, or a reactive nitrogen species (RNS)-dependent promoter, and a corresponding transcription factor.

In some embodiments, the genetically engineered bacteria comprise a stably maintained plasmid or chromosome carrying a gene for producing a payload, such that the payload can be expressed in the host cell, and the host cell is capable of survival and/or growth in vitro, e.g., in medium, and/or in vivo. In some embodiments, a bacterium may comprise multiple copies of the gene encoding the payload. In some embodiments, the gene encoding the payload is expressed on a low-copy plasmid. In some embodiments, the low-copy plasmid may be useful for increasing stability of expression. In some embodiments, the low-copy plasmid may be useful for decreasing leaky expression under non-inducing conditions. In some embodiments, the gene encoding the payload is expressed on a high-copy plasmid. In some embodiments, the high-copy plasmid may be useful for increasing expression of the payload. In some embodiments, the gene encoding the payload is expressed on a chromosome.

In some embodiments, the bacteria are genetically engineered to include multiple mechanisms of action (MOAs), e.g., circuits producing multiple copies of the same product (e.g., to enhance copy number) or circuits performing multiple different functions. For example, the genetically engineered bacteria may include four copies of the gene encoding a particular payload inserted at four different insertion sites. Alternatively, the genetically engineered bacteria may include three copies of the gene encoding a particular payload inserted at three different insertion sites and three copies of the gene encoding a different payload inserted at three different insertion sites.

In some embodiments, under conditions where the payload is expressed, the genetically engineered bacteria of the disclosure produce at least about 1.5-fold, at least about 2-fold, at least about 10-fold, at least about 15-fold, at least about 20-fold, at least about 30-fold, at least about 50-fold, at least about 100-fold, at least about 200-fold, at least about 300-fold, at least about 400-fold, at least about 500-fold, at least about 600-fold, at least about 700-fold, at least about 800-fold, at least about 900-fold, at least about 1,000-fold, or at least about 1,500-fold more of the payload, and/or transcript of the gene(s) in the operon as compared to unmodified bacteria of the same subtype under the same conditions.

In some embodiments, quantitative PCR (qPCR) is used to amplify, detect, and/or quantify mRNA expression levels of the payload gene(s). Primers specific for payload the gene(s) may be designed and used to detect mRNA in a sample according to methods known in the art. In some embodiments, a fluorophore is added to a sample reaction mixture that may contain payload mRNA, and a thermal cycler is used to illuminate the sample reaction mixture with a specific wavelength of light and detect the subsequent emission by the fluorophore. The reaction mixture is heated and cooled to predetermined temperatures for predetermined time periods. In certain embodiments, the heating and cooling is repeated for a predetermined number of cycles. In some embodiments, the reaction mixture is heated and cooled to 90-100° C., 60-70° C., and 30-50° C. for a predetermined number of cycles. In a certain embodiment, the reaction mixture is heated and cooled to 93-97° C., 55-65° C., and 35-45° C. for a predetermined number of cycles. In some embodiments, the accumulating amplicon is quantified after each cycle of the qPCR. The number of cycles at which fluorescence exceeds the threshold is the threshold cycle (CT). At least one CT result for each sample is generated, and the CT result(s) may be used to determine mRNA expression levels of the payload gene(s).

In some embodiments, quantitative PCR (qPCR) is used to amplify, detect, and/or quantify mRNA expression levels of the payload gene(s). Primers specific for payload the gene(s) may be designed and used to detect mRNA in a sample according to methods known in the art. In some embodiments, a fluorophore is added to a sample reaction mixture that may contain payload mRNA, and a thermal cycler is used to illuminate the sample reaction mixture with a specific wavelength of light and detect the subsequent emission by the fluorophore. The reaction mixture is heated and cooled to predetermined temperatures for predetermined time periods. In certain embodiments, the heating and cooling is repeated for a predetermined number of cycles. In some embodiments, the reaction mixture is heated and cooled to 90-100° C., 60-70° C., and 30-50° C. for a predetermined number of cycles. In a certain embodiment, the reaction mixture is heated and cooled to 93-97° C., 55-65° C., and 35-45° C. for a predetermined number of cycles. In some embodiments, the accumulating amplicon is quantified after each cycle of the qPCR. The number of cycles at which fluorescence exceeds the threshold is the threshold cycle (CT). At least one CT result for each sample is generated, and the CT result(s) may be used to determine mRNA expression levels of the payload gene(s).

Multiple Mechanisms of Action

Figure 45:
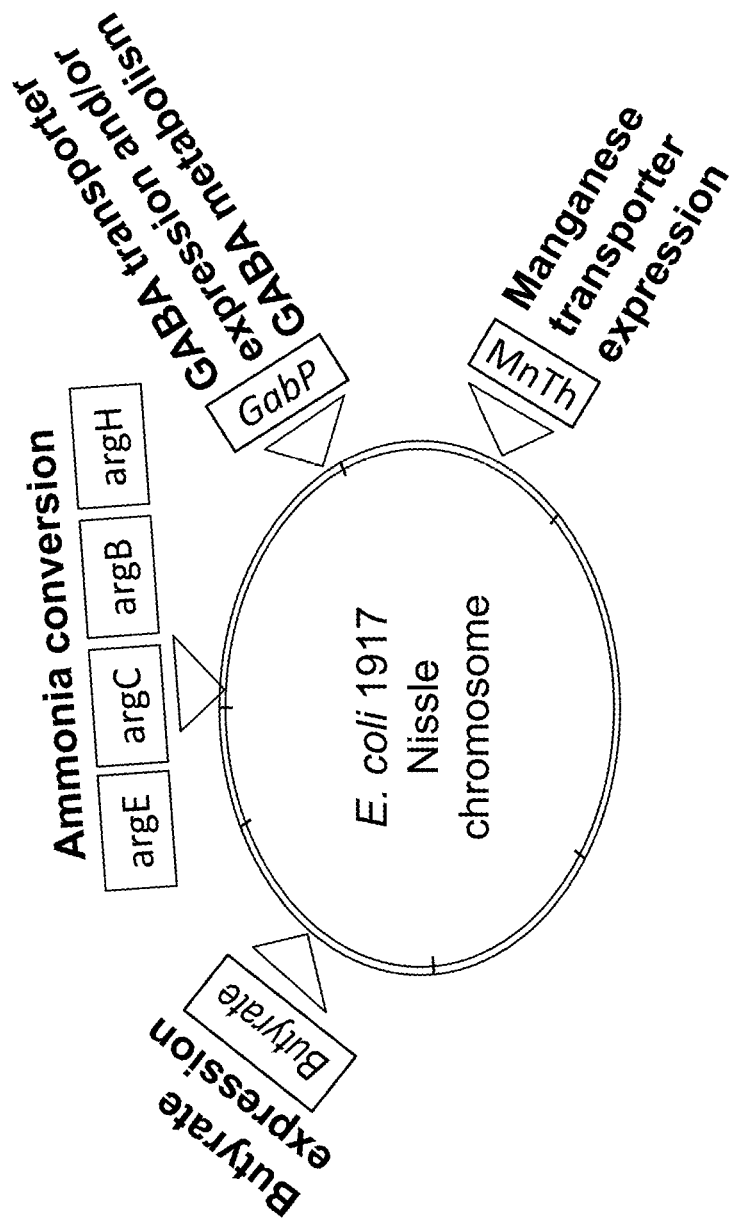
FIG. 45 depicts an exemplary schematic of the E. coli 1917 Nissle chromosome comprising multiple MoAs. In some embodiments, an ammonia conversion circuit, a butyrate production circuit, a GABA transport and/or a GABA metabolic circuit, and a manganese transport circuit are inserted at four or more different chromosomal insertion sites
Figures 46A, 46B:
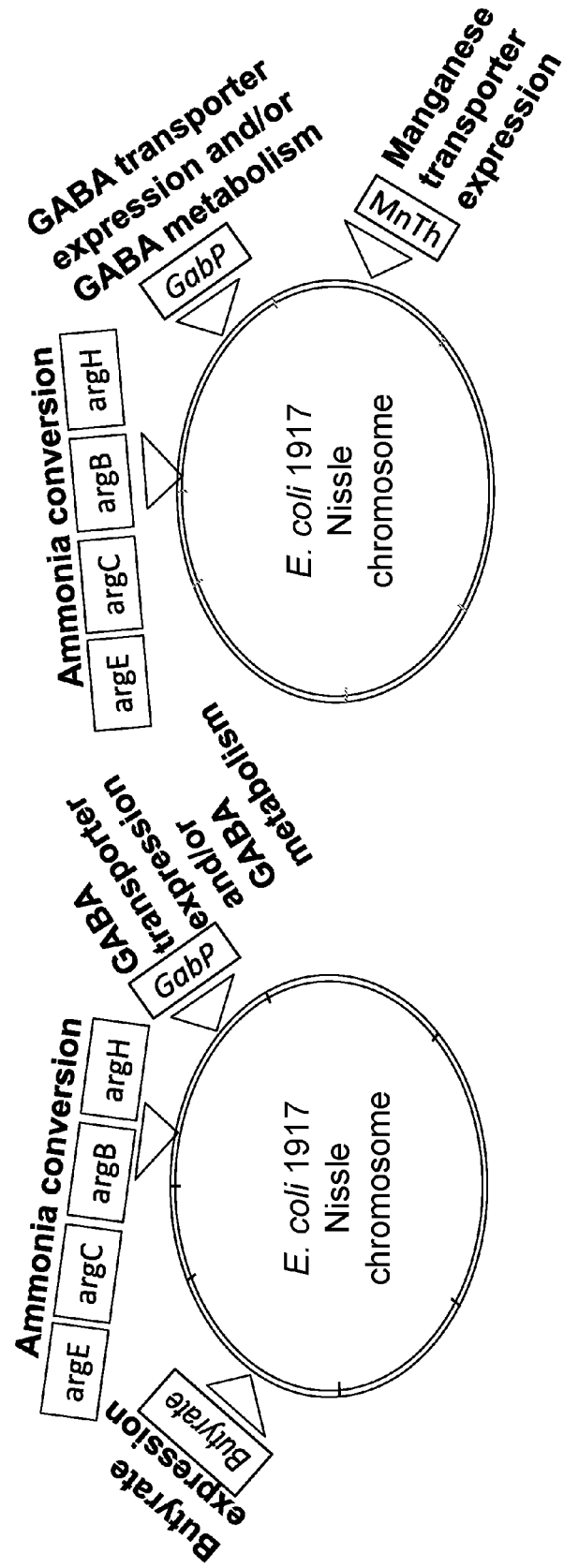
FIGS. 46A and 46B depict an exemplary schematic of the E. coli 1917 Nissle chromosome comprising multiple MoAs.
Figure 47B:
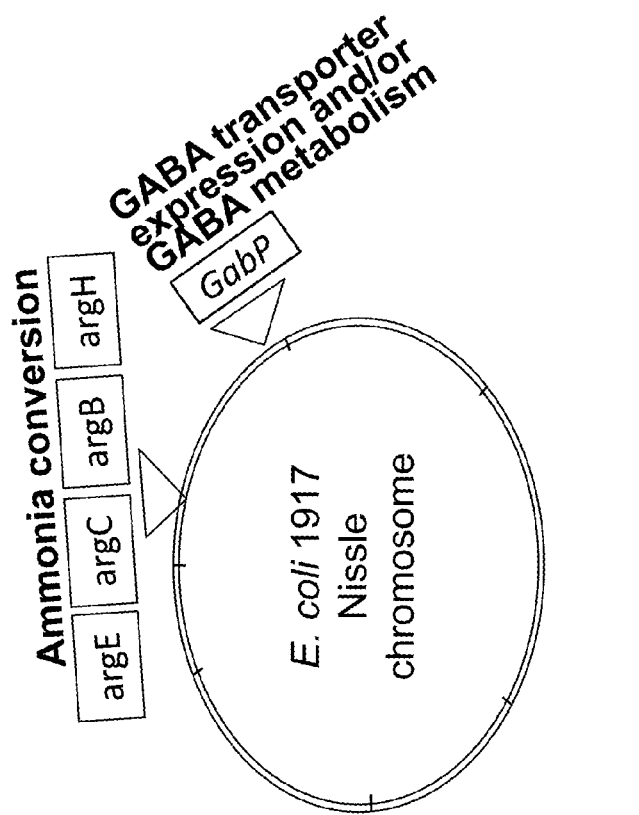
FIGS. 47A and 47B depict an exemplary schematic of the E. coli 1917 Nissle chromosome comprising multiple MoAs.
Figure 47A:
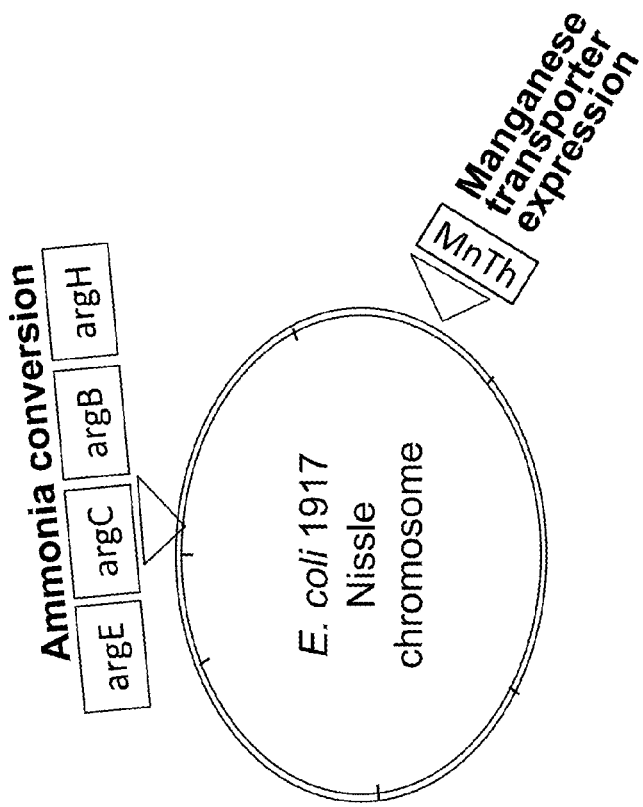
Figure 48A:
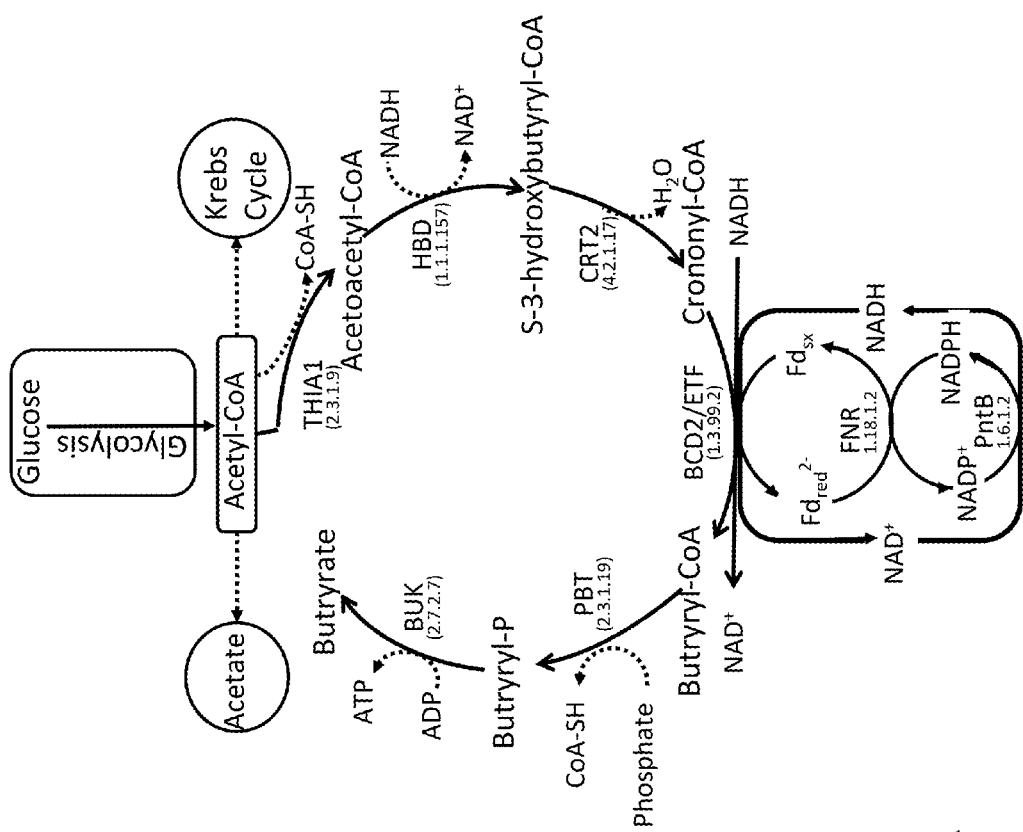
FIG. 48A depicts a metabolic pathway for butyrate production
Figure 48B:
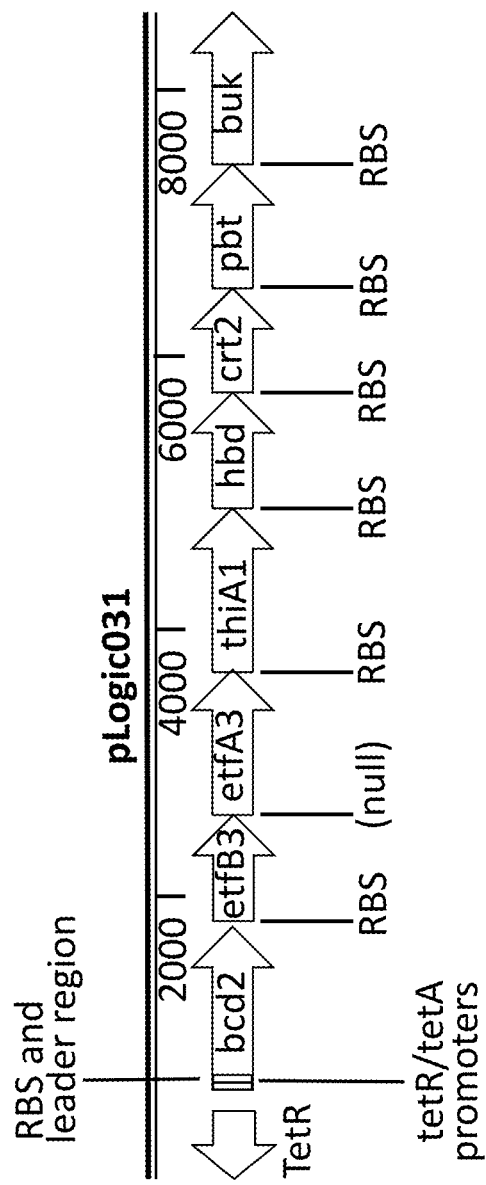
FIGS. 48B and 48C depict two schematics of two different butyrate producing circuits (found in SYN-UCD503 and SYN-UCD504), both under the control of a tetracycline inducible promoter.
Figure 48C:
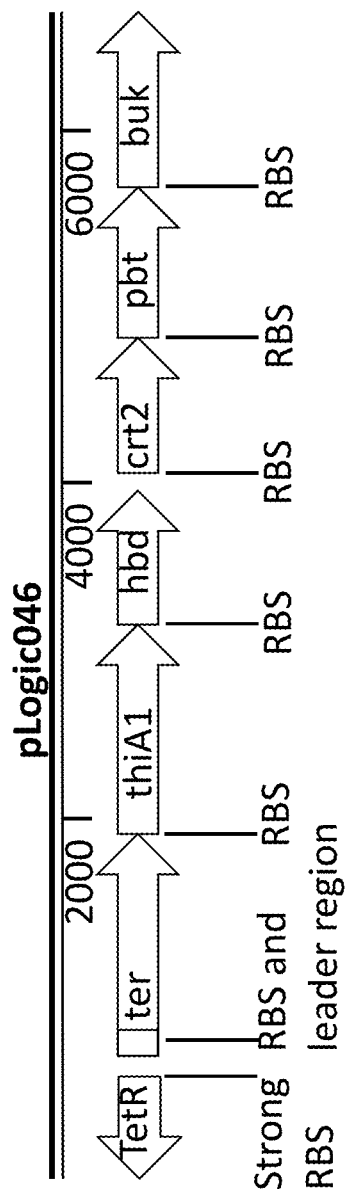
Figure 48D:
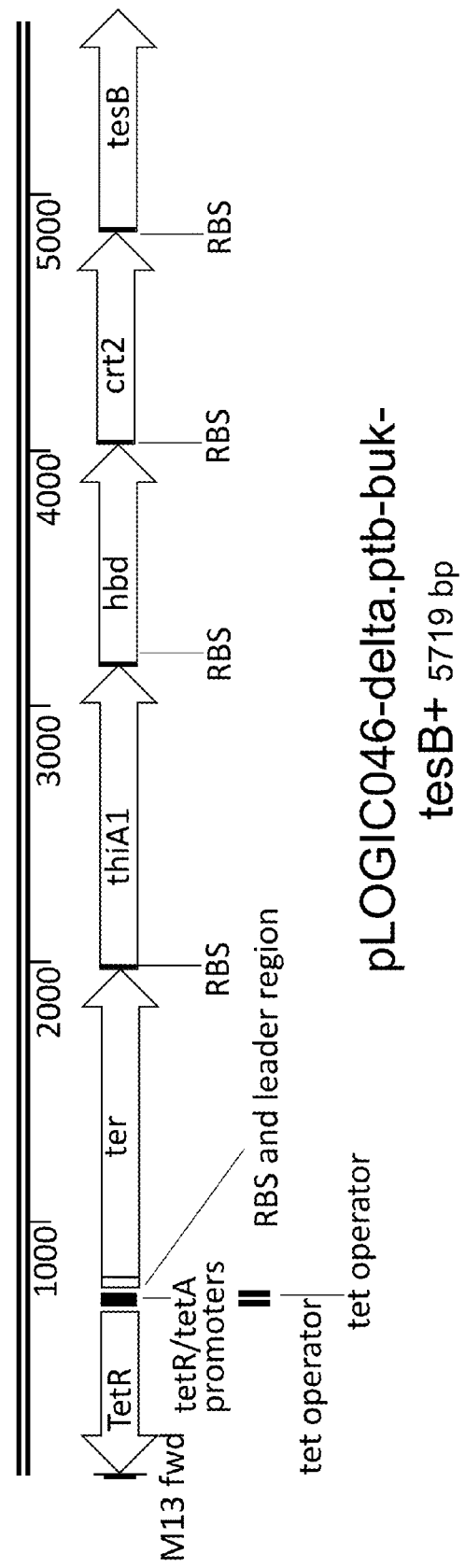
FIG. 48D depicts a schematic of a third butyrate gene cassette (found in SYN-UCD505) under the control of a tetracycline inducible promoter. SYN-UCD503 comprises a bdc2 butyrate cassette under control of tet promoter on a plasmid. A "bdc2 cassette" or "bdc2 butyrate cassette" refres to a butyrate producing cassette that comprises at least the following genes: bcd2, etfB3, etfA3, hbd, crt2, pbt, and buk genes. SYN-UCD504 comprises a ter butyrate cassette (ter gene replaces the bcd2, etfB3, and etfA3 genes) under control of tet promoter on a plasmid. A "ter cassette" or "ter butyrate cassette" refers to a butyrate producing cassete that comprises at least the following genes: ter, thiA1, hbd, crt2, pbt, buk. SYN-UCD505 comprises a tesB butyrate cassette (ter gene is present and tesB gene replaces the pbt gene and the buk gene) under control of tet promoter on a plasmid. A "tes or tesB cassette or "tes or tesB butyrate cassette" refers to a butyrate producing cassette that comprises at least ter, thiA1, hbd, crt2, and tesB genes. An alternative butyrate cassette of the disclosure comprises at least bcd2, etfB3, etfA3, thiA1, hbd, crt2, and tesB genes. In some embodiments, the tes or tesB cassette is under control of an inducible promoter other than tetracycline. Exemplary inducible promoters which may control the expression of the tesB cassette include oxygen level-dependent promoters (e.g., FNR-inducible promoter), promoters induced by HE-specific molecules or metabolites indicative of liver damage (e.g., bilirubin), promoters induced by inflammation or an inflammatory response (RNS, ROS promoters), and promoters induced by a metabolite that may or may not be naturally present (e.g., can be exogenously added) in the gut, e.g., arabinose and tetracycline.
Figure 49A:
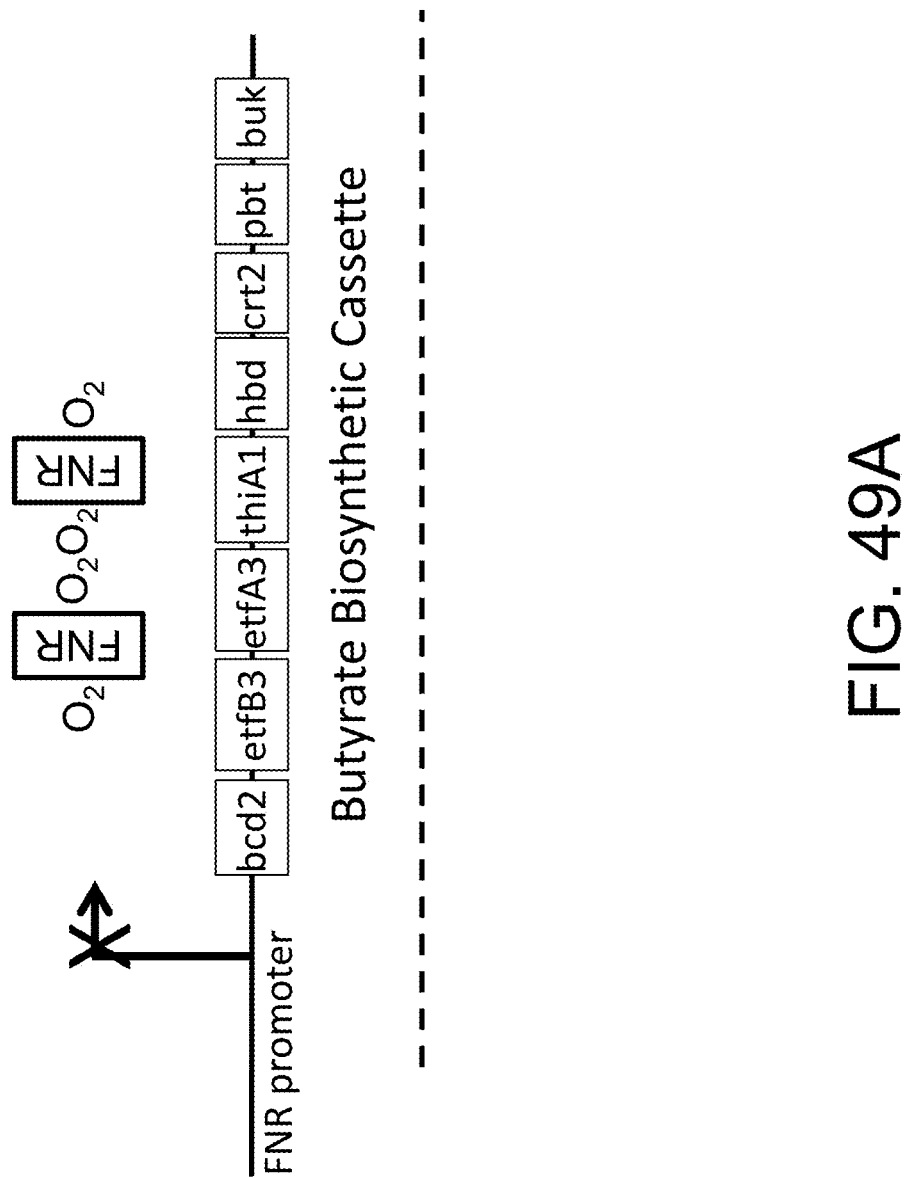
FIGS. 49A-F depict the gene organization of exemplary engineered bacteria of the disclosure and their induction under anaerobic or inflammatory conditions for the production of butyrate.
Figure 49B:
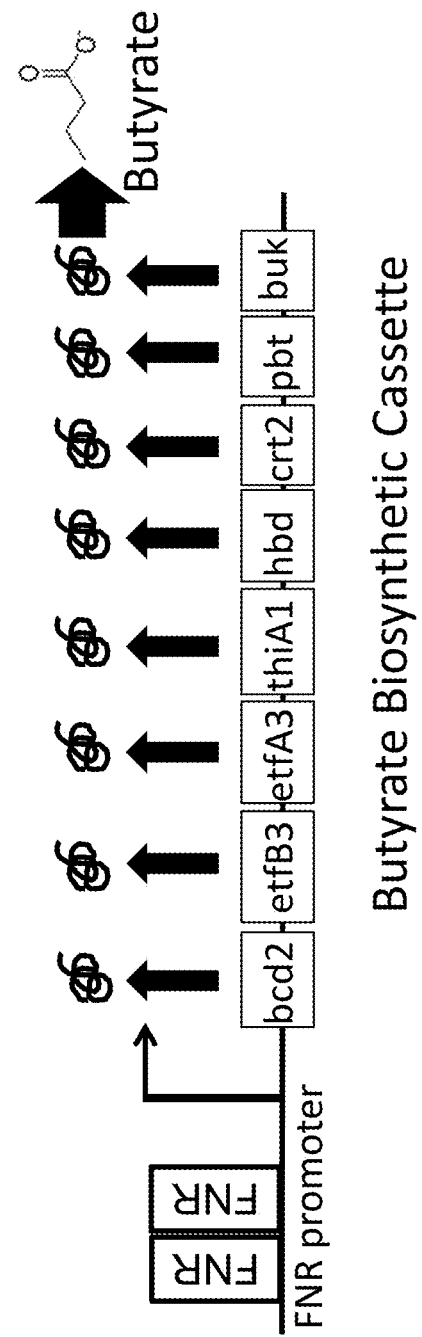
Figure 49C:
Figure 49D:
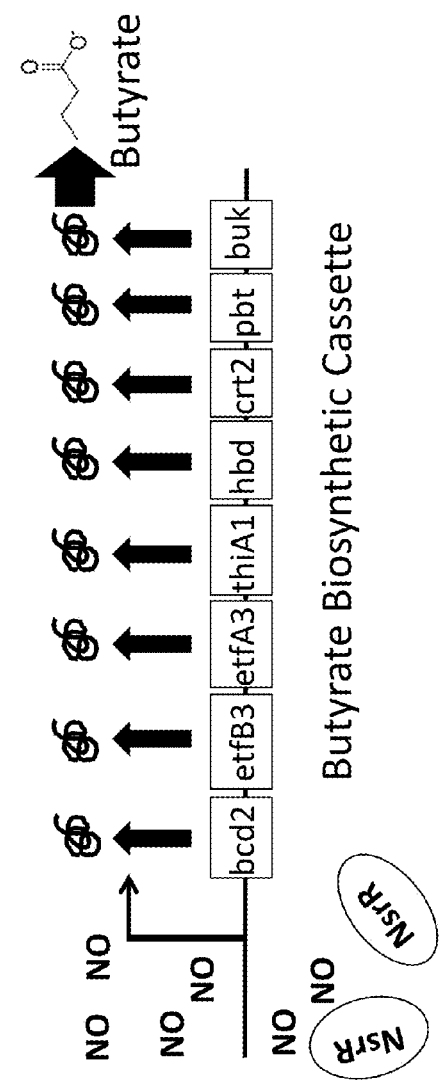
Figure 49E:
Figure 49F:
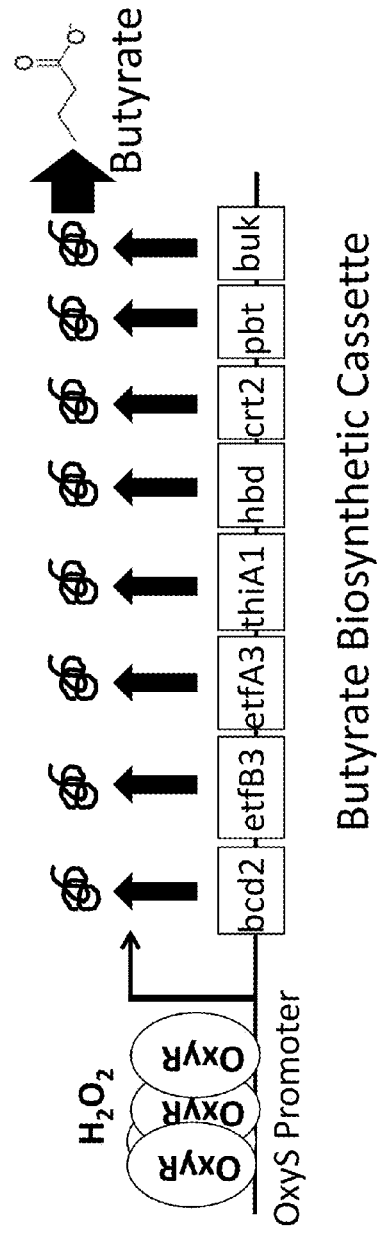
Figures 50A, 50B:
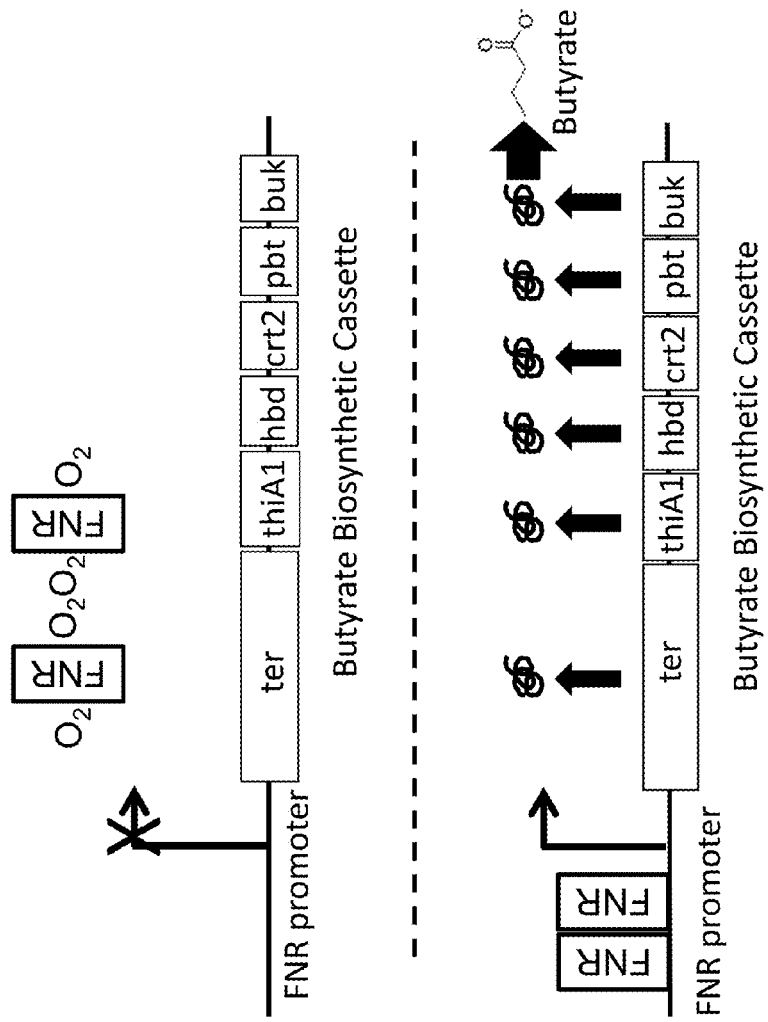

In some embodiments, the bacteria are genetically engineered to include multiple mechanisms of action (MoAs), e.g., circuits producing multiple copies of the same product or circuits performing multiple different functions. Examples of insertion sites include, but are not limited to, malE/K, insB/I, araC/BAD, lacZ, dapA, cea, and other shown in FIG. 18. For example, the genetically engineered bacteria may include four copies of argA$^{fbr}$ inserted at four different insertion sites, e.g., malE/K, insB/I, araC/BAD, and lacZ. Alternatively, the genetically engineered bacteria may include three copies of argA$^{fbr}$ inserted at three different insertion sites, e.g., malE/K, insB/I, and lacZ, and three mutant arginine regulons, e.g., two producing citrulline and one producing arginine, inserted at three different insertion sites dapA, cea, and araC/BAD. In some embodiments, the genetically engineered bacteria may include one or more ammonia conversion circuit(s) inserted at one or more different insertion sites and one or more additional circuits inserted at one or more other insertion sites. For example, the genetically engineered bacteria may include one or more copies of argA$^{fbr}$ (and/or other ammonia conversion circuit(s)) inserted at one or more different insertion sites, and one or more gut barrier enhancing circuits, e.g., one or more butyrate production circuit(s) (or other gut barrier enhancing circuit(s)) at other insertion sites. In other exemplary embodiments, the genetically engineered bacteria may include one or more copies of argA$^{fbr}$ and/or other ammonia conversion circuit(s)) inserted at one or more different insertion sites, and one or more GABA reducing circuits, e.g., GABA transport and/or GABA metabolic circuit(s), inserted at other insertion site(s). In other exemplary embodiments, the genetically engineered bacteria may include one or more copies of argA$^{fbr}$ (and/or other ammonia conversion circuit(s)) inserted at one or more different insertion sites, and one or more manganese transport circuit(s) inserted at other insertion sites (FIG. 47A). In some embodiments, one or more ammonia conversion circuit(s) (e.g., argA$^{fbr}$ and/or other ammonia conversion circuit(s)), one or more gut barrier enhancing circuit (e.g., butyrate, propionate, acetate biosynthetic circuit(s)), one or more GABA reducing circuit(s) (e.g., GABA transport and/or GABA metabolic circuit), and one or more manganese transport circuit(s) are inserted at four or more different chromosomal insertion sites (e.g., FIG. 45). In some embodiments, an ammonia conversion circuit, a gut barrier enhancing circuit, a GABA transport and/or GABA metabolic circuit are inserted at three different chromosomal insertion sites. In some embodiments, an ammonia conversion circuit, a GABA transport/metabolic circuit, and a manganese transport circuit are inserted at three different chromosomal insertion sites (FIG. 46B). In other embodiments, an ammonia conversion circuit, and a manganese transport circuit are inserted at two different chromosomal insertion sites (FIG. 47A). In still other embodiments, an ammonia conversion circuit, and a GABA transport and/or GABA metabolic circuit are inserted at two different chromosomal insertion sites. In still other embodiments, an ammonia conversion circuit, and a gut barrier enhancing circuit are inserted at two different chromosomal insertion sites. In still other embodiments, an ammonia conversion circuit, and a manganese reducing circuit are inserted at two different chromosomal insertion sites.

Table 14 lists non-limiting examples of embodiments of the disclosure.

TABLE 14

Non-limiting examples of embodiments of the disclosure

| Code Name | ARG box | ArgR | argA$^{fb}$ | ThyA | Antibiotic | Other |
|---|---|---|---|---|---|---|
| Control Strains | | | | | | |
| SYN-UCD103 | Wild type ARG Box | Wild type ArgR | none | Wild type ThyA | Strep | none |
| SYN-UCD107 | Wild type ARG Box | Wild type ArgR | none | Wild type ThyA | Kan | none |
| ΔARG box | | | | | | |
| SYN-UCD101 | ΔARG box | Wild type ArgR | none | Wild type ThyA | none | none |
| SYN-UCD102 | ΔARG box | Wild type ArgR | tetracycline-inducible argA$^{fbr}$ on a low copy plasmid | Wild type ThyA | Amp | none |
| SYN-UCD104 | ΔARG box | Wild type ArgR | tetracycline-inducible argA$^{fbr}$ on a low copy plasmid (Amp) | Wild type ThyA | Amp, Cam | Inducible ArgG |
| SYN-UCD105 | ΔARG box | Wild type ArgR | tetracycline-inducible argA$^{fbr}$ on a low copy plasmid (Amp) | Wild type ThyA | Amp | constitutively expressed argG (BBa_J23100 constitutive promoter) |
| ΔArgR | | | | | | |
| SYN-UCD106 | Wild type ARG Box | ΔArgR | none | ΔThyA | Cam | none |
| SYN-UCD201/SYN-UCD312 | Wild type ARG Box | ΔArgR | none | Wild type ThyA | none | none |
| SYN-UCD202 | Wild type ARG Box | ΔArgR | tetracycline-inducible argAfbr on a high-copy plasmid (Amp) | Wild type ThyA | Amp | none |
| SYN-UCD203 | Wild type ARG Box | ΔArgR | tetracycline-inducible argAfbr on a low-copy plasmid (Amp) | Wild type ThyA | Amp | none |
| SYN-UCD204 | Wild type ARG Box | ΔArgR | tet-ArgAfbr on a low-copy plasmid (Amp) | Wild type ThyA | Amp | none |
| SYN-UCD205 | Wild type ARG Box | ΔArgR | PfnrS-ArgAfbr on a low-copy plasmid (Amp) | Wild type ThyA | Amp | none |

TABLE 14-continued

Non-limiting examples of embodiments of the disclosure

| Code Name | ARG box | ArgR | argA$^{fb}$ | ThyA | Anti-biotic | Other |
|---|---|---|---|---|---|---|
| SYN-UCD206 | Wild type ARG Box | ΔArgR | PfnrS-ArgAfbr on a low-copy plasmid (Amp) | ΔThyA | Amp, Cam | none |
| Integrated FNRS-argAfbr | | | | | | |
| SYN-UCD301 | Wild type ARG Box | ΔArgR | PfnrS-ArgAfbr integrated into the chromosome at the malEK locus | Wild type ThyA | Cam | none |
| SYN-UCD302 | Wild type ARG Box | ΔArgR | PfnrS-ArgAfbr integrated into the chromosome at the malEK locus | ΔThyA | Cam | none |
| SYN-UCD303 | Wild type ARG Box | ΔArgR | PfnrS-ArgAfbr integrated into the chromosome at the malEK locus | ΔThyA | Kan | none |
| SYN-UCD305 | Wild type ARG Box | ΔArgR | PfnrS-ArgAfbr integrated into the chromosome at the malEK locus | ΔThyA | None | none |
| SYN-UCD304 | Wild type ARG Box | ΔArgR | PfnrS-ArgAfbr integrated into the chromosome at the malEK locus | Wild type ThyA | None | none |
| SYN-UCD306 | Wild type ARG Box | ΔArgR | PfnrS-ArgAfbr integrated into the chromosome at the malEK locus | Wild type ThyA | Kan | none |
| SYN-UCD307 | Wild type ARG Box | Wild type ArgR | PfnrS-ArgAfbr integrated into the chromosome at the malEK locus | ΔThyA | Kan | none |
| SYN-UCD308 | Wild type ARG Box | Wild type ArgR | PfnrS-ArgAfbr integrated into the chromosome at the malEK locus | ΔThyA | none | none |
| SYN-UCD309 | Wild type ARG Box | Wild type ArgR | PfnrS-ArgAfbr integrated into the chromosome at the malEK locus | Wild type ThyA | Kan | none |

TABLE 14-continued

Non-limiting examples of embodiments of the disclosure

| Code Name | ARG box | ArgR | argA$^{fb}$ | ThyA | Antibiotic | Other |
|---|---|---|---|---|---|---|
| SYN-UCD310 | Wild type ARG Box | Wild type ArgR | PfnrS-ArgAfbr integrated into the chromosome at the malEK locus | Wild type ThyA | none | none |
| SYN-UCD311 | Wild type ARG Box | ΔArgR | none | Wild type ThyA | Kan | none |
| SYN-UCD312/ SYN-UCD201 | Wild type ARG Box | ΔArgR | none | Wild type ThyA | none | none |
| SYN-UCD313 | Wild type ARG Box | ΔArgR | none | ΔThyA | Kan | none |
| SYN-UCD314 | Wild type ARG Box | ΔArgR | none | ΔThyA | none | none |
| Rifaximin resistance | | | | | | |
| SYN-UCD403 | Wild type ARG Box | ΔArgR | PfnrS-ArgAfbr integrated into the chromosome at the malEK locus | ΔThyA | Kan | Rifaximin resistance |
| SYN-UCD405 | Wild type ARG Box | ΔArgR | PfnrS-ArgAfbr integrated into the chromosome at the malEK locus | ΔThyA | None | Rifaximin resistance |
| SYN-UCD404 | Wild type ARG Box | ΔArgR | PfnrS-ArgAfbr integrated into the chromosome at the malEK locus | Wild type ThyA | None | Rifaximin resistance |
| SYN-UCD406 | Wild type ARG Box | ΔArgR | PfnrS-ArgAfbr integrated into the chromosome at the malEK locus | Wild type ThyA | Kan | Rifaximin resistance |
| SYN-UCD407 | Wild type ARG Box | Wild type ArgR | PfnrS-ArgAfbr integrated into the chromosome at the malEK locus | ΔThyA | Kan | Rifaximin resistance |
| SYN-UCD408 | Wild type ARG Box | Wild type ArgR | PfnrS-ArgAfbr integrated into the chromosome at the malEK locus | ΔThyA | none | Rifaximin resistance |
| SYN-UCD409 | Wild type ARG Box | Wild type ArgR | PfnrS-ArgAfbr integrated into the chromosome at the malEK locus | Wild type ThyA | Kan | Rifaximin resistance |

TABLE 14-continued

Non-limiting examples of embodiments of the disclosure

| Code Name | ARG box | ArgR | argA^fb | ThyA | Antibiotic | Other |
|---|---|---|---|---|---|---|
| SYN-UCD410 | Wild type ARG Box | Wild type ArgR | PfnrS-ArgAfbr integrated into the chromosome at the malEK locus | Wild type ThyA | none | Rifaximin resistance |
| SYN-UCD411 | Wild type ARG Box | ΔArgR | none | Wild type ThyA | Kan | Rifaximin resistance |
| SYN-UCD412 | Wild type ARG Box | ΔArgR | none | Wild type ThyA | none | Rifaximin resistance |
| SYN-UCD413 | Wild type ARG Box | ΔArgR | none | ΔThyA | Kan | Rifaximin resistance |
| SYN-UCD414 | Wild type ARG Box | ΔArgR | none | ΔThyA | none | Rifaximin resistance |
| Butyrate Circuits | | | | | | |
| SYN-UCD500 | Wild type ARG Box | Wild type ArgR | none | Wild type ThyA | Amp | Logic156 (pSC101 PydfZ-Bcd butyrate plasmid; amp resistance) |
| SYN-UCD501 | Wild type ARG Box | Wild type ArgR | none | Wild type ThyA | Amp | Logic156 (pSC101 PydfZ-ter butyrate plasmid; amp resistance) |
| SYN-UCD502 | Wild type ARG Box | Wild type ArgR | none | Wild type ThyA | None | PydfZ-ter butyrate cassette integrated on the chromosome |
| SYN-UCD503 | Wild type ARG Box | Wild type ArgR | none | Wild type ThyA | Amp | pLogic031 (bdc2 butyrate cassette under control of tet promoter on a plasmid) |
| SYN-UCD504 | Wild type ARG Box | Wild type ArgR | none | Wild type ThyA | None | pLogic046 (ter butyrate cassette under control of tet promoter on a plasmid) |
| SYN-UCD505 | Wild type ARG Box | Wild type ArgR | none | Wild type ThyA | Amp | pLOGIC046-delta.pbt-buk/tesB+ (tesB butyrate cassette under control of tet promoter on a plasmid) |
| SYN-UCD506 | Wild type ARG Box | Wild type ArgR | none | Wild type ThyA | Amp | Logic156 (pSC101 nirB-Bcd butyrate plasmid; amp resistance) |
| SYN-UCD507 | Wild type ARG Box | Wild type ArgR | none | Wild type ThyA | Amp | pLogic031-nsrR-norB-butyrate construct |
| SYN-UCD508 | Wild type ARG Box | Wild type ArgR | none | Wild type ThyA | Amp | pLogic046-nsrR-norB-butyrate construct |

TABLE 14-continued

Non-limiting examples of embodiments of the disclosure

| Code Name | ARG box | ArgR | argA$^{fb}$ | ThyA | Antibiotic | Other |
|---|---|---|---|---|---|---|
| SYN-UCD509 | Wild type ARG Box | Wild type ArgR | none | Wild type ThyA | Amp | tesB-butyrate cassette integrated into chromosome under control of FNR promoter |
| SYN-UCD510 | Wild type ARG Box | Wild type ArgR | none | Wild type ThyA | None | pLogic031 (bdc2 butyrate cassette under control of tet promoter on a plasmid); nuoB deletion |
| SYN-UCD511 | Wild type ARG Box | Wild type ArgR | none | Wild type ThyA | None | pLogic046 (ter butyrate cassette under control of tet promoter on a plasmid); nuoB deletion |
| Butyrate and Ammonium Circuits | | | | | | |
| SYN-UCD601 | Wild type ARG Box | ΔArgR | PfnrS-ArgAfbr integrated into the chromosome at the malEK locus | ΔThyA | Amp | Logic156 (pSC101 PydfZ-ter butyrate plasmid; amp resistance) |
| SYN-UCD603 | Wild type ARG Box | ΔArgR | PfnrS-ArgAfbr integrated into the chromosome at the malEK locus | ΔThyA | Kan | PydfZ-ter butyrate cassette integrated on the chromosome |
| SYN-UCD605 | Wild type ARG Box | ΔArgR | PfnrS-ArgAfbr integrated into the chromosome at the malEK locus | ΔThyA | None | PydfZ-ter butyrate cassette integrated on the chromosome |
| SYN-UCD604 | Wild type ARG Box | ΔArgR | PfnrS-ArgAfbr integrated into the chromosome at the malEK locus | Wild type ThyA | None | PydfZ-ter butyrate cassette integrated on the chromosome |
| SYN-UCD606 | Wild type ARG Box | ΔArgR | PfnrS-ArgAfbr integrated into the chromosome at the malEK locus | Wild type ThyA | Kan | PydfZ-ter butyrate cassette integrated on the chromosome |
| SYN-UCD607 | Wild type ARG Box | Wild type ArgR | PfnrS-ArgAfbr integrated into the chromosome at the malEK locus | ΔThyA | Kan | PydfZ-ter butyrate cassette integrated on the chromosome |
| SYN-UCD608 | Wild type ARG Box | Wild type ArgR | PfnrS-ArgAfbr integrated into the chromosome at the malEK locus | ΔThyA | none | PydfZ-ter butyrate cassette integrated on the chromosome |
| SYN-UCD609 | Wild type ARG Box | Wild type ArgR | PfnrS-ArgAfbr integrated | Wild type ThyA | Kan | PydfZ-ter butyrate cassette |

TABLE 14-continued

Non-limiting examples of embodiments of the disclosure

| Code Name | ARG box | ArgR | argA[fb] | ThyA | Antibiotic | Other |
|---|---|---|---|---|---|---|
| | | | into the chromosome at the malEK locus | | | integrated on the chromosome |
| SYN-UCD610 | Wild type ARG Box | Wild type ArgR | PfnrS-ArgAfbr integrated into the chromosome at the malEK locus | Wild type ThyA | none | PydfZ-ter butyrate cassette integrated on the chromosome |
| SYN-UCD611 | Wild type ARG Box | ΔArgR | none | Wild type ThyA | Kan | PydfZ-ter butyrate cassette integrated on the chromosome |
| SYN-UCD612 | Wild type ARG Box | ΔArgR | none | Wild type ThyA | none | PydfZ-ter butyrate cassette integrated on the chromosome |
| SYN-UCD613 | Wild type ARG Box | ΔArgR | none | ΔThyA | Kan | PydfZ-ter butyrate cassette integrated on the chromosome |
| SYN-UCD614 | Wild type ARG Box | ΔArgR | none | ΔThyA | none | PydfZ-ter butyrate cassette integrated on the chromosome |
| SYN-UCD703 | Wild type ARG Box | ΔArgR | PfnrS-ArgAfbr integrated into the chromosome at the malEK locus | ΔThyA | Kan | PydfZ-ter butyrate cassette integrated on the chromosome; Rifaximin resistance |
| SYN-UCD705 | Wild type ARG Box | ΔArgR | PfnrS-ArgAfbr integrated into the chromosome at the malEK locus | ΔThyA | None | PydfZ-ter butyrate cassette integrated on the chromosome; Rifaximin resistance |
| SYN-UCD704 | Wild type ARG Box | ΔArgR | PfnrS-ArgAfbr integrated into the chromosome at the malEK locus | Wild type ThyA | None | PydfZ-ter butyrate cassette integrated on the chromosome; Rifaximin resistance |
| SYN-UCD706 | Wild type ARG Box | ΔArgR | PfnrS-ArgAfbr integrated into the chromosome at the malEK locus | Wild type ThyA | Kan | PydfZ-ter butyrate cassette integrated on the chromosome; Rifaximin resistance |
| SYN-UCD707 | Wild type ARG Box | Wild type ArgR | PfnrS-ArgAfbr integrated into the chromosome at the malEK locus | ΔThyA | Kan | PydfZ-ter butyrate cassette integrated on the chromosome; Rifaximin resistance |

TABLE 14-continued

Non-limiting examples of embodiments of the disclosure

| Code Name | ARG box | ArgR | argA$^{fb}$ | ThyA | Antibiotic | Other |
|---|---|---|---|---|---|---|
| SYN-UCD708 | Wild type ARG Box | Wild type ArgR | PfnrS-ArgAfbr integrated into the chromosome at the malEK locus | ΔThyA | none | PydfZ-ter butyrate cassette integrated on the chromosome; Rifaximin resistance |
| SYN-UCD709 | Wild type ARG Box | Wild type ArgR | PfnrS-ArgAfbr integrated into the chromosome at the malEK locus | Wild type ThyA | Kan | PydfZ-ter butyrate cassette integrated on the chromosome; Rifaximin resistance |
| SYN-UCD710 | Wild type ARG Box | Wild type ArgR | PfnrS-ArgAfbr integrated into the chromosome at the malEK locus | Wild type ThyA | none | PydfZ-ter butyrate cassette integrated on the chromosome; Rifaximin resistance |
| SYN-UCD711 | Wild type ARG Box | ΔArgR | none | Wild type ThyA | Kan | PydfZ-ter butyrate cassette integrated on the chromosome; Rifaximin resistance |
| SYN-UCD712 | Wild type ARG Box | ΔArgR | none | Wild type ThyA | none | PydfZ-ter butyrate cassette integrated on the chromosome; Rifaximin resistance |
| SYN-UCD713 | Wild type ARG Box | ΔArgR | none | ΔThyA | Kan | PydfZ-ter butyrate cassette integrated on the chromosome; Rifaximin resistance |
| SYN-UCD714 | Wild type ARG Box | ΔArgR | none | ΔThyA | none | PydfZ-ter butyrate cassette integrated on the chromosome; Rifaximin resistance |
| SYN-UCD715 | Wild type ARG Box | ΔArgR | PfnrS- ArgAfbr integrated into the chromosome at malEK locus | ΔThyA | Kan | tesB-butyrate cassette integrated into chromosome under control of FNR promoter |
| SYN-UCD716 | Wild type ARG Box | ΔArgR | PfnrS- ArgAfbr integrated into the chromosome at malEK locus | ΔThyA | None | tesB-butyrate cassette integrated into chromosome under control of FNR promoter |
| SYN-UCD717 | Wild type ARG Box | ΔArgR | PfnrS- ArgAfbr integrated into the chromosome at malEK locus | Wild type ThyA | None | tesB-butyrate cassette integrated into chromosome under control of FNR promoter |

TABLE 14-continued

Non-limiting examples of embodiments of the disclosure

| Code Name | ARG box | ArgR | argA^fb | ThyA | Antibiotic | Other |
|---|---|---|---|---|---|---|
| SYN-UCD718 | Wild type ARG Box | ΔArgR | PfnrS- ArgAfbr integrated into the chromosome at malEK locus | Wild type ThyA | Kan | tesB-butyrate cassette integrated into chromosome under control of FNR promoter |
| SYN-UCD719 | Wild type ARG Box | Wild type ArgR | PfnrS- ArgAfbr integrated into the chromosome at malEK locus | ΔThyA | Kan | tesB-butyrate cassette integrated into chromosome under control of FNR promoter |
| SYN-UCD720 | Wild type ARG Box | Wild type ArgR | PfnrS- ArgAfbr integrated into the chromosome at malEK locus | ΔThyA | none | tesB-butyrate cassette integrated into chromosome under control of FNR promoter |
| SYN-UCD721 | Wild type ARG Box | Wild type ArgR | PfnrS- ArgAfbr integrated into the chromosome at malEK locus | Wild type ThyA | Kan | tesB-butyrate cassette integrated into chromosome under control of FNR promoter |
| SYN-UCD722 | Wild type ARG Box | Wild type ArgR | PfnrS- ArgAfbr integrated into the chromosome at malEK locus | Wild type ThyA | none | tesB-butyrate cassette integrated into chromosome under control of FNR promoter |
| SYN-UCD723 | Wild type ARG Box | ΔArgR | none | Wild type ThyA | Kan | tesB-butyrate cassette integrated into chromosome under control of FNR promoter |
| SYN-UCD724 | Wild type ARG Box | ΔArgR | none | Wild type ThyA | none | tesB-butyrate cassette integrated into chromosome under control of FNR promoter |
| SYN-UCD725 | Wild type ARG Box | ΔArgR | none | ΔThyA | Kan | tesB-butyrate cassette integrated into chromosome under control of FNR promoter |
| SYN-UCD726 | Wild type ARG Box | ΔArgR | none | ΔThyA | none | tesB-butyrate cassette integrated into chromosome under control of FNR promoter |
| SYN-UCD727 | Wild type ARG Box | ΔArgR | PfnrS- ArgAfbr integrated into the chromosome at malEK locus | ΔThyA | Kan | tesB-butyrate cassette integrated into chromosome under control of FNR promoter; Rifaximin resistance |
| SYN-UCD728 | Wild type ARG Box | ΔArgR | PfnrS- ArgAfbr integrated into the chromosome at malEK locus | ΔThyA | None | tesB-butyrate cassette integrated into chromosome under control of FNR promoter; Rifaximin resistance |

TABLE 14-continued

Non-limiting examples of embodiments of the disclosure

| Code Name | ARG box | ArgR | argA$^{fb}$ | ThyA | Antibiotic | Other |
|---|---|---|---|---|---|---|
| SYN-UCD729 | Wild type ARG Box | ΔArgR | PfnrS- ArgAfbr integrated into the chromosome at malEK locus | Wild type ThyA | None | tesB-butyrate cassette integrated into chromosome under control of FNR promoter; Rifaximin resistance |
| SYN-UCD730 | Wild type ARG Box | ΔArgR | PfnrS- ArgAfbr integrated into the chromosome at malEK locus | Wild type ThyA | Kan | tesB-butyrate cassette integrated into chromosome under control of FNR promoter; Rifaximin resistance |
| SYN-UCD731 | Wild type ARG Box | Wild type ArgR | PfnrS- ArgAfbr integrated into the chromosome at malEK locus | ΔThyA | Kan | tesB-butyrate cassette integrated into chromosome under control of FNR promoter; Rifaximin resistance |
| SYN-UCD732 | Wild type ARG Box | Wild type ArgR | PfnrS- ArgAfbr integrated into the chromosome at malEK locus | ΔThyA | none | tesB-butyrate cassette integrated into chromosome under control of FNR promoter; Rifaximin resistance |
| SYN-UCD733 | Wild type ARG Box | Wild type ArgR | PfnrS- ArgAfbr integrated into the chromosome at malEK locus | Wild type ThyA | Kan | tesB-butyrate cassette integrated into chromosome under control of FNR promoter; Rifaximin resistance |
| SYN-UCD734 | Wild type ARG Box | Wild type ArgR | PfnrS- ArgAfbr integrated into the chromosome at malEK locus | Wild type ThyA | none | tesB-butyrate cassette integrated into chromosome under control of FNR promoter; Rifaximin resistance |
| SYN-UCD735 | Wild type ARG Box | ΔArgR | none | Wild type ThyA | Kan | tesB-butyrate cassette integrated into chromosome under control of FNR promoter; Rifaximin resistance |
| SYN-UCD736 | Wild type ARG Box | ΔArgR | none | Wild type ThyA | none | tesB-butyrate cassette integrated into chromosome under control of FNR promoter; Rifaximin resistance |
| SYN-UCD737 | Wild type ARG Box | ΔArgR | none | ΔThyA | Kan | tesB-butyrate cassette integrated into chromosome under control of FNR promoter; Rifaximin resistance |

TABLE 14-continued

Non-limiting examples of embodiments of the disclosure

| Code Name | ARG box | ArgR | argA$^{fbr}$ | ThyA | Anti-biotic | Other |
|---|---|---|---|---|---|---|
| SYN-UCD38 | Wild type ARG Box | ΔArgR | none | ΔThyA | none | tesB-butyrate cassette integrated into chromosome under control of FNR promoter; Rifaximin resistance |

In some embodiments, butyrate production by the genetically engineered bacteria can be further enhanced by additional modifications. Butyrate production under anaerobic conditions depends on endogenous NADH pools. In some embodiments, the flux through the butyrate pathway may be enhanced by eliminating competing routes for NADH utilization. A non-limiting example is the mutation/deletion of frdA, which utilizes NADH to catalyze the conversion of phosphoenolpyruvate to succinate. In some embodiments, any of the genetically engineered bacteria described herein further comprise a mutation, which eliminates competing routes for NADH utilization, e.g., a mutation/deletion of frdA.

Secretion

In some embodiments, the genetically engineered bacteria further comprise a native secretion mechanism (e.g., gram positive bacteria) or non-native secretion mechanism (e.g., gram negative bacteria) that is capable of secreting the protein(s) of interest or therapeutic protein(s), from the bacterial cytoplasm. Many bacteria have evolved sophisticated secretion systems to transport substrates across the bacterial cell envelope. Substrates, such as small molecules, proteins, and DNA, may be released into the extracellular space or periplasm (such as the gut lumen or other space), injected into a target cell, or associated with the bacterial membrane.

In Gram-negative bacteria, secretion machineries may span one or both of the inner and outer membranes. In some embodiments, the genetically engineered bacteria further comprise a non-native double membrane-spanning secretion system. Double membrane-spanning secretion systems include, but are not limited to, the type I secretion system (T1SS), the type II secretion system (T2SS), the type III secretion system (T3SS), the type IV secretion system (T4SS), the type VI secretion system (T6SS), and the resistance-nodulation-division (RND) family of multi-drug efflux pumps (Pugsley 1993; Gerlach et al., 2007; Collinson et al., 2015; Costa et al., 2015; Reeves et al., 2015; WO2014138324A1, incorporated herein by reference). Examples of such secretion systems are shown in FIGS. 69-73. Mycobacteria, which have a Gram-negative-like cell envelope, may also encode a type VII secretion system (T7SS) (Stanley et al., 2003). With the exception of the T2SS, double membrane-spanning secretions generally transport substrates from the bacterial cytoplasm directly into the extracellular space or into the target cell. In contrast, the T2SS and secretion systems that span only the outer membrane may use a two-step mechanism, wherein substrates are first translocated to the periplasm by inner membrane-spanning transporters, and then transferred to the outer membrane or secreted into the extracellular space. Outer membrane-spanning secretion systems include, but are not limited to, the type V secretion or autotransporter system (T5SS), the curli secretion system, and the chaperone-usher pathway for pili assembly (Saier, 2006; Costa et al., 2015).

In some embodiments, the genetically engineered bacteria of the invention further comprise a type III or a type III-like secretion system (T3SS) from *Shigella, Salmonella, E. coli, Bivrio, Burkholderia, Yersinia, Chlamydia,* or *Pseudomonas*. The T3SS is capable of transporting a protein from the bacterial cytoplasm to the host cytoplasm through a needle complex. The T3SS may be modified to secrete the molecule from the bacterial cytoplasm, but not inject the molecule into the host cytoplasm. Thus, the molecule is secreted into the gut lumen or other extracellular space. In some embodiments, the genetically engineered bacteria comprise said modified T3SS and are capable of secreting the protein(s) of interest or therapeutic protein(s) from the bacterial cytoplasm. In some embodiments, the secreted molecule, such as a heterologous protein or peptide, e.g., the protein of interest or therapeutic protein, comprises a type III secretion sequence that allows the protein(s) of interest or therapeutic protein(s) to be secreted from the bacteria.

In some embodiments, a flagellar type III secretion pathway is used to secrete the molecule of interest. In some embodiments, an incomplete flagellum is used to secrete a therapeutic peptide of interest, by recombinantly fusing the peptide to an N-terminal flagellar secretion signal of a native flagellar component. In this manner, the intracellularly expressed chimeric peptide can be mobilized across the inner and outer membranes into the surrounding host environment.

Figure 70:
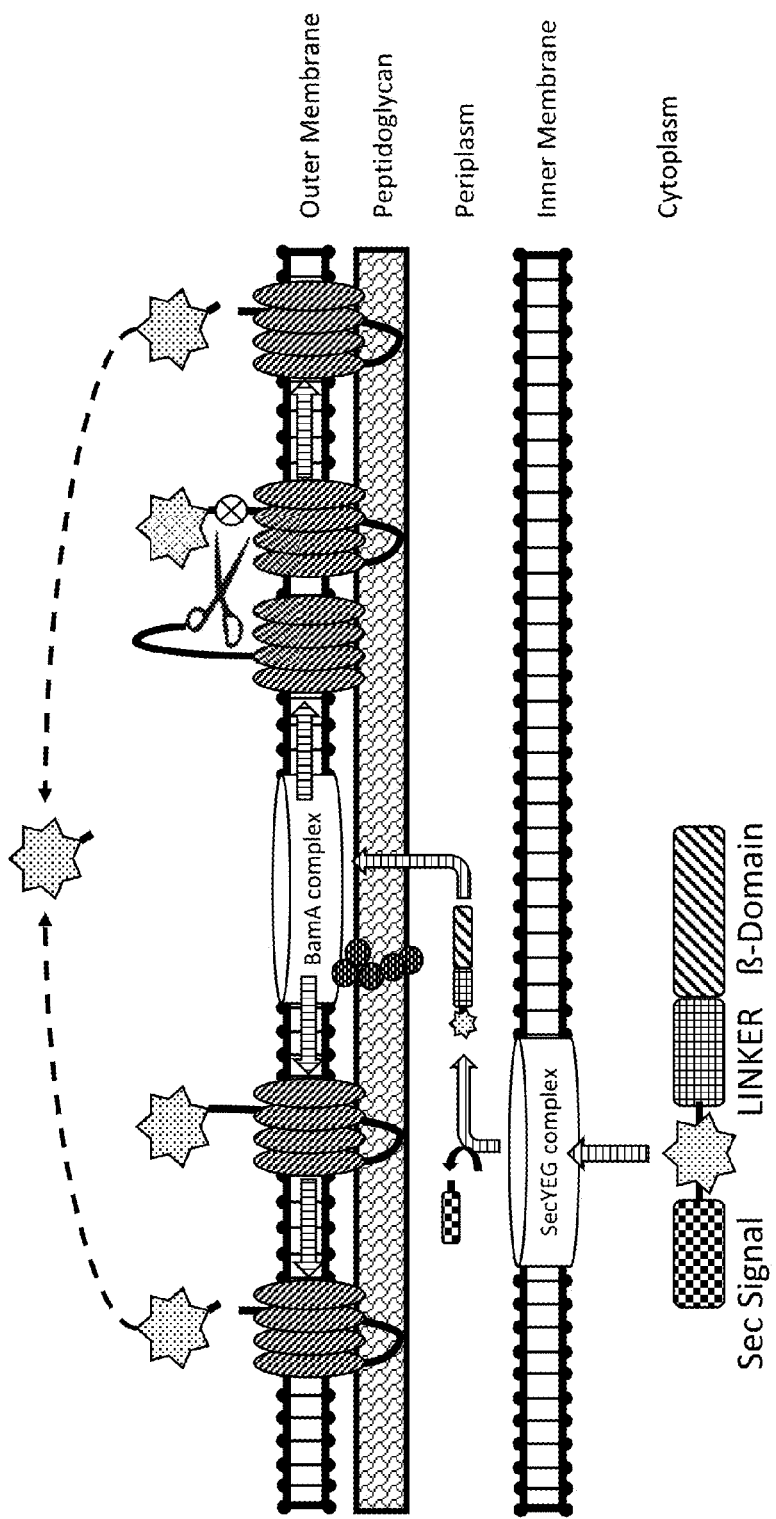
FIG. 70 depicts a schematic of a type V secretion system for the extracellular production of recombinant proteins in which a therapeutic peptide (star) can be fused to an N-terminal secretion signal, a linker and the beta-domain of an autotransporter. In this system, the N-terminal signal sequence directs the protein to the SecA-YEG machinery which moves the protein across the inner membrane into the periplasm, followed by subsequent cleavage of the signal sequence. The beta-domain is recruited to the Bam complex where the beta-domain is folded and inserted into the outer membrane as a beta-barrel structure. The therapeutic peptide is then thread through the hollow pore of the beta-barrel structure ahead of the linker sequence. The therapeutic peptide is freed from the linker system by an autocatalytic cleavage or by targeting of a membrane-associated peptidase (scissors) to a complementary protease cut site in the linker.

In some embodiments, a Type V Autotransporter Secretion System is used to secrete the therapeutic peptide. Due to the simplicity of the machinery and capacity to handle relatively large protein fluxes, the Type V secretion system is attractive for the extracellular production of recombinant proteins. As shown in FIG. 70, a therapeutic peptide (star) can be fused to an N-terminal secretion signal, a linker, and the beta-domain of an autotransporter. The N-terminal signal sequence directs the protein to the SecA-YEG machinery which moves the protein across the inner membrane into the periplasm, followed by subsequent cleavage of the signal sequence. The Beta-domain is recruited to the Bam complex ('Beta-barrel assembly machinery') where the beta-domain is folded and inserted into the outer membrane as a beta-barrel structure. The therapeutic peptide, is threaded through the hollow pore of the beta-barrel structure ahead of the linker sequence. Once exposed to the extracellular environment, the therapeutic peptide, can be freed from the linker system by an autocatalytic cleavage (left side of Bam complex) or by targeting of a membrane-associated peptidase (black scissors; right side of Bam complex) to a complimentary protease cut site in the linker. Thus, in some embodiments, the secreted molecule, such as a heterologous protein or peptide, e.g., the protein of interest or therapeutic protein, comprises an N-terminal secretion signal, a linker, and beta-domain of an autotransporter so as to allow the molecule to be secreted from the bacteria.

Figure 71:
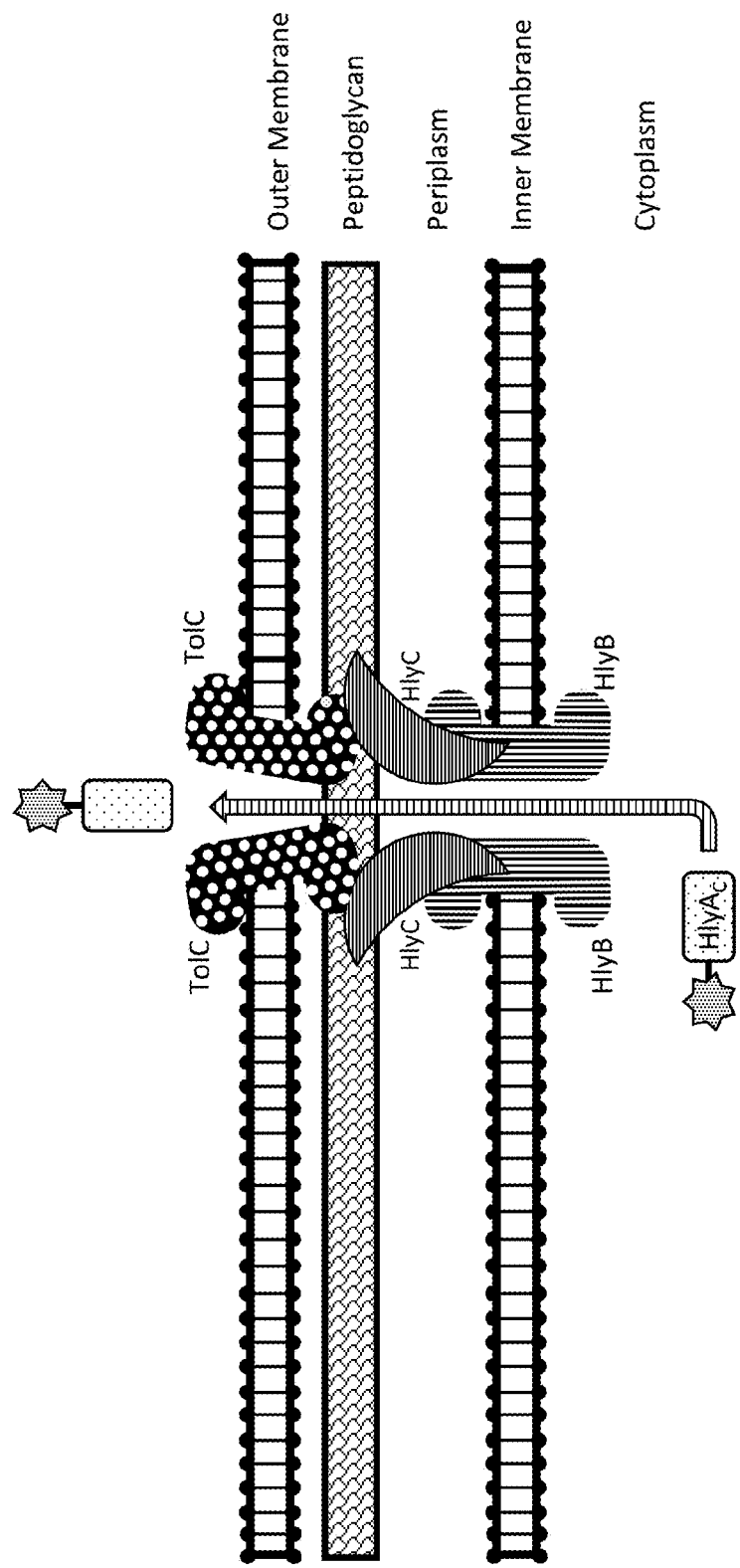
FIG. 71 depicts a schematic of a type I secretion system, which translocates a passenger peptide directly from the cytoplasm to the extracellular space using HlyB (an ATP-binding cassette transporter); HlyD (a membrane fusion protein); and TolC (an outer membrane protein) which form a channel through both the inner and outer membranes. The secretion signal-containing C-terminal portion of HlyA is fused to the C-terminal portion of a therapeutic peptide (star) to mediate secretion of this peptide.
Figure 72:
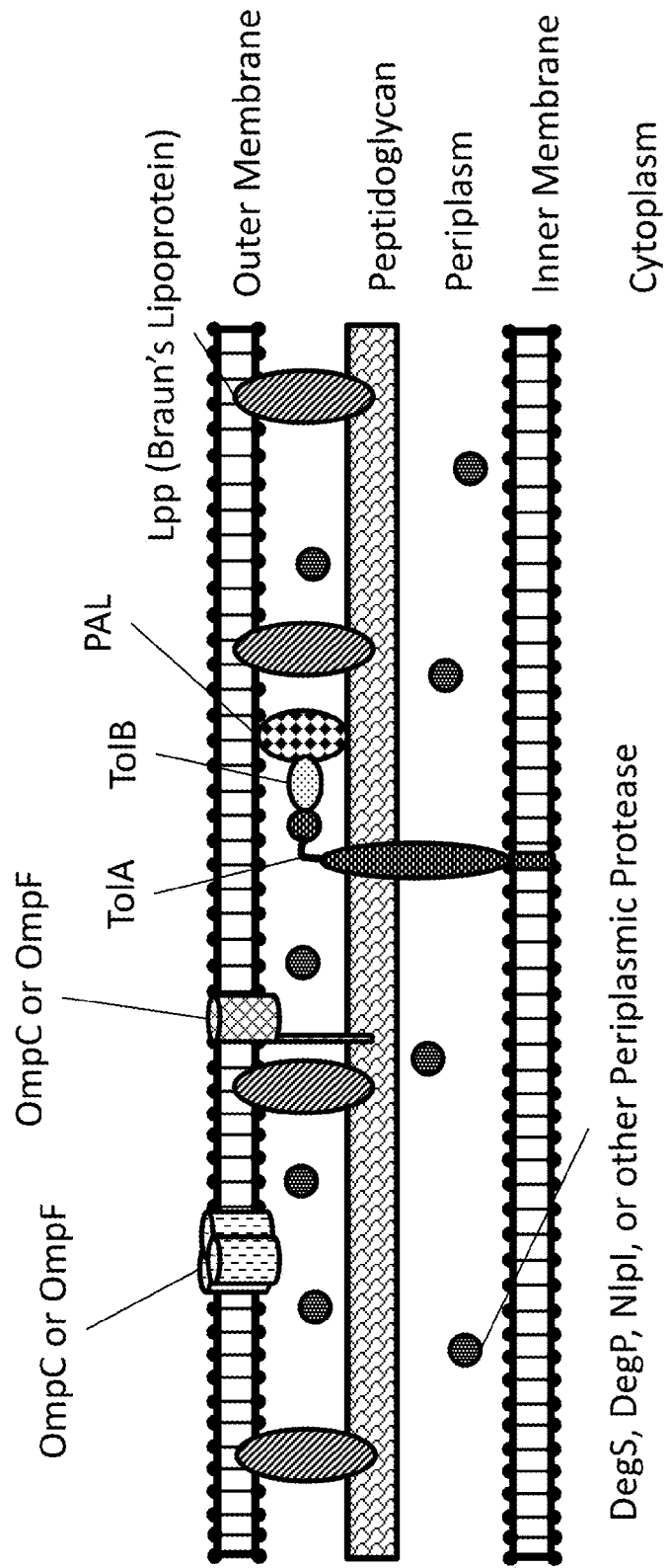
FIG. 72 depicts a schematic of the outer and inner membranes of a gram-negative bacterium, and several deletion targets for generating a leaky or destabilized outer membrane, thereby facilitating the translocation of a therapeutic polypeptides to the extracellular space, e.g., therapeutic polypeptides of eukaryotic origin containing disulphide bonds. Deactivating mutations of one or more genes encoding a protein that tethers the outer membrane to the peptidoglycan skeleton, e.g., lpp, ompC, ompA, ompF, tolA, tolB, paI, and/or one or more genes encoding a periplasmic protease, e.g., degS, degP, nlpI, generates a leaky phenotype. Combinations of mutations may synergistically enhance the leaky phenotype.
Figure 73:
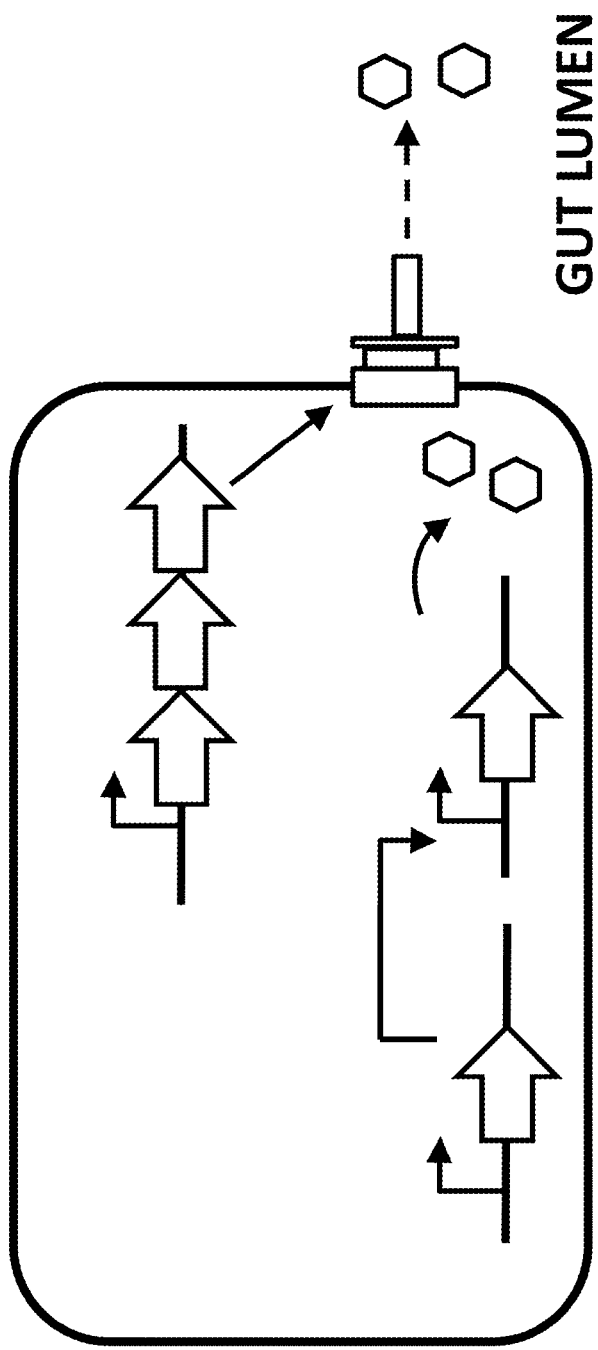
FIG. 73 depicts a modified type 3 secretion system (T3SS) to allow the bacteria to inject secreted therapeutic proteins into the gut lumen. An inducible promoter (small arrow, top), e.g. a FNR-inducible promoter, drives expression of the T3 secretion system gene cassette (3 large arrows, top) that produces the apparatus that secretes tagged peptides out of the cell. An inducible promoter (small arrow, bottom), e.g. a FNR-inducible promoter, drives expression of a regulatory factor, e.g. T7 polymerase, that then activates the expression of the tagged therapeutic peptide (hexagons).
Figure 74:
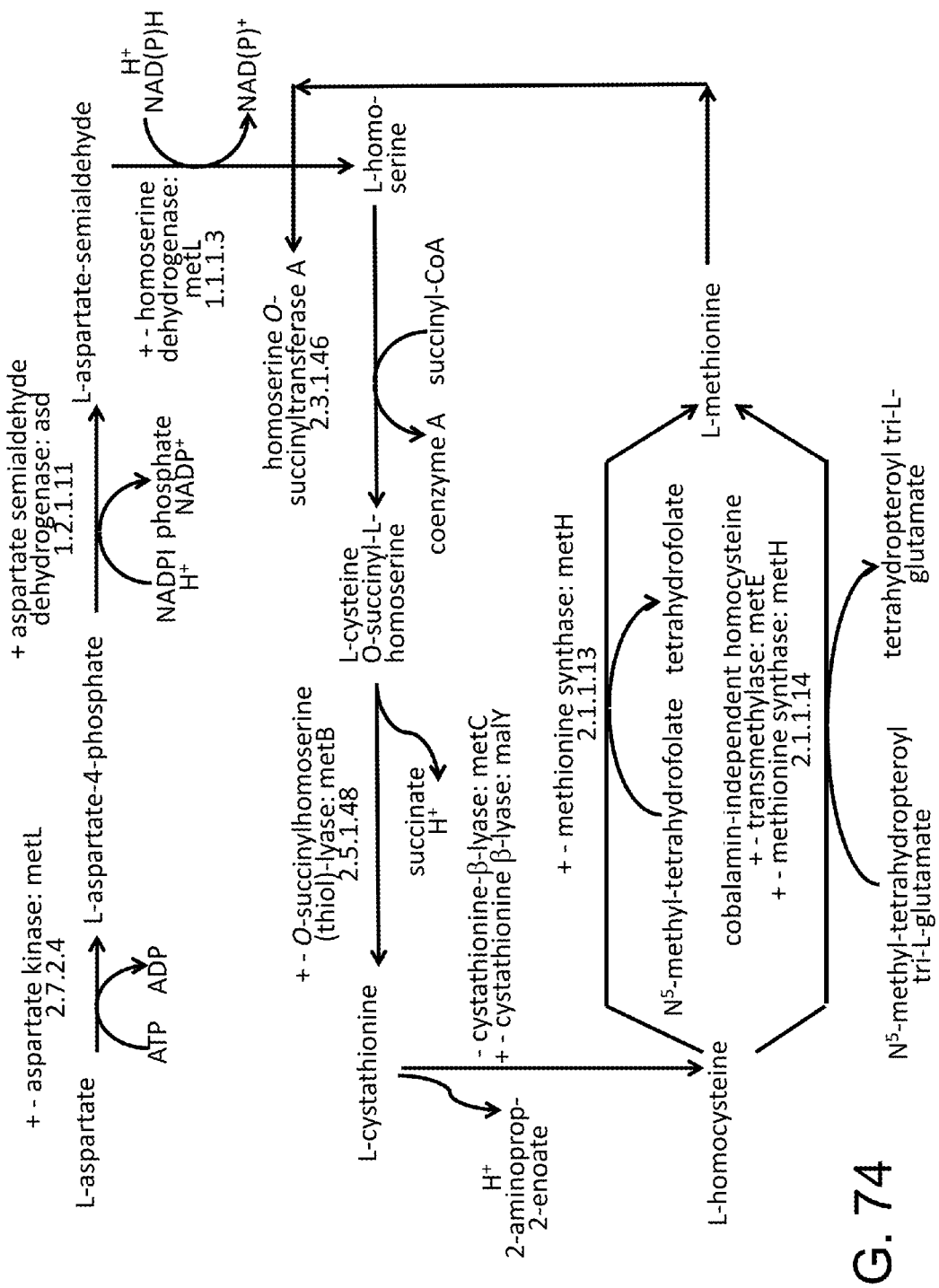
FIG. 74 depicts an exemplary L-homoserine and L-methionine biosynthesis pathway. Circles indicate genes repressed by MetJ, and deletion of metJ leads to constitutive expression of these genes and activation of the pathway.
Figure 75:
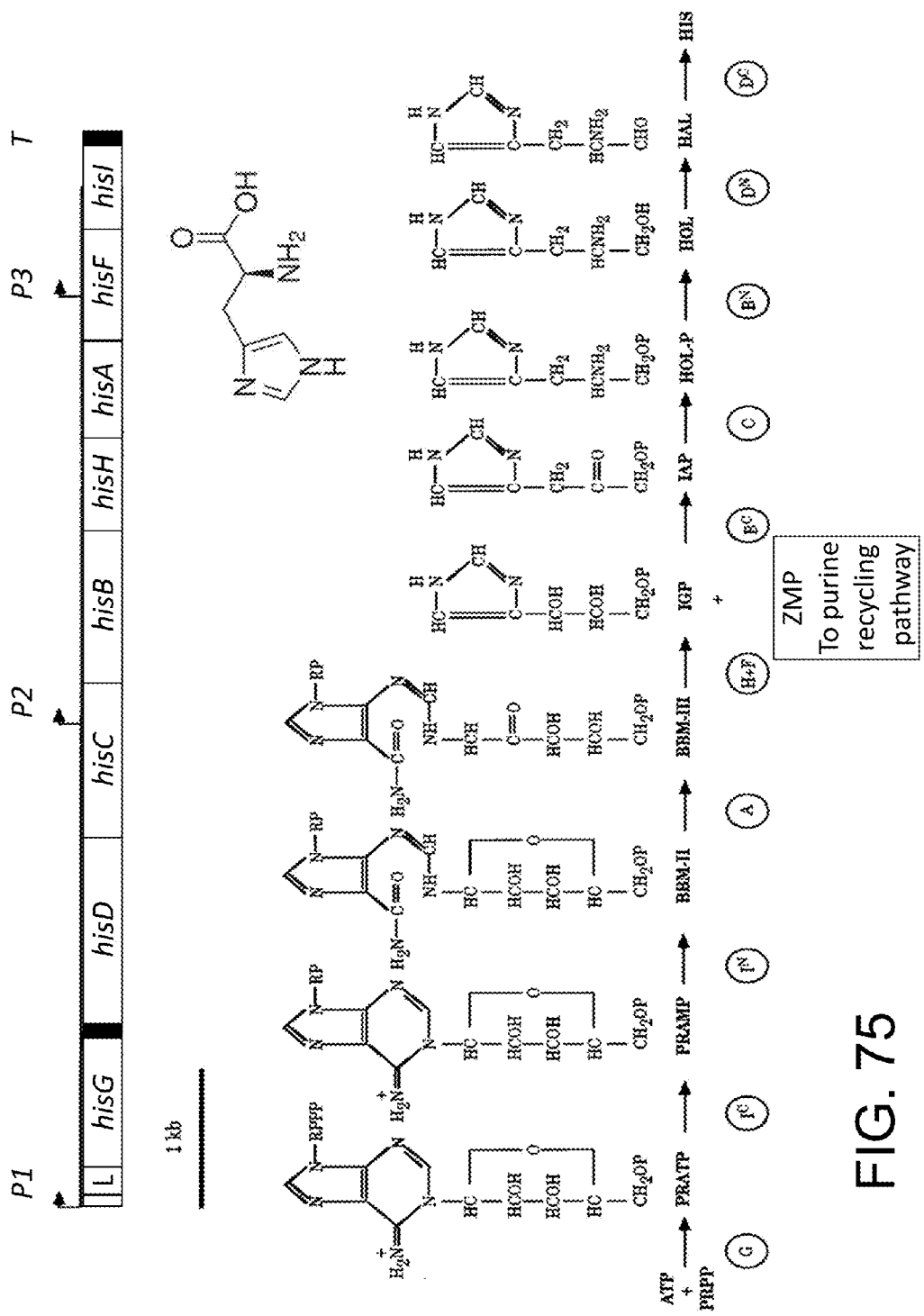
FIG. 75 depicts an exemplary histidine biosynthesis pathway.
Figure 76:
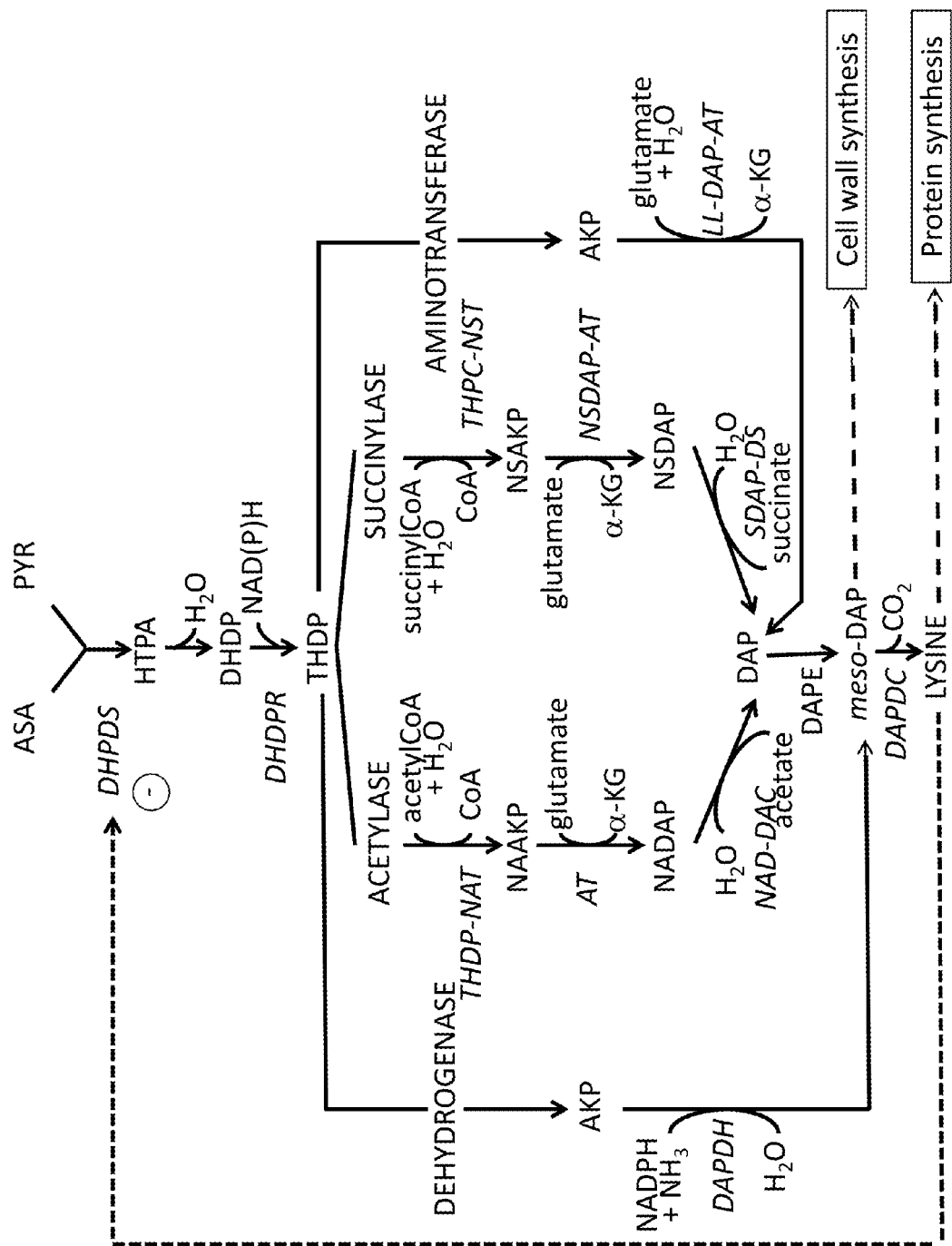
FIG. 76 depicts an exemplary lysine biosynthesis pathway.
Figure 77:
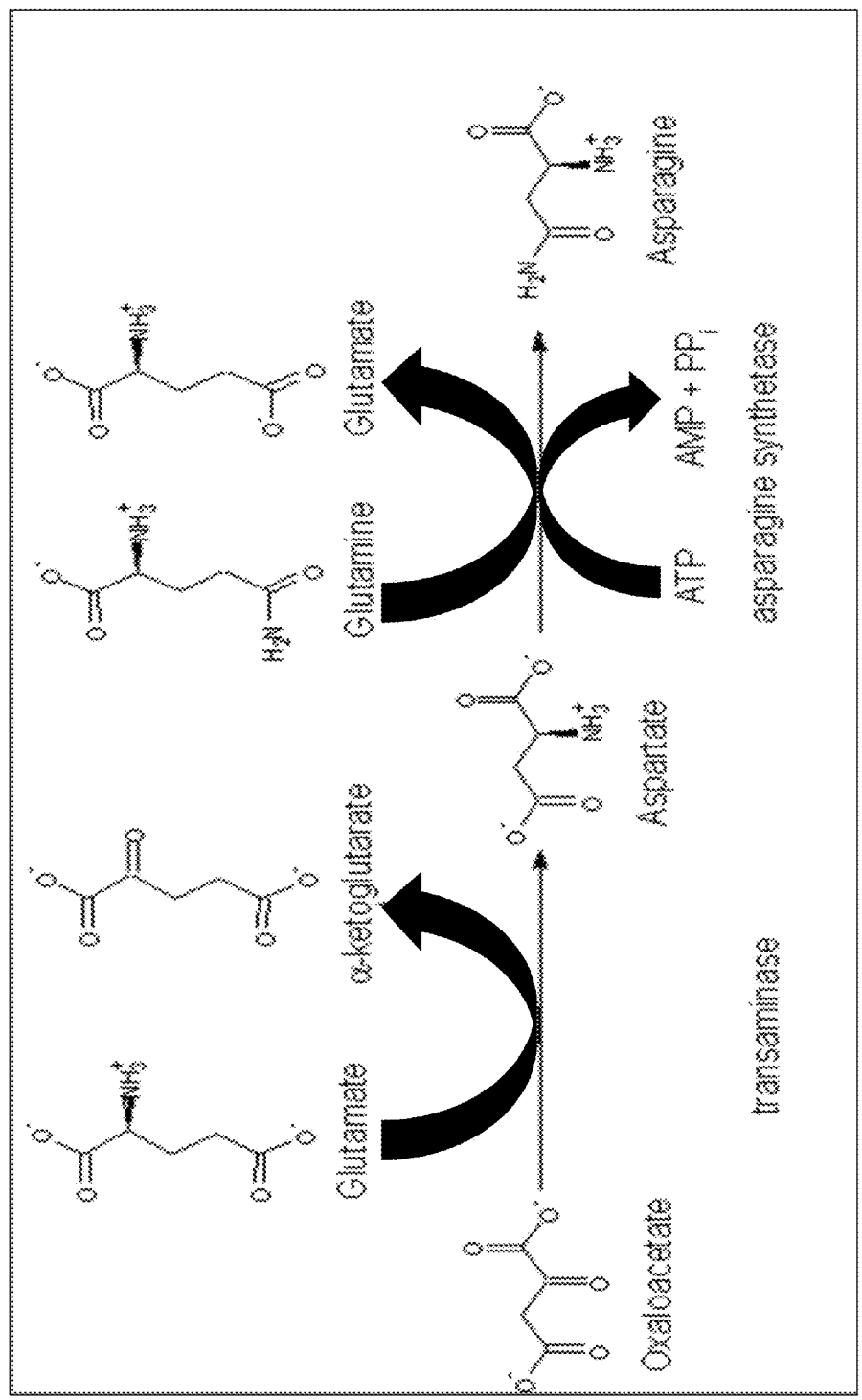
FIG. 77 depicts an exemplary asparagine biosynthesis pathway.
Figure 78:
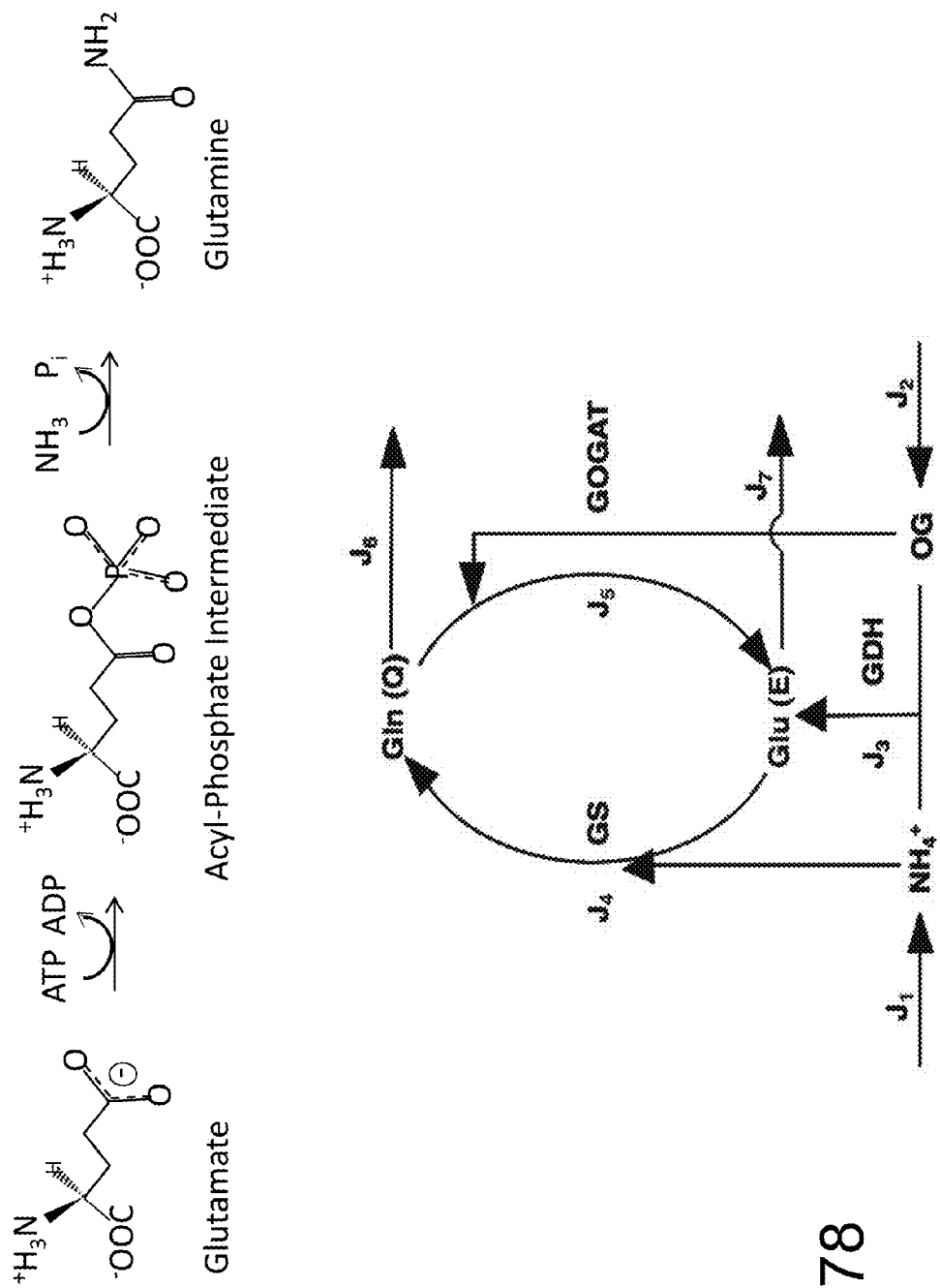
FIG. 78 depicts an exemplary glutamine biosynthesis pathway.
Figure 79:
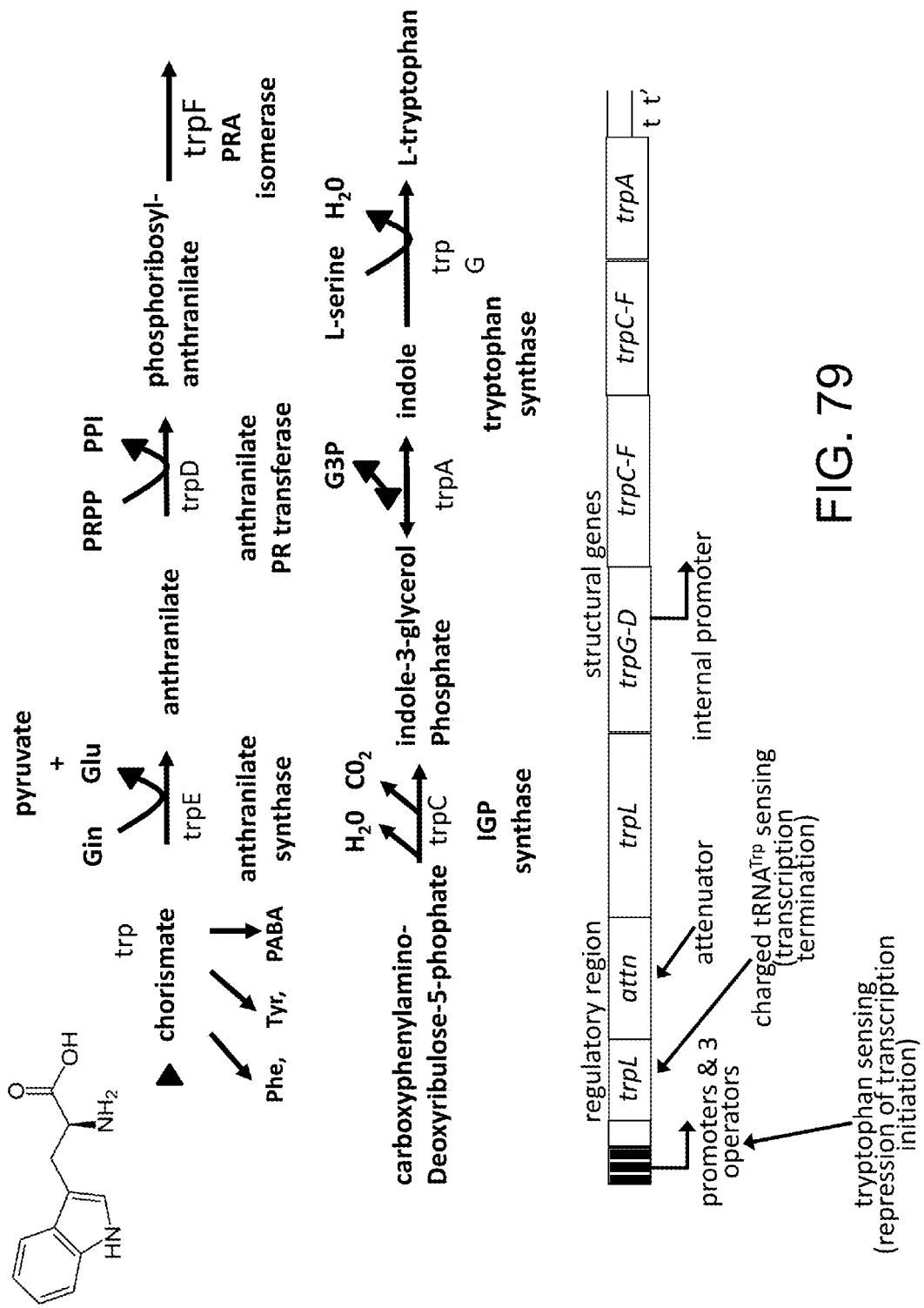
FIG. 79 depicts an exemplary tryptophan biosynthesis pathway.
Figure 80:
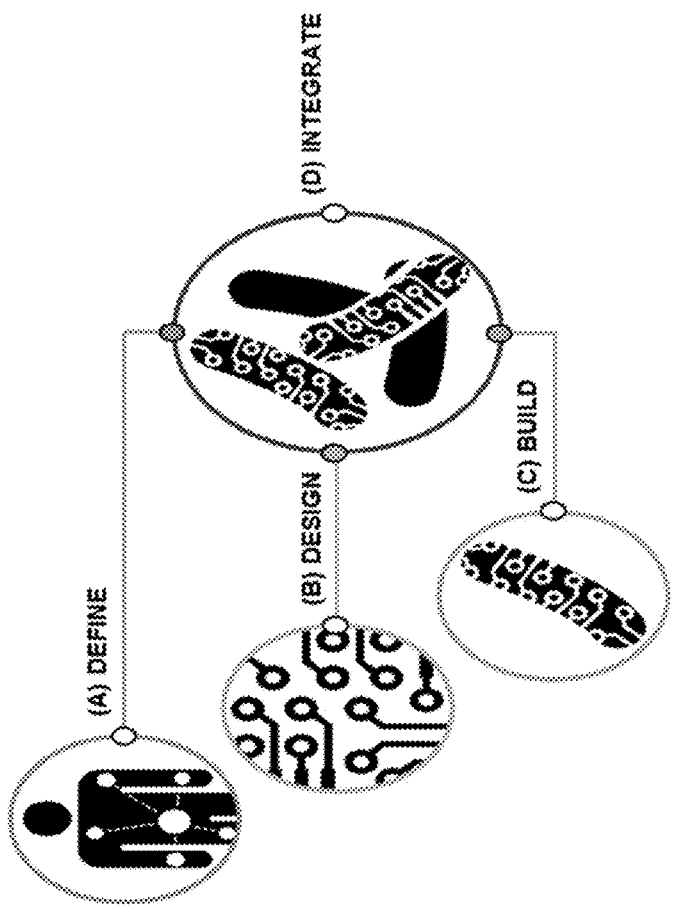
FIG. 80 depicts a schematic of non-limiting processes for designing and producing the genetically engineered bacteria of the present disclosure. The step of "defining" comprises 1. Identification of diverse candidate approaches based on microbial physiology and disease biology; 2. Use of bioinformatics to determine candidate metabolic pathways; the use of prospective tools to determine performance targets required of optimized engineered synthetic biotics. The step of "designing" comprises the use of 1. Cutting-edge DNA assembly to enable combinatorial testing of pathway organization; 2. Mathematical models to predict pathway efficiency; 3. Internal stable of proprietary switches and parts to permit control and tuning of engineered circuits. The step of "Builing" comprises 1. Building core structures "chassies" 2. Stably integrating engineered circuits into optimal chromosomal locations for efficient expression; 3. Employing unique functional assays to assess genetic circuit fidelity and activity. The step of "integrating" comprises 1. Use of chromosomal markers, which enable monitoring of synthetic biotic localization and transit times in animal models; 2. Leveraging expert microbiome network and bioinformatics support to expand understanding of how specific disease states affect GI microbial flora and the behaviors of synthetic biotics in that environment; 3. Activating process development research and optimization in-house during the discovery phase, enabling rapid and seamless transition of development candidates to pre-clinical progression; Drawing upon extensive experience in specialized disease animal model refinement, which supports prudent, high quality testing of candidate synthetic biotics.
Figure 82A:
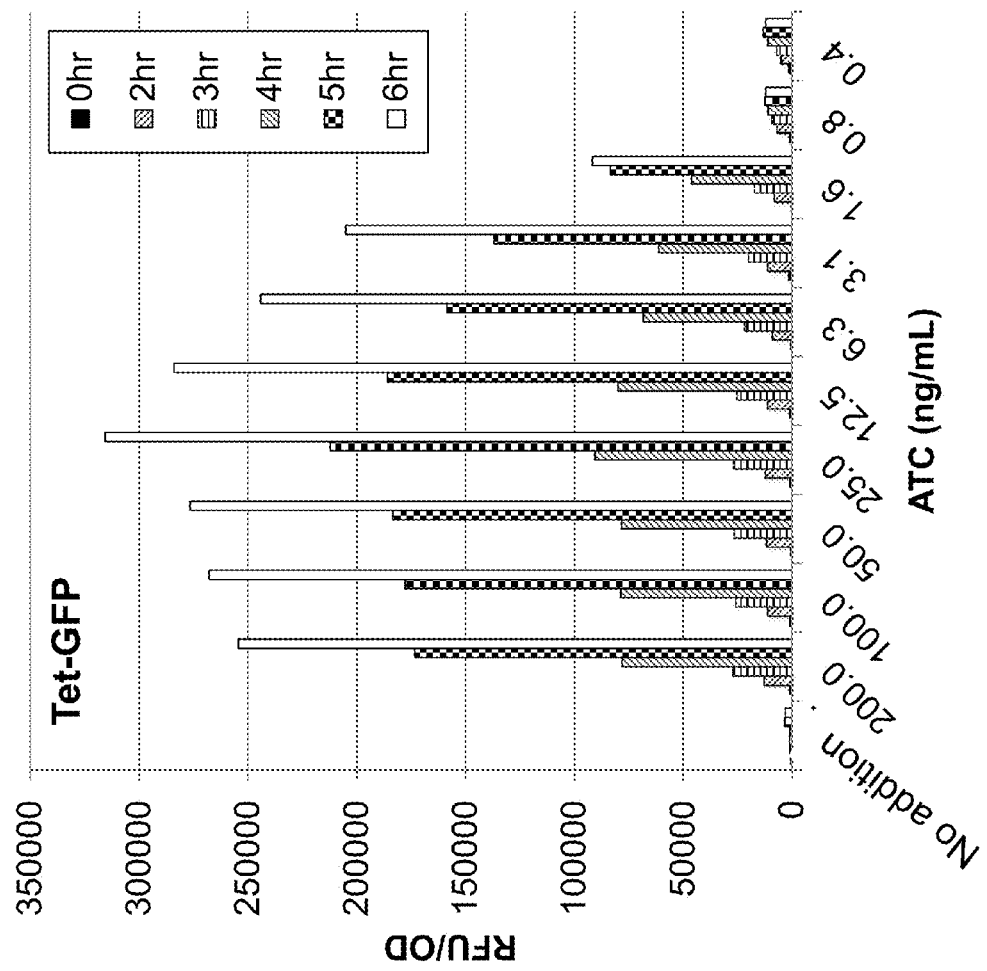
FIGS. 82A-C depict ATC (FIG. 82A) or nitric oxide-inducible (FIG. 82B) reporter constructs. These constructs, when induced by their cognate inducer, lead to expression of GFP. Nissle cells harboring plasmids with either the control, ATC-inducible $P_{tet}$-GFP reporter construct or the nitric oxide inducible $P_{nsrR}$-GFP reporter construct induced across a range of concentrations. Promoter activity is expressed as relative florescence units.
Figure 82B:
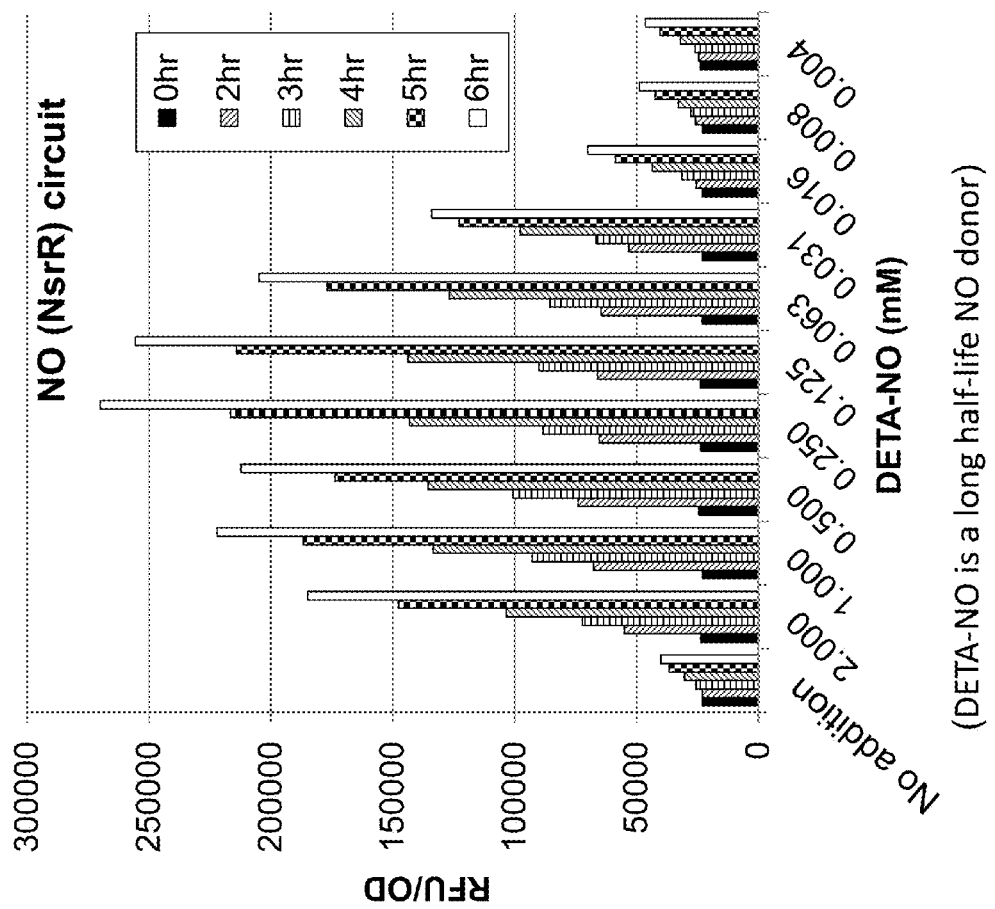
Figure 82C:
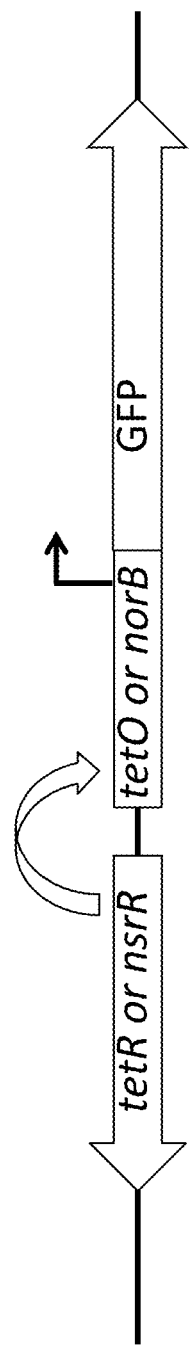
Figure 83:
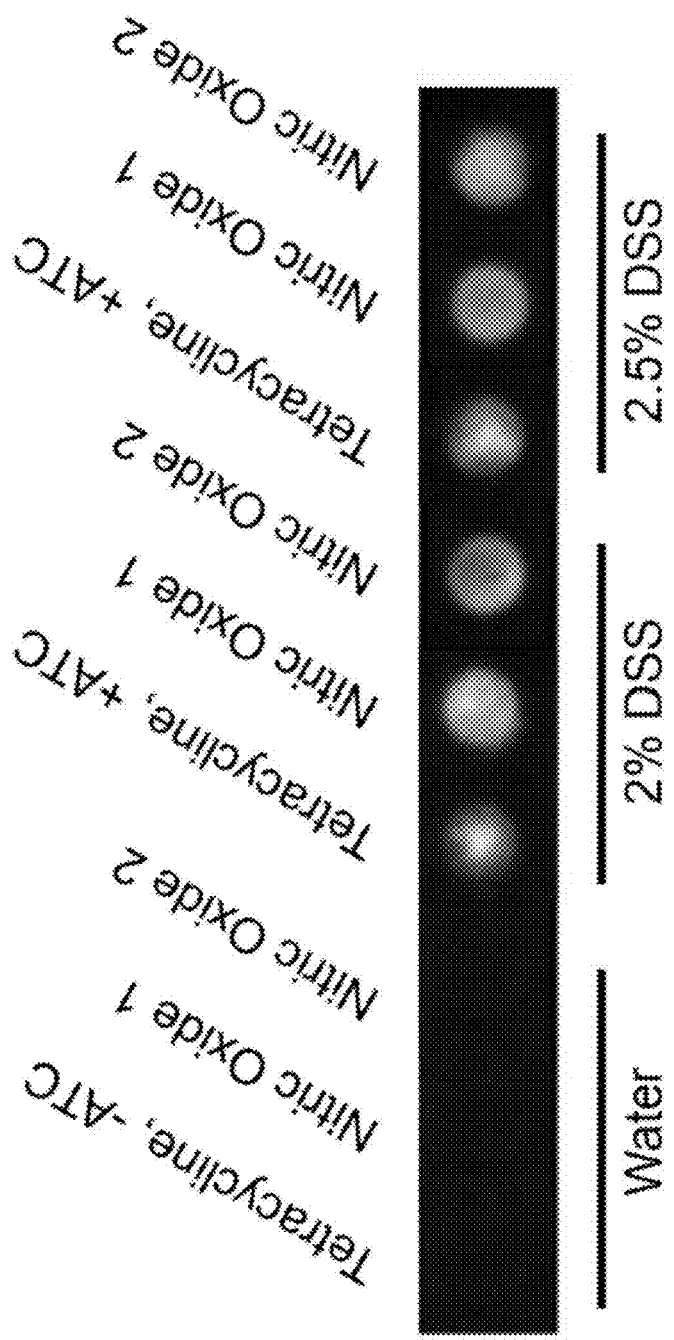
FIG. 83 depicts a dot blot of bacteria harboring a plasmid expressing NsrR under control of a constitutive promoter and the reporter gene gfp (green fluorescent protein) under control of an NsrR-inducible promoter. DSS-treated mice serve as exemplary models for HE. As in HE subjects, the guts of mice are damaged by supplementing drinking water with 2-3% dextran sodium sulfate (DSS). Chemiluminescent is shown for NsrR-regulated promoters induced in DSS-treated mice.
Figure 84:
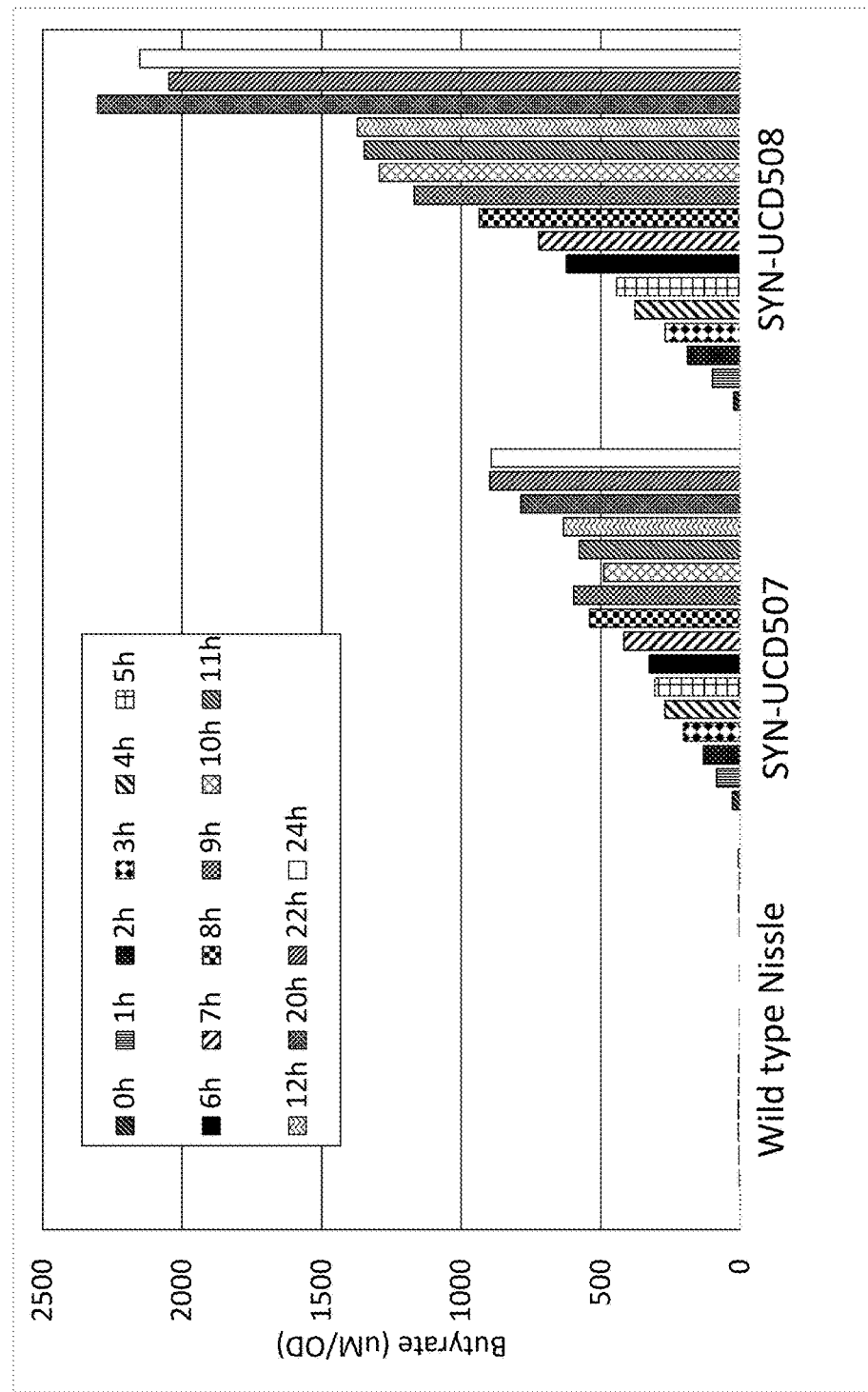
FIG. 84 depicts butyrate production by genetically engineered Nissle comprising the pLogic031-nsrR-norB-butyrate construct (SYN-UCD507) or the pLogic046-nsrR-norB-butyrate construct (SYN-UCD508), which produce more butyrate as compared to wild-type Nissle.

In some embodiments, a Hemolysin-based Secretion System is used to secrete the molecule of interest. Type I Secretion systems offer the advantage of translocating their passenger peptide directly from the cytoplasm to the extracellular space, obviating the two-step process of other secretion types. FIG. 71 shows the alpha-hemolysin (HlyA) of uropathogenic *Escherichia coli*. This pathway uses HlyB, an ATP-binding cassette transporter; HlyD, a membrane fusion protein; and TolC, an outer membrane protein. The assembly of these three proteins forms a channel through both the inner and outer membranes. Natively, this channel is used to secrete HlyA, however, to secrete the therapeutic peptide of the present disclosure, the secretion signal-containing C-terminal portion of HlyA is fused to the C-terminal portion of a therapeutic peptide (star) to mediate secretion of this peptide.

In alternate embodiments, the genetically engineered bacteria further comprise a non-native single membrane-spanning secretion system. Single membrane-spanning exporters may act as a component of a secretion system, or may export substrates independently. Such exporters include, but are not limited to, ATP-binding cassette translocases, flagellum/virulence-related translocases, conjugation-related translocases, the general secretory system (e.g., the SecYEG complex in *E. coli*), the accessory secretory system in mycobacteria and several types of Gram-positive bacteria (e.g., *Bacillus anthracis, Lactobacillus johnsonii, Corynebacterium glutamicum, Streptococcus gordonii, Staphylococcus aureus*), and the twin-arginine translocation (TAT) system (Saier, 2006; Rigel and Braunstein, 2008; Albiniak et al., 2013). It is known that the general secretory and TAT systems can both export substrates with cleavable N-terminal signal peptides into the periplasm, and have been explored in the context of biopharmaceutical production. The TAT system may offer particular advantages, however, in that it is able to transport folded substrates, thus eliminating the potential for premature or incorrect folding. In certain embodiments, the genetically engineered bacteria comprise a TAT or a TAT-like system and are capable of secreting the protein(s) of interest or therapeutic protein(s), from the bacterial cytoplasm. One of ordinary skill in the art would appreciate that the secretion systems disclosed herein may be modified to act in different species, strains, and subtypes of bacteria, and/or adapted to deliver different payloads.

In order to translocate a protein, e.g., therapeutic polypeptide, to the extracellular space, the polypeptide must first be translated intracellularly, mobilized across the inner membrane and finally mobilized across the outer membrane. Many effector proteins (e.g., therapeutic polypeptides)—particularly those of eukaryotic origin—contain disulphide bonds to stabilize the tertiary and quaternary structures. While these bonds are capable of correctly forming in the oxidizing periplasmic compartment with the help of periplasmic chaperones, in order to translocate the polypeptide across the outer membrane the disulphide bonds must be reduced and the protein unfolded again.

One way to secrete properly folded proteins in gram-negative bacteria—particularly those requiring disulphide bonds—is to target the periplasm in a bacterium with a destabilized outer membrane. In this manner the protein is mobilized into the oxidizing environment and allowed to fold properly. In contrast to orchestrated extracellular secretion systems, the protein is then able to escape the periplasmic space in a correctly folded form by membrane leakage. These "leaky" gram-negative mutants are therefore capable of secreting bioactive, properly disulphide-bonded polypeptides. In some embodiments, the genetically engineered bacteria have a "leaky" or destabilized outer membrane. Destabilizing the bacterial outer membrane to induce leakiness can be accomplished by deleting or mutagenizing genes responsible for tethering the outer membrane to the rigid peptidoglycan skeleton, including for example, lpp, ompC, ompA, ompF, tolA, tolB, paI, degS, degP, and nlpI. Lpp is the most abundant polypeptide in the bacterial cell existing at ~500,000 copies per cell and functions as the primary 'staple' of the bacterial cell wall to the peptidoglycan. Silhavy, T. J., Kahne, D. & Walker, S. The bacterial cell envelope. *Cold Spring Harb Perspect Biol* 2, a000414 (2010). TolA-PAL and OmpA complexes function similarly to Lpp and are other deletion targets to generate a leaky phenotype. Additionally, leaky phenotypes have been observed when periplasmic proteases are deactivated. The periplasm is very densely packed with protein and therefore encode several periplasmic proteins to facilitate protein turnover. Removal of periplasmic proteases such as degS, degP or nlpI can induce leaky phenotypes by promoting an excessive build-up of periplasmic protein. Mutation of the proteases can also preserve the effector polypeptide by preventing targeted degradation by these proteases. Moreover, a combination of these mutations may synergistically enhance the leaky phenotype of the cell without major sacrifices in cell viability. Thus, in some embodiments, the engineered bacteria have one or more deleted or mutated membrane genes. In some embodiments, the engineered bacteria have a deleted or mutated lpp gene. In some embodiments, the engineered bacteria have one or more deleted or mutated gene(s), selected from ompA, ompA, and ompF genes. In some embodiments, the engineered bacteria have one or more deleted or mutated gene(s), selected from tolA, tolB, and paI genes. in some embodiments, the engineered bacteria have one or more deleted or mutated periplasmic protease genes. In some embodiments, the engineered bacteria have one or more deleted or mutated periplasmic protease genes selected from degS, degP, and nlpI. In some embodiments, the engineered bacteria have one or more deleted or mutated gene(s), selected from lpp, ompA, ompA, ompF, tolA, tolB, paI, degS, degP, and nlpI genes.

To minimize disturbances to cell viability, the leaky phenotype can be made inducible by placing one or more membrane or periplasmic protease genes, e.g., selected from lpp, ompA, ompA, ompF, tolA, tolB, paI, degS, degP, and nlpI, under the control of an inducible promoter. For example, expression of lpp or other cell wall stability protein or periplasmic protease can be repressed in conditions where the therapeutic polypeptide needs to be delivered (secreted). For instance, under inducing conditions a transcriptional repressor protein or a designed antisense RNA can be expressed which reduces transcription or translation of a target membrane or periplasmic protease gene. Conversely, overexpression of certain peptides can result in a destabilized phenotype, e.g., overexpression of colicins or the third topological domain of TolA, wherein peptide overexpression can be induced in conditions in which the therapeutic polypeptide needs to be delivered (secreted). These sorts of strategies would decouple the fragile, leaky phenotypes from biomass production. Thus, in some embodiments, the engineered bacteria have one or more membrane and/or periplasmic protease genes under the control of an inducible promoter.

Table 15 and Table 16 list secretion systems for Gram positive bacteria and Gram negative bacteria. These can be used to secrete polypeptides, proteins of interest or therapeutic protein(s) from the engineered bacteria, which are reviewed in Milton H. Saier, Jr. Microbe/Volume 1, Number 9, 2006 "Protein Secretion Systems in Gram-Negative Bacteria Gram-negative bacteria possess many protein secretion-membrane insertion systems that apparently evolved independently", the contents of which is herein incorporated by reference in its entirety.

TABLE 15

Secretion systems for gram positive bacteria

| Bacterial Strain | Relevant Secretion System |
|---|---|
| C. novyi-NT (Gram+) | Sec pathway |
| | Twin-arginine (TAT) pathway |
| C. butryicum (Gram+) | Sec pathway |
| | Twin-arginine (TAT) pathway |
| Listeria monocytogenes (Gram+) | Sec pathway |
| | Twin-arginine (TAT) pathway |

TABLE 16

Secretion Systems for Gram negative bacteria
Protein secretary pathways (SP) in gram-negative bacteria and their descendants

| Type (Abbreviation) | Name | TC#[2] | Bacteria | Archaea | Eukarya | # Proteins/ System | Energy Source |
|---|---|---|---|---|---|---|---|
| IMPS - Gram-negative bacterial inner membrane channel-forming translocases | | | | | | | |
| ABC (SIP) | ATP binding cassette translocase | 3.A.1 | + | + | + | 3-4 | ATP |
| SEC (IISP) | General secretory translocase | 3.A.5 | + | + | + | ~12 | GTP OR ATP + PMF |
| Fla/Path (IIISP) | Flagellum/virulence-related translocase | 3.A.6 | + | − | − | >10 | ATP |
| Conj (IVSP) | Conjugation-related translocase | 3.A.7 | + | − | − | >10 | ATP |
| Tat (IISP) | Twin-arginine targeting translocase | 2.A.64 | + | + | + (chloroplasts) | 2-4 | PMF |
| Oxa1 (YidC) | Cytochrome oxidase biogenesis family | 2.A.9 | + | + | + (mitochondria chloroplasts) | 1 | None or PMF |
| MscL | Large conductance mechanosensitive channel family | 1.A.22 | + | + | + | 1 | None |
| Holins | Holin functional superfamily | 1.E.1 •21 | + | − | − | 1 | None |
| Eukaryotic Organelles | | | | | | | |
| MPT | Mitochondrial protein translocase | 3.A.B | − | − | + (mitochondrial) | >20 | ATP |
| CEPT | Chloroplast envelope protein translocase | 3.A.9 | (+) | − | + (chloroplasts) | ≥3 | GTP |
| Bcl-2 | Eukaryotic Bcl-2 family (programmed cell death) | 1.A.21 | − | − | + | 1? | None |
| Gram-negative bacterial outer membrane channel-forming translocases | | | | | | | |
| MTB (IISP) | Main terminal branch of the general secretory translocase | 3.A.15 | +[b] | − | − | ~14 | ATP; PMF |
| FUP | Fimbrial usher protein | 1.B.11 | +[b] | − | − | 1 | None |
| AT-1 | Autotransporter-1 | 1.B.12 | +[b] | − | − | 1 | None |
| AT-2 | Autotransporter-2 | 1.B.40 | +[b] | − | − | 1 | None |
| OMF (ISP) | | 1.B.17 | +[b] | − | +(?) | 1 | None |
| TPS | | 1.B.20 | + | − | + | 1 | None |

TABLE 16-continued

Secretion Systems for Gram negative bacteria
Protein secretary pathways (SP) in gram-negative bacteria and their descendants

| Type (Abbreviation) | Name | TC#[2] | Bacteria | Archaea | Eukarya | # Proteins/ System | Energy Source |
|---|---|---|---|---|---|---|---|
| Secretin (IISP and IISP) | | 1.B.22 | +[b] | | − | 1 | None |
| OmpIP | Outer membrane insertion porin | 1.B.33 | + | − | + (mitochondria; chloroplasts) | ≥4 | None? |

In some embodiments, the genetically engineered bacterial comprise a native or non-native secretion system described herein for the secretion of therapeutic enzyme. In some embodiments, the secretion system is selected from the modified type III flagellar, type I (e.g., hemolysin secretion system), type II, type IV, type V, type VI, and type VII secretion systems, resistance-nodulation-division (RND) multi-drug efflux pumps, a single membrane secretion system, Sec and, TAT secretion systems.

In some embodiments, the therapeutic proteins secreted by the genetically engineered bacteria are modified to increase resistance to proteases, e.g. intestinal proteases.

In some embodiments, the one or more proteins of interest or therapeutic proteins for secretion are under the control of an inducible promoter, as described herein. In one example, the one or more proteins of interest or therapeutic proteins are under the control of the FNR promoter and are produced and secreted under anaerobic conditions. In some embodiments, the one or more proteins of interest or therapeutic proteins for secretion are under the control of a constitutive promoter.

In some embodiments in which the one or more proteins of interest or therapeutic proteins are secreted or exported from the microorganism, the engineered microorganism comprises gene sequence(s) that includes a secretion tag. In some embodiments, the one or more proteins of interest or therapeutic proteins include a "secretion tag" of either RNA or peptide origin to direct the one or more proteins of interest or therapeutic proteins to specific secretion systems. For example, a secretion tag for the Type I Hemolysin secretion system is encoded in the C-terminal 53 amino acids of the alpha hemolysin protein (HlyA). HlyA secretion signal.

HlyB inserts into inner membrane to form a pore, HlyD aligns HlyB with TolC (outer membrane pore) thereby forming a channel through inner and outer membrane. The C-terminal secretion tag can be removed by either an autocatalytic or protease-catalyzed e.g., OmpT cleavage thereby releasing the one or more proteins of interest or therapeutic proteins into the extracellular milieu.

The Type V Auto-secretion System utilizes an N-terminal Sec-dependent peptide tag (inner membrane) and C-terminal tag (outer-membrane). This uses Sec-system to get from cytoplasm to periplasm. C-terminal tag then inserts into the outer membrane forming a pore through which the "passenger protein" threads through. Once across the outer membrane, the passenger (anti-cancer molecule) is released from the membrane-embedded C-terminal tag by either an auto-catalytic, intein-like mechanism or via a membrane-bound protease (I.e., OmpT). The N-terminal tag is removed by the Sec system. Thus, in some embodiments, the secretion system is able to remove this tag before secreting the one or more proteins of interest or therapeutic proteins, from the engineered bacteria. In the Type V auto-secretion-mediated secretion the N-terminal peptide secretion tag is removed upon translocation of the "passenger" peptide from the cytoplasm into the periplasmic compartment by the native Sec system. Further, once the auto-secretor is translocated across the outer membrane the C-terminal secretion tag can be removed by either an autocatalytic or protease-catalyzed e.g., OmpT cleavage thereby releasing the anti-cancer molecule(s) into the extracellular milieu.

In the Flagellar modified Type III Secretion, the tag is encoded in 5'untranslated region of the mRNA and thus there is no peptide tag to cleave/remove. This modified system does not contain the "syringe" portion and instead uses the basal body of the flagella structure as the pore to translocate across both membranes and out through the forming flagella. If the fliC/fliD genes (encoding the flagella "tail"/whip) are disrupted the flagella cannot fully form and this promotes overall secretion. In some embodiments, the tail portion can be removed entirely. In the Type III traditional secretion system, the basal body closely resembles the flagella, however, instead of a "tail"/whip, the traditional T3SS has a syringe to inject the passenger proteins into host cells. The secretion tag is encoded by an N-terminal peptide (lengths vary and there are several different tags, see PCT/US14/020972). The N-terminal tag is not removed from the polypeptides in this secretion system.

In some embodiments the one or more proteins of interest or therapeutic proteins contain expressed as fusion protein with the 53 amino acids of the C termini of alpha-hemolysin (hlyA) of E. coli CFT073 (C terminal secretion tag).

Essential Genes and Auxotrophs

As used herein, the term "essential gene" refers to a gene which is necessary to for cell growth and/or survival. Bacterial essential genes are well known to one of ordinary skill in the art, and can be identified by directed deletion of genes and/or random mutagenesis and screening (see, for example, Zhang and Lin, 2009, DEG 5.0, a database of essential genes in both prokaryotes and eukaryotes, Nucl. Acids Res., 37:D455-D458 and Gerdes et al., Essential genes on metabolic maps, Curr. Opin. Biotechnol., 17(5): 448-456, the entire contents of each of which are expressly incorporated herein by reference).

An "essential gene" may be dependent on the circumstances and environment in which an organism lives. For example, a mutation of, modification of, or excision of an essential gene may result in the recombinant bacteria of the disclosure becoming an auxotroph. An auxotrophic modification is intended to cause bacteria to die in the absence of an exogenously added nutrient essential for survival or growth because they lack the gene(s) necessary to produce that essential nutrient.

Exemplary bacterial genes which may be disrupted or deleted to produce an auxotrophic strain are shown below.

These include, but are not limited to, genes required for oligonucleotide synthesis, amino acid synthesis, and cell wall synthesis.

An auxotrophic modification is intended to cause bacteria to die in the absence of an exogenously added nutrient essential for survival or growth because they lack the gene(s) necessary to produce that essential nutrient. In some embodiments, any of the genetically engineered bacteria described herein also comprise a deletion or mutation in a gene required for cell survival and/or growth. In one embodiment, the essential gene is a DNA synthesis gene, for example, thyA. In another embodiment, the essential gene is a cell wall synthesis gene, for example, dapA. In yet another embodiment, the essential gene is an amino acid gene, for example, serA or MetA. Any gene required for cell survival and/or growth may be targeted, including but not limited to, cysE, glnA, ilvD, leuB, lysA, serA, metA, glyA, hisB, ilvA, pheA, proA, thrC, trpC, tyrA, thyA, uraA, dapA, dapB, dapD, dapE, dapF, flhD, metB, metC, proAB, and thi1, as long as the corresponding wild-type gene product is not produced in the bacteria. Table 17 lists depicts exemplary bacterial genes which may be disrupted or deleted to produce an auxotrophic strain. These include, but are not limited to, genes required for oligonucleotide synthesis, amino acid synthesis, and cell wall synthesis.

TABLE 17

Non-limiting Examples of Bacterial Genes Useful for Generation of an Auxotroph

| Amino Acid | Oligonucleotide | Cell Wall |
|---|---|---|
| cysE | thyA | dapA |
| glnA | uraA | dapB |
| ilvD |  | dapD |
| leuB |  | dapE |
| lysA |  | dapF |
| serA |  |  |
| metA |  |  |
| glyA |  |  |
| hisB |  |  |
| ilvA |  |  |
| pheA |  |  |
| proA |  |  |
| thrC |  |  |
| trpC |  |  |
| tyrA |  |  |

Table 18 shows the survival of various amino acid auxotrophs in the mouse gut, as detected 24 hrs and 48 hrs post-gavage. These auxotrophs were generated using BW25113, a non-Nissle strain of *E. coli*.

TABLE 18

Survival of amino acid auxotrophs in the mouse gut

| Gene | AA Auxotroph | Pre-Gavage | 24 hours | 48 hours |
|---|---|---|---|---|
| argA | Arginine | Present | Present | Absent |
| cysE | Cysteine | Present | Present | Absent |
| glnA | Glutamine | Present | Present | Absent |
| glyA | Glycine | Present | Present | Absent |
| hisB | Histidine | Present | Present | Present |
| ilvA | Isoleucine | Present | Present | Absent |
| leuB | Leucine | Present | Present | Absent |
| lysA | Lysine | Present | Present | Absent |
| metA | Methionine | Present | Present | Present |
| pheA | Phenylalanine | Present | Present | Present |
| proA | Proline | Present | Present | Absent |
| serA | Serine | Present | Present | Present |
| thrC | Threonine | Present | Present | Present |
| trpC | Tryptophan | Present | Present | Present |
| tyrA | Tyrosine | Present | Present | Present |
| ilvD | Valine/Isoleucine/Leucine | Present | Present | Absent |
| thyA | Thiamine | Present | Absent | Absent |
| uraA | Uracil | Present | Absent | Absent |
| flhD | FlhD | Present | Present | Present |

For example, thymine is a nucleic acid that is required for bacterial cell growth; in its absence, bacteria undergo cell death. The thyA gene encodes thimidylate synthetase, an enzyme that catalyzes the first step in thymine synthesis by converting dUMP to dTMP (Sat et al., 2003). In some embodiments, the bacterial cell of the disclosure is a thyA auxotroph in which the thyA gene is deleted and/or replaced with an unrelated gene. A thyA auxotroph can grow only when sufficient amounts of thymine are present, e.g., by adding thymine to growth media in vitro, or in the presence of high thymine levels found naturally in the human gut in vivo. In some embodiments, the bacterial cell of the disclosure is auxotrophic in a gene that is complemented when the bacterium is present in the mammalian gut. Without sufficient amounts of thymine, the thyA auxotroph dies. In some embodiments, the auxotrophic modification is used to ensure that the bacterial cell does not survive in the absence of the auxotrophic gene product (e.g., outside of the gut).

Diaminopimelic acid (DAP) is an amino acid synthetized within the lysine biosynthetic pathway and is required for bacterial cell wall growth (Meadow et al., 1959; Clarkson et al., 1971). In some embodiments, any of the genetically engineered bacteria described herein is a dapD auxotroph in which dapD is deleted and/or replaced with an unrelated gene. A dapD auxotroph can grow only when sufficient amounts of DAP are present, e.g., by adding DAP to growth media in vitro. Without sufficient amounts of DAP, the dapD auxotroph dies. In some embodiments, the auxotrophic modification is used to ensure that the bacterial cell does not survive in the absence of the auxotrophic gene product (e.g., outside of the gut).

In other embodiments, the genetically engineered bacterium of the present disclosure is a uraA auxotroph in which uraA is deleted and/or replaced with an unrelated gene. The uraA gene codes for UraA, a membrane-bound transporter that facilitates the uptake and subsequent metabolism of the pyrimidine uracil (Andersen et al., 1995). A uraA auxotroph can grow only when sufficient amounts of uracil are present, e.g., by adding uracil to growth media in vitro. Without sufficient amounts of uracil, the uraA auxotroph dies. In some embodiments, auxotrophic modifications are used to ensure that the bacteria do not survive in the absence of the auxotrophic gene product (e.g., outside of the gut).

In complex communities, it is possible for bacteria to share DNA. In very rare circumstances, an auxotrophic bacterial strain may receive DNA from a non-auxotrophic strain, which repairs the genomic deletion and permanently rescues the auxotroph. Therefore, engineering a bacterial strain with more than one auxotroph may greatly decrease the probability that DNA transfer will occur enough times to rescue the auxotrophy. In some embodiments, the genetically engineered bacteria of the invention comprise a deletion or mutation in two or more genes required for cell survival and/or growth.

Other examples of essential genes include, but are not limited to yhbV, yagG, hemB, secD, secF, ribD, ribE, thiL, dxs, ispA, dnaX, adk, hemH, lpxH, cysS, fold, rplT, infC, thrS, nadE, gapA, yeaZ, aspS, argS, pgsA, yefM, metG, folE, yejM, gyrA, nrdA, nrdB, folC, accD, fabB, gltX, ligA, zipA, dapE, dapA, der, hisS, ispG, suhB, tadA, acpS, era, rnc, ftsB, eno, pyrG, chpR, lgt, fbaA, pgk, yqgD, metK, yqgF, plsC, ygiT, pare, ribB, cca, ygjD, tdcF, yraL, yihA, ftsN, murI, murB, birA, secE, nusG, rplJ, rplL, rpoB, rpoC, ubiA, plsB, lexA, dnaB, ssb, alsK, groS, psd, orn, yjeE, rpsR, chpS, ppa, valS, yjgP, yjgQ, dnaC, ribF, lspA, ispH, dapB, folA, imp, yabQ, ftsL, ftsI, murE, murF, mraY, murD, ftsW, murG, murC, ftsQ, ftsA, ftsZ, lpxC, secM, secA, can, folk, hemL, yadR, dapD, map, rpsB, infB, nusA, ftsH, obgE, rpmA, rplU, ispB, murA, yrbB, yrbK, yhbN, rpsI, rplM, degS, mreD, mreC, mreB, accB, accC, yrdC, def, fmt, rplQ, rpoA, rpsD, rpsK, rpsM, entD, mrdB, mrdA, nadD, hlepB, rpoE, pssA, yfiO, rplS, trmD, rpsP, ffh, grpE, yfjB, csrA, ispF, ispD, rplW, rplD, rplC, rpsJ, fusA, rpsG, rpsL, trpS, yrfF, asd, rpoH, ftsX, ftsE, ftsY, frr, dxr, ispU, rfaK, kdtA, coaD, rpmB, dfp, dut, gmk, spot, gyrB, dnaN, dnaA, rpmH, mpA, yidC, tnaB, glmS, glmU, wzyE, hemD, hemC, yigP, ubiB, ubiD, hemG, secY, rplO, rpmD, rpsE, rplR, rplF, rpsH, rpsN, rplE, rplX, rplN, rpsQ, rpmC, rplP, rpsC, rplV, rpsS, rplB, cdsA, yaeL, yaeT, lpxD, fabZ, lpxA, lpxB, dnaE, accA, tilS, proS, yafF, tsf, pyrH, olA, rlpB, leuS, lnt, glnS, fldA, cydA, infA, cydC, ftsK, lolA, serS, rpsA, msbA, lpxK, kdsB, mukF, mukE, mukB, asnS, fabA, mviN, rne, yceQ, fabD, fabG, acpP, tmk, holB, lolC, lolD, lolE, purB, ymfK, minE, mind, pth, rsA, ispE, lolB, hemA, prfA, prmC, kdsA, topA, ribA, fabI, racR, dicA, ydfB, tyrS, ribC, ydiL, pheT, pheS, yhhQ, bcsB, glyQ, yibJ, and gpsA. Other essential genes are known to those of ordinary skill in the art.

In some embodiments, the genetically engineered bacterium of the present disclosure is a synthetic ligand-dependent essential gene (SLiDE) bacterial cell. SLiDE bacterial cells are synthetic auxotrophs with a mutation in one or more essential genes that only grow in the presence of a particular ligand (see Lopez and Anderson "Synthetic Auxotrophs with Ligand-Dependent Essential Genes for a BL21 (DE3 Biosafety Strain," ACS Synthetic Biology (2015) DOI: 10.1021/acssynbio.5b00085, the entire contents of which are expressly incorporated herein by reference).

In some embodiments, the SLiDE bacterial cell comprises a mutation in an essential gene. In some embodiments, the essential gene is selected from the group consisting of pheS, dnaN, tyrS, metG, and adk. In some embodiments, the essential gene is dnaN comprising one or more of the following mutations: H191N, R240C, I317S, F319V, L340T, V347I, and S345C. In some embodiments, the essential gene is dnaN comprising the mutations H191N, R240C, I317S, F319V, L340T, V347I, and S345C. In some embodiments, the essential gene is pheS comprising one or more of the following mutations: F125G, P183T, P184A, R186A, and I188L. In some embodiments, the essential gene is pheS comprising the mutations F125G, P183T, P184A, R186A, and I188L. In some embodiments, the essential gene is tyrS comprising one or more of the following mutations: L36V, C38A, and F40G. In some embodiments, the essential gene is tyrS comprising the mutations L36V, C38A, and F40G. In some embodiments, the essential gene is metG comprising one or more of the following mutations: E45Q, N47R, I49G, and A51C. In some embodiments, the essential gene is metG comprising the mutations E45Q, N47R, I49G, and A51C. In some embodiments, the essential gene is adk comprising one or more of the following mutations: I4L, L5I, and L6G. In some embodiments, the essential gene is adk comprising the mutations I4L, L5I, and L6G.

In some embodiments, the genetically engineered bacterium is complemented by a ligand. In some embodiments, the ligand is selected from the group consisting of benzothiazole, indole, 2-aminobenzothiazole, indole-3-butyric acid, indole-3-acetic acid, and L-histidine methyl ester. For example, bacterial cells comprising mutations in metG (E45Q, N47R, I49G, and A51C) are complemented by benzothiazole, indole, 2-aminobenzothiazole, indole-3-butyric acid, indole-3-acetic acid or L-histidine methyl ester. Bacterial cells comprising mutations in dnaN (H191N, R240C, I317S, F319V, L340T, V347I, and S345C) are complemented by benzothiazole, indole or 2-aminobenzothiazole. Bacterial cells comprising mutations in pheS (F125G, P183T, P184A, R186A, and I188L) are complemented by benzothiazole or 2-aminobenzothiazole. Bacterial cells comprising mutations in tyrS (L36V, C38A, and F40G) are complemented by benzothiazole or 2-aminobenzothiazole. Bacterial cells comprising mutations in adk (I4L, L5I, and L6G) are complemented by benzothiazole or indole.

In some embodiments, the genetically engineered bacterium comprises more than one mutant essential gene that renders it auxotrophic to a ligand. In some embodiments, the bacterial cell comprises mutations in two essential genes. For example, in some embodiments, the bacterial cell comprises mutations in tyrS (L36V, C38A, and F40G) and metG (E45Q, N47R, I49G, and A51C). In other embodiments, the bacterial cell comprises mutations in three essential genes. For example, in some embodiments, the bacterial cell comprises mutations in tyrS (L36V, C38A, and F40G), metG (E45Q, N47R, I49G, and A51C), and pheS (F125G, P183T, P184A, R186A, and I188L).

Figure 66A:
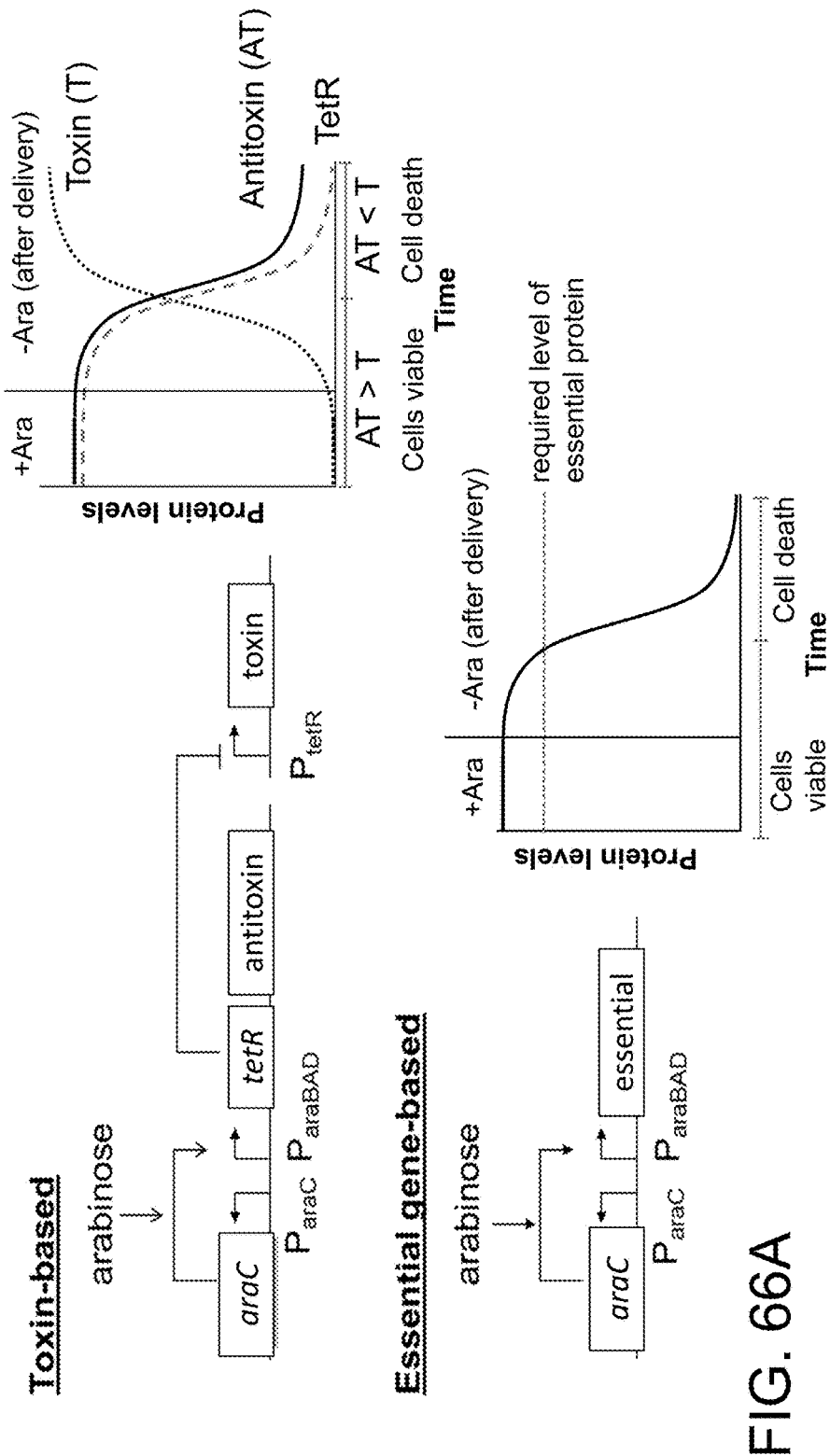
FIG. 66A depicts another non-limiting embodiment of the disclosure, wherein the expression of a heterologous gene is activated by an exogenous environmental signal. In the absence of arabinose, the AraC transcription factor adopts a conformation that represses transcription. In the presence of arabinose, the AraC transcription factor undergoes a conformational change that allows it to bind to and activate the ParaBAD promoter ($P_{araBAD}$), which induces expression of the Tet repressor (TetR) and an anti-toxin. The anti-toxin builds up in the recombinant bacterial cell, while TetR prevents expression of a toxin (which is under the control of a promoter having a TetR binding site). However, when arabinose is not present, both the anti-toxin and TetR are not expressed. Since TetR is not present to repress expression of the toxin, the toxin is expressed and kills the cell.
Figure 66B:
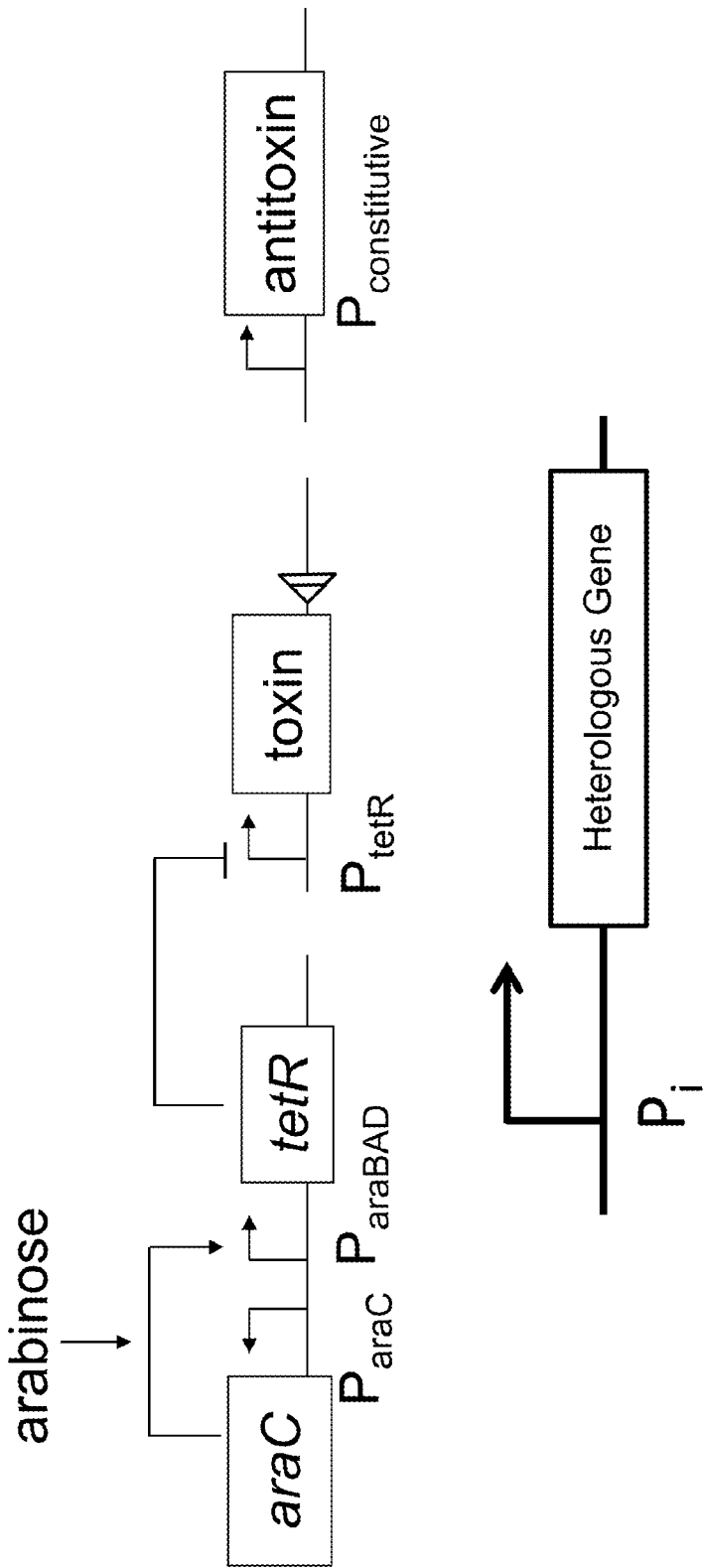
FIG. 66B depicts a non-limiting embodiment of the disclosure, where an anti-toxin is expressed from a constitutive promoter, and expression of a heterologous gene is activated by an exogenous environmental signal. In the absence of arabinose, the AraC transcription factor adopts a conformation that represses transcription. In the presence of arabinose, the AraC transcription factor undergoes a conformational change that allows it to bind to and activate the araBAD promoter, which induces expression of TetR, thus preventing expression of a toxin. However, when arabinose is not present, TetR is not expressed, and the toxin is expressed, eventually overcoming the anti-toxin and killing the cell. The constitutive promoter regulating expression of the anti-toxin should be a weaker promoter than the promoter driving expression of the toxin. The araC gene is under the control of a constitutive promoter in this circuit.
Figure 66C:
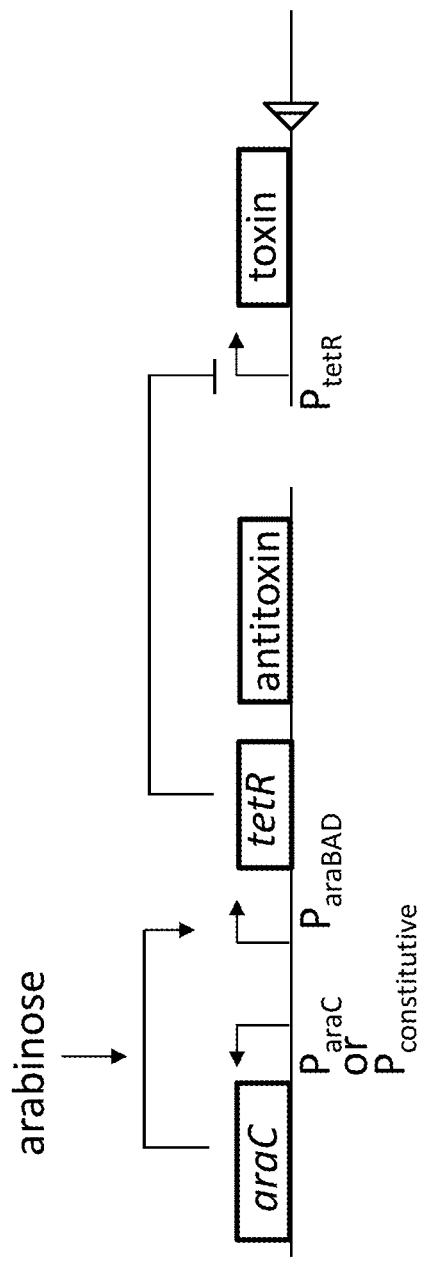
FIG. 66C depicts another non-limiting embodiment of the disclosure, wherein the expression of a heterologous gene is activated by an exogenous environmental signal. In the absence of arabinose, the AraC transcription factor adopts a conformation that represses transcription. In the presence of arabinose, the AraC transcription factor undergoes a conformational change that allows it to bind to and activate the araBAD promoter, which induces expression of the Tet repressor (TetR) and an anti-toxin. The anti-toxin builds up in the recombinant bacterial cell, while TetR prevents expression of a toxin (which is under the control of a promoter having a TetR binding site). However, when arabinose is not present, both the anti-toxin and TetR are not expressed. Since TetR is not present to repress expression of the toxin, the toxin is expressed and kills the cell. The araC gene is either under the control of a constitutive promoter or an inducible promoter (e.g., AraC promoter) in this circuit.

In some embodiments, the genetically engineered bacterium is a conditional auxotroph whose essential gene(s) is replaced using the arabinose system, e.g., as shown in FIG. 66.

In some embodiments, the genetically engineered bacterium of the disclosure is an auxotroph and also comprises kill-switch circuitry, such as any of the kill-switch components and systems described herein. For example, the recombinant bacteria may comprise a deletion or mutation in an essential gene required for cell survival and/or growth, for example, in a DNA synthesis gene, for example, thyA, cell wall synthesis gene, for example, dapA and/or an amino acid gene, for example, serA or MetA and may also comprise a toxin gene that is regulated by one or more transcriptional activators that are expressed in response to an environmental condition(s) and/or signal(s) (such as the described arabinose system) or regulated by one or more recombinases that are expressed upon sensing an exogenous environmental condition(s) and/or signal(s) (such as the recombinase systems described herein and in FIGS. 62-65. Other embodiments are described in Wright et al., "GeneGuard: A Modular Plasmid System Designed for Biosafety," ACS Synthetic Biology (2015) 4: 307-316, the entire contents of which are expressly incorporated herein by reference). In some embodiments, the genetically engineered bacterium of the disclosure is an auxotroph and also comprises kill-switch circuitry, such as any of the kill-switch components and systems described herein, as well as another biosecurity system, such a conditional origin of replication (Wright et al., 2015).

Figure 60A:
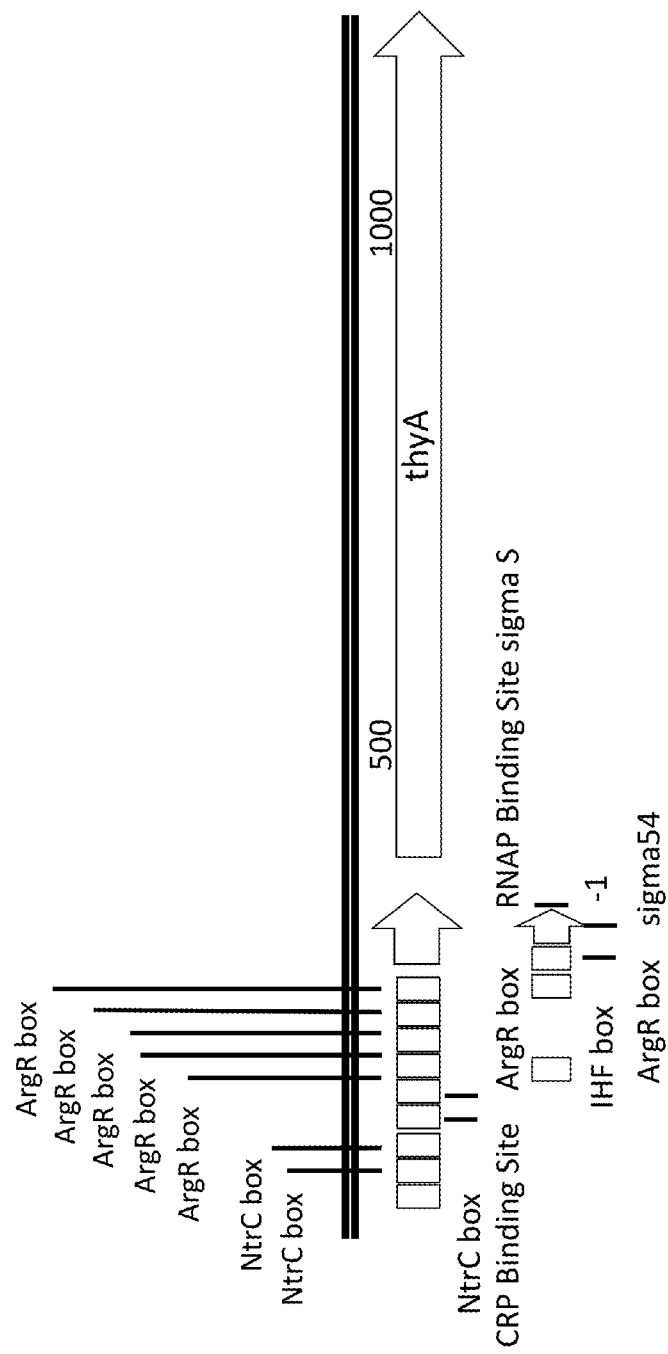
FIGS. 60A and 60B depict diagrams of exemplary constructs which may be used to produce a positive feedback auxotroph and select for high arginine production.
Figure 60B:
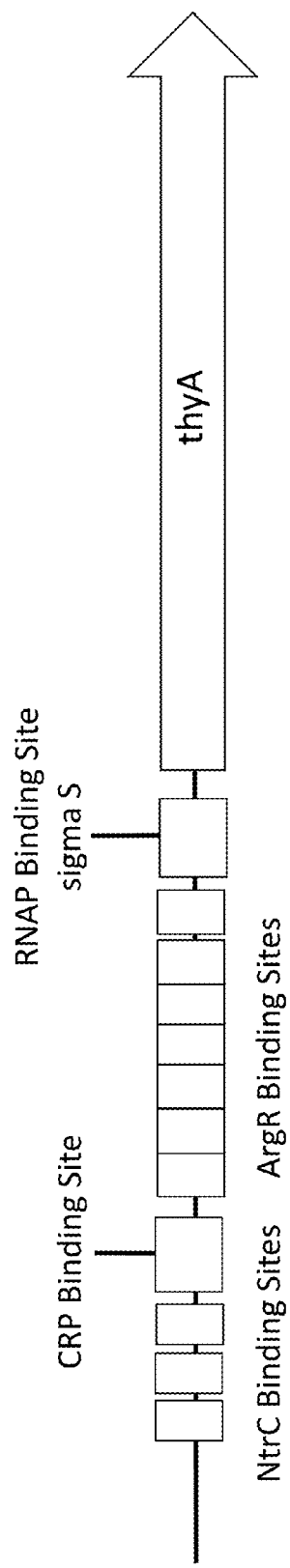
Figure 61:
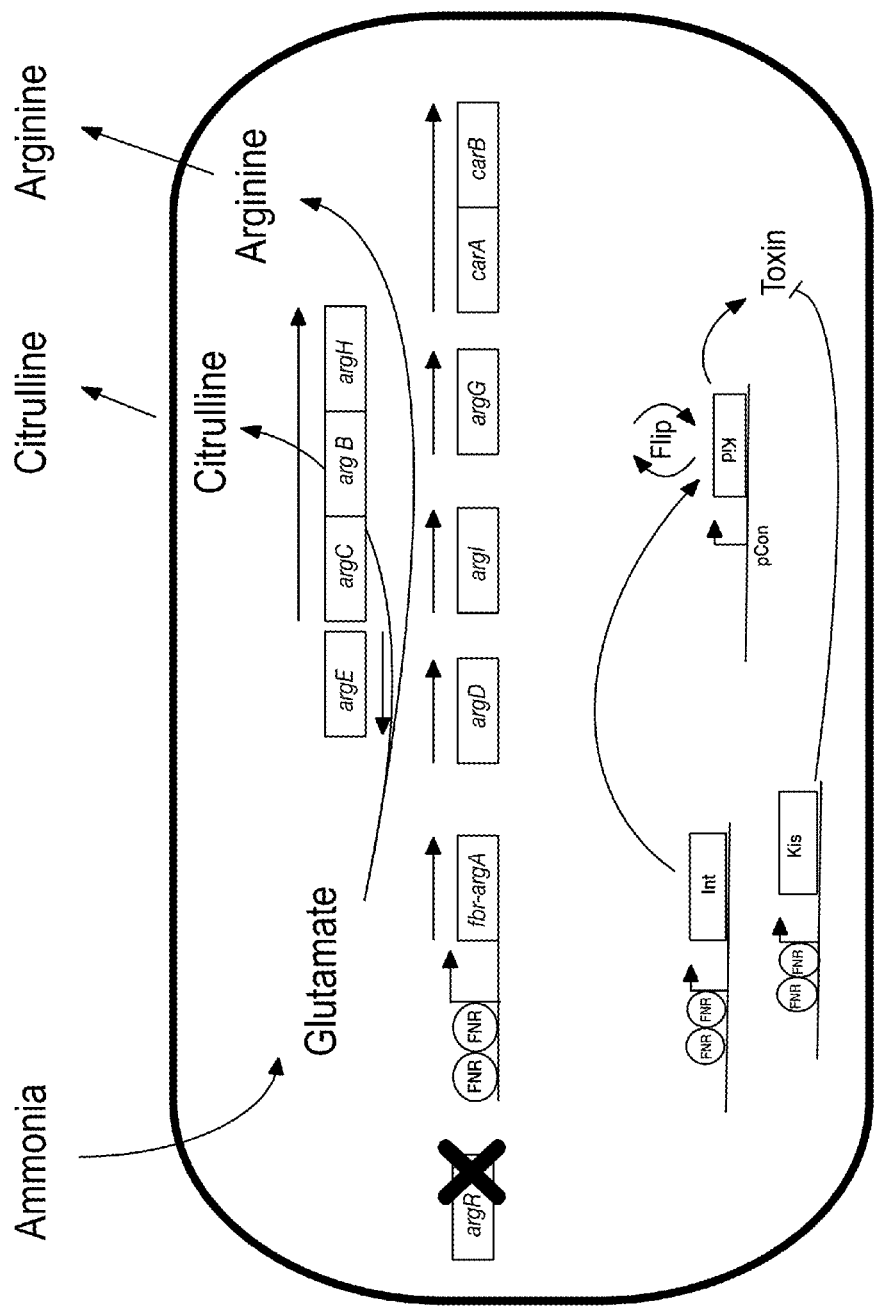
FIG. 61 depicts another exemplary embodiment of an engineered bacterial strain to target urea cycle disorder (UCD), via the conversion of ammonia to desired products, such as citrulline or arginine. The strain is deleted for the argR gene and expressing the feedback-resistant argAfbr gene. In some embodiments, this strain further comprises one or more auxotrophic modifications on the chromosome. The synthetic biotic engineered to target urea cycle disorder (UCD) also has the kill-switch embodiment described in FIG. 65. In this example, the Int recombinase and the Kid-Kis toxin-antitoxin system are used in a recombinant bacterial cell for treating UCD. The recombinant bacterial cell is engineered to consume excess ammonia to produce beneficial byproducts to improve patient outcomes. The recombinant bacterial cell also comprises a highly controllable kill switch to ensure safety. In response to a low oxygen environment (e.g., such as that found in the gut), the FNR promoter induces expression of the Int recombinase and also induces expression of the Kis anti-toxin. The Int recombinase causes the Kid toxin gene to flip into an activated conformation, but the presence of the accumulated Kis anti-toxin suppresses the activity of the expressed Kid toxin. In the presence of oxygen (e.g., outside the gut), expression of the anti-toxin is turned off. Since the toxin is constitutively expressed, it continues to accumulate and kills the bacterial cell.
Figure 62:
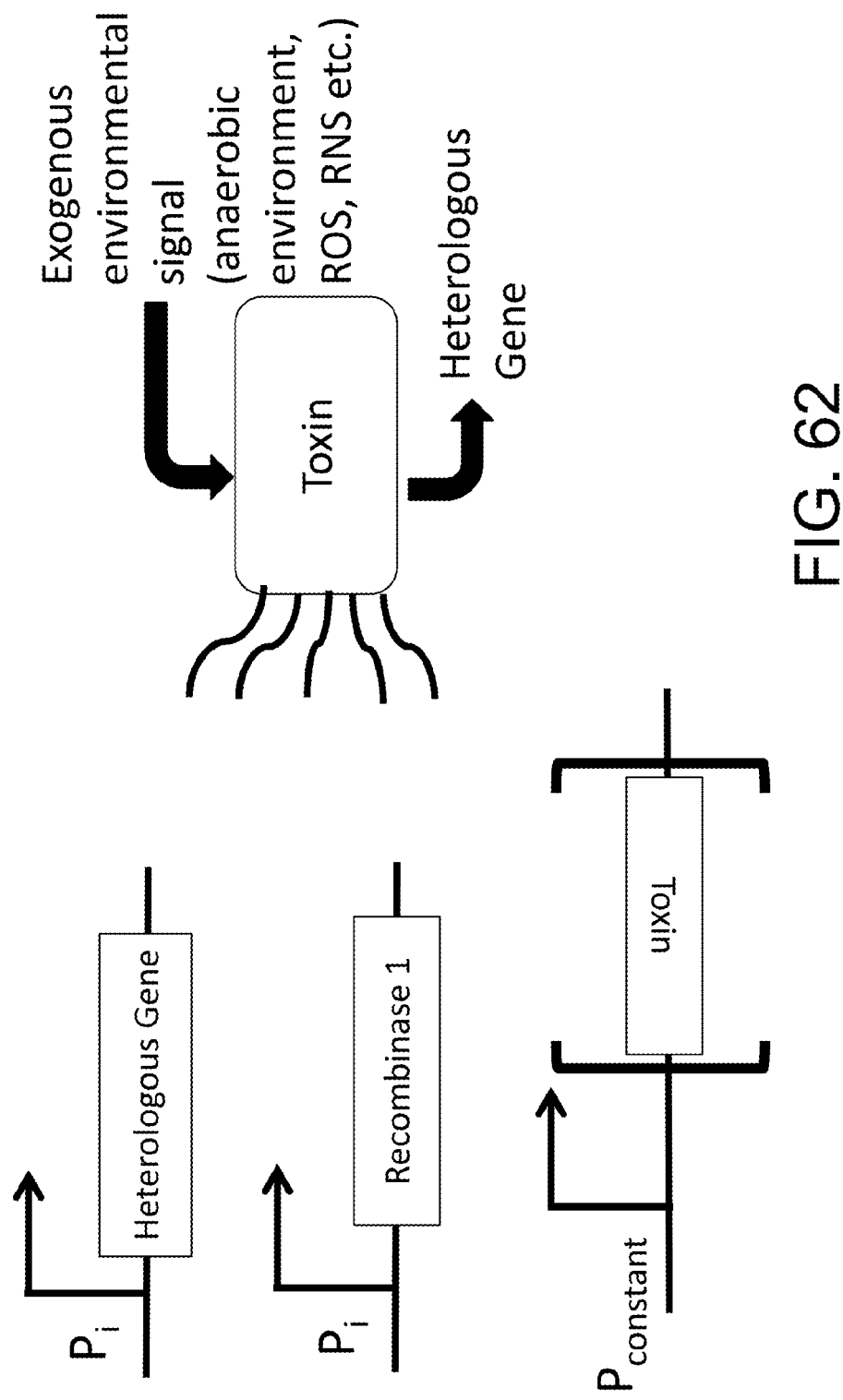
FIG. 62 depicts one non-limiting embodiment of the disclosure, where an exogenous environmental condition or one or more environmental signals activates expression of a heterologous gene and at least one recombinase from an inducible promoter or inducible promoters. The recombinase then flips a toxin gene into an activated conformation, and the natural kinetics of the recombinase create a time delay in expression of the toxin, allowing the heterologous gene to be fully expressed. Once the toxin is expressed, it kills the cell.
Figure 63:
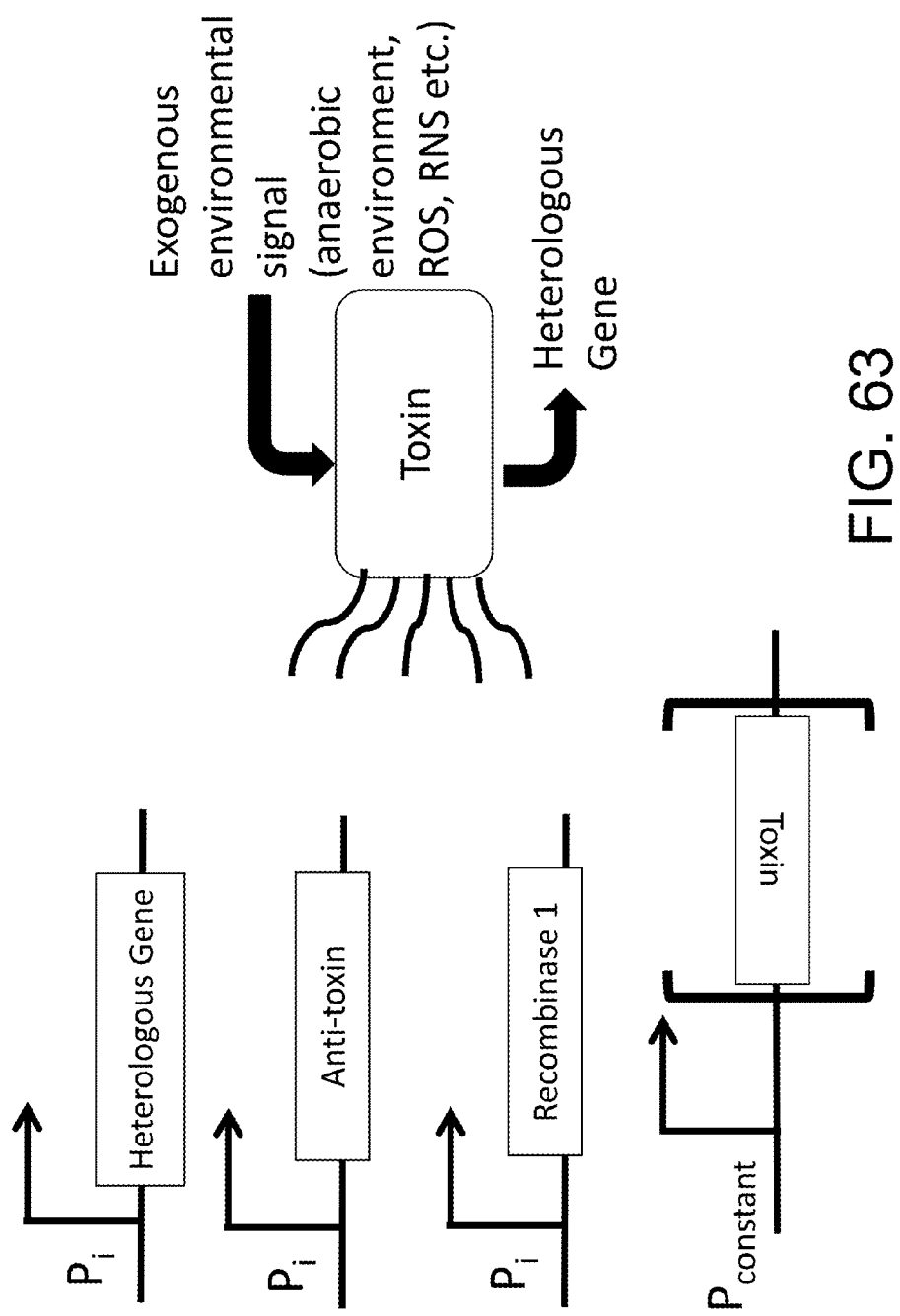
FIG. 63 depicts another non-limiting embodiment of the disclosure, where an exogenous environmental condition or one or more environmental signals activates expression of a heterologous gene, an anti-toxin, and at least one recombinase from an inducible promoter or inducible promoters. The recombinase then flips a toxin gene into an activated conformation, but the presence of the accumulated anti-toxin suppresses the activity of the toxin. Once the exogenous environmental condition or cue(s) is no longer present, expression of the anti-toxin is turned off. The toxin is constitutively expressed, continues to accumulate, and kills the bacterial cell.
Figure 64:
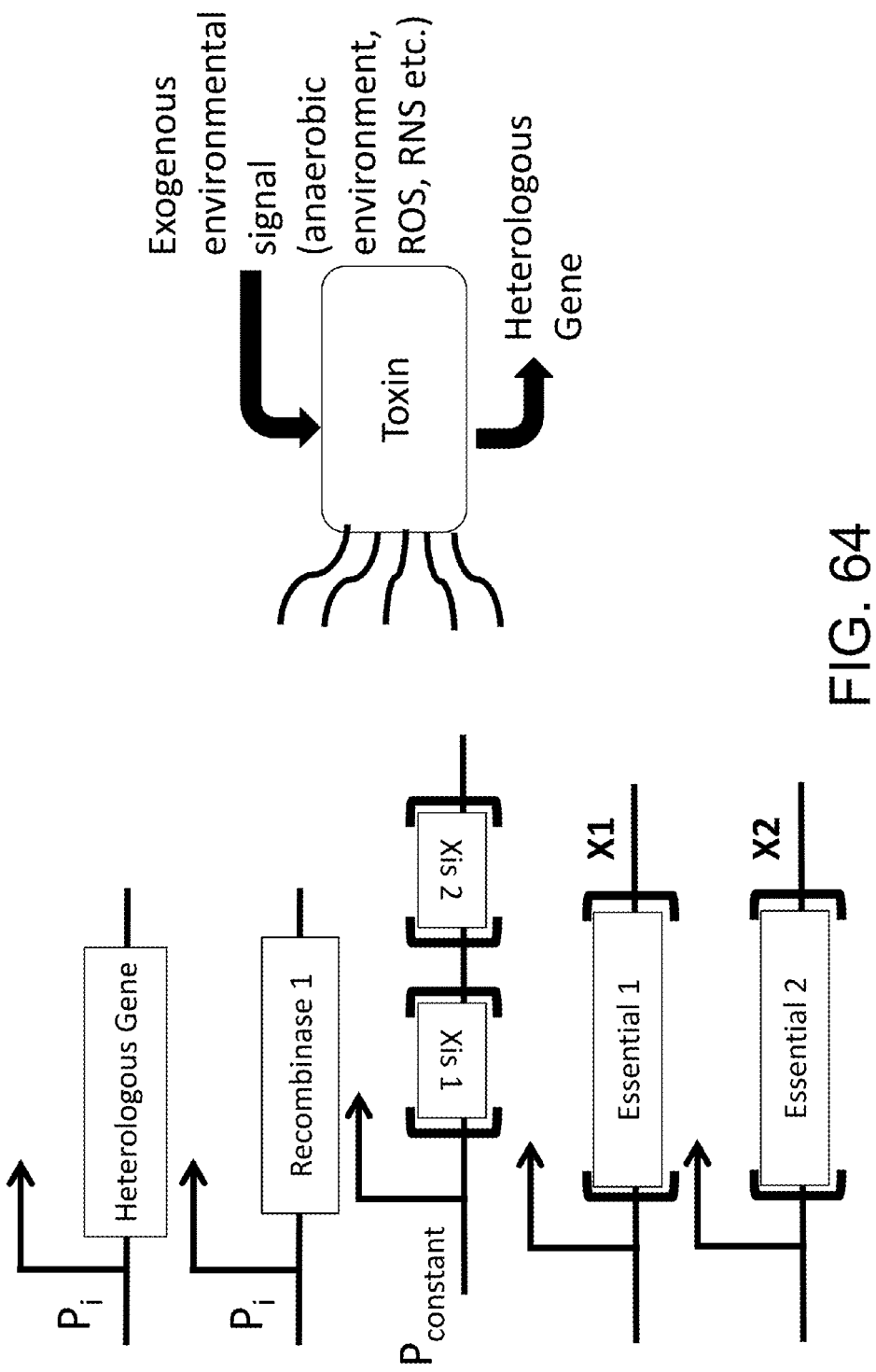
FIG. 64 depicts another non-limiting embodiment of the disclosure, where an exogenous environmental condition or one or more environmental signals activates expression of a heterologous gene and at least one recombinase from an inducible promoter or inducible promoters. The recombinase then flips at least one excision enzyme into an activated conformation. The at least one excision enzyme then excises one or more essential genes, leading to senescence, and eventual cell death. The natural kinetics of the recombinase and excision genes cause a time delay, the kinetics of which can be altered and optimized depending on the number and choice of essential genes to be excised, allowing cell death to occur within a matter of hours or days. The presence of multiple nested recombinases can be used to further control the timing of cell death.
Figure 65:
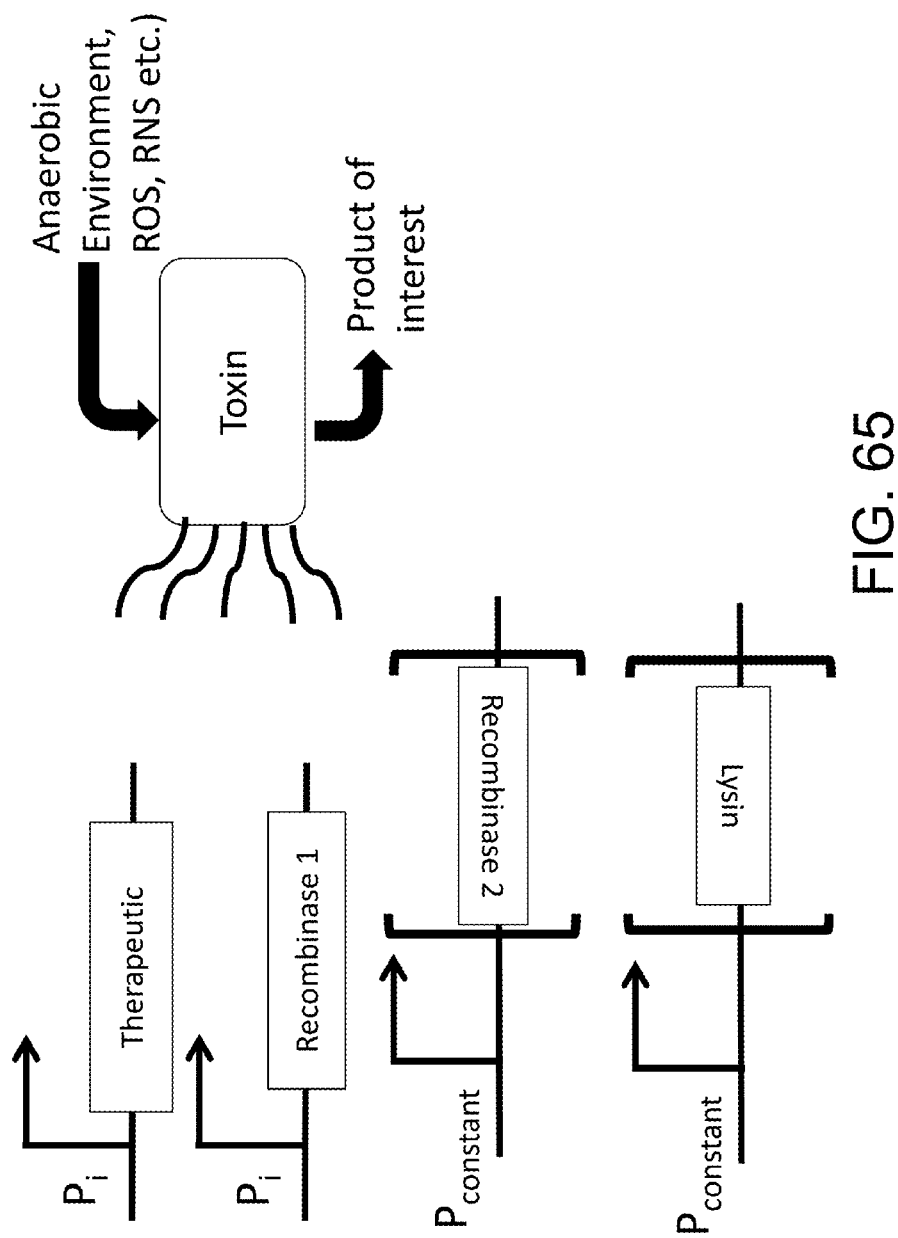
FIG. 65 depicts a schematic of an activation-based kill switch, in which R is any inducible promoter, e.g., a FNR-responsive promoter. When the therapeutic is induced, the anti-toxin and recombinases are turned on, which results in the toxin being 'flipped' to the ON position after 4-6 hours, which results in a build-up of anti-toxin before the toxin is expressed. In absence of the inducing signal, only toxin is made and the cell dies.

In other embodiments, auxotrophic modifications may also be used to screen for mutant bacteria that consume excess ammonia. In a more specific aspect, auxotrophic modifications may be used to screen for mutant bacteria that consume excess ammonia by overproducing arginine. As described herein, many genes involved in arginine metabolism are subject to repression by arginine via its interaction with ArgR. The astC gene promoter is unique in that the arginine-ArgR complex acts as a transcriptional activator, as opposed to a transcriptional repressor. AstC encodes succinylornithine aminotransferase, the third enzyme of the ammonia-producing arginine succinyltransferase (AST) pathway and the first of the astCADBE operon in E. coli (Schneider et al., 1998). In certain embodiments, the genetically engineered bacteria are auxotrophic for a gene, and express the auxotrophic gene product under the control of an astC promoter. In these embodiments, the auxotrophy is subject to a positive feedback mechanism and used to select for mutant bacteria which consume excess ammonia by overproducing arginine. A non-limiting example of a positive feedback auxotroph is shown in FIGS. 60A and 60B.

Genetic Regulatory Circuits

In some embodiments, the genetically engineered bacteria comprise multilayered genetic regulatory circuits for expressing the constructs described herein (see, e.g., U.S. Provisional Application No. 62/184,811, incorporated herein by reference in its entirety).

In certain embodiments, the invention provides methods for selecting genetically engineered bacteria that overproduce arginine. In some embodiments, the invention provides methods for selecting genetically engineered bacteria that consume excess ammonia via an alternative metabolic pathway, e.g., a histidine biosynthesis pathway, a methionine biosynthesis pathway, a lysine biosynthesis pathway, an asparagine biosynthesis pathway, a glutamine biosynthesis pathway, and a tryptophan biosynthesis pathway. In some embodiments, the invention provides genetically engineered bacteria comprising a mutant arginine regulon and an ArgR-regulated two-repressor activation genetic regulatory circuit. The two-repressor activation genetic regulatory circuit is useful to screen for mutant bacteria that reduce ammonia or rescue an auxotroph. In some constructs, high levels of arginine and the resultant activation of ArgR by arginine can cause expression of a detectable label or an essential gene that is required for cell survival.

The two-repressor activation regulatory circuit comprises a first ArgR and a second repressor, e.g., the Tet repressor. In one aspect of these embodiments, ArgR inhibits transcription of a second repressor, which inhibits the transcription of a particular gene of interest, e.g., a detectable product, which may be used to screen for mutants that consume excess ammonia, and/or an essential gene that is required for cell survival. Any detectable product may be used, including but not limited to, luciferase, β-galactosidase, and fluorescent proteins such as GFP. In some embodiments, the second repressor is a Tet repressor protein (TetR). In this embodiment, an ArgR-repressible promoter comprising wild-type ARG boxes drives the expression of TetR, and a TetR-repressible promoter drives the expression of at least one gene of interest, e.g., GFP. In the absence of ArgR binding (which occurs at low arginine concentrations), tetR is transcribed, and TetR represses GFP expression. In the presence of ArgR binding (which occurs at high arginine concentrations), tetR expression is repressed, and GFP is generated. Examples of other second repressors useful in these embodiments include, but are not limited to, ArsR, AscG, LacI, CscR, DeoR, DgoR, FruR, GalR, GatR, Cl, LexA, RafR, QacR, and PtxS (US20030166191). In some embodiments, the mutant arginine regulon comprising a switch is subjected to mutagenesis, and mutants that reduce ammonia by overproducing arginine are selected based upon the level of detectable product, e.g., by flow cytometry, fluorescence-activated cell sorting (FACS) when the detectable product fluoresces.

In some embodiments, the gene of interest is one required for survival and/or growth of the bacteria. Any such gene may be used, including but not limited to, cysE, glnA, ilvD, leuB, lysA, serA, metA, glyA, hisB, ilvA, pheA, proA, thrC, trpC, tyrA, thyA, uraA, dapA, dapB, dapD, dapE, dapF, flhD, metB, metC, proAB, and thi1, as long as the corresponding wild-type gene has been removed or mutated so as not to produce the gene product except under control of ArgR. In some embodiments, an ArgR-repressible promoter comprising wild-type ARG boxes drives the expression of a TetR protein, and a TetR-repressible promoter drives the expression of at least one gene required for survival and/or growth of the bacteria, e.g., thyA, uraA (Sat et al., 2003). In some embodiments, the genetically engineered bacterium is auxotrophic in a gene that is not complemented when the bacterium is present in the mammalian gut, wherein said gene is complemented by a second inducible gene present in the bacterium; transcription of the second gene is ArgR-repressible and induced in the presence of sufficiently high concentrations of arginine (thus complementing the auxotrophic gene). In some embodiments, the mutant arginine regulon comprising a two-repressor activation circuit is subjected to mutagenesis, and mutants that reduce excess ammonia are selected by growth in the absence of the gene product required for survival and/or growth. In some embodiments, the mutant arginine regulon comprising a two-repressor activation circuit is used to ensure that the bacteria do not survive in the absence of high levels of arginine (e.g., outside of the gut).

Host-Plasmid Mutual Dependency

In some embodiments, the genetically engineered bacteria of the invention also comprise a plasmid that has been modified to create a host-plasmid mutual dependency. In certain embodiments, the mutually dependent host-plasmid platform is GeneGuard (Wright et al., 2015). In some embodiments, the GeneGuard plasmid comprises (i) a conditional origin of replication, in which the requisite replication initiator protein is provided in trans; (ii) an auxotrophic modification that is rescued by the host via genomic translocation and is also compatible for use in rich media; and/or (iii) a nucleic acid sequence which encodes a broad-spectrum toxin. The toxin gene may be used to select against plasmid spread by making the plasmid DNA itself disadvantageous for strains not expressing the anti-toxin (e.g., a wild-type bacterium). In some embodiments, the GeneGuard plasmid is stable for at least 100 generations without antibiotic selection. In some embodiments, the GeneGuard plasmid does not disrupt growth of the host. The GeneGuard plasmid is used to greatly reduce unintentional plasmid propagation in the genetically engineered bacteria of the invention.

The mutually dependent host-plasmid platform may be used alone or in combination with other biosafety mechanisms, such as those described herein (e.g., kill switches, auxotrophies). In some embodiments, the genetically engineered bacteria comprise a GeneGuard plasmid. In other embodiments, the genetically engineered bacteria comprise a GeneGuard plasmid and/or one or more kill switches. In other embodiments, the genetically engineered bacteria comprise a GeneGuard plasmid and/or one or more auxotrophies. In still other embodiments, the genetically engineered bacteria comprise a GeneGuard plasmid, one or more kill switches, and/or one or more auxotrophies.

Figure 68:
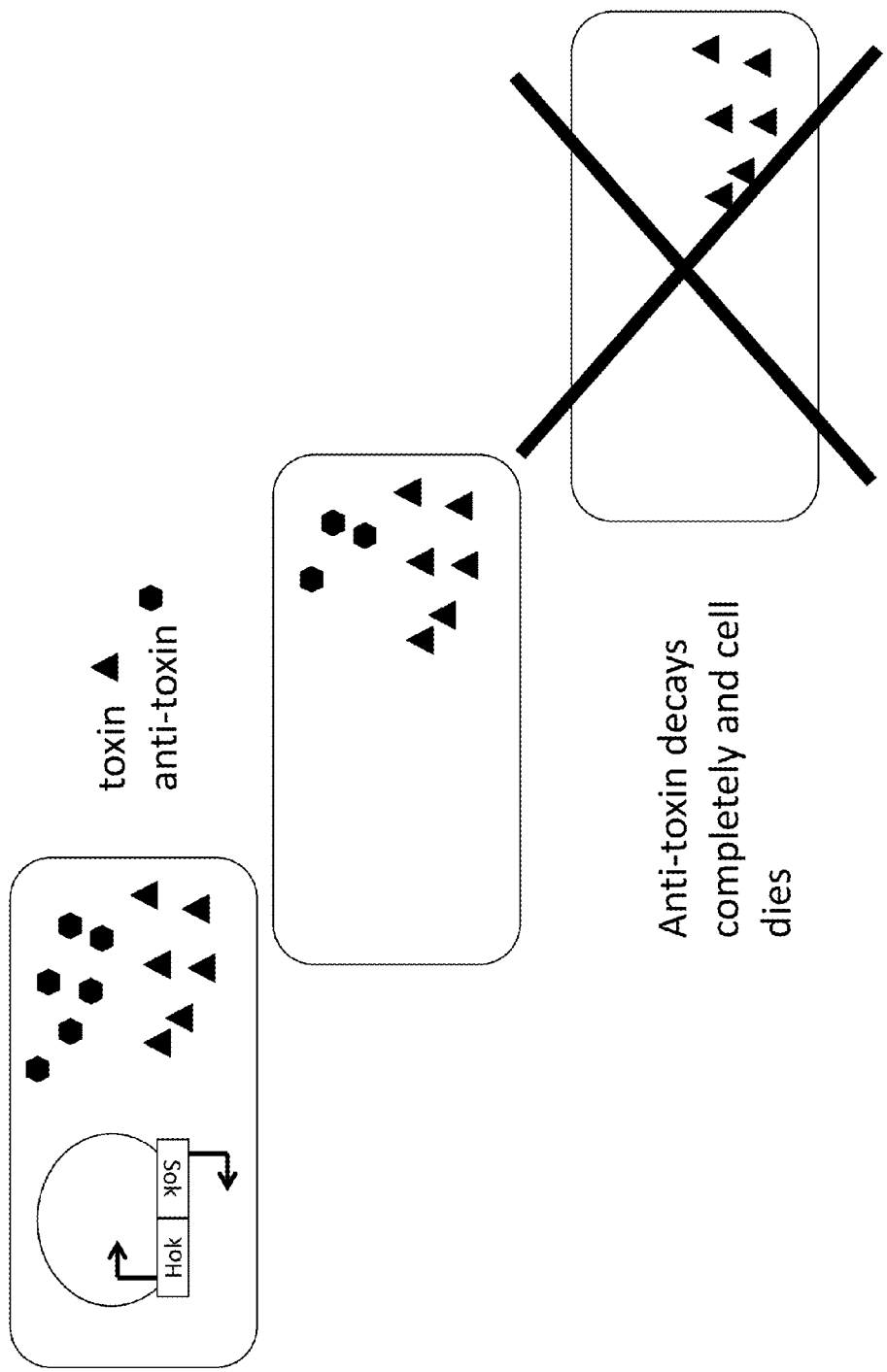
FIG. 68 depicts a one non-limiting embodiment of the disclosure, which comprises a plasmid stability system with a plasmid that produces both a short-lived anti-toxin and a long-lived toxin. When the cell loses the plasmid, the anti-toxin is no longer produced, and the toxin kills the cell. In one embodiment, the genetically engineered bacteria produce an equal amount of a Hok toxin and a short-lived Sok antitoxin. In the upper panel, the cell produces equal amounts of toxin and anti-toxin and is stable. In the center panel, the cell loses the plasmid and anti-toxin begins to decay. In the lower panel, the anti-toxin decays completely, and the cell dies.
Figure 69:
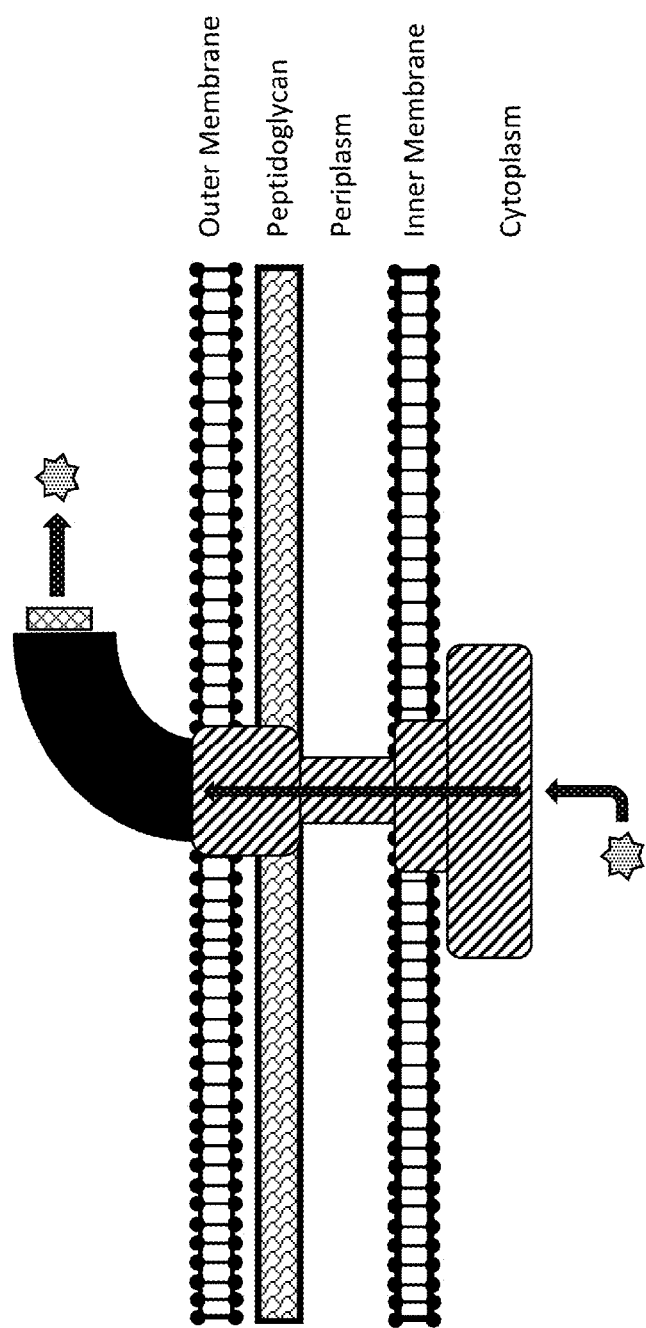
FIG. 69 depicts a schematic of a secretion system based on the flagellar type III secretion in which an incomplete flagellum is used to secrete a therapeutic peptide of interest (star) by recombinantly fusing the peptide to an N-terminal flagellar secretion signal of a native flagellar component so that the intracellularly expressed chimeric peptide can be mobilized across the inner and outer membranes into the surrounding host environment.

Synthetic gene circuits express on plasmids may function well in the short term but lose ability and/or function in the long term (Danino et al., 2015). In some embodiments, the genetically engineered bacteria comprise stable circuits for expressing genes of interest over prolonged periods. In some embodiments, the genetically engineered bacteria are capable of producing a gut enhancer molecule and further comprise a toxin-anti-toxin system that simultaneously produces a toxin (hok) and a short-lived anti-toxin (sok), wherein loss of the plasmid causes the cell to be killed by the long-lived toxin (Danino et al., 2015; FIG. 68). In some embodiments, the genetically engineered bacteria further comprise alp7 from *B. subtilis* plasmid pL20 and produces filaments that are capable of pushing plasmids to the poles of the cells in order to ensure equal segregation during cell division (Danino et al., 2015).

Kill Switch

In some embodiments, the genetically engineered bacteria of the invention also comprise a kill switch (see, e.g., U.S. Provisional Application Nos. 62/183,935, 62/263,329, and 62/277,654, each of which is incorporated herein by reference in their entireties). The kill switch is intended to actively kill engineered microbes in response to external stimuli. As opposed to an auxotrophic mutation where bacteria die because they lack an essential nutrient for survival, the kill switch is triggered by a particular factor in the environment that induces the production of toxic molecules within the microbe that cause cell death.

Bacteria engineered with kill switches have been engineered for in vitro research purposes, e.g., to limit the spread of a biofuel-producing microorganism outside of a laboratory environment. Bacteria engineered for in vivo administration to treat a disease or disorder may also be programmed to die at a specific time after the expression and delivery of a heterologous gene or genes, for example, a therapeutic gene(s) or after the subject has experienced the therapeutic effect. For example, in some embodiments, the kill switch is activated to kill the bacteria after a period of time following oxygen level-dependent expression of $\text{arg}^{Afbr}$. In some embodiments, the kill switch is activated in a delayed fashion following oxygen level-dependent expression of $\text{arg}^{Afbr}$, for example, after the production of arginine or citrulline. Alternatively, the bacteria may be engineered to die after the bacteria has spread outside of a disease site. Specifically, it may be useful to prevent long-term colonization of subjects by the microorganism, spread of the microorganism outside the area of interest (for example, outside the gut) within the subject, or spread of the microorganism outside of the subject into the environment (for example, spread to the environment through the stool of the subject). Examples of such toxins that can be used in kill-switches include, but are not limited to, bacteriocins, lysins, and other molecules that cause cell death by lysing cell membranes, degrading cellular DNA, or other mechanisms. Such toxins can be used individually or in combination. The switches that control their production can be based on, for example, transcriptional activation (toggle switches; see, e.g., Gardner et al., 2000), translation (riboregulators), or DNA recombination (recombinase-based switches), and can sense environmental stimuli such as anaerobiosis or reactive oxygen species. These switches can be activated by a single environmental factor or may require several activators in AND, OR, NAND and NOR logic configurations to induce cell death. For example, an AND riboregulator switch is activated by tetracycline, isopropyl β-D-1-thiogalactopyranoside (IPTG), and arabinose to induce the expression of lysins, which permeabilize the cell membrane and kill the cell. IPTG induces the expression of the endolysin and holin mRNAs, which are then derepressed by the addition of arabinose and tetracycline. All three inducers must be present to cause cell death. Examples of kill switches are known in the art (Callura et al., 2010). In some embodiments, the kill switch is activated to kill the bacteria after a period of time following oxygen level-dependent expression of $\text{arg}^{Afbr}$. In some embodiments, the kill switch is activated in a delayed fashion following oxygen level-dependent expression of $\text{arg}A^{fbr}$.

Kill-switches can be designed such that a toxin is produced in response to an environmental condition or external signal (e.g., the bacteria is killed in response to an external cue) or, alternatively designed such that a toxin is produced once an environmental condition no longer exists or an external signal is ceased.

Thus, in some embodiments, the genetically engineered bacteria of the disclosure are further programmed to die after sensing an exogenous environmental signal, for example, in a low-oxygen environment. In some embodiments, the genetically engineered bacteria of the present disclosure, e.g., bacteria expressing $\text{arg}A^{fbr}$ and repressor ArgR, comprise one or more genes encoding one or more recombinase(s), whose expression is induced in response to an environmental condition or signal and causes one or more recombination events that ultimately leads to the expression of a toxin which kills the cell. In some embodiments, the at least one recombination event is the flipping of an inverted heterologous gene encoding a bacterial toxin which is then constitutively expressed after it is flipped by the first recombinase. In one embodiment, constitutive expression of the bacterial toxin kills the genetically engineered bacterium. In these types of kill-switch systems once the engineered bacterial cell senses the exogenous environmental condition and expresses the heterologous gene of interest, the recombinant bacterial cell is no longer viable.

In another embodiment in which the genetically engineered bacteria of the present disclosure, e.g., bacteria expressing $\text{arg}A^{fbr}$ and repressor ArgR, express one or more recombinase(s) in response to an environmental condition or signal causing at least one recombination event, the genetically engineered bacterium further expresses a heterologous gene encoding an anti-toxin in response to an exogenous environmental condition or signal. In one embodiment, the at least one recombination event is flipping of an inverted heterologous gene encoding a bacterial toxin by a first recombinase. In one embodiment, the inverted heterologous gene encoding the bacterial toxin is located between a first forward recombinase recognition sequence and a first reverse recombinase recognition sequence. In one embodiment, the heterologous gene encoding the bacterial toxin is constitutively expressed after it is flipped by the first recombinase. In one embodiment, the anti-toxin inhibits the activity of the toxin, thereby delaying death of the genetically engineered bacterium. In one embodiment, the genetically engineered bacterium is killed by the bacterial toxin when the heterologous gene encoding the anti-toxin is no longer expressed when the exogenous environmental condition is no longer present.

In another embodiment, the at least one recombination event is flipping of an inverted heterologous gene encoding a second recombinase by a first recombinase, followed by the flipping of an inverted heterologous gene encoding a bacterial toxin by the second recombinase. In one embodiment, the inverted heterologous gene encoding the second recombinase is located between a first forward recombinase recognition sequence and a first reverse recombinase recognition sequence. In one embodiment, the inverted heterologous gene encoding the bacterial toxin is located between a second forward recombinase recognition sequence and a second reverse recombinase recognition sequence. In one embodiment, the heterologous gene encoding the second recombinase is constitutively expressed after it is flipped by the first recombinase. In one embodiment, the heterologous gene encoding the bacterial toxin is constitutively expressed after it is flipped by the second recombinase. In one embodiment, the genetically engineered bacterium is killed by the bacterial toxin. In one embodiment, the genetically engineered bacterium further expresses a heterologous gene encoding an anti-toxin in response to the exogenous environmental condition. In one embodiment, the anti-toxin inhibits the activity of the toxin when the exogenous environmental condition is present, thereby delaying death of the genetically engineered bacterium. In one embodiment, the genetically engineered bacterium is killed by the bacterial toxin when the heterologous gene encoding the anti-toxin is no longer expressed when the exogenous environmental condition is no longer present.

In one embodiment, the at least one recombination event is flipping of an inverted heterologous gene encoding a second recombinase by a first recombinase, followed by flipping of an inverted heterologous gene encoding a third recombinase by the second recombinase, followed by flipping of an inverted heterologous gene encoding a bacterial toxin by the third recombinase.

In one embodiment, the at least one recombination event is flipping of an inverted heterologous gene encoding a first excision enzyme by a first recombinase. In one embodiment, the inverted heterologous gene encoding the first excision enzyme is located between a first forward recombinase recognition sequence and a first reverse recombinase recognition sequence. In one embodiment, the heterologous gene encoding the first excision enzyme is constitutively expressed after it is flipped by the first recombinase. In one embodiment, the first excision enzyme excises a first essential gene. In one embodiment, the programmed recombinant bacterial cell is not viable after the first essential gene is excised.

In one embodiment, the first recombinase further flips an inverted heterologous gene encoding a second excision enzyme. In one embodiment, the wherein the inverted heterologous gene encoding the second excision enzyme is located between a second forward recombinase recognition sequence and a second reverse recombinase recognition sequence. In one embodiment, the heterologous gene encoding the second excision enzyme is constitutively expressed after it is flipped by the first recombinase. In one embodiment, the genetically engineered bacterium dies or is no longer viable when the first essential gene and the second essential gene are both excised. In one embodiment, the genetically engineered bacterium dies or is no longer viable when either the first essential gene is excised or the second essential gene is excised by the first recombinase.

In one embodiment, the genetically engineered bacterium dies after the at least one recombination event occurs. In another embodiment, the genetically engineered bacterium is no longer viable after the at least one recombination event occurs.

In any of these embodiment, the recombinase can be a recombinase selected from the group consisting of: BxbI, PhiC31, TP901, BxbI, PhiC31, TP901, HK022, HP1, R4, Int1, Int2, Int3, Int4, Int5, Int6, Int7, Int8, Int9, Int10, Int11, Int12, Int13, Int14, Int15, Int16, Int17, Int18, Int19, Int20, Int21, Int22, Int23, Int24, Int25, Int26, Int27, Int28, Int29, Int30, Int31, Int32, Int33, and Int34, or a biologically active fragment thereof.

Figure 67:
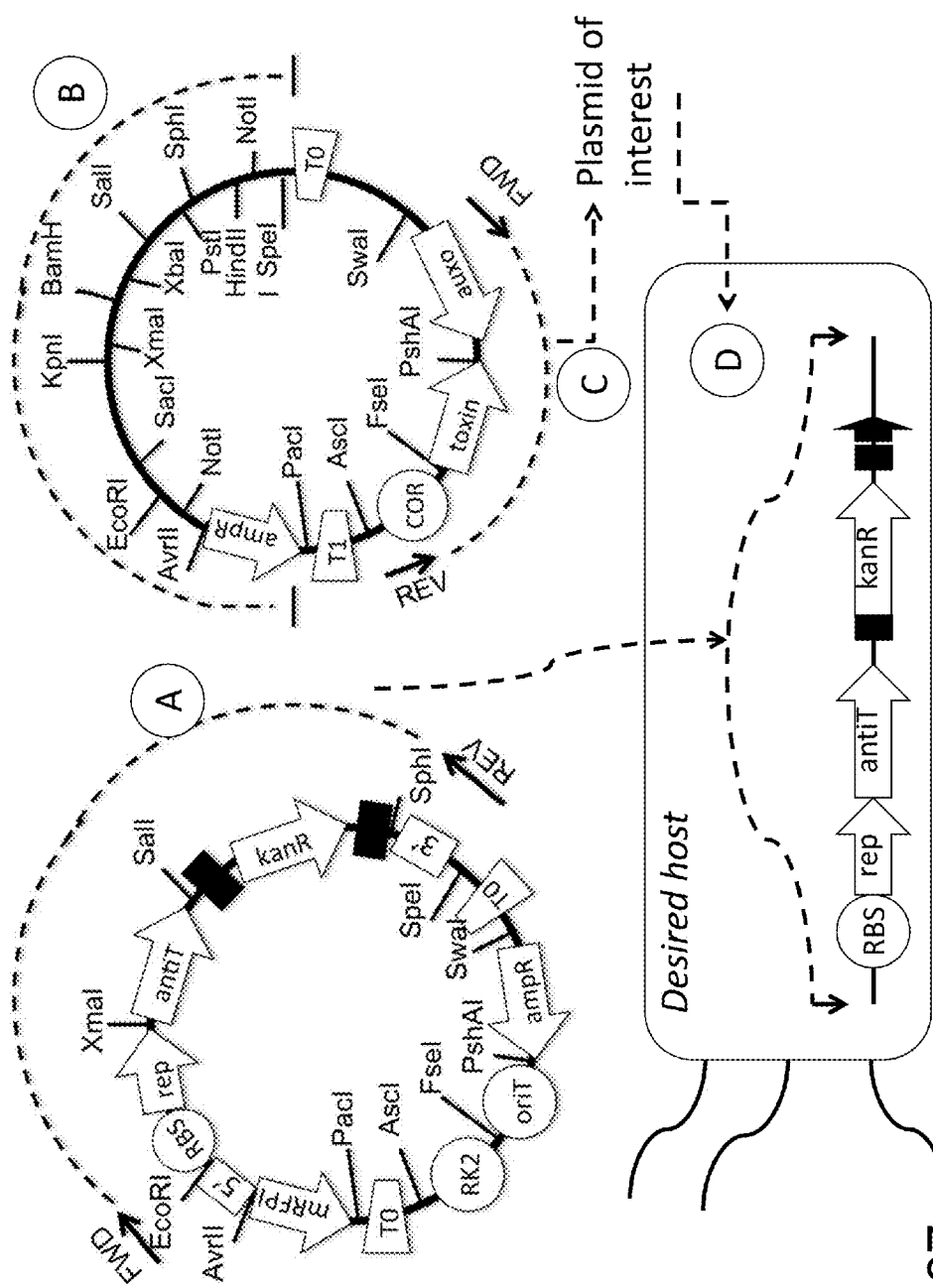
FIG. 67 depicts the use of GeneGuards as an engineered safety component. All engineered DNA is present on a plasmid which can be conditionally destroyed. See, e.g., Wright et al., "GeneGuard: A Modular Plasmid System Designed for Biosafety," ACS Synthetic Biology (2015) 4: 307-316.

In the above-described kill-switch circuits, a toxin is produced in the presence of an environmental factor or signal. In another aspect of kill-switch circuitry, a toxin may be repressed in the presence of an environmental factor (not produced) and then produced once the environmental condition or external signal is no longer present. An exemplary kill-switch in which the toxin is repressed in the presence of an external factor or signal (and activated once the external signal is removed) is shown in FIGS. 66-68. The disclosure provides recombinant bacterial cells which express one or more heterologous gene(s) upon sensing arabinose or other sugar in the exogenous environment. In this aspect, the recombinant bacterial cells contain the araC gene, which encodes the AraC transcription factor, as well as one or more genes under the control of the araBAD promoter. In the absence of arabinose, the AraC transcription factor adopts a conformation that represses transcription of genes under the control of the araBAD promoter. In the presence of arabinose, the AraC transcription factor undergoes a conformational change that allows it to bind to and activate the araBAD promoter, which induces expression of the desired gene, for example tetR, which represses expression of a toxin gene. In this embodiment, the toxin gene is repressed in the presence of arabinose or other sugar. In an environment where arabinose is not present, the tetR gene is not activated and the toxin is expressed, thereby killing the bacteria. The arabinose system can also be used to express an essential gene, in which the essential gene is only expressed in the presence of arabinose or other sugar and is not expressed when arabinose or other sugar is absent from the environment.

Thus, in some embodiments in which one or more heterologous gene(s) are expressed upon sensing arabinose in the exogenous environment, the one or more heterologous genes are directly or indirectly under the control of the araBAD promoter. In some embodiments, the expressed heterologous gene is selected from one or more of the following: a heterologous therapeutic gene, a heterologous gene encoding an anti-toxin, a heterologous gene encoding a repressor protein or polypeptide, for example, a TetR repressor, a heterologous gene encoding an essential protein not found in the bacterial cell, and/or a heterologous encoding a regulatory protein or polypeptide.

Figure 13:
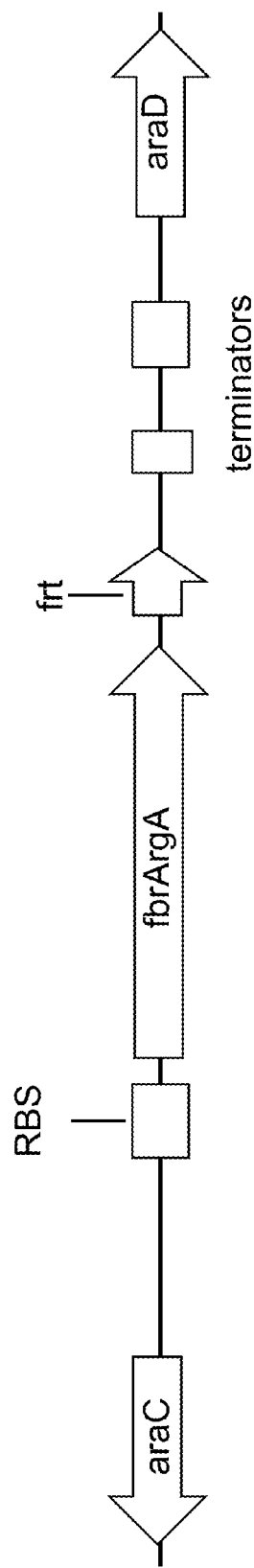
FIG. 13 depicts a schematic diagram of an exemplary BAD promoter-driven argA$^{fbr}$ construct. In this embodiment, the argA$^{fbr}$ gene is inserted between the araC and araD genes. ArgA$^{fbr}$ is flanked by a ribosome binding site, a FRT site, and one or more transcription terminator sequences.
Figure 14:
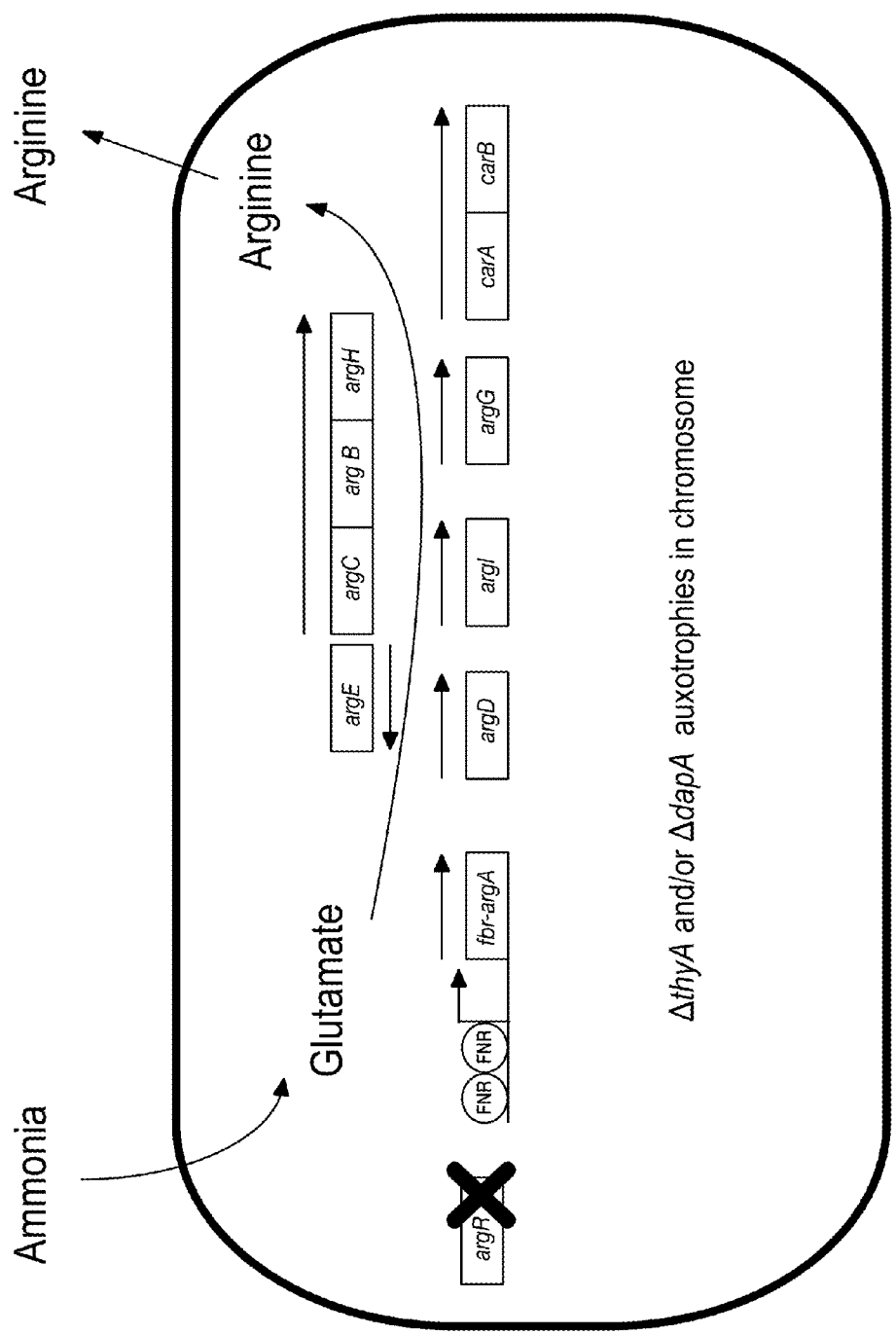
FIG. 14 depicts an exemplary embodiment of an engineered bacterial strain deleted for the argR gene and expressing the feedback-resistant argA$^{fbr}$ gene. In some embodiments, this strain further comprises one or more auxotrophic modifications on the chromosome. This strain is useful for the consumption of ammonia and the production of arginine.
Figure 15:
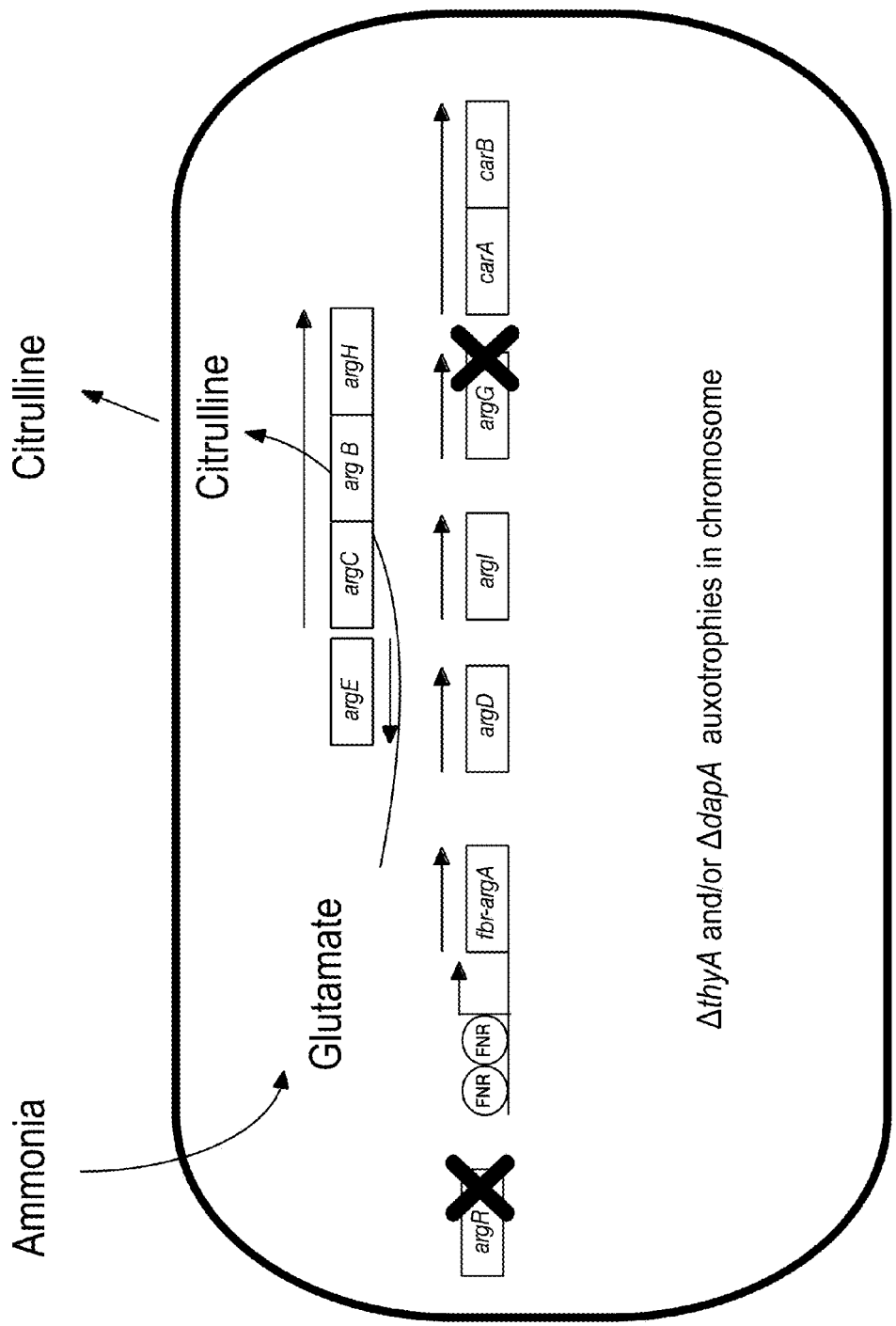
FIG. 15 depicts an exemplary embodiment of an engineered bacterial strain deleted for the argR and argG genes, and expressing the feedback-resistant argA$^{fbr}$ gene. In some embodiments, this strain further comprises one or more auxotrophic modifications on the chromosome. This strain is useful for the consumption of ammonia and the production of citrulline.
Figure 16:
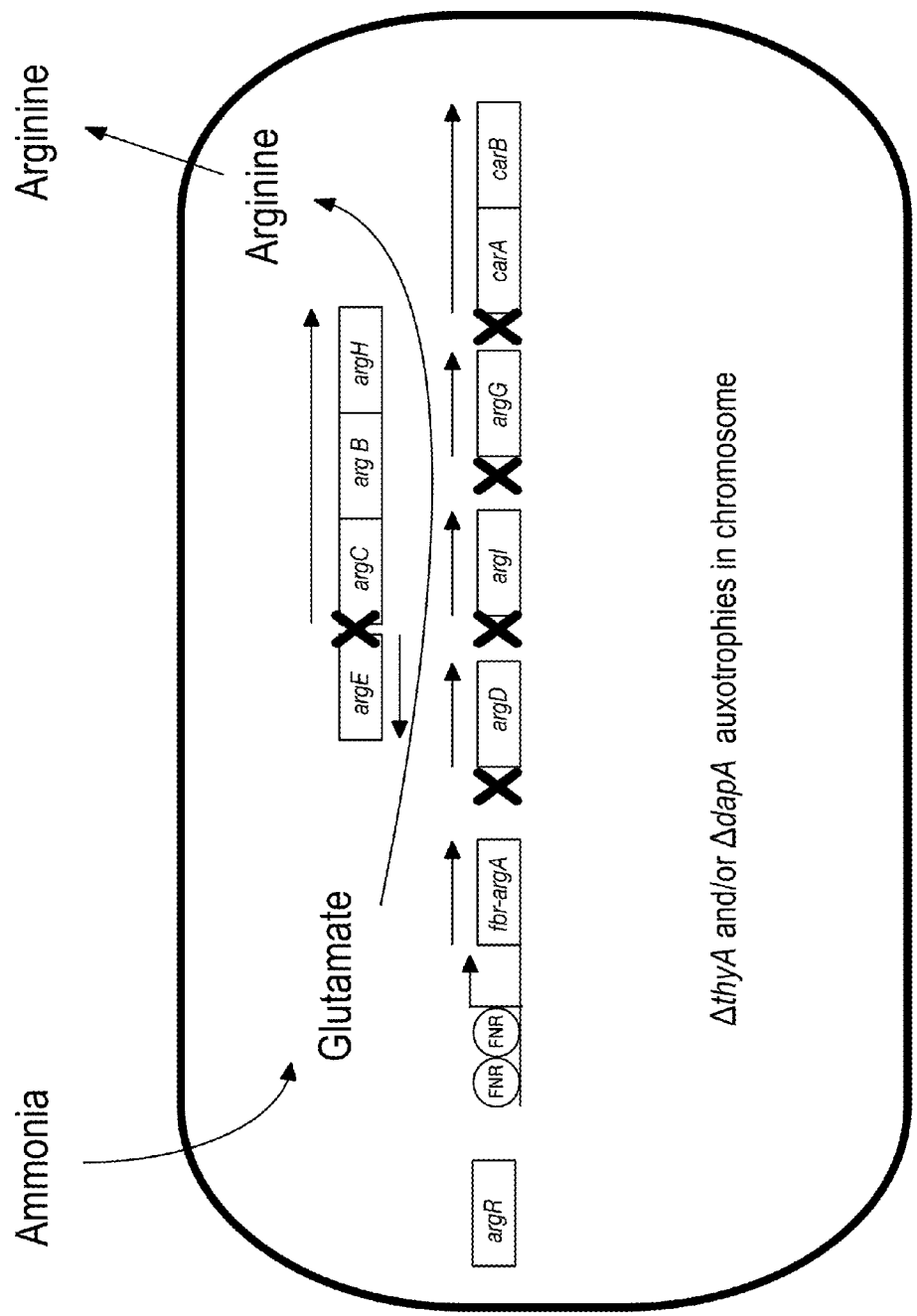
FIG. 16 depicts an exemplary embodiment of an engineered bacterial strain which lacks ArgR binding sites and expresses the feedback-resistant argA$^{fbr}$ gene. In some embodiments, this strain further comprises one or more auxotrophic modifications on the chromosome. This strain is useful for the consumption of ammonia and the production of arginine.
Figure 17:
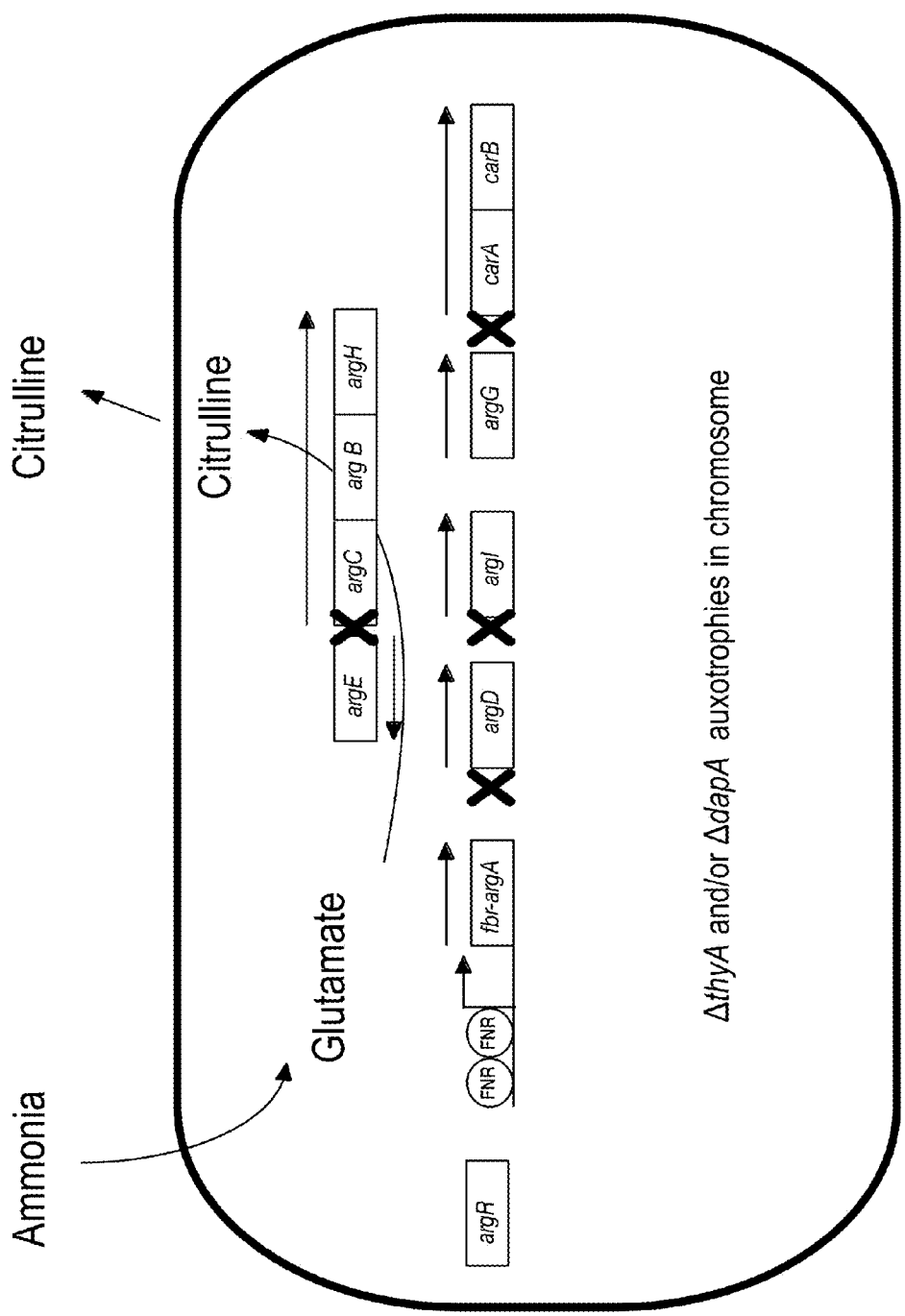
FIG. 17 depicts an exemplary embodiment of an engineered bacterial strain which lacks ArgR binding sites in all of the arginine biosynthesis operons except for argG, and expresses the feedback-resistant argA$^{fbr}$ gene. In some embodiments, this strain further comprises one or more auxotrophic modifications on the chromosome. This strain is useful for the consumption of ammonia and the production of citrulline.

In some embodiments, the argA$^{fbr}$ gene is directly or indirectly under the control of the araBAD promoter. FIG. 13 depicts a schematic diagram of an exemplary BAD promoter-driven argA$^{fbr}$ construct. In this embodiment, the argA$^{fbr}$ gene is inserted between the araC and araD genes. ArgA$^{fbr}$ is flanked by a ribosome binding site, a FRT site, and one or more transcription terminator sequences. The nucleic acid sequence of an exemplary BAD promoter-driven argA$^{fbr}$ construct is shown in Table 19. All bolded sequences are Nissle genomic DNA. A portion of the araC gene is bolded and underlined, the argA$^{fbr}$ gene is boxed, and the bolded sequence in between is the promoter that is activated by the presence of arabinose. The ribosome binding site is in italics, the terminator sequences are highlighted, and the FRT site is boxed. A portion of the araD gene is boxed in dashes. In some embodiments, genetically engineered bacteria comprise a nucleic acid sequence that is at least about 80%, at least about 85%, at least about 90%, at least about 95%, or at least about 99% homologous to the BAD promoter sequence of SEQ ID NO: 67 or a functional fragment thereof. In some embodiments, genetically engineered bacteria comprise the BAD promoter sequence of SEQ ID NO: 67 or a functional fragment thereof.

TABLE 19

Nucleotide sequence of exemplary BAD promoter-driven argA$^{fbr}$ (SEQ ID NO: 67)

cgacggtggcgataggcatccgggtggtgctcaaaagcagcttcgcctgactgatgcgct ggtcctcgcgccagcttaatacgctaatccctaactgctggcggaacaaatgcgacagac gcgacggcgacaggcagacatgctgtgcgacgctggcgatatcaaaattactgtctgcca ggtgatcgctgatgtactgacaagcctcgcgtacccgattatccatcggtggatggagcg actcgttaatcgcttccatgcgccgcagtaacaattgctcaagcagatttatcgccagca attccgaatagcgcccttcccttgtccggcattaatgatttgcccaaacaggtcgctga aatgcggctggtgcgcttcatccgggcgaaagaaaccggtattggcaaatatcgacggcc agttaagccattcatgccagtaggcgcgcggacgaaagtaaacccactggtgataccatt cgtgagcctccggatgacgaccgtagtgatgaatctctccaggcgggaacagcaaaatat cacccggtcggcagacaaattctcgtccctgattttcaccaccccctgaccgcgaatgg tgagattgagaatataacctttcattcccagcggtcggtcgataaaaaaatcgagataac cgttggcctcaatcggcgttaaaccgccaccagatgggcgttaaacgagtatcccggca gcagggatcattttgcgcttcagccatacttttcatactcccgccattcagagaagaaa ccaattgtccatattgcatcagacattgccgtcactgcgtcttttactggctcttctcgc taacccaaccggtaacccgcttattaaaagcattctgtaacaaagcgggaccaaagcca tgacaaaaacgcgtaacaaaagtgtctataatcacggcagaaaagtccacattgattatt tgcacggcgtcacactttgctatgccatagcattttatccataagattagcggatccag cctgacgcttttttcgcaactctctactgtttctccata*cccgtttttttggatggagt*

*gaaacg*| ATGGTAAAGGAACGTAAAACCGAGTTGGTCGAGGG |

| ATTCCGCCATTCGGTTCCCTGTATCAATACCCACCGGGGAAAAACGTTTGTCATCATGC |
| TCGGCGGTGAAGCCATTGAGCATGAGAATTTCTCCAGTATCGTTAATGATATCGGGTTG |

| TTGCACAGCCTCGGCATCCGTCTGGTGGTGGTCTATGGCGCACGTCCGCAGATCGACGC |
| AAATCTGGCTGCGCATCACCACGAACCGCTGTATCACAAGAATATACGTGTGACCGACG |

| CCAAAACACTGGAACTGGTGAAGCAGGCTGCGGGAACATTGCAACTGGATATTACTGCT |
| CGCCTGTCGATGAGTCTCAATAACACGCCGCTGCAGGGCGCGCATATCAACGTCGTCAG |

| TGGCAATTTTATTATTGCCCAGCCGCTGGGCGTCGATGACGGCGTGGATTACTGCCATA |
| GCGGGCGTATCCGGCGGATTGATGAAGACGCGATCCATCGTCAACTGGACAGCGGTGCA |

| ATAGTGCTAATGGGGCCGGTCGCTGTTTCAGTCACTGGCGAGAGCTTTAACCTGACCTC |
| GGAAGAGATTGCCACTCAACTGGCCATCAAACTGAAAGCTGAAAAGATGATTGGTTTTT |

| GCTCTTCCCAGGGCGTCACTAATGACGACGGTGATATTGTCTCCGAACTTTTCCCTAAC |
| GAAGCGCAAGCGCGGGTAGAAGCCCAGGAAGAGAAAGGCGATTACAACTCCGGTACGGT |

| GCGCTTTTTGCGTGGCGCAGTGAAAGCCTGCCGCAGCGGCGTGCGTCGCTGTCATTTAA |
| TCAGTTATCAGGAAGATGGCGCGCTGTTGCAAGAGTTGTTCTCACGCGACGGTATCGGT |

| ACGCAGATTGTGATGGAAAGCGCCGAGCAGATTCGTCGCGCAACAATCAACGATATTGG |
| CGGTATTCTGGAGTTGATTCGCCCACTGGAGCAGCAAGGTATTCTGGTACGCCGTTCTC |

TABLE 19-continued

Nucleotide sequence of exemplary BAD promoter-driven argA^fbr
(SEQ ID NO: 67)

GCGAGCAGCTGGAGATGGAAATCGACAAATTCACCATTATTCAGCGCGATAACACGACT
ATTGCCTGCGCCGCGCTCTATCCGTTCCCGGAAGAGAAGATTGGGGAAATGGCCTGTGT

GGCAGTTCACCCGGATTACCGCAGTTCATCAAGGGGTGAAGTTCTGCTGGAACGCATTG
CCGCTCAGGCTAAGCAGAGCGGCTTAAGCAAATTGTTTGTGCTGACCACGCGCAGTATT

CACTGGTTCCAGGAACGTGGATTTACCCCAGTGGATATTGATTTACTGCCCGAGAGCAA
AAAGCAGTTGTACAACTACCAGCGTAAATCCAAAGTGTTGATGGCGGATTTAGGGTAAT

GGGAATTAGCCATGGTCCATATGAATATCCTCCTTAGTTCCTATTCC gaagttcctatt ccgaagttcctattctctagaaagtataggaacttc GAAGCAGCTCCAGCCTACACAAT CGCTCAAGACGTGTAATGCTGCAATCTGCATGCAAGCTTGGCACTGGCCACGCAAAAAG
GCCATCCGTCAGGATGGCCTTCTGCTTAATTTGATGCCTGGCAGTTTATGGCGGGCGTC
CTGCCCGCCACCCTCCGGGCCGTTGCTTCGCAACGTTCAAATCCGCTCCCGGCGGATTT
GTCCTACTCAGGAGACCGTTCACCGACAAACAACAGATAAAACGAAAGGCCCAGTCTTT
CGACTGAGCCTTTCGTTTTATTTGATGCCTGGCAGTTCCCTACTCTCGCATGctcgagc catgggacgtcaggtattagaagccaacctggcgctgccaaaacacaacctggtcacg
ctcacctggggcaatgtcagcgccgttgatcgcgggcgcggcgtcctggtgatcaaacc ttccggcgtcgactacagcatcatgaccgctgacgatatggtcgtggtcagcatcgaaa
ccggtgaagtggttgaaggtacgaaaaagccctcctccgacacgccaactcaccggctg ctctatcaggcattcccgtctattggcggcattgtgcacacacactcgcgccacgccac
catctgggcgcaggcgggccagtcgattccagcagccggcaccacccacgccgactatt tctacggcaccattccctgcacccgcaaaatgaccgacgcagaaatcaacggtgaatat
gagtgggaaaccggtaacgtcatcgtagaaaccttcgaaaaacagggtatcaatgcagc gcaaatgcccggcgtgctggtccattctcacggcccatttgcatggggaaaaaacgccg
aagatgcggtgcataacgccatcgtgctggaagaagtcgcttatatggggatattctgc cgtcagttagcgccgcagttaccggatatgcagcaaacgctgctggataaacactatct
gcgtaagcatggcgcgaaggcatattacgggcagtaa

---

Arabinose inducible promoters are known in the art, including $P_{ara}$, $P_{araB}$, $P_{araC}$, and $P_{araBAD}$. In one embodiment, the arabinose inducible promoter is from *E. coli*. In some embodiments, the $P_{araC}$ promoter and the $P_{araBAD}$ promoter operate as a bidirectional promoter, with the $P_{araBAD}$ promoter controlling expression of a heterologous gene(s) in one direction, and the $P_{araC}$ (in close proximity to, and on the opposite strand from the $P_{araBAD}$ promoter), controlling expression of a heterologous gene(s) in the other direction. In the presence of arabinose, transcription of both heterologous genes from both promoters is induced. However, in the absence of arabinose, transcription of both heterologous genes from both promoters is not induced.

In one exemplary embodiment of the disclosure, the engineered bacteria of the present disclosure contains a kill-switch having at least the following sequences: a $P_{araBAD}$ promoter operably linked to a heterologous gene encoding a tetracycline repressor protein (TetR), a $P_{araC}$ promoter operably linked to a heterologous gene encoding AraC transcription factor, and a heterologous gene encoding a bacterial toxin operably linked to a promoter which is repressed by the tetracycline repressor protein ($P_{TetR}$). In the presence of arabinose, the AraC transcription factor activates the $P_{araBAD}$ promoter, which activates transcription of the TetR protein which, in turn, represses transcription of the toxin. In the absence of arabinose, however, AraC suppresses transcription from the $P_{araBAD}$ promoter and no TetR protein is expressed. In this case, expression of the heterologous toxin gene is activated, and the toxin is expressed. The toxin builds up in the recombinant bacterial cell, and the recombinant bacterial cell is killed. In one embodiment, the araC gene encoding the AraC transcription factor is under the control of a constitutive promoter and is therefore constitutively expressed.

In one embodiment of the disclosure, the recombinant bacterial cell further comprises an anti-toxin under the control of a constitutive promoter. In this situation, in the presence of arabinose, the toxin is not expressed due to repression by TetR protein, and the anti-toxin protein builds-up in the cell. However, in the absence of arabinose, TetR protein is not expressed, and expression of the toxin is induced. The toxin begins to build-up within the recombinant bacterial cell. The recombinant bacterial cell is no longer viable once the toxin protein is present at either equal or greater amounts than that of the anti-toxin protein in the cell, and the recombinant bacterial cell will be killed by the toxin.

In another embodiment of the disclosure, the recombinant bacterial cell further comprises an anti-toxin under the control of the $P_{araBAD}$ promoter. In this situation, in the presence of arabinose, TetR and the anti-toxin are expressed, the anti-toxin builds up in the cell, and the toxin is not expressed due to repression by TetR protein. However, in the absence of arabinose, both the TetR protein and the anti-toxin are not expressed, and expression of the toxin is induced. The toxin begins to build-up within the recombinant bacterial cell. The recombinant bacterial cell is no longer viable once the toxin protein is expressed, and the recombinant bacterial cell will be killed by the toxin.

In another exemplary embodiment of the disclosure, the engineered bacteria of the present disclosure contain a kill-switch having at least the following sequences: a $P_{araBAD}$ promoter operably linked to a heterologous gene encoding an essential polypeptide not found in the recombinant bacterial cell (and required for survival), and a P araC promoter operably linked to a heterologous gene encoding the AraC transcription factor. In the presence of arabinose, the AraC transcription factor activates the $P_{araBAD}$ promoter, which activates transcription of the heterologous gene encoding the essential polypeptide, allowing the recombinant bacterial cell to survive. In the absence of arabinose, however, AraC suppresses transcription from the $P_{araBAD}$ promoter and the essential protein required for survival is not expressed. In this case, the recombinant bacterial cell dies in the absence of arabinose. In some embodiments, the sequence of $P_{araBAD}$ promoter operably linked to a heterologous gene encoding an essential polypeptide not found in the recombinant bacterial cell can be present in the bacterial cell in conjunction with the TetR/toxin kill-switch system described directly above. In some embodiments, the sequence of $P_{araBAD}$ promoter operably linked to a heterologous gene encoding an essential polypeptide not found in the recombinant bacterial cell can be present in the bacterial cell in conjunction with the TetR/toxin/anti-toxin kill-switch system described directly above.

In yet other embodiments, the bacteria may comprise a plasmid stability system with a plasmid that produces both a short-lived anti-toxin and a long-lived toxin. In this system, the bacterial cell produces equal amounts of toxin and anti-toxin to neutralize the toxin. However, if/when the cell loses the plasmid, the short-lived anti-toxin begins to decay. When the anti-toxin decays completely the cell dies as a result of the longer-lived toxin killing it.

In some embodiments, the engineered bacteria of the present disclosure, for example, bacteria expressing $argA^{fbr}$ and repressor ArgR further comprise the gene(s) encoding the components of any of the above-described kill-switch circuits.

In any of the above-described embodiments, the bacterial toxin is selected from the group consisting of a lysin, Hok, Fst, TisB, LdrD, Kid, SymE, MazF, FlmA, Ibs, XCV2162, dinJ, CcdB, MazF, ParE, YafO, Zeta, hicB, relB, yhaV, yoeB, chpBK, hipA, microcin B, microcin B17, microcin C, microcin C7-C51, microcin J25, microcin ColV, microcin 24, microcin L, microcin D93, microcin L, microcin E492, microcin H47, microcin 147, microcin M, colicin A, colicin E1, colicin K, colicin N, colicin U, colicin B, colicin Ia, colicin Ib, colicin 5, colicin10, colicin S4, colicin Y, colicin E2, colicin E7, colicin E8, colicin E9, colicin E3, colicin E4, colicin E6; colicin E5, colicin D, colicin M, and cloacin DF13, or a biologically active fragment thereof.

In any of the above-described embodiments, the anti-toxin is selected from the group consisting of an anti-lysin, Sok, RNAII, IstR, RdlD, Kis, SymR, MazE, FlmB, Sib, ptaRNA1, yafQ, CcdA, MazE, ParD, yafN, Epsilon, HicA, relE, prlF, yefM, chpBI, hipB, MccE, $MccE^{CTD}$, MccF, Cai, ImmE1, Cki, Cni, Cui, Cbi, Iia, Imm, Cfi, Im10, Csi, Cyi, Im2, Im7, Im8, Im9, Im3, Im4, ImmE6, cloacin immunity protein (Cim), ImmE5, ImmD, and Cmi, or a biologically active fragment thereof.

In one embodiment, the bacterial toxin is bactericidal to the genetically engineered bacterium. In one embodiment, the bacterial toxin is bacteriostatic to the genetically engineered bacterium.

In some embodiments, the engineered bacteria provided herein have an arginine regulon comprising one or more nucleic acid mutations that reduce or eliminate arginine-mediated repression of each of the operons that encode the enzymes responsible for converting glutamate to arginine and/or an intermediate byproduct, e.g., citrulline, in the arginine biosynthesis pathway, such that the mutant arginine regulon produces more arginine and/or intermediate byproduct than an unmodified regulon from the same bacterial subtype under the same conditions. In some embodiments, the genetically engineered bacteria comprise an arginine feedback resistant N-acetylglutamate synthase mutant, e.g., $argA^{fbr}$. In some embodiments, the genetically engineered bacteria comprise a mutant arginine regulon comprising one or more nucleic acid mutations in at least one ARG box for each of the operons that encode the arginine biosynthesis enzymes N-acetylglutamate kinase, N-acetylglutamylphosphate reductase, acetylornithine am inotransferase, N-acetylornithinase, ornithine transcarbamylase, argininosuccinate synthase, argininosuccinate lyase, and carbamoylphosphate synthase, thereby derepressing the regulon and enhancing arginine and/or intermediate byproduct biosynthesis. In some embodiments, the genetically engineered bacteria further comprise an arginine feedback resistant N-acetylglutamate synthase mutant. In some embodiments, the arginine feedback resistant N-acetylglutamate synthase mutant is controlled by an oxygen level-dependent promoter. In some embodiments, the arginine feedback resistant N-acetylglutamate synthase mutant is controlled by a promoter that is induced under low-oxygen or anaerobic conditions. In some embodiments, the promoter is selected from the fumarate and nitrate reductase regulator (FNR) promoter, arginine deiminiase and nitrate reduction (ANR) promoter, and dissimilatory nitrate respiration regulator (DNR) promoter. In some embodiments, the arginine feedback resistant N-acetylglutamate synthase mutant is $argA^{fbr}$.

In some embodiments, the genetically engineered bacteria comprise a mutant arginine regulon comprising one or more nucleic acid mutations in at least one ARG box for each of the operons that encode the arginine biosynthesis enzymes and an arginine feedback resistant N-acetylglutamate synthase mutant. In some embodiments, the genetically engineered bacteria comprise a mutant arginine regulon, wherein the bacterium comprises a gene encoding a functional N-acetylglutamate synthetase that is mutated to reduce arginine feedback inhibition as compared to a wild-type N-acetylglutamate synthetase from the same bacterial subtype under the same conditions, wherein expression of the gene encoding the mutated N-acetylglutamate synthetase is controlled by a promoter that is induced under low-oxygen or anaerobic conditions, wherein the mutant arginine regulon comprises one or more operons comprising genes that encode arginine biosynthesis enzymes N-acetylglutamate kinase, N-acetylglutamate phosphate reductase, acetylornithine aminotransferase, N-acetylornithinase, carbamoylphosphate synthase, ornithine transcarbamylase, argininosuccinate synthase, and argininosuccinate lyase, and wherein each operon comprises one or more mutated ARG box(es) characterized by one or more nucleic acid mutations that reduces arginine-mediated repression of the operon via ArgR repressor binding, and retains RNA polymerase binding with sufficient affinity to promote transcription of the genes in the operon.

In some embodiments, the genetically engineered bacteria is an auxotroph comprising a mutant arginine regulon comprising one or more nucleic acid mutations in at least one ARG box for each of the operons that encode the arginine biosynthesis enzymes and an arginine feedback resistant N-acetylglutamate synthase mutant. In one embodiment, the genetically engineered bacteria comprising a mutant arginine regulon comprising one or more nucleic acid mutations in at least one ARG box for each of the operons that encode the arginine biosynthesis enzymes and an arginine feedback resistant N-acetylglutamate synthase mutant is an auxotroph selected from a cysE, glnA, ilvD, leuB, lysA, serA, metA, glyA, hisB, ilvA, pheA, proA, thrC, trpC, tyrA, thyA, uraA, dapA, dapB, dapD, dapE, dapF, flhD, metB, metC, proAB, and thi1 auxotroph. In some embodiments, the engineered bacteria have more than one auxotrophy, for example, they may be a ΔthyA and ΔdapA auxotroph.

In some embodiments, the genetically engineered bacteria comprising a mutant arginine regulon comprising one or more nucleic acid mutations in at least one ARG box for each of the operons that encode the arginine biosynthesis enzymes and an arginine feedback resistant N-acetylglutamate synthase mutant further comprises a kill-switch circuit, such as any of the kill-switch circuits provided herein. For example, in some embodiments, the genetically engineered bacteria further comprise one or more genes encoding one or more recombinase(s) under the control of an inducible promoter and an inverted toxin sequence. In some embodiments, the genetically engineered bacteria further comprise one or more genes encoding an anti-toxin. In some embodiments, the engineered bacteria further comprise one or more genes encoding one or more recombinase(s) under the control of an inducible promoter and one or more inverted excision genes, wherein the excision gene(s) encode an enzyme that deletes an essential gene. In some embodiments, the genetically engineered bacteria further comprise one or more genes encoding an anti-toxin. In some embodiments, the engineered bacteria further comprise one or more genes encoding a toxin under the control of a promoter having a TetR repressor binding site and a gene encoding the TetR under the control of an inducible promoter that is induced by arabinose, such as $P_{araBAD}$. In some embodiments, the genetically engineered bacteria further comprise one or more genes encoding an anti-toxin.

In some embodiments, the genetically engineered bacteria is an auxotroph comprising a mutant arginine regulon comprising one or more nucleic acid mutations in at least one ARG box for each of the operons that encode the arginine biosynthesis enzymes and an arginine feedback resistant N-acetylglutamate synthase mutant and further comprises a kill-switch circuit, such as any of the kill-switch circuits described herein.

In some embodiments of the above described genetically engineered bacteria, the gene encoding the arginine feedback resistant N-acetylglutamate synthetase is present on a plasmid in the bacterium and operatively linked on the plasmid to the promoter that is induced under low-oxygen or anaerobic conditions. In other embodiments, the gene encoding the arginine feedback resistant N-acetylglutamate synthetase is present in the bacterial chromosome and is operatively linked in the chromosome to the promoter that is induced under low-oxygen or anaerobic conditions.

In some embodiments, the genetically engineered bacteria comprise a mutant arginine repressor comprising one or more nucleic acid mutations such that arginine repressor function is decreased or inactive, or the genetically engineered bacteria do not have an arginine repressor (e.g., the arginine repressor gene has been deleted), resulting in derepression of the regulon and enhancement of arginine and/or intermediate byproduct biosynthesis. In some embodiments, the genetically engineered bacteria further comprise an arginine feedback resistant N-acetylglutamate synthase mutant. In some embodiments, the arginine feedback resistant N-acetylglutamate synthase mutant is controlled by an oxygen level-dependent promoter. In some embodiments, the arginine feedback resistant N-acetylglutamate synthase mutant is controlled by a promoter that is induced under low-oxygen or anaerobic conditions. In some embodiments, the promoter is selected from the fumarate and nitrate reductase regulator (FNR) promoter, arginine deiminiase and nitrate reduction (ANR) promoter, and dissimilatory nitrate respiration regulator (DNR) promoter. In some embodiments, the arginine feedback resistant N-acetylglutamate synthase mutant is $argA^{fbr}$.

In some embodiments, the genetically engineered bacteria comprise a mutant or deleted arginine repressor and an arginine feedback resistant N-acetylglutamate synthase mutant. In some embodiments, the genetically engineered bacterium comprise an arginine regulon, wherein the bacterium comprises a gene encoding a functional N-acetylglutamate synthetase with reduced arginine feedback inhibition as compared to a wild-type N-acetylglutamate synthetase from the same bacterial subtype under the same conditions, wherein expression of the gene encoding arginine feedback resistant N-acetylglutamate synthetase is controlled by a promoter that is induced by exogenous environmental conditions and wherein the bacterium has been genetically engineered to lack a functional ArgR repressor.

In some embodiments, the genetically engineered bacteria comprising a mutant or deleted arginine repressor and an arginine feedback resistant N-acetylglutamate synthase mutant is an auxotroph. In one embodiment, the genetically engineered bacteria comprising a mutant or deleted arginine repressor and an arginine feedback resistant N-acetylglutamate synthase mutant is an auxotroph selected from a cysE, glnA, ilvD, leuB, lysA, serA, metA, glyA, hisB, ilvA, pheA, proA, thrC, trpC, tyrA, thyA, uraA, dapA, dapB, dapD, dapE, dapF, flhD, metB, metC, proAB, and thi1 auxotroph. In some embodiments, the engineered bacteria have more than one auxotrophy, for example, they may be a ΔthyA and ΔdapA auxotroph.

In some embodiments, the genetically engineered bacteria comprising a mutant or deleted arginine repressor and an arginine feedback resistant N-acetylglutamate synthase mutant further comprise a kill-switch circuit, such as any of the kill-switch circuits provided herein. For example, in some embodiments, the genetically engineered bacteria further comprise one or more genes encoding one or more recombinase(s) under the control of an inducible promoter, and an inverted toxin sequence. In some embodiments, the genetically engineered bacteria further comprise one or more genes encoding an anti-toxin. In some embodiments, the engineered bacteria further comprise one or more genes encoding one or more recombinase(s) under the control of an inducible promoter and one or more inverted excision genes, wherein the excision gene(s) encode an enzyme that deletes an essential gene. In some embodiments, the genetically engineered bacteria further comprise one or more genes encoding an anti-toxin. In some embodiments, the engineered bacteria further comprise one or more genes encoding a toxin under the control of a promoter having a TetR repressor binding site and a gene encoding the TetR under the control of an inducible promoter that is induced by arabinose, such as $P_{araBAD}$. In some embodiments, the genetically engineered bacteria further comprise one or more genes encoding an anti-toxin.

In some embodiments, the genetically engineered bacterium is an auxotroph comprising a mutant or deleted arginine repressor and an arginine feedback resistant N-acetylglutamate synthase mutant and further comprises a kill-switch circuit, such as any of the kill-switch circuits described herein.

In some embodiments of the above described genetically engineered bacteria, the gene encoding the arginine feedback resistant N-acetylglutamate synthetase is present on a plasmid in the bacterium and operatively linked on the plasmid to the promoter that is induced under low-oxygen or anaerobic conditions. In other embodiments, the gene encoding the arginine feedback resistant N-acetylglutamate synthetase is present in the bacterial chromosome and is operatively linked in the chromosome to the promoter that is induced under low-oxygen or anaerobic conditions.

Ammonia Transport

Ammonia transporters may further be expressed or modified in the genetically engineered bacteria of the invention in order to enhance ammonia transport into the cell. AmtB is a membrane transport protein that transports ammonia into bacterial cells. In some embodiments, the genetically engineered bacteria of the invention also comprise multiple copies of the native amtB gene. In some embodiments, the genetically engineered bacteria of the invention also comprise an amtB gene from a different bacterial species. In some embodiments, the genetically engineered bacteria of the invention comprise multiple copies of an amtB gene from a different bacterial species. In some embodiments, the native amtB gene in the genetically engineered bacteria of the invention is not modified. In some embodiments, the genetically engineered bacteria of the invention comprise an amtB gene that is controlled by its native promoter, an inducible promoter, or a promoter that is stronger than the native promoter, e.g., a GlnRS promoter, a P(Bla) promoter, or a constitutive promoter.

In some embodiments, the native amtB gene in the genetically engineered bacteria is not modified, and one or more additional copies of the native amtB gene are inserted into the genome under the control of the same inducible promoter that controls expression of $argA^{fbr}$, e.g., a FNR promoter, or a different inducible promoter than the one that controls expression of $argA^{fbr}$ or a constitutive promoter. In alternate embodiments, the native amtB gene is not modified, and a copy of a non-native amtB gene from a different bacterial species is inserted into the genome under the control of the same inducible promoter that controls expression of $argA^{fbr}$, e.g., a FNR promoter, or a different inducible promoter than the one that controls expression of $argA^{fbr}$ or a constitutive promoter.

In some embodiments, the native amtB gene in the genetically engineered bacteria is not modified, and one or more additional copies of the native amtB gene are present in the bacteria on a plasmid and under the control of the same inducible promoter that controls expression of $argA^{fbr}$, e.g., a FNR promoter, or a different inducible promoter than the one that controls expression of $argA^{fbr}$ or a constitutive promoter. In alternate embodiments, the native amtB gene is not modified, and a copy of a non-native amtB gene from a different bacterial species is present in the bacteria on a plasmid and under the control of the same inducible promoter that controls expression of $argA^{fbr}$, e.g., a FNR promoter, or a different inducible promoter than the one that controls expression of $argA^{fbr}$ or a constitutive promoter.

In some embodiments, the native amtB gene is mutagenized, the mutants exhibiting increased ammonia transport are selected, and the mutagenized amtB gene is isolated and inserted into the genetically engineered bacteria. In some embodiments, the native amtB gene is mutagenized, mutants exhibiting increased ammonia transport are selected, and those mutants are used to produce the bacteria of the invention. The ammonia transporter modifications described herein may be present on a plasmid or chromosome.

In some embodiments, the genetically engineered bacterium is E. coli Nissle, and the native amtB gene in E. coli Nissle is not modified; one or more additional copies the native E. coli Nissle amtB genes are inserted into the E. coli Nissle genome under the control of the same inducible promoter that controls expression of $argA^{fbr}$, e.g., a FNR promoter, or a different inducible promoter than the one that controls expression of $argA^{fbr}$ or a constitutive promoter. In an alternate embodiment, the native amtB gene in E. coli Nissle is not modified, and a copy of a non-native amtB gene from a different bacterium, e.g., Lactobacillus plantarum, is inserted into the E. coli Nissle genome under the control of the same inducible promoter that controls expression of $argA^{fbr}$, e.g., a FNR promoter, or a different inducible promoter than the one that controls expression of $argA^{fbr}$ or a constitutive promoter.

In some embodiments, the genetically engineered bacterium is E. coli Nissle, and the native amtB gene in E. coli Nissle is not modified; one or more additional copies the native E. coli Nissle amtB genes are present in the bacterium on a plasmid and under the control of the same inducible promoter that controls expression of $argA^{fbr}$, e.g., a FNR promoter, or a different inducible promoter than the one that controls expression of $argA^{fbr}$, or a constitutive promoter. In an alternate embodiment, the native amtB gene in E. coli Nissle is not modified, and a copy of a non-native amtB gene from a different bacterium, e.g., Lactobacillus plantarum, are present in the bacterium on a plasmid and under the control of the same inducible promoter that controls expression of $argA^{fbr}$, e.g., a FNR promoter, or a different inducible promoter than the one that controls expression of $argA^{fbr}$, or a constitutive promoter.

Pharmaceutical Compositions and Formulations

Pharmaceutical compositions comprising the genetically engineered bacteria described herein may be used to treat, manage, ameliorate, and/or prevent a disorder associated with hyperammonemia or symptom(s) associated with hyperammonemia. Pharmaceutical compositions comprising one or more genetically engineered bacteria, alone or in combination with prophylactic agents, therapeutic agents, and/or pharmaceutically acceptable carriers are provided.

In certain embodiments, the pharmaceutical composition comprises one species, strain, or subtype of bacteria that are engineered to comprise the genetic modifications described herein. In alternate embodiments, the pharmaceutical composition comprises two or more species, strains, and/or subtypes of bacteria that are each engineered to comprise the genetic modifications described herein.

The pharmaceutical compositions described herein may be formulated in a conventional manner using one or more physiologically acceptable carriers comprising excipients and auxiliaries, which facilitate processing of the active ingredients into compositions for pharmaceutical use. Methods of formulating pharmaceutical compositions are known in the art (see, e.g., "Remington's Pharmaceutical Sciences," Mack Publishing Co., Easton, Pa.). In some embodiments, the pharmaceutical compositions are subjected to tabletting, lyophilizing, direct compression, conventional mixing, dissolving, granulating, levigating, emulsifying, encapsulating, entrapping, or spray drying to form tablets, granulates, nanoparticles, nanocapsules, microcapsules, microtablets, pellets, or powders, which may be enterically coated or uncoated. Appropriate formulation depends on the route of administration.

The genetically engineered bacteria described herein may be formulated into pharmaceutical compositions in any suitable dosage form (e.g., liquids, capsules, sachet, hard capsules, soft capsules, tablets, enteric coated tablets, suspension powders, granules, or matrix sustained release formations for oral administration) and for any suitable type of administration (e.g., oral, topical, injectable, immediate-release, pulsatile-release, delayed-release, or sustained release). Suitable dosage amounts for the genetically engineered bacteria may range from about $10^5$ to $10^{12}$ bacteria, e.g., approximately $10^5$ bacteria, approximately $10^6$ bacteria, approximately $10^7$ bacteria, approximately $10^8$ bacteria, approximately $10^9$ bacteria, approximately $10^{10}$ bacteria, approximately $10^{11}$ bacteria, or approximately $10^{11}$ bacteria. The composition may be administered once or more daily, weekly, or monthly. The composition may be administered before, during, or following a meal. In one embodiment, the pharmaceutical composition is administered before the subject eats a meal. In one embodiment, the pharmaceutical composition is administered currently with a meal. In one embodiment, the pharmaceutical composition is administered after the subject eats a meal.

The composition may be administered once or more daily, weekly, or monthly. The genetically engineered bacteria may be formulated into pharmaceutical compositions comprising one or more pharmaceutically acceptable carriers, thickeners, diluents, buffers, buffering agents, surface active agents, neutral or cationic lipids, lipid complexes, liposomes, penetration enhancers, carrier compounds, and other pharmaceutically acceptable carriers or agents. For example, the pharmaceutical composition may include, but is not limited to, the addition of calcium bicarbonate, sodium bicarbonate, calcium phosphate, various sugars and types of starch, cellulose derivatives, gelatin, vegetable oils, polyethylene glycols, and surfactants, including, for example, polysorbate 20. In some embodiments, the genetically engineered bacteria of the invention may be formulated in a solution of sodium bicarbonate, e.g., 1 molar solution of sodium bicarbonate (to buffer an acidic cellular environment, such as the stomach, for example). The genetically engineered bacteria may be administered and formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

The genetically engineered bacteria disclosed herein may be administered topically and formulated in the form of an ointment, cream, transdermal patch, lotion, gel, shampoo, spray, aerosol, solution, emulsion, or other form well-known to one of skill in the art. See, e.g., "Remington's Pharmaceutical Sciences," Mack Publishing Co., Easton, Pa. In an embodiment, for non-sprayable topical dosage forms, viscous to semi-solid or solid forms comprising a carrier or one or more excipients compatible with topical application and having a dynamic viscosity greater than water are employed. Suitable formulations include, but are not limited to, solutions, suspensions, emulsions, creams, ointments, powders, liniments, salves, etc., which may be sterilized or mixed with auxiliary agents (e.g., preservatives, stabilizers, wetting agents, buffers, or salts) for influencing various properties, e.g., osmotic pressure. Other suitable topical dosage forms include sprayable aerosol preparations wherein the active ingredient in combination with a solid or liquid inert carrier, is packaged in a mixture with a pressurized volatile (e.g., a gaseous propellant, such as freon) or in a squeeze bottle. Moisturizers or humectants can also be added to pharmaceutical compositions and dosage forms. Examples of such additional ingredients are well known in the art. In one embodiment, the pharmaceutical composition comprising the recombinant bacteria of the invention may be formulated as a hygiene product. For example, the hygiene product may be an antibacterial formulation, or a fermentation product such as a fermentation broth. Hygiene products may be, for example, shampoos, conditioners, creams, pastes, lotions, and lip balms.

The genetically engineered bacteria disclosed herein may be administered orally and formulated as tablets, pills, dragees, capsules, liquids, gels, syrups, slurries, suspensions, etc. Pharmacological compositions for oral use can be made using a solid excipient, optionally grinding the resulting mixture, and processing the mixture of granules, after adding suitable auxiliaries if desired, to obtain tablets or dragee cores. Suitable excipients include, but are not limited to, fillers such as sugars, including lactose, sucrose, mannitol, or sorbitol; cellulose compositions such as maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP) or polyethylene glycol (PEG). Disintegrating agents may also be added, such as cross-linked polyvinylpyrrolidone, agar, alginic acid or a salt thereof such as sodium alginate.

Tablets or capsules can be prepared by conventional means with pharmaceutically acceptable excipients such as binding agents (e.g., pregelatinised maize starch, polyvinylpyrrolidone, hydroxypropyl methylcellulose, carboxymethylcellulose, polyethylene glycol, sucrose, glucose, sorbitol, starch, gum, kaolin, and tragacanth); fillers (e.g., lactose, microcrystalline cellulose, or calcium hydrogen phosphate); lubricants (e.g., calcium, aluminum, zinc, stearic acid, polyethylene glycol, sodium lauryl sulfate, starch, sodium benzoate, L-leucine, magnesium stearate, talc, or silica); disintegrants (e.g., starch, potato starch, sodium starch glycolate, sugars, cellulose derivatives, silica powders); or wetting agents (e.g., sodium lauryl sulphate). The tablets may be coated by methods well known in the art. A coating shell may be present, and common membranes include, but are not limited to, polylactide, polyglycolic acid, polyanhydride, other biodegradable polymers, alginate-polylysine-alginate (APA), alginate-polymethylene-co-guanidine-alginate (A-PMCG-A), hydroymethylacrylate-methyl methacrylate (HEMA-MMA), multilayered HEMA-MMA-MAA, polyacrylonitrilevinylchloride (PAN-PVC), acrylonitrile/sodium methallylsulfonate (AN-69), polyethylene glycol/poly pentamethylcyclopentasiloxane/polydimethylsiloxane (PEG/PD5/PDMS), poly N,N-dimethyl acrylamide (PDMAAm), siliceous encapsulates, cellulose sulphate/sodium alginate/ polymethylene-co-guanidine (CS/A/PMCG), cellulose acetate phthalate, calcium alginate, k-carrageenan-locust bean gum gel beads, gellan-xanthan beads, poly(lactide-co-glycolides), carrageenan, starch polyanhydrides, starch polymethacrylates, polyamino acids, and enteric coating polymers.

In some embodiments, the genetically engineered bacteria are enterically coated for release into the gut or a particular region of the gut, for example, the large intestine. The typical pH profile from the stomach to the colon is about 1-4 (stomach), 5.5-6 (duodenum), 7.3-8.0 (ileum), and 5.5-6.5 (colon). In some diseases, the pH profile may be modified. In some embodiments, the coating is degraded in specific pH environments in order to specify the site of release. In some embodiments, at least two coatings are used. In some embodiments, the outside coating and the inside coating are degraded at different pH levels.

Liquid preparations for oral administration may take the form of solutions, syrups, suspensions, or a dry product for constitution with water or other suitable vehicle before use. Such liquid preparations may be prepared by conventional means with pharmaceutically acceptable agents such as suspending agents (e.g., sorbitol syrup, cellulose derivatives, or hydrogenated edible fats); emulsifying agents (e.g., lecithin or acacia); non-aqueous vehicles (e.g., almond oil, oily esters, ethyl alcohol, or fractionated vegetable oils); and preservatives (e.g., methyl or propyl-p-hydroxybenzoates or sorbic acid). The preparations may also contain buffer salts, flavoring, coloring, and sweetening agents as appropriate. Preparations for oral administration may be suitably formulated for slow release, controlled release, or sustained release of the genetically engineered bacteria described herein.

In one embodiment, the genetically engineered bacteria of the disclosure may be formulated in a composition suitable for administration to pediatric subjects. As is well known in the art, children differ from adults in many aspects, including different rates of gastric emptying, pH, gastrointestinal permeability, etc. (Ivanovska et al., 2014). Moreover, pediatric formulation acceptability and preferences, such as route of administration and taste attributes, are critical for achieving acceptable pediatric compliance. Thus, in one embodiment, the composition suitable for administration to pediatric subjects may include easy-to-swallow or dissolvable dosage forms, or more palatable compositions, such as compositions with added flavors, sweeteners, or taste blockers. In one embodiment, a composition suitable for administration to pediatric subjects may also be suitable for administration to adults.

In one embodiment, the composition suitable for administration to pediatric subjects may include a solution, syrup, suspension, elixir, powder for reconstitution as suspension or solution, dispersible/effervescent tablet, chewable tablet, gummy candy, lollipop, freezer pop, troche, chewing gum, oral thin strip, orally disintegrating tablet, sachet, soft gelatin capsule, sprinkle oral powder, or granules. In one embodiment, the composition is a gummy candy, which is made from a gelatin base, giving the candy elasticity, desired chewy consistency, and longer shelf-life. In some embodiments, the gummy candy may also comprise sweeteners or flavors.

In one embodiment, the composition suitable for administration to pediatric subjects may include a flavor. As used herein, "flavor" is a substance (liquid or solid) that provides a distinct taste and aroma to the formulation. Flavors also help to improve the palatability of the formulation. Flavors include, but are not limited to, strawberry, vanilla, lemon, grape, bubble gum, and cherry.

In certain embodiments, the genetically engineered bacteria may be orally administered, for example, with an inert diluent or an assimilable edible carrier. The compound may also be enclosed in a hard or soft shell gelatin capsule, compressed into tablets, or incorporated directly into the subject's diet. For oral therapeutic administration, the compounds may be incorporated with excipients and used in the form of ingestible tablets, buccal tablets, troches, capsules, elixirs, suspensions, syrups, wafers, and the like. To administer a compound by other than parenteral administration, it may be necessary to coat the compound with, or co-administer the compound with, a material to prevent its inactivation.

In another embodiment, the pharmaceutical composition comprising the recombinant bacteria of the invention may be a comestible product, for example, a food product. In one embodiment, the food product is milk, concentrated milk, fermented milk (yogurt, sour milk, frozen yogurt, lactic acid bacteria-fermented beverages), milk powder, ice cream, cream cheeses, dry cheeses, soybean milk, fermented soybean milk, vegetable-fruit juices, fruit juices, sports drinks, confectionery, candies, infant foods (such as infant cakes), nutritional food products, animal feeds, or dietary supplements. In one embodiment, the food product is a fermented food, such as a fermented dairy product. In one embodiment, the fermented dairy product is yogurt. In another embodiment, the fermented dairy product is cheese, milk, cream, ice cream, milk shake, or kefir. In another embodiment, the recombinant bacteria of the invention are combined in a preparation containing other live bacterial cells intended to serve as probiotics. In another embodiment, the food product is a beverage. In one embodiment, the beverage is a fruit juice-based beverage or a beverage containing plant or herbal extracts. In another embodiment, the food product is a jelly or a pudding. Other food products suitable for administration of the recombinant bacteria of the invention are well known in the art. For example, see U.S. 2015/0359894 and US 2015/0238545, the entire contents of each of which are expressly incorporated herein by reference. In yet another embodiment, the pharmaceutical composition of the invention is injected into, sprayed onto, or sprinkled onto a food product, such as bread, yogurt, or cheese.

In some embodiments, the composition is formulated for intraintestinal administration, intrajejunal administration, intraduodenal administration, intrailleal administration, gastric shunt administration, or intracolic administration, via nanoparticles, nanocapsules, microcapsules, or microtablets, which are enterically coated or uncoated. The pharmaceutical compositions may also be formulated in rectal compositions such as suppositories or retention enemas, using, e.g., conventional suppository bases such as cocoa butter or other glycerides. The compositions may be suspensions, solutions, or emulsions in oily or aqueous vehicles, and may contain suspending, stabilizing and/or dispersing agents.

The genetically engineered bacteria described herein may be administered intranasally, formulated in an aerosol form, spray, mist, or in the form of drops, and conveniently delivered in the form of an aerosol spray presentation from pressurized packs or a nebuliser, with the use of a suitable propellant (e.g., dichlorodifluoromethane, trichlorofluoromethane, dichlorotetrafluoroethane, carbon dioxide or other suitable gas). Pressurized aerosol dosage units may be determined by providing a valve to deliver a metered amount. Capsules and cartridges (e.g., of gelatin) for use in an inhaler or insufflator may be formulated containing a powder mix of the compound and a suitable powder base such as lactose or starch.

The genetically engineered bacteria may be administered and formulated as depot preparations. Such long acting formulations may be administered by implantation or by injection, including intravenous injection, subcutaneous injection, local injection, direct injection, or infusion. For example, the compositions may be formulated with suitable polymeric or hydrophobic materials (e.g., as an emulsion in an acceptable oil) or ion exchange resins, or as sparingly soluble derivatives (e.g., as a sparingly soluble salt).

In some embodiments, disclosed herein are pharmaceutically acceptable compositions in single dosage forms. Single dosage forms may be in a liquid or a solid form. Single dosage forms may be administered directly to a patient without modification or may be diluted or reconstituted prior to administration. In certain embodiments, a single dosage form may be administered in bolus form, e.g., single injection, single oral dose, including an oral dose that comprises multiple tablets, capsule, pills, etc. In alternate embodiments, a single dosage form may be administered over a period of time, e.g., by infusion.

Single dosage forms of the pharmaceutical composition may be prepared by portioning the pharmaceutical composition into smaller aliquots, single dose containers, single dose liquid forms, or single dose solid forms, such as tablets, granulates, nanoparticles, nanocapsules, microcapsules, microtablets, pellets, or powders, which may be enterically coated or uncoated. A single dose in a solid form may be reconstituted by adding liquid, typically sterile water or saline solution, prior to administration to a patient.

In other embodiments, the composition can be delivered in a controlled release or sustained release system. In one embodiment, a pump may be used to achieve controlled or sustained release. In another embodiment, polymeric materials can be used to achieve controlled or sustained release of the therapies of the present disclosure (see, e.g., U.S. Pat. No. 5,989,463). Examples of polymers used in sustained release formulations include, but are not limited to, poly(2-hydroxy ethyl methacrylate), poly(methyl methacrylate), poly(acrylic acid), poly(ethylene-co-vinyl acetate), poly(methacrylic acid), polyglycolides (PLG), polyanhydrides, poly(N-vinyl pyrrolidone), poly(vinyl alcohol), polyacrylamide, poly(ethylene glycol), polylactides (PLA), poly(lactide-co-glycolides) (PLGA), and polyorthoesters. The polymer used in a sustained release formulation may be inert, free of leachable impurities, stable on storage, sterile, and biodegradable. In some embodiments, a controlled or sustained release system can be placed in proximity of the prophylactic or therapeutic target, thus requiring only a fraction of the systemic dose. Any suitable technique known to one of skill in the art may be used.

Dosage regimens may be adjusted to provide a therapeutic response. Dosing can depend on several factors, including severity and responsiveness of the disease, route of administration, time course of treatment (days to months to years), and time to amelioration of the disease. For example, a single bolus may be administered at one time, several divided doses may be administered over a predetermined period of time, or the dose may be reduced or increased as indicated by the therapeutic situation. The specification for the dosage is dictated by the unique characteristics of the active compound and the particular therapeutic effect to be achieved. Dosage values may vary with the type and severity of the condition to be alleviated. For any particular subject, specific dosage regimens may be adjusted over time according to the individual need and the professional judgment of the treating clinician. Toxicity and therapeutic efficacy of compounds provided herein can be determined by standard pharmaceutical procedures in cell culture or animal models. For example, $LD_{50}$, $ED_{50}$, $EC_{50}$, and $IC_{50}$ may be determined, and the dose ratio between toxic and therapeutic effects ($LD_{50}/ED_{50}$) may be calculated as the therapeutic index. Compositions that exhibit toxic side effects may be used, with careful modifications to minimize potential damage to reduce side effects. Dosing may be estimated initially from cell culture assays and animal models. The data obtained from in vitro and in vivo assays and animal studies can be used in formulating a range of dosage for use in humans.

The ingredients are supplied either separately or mixed together in unit dosage form, for example, as a dry lyophilized powder or water-free concentrate in a hermetically sealed container such as an ampoule or sachet indicating the quantity of active agent. If the mode of administration is by injection, an ampoule of sterile water for injection or saline can be provided so that the ingredients may be mixed prior to administration.

The pharmaceutical compositions may be packaged in a hermetically sealed container such as an ampoule or sachet indicating the quantity of the agent. In one embodiment, one or more of the pharmaceutical compositions is supplied as a dry sterilized lyophilized powder or water-free concentrate in a hermetically sealed container and can be reconstituted (e.g., with water or saline) to the appropriate concentration for administration to a subject. In an embodiment, one or more of the prophylactic or therapeutic agents or pharmaceutical compositions is supplied as a dry sterile lyophilized powder in a hermetically sealed container stored between 2° C. and 8° C. and administered within 1 hour, within 3 hours, within 5 hours, within 6 hours, within 12 hours, within 24 hours, within 48 hours, within 72 hours, or within one week after being reconstituted. Cryoprotectants can be included for a lyophilized dosage form, principally 0-10% sucrose (optimally 0.5-1.0%). Other suitable cryoprotectants include trehalose and lactose. Other suitable bulking agents include glycine and arginine, either of which can be included at a concentration of 0-0.05%, and polysorbate-80 (optimally included at a concentration of 0.005-0.01%). Additional surfactants include but are not limited to polysorbate 20 and BRIJ surfactants. The pharmaceutical composition may be prepared as an injectable solution and can further comprise an agent useful as an adjuvant, such as those used to increase absorption or dispersion, e.g., hyaluronidase.

Methods of Treatment

Another aspect of the invention provides methods of treating a disease or disorder associated with hyperammonemia. In some embodiments, the invention provides methods for reducing, ameliorating, or eliminating one or more symptom(s) associated with these diseases or disorders. In some embodiments, the disorder is a urea cycle disorder such as argininosuccinic aciduria, arginase deficiency, carbamoylphosphate synthetase deficiency, citrullinemia, N-acetylglutamate synthetase deficiency, and ornithine transcarbamylase deficiency. In alternate embodiments, the disorder is a liver disorder such as hepatic encephalopathy, acute liver failure, or chronic liver failure; organic acid disorders; isovaleric aciduria; 3-methylcrotonylglycinuria; methylmalonic acidemia; propionic aciduria; fatty acid oxidation defects; carnitine cycle defects; carnitine deficiency; β-oxidation deficiency; lysinuric protein intolerance; pyrroline-5-carboxylate synthetase deficiency; pyruvate carboxylase deficiency; ornithine aminotransferase deficiency; carbonic anhydrase deficiency; hyperinsulinism-hyperammonemia syndrome; mitochondrial disorders; valproate therapy; asparaginase therapy; total parenteral nutrition; cystoscopy with glycine-containing solutions; post-lung/bone marrow transplantation; portosystemic shunting; urinary tract infections; ureter dilation; multiple myeloma; chemotherapy; infection; neurogenic bladder; or intestinal bacterial overgrowth. In some embodiments, the symptom(s) associated thereof include, but are not limited to, seizures, ataxia, stroke-like lesions, coma, psychosis, vision loss, acute encephalopathy, cerebral edema, as well as vomiting, respiratory alkalosis, and hypothermia.

The method may comprise preparing a pharmaceutical composition with at least one genetically engineered species, strain, or subtype of bacteria described herein, and administering the pharmaceutical composition to a subject in a therapeutically effective amount. In some embodiments, the genetically engineered bacteria of the invention are administered orally, e.g., in a liquid suspension. In some embodiments, the genetically engineered bacteria of the invention are lyophilized in a gel cap and administered orally. In some embodiments, the genetically engineered bacteria of the invention are administered via a feeding tube or gastric shunt. In some embodiments, the genetically engineered bacteria of the invention are administered rectally, e.g., by enema. In some embodiments, the genetically engineered bacteria of the invention are administered topically, intraintestinally, intrajejunally, intraduodenally, intraileally, and/or intracolically.

In certain embodiments, administering the pharmaceutical composition to the subject reduces ammonia concentrations in a subject. In some embodiments, the methods of the present disclosure may reduce the ammonia concentration in a subject by at least about 10%, 20%, 25%, 30%, 40%, 50%, 60%, 70%, 75%, 80%, 85%, 90%, 95%, or more as compared to levels in an untreated or control subject. In some embodiments, reduction is measured by comparing the ammonia concentration in a subject before and after administration of the pharmaceutical composition. In some embodiments, the method of treating or ameliorating hyperammonemia allows one or more symptoms of the condition or disorder to improve by at least about 10%, 20%, 30%, 40%, 50%, 60%, 70%, 80%, 90%, 95%, or more.

Before, during, and after the administration of the pharmaceutical composition, ammonia concentrations in the subject may be measured in a biological sample, such as blood, serum, plasma, urine, fecal matter, peritoneal fluid, intestinal mucosal scrapings, a sample collected from a tissue, and/or a sample collected from the contents of one or more of the following: the stomach, duodenum, jejunum, ileum, cecum, colon, rectum, and anal canal. In some embodiments, the methods may include administration of the compositions of the invention to reduce ammonia concentrations in a subject to undetectable levels, or to less than about 1%, 2%, 5%, 10%, 20%, 25%, 30%, 40%, 50%, 60%, 70%, 75%, or 80% of the subject's ammonia concentrations prior to treatment.

Figure 34:
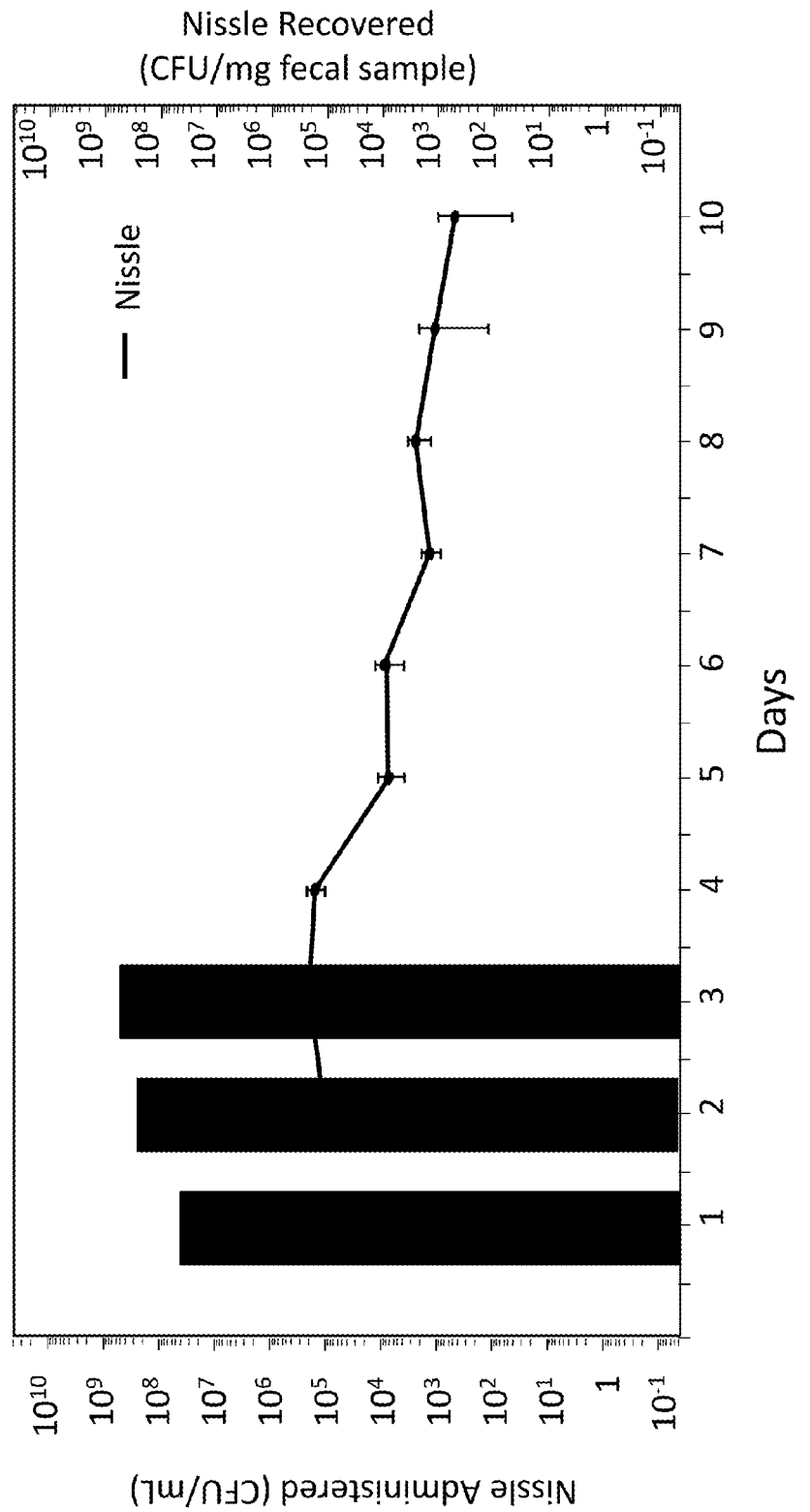
FIG. 34 depicts a graph of Nissle residence in vivo. Streptomycin-resistant Nissle was administered to mice via oral gavage without antibiotic pre-treatment. Fecal pellets from six total mice were monitored post-administration to determine the amount of administered Nissle still residing within the mouse gastrointestinal tract. The bars represent the number of bacteria administered to the mice. The line represents the number of Nissle recovered from the fecal samples each day for 10 consecutive days.

In certain embodiments, the genetically engineered bacteria comprising the mutant arginine regulon is *E. coli* Nissle. The genetically engineered bacteria may be destroyed, e.g., by defense factors in the gut or blood serum (Sonnenborn et al., 2009), or by activation of a kill switch, several hours or days after administration. Thus, the pharmaceutical composition comprising the mutant arginine regulon may be re-administered at a therapeutically effective dose and frequency. Length of Nissle residence in vivo in mice is shown in FIGS. 34 and 35. In alternate embodiments, the genetically engineered bacteria are not destroyed within hours or days after administration and may propagate and colonize the gut.

The pharmaceutical composition may be administered alone or in combination with one or more additional therapeutic agents, including but not limited to, sodium phenylbutyrate, sodium benzoate, and glycerol phenylbutyrate. An important consideration in the selection of the one or more additional therapeutic agents is that the agent(s) should be compatible with the genetically engineered bacteria of the invention, e.g., the agent(s) must not kill the bacteria.

In one embodiment, the genetically engineered bacteria are administered for prevention, treatment or management of HE. In some embodiments, the genetically engineered bacteria are administered in combination with another therapeutic approach to prevent HE reoccurrence. In one embodiment, the genetically engineered bacteria are administered in combination with branched-chain amino acid supplementation. In one embodiment, the genetically engineered bacteria are administered in combination with acetyl-l-carnitine and/or sodium benzoate and/or zinc and/or acarbose and/or ornithine aspartate. In one embodiment, the genetically engineered bacteria are administered in combination with non-absorbable disaccharides, which are commonly applied to both treat and prevent HE in patients. In one embodiment, the genetically engineered bacteria are administered in combination with lactulose and/or lactitol.

In one embodiment, the genetically engineered bacteria are administered in combination with one or more antibiotics, for example for the treatment of HE. Examples of such antibiotics include, but are not limited to, non-absorbable antibiotics, such as aminoglicosides, e.g., neomycin and/or paramomycin. In one embodiment, the antibiotic is rifamycin. In one embodiment, the antibiotic is a rifamycin derivative, e.g., a synthetic derivative, including but not limited to, rifaximin.

Rifaximin has been shown to significantly reduce the risk of an episode of hepatic encephalopathy, as compared with placebo, over a 6-month period (Bass et a., Rifaximin Treatment in Hepatic Encephalopathy; N Engl J Med 2010; 362:1071-1081). Rifaximin is a semi-synthetic derivative of rifampin and acts by binding to the beta-subunit of bacterial DNA-dependent RNA polymerase, and thereby blocking transcription. As a result, bacterial protein synthesis and growth is inhibited.

Rifaximin has been shown to be active against *E. coli* both in vitro and in clinical studies. It therefore is understood that, for a combination treatment with rifaximin to be effective, the genetically engineered bacteria must further comprise a rifaximin resistance.

Resistance to rifaximin is caused primarily by mutations in the rpoB gene. This changes the binding site on DNA dependent RNA polymerase and decreases rifaximin binding affinity, thereby reducing efficacy. In one embodiment, the rifaximin resistance is a mutation in the rpoB gene. Non-limiting examples of such mutations are described in e.g., Rodriguez-Verdugo, Evolution of *Escherichia coli* rifampicin resistance in an antibiotic-free environment during thermal stress. BMC Evol Biol. 2013 Feb. 22; 13:50. Of note, mutations in the same three codons of the rpoB consensus sequence occur repeatedly in unrelated rifaximin-resistant clinical isolates of several different bacterial species (as reviewed in Goldstein, Resistance to rifampicin: a review; The Journal of Antibiotics (2014), 1-6, the contents of which is herein incorporated by reference in its entirety. In some embodiments, the genetically engineered bacteria comprise a known rifaximin resistance mutation, e.g., in the rpoB gene. In other embodiments, a screen can be employed, exposing the genetically engineered bacteria to increasing amounts of rifaximin, to identify a useful mutation which confers rifaximin resistance.

In some embodiments, the pharmaceutical composition is administered with food. In alternate embodiments, the pharmaceutical composition is administered before or after eating food. The pharmaceutical composition may be administered in combination with one or more dietary modifications, e.g., low-protein diet and amino acid supplementation. The dosage of the pharmaceutical composition and the frequency of administration may be selected based on the severity of the symptoms and the progression of the disorder. The appropriate therapeutically effective dose and/or frequency of administration can be selected by a treating clinician.

Table 20 shows non-limiting examples of target degradation rates, based on levels of phenylalanine on average in) in hyperammonemic patients (UCD<HE).

TABLE 20

Target Ammonia Degradation/Arginine Production Rates

| Parameter | Value |
| --- | --- |
| Maximum burden of $NH_4^+$ (in blood) in hyperammonemic patients (UCD < HE) | 825 μmols total excess $NH_4^+$ Total blood ammonia levels: ~1000 μmols; 5 L blood (adult) |
| Arginine production target: $NH_4^+$ burden | 275 μmol/day (1 Arg = 3 $NH_4^+$) |
| Target arginine production rate: $NH_4^+$ burden | 275 μmol/day/$10^{11}$ bacteria |
| Lab assay target: $NH_4^+$ burden | 0.11 μmol/hr/$10^9$ bacteria |
| Current arginine production rate | 1.25 μmol/hr/$10^9$ bacteria |
| Maximum flux of $NH_4^+$ (in blood from colon); in healthy individuals > UCD | 800 μmols/hr |
| Arginine production target: $NH_4^+$ flux | 267 μmols/hr |
| Target arginine production rate: $NH_4^+$ flux | 267 μmols/hr/$10^{11}$ bacteria |
| Lab assay target: $NH_4^+$ flux | 2.67 mol/hr/$10^9$ bacteria |

Treatment In Vivo

The genetically engineered bacteria of the invention may be evaluated in vivo, e.g., in an animal model. Any suitable animal model of a disease or condition associated with hyperammonemia may be used (see, e.g., Deignan et al., 2008; Nicaise et al., 2008), for example, a mouse model of acute liver failure and hyperammonemia. This acute liver failure and hyperammonemia may be induced by treatment with thiol acetamide (TAA) (Basile et al., 1990; Nicaise et al., 2008). Alternatively, liver damage may be modeled using physical bile duct ligation (Rivera-Mancía et al., 2012). Hyperammonemia may also be induced by oral supplementation with ammonium acetate and/or magnesium chloride (Azorín et al., 1989; Rivera-Mancía et al., 2012).

Additionally, CCl4 is often used to induce hepatic fibrosis and cirrhosis in animals (Nhung et al., Establishment of a standardized mouse model of hepatic fibrosis for biomedical research; Biomedical Research and Therapy 2014, 1(2):43-49).

The genetically engineered bacteria of the invention may be administered to the animal, e.g., by oral gavage, and treatment efficacy determined, e.g., by measuring ammonia in blood samples and/or arginine, citrulline, or other byproducts in fecal samples.

Full citations for the references cited throughout the specification include:

1. Alifano et al. Histidine biosynthetic pathway and genes: structure, regulation, and evolution. Microbiol Rev. 1996 March; 60(1):44-69. PMID: 8852895.
2. Altenhoefer et al. The probiotic *Escherichia coli* strain Nissle 1917 interferes with invasion of human intestinal epithelial cells by different enteroinvasive bacterial pathogens. FEMS Immunol Med Microbiol. 2004 Apr. 9; 40(3):223-229. PMID: 15039098.
3. Andersen et al. Uracil uptake in *Escherichia coli* K-12: isolation of uraA mutants and cloning of the gene. J Bacteriol. 1995 April; 177(8):2008-2013. PMID: 7721693.
4. Arthur et al. Intestinal inflammation targets cancer-inducing activity of the microbiota. Science. 2012 Oct. 5; 338(6103):120-123. PMID: 22903521.
5. Aoyagi et al. Gastrointestinal urease in man. Activity of mucosal urease. Gut. 1966 December; 7(6):631-635. PMID: 5957514.
6. Arai et al. Expression of the nir and nor genes for denitrification of *Pseudomonas aeruginosa* requires a novel CRP/FNR-related transcriptional regulator, DNR, in addition to ANR. FEBS Lett. 1995 Aug. 28; 371(1):73-76. PMID: 7664887.
7. Aschner et al. Manganese uptake and distribution in the central nervous system (CNS). Neurotoxicology. 1999 April-June; 20(2-3):173-180. PMID: 10385881.
8. Azorin et al. A simple animal model of hyperammonemia. Hepatology. 1989 September; 10(3):311-314. PMID: 2759549.
9. Bansky et al. Reversal of hepatic coma by benzodiazepene antagonists (Rol5-1788). Lancet. 1985; 1:1324-1325.
10. Basile et al. Brain concentrations of benzodiazepines are elevated in an animal model of hepatic encephalopathy. Proc Natl Acad Sci USA. 1990 July; 87(14):5263-5267. PMID: 1973539.
11. Bearden S W, Perry R D. The Yfe system of *Yersinia pestis* transports iron and manganese and is required for full virulence of plague. Mol Microbiol. 1999 April; 32(2):403-414. PMID: 10231495.
12. Berk D P, Chalmers T. Deafness complicating antibiotic therapy of hepatic encephalopathy. Ann Intern Med. 1970 September; 73(3):393-396. PMID: 5455989.
13. Blanc et al. Lactitol or lactulose in the treatment of chronic hepatic encephalopathy: results of a meta-analysis. Hepatology. 1992 February; 15(2):222-228. PMID: 1531204.
14. Caldara et al. The arginine regulon of *Escherichia coli*: whole-system transcriptome analysis discovers new genes and provides an integrated view of arginine regulation. Microbiology. 2006 November; 152(Pt 11):3343-3354. PMID: 17074904.
15. Caldara et al. Arginine biosynthesis in *Escherichia coli*: experimental perturbation and mathematical modeling. J Biol Chem. 2008 Mar. 7; 283(10):6347-6358. PMID: 18165237.
16. Caldovic et al. N-acetylglutamate synthase: structure, function and defects. Mol Genet Metab. 2010; 100 Suppl 1:S13-S19. Review. PMID: 20303810.
17. Callura et al. Tracking, tuning, and terminating microbial physiology using synthetic riboregulators. Proc Natl Acad Sci USA. 2010 Sep. 7; 107(36):15898-15903. PMID: 20713708.
18. Cash et al. Current concepts in the assessment and treatment of hepatic encephalopathy. QJM. 2010 January; 103(1):9-16. PMID: 19903725.
19. Castiglione et al. The transcription factor DNR from *Pseudomonas aeruginosa* specifically requires nitric oxide and haem for the activation of a target promoter in 19. *Escherichia coli*. Microbiology. 2009 September; 155(Pt 9):2838-2844. PMID: 19477902.
20. Cellier et al. Resistance to intracellular infections: comparative genomic analysis of Nramp. Trends Genet. 1996 June; 12(6):201-204. PMID: 8928221.
21. Charlier et al. Arginine regulon of *Escherichia coli* K-12. A study of repressor-operator interactions and of in vitro binding affinities versus in vivo repression. J Mol Biol. 1992 Jul. 20; 226(2):367-386. PMID: 1640456.
22. Chiang et al. Dysregulation of C/EBPalpha by mutant Huntingting causes the urea cycle deficiency in Huntington's disease. Hum Mol Genet. 2007 Mar. 1; 16(5):483-498. PMID: 17213233.
23. Collinson et al. Channel crossing: how are proteins shipped across the bacterial plasma membrane? Philos Trans R Soc Lond B Biol Sci. 2015; 370:20150025. PMID: 26370937.
24. Córdoba J, Minguez B. Hepatic Encephalopathy. Semin Liver Dis. 2008; 28(1):70-80. PMID: 18293278.
25. Costa et al. Secretion systems in Gram-negative bacteria: structural and mechanistic insights. Nat Rev Microbiol. 2015; 13(6):343-359. PMID: 25978706.
26. Crabeel et al. Characterization of the *Saccharomyces cerevisiae* ARG7 gene encoding ornithine acetyltransferase, an enzyme also endowed with acetylglutamate synthase activity. Eur J Biochem. 1997 Dec. 1; 250(2): 232-241. PMID: 9428669.
27. Cuevas-Ramos et al. *Escherichia coli* induces DNA damage in vivo and triggers genomic instability in mammalian cells. Proc Natl Acad Sci USA. 2010 Jun. 22; 107(25):11537-42. PMID: 20534522.
28. Cunin et al. Molecular basis for modulated regulation of gene expression in the arginine regulon of *Escherichia coli* K-12. Nucleic Acids Res. 1983 Aug. 11; 11(15):5007-5019. PMID: 6348703.
29. Cunin et al. Biosynthesis and metabolism of arginine in bacteria. Microbiol Rev. 1986 September; 50(3):314-52. Review. Erratum in: Microbiol Rev. 1987 March; 51(1): 178. PMID: 3534538.
30. Danino et al. Programmable probiotics for detection of cancer in urine. Sci Transl Med. 2015 May 27; 7(289): 289ra84. PMID: 26019220.
31. Deignan et al. Contrasting features of urea cycle disorders in human patients. Mol Genet Metab. 2008 January; 93(1):7-14. PMID: 17933574.
32. Deutscher. The mechanisms of carbon catabolite repression in bacteria. Curr Opin Microbiol. 2008 April; 11(2): 87-93. PMID: 18359269.
33. Diaz et al. Ammonia control and neurocognitive outcome among urea cycle disorder patients treated with glycerol phenylbutyrate. Hepatology. 2013 June; 57(6): 2171-9. PMID: 22961727.
34. Dinleyici et al. *Saccharomyces boulardii* CNCM I-745 in different clinical conditions. Expert Opin Biol Ther. 2014 November; 14(11): 1593-609. PMID: 24995675.
35. Doolittle. A new allele of the sparse fur gene in the mouse. J Hered. 1974 May-June; 65(3):194-5. PMID: 4603259.
36. Eckhardt et al. Isolation and characterization of mutants with a feedback resistant N-acetylglutamate synthase in *Escherichia coli* K 12. Mol Gen Genet. 1975 Jun. 19; 138(3):225-32. PMID: 1102931.
37. Eiglmeier et al. Molecular genetic analysis of FNR-dependent promoters. Mol Microbiol. 1989 July; 3(7): 869-78. PMID: 2677602.
38. Fraga et al. (2008). Real-Time PCR. Current Protocols Essential Laboratory Techniques (10.3.1-10.3.33). John Wiley & Sons, Inc.
39. Galimand et al. Positive FNR-like control of anaerobic arginine degradation and nitrate respiration in *Pseudomonas aeruginosa*. J Bacteriol. 1991 March; 173(5):1598-606. PMID: 1900277.
40. Gamper et al. Anaerobic regulation of transcription initiation in the arcDABC operon of *Pseudomonas aeruginosa*. J Bacteriol. 1991 August; 173(15):4742-50. PMID: 1906871.
41. Gardner et al. Construction of a genetic toggle switch in *Escherichia coli*. Nature. 2000; 403:339-42. PMID: 10659857.
42. Görke B et al. Carbon catabolite repression in bacteria: many ways to make the most out of nutrients. Nat Rev Microbiol. 2008 August; 6(8):613-24. PMID: 18628769.
43. Häberle et al. Suggested guidelines for the diagnosis and management of urea cycle disorders. Orphanet J Rare Dis. 2012 May 29; 7:32. Review. PMID: 22642880.
44. Häberle J. Clinical and biochemical aspects of primary and secondary hyperammonemic disorders. Arch Biochem Biophys. 2013 Aug. 15; 536(2):101-8. Review. PMID: 23628343.
45. Hasegawa et al. Activation of a consensus FNR-dependent promoter by DNR of *Pseudomonas aeruginosa* in response to nitrite. FEMS Microbiol Lett. 1998 Sep. 15; 166(2):213-7. PMID: 9770276.
46. Hodges et al. The spfash mouse: a missense mutation in the ornithine transcarbamylase gene also causes aberrant mRNA splicing. Proc Natl Acad Sci USA. 1989 June; 86(11):4142-6. PMID: 2471197.
47. Hoeren et al. Sequence and expression of the gene encoding the respiratory nitrous-oxide reductase from *Paracoccus denitrificans*. Eur J Biochem. 1993 Nov. 15; 218(1):49-57. PMID: 8243476.
48. Hoffmann et al. Defects in amino acid catabolism and the urea cycle. Handb Clin Neurol. 2013; 113:1755-73. Review. PMID: 23622399.
49. Hosseini et al. Proprionate as a health-promoting microbial metabolite in the human gut. Nutr Rev. 2011 May; 69(5):245-58. PMID: 21521227.
50. Isabella et al. Deep sequencing-based analysis of the anaerobic stimulon in *Neisseria gonorrhoeae*. BMC Genomics. 2011 Jan. 20; 12:51. PMID: 21251255.
51. Konieczna et al. Bacterial urease and its role in long-lasting human diseases. Curr Protein Pept Sci. 2012 December; 13(8):789-806. Review. PMID: 23305365.
52. Lazier et al. Hyperammonemic encephalopathy in an adenocarcinoma patient managed with carglumic acid. Curr Oncol. 2014 October; 21(5):e736-9. PMID: 25302046.
53. Leonard (2006). Disorders of the urea cycle and related enzymes. *Inborn Metabolic Diseases*, 4$^{th}$ ed (pp. 263-272). Springer Medizin Verlag Heidelberg.
54. Lim et al. Nucleotide sequence of the argR gene of *Escherichia coli* K-12 and isolation of its product, the arginine repressor. Proc Natl Acad Sci USA. 1987 October; 84(19):6697-701. PMID: 3116542.
55. Makarova et al. Conservation of the binding site for the arginine repressor in all bacterial lineages. Genome Biol. 2001; 2(4). PMID: 11305941.
56. Maas et al. Studies on the mechanism of repression of arginine biosynthesis in *Escherichia coli*. Dominance of repressibility in diploids. J Mol Biol. 1964 March; 8:365-70. PMID: 14168690.

57. Maas. The arginine repressor of *Escherichia coli*. Microbiol Rev. 1994 December; 58(4):631-40. PMID: 7854250.
58. Meng et al. Nucleotide sequence of the *Escherichia coli* cad operon: a system for neutralization of low extracellular pH. J Bacteriol. 1992 April; 174(8):2659-69. PMID: 1556085.
59. Moore et al. Regulation of FNR dimerization by subunit charge repulsion. J Biol Chem. 2006 Nov. 3; 281(44): 33268-75. PMID: 16959764.
60. Mountain et al. Cloning of a *Bacillus subtilis* restriction fragment complementing auxotrophic mutants of eight *Escherichia coli* genes of arginine biosynthesis. Mol Gen Genet. 1984; 197(1):82-9. PMID: 6096675.
61. Nagamani et al. Optimizing therapy for argininosuccinic aciduria. Mol Genet Metab. 2012 September; 107(1-2): 10-4. Review. PMID: 22841516.
62. Nicaise et al. Control of acute, chronic, and constitutive hyperammonemia by wild-type and genetically engineered *Lactobacillus plantarum* in rodents. Hepatology. 2008 October; 48(4):1184-92. PMID: 18697211.
63. Nicoloff et al. Two arginine repressors regulate arginine biosynthesis in *Lactobacillus plantarum*. J Bacteriol. 2004 September; 186(18):6059-69. PMID: 15342575.
64. Nougayrede et al. *Escherichia coli* induces DNA double-strand breaks in eukaryotic cells. Science. 2006 Aug. 11; 313(5788):848-51. PMID: 16902142.
65. Olier et al. Genotoxicity of *Escherichia coli* Nissle 1917 strain cannot be dissociated from its probiotic activity. Gut Microbes. 2012 November-December; 3(6):501-9. PMID: 22895085.
66. Pham et al. Multiple myeloma-induced hyperammonemic encephalopathy: an entity associated with high in-patient mortality. Leuk Res. 2013 October; 37(10):1229-32. Review. PMID: 23932549.
67. Rajagopal et al. Use of inducible feedback-resistant N-acetylglutamate synthetase (argA) genes for enhanced arginine biosynthesis by genetically engineered *Escherichia coli* K-12 strains. Appl Environ Microbiol. 1998 May; 64(5):1805-11. PMID: 9572954.
68. Ray et al. The effects of mutation of the anr gene on the aerobic respiratory chain of *Pseudomonas aeruginosa*. FEMS Microbiol Lett. 1997 Nov. 15; 156(2):227-32. PMID: 9513270.
69. Reister et al. Complete genome sequence of the Gram-negative probiotic *Escherichia coli* strain Nissle 1917. J Biotechnol. 2014 Oct. 10; 187:106-7. PMID: 25093936.
70. Rembacken et al. Non-pathogenic *Escherichia coli* versus mesalazine for the treatment of ulcerative colitis: a randomised trial. Lancet. 1999 Aug. 21; 354(9179):635-9. PMID: 10466665.
71. Remington's Pharmaceutical Sciences, 22$^{nd}$ ed. Mack Publishing Co.
72. Salmon et al. Global gene expression profiling in *Escherichia coli* K12. The effects of oxygen availability and FNR. J Biol Chem. 2003 Aug. 8; 278(32):29837-55. PMID: 12754220.
73. Sat et al. The *Escherichia coli* mazEF suicide module mediates thymineless death. J Bacteriol. 2003 March; 185(6):1803-7. PMID: 12618443.
74. Sawers. Identification and molecular characterization of a transcriptional regulator from *Pseudomonas aeruginosa* PAO1 exhibiting structural and functional similarity to the FNR protein of *Escherichia coli*. Mol Microbiol. 1991 June; 5(6):1469-81. PMID: 1787797.
75. Schneider et al. Arginine catabolism and the arginine succinyltransferase pathway in *Escherichia coli*. J Bacteriol. 1998 August; 180(16): 4278-86. PMID: 9696779.
76. Schultz. Clinical use of *E. coli* Nissle 1917 in inflammatory bowel disease. Inflamm Bowel Dis. 2008 July; 14(7):1012-8. Review. PMID: 18240278.
77. Sonnenborn et al. The non-pathogenic *Escherichia coli* strain Nissle 1917-features of a versatile probiotic. Microbial Ecology in Health and Disease. 2009; 21:122-58.
78. Suiter et al. Fitness consequences of a regulatory polymorphism in a seasonal environment. Proc Natl Acad Sci USA. 2003 Oct. 28; 100(22):12782-6. PMID: 14555766.
79. Summerskill. On the origin and transfer of ammonia in the human gastrointestinal tract. Medicine (Baltimore). 1966 November; 45(6):491-6. PMID: 5925900.
80. Szwajkajzer et al. Quantitative analysis of DNA binding by the *Escherichia coli* arginine repressor. J Mol Biol. 2001 Oct. 5; 312(5):949-62. PMID: 11580241.
81. Tian et al. Binding of the arginine repressor of *Escherichia coli* K12 to its operator sites. J Mol Biol. 1992 Jul. 20; 226(2):387-97. PMID: 1640457.
82. Tian et al. Explanation for different types of regulation of arginine biosynthesis in *Escherichia coli* B and *Escherichia coli* K12 caused by a difference between their arginine repressors. J Mol Biol. 1994 Jan. 7; 235(1):221-30. PMID: 8289243.
83. Torres-Vega et al. Delivery of glutamine synthetase gene by baculovirus vectors: a proof of concept for the treatment of acute hyperammonemia. Gene Ther. 2014 Oct. 23; 22(1):58-64. PMID: 25338921.
84. Trunk et al. Anaerobic adaptation in *Pseudomonas aeruginosa*: definition of the Anr and Dnr regulons. Environ Microbiol. 2010 June; 12(6):1719-33. PMID: 20553552.
85. Tuchman et al. Enhanced production of arginine and urea by genetically engineered *Escherichia coli* K-12 strains. Appl Environ Microbiol. 1997 January; 63(1):33-8. PMID: 8979336.
86. Ukena et al. Probiotic *Escherichia coli* Nissle 1917 inhibits leaky gut by enhancing mucosal integrity. PLoS One. 2007 Dec. 12; 2(12):e1308. PMID: 18074031.
87. Unden et al. Alternative respiratory pathways of *Escherichia coli*: energetics and transcriptional regulation in response to electron acceptors. Biochim Biophys Acta. 1997 Jul. 4; 1320(3):217-34. Review. PMID: 9230919.
88. Vander Wauven et al. *Pseudomonas aeruginosa* mutants affected in anaerobic growth on arginine: evidence for a four-gene cluster encoding the arginine deiminase pathway. J Bacteriol. 1984 December; 160(3):928-34. PMID: 6438064.
89. Walker. Severe hyperammonaemia in adults not explained by liver disease. Ann Clin Biochem. 2012 May; 49(Pt 3):214-28. Review. PMID: 22349554.
90. Winteler et al. The homologous regulators ANR of *Pseudomonas aeruginosa* and FNR of *Escherichia coli* have overlapping but distinct specificities for anaerobically inducible promoters. Microbiology. 1996 March; 142 (Pt 3):685-93. PMID: 8868444.
91. Wu et al. Direct regulation of the natural competence regulator gene tfoX by cyclic AMP (cAMP) and cAMP receptor protein in Vibrios. Sci Rep. 2015 Oct. 7; 5:14921. PMID: 26442598.
92. Zimmermann et al. Anaerobic growth and cyanide synthesis of *Pseudomonas aeruginosa* depend on anr, a regulatory gene homologous with fnr of *Escherichia coli*. Mol Microbiol. 1991 June; 5(6):1483-90. PMID: 1787798.
93. Wright O, Delmans M, Stan G B, Ellis T. GeneGuard: A modular plasmid system designed for biosafety. ACS Synth Biol. 2015 Mar. 20; 4(3):307-16. PMID: 24847673.

94. Liu Y, White R H, Whitman W B. Methanococci use the diaminopimelate aminotransferase (DapL) pathway for lysine biosynthesis. J Bacteriol. 2010 July; 192(13):3304-10. PMID: 20418392.
95. Dogovski et al. (2012) Enzymology of Bacterial Lysine Biosynthesis, Biochemistry, Prof. Deniz Ekinci (Ed.), ISBN: 978-953-51-0076-8, InTech, Available from:
96. http://www.intechopen.com/books/biochemistry/enzymology-of-bacterial-lysine-biosynthesis.
97. Feng et al. Role of phosphorylated metabolic intermediates in the regulation of glutamine synthetase synthesis in Escherichia coli. J Bacteriol. 1992 October; 174(19): 6061-70. PMID: 1356964.
98. Lodeiro et al. Robustness in Escherichia coli glutamate and glutamine synthesis studied by a kinetic model. J Biol Phys. 2008 April; 34(1-2):91-106. PMID: 19669495.
99. Reboul et al. Structural and dynamic requirements for optimal activity of the essential bacterial enzyme dihydrodipicolinate synthase. PLoS Comput Biol. 2012; 8(6): e1002537. PMID: 22685390.
100. Saint-Girons et al. Structure and autoregulation of the metJ regulatory gene in Escherichia coli. J Biol Chem. 1984 Nov. 25; 259(22):14282-5. PMID: 6094549.
101. Shoeman et al. Regulation of methionine synthesis in Escherichia coli: Effect of metJ gene product and S-adenosylmethionine on the expression of the metF gene. Proc Natl Acad Sci USA. 1985 June; 82(11):3601-5. PMID: 16593564.
102. van Heeswijk et al. Nitrogen assimilation in Escherichia coli: putting molecular data into a systems perspective. Microbiol Mol Biol Rev. 2013 December; 77(4): 628-95. PMID: 24296575.

EXAMPLES

The following examples provide illustrative embodiments of the disclosure. One of ordinary skill in the art will recognize the numerous modifications and variations that may be performed without altering the spirit or scope of the disclosure. Such modifications and variations are encompassed within the scope of the disclosure. The Examples do not in any way limit the disclosure.

Arginine Repressor Binding Sites (ARG Boxes)

Example 1

ARG Box Mutations

The wild-type genomic sequences comprising ArgR binding sites for each arginine biosynthesis operon in E. coli Nissle is shown in Table 3. Modifications to those sequences are designed according to the following parameters. For each wild-type sequence, the ARG boxes are shown in italics. The ARG boxes of the arginine regulon overlap with the promoter region of each operon. The underlined sequences represent RNA polymerase binding sites and those sequences were not altered. Bases that are protected from DNA methylation during ArgR binding are highlighted, and bases that are protected from hydroxyl radical attack during ArgR binding are bolded. The highlighted and bolded bases were the primary targets for mutations to disrupt ArgR binding.

Example 2

Lambda Red Recombination

Lambda red recombination is used to make chromosomal modifications, e.g., ARG box mutations. Lambda red is a procedure using recombination enzymes from a bacteriophage lambda to insert a piece of custom DNA into the chromosome of E. coli. A pKD46 plasmid is transformed into the E. coli Nissle host strain. E. coli Nissle cells are grown overnight in LB media. The overnight culture is diluted 1:100 in 5 mL of LB media and grown until it reaches an $OD_{600}$ of 0.4-0.6. All tubes, solutions, and cuvettes are pre-chilled to 4° C. The E. coli cells are centrifuged at 2,000 rpm for 5 min. at 4° C., the supernatant is removed, and the cells are resuspended in 1 mL of 4° C. water. The E. coli are centrifuged at 2,000 rpm for 5 min. at 4° C., the supernatant is removed, and the cells are resuspended in 0.5 mL of 4° C. water. The E. coli are centrifuged at 2,000 rpm for 5 min. at 4° C., the supernatant is removed, and the cells are resuspended in 0.1 mL of 4° C. water. The electroporator is set to 2.5 kV. 1 ng of pKD46 plasmid DNA is added to the E. coli cells, mixed by pipetting, and pipetted into a sterile, chilled cuvette. The dry cuvette is placed into the sample chamber, and the electric pulse is applied. 1 mL of room-temperature SOC media is immediately added, and the mixture is transferred to a culture tube and incubated at 30° C. for 1 hr. The cells are spread out on a selective media plate and incubated overnight at 30° C.

DNA sequences comprising the desired ARG box sequences shown in Table 3 were ordered from a gene synthesis company. For the argA operon, the mutant regulatory region comprises the following nucleic acid sequence (SEQ ID NO: 2):

gcaaaaaaacaCTTtaaaaaCTTaataatttcCTTtaatcaCTTaaagag gtgtaccgtg.

The lambda enzymes are used to insert this construct into the genome of E. coli Nissle through homologous recombination. The construct is inserted into a specific site in the genome of E. coli Nissle based on its DNA sequence. To insert the construct into a specific site, the homologous DNA sequence flanking the construct is identified. The homologous sequence of DNA includes approximately 50 bases on either side of the mutated sequence. The homologous sequences are ordered as part of the synthesized gene. Alternatively, the homologous sequences may be added by PCR. The construct is used to replace the natural sequence upstream of argA in the E. coli Nissle genome. The construct includes an antibiotic resistance marker that may be removed by recombination. The resulting mutant argA construct comprises approximately 50 bases of homology upstream of argA, a kanamycin resistance marker that can be removed by recombination, gcaaaaaaacaCTTtaaaaaCTTaataatttcCTTtaatcaCTTaaagaggtgtaccgtg (SEQ ID NO: 2), and approximately 50 bases of homology to argA.

In some embodiments, the ARG boxes were mutated in the argG regulatory region as described above, and a BBa_J23100 constitutive promoter was inserted into the regulatory region using lambda red recombination (SYN-UCD105). These bacteria were capable of producing arginine. In alternate embodiments, the argG regulatory region (SEQ ID NO: 16) remained ArgR-repressible (SYN-UCD104), and the bacteria were capable of producing citrulline.

Example 3

Transforming E. coli Nissle

The mutated ARG box construct is transformed into E. coli Nissle comprising pKD46. All tubes, solutions, and cuvettes are pre-chilled to 4° C. An overnight culture is diluted 1:100 in 5 mL of LB media containing ampicillin and grown until it reaches an $OD_{600}$ of 0.1. 0.05 mL of 100× L-arabinose stock solution is added to induce pKD46 lambda red expression. The culture is grown until it reaches an $OD_{600}$ of 0.4-0.6. The *E. coli* cells are centrifuged at 2,000 rpm for 5 min. at 4° C., the supernatant is removed, and the cells are resuspended in 1 mL of 4° C. water. The *E. coli* are centrifuged at 2,000 rpm for 5 min. at 4° C., the supernatant is removed, and the cells are resuspended in 0.5 mL of 4° C. water. The *E. coli* are centrifuged at 2,000 rpm for 5 min. at 4° C., the supernatant is removed, and the cells are resuspended in 0.1 mL of 4° C. water. The electroporator is set to 2.5 kV. 0.5 µg of the mutated ARG box construct is added to the cells, mixed by pipetting, and pipetted into a sterile, chilled cuvette. The dry cuvette is placed into the sample chamber, and the electric pulse is applied. 1 mL of room-temperature SOC media is immediately added, and the mixture is transferred to a culture tube and incubated at 37° C. for 1 hr. The cells are spread out on an LB plate containing kanamycin and incubated overnight.

Example 4

Verifying Mutants

The presence of the mutation is verified by colony PCR. Colonies are picked with a pipette tip and resuspended in 20 µl of cold $ddH_2O$ by pipetting up and down. 3 µL of the suspension is pipetted onto an index plate with appropriate antibiotic for use later. The index plate is grown at 37° C. overnight. A PCR master mix is made using 5 µL of 10×PCR buffer, 0.6 µl of 10 mM dNTPs, 0.4 µL of 50 mM $Mg_2SO_4$, 6.0 µL of 10× enhancer, and 3.0 µL of $ddH_2O$ (15 µL of master mix per PCR reaction). A 10 µM primer mix is made by mixing 2 µL of primers unique to the argA mutant construct (100 µM stock) into 16 µL of $ddH_2O$. For each 20 µL reaction, 15 µL of the PCR master mix, 2.0 µL of the colony suspension (template), 2.0 µL of the primer mix, and 1.0 µL of Pfx Platinum DNA Pol are mixed in a PCR tube. The PCR thermocycler is programmed as follows, with steps 2-4 repeating 34 times: 1) 94° C. at 5:00 min., 2) 94° C. at 0:15 min., 3) 55° C. at 0:30 min., 4) 68° C. at 2:00 min., 5) 68° C. at 7:00 min., and then cooled to 4° C. The PCR products are analyzed by gel electrophoresis using 10 µL of each amplicon and 2.5 µL 5× dye. The PCR product only forms if the mutation has inserted into the genome.

Example 5

Removing Selection Marker

The antibiotic resistance gene is removed with pCP20. Each strain with the mutated ARG boxes is grown in LB media containing antibiotics at 37° C. until it reaches an $OD_{600}$ of 0.4-0.6. All tubes, solutions, and cuvettes are pre-chilled to 4° C. The cells are centrifuged at 2,000 rpm for 5 min. at 4° C., the supernatant is removed, and the cells are resuspended in 1 mL of 4° C. water. The *E. coli* are centrifuged at 2,000 rpm for 5 min. at 4° C., the supernatant is removed, and the cells are resuspended in 0.5 mL of 4° C. water. The *E. coli* are centrifuged at 2,000 rpm for 5 min. at 4° C., the supernatant is removed, and the cells are resuspended in 0.1 mL of 4° C. water. The electroporator is set to 2.5 kV. 1 ng of pCP20 plasmid DNA is added to the cells, mixed by pipetting, and pipetted into a sterile, chilled cuvette. The dry cuvette was placed into the sample chamber, and the electric pulse was applied. 1 mL of room-temperature SOC media is immediately added, and the mixture is transferred to a culture tube and incubated at 30° C. for 1-3 hrs. The cells are spread out on an LB plate containing kanamycin and incubated overnight. Colonies that do not grow to a sufficient $OD_{600}$ overnight are further incubated for an additional 24 hrs. 200 µL of cells are spread on ampicillin plates, 200 µL of cells are spread on kanamycin plates, and both are grown at 37° C. overnight. The ampicillin plate contains cells with pCP20. The kanamycin plate provides an indication of how many cells survived the electroporation. Transformants from the ampicillin plate are purified non-selectively at 43° C. and allowed to grow overnight.

Example 6

Verifying Transformants

The purified transformants are tested for sensitivity to ampicillin and kanamycin. A colony from the plate grown at 43° C. is picked and resuspended in 10 µL of LB media. 3 µL of the cell suspension is pipetted onto each of three plates: 1) an LB plate with kanamycin incubated at 37° C., which tests for the presence or absence of the kanR gene in the genome of the host strain; 2) an LB plate with ampicillin incubated at 30° C., which tests for the presence or absence of the ampR gene from the pCP20 plasmid; and 3) an LB plate without antibiotic incubated at 37° C. If no growth is observed on the kanamycin or ampicillin plates for a particular colony, then both the kanR gene and the pCP20 plasmid were lost, and the colony is saved for further analysis. The saved colonies are restreaked onto an LB plate to obtain single colonies and grown overnight at 37° C. The presence of the mutated genomic ARG box is confirmed by sequencing the argA region of the genome.

The methods for lambda red recombination, transforming *E. coli* Nissle, verifying the mutation, removing the selection marker, and verifying/sequencing the transformants are repeated for each of the ARG box mutations and operons shown in Table 3. The resulting bacteria comprise mutations in each ARG box for one or more operons encoding the arginine biosynthesis enzymes, such that ArgR binding to the ARG boxes is reduced and total ArgR binding to the regulatory region of said operons is reduced.

Example 7

Arginine Feedback Resistant N-Acetylglutamate Synthetase (argA$^{fbr}$)

In addition to the ARG box mutations described above, the *E. coli* Nissle bacteria further comprise an arginine feedback resistant N-acetylglutamate synthetase (argA$^{fbr}$, SEQ ID NO: 30) gene expressed under the control of each of the following promoters: tetracycline-inducible promoter, FNR promoter selected from SEQ ID NOs: 18-29. As discussed herein, other promoters may be used.

The argA$^{fbr}$ gene is expressed on a high-copy plasmid, a low-copy plasmid, or a chromosome. SYN-UCD101 comprises wild-type ArgR, wild-type ArgA, tetracycline-inducible argA$^{fbr}$ on a plasmid, and mutations in each ARG box for each arginine biosynthesis operon. The plasmid does not comprise functional ArgR binding sites, i.e., ARG boxes. SYN-UCD101 was used to generate SYN-UCD102, which comprises wild-type ArgR, wild-type ArgA, tetracycline-inducible argA$^{fbr}$ on a plasmid, and mutations in each ARG box for each arginine biosynthesis operon. The plasmid further comprises functional ArgR binding sites, i.e., ARG boxes. In some instances, the presence and/or build-up of functional ArgR may result in off-target binding at sites other than the ARG boxes. Introducing functional ARG boxes in this plasmid may be useful for reducing or eliminating off-target ArgR binding, i.e., by acting as an ArgR sink. SYN-UCD104 comprises wild-type ArgR, wild-type ArgA, tetracycline-inducible argA$^{fbr}$ on a low-copy plasmid, tetracycline-inducible argG, and mutations in each ARG box for each arginine biosynthesis operon except for argG. SYN-UCD105 comprises wild-type ArgR, wild-type ArgA, tetracycline-inducible argA$^{fbr}$ on a low-copy plasmid, constitutively expressed argG (SEQ ID NO: 17 comprising the BBa_J23100 constitutive promoter), and mutations in each ARG box for each arginine biosynthesis operon. SYN-UCD103 is a control Nissle construct.

The argA$^{fbr}$ gene is inserted into the bacterial genome at one or more of the following insertion sites in *E. coli* Nissle: malE/K, araC/BAD, lacZ, thyA, malP/T. Any suitable insertion site may be used, see, e.g., FIG. 18. The insertion site may be anywhere in the genome, e.g., in a gene required for survival and/or growth, such as thyA (to create an auxotroph); in an active area of the genome, such as near the site of genome replication; and/or in between divergent promoters in order to reduce the risk of unintended transcription, such as between AraB and AraC of the arabinose operon. At the site of insertion, DNA primers that are homologous to the site of insertion and to the argA$^{fbr}$ construct are designed. A linear DNA fragment containing the construct with homology to the target site is generated by PCR, and lambda red recombination is performed as described above.

The resulting *E. coli* Nissle bacteria are genetically engineered to include nucleic acid mutations that reduce arginine-mediated repression—via ArgR binding and arginine binding to N-acetylglutamate synthetase—of one or more of the operons that encode the arginine biosynthesis enzymes, thereby enhancing arginine and/or citrulline biosynthesis.

Arginine Repressor (ArgR) sequences The wild-type argR nucleotide sequence in *E. coli* Nissle and the nucleotide sequence following argR deletion are shown below in Table 21 and Table 22.

TABLE 21

Wild-type argR nucleotide sequence

| SEQ ID NO: 69 | Sequence |
|---|---|
| argR nucleotide sequence | atgcgaagctcggctaagcaagaagaactagtta aagcatttaaagcattacttaaagaagagaaatt tagctcccagggcgaaatcgtcgccgcgttgcag gagcaaggctttgacaatattaatcagtctaaag tctcgcggatgttgaccaagtttggtgctgtacg tacacgcaatgccaaaatggaaatggtttactgc ctgccagctgaactgggtgtaccaaccacctcca gtccattgaagaatctggtactggatatcgacta caacgatgcagttgtcgtgattcataccagccct ggtgcggcgcagttaattgctcgcctgctggact cactgggcaaagcagaaggtattctgggcaccat cgctggcgatgacaccatctttactacccctgct aacggtttcaccgtcaaagagctgtacgaagcga ttttagagctgttcgaccaggagctttaa |

TABLE 22

Nucleotide sequence following argR deletion

| SEQ ID NO: 124 | Sequence |
|---|---|
| argR-deleted nucleotide sequence | atgcgaagctcggctaagcaagaagagagctg ttcgaccaggagctttaa |

Example 9

Deleting ArgR

A pKD46 plasmid is transformed into the *E. coli* Nissle host strain. *E. coli* Nissle cells are grown overnight in LB media. The overnight culture is diluted 1:100 in 5 mL of LB media and grown until it reaches an OD$_{600}$ of 0.4-0.6. All tubes, solutions, and cuvettes are pre-chilled to 4° C. The *E. coli* cells are centrifuged at 2,000 rpm for 5 min. at 4° C., the supernatant is removed, and the cells are resuspended in 1 mL of 4° C. water. The *E. coli* are centrifuged at 2,000 rpm for 5 min. at 4° C., the supernatant is removed, and the cells are resuspended in 0.5 mL of 4° C. water. The *E. coli* are centrifuged at 2,000 rpm for 5 min. at 4° C., the supernatant is removed, and the cells are resuspended in 0.1 mL of 4° C. water. The electroporator is set to 2.5 kV. 1 ng of pKD46 plasmid DNA is added to the *E. coli* cells, mixed by pipetting, and pipetted into a sterile, chilled cuvette. The dry cuvette is placed into the sample chamber, and the electric pulse is applied. 1 mL of room-temperature SOC media is immediately added, and the mixture is transferred to a culture tube and incubated at 30° C. for 1 hr. The cells are spread out on a selective media plate and incubated overnight at 30° C.

Approximately 50 bases of homology upstream and downstream of the ArgR gene are added by PCR to the kanamycin resistance gene in the pKD4 plasmid to generate the following KanR construct: (~50 bases upstream of ArgR) (terminator) (kanR gene flanked by FRT sites from pKD4) (DNA downstream of argR).

In some embodiments, both argR and argG genes are deleted using lambda red recombination as described above, and the bacteria are capable of producing citrulline.

Example 10

Bacterial Strains Having Arginine Feedback Resistant N-Acetylglutamate Synthetase (argA$^{fbr}$) and ArgR Deletion In addition to the ArgR deletion described above, the *E. coli* Nissle bacteria further comprise an arginine feedback resistant N-acetylglutamate synthetase (argA$^{fbr}$, SEQ ID NO: 30) gene expressed under the control of each of the following promoters: tetracycline-inducible promoter, FNR promoter selected from SEQ ID NOs: 18-29. As discussed herein, other promoters may be used.

The argA$^{fbr}$ gene is expressed on a high-copy plasmid, a low-copy plasmid, or a chromosome. ArgR is deleted (ΔArgR) in each of SYN-UCD201, SYN-UCD202, and SYN-UCD203. SYN-UCD201 further comprises wild-type argA, but lacks inducible argA$^{fbr}$. SYN-UCD202 comprises ΔArgR and argA$^{fbr}$ expressed under the control of a tetracycline-inducible promoter on a high-copy plasmid. SYN-UCD203 comprises ΔArgR and argA$^{fbr}$ expressed under the control of a tetracycline-inducible promoter on a low-copy plasmid. SYN-UCD204 comprises ΔArgR and argA$^{fbr}$ expressed under the control of a tetracycline-inducible promoter on a low-copy plasmid. SYN-UCD205 comprises ΔArgR and argA$^{fbr}$ expressed under the control of a FNR-inducible promoter (fnrS2) on a low-copy plasmid.

The argA$^{fbr}$ gene is inserted into the bacterial genome at one or more of the following insertion sites in *E. coli* Nissle: malE/K, araC/BAD, lacZ, thyA, malP/T. Any suitable insertion site may be used, see, e.g., FIG. 18. The insertion site may be anywhere in the genome, e.g., in a gene required for survival and/or growth, such as thyA (to create an auxotroph); in an active area of the genome, such as near the site of genome replication; and/or in between divergent promoters in order to reduce the risk of unintended transcription, such as between AraB and AraC of the arabinose operon. At the site of insertion, DNA primers that are homologous to the site of insertion and to the argA$^{fbr}$ construct are designed. A linear DNA fragment containing the construct with homology to the target site is generated by PCR, and lambda red recombination is performed as described above. The resulting *E. coli* Nissle bacteria have deleted ArgR and inserted feedback resistant N-acetylglutamate synthetase, thereby increasing arginine or citrulline biosynthesis.

Example 11

Generation of ΔThyA

An auxotrophic mutation causes bacteria to die in the absence of an exogenously added nutrient essential for survival or growth because they lack the gene(s) necessary to produce that essential nutrient. In order to generate genetically engineered bacteria with an auxotrophic modification, the thyA, a gene essential for oligonucleotide synthesis was deleted. Deletion of the thyA gene in *E. coli* Nissle yields a strain that cannot form a colony on LB plates unless they are supplemented with thymidine.

A thyA::cam PCR fragment was amplified using 3 rounds of PCR as follows. Sequences of the primers used at a 100 um concentration are found in Table 23.

TABLE 23

Primer Sequences

| Name | Sequence | Description | SEQ ID NO |
|---|---|---|---|
| SR36 | tagaactgatgcaaaaaggct tcgacgaaggcacacagaTG TGTAGGCTGGAGCTG CTTC | Round 1: binds on pKD3 | SEQ ID NO: 68 |
| SR38 | gtttcgtaattagatagccacc ggcgctttaatgcccggaCAT ATGAATATCCTCCTTAG | Round 1: binds on pKD3 | SEQ ID NO: 125 |
| SR33 | caacacgtttcctgaggaacc atgaaacagtatttagaactg atgcaaaaag | Round 2: binds to round 1 PCR product | SEQ ID NO: 70 |
| SR34 | cgcacactggcgtcggctctgg caggatgtttcgtaattagat agc | Round 2: binds to round 1 PCR product | SEQ ID NO: 71 |
| SR43 | atatcgtcgcagcccacagcaa cacgtttcctgagg | Round 3: binds to round 2 PCR product | SEQ ID NO: 72 |

TABLE 23-continued

Primer Sequences

| Name | Sequence | Description | SEQ ID NO |
|---|---|---|---|
| SR44 | aagaatttaacggagggcaaa aaaaaccgacgcacact ggcgtcggc | Round 3: binds to round 2 PCR product | SEQ ID NO: 73 |

For the first PCR round, 4×50 ul PCR reactions containing 1 ng pKD3 as template, 25 ul 2× phusion, 0.2 ul primer SR36 and SR38, and either 0, 0.2, 0.4 or 0.6 ul DMSO were brought up to 50 ul volume with nuclease free water and amplified under the following cycle conditions:
step1: 98c for 30 s
step2: 98c for 10 s
step3: 55c for 15 s
step4: 72c for 20 s
repeat step 2-4 for 30 cycles
step5: 72c for 5 min Subsequently, 5 ul of each PCR reaction was run on an agarose gel to confirm PCR product of the appropriate size. The PCR product was purified from the remaining PCR reaction using a Zymoclean gel DNA recovery kit according to the manufacturer's instructions and eluted in 30 ul nuclease free water.

For the second round of PCR, 1 ul purified PCR product from round 1 was used as template, in 4×50 ul PCR reactions as described above except with 0.2 ul of primers SR33 and SR34. Cycle conditions were the same as noted above for the first PCR reaction. The PCR product run on an agarose gel to verify amplification, purified, and eluted in 30 ul as described above.

For the third round of PCR, 1 ul of purified PCR product from round 2 was used as template in 4×50 ul PCR reactions as described except with primer SR43 and SR44. Cycle conditions were the same as described for rounds 1 and 2. Amplification was verified, the PCR product purified, and eluted as described above. The concentration and purity was measured using a spectrophotometer. The resulting linear DNA fragment, which contains 92 bp homologous to upstream of thyA, the chloramphenicol cassette flanked by frt sites, and 98 bp homologous to downstream of the thyA gene, was transformed into a *E. coli* Nissle 1917 strain containing pKD46 grown for recombineering. Following electroporation, 1 ml SOC medium containing 3 mM thymidine was added, and cells were allowed to recover at 37 C for 2 h with shaking. Cells were then pelleted at 10,000×g for 1 minute, the supernatant was discarded, and the cell pellet was resuspended in 100 ul LB containing 3 mM thymidine and spread on LB agar plates containing 3 mM thy and 20 ug/ml chloramphenicol. Cells were incubated at 37 C overnight. Colonies that appeared on LB plates were restreaked. + cam 20 ug/ml+ or − thy 3 mM. (thyA auxotrophs will only grow in media supplemented with thy 3 mM).

Next, the antibiotic resistance was removed with pCP20 transformation. pCP20 has the yeast Flp recombinase gene, FLP, chloramphenicol and ampicillin resistant genes, and temperature sensitive replication. Bacteria were grown in LB media containing the selecting antibiotic at 37° C. until OD600=0.4-0.6. 1 mL of cells were washed as follows: cells were pelleted at 16,000×g for 1 minute. The supernatant was discarded and the pellet was resuspended in 1 mL ice-cold 10% glycerol. This wash step was repeated 3× times. The final pellet was resuspended in 70 ul ice-cold 10% glycerol. Next, cells were electroporated with 1 ng pCP20 plasmid DNA, and 1 mL SOC supplemented with 3 mM thymidine was immediately added to the cuvette. Cells were resuspended and transferred to a culture tube and grown at 30° C. for 1 hours. Cells were then pelleted at 10,000×g for 1 minute, the supernatant was discarded, and the cell pellet was resuspended in 100 ul LB containing 3 mM thymidine and spread on LB agar plates containing 3 mM thy and 100 ug/ml carbenicillin and grown at 30° C. for 16-24 hours. Next, transformants were colony purified non-selectively (no antibiotics) at 42° C.

To test the colony-purified transformants, a colony was picked from the 42° C. plate with a pipette tip and resuspended in 10 µL LB. 3 µL of the cell suspension was pipetted onto a set of 3 plates: Cam, (37° C.; tests for the presence/absence of CamR gene in the genome of the host strain), Amp, (30° C., tests for the presence/absence of AmpR from the pCP20 plasmid) and LB only (desired cells that have lost the chloramphenicol cassette and the pCP20 plasmid), 37° C. Colonies were considered cured if there is no growth in neither the Cam or Amp plate, picked, and restreaked on an LB plate to get single colonies, and grown overnight at 37° C.

Example 12

Quantifying Ammonia

The genetically engineered bacteria described above were grown overnight in 5 mL LB. The next day, cells were pelleted and washed in M9+glucose, pelleted, and resuspended in 3 mL M9+glucose. Cell cultures were incubated with shaking (250 rpm) for 4 hrs and incubated aerobically or anaerobically in a Coy anaerobic chamber (supplying 90% $N_2$, 5% $CO_2$, 5% $H_2$) at 37° C. At baseline (t=0), 2 hours, and 4 hours, the $OD_{600}$ of each cell culture was measured in order to determine the relative abundance of each cell.

Figure 25:
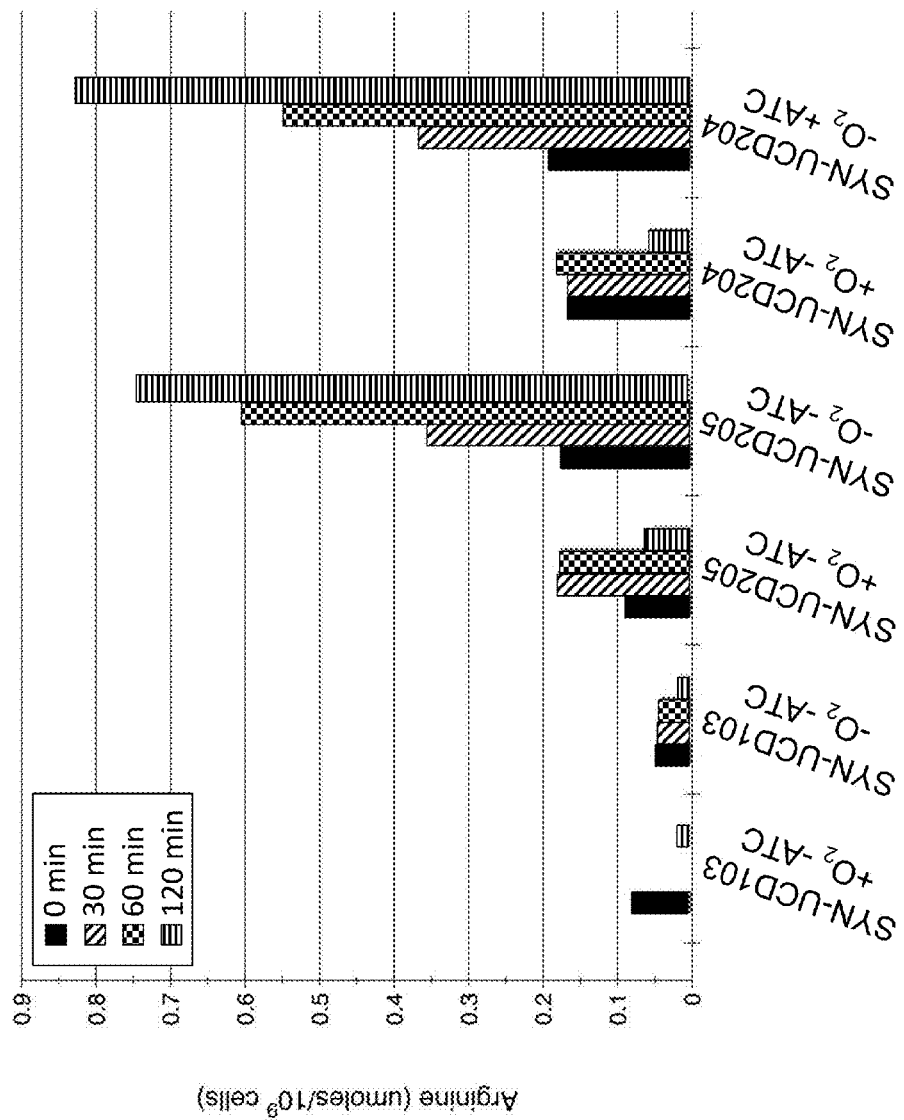
FIG. 25 depicts a bar graph of in vitro arginine levels produced by streptomycin-resistant Nissle (SYN-UCD103), SYN-UCD205, and SYN-UCD204 under inducing (+ATC) and non-inducing (−ATC) conditions, in the presence (+O$_2$) or absence (−O$_2$) of oxygen. SYN-UCD103 is a control Nissle construct. SYN-UCD205 comprises ΔArgR and argA$^{fbr}$ expressed under the control of a FNR-inducible promoter on a low-copy plasmid. SYN204 comprises ΔArgR and argA$^{fbr}$ expressed under the control of a tetracycline-inducible promoter on a low-copy plasmid.
Figure 26:
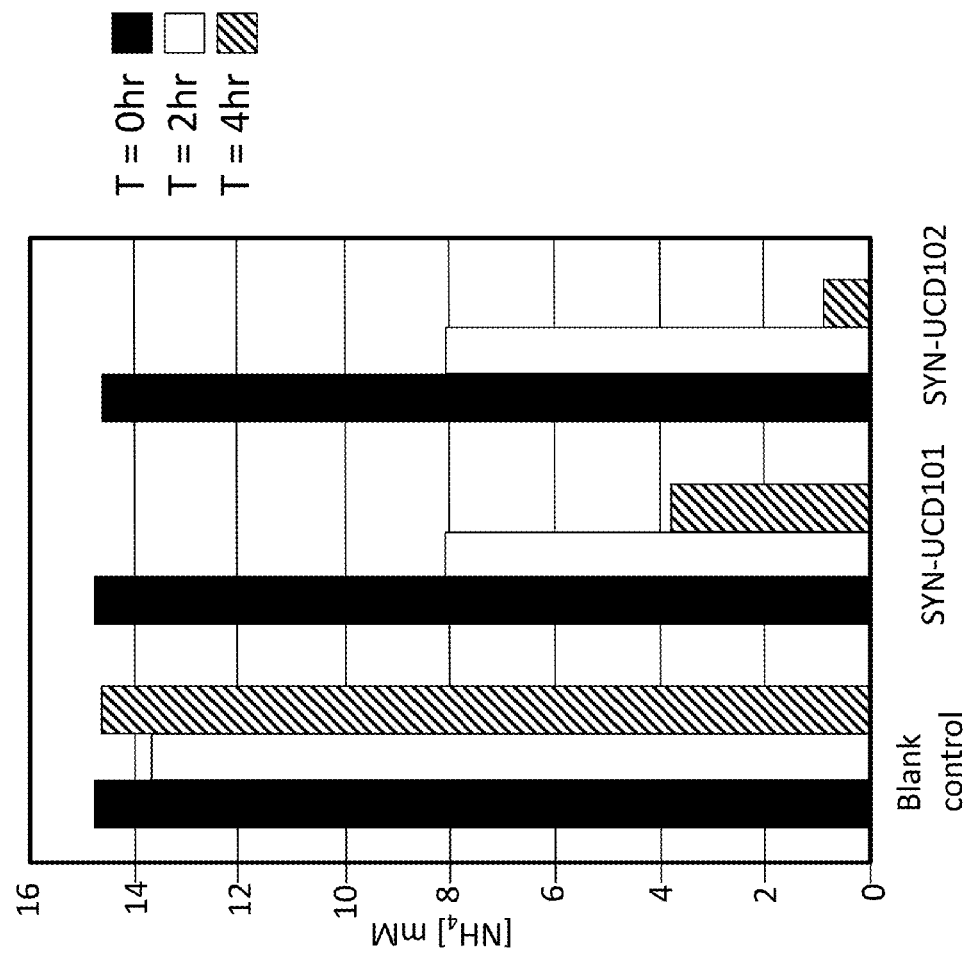
FIG. 26 depicts a bar graph of in vitro ammonia levels in culture media from SYN-UCD101, SYN-UCD102, and blank controls at baseline, two hours, and four hours. Both SYN-UCD101 and SYN-UCD102 are capable of consuming ammonia in vitro. SYN-UCD101 comprises wild type ArgR, and wild type ThyA, and no ArgAfbr; SYN-UCD102 comprises wild type ArgR, tetracycline-inducible argAfbr on a low copy plasmid, and wild type ThyA.
Figure 27:
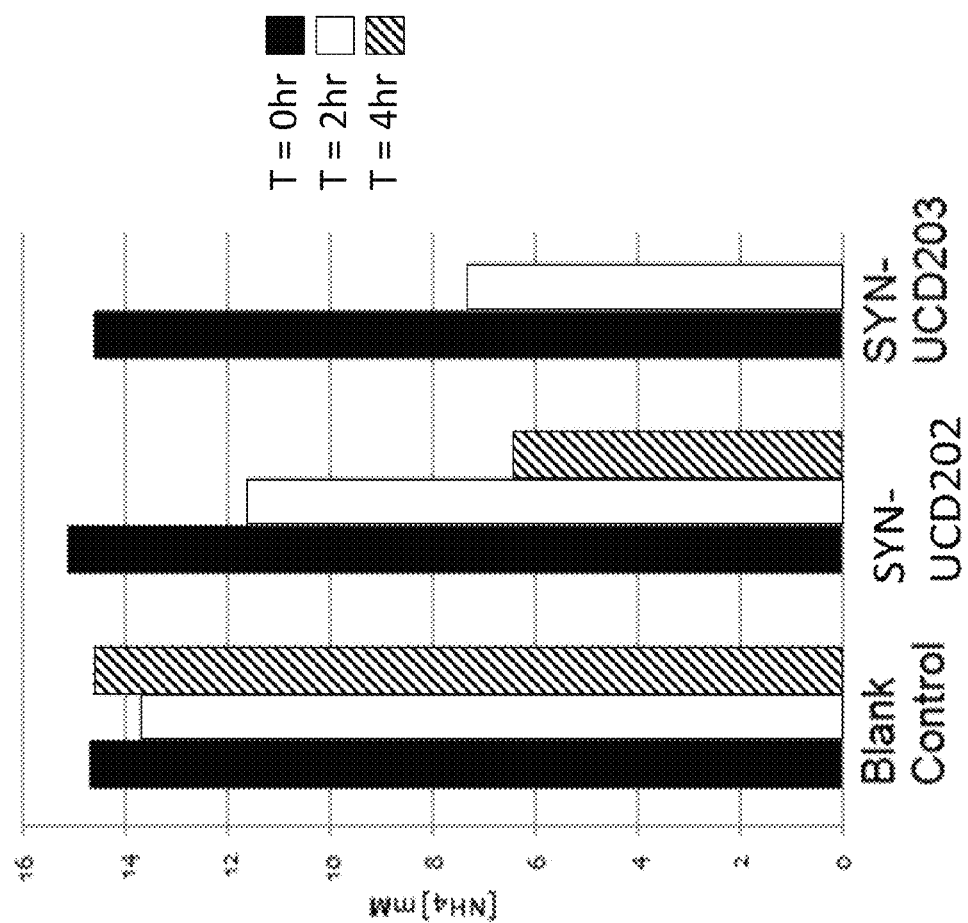
FIG. 27 depicts a bar graph of in vitro ammonia levels in culture media from SYN-UCD202, SYN-UCD203, and blank controls at baseline, two hours, and four hours. Both SYN-UCD202 and SYN-UCD203 are capable of consuming ammonia in vitro. SYN-UCD202 and SYN-UCD203 both comprise ΔArgR, tetracycline-inducible argAfbr on a high-copy plasmid or low copy plasmid, respectively, Amp resistance, and wild type ThyA.

At t=0, 2 hrs, and 4 hrs, a 1 mL aliquot of each cell culture was analyzed on the Nova Biomedical Bioprofile Analyzer 300 in order to determine the concentration of ammonia in the media. Both SYN-UCD101 and SYN-UCD102 were capable of consuming ammonia in vitro (FIG. 26). FIGS. 25, 26, and 27 depict bar graphs of ammonia concentrations using SYN-UCD202, SYN-UCD204, SYN-UCD103, and blank controls.

Example 13

Quantifying Arginine and Citrulline

In some embodiments, the genetically engineered bacteria described above are grown overnight in LB at 37° C. with shaking. The bacteria are diluted 1:100 in 5 mL LB and grown at 37° C. with shaking for 1.5 hr. The bacteria cultures are induced as follows: (1) bacteria comprising FNR-inducible argA$^{fbr}$ are induced in LB at 37° C. for up to 4 hrs in anaerobic conditions in a Coy anaerobic chamber (supplying 90% $N_2$, 5% $CO_2$, 5% $H_2$, and 20 mM nitrate) at 37° C.; (2) bacteria comprising tetracycline-inducible argA$^{fbr}$ are induced with anhydrotetracycline (100 ng/mL); (3) bacteria comprising arabinose-inducible argA$^{fbr}$ are induced with 1% arabinose in media lacking glucose. After induction, bacterial cells are removed from the incubator and spun down at maximum speed for 5 min. The cells are resuspended in 1 mL M9 glucose, and the $OD_{600}$ is measured. Cells are diluted until the $OD_{600}$ is between 0.6-0.8. Resuspended cells in M9 glucose media are grown aerobically with shaking at 37 C. 100 µL of the cell resuspension is removed and the $OD_{600}$ is measured at time=0. A 100 µL aliquot is frozen at −20° C. in a round-bottom 96-well plate for mass spectrometry analysis (LC-MS/MS). At each subsequent time point, 100 µL of the cell suspension is removed and the $OD_{600}$ is measured; a 100 µL aliquot is frozen at −20 C in a round-bottom 96-well plate for mass spectrometry analysis. Samples are analyzed for arginine and/or citrulline concentrations. At each time point, normalized concentrations as determined by mass spectrometry vs. $OD_{600}$ are used to determine the rate of arginine and/or citrulline production per cell per unit time.

In some embodiments, the genetically engineered bacteria described above are streaked from glycerol stocks for single colonies on agar. A colony is picked and grown in 3 mL LB for 4 hrs or overnight, then centrifuged for 5 min at 2,500 rcf. The cultures are washed in M9 media with 0.5% glucose. The cultures are resuspended in 3 mL of M9 media with 0.5% glucose, and the $OD_{600}$ is measured. The cultures are diluted in M9 media with 0.5% glucose, with or without ATC (100 ng/mL), with or without 20 mM glutamine, so that all of the $OD_{600}$ are between 0.4 and 0.5. A 0.5 mL aliquot of each sample is removed, centrifuged for 5 min. at 14,000 rpm, and the supernatant is removed and saved. The supernatant is frozen at −80° C., and the cell pellets are frozen at −80° C. (t=0). The remaining cells are grown with shaking (250 rpm) for 4-6 hrs and incubated aerobically or anaerobically in a Coy anaerobic chamber (supplying 90% $N_2$, 5% $CO_2$, 5% $H_2$) at 37° C. One 0.5 mL aliquot is removed from each sample every two hours and the $OD_{600}$ is measured. The aliquots are centrifuged for 5 min at 14,000 rpm, and the supernatant is removed. The supernatant is frozen at −80° C., and the cell pellets are frozen at −80° C. (t=2, 4, and 6 hrs). The samples are placed on ice, and arginine and citrulline levels are determined using mass spectrometry.

For bacterial culture supernatants, samples of 500, 100, 20, 4, and 0.8 µg/mL arginine and citrulline standards in water are prepared. In a round-bottom 96-well plate, 20 µL of sample (bacterial supernatant or standards) is added to 80 µL of water with L-Arginine-$^{13}C_6$, $^{15}N_4$ (Sigma) and L-Citrulline-2,3,3,4,4,5,5-d7 (CDN isotope) internal standards at a final 2 µg/mL concentration. The plate is heat-sealed with a PierceASeal foil and mixed well. In a V-bottom 96-well polypropylene plate, 5 µL of diluted samples is added to 95 µL of derivatization mix (85 µL 10 mM NaHCO$_3$ pH 9.7 and 10 µL 10 mg/mL dansyl-chloride (diluted in acetonitrile). The plate is heat-sealed with a ThermASeal foil and mixed well. The samples are incubated at 60° C. for 45 min for derivatization and centrifuged at 4000 rpm for 5 min. In a round-bottom 96-well plate, 20 µL of the derivatized samples are added to 180 µL of water with 0.1% formic acid. The plate is heat-sealed with a ClearASeal sheet and mixed well.

Arginine and citrulline are measured by liquid chromatography coupled to tandem mass spectrometry (LC-MS/MS) using a Thermo TSQ Quantum Max triple quadrupole mass spectrometer. Table 24 below provides a summary of a LC-MS/MS method.

TABLE 24 a LC-MS/MS Method Summary

HPLC

| Column | Luna C18(2) column, 5 μm (50 × 2.1 mm) |
|---|---|
| Mobile Phase A | 100% H$_2$O, 0.1% Formic Acid) |
| Mobile Phase B | 100% ACN, 0.1% Formic Acid |

HPLC Method

| Total Time (min) | Flow Rate (μL/min) | A % | B % |
|---|---|---|---|
| 0.00 | 400 | 90.0 | 10.0 |
| 0.50 | 400 | 90.0 | 10.0 |
| 2.00 | 400 | 10.0 | 90.0 |
| 3.25 | 400 | 10.0 | 90.0 |
| 3.26 | 400 | 90.0 | 10.0 |
| 4.30 | 400 | 90.0 | 10.0 |

| Injection Volume | 10 μL |
|---|---|

Tandem Mass Spectrometry

| Ion Source | HESI-II |
|---|---|
| Polarity | Positive |
| SRM transitions | L-Arginine: 408.1/170.1 |
| | L-Arginine-$^{13}$C$_6$, $^{15}$N$_4$: 418.1/170.0 |
| | L-Citrulline: 409.1/170.2 |
| | L-Citrulline-2,3,3,4,4,5,5-d7: 416.1/170.1 |

Intracellular arginine and secreted (supernatant) arginine production in the genetically engineered bacteria in the presence or absence an ATC or anaerobic inducer is measured and compared to control bacteria of the same strain under the same conditions.

Total arginine production over 6 hrs in the genetically engineered bacteria in the genetically engineered bacteria in the presence or absence an ATC or anaerobic inducer is measured and compared to control bacteria of the same strain under the same conditions.

Example 14

Efficacy of Genetically Engineered Bacteria in a Mouse Model of Hyperammonemia and Acute Liver Failure Wild-type C57BL6/J mice are treated with thiol acetamide (TAA), which causes acute liver failure and hyperammonemia (Nicaise et al., 2008). The TAA mouse model is an industry-accepted in vivo model for HE. Mice are treated with unmodified control Nissle bacteria or Nissle bacteria engineered to produce high levels of arginine or citrulline as described above.

On day 1, 50 mL of the bacterial cultures are grown overnight and pelleted. The pellets are resuspended in 5 mL of PBS at a final concentration of approximately $10^{11}$ CFU/mL. Blood ammonia levels in mice are measured by mandibular bleed, and ammonia levels are determined by the PocketChem Ammonia Analyzer (Arkray). Mice are gavaged with 100 μL of bacteria (approximately $10^{10}$ CFU). Drinking water for the mice is changed to contain 0.1 mg/mL anhydrotetracycline (ATC) and 5% sucrose for palatability.

On day 2, the bacterial gavage solution is prepared as described above, and mice are gavaged with 100 μL of bacteria. The mice continue to receive drinking water containing 0.1 mg/mL ATC and 5% sucrose.

On day 3, the bacterial gavage solution is prepared as described above, and mice are gavaged with 100 μL of bacteria. The mice continue to receive drinking water containing 0.1 mg/mL ATC and 5% sucrose. Mice receive an intraperitoneal (IP) injection of 100 μL of TAA (250 mg/kg body weight in 0.5% NaCl).

On day 4, the bacterial gavage solution is prepared as described above, and mice are gavaged with 100 μL of bacteria. The mice continue to receive drinking water containing 0.1 mg/mL ATC and 5% sucrose. Mice receive another IP injection of 100 μL of TAA (250 mg/kg body weight in 0.5% NaCl). Blood ammonia levels in the mice are measured by mandibular bleed, and ammonia levels are determined by the PocketChem Ammonia Analyzer (Arkray).

On day 5, blood ammonia levels in mice are measured by mandibular bleed, and ammonia levels are determined by the PocketChem Ammonia Analyzer (Arkray). Fecal pellets are collected from mice to determine arginine content by liquid chromatography-mass spectrometry (LC-MS). Ammonia levels in mice treated with genetically engineered Nissle and unmodified control Nissle are compared.

Example 15

Efficacy of Genetically Engineered Bacteria in a Mouse Model of Hyperammonemia and UCD Ornithine transcarbamylase is urea cycle enzyme, and mice comprising an spf-ash mutation exhibit partial ornithine transcarbamylase deficiency, which serves as a model for human UCD. Mice are treated with unmodified control Nissle bacteria or Nissle bacteria engineered to produce high levels of arginine or citrulline as described above.

Figure 29:
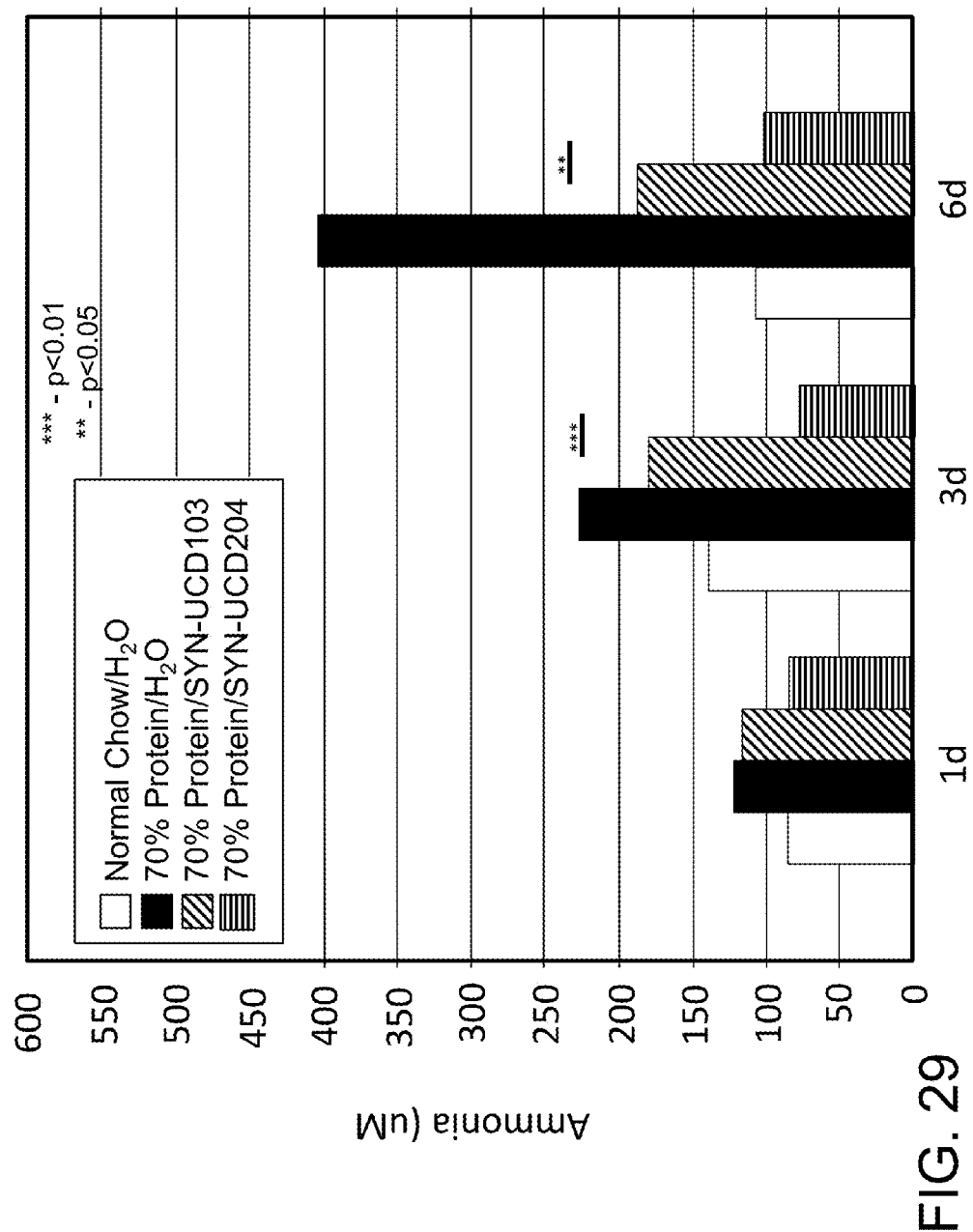
FIG. 29 depicts a bar graph of ammonia levels in hyperammonemic spf$^{ash}$ mice. Fifty-six spf$^{ash}$ mice were separated into four groups. Group 1 was fed normal chow, and groups 2-4 were fed 70% protein chow following an initial blood draw. Groups were gavaged twice daily, with water, streptomycin-resistant Nissle control (SYN-UCD103), or SYN-UCD204, and blood was drawn 4 hours following the first gavage. SYN-UCD204, comprising ΔArgR and argA$^{fbr}$ expressed under the control of a tetracycline-inducible promoter on a low-copy plasmid, significantly reduced blood ammonia to levels below the hyperammonemia threshold.

60 spf-ash mice were treated with the genetically engineered bacteria of the invention (SYN-UCD103, SYN-UCD204) or H2O control at 100 ul PO QD: H2O control, normal chow (n=15); H2O control, high protein chow (n=15); SYN-UCD103, high protein chow (n=15); SYN-UCD204, high protein chow (n=15). On Day 1, mice were weighed and sorted into groups to minimize variance in mouse weight per cage. Mice were gavaged and water with 20 mg/L ATC was added to the cages. On day 2, mice were gavaged in the morning and afternoon. On day 3, mice were gavaged in the morning and weighed, and blood was drawn 4 h post-dosing to obtain baseline ammonia levels. Mice were gavaged in the afternoon and chow changed to 70% protein chow. On day 4, mice were gavaged in the morning and afternoon. On day 5, mice were gavaged in the morning and weighed, and blood was drawn 4 h post-dosing to obtain ammonia levels. On days 6 and 7, mice were gavaged in the morning. On day 8, mice were gavaged in the morning and weighed, and blood was drawn 4 h post-dosing to obtain ammonia levels. On day 9, mice were gavaged in the morning and afternoon. On day 10, mice were gavaged in the morning and weighed, and blood was drawn 4 h post-dosing to obtain ammonia levels. On day 12, mice were gavaged in the morning and afternoon. On day 13, mice were gavaged in the morning and weighed, and blood was drawn 4 h post-dosing to obtain ammonia levels. Blood ammonia levels, body weight, and survival rates are analyzed (FIG. 29).

Example 16

Efficacy of Genetically Engineered Bacteria in a Mouse Model of Hyperammonemia and UCD (Spf-Ash) Maintained on a High Protein Diet The hyperammonia/UCD (spf-ash) model described in Example 14 was used to assess the in vivo efficacy of genetically engineered bacteria encoding ArgAfbr driven by a fnr promoter on a low copy plasmid on ammonia levels upon administration of a high protein diet.

Two strains encoding ArgAfbr driven by a fnr promoter on a low copy plasmid, SYN-UCD206 (comprising ΔArgR and ΔThyA and argAfbr expressed under the control of a FNR-inducible promoter (fnrS2) on a low-copy plasmid) and SYN-UCD205 (comprising ΔArgR and argAfbr expressed under the control of a FNR-inducible promoter (fnrS2) on a low-copy plasmid) were compared to determine whether thymidine auxotrophy can influence the efficacy of ammonia removal from the blood.

Spf-ash mice were treated by oral administration with the genetically engineered bacteria (SYN-UCD205, SYN-UCD206) or H2O control. Normal or high protein chow was provided as follows: SYN-UCD205, high protein chow (n=10); SYN-UCD206, high protein chow (n=10); H2O control, normal chow (n=10); H2O control, high protein chow (n=10). For SYN-UCD205 and SYN-UCD206, a dose of 100 ul of >1×10$^{10}$ cells/ml was administered twice a day for 12 days, with the exception of days 1, 5, 6, and 7, where bacteria were administered once. On Day 1, mice were weighed and randomized. T=0 NH4 levels were determined from mandibular bleeds using the PocketChem Ammonia Analyzer (Arkray), and mice were subsequently and gavaged. On day 2, mice were gavaged in the morning and afternoon. On day 3, mice were gavaged in the morning and afternoon and the chow was changed from normal chow to 70% protein chow. On day 4, mice were gavaged in the morning and afternoon. On day 5, mice were gavaged in the morning and weighed, and blood was drawn 4 h post-dosing to obtain ammonia levels. On days 8 through 12, mice were gavaged in the morning and afternoon.

Figure 30:
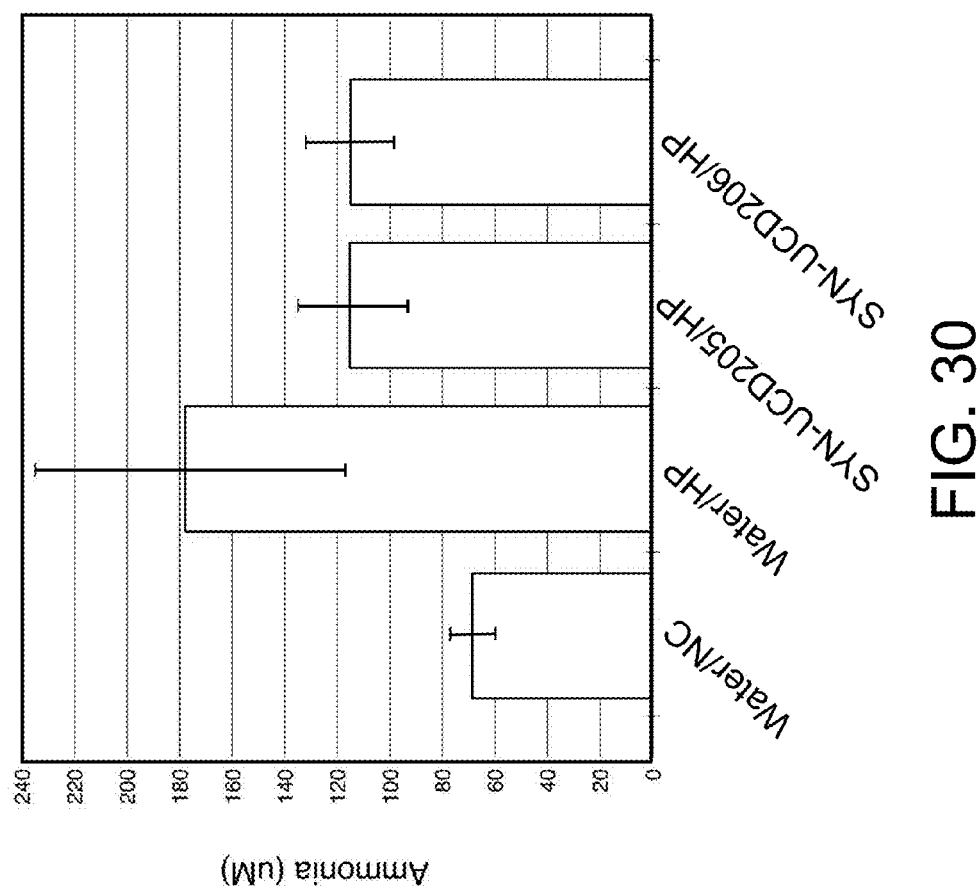
FIG. 30 depicts a bar graph of ammonia levels in hyperammonemic spf$^{ash}$ mice on a high protein diet. Mice were treated with SYN-UCD204 (comprising ΔArgR, PfnrS-ArgAfbr on a low-copy plasmid and wild type ThyA), SYN-UCD206 (comprising ΔArgR, PfnrS-ArgAfbr on a low-copy plasmid and ΔThyA) or water, then switched to high protein chow after 2 days.

As seen in FIG. 30, ammonia levels of spf-ash mice in a high protein diet were reduced 48 hours after switch to high protein chow in the SYN-UCD205 and SYN-UCD206 groups as compared to the H2O high protein diet control group, indicating that the FNR inducible promoter can drive ArgAfbr expression, resulting in decreased ammonia levels in the blood of the mice treated with the engineered bacteria. The observed reduction in ammonia levels was similar in both SYN-UCD205 and SYN-UCD206, indicating that ThyA auxotrophy does not have a significant effect on efficacy of SYN-UCD206.

Example 17

Engineering Bacterial Strains Using Chromosomal Insertions

Bacterial strains, in which ArgAfbr is integrated directly into the *E. coli* Nissle genome under the control of an FNR-responsive promoter at the MALEK site were constructed.

To create a vector capable of integrating the PfnrS-ArgAfbr into the chromosome at the Nissle MalE and MalK loci, Gibson assembly was used to add 1000 bp sequences of DNA homologous to the Nissle MALE/K locus to both sides of a flippase recombination target (FRT) site-flanked chloramphenicol resistance (cmR) cassette on a knock-in knock-out (KIKO) plasmid. Gibson assembly was then used to clone the PfnrS-ArgAfbr DNA sequence between these homology arms, adjacent to the FRT-cmR-FRT site. Successful insertion of the fragment was validated by sequencing. PCR is used to amplify the entire MalEK::FRT-cmR-FRT::PfnrS-ArgAfbr::MalK region. This knock-in PCR fragment was used to transform an electrocompetent Nissle strain that contains a temperature-sensitive plasmid encoding the lambda red recombinase genes. After transformation, cells were grown for 2 hrs at 37° C. Growth at 37° C. cures the temperature-sensitive plasmid. Transformants with successful chromosomal integration of the fragment were selected on chloramphenicol at 20 μg/m L.

In some embodiments, recombinase-based switches may be used to activate PfnrS-ArgAfbr expression. To construct a strain allowing recombinase-based switches to regulate ArgAfbr expression, the PfnrS-driven Int5 gene and the rrnBUP-driven, recombinase site-flanked ArgAfbrare synthesized by Genewiz (Cambridge, Mass.). Gibson assembly is used to add 1000 bp sequences of DNA homologous to the Nissle malE and malK loci on either side of the PfnrS-Int5, rrnBUP-ArgAfbr sequence and to clone this sequence between the homology arms. Successful insertion of the fragment into a KIKO plasmid is validated by sequencing. PCR is used to amplify the entire PfnrS-Int5, rrnBUP-ArgAfbr region. This knock-in PCR fragment is used to transform an electrocompetent Nissle strain expressing the lambda red recombinase genes. After transformation, cells are grown for 2 hrs at 37° C. Transformants with successful integration of the PfnrS-ArgAfbr at the malEK intergenic region are selected on kanamycin at 50 μg/mL. This strategy may also be used to construct a recombinase-based strain requiring T7 polymerase activity for ArgAfbr expression.

Example 18

Comparison of In Vitro Efficacy of Chromosomal Insertion and Plasmid-Bearing Engineered Bacterial Strains To compare the in vitro efficacy between engineered bacterial strains harboring a chromosomal insertion of ArgAfbr driven by an fnr inducible promoter at the malEK locus and strains with a low copy plasmid comprising ArgAfbr driven by an fnr inducible promoter, arginine levels in the media were measured at various time points post anaerobic induction. Additionally, to assess whether auxotrophy for thymidine may have an effect on arginine production efficiency, arginine production of engineered bacterial strains with or without a ThyA deletion, comprising the fnr-ArgAfbr on a low copy plasmid or integrated on the chromosome, were compared.

Overnight cultures were diluted 1:100 in LB and grown with shaking (250 rpm) at 37° C. After 1.5 hrs of growth, the bacteria cultures were induced as follows: (1) bacteria comprising FNR-inducible argAfbr were induced in LB at 37° C. for 4 hrs in anaerobic conditions in a Coy anaerobic chamber (supplying 90% N2, 5% CO2, 5% H2, and 20 mM nitrate) at 37° C.; (2) bacteria comprising tetracycline-inducible argAfbr were induced with anhydrotetracycline (100 ng/m L). After induction, bacteria were removed from the incubator and spun down at maximum speed for 5 min. The cells were resuspended in 1 mL M9 glucose, and the OD600 was measured. Cells were diluted until the OD600 was between 0.6-0.8. Resuspended cells in M9 glucose media were grown aerobically with shaking at 37 C. 100 μL of the cell resuspension was removed and the OD600 is measured at time=0. A 100 μL aliquot was frozen at −20° C. in a round-bottom 96-well plate for mass spectrometry analysis (LC-MS/MS). At each subsequent time point (e.g., 30, 60, and 120 min), 100 μL of the cell suspension was removed and the OD600 was measured; a 100 μL aliquot was frozen at −20 C in a round-bottom 96-well plate for mass spectrometry analysis. Samples were analyzed for arginine concentrations. At each time point, normalized concentrations as determined by mass spectrometry vs. OD600 were used to determine the rate of arginine production per cell per unit time. A summary of the LC-MS/MS method is provided above.

Arginine production at 30, 60, and 120 min post induction was compared between (1) Syn-UCD301 (SYN825; comprising ΔArgR and argAfbr expressed under the control of a FNR-inducible promoter integrated into the chromosome at the malEK locus), (2) SYN-UCD205 (comprising ΔArgR and argAfbr expressed under the control of a FNR-inducible promoter on a low-copy plasmid), and (3) SYN-UCD206 (comprising ΔArgR and ΔThyA and argAfbr expressed under the control of a FNR-inducible promoter on a low-copy plasmid. SYN-UCD103 was used as is a control Nissle construct and results are shown in FIG. 31A.

Figure 31A:
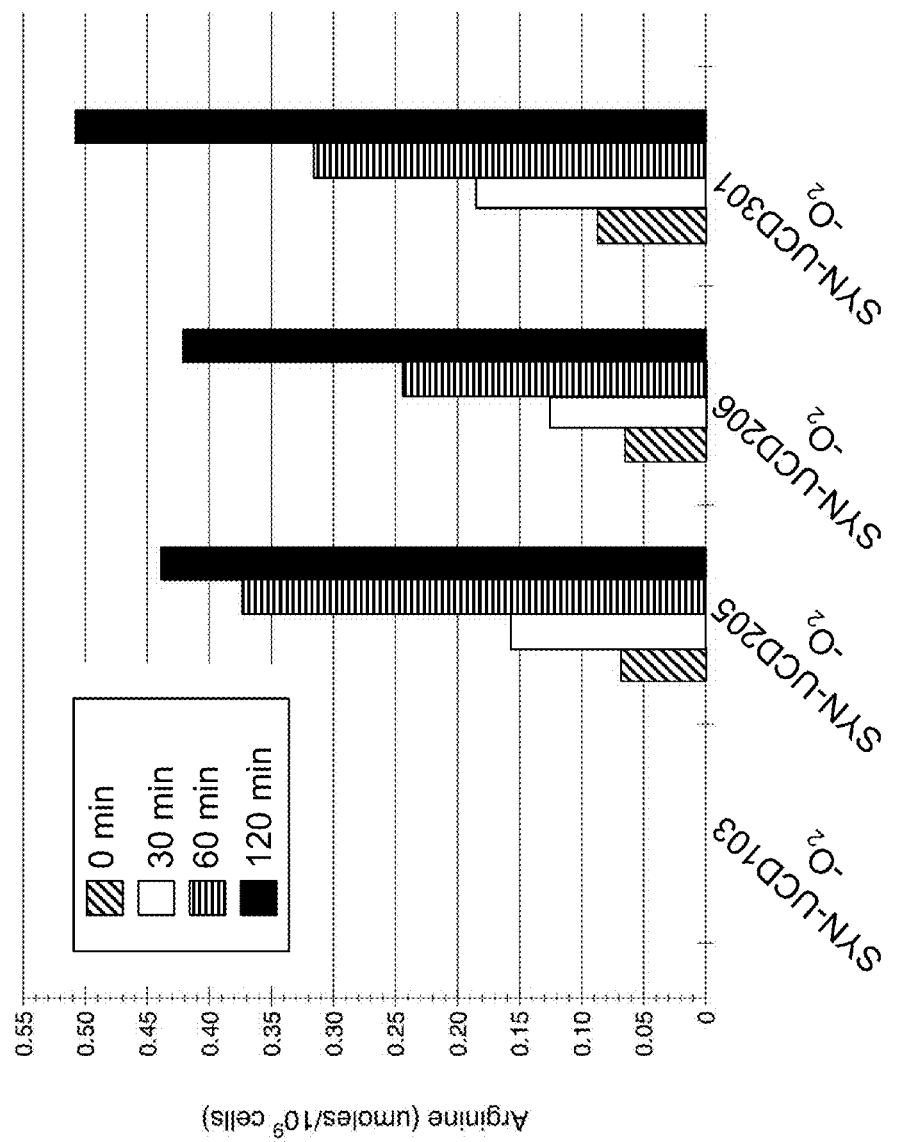
FIGS. 31A and 31B depict bar graphs of ammonia levels in the media at various time points post anaerobic induction.

FIG. 31A shows the levels of arginine production of SYN-UCD205, SYN-UCD206, and SYN-UCD301 measured at 0, 30, 60, and 120 minutes. Arginine production was comparable between all three strains, with the greatest arginine production seen with SYN-UCD301 at 120 minutes, indicating that chromosomal integration of FNR ArgA fbr results in similar levels of arginine production as seen with the low copy plasmid strains expressing the same construct, and may even slightly increase the rate of arginine production. SYN-UCD206 exhibited attenuated arginine production as compared to SYN-UCD205 and SYN-UCD-301 (lower arginine levels at 60 minutes), but reached comparable arginine production levels at 120 minutes, indicating that ΔThyA may have a slight attenuating effect on arginine production. No arginine production was detected for the SYN-UCD103 control.

Next, samples were prepared as described above and arginine production at 120 min post induction was compared between (1) SYN-UCD204 (comprising ΔArgR and argAfbr expressed under the control of a tetracycline-inducible promoter on a low-copy plasmid), and (2) SYN-UCD301 (comprising ΔArgR, CmR and argAfbr expressed under the control of a FNR-inducible promoter integrated into the chromosome at the malEK locus), (3) SYN-UCD302 (comprising ΔArgR, ΔThyA, CmR (chloramphenicol resistance) and argAfbr expressed under the control of a FNR-inducible promoter integrated into the chromosome at the malEK locus), and (4) SYN-UCD303 (comprising ΔArgR, ΔThyA, KanR (kanamycin resistance) and argAfbr expressed under the control of a FNR-inducible promoter integrated into the chromosome at the malEK locus).

Figure 31B:
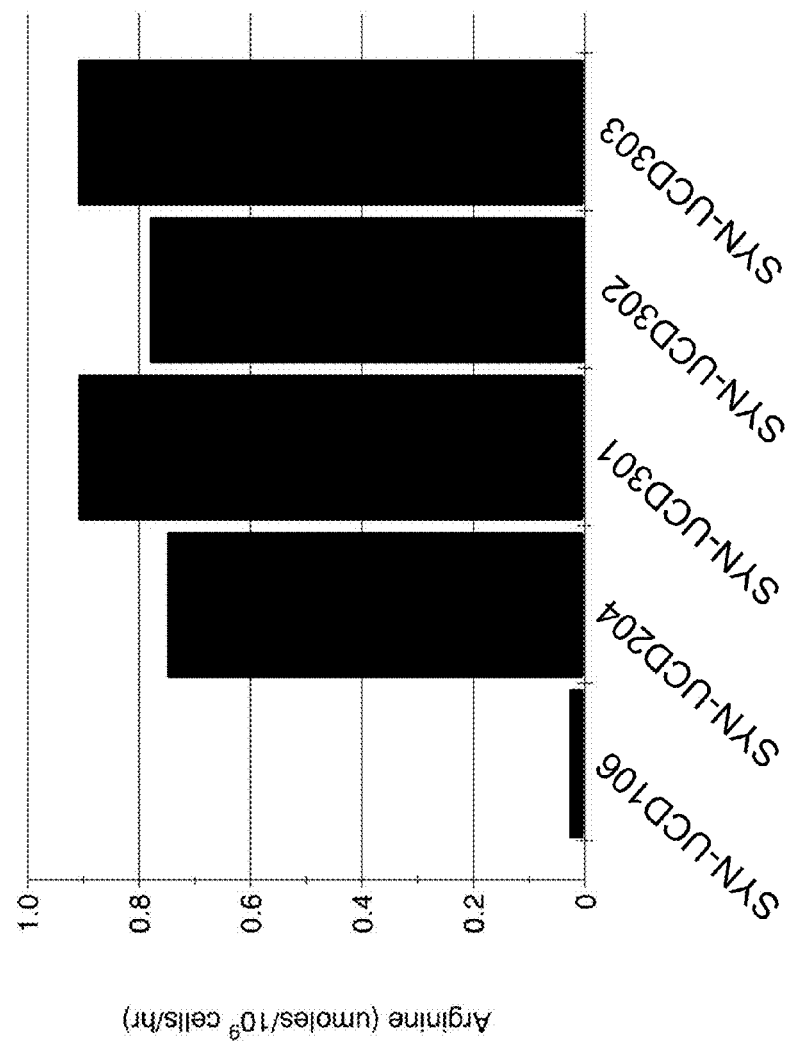

SYN-UCD106, comprising ΔArgR and ΔThyA was used as is a control Nissle construct. Results are shown in FIG. 31B. As seen in FIG. 31B, arginine production was elevated to between 0.7 and 0.9 umol/1×109 cells, indicating that arginine production is at similar levels in strains bearing ArgAfbr on a plasmid and strains with integrated copies of ArgAfbr.

Example 19

Efficacy of Genetically Engineered Bacteria in a Mouse Model of Hyperammonemia and UCD (Spf-Ash) Maintained on a High Protein Diet The hyperammonia/UCD (spf-ash) model described in Example 14 was used to assess the in vivo efficacy of genetically engineered bacteria encoding ArgAfbr driven by a fnr promoter integrated into the bacterial chromosome on ammonia levels upon administration of a high protein diet. Mice were treated with unmodified control Nissle bacteria or Nissle bacteria engineered to produce high levels of arginine or citrulline as described above.

Two strains, one with a ThyA deletion (SYN-UCD303) and one without a ThyA deletion (SYN-UCD301) were tested for efficacy and compared to determine whether ΔThyA may influence the efficacy of ammonia removal from the blood with these stains harboring chromosomal fnr-ArgAfbr.

Figure 32A:
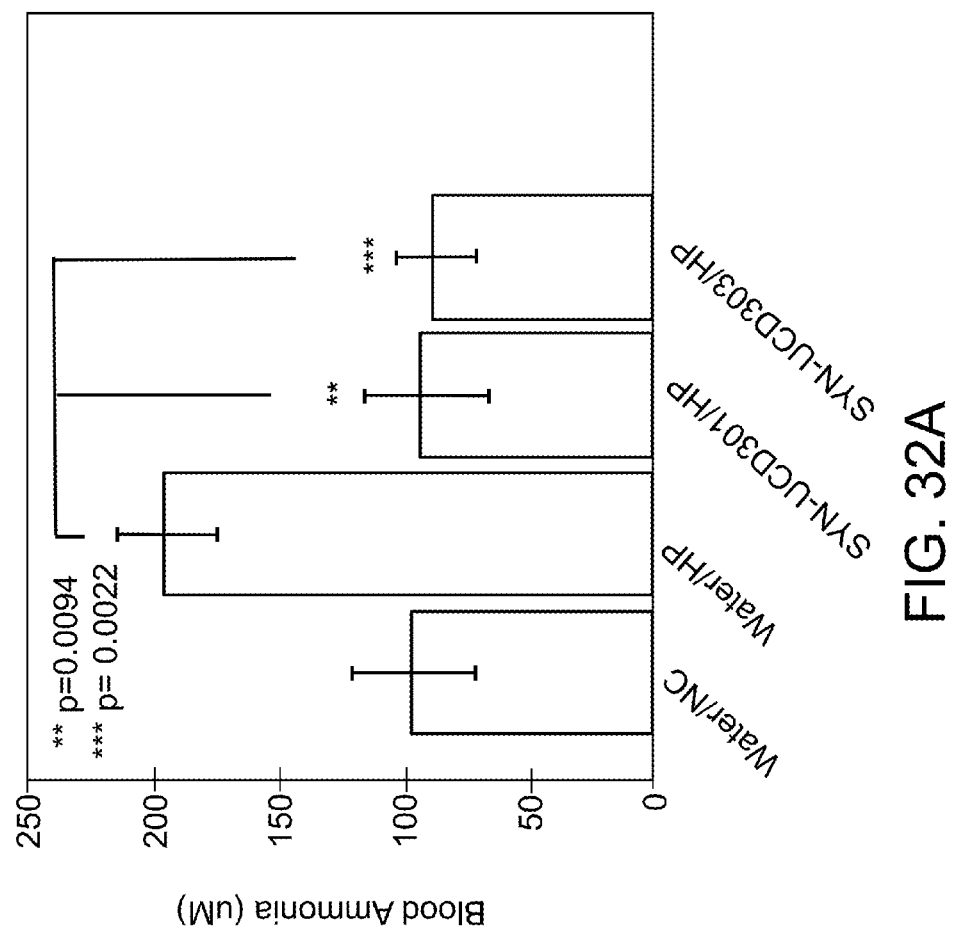
FIGS. 32A and 32B depicts a bar graph of ammonia levels and a survival curve for hyperammonemic spf$^{ash}$ mice on a normal (NC) or high protein (HP) diet. Two strains with an integrated copy of FNR-ArgAfbr, one with (SYN-UCD303) and one without a ThyA deletion (SYN-UCD301) were compared.
Figure 32B:
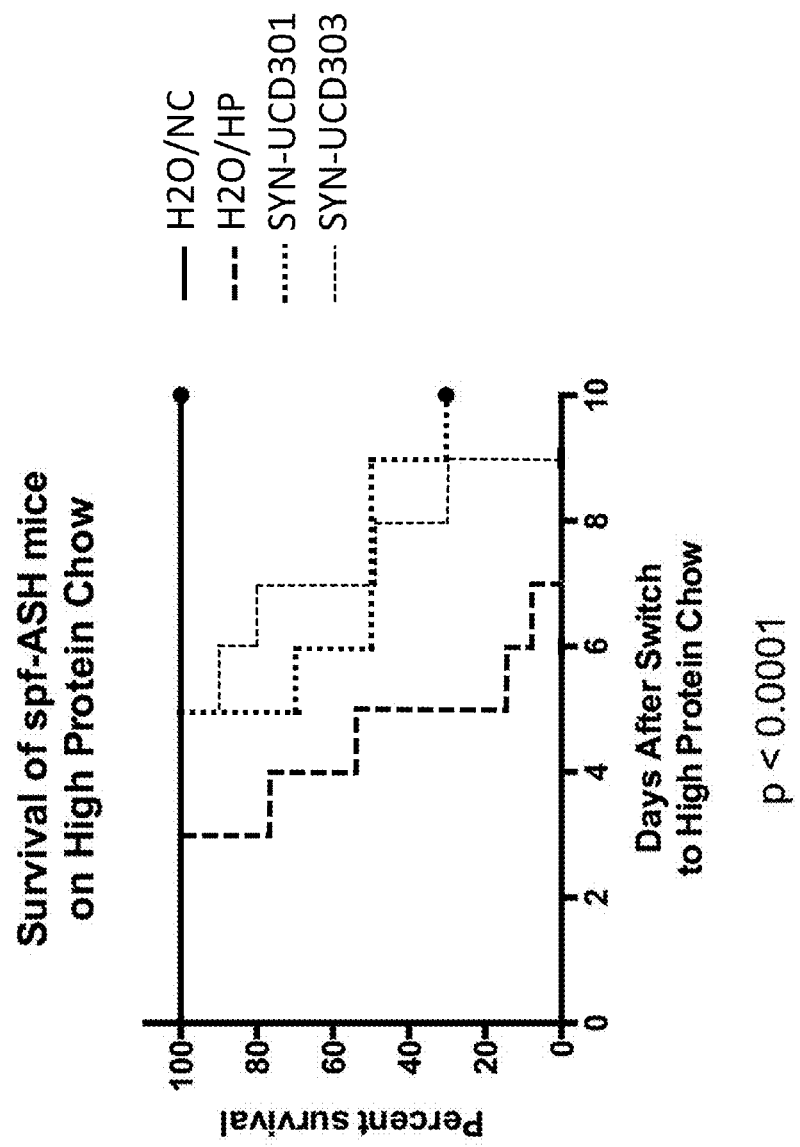

Spf-ash mice were treated by oral administration with the genetically engineered bacteria (SYN-UCD301, SYN-UCD303) or H2O control. Normal and high protein chow was provided as follows: SYN-UCD301, high protein chow (n=10); SYN-UCD303, high protein chow (n=10); H2O control, normal chow (n=10); H2O control, high protein chow (n=10). For SYN-UCD301, SYN-UCD303, and SYN-UCD106, a dose of 100 ul of >1×10$^{10}$ cells/ml was administered twice a day for 12 days, with the exception of days 1, 5, 6, and 7, where bacteria were administered once. Essentially the same protocol was followed as described in Example 16, with blood being drawn on day 5 to obtain ammonia levels (FIG. 32A). On day 10, survival rates were analyzed and a time course of survival is shown in FIG. 32B.

As depicted in FIG. 32A, ammonia levels of spf-ash mice in a high protein diet were reduced in the SYN-UCD301 and SYN-UCD303 groups as compared to the H2O high protein diet control group, indicating that the FNR inducible promoter can drive ArgAfbr expression when the construct is integrated into the chromosome, resulting in decreased ammonia levels in the blood of the mice treated with the engineered bacteria. The observed reduction in ammonia levels was similar in both SYN-UCD301 and SYN-UCD303, indicating that ThyA auxotrophy does not have a significant effect on efficacy of SYN-UCD303. As seen in FIG. 32B, SYN-UCD301 and SYN-UCD303 showed prolonged survival as compared to controls. Experiments were conducted twice sequentially with similar results.

Example 20

Comparison of Efficacy at Various Doses

To determine the lowest dose which can be used, while achieving optimal arginine production in the hyperammonia/UCD (spf-ash) model described in Example 14, three doses of SYN-UCD303 were administered.

Figure 33:
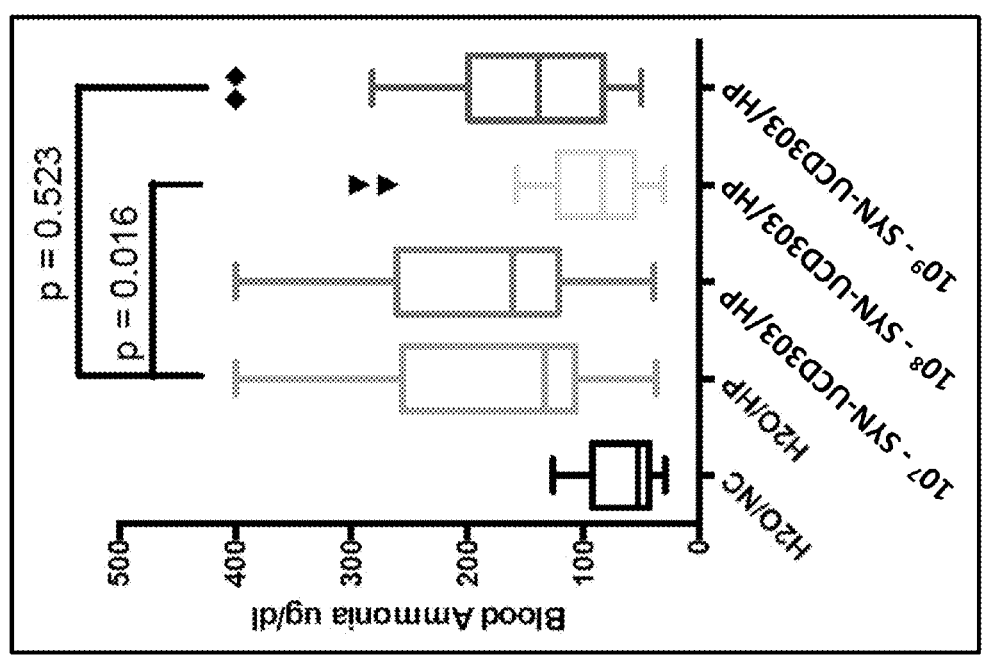
FIG. 33 depicts a graph of bood ammonia levels in an hyperammonemic spf$^{ash}$ mice on a normal (NC) or high protein (HP) diet. For SYN-UCD303, doses of 1×10$^7$, 1×10$^8$, 1×10$^9$, and 1×10$^{10}$ cells were administered daily over a time course of 12 days. Blood ammonia levels were measured on day 5. Both doses of 1×10$^8$ and 1×10$^9$ were sufficient to result in a significant reduction of blood ammonia levels in this model. SYN-UCD303 comprises ΔArgR, PfnrS-ArgAfbr integrated into the chromosome at the malEK locus, ΔThyA, and Kanamycin resistance.

Spf-ash mice were treated by gavage with the genetically engineered bacteria (SYN-UCD303) or H2O control. For SYN-UCD303, doses of 1×10$^7$, 1×10$^8$, 1×10$^9$, and 1×10$^{10}$ CFUs were administered in a volume of 100 ul twice a day for 12 days, with the exception of days 1, 5, 6, and 7, where bacteria were administered once. Normal chow or high protein chow was provided as follows: SYN-UCD303 (1×10$^7$ CFU), high protein chow (n=10); SYN-UCD303 (1×10$^8$ CFU), high protein chow (n=10); SYN-UCD303 (1×10$^9$ CFU), high protein chow (n=10); H2O control, normal chow (n=10); H2O control, high protein chow (n=10). Essentially the same protocol was followed as described in Example 16, with blood being drawn on day 5 to obtain ammonia levels. Blood ammonia levels were analyzed for each dose on day 5. Results are depicted in FIG. 33. Both doses of 1×10$^8$ and 1×10$^9$ were sufficient to result in a significant reduction of blood ammonia levels in this model.

Example 21

Nissle Residence

Unmodified *E. coli* Nissle and the genetically engineered bacteria of the invention may be destroyed, e.g., by defense factors in the gut or blood serum. The residence time of bacteria in vivo may be calculated. A non-limiting example using a streptomycin-resistant strain of *E. coli* Nissle is described below. In alternate embodiments, residence time is calculated for the genetically engineered bacteria of the invention.

C57BL/6 mice were acclimated in the animal facility for 1 week. After one week of acclimation (i.e., day 0), streptomycin-resistant Nissle (SYN-UCD103) was administered to the mice via oral gavage on days 1-3. Mice were not pre-treated with antibiotic. The amount of bacteria administered, i.e., the inoculant, is shown in Table 25. In order to determine the CFU of the inoculant, the inoculant was serially diluted, and plated onto LB plates containing streptomycin (300 μg/mL). The plates were incubated at 37° C. overnight, and colonies were counted.

TABLE 25

| CFU administered via oral gavage CFU administered via oral gavage | | | |
|---|---|---|---|
| Strain | Day 1 | Day 2 | Day 3 |
| SYN-UCD103 | 1.30E+08 | 8.50E+08 | 1.90E+09 |

On days 2-10, fecal pellets were collected from up to 6 mice (ID NOs. 1-6; Table 14). The pellets were weighed in tubes containing PBS and homogenized. In order to determine the CFU of Nissle in the fecal pellet, the homogenized fecal pellet was serially diluted, and plated onto LB plates containing streptomycin (300 μg/mL). The plates were incubated at 37° C. overnight, and colonies were counted.

Fecal pellets from day 1 were also collected and plated on LB plates containing streptomycin (300 μg/mL) to determine if there were any strains native to the mouse gastrointestinal tract that were streptomycin resistant. The time course and amount of administered Nissle still residing within the mouse gastrointestinal tract is shown in Table 26.

FIG. 34 depicts a graph of Nissle residence in vivo. Streptomycin-resistant Nissle was administered to mice via oral gavage without antibiotic pre-treatment. Fecal pellets from six total mice were monitored post-administration to determine the amount of administered Nissle still residing within the mouse gastrointestinal tract. The bars represent the number of bacteria administered to the mice. The line represents the number of Nissle recovered from the fecal samples each day for 10 consecutive days.

TABLE 26

| Nissle residence in vivo | | | | |
|---|---|---|---|---|
| ID | Day 2 | Day 3 | Day 4 | Day 5 |
| 1 | 2.40E+05 | 6.50E+03 | 6.00E+04 | 2.00E+03 |
| 2 | 1.00E+05 | 1.00E+04 | 3.30E+04 | 3.00E+03 |
| 3 | 6.00E+04 | 1.70E+04 | 6.30E+04 | 2.00E+02 |
| 4 | 3.00E+04 | 1.50E+04 | 1.10E+05 | 3.00E+02 |
| 5 |  | 1.00E+04 | 3.00E+05 | 1.50E+04 |
| 6 |  | 1.00E+06 | 4.00E+05 | 2.30E+04 |
| Avg | 1.08E+05 | 1.76E+05 | 1.61E+05 | 7.25E+03 |

| ID | Day 6 | Day 7 | Day 8 | Day 9 | Day 10 |
|---|---|---|---|---|---|
| 1 | 9.10E+03 | 1.70E+03 | 4.30E+03 | 6.40E+03 | 2.77E+03 |
| 2 | 6.00E+03 | 7.00E+02 | 6.00E+02 | 0.00E+00 | 0.00E+00 |
| 3 | 1.00E+02 | 2.00E+02 | 0.00E+00 | 0.00E+00 | 0.00E+00 |
| 4 | 1.50E+03 | 1.00E+02 |  | 0.00E+00 | 0.00E+00 |
| 5 | 3.10E+04 | 3.60E+03 |  | 0.00E+00 | 0.00E+00 |
| 6 | 1.50E+03 | 1.40E+03 | 4.20E+03 | 1.00E+02 | 0.00E+00 |
| Avg | 8.20E+03 | 1.28E+03 | 2.28E+03 | 1.08E+03 | 4.62E+02 |

Example 22

Intestinal Residence and Survival of Bacterial Strains In Vivo

Figure 35A:
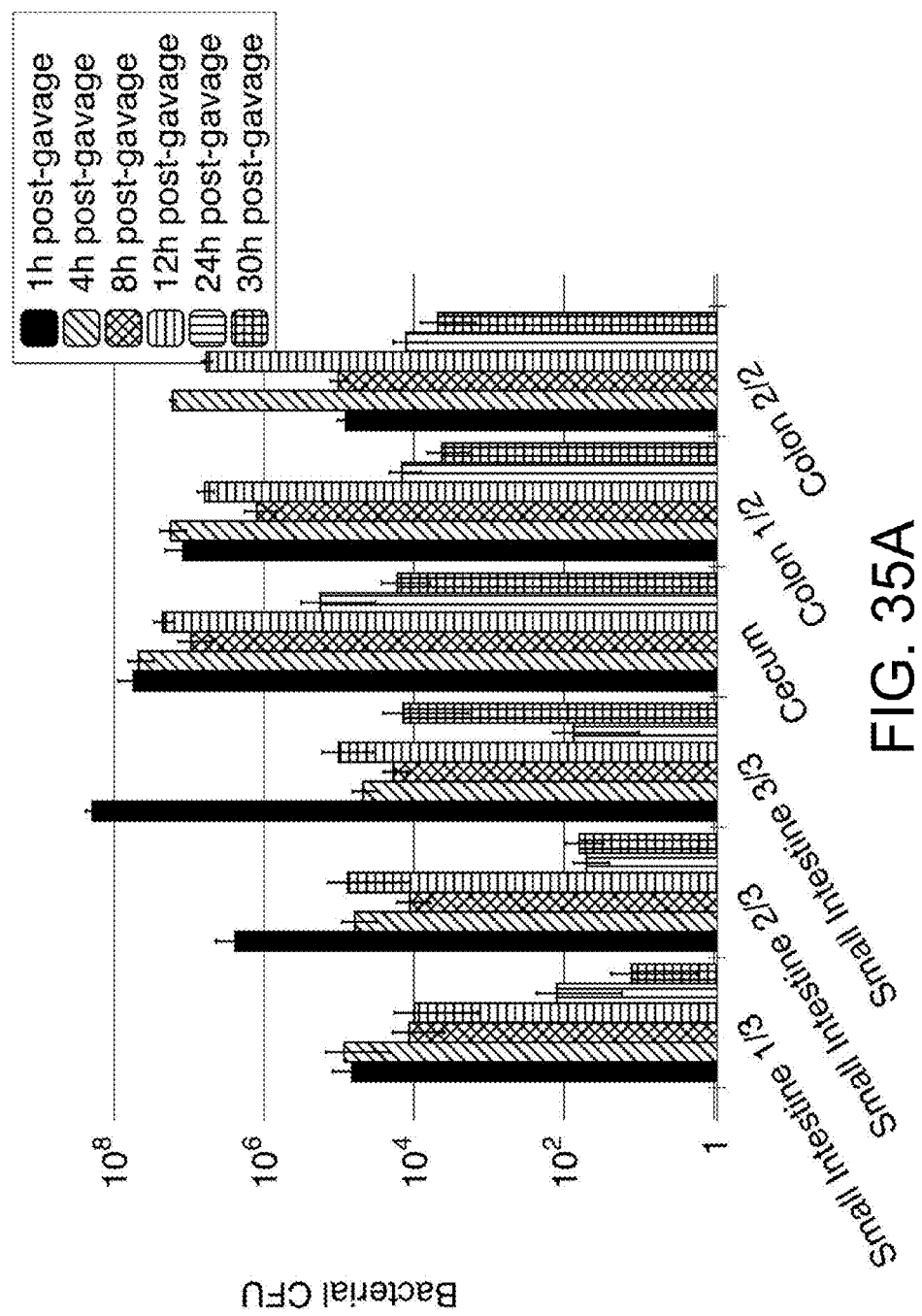
FIGS. 35A, 35B, and 35C depict bar graphs of bacterial residence in various compartments of the intestinal tract at 1, 4, 8, 12, 24, and 30 hours post gavage. Mice were treated with approximately 10$^9$ CFU, and at each timepoint, animals (n=4) were euthanized, and intestine, cecum, and colon were removed. The small intestine was cut into three sections, and the large intestine and colon each into two sections. Intestinal effluents gathered and CFUs in each compartment were determined by serial dilution plating.
Figure 35B:
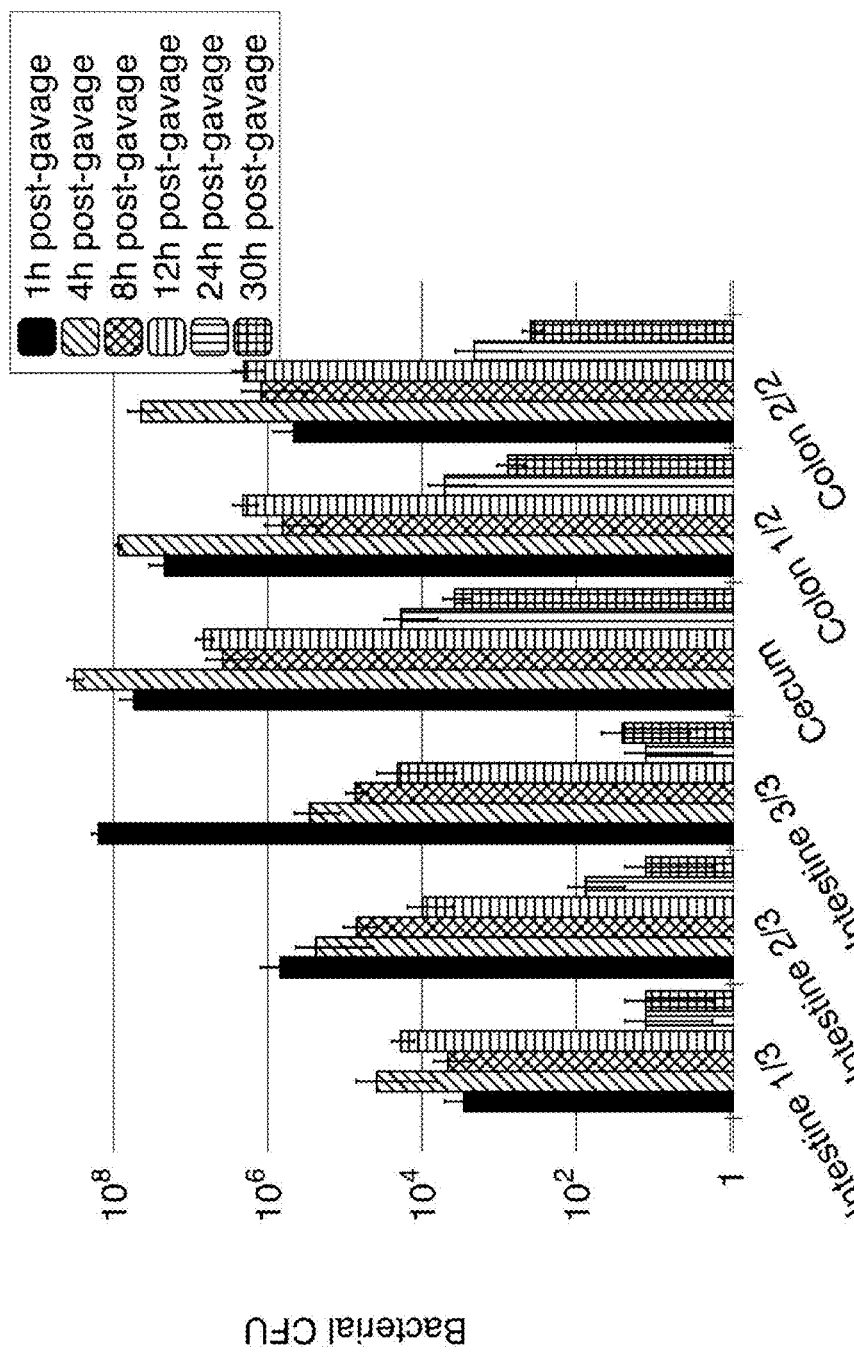
Figure 35C:
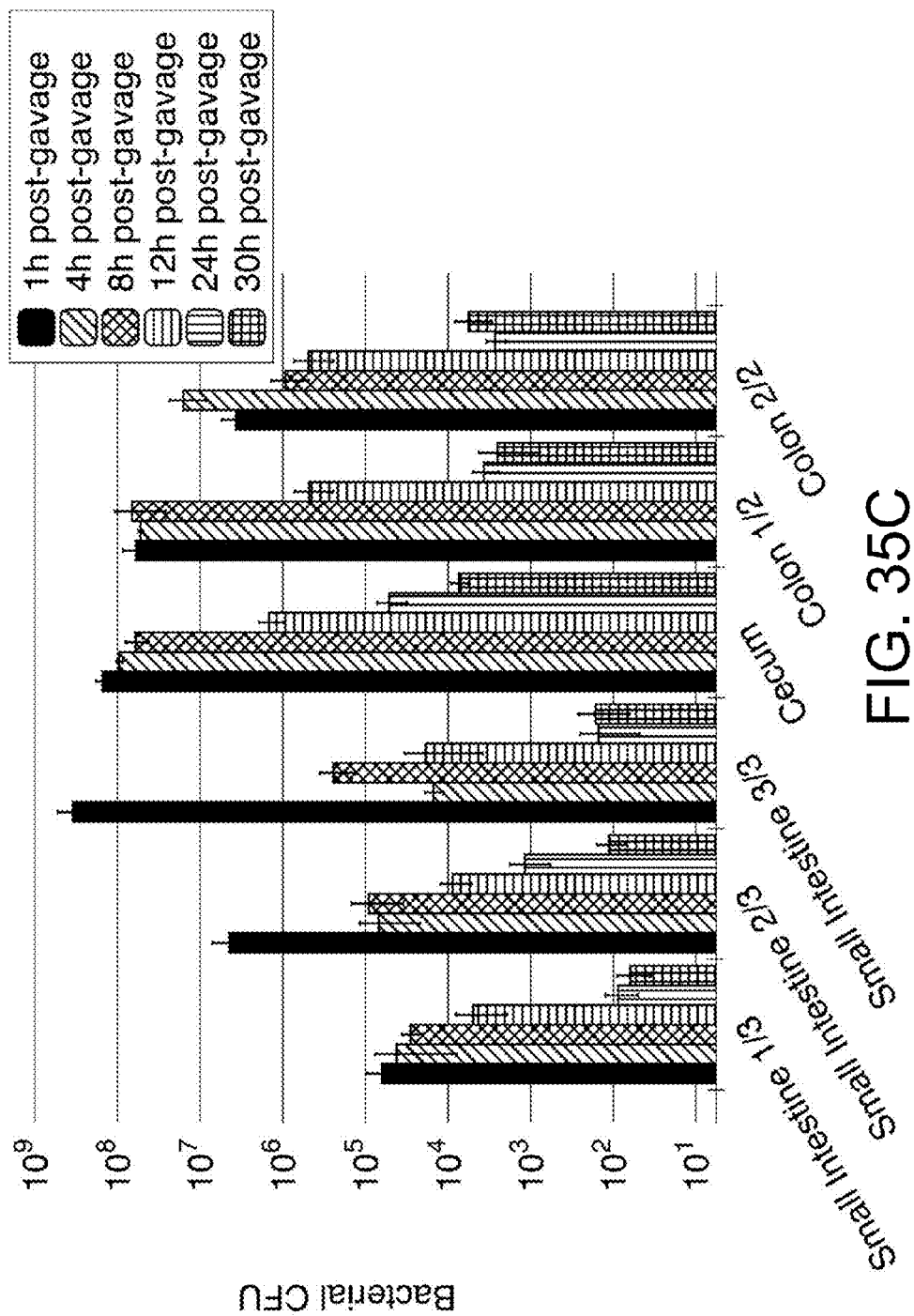

Localization and intestinal residence time of SYN-UCD303 (integrated fnrS inducible promoter driving ArgAfbr, kanamycin resistance, ΔThyA, FIG. 35C) was compared to SYN-UCD106 (ΔArgR, ΔThyA, and chloramphenicol resistance, FIG. 35B) and SYN-UCD103 (streptomycin resistant Nissle, FIG. 35A). Mice were gavaged, sacrificed at various time points, and effluents were collected from various areas of the small intestine cecum and colon.

Bacterial cultures were grown overnight and pelleted. The pellets were resuspended in PBS at a final concentration of approximately $10^{10}$ CFU/mL. Mice (C57BL6/J, 10-12 weeks old) were gavaged with 100 μL of bacteria (approximately 109 CFU). Drinking water for the mice was changed to contain 0.1 mg/mL anhydrotetracycline (ATC) and 5% sucrose for palatability. At each timepoint (1, 4, 8, 12, 24, and 30 hours post-gavage), animals (n=4) were euthanized, and intestine, cecum, and colon were removed. The small intestine was cut into three sections, and the large intestine and colon each into two sections. Each section was flushed with 0.5 ml cold PBS and collected in separate 1.5 ml tubes. The cecum was harvested, contents were squeezed out, and flushed with 0.5 ml cold PBS and collected in a 1.5 ml tube. Intestinal effluents were placed on ice for serial dilution plating.

In order to determine the CFU of bacteria in each effluent, the effluent was serially diluted, and plated onto LB plates containing kanamycin. The plates were incubated at 37° C. overnight, and colonies were counted. The amount of bacteria and residence time of SYN-UCD103, SYN-UCD106, and SYN-UCD303 seen in each compartment is shown in FIG. 35. As seen in FIG. 35, all three strains behave in a similar manner. Comparing FIG. 35A with FIG. 35B, ΔThyA auxotrophy and ΔArgR does not seem to have any substantial effect on residency and transit time.

Example 23

Effect of Auxotrophy on Intestinal Residence Time

To determine if auxotrophy may have an effect on localization and time of residence, the mouse model described above is used to compare the residency of SYN-UCD303 (ΔThyA) with SYN-UCD304 (wild type ThyA). SYN-UCD103 (streptomycin resistant control Nissle) is administered in parallel to determine whether the Arg R deletion and argAfbr have an effect on residence.

Bacteria are prepared and mice are gavaged, euthanized and intestinal effluents collected at various time points as described in Example 22. To determine the CFU of bacteria in each effluent, the effluent is serially diluted and plated as described in Example 20. For SYN-UCD103 streptomycin containing plates and for SYN-UCD301 chloramphenicol containing plates are used.

Example 24

TAA Model of Hyperammonemia

TAA treatment of mice has previously been employed in the literature to model increased blood ammonia levels associated with UCDs, acute and chronic liver disease and HE (Wallace M C, et al., Lab Anim. 2015 April; 49(1 Suppl):21-9. Standard operating procedures in experimental liver research: thioacetamide model in mice and rat)s. In some embodiments, a TAA-induced mouse model of hyperammonemia is employed to investigate the ability of the genetically engineered bacteria to reduce blood ammonia levels. The TAA serves as an alternative to the spf-ash model. Because spf-ash is a genetic model, the numbers of mice are limiting so developing an inducible model in wild-type mice would greatly facilitate in vivo testing of potential strains of interest.

To investigate the effects of engineered bacteria on prolonged elevations of blood ammonia, the bacteria are administered to C57BL6 mice that are also administered a dose of 300 mpk thioacetamide (TAA).

C57BL6 (10 weeks old) are administered one daily dose of SYN-UCD103 or SYN-UCD303 (100 ul of $>1\times10^{10}$ cells/ml) or vehicle control. Alternatively, mice are administered 2 daily doses of bacteria (100 ul of $>1\times10^{10}$ cells/ml) (n=5 for each treatment group), once in the AM and once in the PM. After three days of pre-dosing with the bacteria, the mice are treated intraperitoneally with thioacetamide (TAA) at 300 mpk or with H2O as control. Alternatively, the mice are treated twice daily, once in the AM and once in the PM with 250 mpk. The duration of the study is five days. Ammonium levels are measured and overall health survival, body weight change is monitored.

In brief, animals are acclimated for 7 days. On day 1 of the time course, animals are weighed, bled to measure baseline ammonia and collect fecal pellets (per cage), and are randomized based on initial blood ammonia levels. Animals are dosed by oral gavage either once or twice (AM and PM) with H2O, SYN-UCD103 or SYN-UCD303 (100 ul/dose/animal). Water is changed to H2O (+)20 mg/ml ATC. On day 2, animals are dosed by oral gavage either once or twice (AM and PM) with H2O, SYN-UCD103 or SYN-UCD303 (100 ul/dose/animal). On day 3, animals are weighed and dosed by oral gavage either once or twice (AM and PM) with H2O, SYN-UCD103 or SYN-UCD303 (100 ul/dose/animal). Additionally, animals are dosed intraperitoneally with 300 mpk TAA (or saline control). Alternatively, animals are dosed with 250 mpk TAA (or saline control) once in the AM and once in the PM. On day 4, animals are weighed, bled, and blood ammonia is measured. Fecal pellets are collected per cage. Animals are dosed per oral gavage either once or twice (AM and PM) with H2O, SYN-UCD103 or SYN-UCD303 (100 ul/dose/animal). Animals may also be dosed with 250 mpk TAA (or saline control). On day 5, animals are weighed, bled, and blood ammonia levels are measured. Fecal pellets are collected (per cage). Animals are dosed by oral gavage either once or twice (AM and PM) with H2O, SYN-UCD103 or SYN-UCD303 (100 ul/dose/animal). Ammonium levels, bacterial load in the fecal pellets, and overall health survival, and body weight changes are monitored.

Example 25

Model of Hyperammonemia Using Arginase Inhibitors

As an alternative to the genetic spf-ash model, arginase inhibitors +/- high protein chow are used as an inducible model of hyperammonemia. Arginase inhibitors fall into at least 2 classes (described in Steppan et al., Front Immunol. 2013; 4: 278. Development of Novel Arginase Inhibitors for Therapy of Endothelial Dysfunction). The first group of arginase inhibitors consisted of the boronic acid analogs of 1-arginine (2)S-amino-6-hexanoic acid (ABH) and S-2-BEC both of which inhibit the catalytic activity of arginase. Another category of arginase inhibitors, that is mainly represented by N-hydroxy-l-arginine (NOHA) and N-hydroxy-nor-l-arginine (nor-NOHA), is characterized by N-hydroxy-guanidinium side chains and inhibit arginase by displacing the metal-bridging hydroxide ion of arginase with their N-hydroxy group. The model development study employs an arginase inhibitor from each group, BEC and nor-NOHA +/- high protein chow (70% protein).

To determine if engineered bacteria can change ammonium levels in the blood, inducible models using an arginase inhibitor from each group, BEC and nor-NOHA, +/- high protein chow (70% protein) (70% protein) in wild type mice are employed. C57BL6 (Female, 8 weeks) are treated by oral gavage with the genetically engineered bacteria (100 ul of $>1\times10^{10}$ cells/ml) or a vehicle control and intraperitoneally either with BEC or norNOHA, and are kept either on a normal chow (n=5 per treatment group) or a high protein chow diet (n=5 per treatment group). Administration groups are as follows for SYN-UCD303 and a vehicle control-treated animals: normal chow (n=5); high protein chow (70% protein chow; n=5); high protein chow (+)BEC (n=5); high protein chow (+)norNOHA (n=5).

On day 1 of the time course, animals are weighed, bled to measure baseline ammonia, and are randomized based on initial blood ammonia levels. Fecal pellets are collected (per cage). Animals are dosed by oral gavage with H2O, SYN-UCD303 or SYN-UCD103 (100 ul/dose/animal). Water is changed to H2O (+)20 mg/ml ATC. On day 2, animals are dosed by oral gavage either once or twice (AM and PM) with H2O, SYN-UCD303 or SYN-UCD103 (100 ul/dose/animal). On day 3, animals are weighed and dosed by oral gavage either once or twice (AM and PM) with H2O, SYN-UCD303 or SYN-UCD103 (100 ul/dose/animal). Additionally, animals are dosed intraperitoneally with BEC (25 mpk) or norNOHA (100 mpk) or saline control. For the high protein diet groups, the chow is changed from normal chow to 70% protein chow. On day 4, animals are weighed, bled, and blood ammonia is measured. Fecal pellets are collected per cage. Animals are dosed per oral gavage either once or twice (AM and PM) with H2O, SYN-UCD303 or SYN-UCD103 (100 ul/dose/animal). Animals are dosed intraperitoneally with BEC (25 mpk) or norNOHA (100 mpk). On day 4, animals are dosed per oral gavage either once or twice (AM and PM) with H2O, SYN-UCD303 or SYN-UCD103 (100 ul/dose/animal). Animals are weighed, bled 1 h post dose, and blood ammonia is measured. Fecal pellets are collected per cage. Animals are also dosed intraperitoneally with BEC (25 mpk) or norNOHA (100 mpk). On day 5, Animals are dosed by oral gavage either once or twice (AM and PM) with H2O, SYN-UCD303 or SYN-UCD103 (100 ul/dose/animal). Animals are weighed, bled 1 h post dose, and ammonia levels are measured.

Figure 28A:
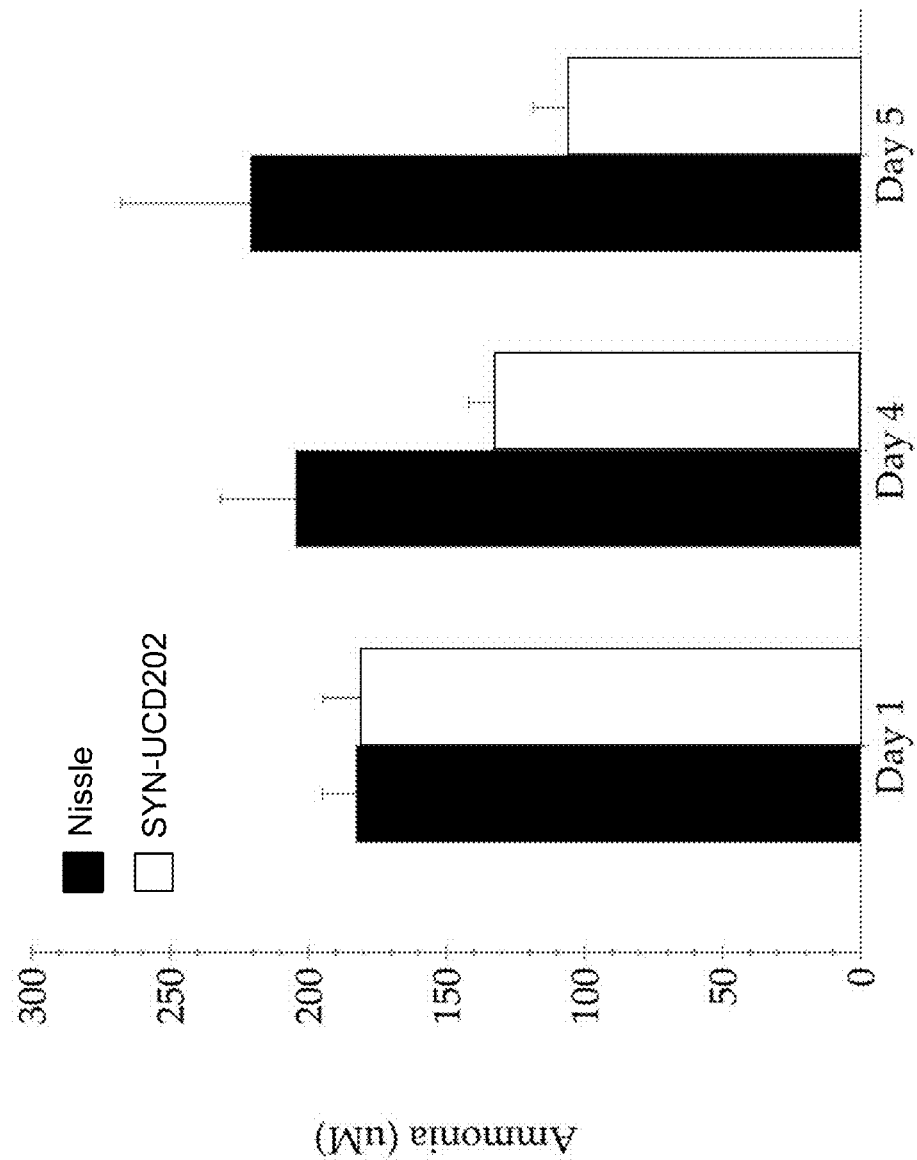
FIGS. 28A, 28B, and 28C depict bar graphs of ammonia levels in hyperammonemic TAA mice.
Figure 28B:
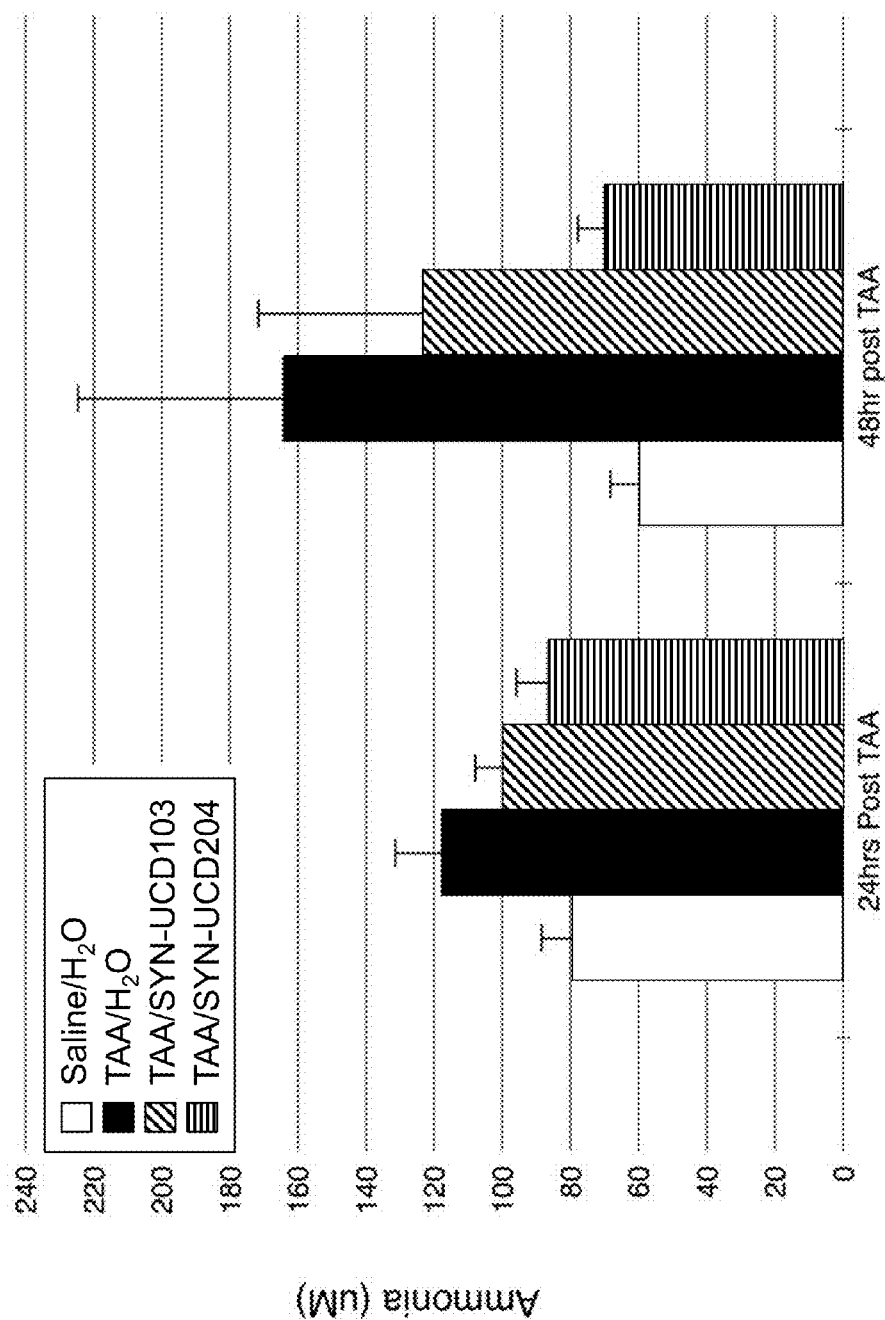
Figure 28C:
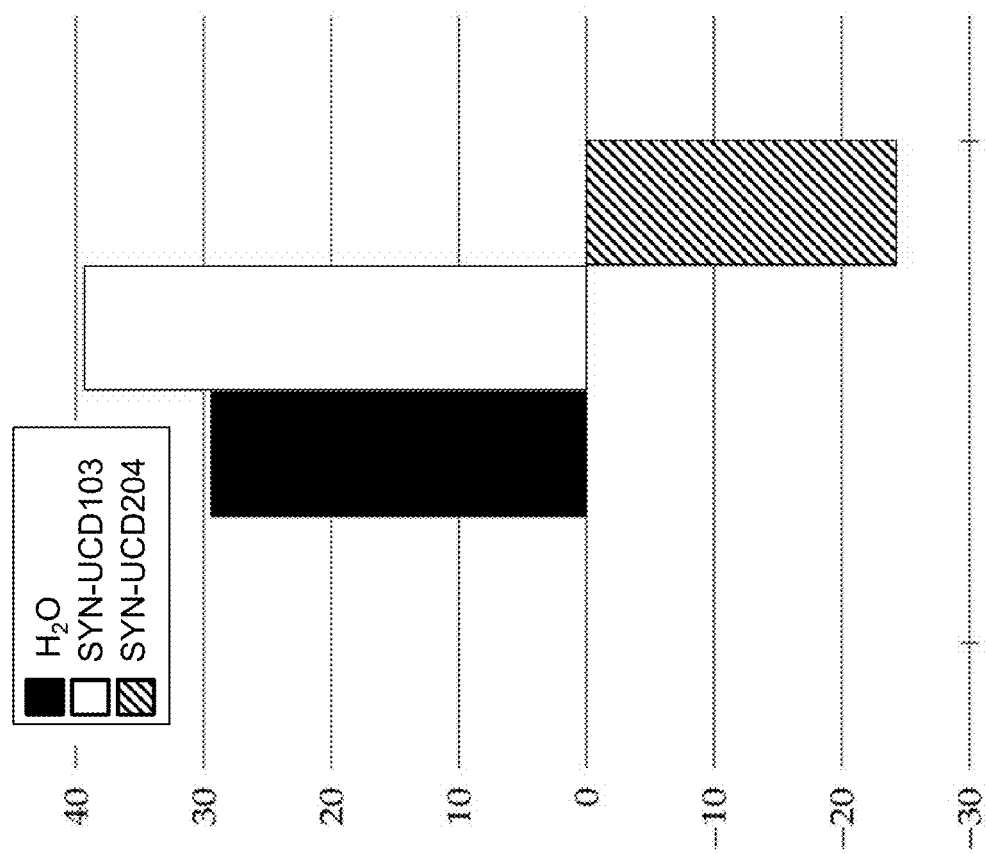

A similar study was conducted using strains SYN-UCD202, SYN-UCD204, and SYN-UCD103, and results are shown in FIG. 28.

Example 26

Effect of Proliferation Potential and Metabolic Activity on Arginine Production The requirement of cell division and/or active metabolism for arginine production from the genetically engineered bacteria was investigated in strain SYNUCD-303.

SYNUCD-301 were incubated with 70% isopropanol or phosphate buffered saline (PBS) as a control for 1 hour with shaking. 70% isopropanol disrupted the cellular membrane, which prevented cell division, but should allow cell metabolism. PBS incubation had no effect on the cells (not shown). After treatment, the cells were mixed at specific ratios in M9 media supplemented with 0.5% glucose and 3 mM thymidine. Cells were incubated with shaking at 37 C for 2 hours. Cells can use the ammonium chloride contained in the M9 media to form arginine. Arginine concentration was measured in the media at time zero and again after the 2 hour incubation, and the amount of arginine produced per hour per billion cells was calculated. As seen in FIGS. 36A and 36B, a greater ratio of isopropanol treated cells to untreated in a culture results in fewer CFUs as determined by plating, and lower levels of arginine production. Arginine production relative to amount of bacteria present remained constant across the various cultures (FIG. 36C). These results indicate that only viable bacteria are contributing to arginine production.

Example 27

Repeat-Dose Pharmacokinetic and Pharmacodynamic Study of SYN-UCD-303 Following Daily Nasogastric Gavage Dose Administration for 28-Days in Cynomolgus Monkeys (Non-GLP)

To evaluate any potential toxicities arising from administration of the genetically engineered bacteria or E coli Nissle alone, the pharmacokinetics and pharmacodynamics of SYN-UCD303 and an E. coli Nissle with kanamycin resistance (SYN-UCD107) were studied following daily nasogastric gavage (NG) dose administration for 28-days to female cynomolgus monkeys. Cynomolgus monkeys were selected because this species is closely related, both phylogenetically and physiologically, to humans and is a species commonly used for nonclinical toxicity evaluations. The genetically engineered bacteria were administered by nasal gastric gavage, consistent with the proposed route of administration in humans. Animals overall well-being (clinical observations), weight clinical pathology (serum chemistry, hematology, and coagulation) were tracked. Fecal samples were examined for bacterial load. Plasma is analyzed for ammonia levels.

A. Materials, Animals and Dosing Regimen:

The study was conducted in compliance with nonclinical Laboratory Studies Good Laboratory Practice Regulations issued by the U.S. Food and Drug Administration (Title 21 of the Code of Federal Regulations, Part 58; effective Jun. 20, 1979) and the OECD Principles on Good Laboratory Practice (C[97]186/Final; effective 1997). The animals were individually housed based on the recommendations set forth in the Guide for the Care and Use of Laboratory Animals (National Research Council 2011).

Animals used in the study were Female Purpose-bred, non-naive cynomolgus monkey (Macaca fascicularis) with 3 to 6 kg (at initial physical exam) 3 to 8 years (at initial physical exam) of age (SNBL USA stock, Origin: Cambodia).

For control of bias, animals were randomized to groups in a weight-stratified manner to achieve similar group body weight distributions. The number of animals selected for randomization and their weights and ages are included in Table 27.

TABLE 27

Animals for randomization

| Sex | Number of Animals | Age | Weight |
|---|---|---|---|
| Female | 17 | 3 to 6 years | 3.1 to 4.7 kg |

Animals were identified by unique tattoo numbers.

Seventeen animals were acclimated for 7 days prior to dose initiation and fifteen animals were assigned to treatment groups. Spare animals were removed from the study after Day 1.

For the duration of the study, animals were offered PMI LabDiet® Fiber-Plus® Monkey Diet 5049 biscuits twice daily. Animal were fasted for at least 2 hours prior to dose administration and fed within 1 hour post dose. Animals also were fasted as required by specific procedures (e.g., prior to blood draws for serum chemistry, fecal collection). The diet was routinely analyzed for contaminants and found to be within manufacturer's specifications. No contaminants were expected to be present at levels that would interfere with the outcome of the study.

Fresh drinking water was provided ad libitum to all animals. The water was routinely analyzed for contaminants. No contaminants were present at levels that would interfere with the outcome of the study. Animals were given fruits, vegetables, other dietary supplements, and cage enrichment devices throughout the course of the study.

Previously quarantined animals were acclimated to the study room for 7 days prior to initiation of dosing (day 1). The last dosing occurred on day 28. A stratified randomization scheme incorporating body weights was used to assign animals to study groups. Animals were assigned to groups and treated as indicated in Table 28.

TABLE 28

Group Assignments

| Group | Test/Control Articles | Dose Level (cfu/Animal) | Conc. (cfu/mL) | Volume (mL/Animal) | Flush* Bicarb. Conc. (M) | Flush* Volume (mL/Animal) | Number of Females (Animal NO.) |
|---|---|---|---|---|---|---|---|
| 1 | Control Article* | 0 | 0 | 10 | 0.36 | 5 | 3 (1, 3, 5) |
| 2 | SYN-UCD107 | $1 \times 10^9$ | $1 \times 10^9$ | 1 | 0.12 | 14 | 3 (1, 3, 5) |
| 3 | SYN-UCD107 | $1 \times 10^{12}$ | $1 \times 10^{11}$ | 10 | 0.36 | 5 | 3 (1, 3, 5) |
| 4 | SYN-UCD303 | $1 \times 10^9$ | $1 \times 10^9$ | 1 | 0.12 | 14 | 3 (19, 21, 23) |
| 5 | SYN-UCD303 | $1 \times 10^{12}$ | $1 \times 10^{11}$ | 10 | 0.36 | 5 | 3 (25, 27, 29) |

*Concentration of Sodium Bicarbonate: .36M or 0.12M (0.36M for the control article)

SYN-UCD107 and SYN-UCD303 stocks were prepared at 1×109 cfu/mL and 1×10$^{11}$ cfu/mL in 15% glycerol in 1×PBS with 2.2% glucose and 3 mM thymidine and were kept at 86 to −60° C. (see Table 28). PBS made in 20% glycerol with sodium bicarbonate was used as a control vehicle. Carbonate concentration was 0.36M and 0.12M for sodium bicarbonate (see Table 28). On the day of each dosing, bacteria and vehicle control were removed from the freezer and put on ice and thawed and placed on ice until dosing.

Animals were dosed at 0, 1×10$^9$, or 1×10$^{12}$ cfu/animal. All animals were dosed via nasal gastric gavage (NG) followed by control/vehicle flush once daily for 28-days. The concentration of bicarbonate and volume for each group is specified in Table 28. Vials were inverted at least 3 times prior to drawing the dose in the syringe. The dose site and dose time (end of flush time) was recorded. On Day 6, Animals 19, 21, and 23 in Group 4 (SYN-UCD303, 1×109/animal) received 5 mL bicarbonate flush instead of 14 mL followed by test article dose administration.

B. Analysis

Overall Condition and Weight

Overall condition: Clinical observations were performed twice daily, beginning on Day −6 through 44. The first observation was in the AM. The second observation was no sooner than 4 hours after the AM observation. During the dosing phase, the second observation was performed 4 hour (±10 minutes) post dose administration. Additional clinical observations were performed, as necessary.

No test article-related clinical observations were identified in this study.

Incidental and/or procedural findings, commonly noted in similarly housed animals, occurred sporadically among individuals, were noted in control animals, were also present during the acclimation phase, and did not increase in severity and incidence among dose groups. These included findings related to skin (scab/crust, wounds, abrasions, abnormal skin discoloration, bruising), hair loss, kinked tail, sunken eyes, inappetence, emesis, and urogenital discharge.

Weight: Body weights were measured on Days −6, 1, 8, 11, 15, 22, 29, 36, and 43 prior to the first feeding and dose administration, as applicable.

No test article-related effects on body weights were identified in this study. Decreases of 5 to 10% body weight, relative to baseline (Day 1), was apparent across all groups, including control, by Day 36 and determined to be study procedure-related. Compared to Day 36, an upward trend was noted in the available body weight data on Day 43, albeit values did not completely return to baseline.

Clinical Pathology

Blood Collection: Animals were fasted overnight prior to daily dose administration and at least 4 hours prior to each series of collections that included specimens for serum chemistry and plasma bioanalysis. In these instances, associated clinical pathology evaluations were from fasted animals. Blood was collected by venipuncture from a peripheral vein of restrained, conscious animals via a single draw (if possible) and divided into appropriate tubes for analysis, as follows: Hematology: approximately 1.3 mL, K2EDTA tube; Coagulation: approximately 1.8 mL, 3.2% sodium citrate tube; Serum chemistry: approximately 1.0 mL, serum separator tube (SST); Plasma sample: approximately 1.0 mL, Lithium Heparin; The blood for clinical pathology assessment was processed to serum or plasma, or used intact, according to SNBL USA SOPs.

Whenever possible, blood was collected via a single draw and then divided appropriately. Specimen collection frequency is summarized in Table 29.

TABLE 29

Specimen collection frequency

| Time Point | Hematology | Coagulation | Serum Chemistry | Plasma Sample (on ice) | Fecal sample (on ice) |
|---|---|---|---|---|---|
| Acclimation Week 1 | 1x | 1x | 1x | 1x | 1x |
| Dosing Week 1 | Day 2 (Predose) | Day 2 (Predose) | Day 2 (Predose) | Days 2 and 7 (Predose) | Days 2, 4 and 7 (Postdose) |
| Dosing Week 2 | Day 14 (Predose) | Day 14 (Predose) | Day 14 (Predose) | Day 14 (Predose) | Day 14 (Postdose) |
| Dosing Week 3 | — | — | — | — | Once daily Days 18 through 21 (Predose) |
| Dosing Week 4 | — | — | — | Day28 (Predose) | Once daily Days 22 through 28 (Predose) |
| Dosing Weeks 5 | Day 30 | Day 30 | Day 30 | Day 30 | Once daily Days 29,, 30, and 35 |
| Dosing Weeks 6 | — | — | — | — | Day 40 |
| Dosing Weeks 6 | — | — | — | — | Days 46 and 50 |

— = Not applicable
x =Number of times procedure performed within the week

Table 30 Summarizes the Clinical Pathology Assay Information.

TABLE 30

Clinical pathology assay information

| Assay | Analyzed Sample Collection Days | Parameters Measured | Residual Sample Disposition |
|---|---|---|---|
| Hematology | Days −6, 2, 14, and 30 | Hematocrit, Hemoglobin, Mean corpuscular hemoglobin, Mean corpuscular hemoglobin concentration, Mean corpuscular volume, Mean platelet volume, Platelets, Red blood cells, Red cell distribution width, Reticulocyte absolute count, Reticulocyte percent, White blood cells, and Differential leukocyte absolute count: Basophils, Eosinophils, Lymphocytes, Monocytes, and Neutrophils | Stored at 2 to 8° C.[a] |
| Coagulation | Days −6, 2, 14, and 30 | Activated partial thromboplastin time, Fibrinogen, and Prothrombin time | Stored at −60 to −86° C.[a] |
| Serum Chemistry | Days −6, 2, 14, and 30 | Alanine Aminotransferase, Albumin, Albumin/Globulin Ratio, Alkaline Phosphatase, Aspartate Aminotransferase, Blood Urea Nitrogen, Calcium, Chloride, Creatine Kinase, Creatinine, Gamma Glutamyltransferase, Globulin, Glucose, Inorganic Phosphorus, Potassium, Sodium, Total Bilirubin, Total Cholesterol, Total Protein, and Triglyceride | Stored at −60 to −86° C.[a] |

[a]Residual samples were discarded prior to study finalization

No test article-related effects in hematology, coagulation, and serum chemistry parameters were identified in this study.

Plasma Samples: Animals were fasted for 4 hours prior to removal of the sample. Approximately 1 mL of blood were collected from the femoral vein and transferred into 2 mL lithium heparin tubes on Days −1 and 30, and prior to dose administration on Days 2, 7, 14, and 28. After collection of the target volume of blood in the tube, approximately 0.05 (on Days −1 and 2) or 0.1 mL (on Days 7, 14, 28, and 30) of mineral oil was added to cover the surface of blood in the tubes. Tubes were not inverted and were placed on wet ice. The samples were centrifuged within 15 minutes of collection at 2 to 8° C. to obtain plasma and the plasma was maintained on dry ice prior to storage at −60 to −86° C.

Analysis of specimens is conducted using a blood ammonia analyzer instrument.

Fecal Sample Collection: Two fecal samples per animal were collected at the target time points listed in Table 29. Sample collection dates and times were recorded. 50 mL falcon tube with approximately 5 mL PBS were used as the container (If feces is liquid, no PBS is added). To get the fecal sample weight, pre- and post-sampling weight of container was taken. Samples were collected from the bottom of the cage from each animal. To get fresh and un-contaminated samples, remaining food was removed and the cage pan was cleaned and squeegeed to remove debris and/or water before the collection. On Days −5, 2, 4, 7, and 14, food removals and pan cleanings were performed after the first feeding and/or dose administration. On Days 18, 20, 24, 28, 30, 35, 40, 46, and 50, the food removals and pan cleanings were performed the night before each collection. Visually fresh fecal samples were also collected in the morning before any procedures, except clinical observations, occurred.

Fecal Swab Collection: When fecal samples were not collected by the end of the scheduled day, fecal swab samples were collected with a cotton tip applicator from the rectum of animals restrained in a procedure cage.

Samples were put on wet ice immediately after the collection. Samples were stored at −20 to −15° C. until analysis. Analysis of specimens was conducted using a PCR analytical method as described in Example 31.

Two fecal samples per animal were collected on Day −5 and after dose administration on Days 2, 4, 7, and 14, and three fecal samples per animal were collected on Days 29, 30, 35, 40, 46, and 50, and prior to dose administration on Days 18 through 28. Fifty milliliter falcon tubes with approximately 5 mL PBS were used for the collections on Days −5 through 14, and 50 mL falcon tubes with approximately 5 mL PBS for Tube 1, 20 mL of 50% glycerol and 10 mM thymidine for Tube 2, and 20 mL of 50% glycerol/PBS for Tube 3, were used for the collections on Days 18 through 50. Specimens were put on wet ice immediately after the collection and the contents of each tube collected on Days 18 through 50 were broken-up and mixed using a sterile tongue depressor.

Since no fecal samples were collected from the animals listed in Table 29 by the end of the collection day, two fecal swab samples were collected per animal. After sample collection, the cotton part of the swab was transferred to a 5 mL cryovial with 1 mL of PBS and immediately put on wet ice.

Figure 37:
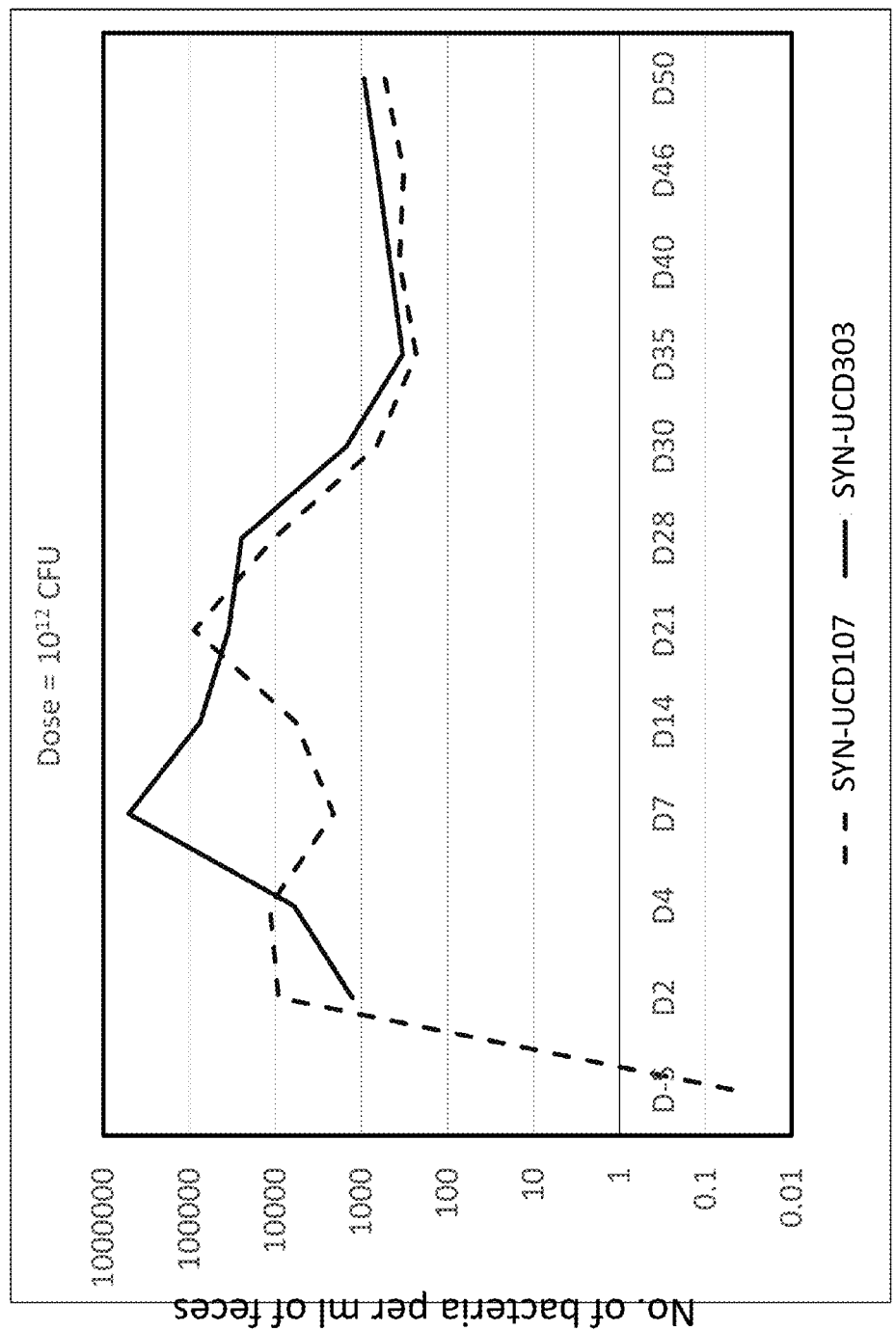
FIG. 37. Depicts the number of bacteria quantified in fecal samples collected in a non-human primate toxicity study. Pharmacokinetics and pharmacodynamics resulting from administration of SYN-UCD107 (a kanamycin resistant Nissle) and SYN-UCD303 (comprising ΔArgR, PfnrS-ArgAfbr integrated into the chromosome at the malEK locus, ΔThyA, and Kanamycin resistance) was compared over 50 days. Results indicate that under these dosing conditions, similar amounts of bacteria were recovered with the auxotroph SYN-UCD303 as control kanamycin resistant Nissle in the feces. Similar results have been observed in mice.
Figure 38:
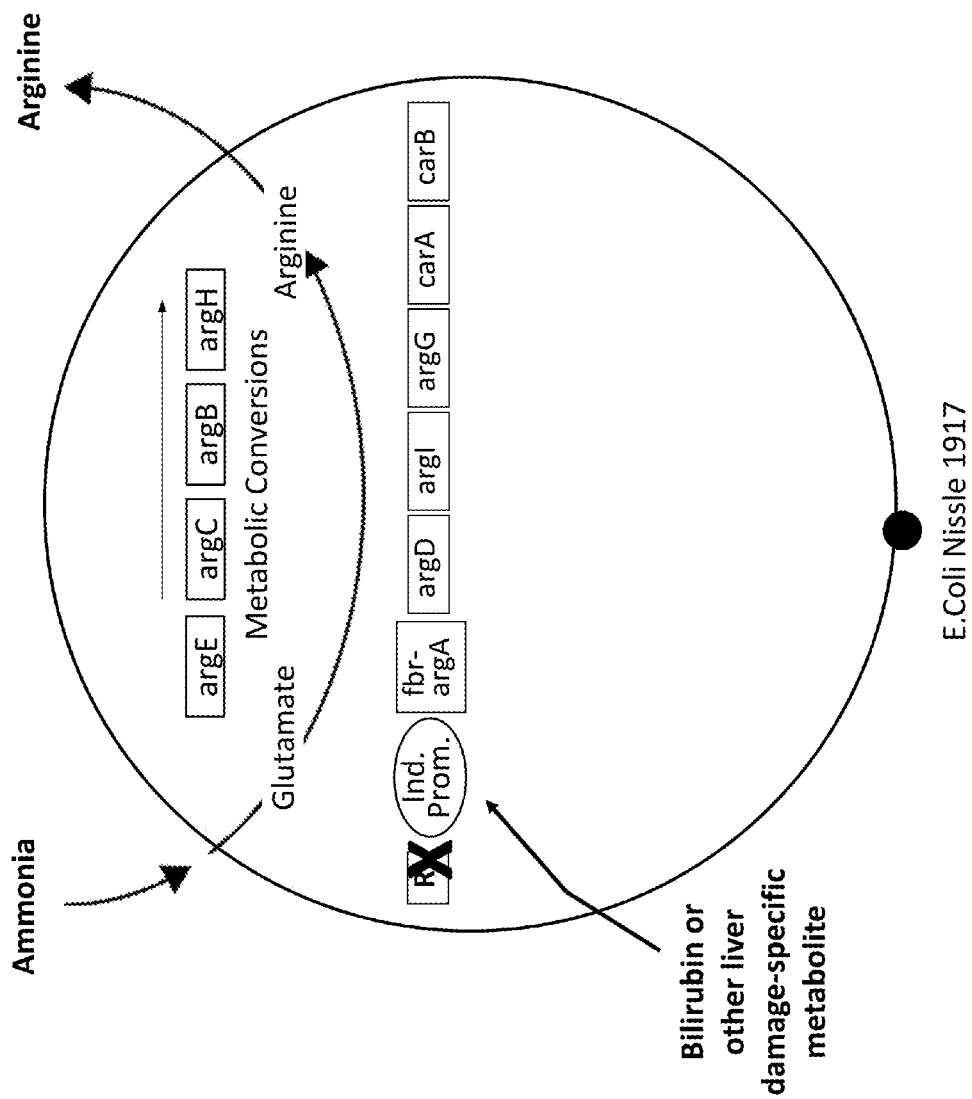
FIG. 38 depicts an exemplary synthetic genetic circuit for treating hepatic encephalopathy and other disorders characterized by hyperammonemia. In the ammonia conversion circuit, ammonia is taken up by a bacterium (e.g., E. coli Nissle), converted to glutamate, and glutamate is subsequently metabolized to arginine. Arginine ultimately exits the bacterial cell.
Figure 39:
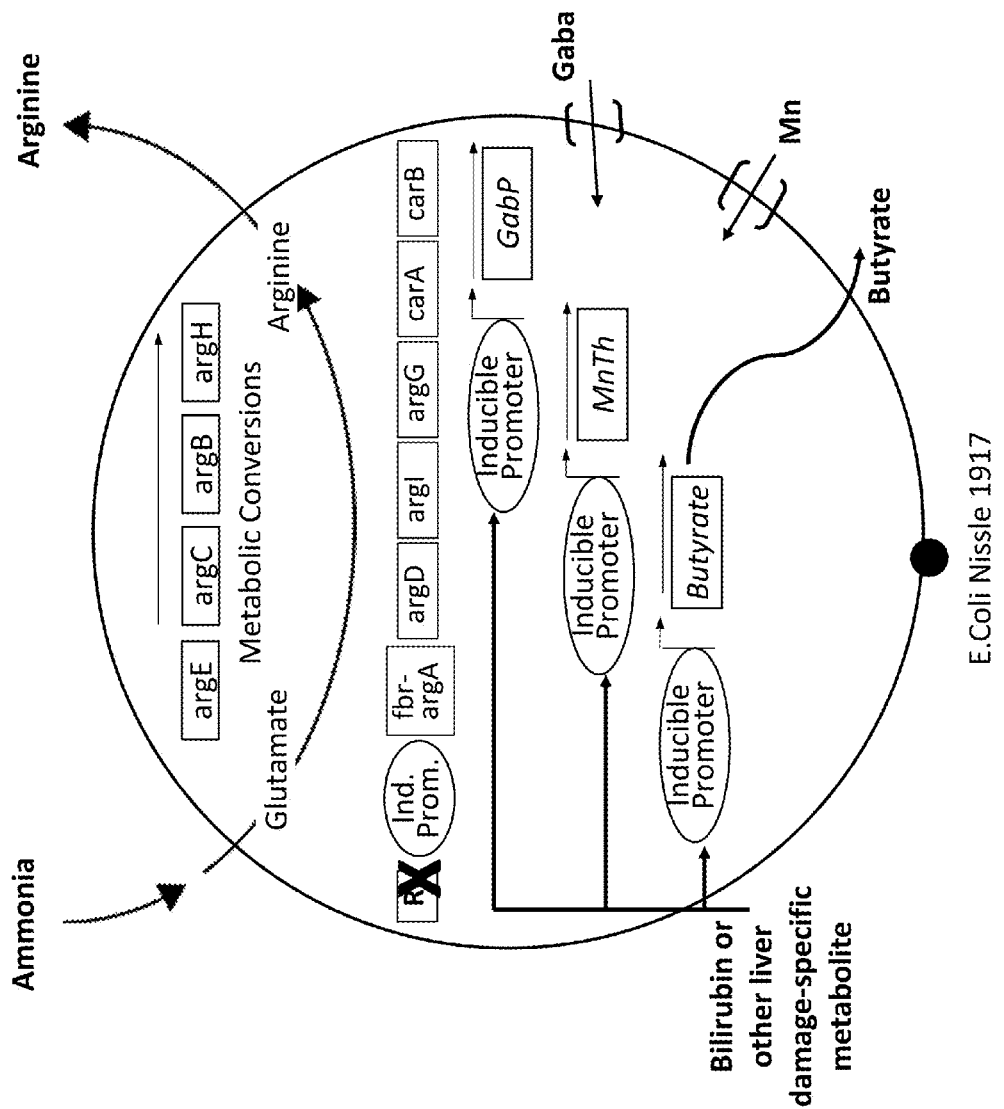
FIG. 39 depicts one embodiment of the invention. In this embodiment, the genetically engineered bacteria comprise four exemplary circuits for the treatment of hepatic encephalopathy. In one circuit, ammonia is taken up by the bacterium, converted to glutamate, and glutamate is subsequently metabolized to arginine. Arginine ultimately exits the bacterial cell. In a second circuit, the GABA membrane transport protein (GabP) is expressed by the gabP gene, and facilitates GABA transport into the cell. In a third circuit, the bacterial manganese transport protein (MntH) is expressed by the mntH gene, and facilitates manganese transport into the cell. In a fourth circuit, expression of a butyrate gene cassette results in the production of butyrate, and release of this gut barrier enhancer molecule outside of the cell. In some embodiments, all four circuits are each under the control of the same inducible promoter. In other embodiments, the four circuits may be under the control of different inducible promoters. Exemplary inducible promoters include oxygen level-dependent promoters (e.g., FNR-inducible promoter), promoters induced by HE-specific molecules or metabolites indicative of liver damage (e.g., bilirubin), promoters induced by inflammation or an inflammatory response, and promoters induced by a metabolite that may or may not be naturally present (e.g., can be exogenously added) in the gut, e.g., arabinose.
Figure 40:
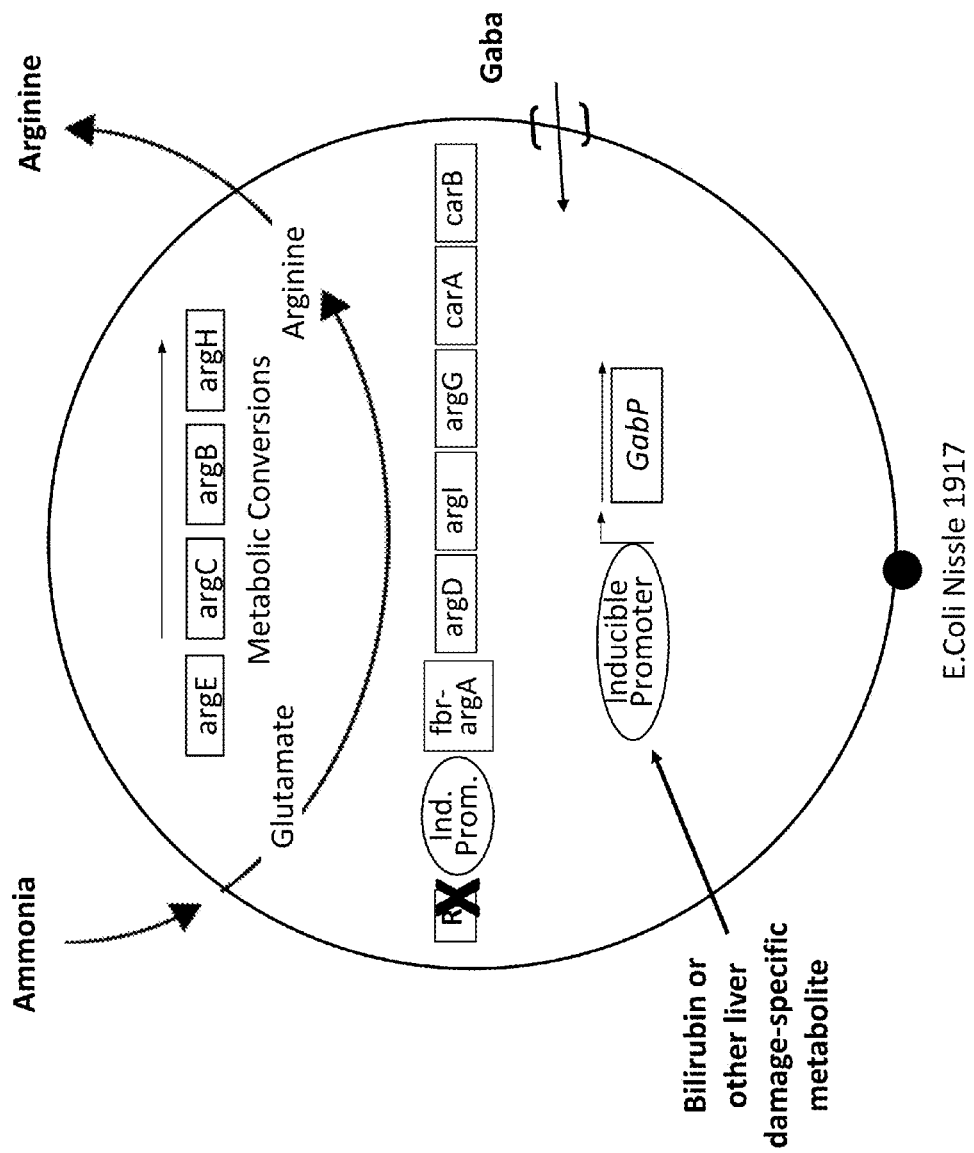
FIG. 40 depicts one embodiment of the invention. In this embodiment, the genetically engineered bacteria comprise two exemplary circuits for the treatment of hepatic encephalopathy. In one circuit, ammonia is taken up by the bacterium, converted to glutamate, and glutamate is subsequently metabolized to arginine. Arginine ultimately exits the bacterial cell. In a second circuit, the GABA membrane transport protein (GabP) is expressed by the gabP gene, and facilitates GABA transport into the cell. In some embodiments, both circuits are under the control of the same inducible promoter. In other embodiments, the two circuits may each be under the control of a different inducible promoter. Exemplary inducible promoters include oxygen level-dependent promoters (e.g., FNR-inducible promoter), promoters induced by HE-specific molecules or metabolites indicative of liver damage (e.g., bilirubin), promoters induced by inflammation or an inflammatory response, and promoters induced by a metabolite that may or may not be naturally present (e.g., can be exogenously added) in the gut, e.g., arabinose. In other embodiments, the genetically engineered bacteria may further comprise an additional circuit for reducing the level of GABA, e.g., a circuit for metabolizing (catabolizing) GABA.

Results are shown in FIG. 37, and show that the amount of bacteria quantified from fecal samples follows a similar pattern for Kanamycin resistant control Nissle (SYN-UCD107) and SYN-UCD303. Bacteria in the fecal samples reach a level of less than 1000 bacteria/per ml of feces by day 35. Results indicate that under these dosing conditions, similar amounts of bacteria were recovered with the auxotroph SYN-UCD303 as control kanamycin resistant Nissle in the feces. Similar results have been observed in mice. In conclusion, SYN-UCD303 appeared to be present in the NHP feces at nearly the same concentration as Nissle (SYN-UCD107).

In overall conclusion, the test article, SYN-UCD303, was well tolerated by female cynomolgus monkeys after 28 days of daily NG dose administration at doses up to $1 \times 10^{12}$ CFU/animal. No test article-related mortality occurred and no test article-related effects were identified upon clinical observation, body weight, and clinical pathology assessment.

Example 28

Repeat-Dose Pharmacokinetic and Pharmacodynamic Study of SYN-UCD-303 Following Daily Nasogastric Gavage Dose Administration for 28-Days in Cynomolgus Monkeys (Non-GLP)

Pharmacokinetics and pharmacodynamics of SYN-UCD303, SYN-UCD304, SYN-UCD305, and SYN-UCD306 and are studied following daily nasogastric gavage (NG) dose administration for 28-days to female cynomolgus monkeys essentially as described in Example 27. Cynomolgus monkeys are selected because this species is closely related, both phylogenetically and physiologically, to humans and is a species commonly used for nonclinical toxicity evaluations. The genetically engineered bacteria are administered by nasal gastric gavage, consistent with the proposed route of administration in humans. Animals overall well-being (clinical observations), weight clinical pathology (serum chemistry, hematology, and coagulation) are tracked. Plasma is analyzed for ammonia levels, and fecal samples are examined for bacterial load.

Example 29

4-Week Toxicity Study in Cynomolgus Monkeys with a 4-Week Recovery (GLP)

To evaluate any potential toxicities arising from administration of the genetically engineered bacteria, the pharmacokinetics and pharmacodynamics of SYN-UCD303 is studied following daily nasogastric gavage (NG) dose administration for 28-days to female cynomolgus monkeys under GLP conditions.

In other embodiments, the study is conducted SYN-UCD304, SYN-UCD305, and/or SYN-UCD306.

The study is conducted in compliance with nonclinical Laboratory Studies Good Laboratory Practice Regulations issued by the U.S. Food and Drug Administration (Title 21 of the Code of Federal Regulations, Part 58; effective Jun. 20, 1979) and the OECD Principles on Good Laboratory Practice (C[97]186/Final; effective 1997). The animals are individually housed based on the recommendations set forth in the Guide for the Care and Use of Laboratory Animals (National Research Council 2011).

Animals are administered SYN-UCD303 or control vehicle essentially as described in the Example 27, except that all materials are manufactured under GMP standards. Dosing is tabulated in Table 31. Additionally, animals are acclimated for 14 days and the dosing period is daily for 28 days followed by a recovery period of 28 days. Additionally, animals are euthanized at the end of the study to conduct histological analysis.

TABLE 31

Dosing Period and Regimen

| ACCLIMATION | 14 days |
| TEST ARTICLE PREP | Daily |
| DOSING PERIOD | Daily for 28 days |
| RECOVERY PERIOD | 28 days |
| REGULATIONS | FDA GLP |

| TEST GROUP | DOSE ARTICLE | DOSE LEVEL | DOSE ROUTE | NUMBER OF ANIMALS MALES (♂) | FEMALES (♀) |
|---|---|---|---|---|---|
| 1 | Vehicle | 0 | NG | $3^a + 2^b$ | $3^a + 2^b$ |
| 2 | SYN-UCD303 | $1 \times 10^9$ | NG | $3^a$ | $3^a$ |
| 3 | SYN-UCD303 | $1 \times 10^{10}$ | NG | $3^a$ | $3^a$ |
| 4 | SYN-UCD303 | $1 \times 10^{11}$ | NG | $3^a + 2^b$ | $3^a + 2^b$ |

$^a$Terminal Necropsy, Day 29
$^b$Recovery Necropsy, Day 56

Study Analysis is conducted as described in Table 32. Hematology, Coagulation, Serum Chemistry and Plasma Samples parameters are essentially as described in Example 27, and are analyzed using the methods described in Example 27. Collection and analysis of fecal samples is essentially conducted as described in Example 27.

TABLE 32

Study Analysis

| PROCEDURE | TIME POINTS |
|---|---|
| DOSE CONCENTRATION ANALYSIS | Day 1 and Day 28 |
| CLINICAL OBSERVATIONS | Twice Daily (cageside observations) |
| FOOD CONSUMPTION | Daily (qualitative) |
| BODY WEIGHTS | Weekly |
| OPHTHALMOLOGY | Once during acclimation, Week 4, and Week 8 |
| ECGs/HR/BP | Once during acclimation, Week 4, and Week 8 |
| HEMATOLOGY | Twice during acclimation, Day 2 (pre-dose), Day 15 (pre-dose), Day 29, Day 42, and Day 56 |
| COAGULATION | Twice during acclimation, Day 2 (pre-dose), Day 15 (pre-dose), Day 29, Day 42, and Day 56 |
| SERUM CHEMISTRY | Twice during acclimation, Day 2 (pre-dose), Day 15 (pre-dose), Day 29, Day 42, and Day 56 |
| BODY (RECTAL) TEMPERATURE | Twice during acclimation (with at least 7 days between measurements); once weekly during dosing (~6 hrs post-dose), and Weeks 5 and 8 |
| STOOL SAMPLE COLLECTION (BACTERIAL CULTURE) | Once during acclimation, prior to dosing on Days 2, 7, and 14, Day 29, Day 33, and Week 8 Rectal/Fecal swabs are collected via cotton tip applicator; the cotton part of the swab is transferred to a tube with an appropriate broth/media and immediately put on wet ice. Fecal samples are stored at 2 to 8° C. until time of analysis. |
| CYTOKINE BLOOD COLLECTIONS | Once during acclimation, Days 1, 3, 7, 14 and 28 (6 hrs post-dose), and Day 56 |
| ARCHIVE BLOOD SAMPLE COLLECTION (SAMPLE TO BE HELD FOR POSSIBLE ANALYSIS) | Once during acclimation, Days 1, 3, 7, 14 and 28 (6 hrs post-dose), and Day 56; Blood samples are processed to serum; samples are stored frozen. |

TABLE 32-continued

Study Analysis

| PROCEDURE | TIME POINTS |
|---|---|
| NECROPSY & TISSUE COLLECTION | All animals (e.g., colon, intestine, cecum, liver, spleen) |
| ORGAN WEIGHTS | All animals |
| TISSUE COLLECTION FOR PK/PD ASSESSMENT | All animals |
| HISTOPATHOLOGY | All animals |
| STATISTICAL ANALYSIS | Comparative (Anova/Bartletts) |

Example 30

4-Week Repeat Dose Toxicity Study in Mice with a 2-Week Recovery (GLP)

To evaluate any potential toxicities arising from administration of the genetically engineered bacteria, the pharmacokinetics and pharmacodynamics of SYN-UCD303 is studied following daily gavage dose administration for 4 weeks followed by a two week recovery under GLP conditions.

All materials are manufactured under GLP conditions. CD-1 Mice, 6-8 weeks of age at initiation of study are acclimated for 7 days. Groups of males and female mice are studied separately. SYN-UCD303 or vehicle control are administered as described in Table 33.

In certain embodiments, the study is conducted SYN-UCD304, SYN-UCD305, and/or SYN-UCD306.

TABLE 33

Study Design

| GROUP | TEST ARTICLE | DOSE LEVEL (MG/KG) | DOSE ROUTE | NUMBER OF ANIMALS MALES ($\male$) | FEMALES ($\female$) |
|---|---|---|---|---|---|
| 1 | Vehicle | 0 | NG | $10^a + 6^b$ | $10^a + 6^b$ |
| 2 | SYN-UCD303 | $1 \times 10^9$ | NG | $10^a + 6^b$ | $10^a + 6^b$ |
| 3 | SYN-UCD303 | $1 \times 10^{10}$ | NG | $10^a + 6^b$ | $10^a + 6^b$ |
| 4 | SYN-UCD303 | $1 \times 10^{11}$ | NG | $10^a + 6^b$ | $10^a + 6^b$ |

$^a$Toxicity (Tox) Animals, Terminal Necropsy Day 29;
$^b$Toxicity (Tox) Animals, Recovery Necropsy Day 42

The study analysis is described in Table 34. Hematology, Coagulation, Serum Chemistry and Plasma Samples parameters are essentially as described in Example 27, and are analyzed using the methods described in Example 27. Collection and analysis of fecal samples is essentially conducted as described in Example 27. Histology is conducted as in Example 29.

TABLE 34

Study Analysis

| PROCEDURE | TIME POINTS |
|---|---|
| DOSE CONCENTRATION ANALYSIS | Day 1 and Day 28 |
| CLINICAL OBSERVATIONS | Daily (Cageside Observations) |
| FOOD CONSUMPTION | Weekly (Quantitative) |
| BODY WEIGHTS | Twice during acclimation, weekly during study and recovery |
| OPHTHALMOLOGY | Once during acclimation, Week 4, and Week 8 |

TABLE 34-continued

Study Analysis

| PROCEDURE | TIME POINTS |
|---|---|
| HEMATOLOGY | At each necropsy; Day 29: 5 animals/sex/group; Day 42: 3 animals/sex/group; Standard panel as in Example 27 |
| COAGULATION | At each necropsy; Day 29: 5 animals/sex/group; Day 42: 3 animals/sex/group; Standard panel as in Example 27 |
| SERUM CHEMISTRY | At each necropsy; Day 29: 5 animals/sex/group; Day 56: 3 animals/sex/group; Standard panel as in Example 27 |
| FECAL SAMPLE COLLECTION (BACTERIAL CULTURE) | Once during acclimation, Days 2, 7, 14, 29, 33, and 42. Samples will be collected for up to a 2 hour period. For sample collection, animals, as a group of 6, are placed in or above a sterile surface. Fecal pellets (for each sex and group) are transferred to a tube with an appropriate broth/media and immediately put on wet ice. |
| NECROPSY AND TISSUE COLLECTION | At each necropsy Standard panel as in Example 29 |
| ORGAN WEIGHTS | At each necropsy Standard panel as in Example 29. |
| HISTOPATHOLOGY | Tox animals: Control & High dose groups only Example 29. |
| STATISTICAL ANALYSIS | Comparative (Anova/Bartletts) |

Example 31

Determination of Presence of Nissle in Fecal Samples of Non-Human Primates

To analyze fecal samples from non-human primates (NHPs) for the presence of Nissle, the number of bacteria from NHP samples was quantified based on the quantity of DNA in the sample using qPCR. In some embodiments, this protocol is used for the analysis of fecal samples from other mammals, including, but not limited to, mice and humans.

Sample Homogenization: Fecal samples (stored at −20° C.) were thawed at room temperature for 90 minutes. For solid fecal samples, the approximate solid volume was estimated, and phosphate buffered saline (PBS) was added to double the volume. For liquid fecal samples, no additional PBS was added. Samples were then vortexed for 30 seconds per tube. Fecal samples were homogenized using a disposable Pestle (Fisher 12-141-363) in PBS in Eppendorf tubes and kept on ice for subsequent procedures.

DNA purification: The homogenized samples (250 µL) were removed using sterilized filter tips (Racked Gilson Expert Sterilized Filter Tips) cut at the first gradation line and transferred to Eppendorf tubes. DNA was purified from the homogenized samples (250 µl) using the MoBio PowerLyzer PowerSoil DNA Isolation Kit (12855-100) following manufacturer's protocol. The amount of purified DNA recovered from each sample was quantified by measuring the OD260 of the sample on a Eppendorf BioSpectrometer Basic.

PCR reaction: Two reactions (Reaction 1 and Reaction 2) were assembled and run in triplicate. The first reaction served to quantify the amount of Nissle, and the second to quantify the total amount of bacteria present in the fecal samples. For the first qPCR reaction, purified DNA (5 ng), 0.4 µL of Primer 1 (10 µM), 0.4 µL of Primer 2 (10 µM), and 10 μL of SYBR Green PCR Master Mix (Thermo Fisher Scientific: 4368577) were brought up to 20 μL with water. For the second qPCR reaction, purified DNA (5 ng), 0.4 μL of Primer 3 (10 μM), 0.4 μL of Primer 4 (10 μM), and 10 μL of SYBR Green PCR Master Mix (Thermo Fisher Scientific: 4368577) were brought up to 20 μL with water.

The sequences of primers used in the reactions at a concentration of 10 μM are found in Table 35.

TABLE 35

Primer Sequences

| Primer Name | Primer Sequence | Size of Product | Identifies | SEQ ID NO |
|---|---|---|---|---|
| 1 | GCAACTGGCCCGTAATT | 191 bp | Nissle | 74 |
| 2 | ATCCACGCATCGCACG TAGGTTT | | | 75 |
| 3 | ggcaggcctaacacatgc aag | 240 bp | Total Bacteria | 76 |
| 4 | gtcgcctaggtgagcctt tacc | | | 77 |

For quantification of the amount of bacterial DNA amplified, a standard curve was run for each reaction. To generate the standard curve, Fragment #1 (synthesized at a set concentration) (Table 36) was diluted in 10-fold serial dilutions, resulting in the following amounts: no DNA, 1 copy of Fragment #1, 10 copies of Fragment #1, 100 copies of Fragment #1, and so on, until the eighth well has 106 copies of fragment #1. Standard DNAs were then added to the qPCR reaction mix for Reaction #1.

TABLE 36

Standard DNA Sequence (Fragment #1)

| Description | Sequence | SEQ ID NO |
|---|---|---|
| Fragment 1 | gcaactggcccgtaattatccatagctgtag tgatcactcggtccgaattaaacgcaatgat ggcgagctgagaacgattagcatcaaacg ctttaacgaagattttgaacgagtggagcat gatgagtatcgcaaaatatgtgccgaaata gagcaggaaacaaacctgaaaaacctac gtgcgatgcgt | 78 |

PCR reaction conditions for standard curve, and Reactions 1 and 2 are shown in Table 37.

TABLE 37

PCR Reaction Conditions

| Temperature (° C.) | Time (seconds) | Transition Speed (° C./second) | Repeats |
|---|---|---|---|
| 95 | 15 | N/A | 40 |
| 60 | 60 | N/A | |
| Melt Curve | | | |
| 95 | 15 | N/A | 1 |
| 60 | 60 | 0.3 | |
| 95 | 15 | | |

As a quality control measure, the melt-curves of the test qPCR reactions were compared to the positive control for each primer set, to ensure that the melt-curve of the positive controls matched the melt-curve of the test samples. The presence and quantity of Nissle and total bacteria was determined by analyzing CT values (Cycle threshold values) against the standard curve.

Example 32

Construction of Vectors for Overproducing Butyrate

In addition to the ammonia conversion circuit, GABA transport circuit, GABA metabolic circuit, and/or manganese transport circuit described above, the *E. coli* Nissle bacteria further comprise one or more circuits for producing a gut barrier enhancer molecule.

To facilitate inducible production of butyrate in *E. coli* Nissle, the eight genes of the butyrate production pathway from *Peptoclostridium difficile* 630 (bcd2, etfB3, etfA3, thiA1, hbd, crt2, bpt, and buk; NCBI), as well as transcriptional and translational elements, were synthesized (Gen9, Cambridge, Mass.) and cloned into vector pBR322. The butyrate gene cassette is placed under the control of a FNR regulatory region selected from SEQ ID NOs: 18-29 (Table 6). In certain constructs, the FNR-responsive promoter is further fused to a strong ribosome binding site sequence. For efficient translation of butyrate genes, each synthetic gene in the operon was separated by a 15 base pair ribosome binding site derived from the T7 promoter/translational start site.

In certain constructs, the butyrate gene cassette is placed under the control of an RNS-responsive regulatory region, e.g., norB, and the bacteria further comprises a gene encoding a corresponding RNS-responsive transcription factor, e.g., nsrR (see, e.g., Tables 38 and 39). In certain constructs, the butyrate gene cassette is placed under the control of an ROS-responsive regulatory region, e.g., oxyS, and the bacteria further comprises a gene encoding a corresponding ROS-responsive transcription factor, e.g., oxyR (see, e.g., Tables 14-17). In certain constructs, the butyrate gene cassette is placed under the control of a tetracycline-inducible or constitutive promoter.

TABLE 38 pLogic031-nsrR-norB-butyrate construct (SEQ ID NO: 79)

| Description | Nucleotide sequences of pLogic031-nsrR-norB-butyrate construct (SEQ ID NO: 79) |
|---|---|
| Nucleic acid sequence of an exemplary RNS-regulated construct comprising a gene encoding nsrR, a regulatory region of norB, and a | ttatta<u>tcgcaccgcaatcgggatttttcgattcataaagcaggt</u> <u>cgtaggtcggcttgttgagcaggtcttgcagcgtgaaaccgtcc</u> <u>agatacgtgaaaaacgacttcattgcaccgccgagtatgcccgt</u> <u>cagccggcaggacggcgtaatcaggcattcgttgttcgggccca</u> |

TABLE 38 -continued pLogic031-nsrR-norB-butyrate construct (SEQ ID NO: 79)

| Description | Nucleotide sequences of pLogic031-nsrR-norB-butyrate construct (SEQ ID NO: 79) |
|---|---|
| butyrogenic gene cassette (pLogic031-nsrR-norB-butyrate construct; SEQ ID NO: 79). The sequence encoding NsrR is underlined and bolded, and the NsrR binding site, i.e., a regulatory region of norB is boxed. | tacactcgaccagctgcatcggttcgaggtggcggacgaccgcg<br><br>ccgatattgatgcgttcgggcggcgcggccagcctcagcccgcc<br><br>gcctttcccgcgtacgctgtgcaagaacccgcctttgaccagcg<br><br>cggtaaccactttcatcaaatggcttttggaaatgccgtaggtc<br><br>gaggcgatggtggcgatattgaccagcgcgtcgtcgttgacggc<br><br>ggtgtagatgaggacgcgcagcccgtagtcggtatgttgggtca<br><br>gatacatacaacctccttagtacatgcaaaattatttctagagc<br><br>aacatacgagccggaagcataaagtgtaaagcctggggtgccta<br><br>atgagttgagttgaggaattataacaggaagaaatattcctcat<br><br>acgcttgtaattcctctatggttgttgacaattaatcatcggct<br><br>cgtataatg|ataacattcatattttgtgaattttaaa|ctcta<br><br>gaaataattttgtttaactttaagaaggagatatacatatggat<br><br>ttaaattctaaaaaatatcagatgcttaaagagctatatgtaag<br><br>cttcgctgaaaatgaagttaaacctttagcaacagaacttgatg<br><br>aagaagaaagatttccttatgaaacagtggaaaaaatggcaaaa<br><br>gcaggaatgatgggtataccatatccaaaagaatatggtggaga<br><br>aggtggagacactgtaggatatataatggcagttgaagaattgt<br><br>ctagagtttgtggtactacaggagttatattatcagctcataca<br><br>tctcttggctcatggcctatatcaatatggtaatgaagaaca<br><br>aaaacaaaaattcttaagaccactagcaagtggagaaaaattag<br><br>gagcatttggtcttactgagcctaatgctggtacagatgcgtct<br><br>ggccaacaaacaactgctgttttagacggggatgaatacatact<br><br>taatggctcaaaaatatttataacaaacgcaatagctggtgaca<br><br>tatatgtagtaatggcaatgactgataaatctaaggggaacaaa<br><br>ggaatatcagcatttatagttgaaaaaggaactcctgggtttag<br><br>ctttggagttaaagaaaagaaaatgggtataagaggttcagcta<br><br>cgagtgaattaatatttgaggattgcagaatacctaaagaaaat<br><br>ttacttggaaaagaaggtcaaggatttaagatagcaatgtctac<br><br>tcttgatggtggtagaattggtatagctgcacaagctttaggtt<br><br>tagcacaaggtgctcttgatgaaactgttaaatatgtaaaagaa<br><br>agagtacaatttggtagaccattatcaaaattccaaaatacaca<br><br>attccaattagctgatatggaagttaaggtacaagcggctagac<br><br>accttgtatatcaagcagctataaataaagacttaggaaaacct<br><br>tatggagtagaagcagcaatggcaaaattatttgcagctgaaac<br><br>agctatggaagttactacaaaagctgtacaacttcatggaggat<br><br>atggatacactcgtgactatccagtagaaagaatgatgagagat<br><br>gctaagataactgaaatatatgaaggaactagtgaagttcaaag |

TABLE 38 -continued pLogic031-nsrR-norB-butyrate construct (SEQ ID NO: 79)

| Description | Nucleotide sequences of pLogic031-nsrR-norB-butyrate construct (SEQ ID NO: 79) |
|---|---|
| | aatggttatttcaggaaaactattaaaatagtaagaaggagata |
| | tacatatggaggaaggatttatgaatatagtcgtttgtataaaa |
| | caagttccagatacaacagaagttaaactagatcctaatacagg |
| | tactttaattagagatggagtaccaagtataataaaccctgatg |
| | ataaagcaggtttagaagaagctataaaattaaaagaagaaatg |
| | ggtgctcatgtaactgttataacaatgggacctcctcaagcaga |
| | tatggctttaaaagaagctttagcaatgggtgcagatagaggta |
| | tattattaacagatagagcatttgcgggtgctgatacttgggca |
| | acttcatcagcattagcaggagcattaaaaaatatagattttga |
| | tattataatagctggaagacaggcgatagatggagatactgcac |
| | aagttggacctcaaatagctgaacatttaaatcttccatcaata |
| | acatatgctgaagaaataaaaactgaaggtgaatatgtattagt |
| | aaaaagacaatttgaagattgttgccatgacttaaaagttaaaa |
| | tgccatgccttataacaactcttaaagatatgaacacaccaaga |
| | tacatgaaagttggaagaatatatgatgctttcgaaaatgatgt |
| | agtagaaacatggactgtaaaagatatagaagttgacccttcta |
| | atttaggtcttaaaggttctccaactagtgtatttaaatcattt |
| | acaaaatcagttaaaccagctggtacaatatacaatgaagatgc |
| | gaaaacatcagctggaattatcatagataaattaaaagagaagt |
| | atatcatataataagaaggagatatacatatgggtaacgtttta |
| | gtagtaatagaacaaagagaaaatgtaattcaaactgtttcttt |
| | agaattactaggaaaggctacagaaatagcaaaagattatgata |
| | caaaagtttctgcattacttttaggtagtaaggtagaaggttta |
| | atagatacattagcacactatggtgcagatgaggtaatagtagt |
| | agatgatgaagctttagcagtgtatacaactgaaccatatacaa |
| | aagcagcttatgaagcaataaaagcagctgaccctatagttgta |
| | ttatttggtgcaacttcaataggtagagatttagcgcctagagt |
| | ttctgctagaatacatacaggtcttactgctgactgtacaggtc |
| | ttgcagtagctgaagatacaaaattattattaatgacaagacct |
| | gcctttggtggaaatataatggcaacaatagtttgtaaagattt |
| | cagacctcaaatgtctacagttagaccagggggttatgaagaaaa |
| | atgaacctgatgaaactaaagaagctgtaattaaccgtttcaag |
| | gtagaatttaatgatgctgataaattagttcaagttgtacaagt |
| | aataaaagaagctaaaaaacaagttaaaatagaagatgctaaga |
| | tattagtttctgctggacgtggaatgggtggaaaagaaaactta |
| | gacatactttatgaattagctgaaattataggtggagaagtttc |
| | tggttctcgtgccactatagatgcaggttggttagataaagcaa |

TABLE 38 -continued pLogic031-nsrR-norB-butyrate construct (SEQ ID NO: 79)

| Description | Nucleotide sequences of pLogic031-nsrR-norB-butyrate construct (SEQ ID NO: 79) |
|---|---|
| | gacaagttggtcaaactggtaaaactgtaagaccagaccttat |
| | atagcatgtggtatatctggagcaatacaacatatagctggtat |
| | ggaagatgctgagtttatagttgctataaataaaaatccagaag |
| | ctccaatatttaaatatgctgatgttggtatagttggagatgtt |
| | cataaagtgcttccagaacttatcagtcagttaagtgttgcaaa |
| | agaaaaggtgaagttttagctaactaataagaaggagatatac |
| | atatgagagaagtagtaattgccagtgcagctagaacagcagta |
| | ggaagttttggaggagcatttaaatcagtttcagcggtagagtt |
| | aggggtaacagcagctaaagaagctataaaaagagctaacataa |
| | ctccagatatgatagatgaatctcttttaggggagtacttaca |
| | gcaggtcttggacaaaatatagcaagacaaatagcattaggagc |
| | aggaataccagtagaaaaaccagctatgactataaatatagttt |
| | gtggttctggattaagatctgtttcaatggcatctcaacttata |
| | gcattaggtgatgctgatataatgttagttggtggagctgaaaa |
| | catgagtatgtctccttatttagtaccaagtgcgagatatggtg |
| | caagaatgggtgatgctgcttttgttgattcaatgataaaagat |
| | ggattatcagacatatttaataactatcacatgggtattactgc |
| | tgaaaacatagcagagcaatggaatataactagagaagaacaag |
| | atgaattagctcttgcaagtcaaaataaagctgaaaaagctcaa |
| | gctgaaggaaaatttgatgaagaaatagttcctgttgttataaa |
| | aggaagaaaaggtgacactgtagtagataaagatgaatatatta |
| | agcctggcactacaatggagaaacttgctaagttaagacctgca |
| | tttaaaaaagatggaacagttactgctggtaatgcatcaggaat |
| | aaatgatggtgctgctatgttagtagtaatggctaaagaaaaag |
| | ctgaagaactaggaatagagcctcttgcaactatagtttcttat |
| | ggaacagctggtgttgaccctaaaataatgggatatggaccagt |
| | tccagcaactaaaaaagctttagaagctgctaatatgactattg |
| | aagatatagatttagttgaagctaatgaggcatttgctgcccaa |
| | tctgtagctgtaataagagacttaaatatagatatgaataaagt |
| | taatgttaatggtggagcaatagctataggacatccaataggat |
| | gctcaggagcaagaatacttactacacttttatatgaaatgaag |
| | agaagagatgctaaaactggtcttgctcactttgtataggcgg |
| | tggaatgggaactactttaatagttaagagatagtaagaaggag |
| | atatacatatgaaattagctgtaataggtagtggaactatggga |
| | agtggtattgtacaaacttttgcaagttgtggacatgatgtatg |
| | tttaaagagtagaactcaaggtgctatagataaatgtttagctt |
| | tattagataaaaatttaactaagttagttactaagggaaaaatg |
| | gatgaagctacaaaagcagaaatattaagtcatgttagttcaac |

TABLE 38 -continued pLogic031-nsrR-norB-butyrate construct (SEQ ID NO: 79)

| Description | Nucleotide sequences of pLogic031-nsrR-norB-butyrate construct (SEQ ID NO: 79) |
|---|---|
| | tactaattatgaagatttaaaagatatggatttaataatagaag |
| | catctgtagaagacatgaatataaagaaagatgttttcaagtta |
| | ctagatgaattatgtaaagaagatactatcttggcaacaaatac |
| | ttcatcattatctataacagaaatagcttcttctactaagcgcc |
| | cagataaagttataggaatgcatttctttaatccagttcctatg |
| | atgaaattagttgaagttataagtggtcagttaacatcaaaagt |
| | tactttttgatacagtatttgaattatctaagagtatcaataaag |
| | taccagtagatgtatctgaatctcctggatttgtagtaaataga |
| | atacttatacctatgataaatgaagctgttggtatatatgcaga |
| | tggtgttgcaagtaaagaagaaatagatgaagctatgaaattag |
| | gagcaaaccatccaatgggaccactagcattaggtgatttaatc |
| | ggattagatgttgttttagctataatgaacgttttatatactga |
| | atttggagatactaaatatagacctcatccacttttagctaaaa |
| | tggttagagctaatcaattaggaagaaaaactaagataggattc |
| | tatgattataataataataagaaggagatatacatatgagtac |
| | aagtgatgttaaagtttatgagaatgtagctgttgaagtagatg |
| | gaaatatatgtacagtgaaaatgaatagacctaaagcccttaat |
| | gcaataaattcaaagactttagaagaactttatgaagtatttgt |
| | agatattaataatgatgaaactattgatgttgtaatattgacag |
| | gggaaggaaaggcatttgtagctggagcagatattgcatacatg |
| | aaagatttagatgctgtagctgctaaagattttagtatcttagg |
| | agcaaaagcttttggagaaatagaaaatagtaaaaaagtagtga |
| | tagctgctgtaaacggatttgctttaggtggaggatgtgaactt |
| | gcaatggcatgtgatataagaattgcatctgctaaagctaaatt |
| | tggtcagccagaagtaactcttggaataactccaggatatggag |
| | gaactcaaaggcttacaagattggttggaatggcaaaagcaaaa |
| | gaattaatctttacaggtcaagttataaaagctgatgaagctga |
| | aaaaatagggctagtaaatagagtcgttgagccagacattttaa |
| | tagaagaagttgagaaattagctaagataatagctaaaaatgct |
| | cagcttgcagttagatactctaaagaagcaatacaacttggtgc |
| | tcaaactgatataaatactggaatagatatagaatctaatttat |
| | ttggtctttgtttttcaactaaagaccaaaaagaaggaatgtca |
| | gctttcgttgaaaagagagaagctaactttataaaagggtaata |
| | agaaggagatatacatatgagaagttttgaagaagtaattaagt |
| | ttgcaaaagaaagaggacctaaaactatatcagtagcatgttgc |
| | caagataaagaagttttaatggcagttgaaatggctagaaaaga |
| | aaaaatagcaaatgccatttttagtaggagatatagaaaagacta |

TABLE 38 -continued

| pLogic031-nsrR-norB-butyrate construct (SEQ ID NO: 79) | |
|---|---|
| Description | Nucleotide sequences of pLogic031-nsrR-norB-butyrate construct (SEQ ID NO: 79) |
| | aagaaattgcaaaaagcatagacatggatatcgaaaattatgaa |
| | ctgatagatataaaagatttagcagaagcatctctaaaatctgt |
| | tgaattagtttcacaaggaaaagccgacatggtaatgaaaggct |
| | tagtagacacatcaataatactaaaagcagttttaaataaagaa |
| | gtaggtcttagaactggaaatgtattaagtcacgtagcagtatt |
| | tgatgtagagggatatgatagattattttcgtaactgacgcag |
| | ctatgaacttagctcctgatacaaatactaaaaagcaaatcata |
| | gaaaatgcttgcacagtagcacattcattagatataagtgaacc |
| | aaaagttgctgcaatatgcgcaaaagaaaagtaaatccaaaaa |
| | tgaaagatacagttgaagctaaagaactagaagaaatgtatgaa |
| | agaggagaaatcaaaggttgtatggttggtgggccttttgcaat |
| | tgataatgcagtatctttagaagcagctaaacataaaggtataa |
| | atcatcctgtagcaggacgagctgatatattattagccccagat |
| | attgaaggtggtaacatattatataaagctttggtattcttctc |
| | aaaatcaaaaaatgcaggagttatagttggggctaaagcaccaa |
| | taatattaacttctagagcagacagtgaagaaactaaactaaac |
| | tcaatagctttaggtgttttaatggcagcaaaggcataataaga |
| | aggagatatacatatgagcaaaatatttaaaatcttaacaataa |
| | atcctggttcgacatcaactaaaatagctgtatttgataatgag |
| | gatttagtatttgaaaaaacttaagacattcttcagaagaaat |
| | aggaaaatatgagaaggtgtctgaccaatttgaatttcgtaaac |
| | aagtaatagaagaagctctaaaagaaggtggagtaaaaacatct |
| | gaattagatgctgtagtaggtagaggaggacttcttaaacctat |
| | aaaaggtggtacttattcagtaagtgctgctatgattgaagatt |
| | taaaagtgggagttttaggagaacacgcttcaaacctaggtgga |
| | ataatagcaaaacaaataggtgaagaagtaaatgttccttcata |
| | catagtagaccctgttgttgtagatgaattagaagatgttgcta |
| | gaatttctggtatgcctgaaataagtagagcaagtgtagtacat |
| | gctttaaatcaaaaggcaatagcaagaagatatgctagagaaat |
| | aaacaagaaatatgaagatataaatcttatagttgcacacatgg |
| | gtggaggagtttctgttggagctcataaaaatggtaaaatagta |
| | gatgttgcaaacgcattagatggagaaggacctttctctccaga |
| | aagaagtggtggactaccagtaggtgcattagtaaaaatgtgct |
| | ttagtggaaaatatactcaagatgaaattaaaagaaaataaaa |
| | ggtaatggcggactagttgcatacttaaacactaatgatgctag |
| | agaagttgaagaaagaattgaagctggtgatgaaaaagctaaat |
| | tagtatatgaagctatggcatatcaaatctctaaagaaatagga |
| | gctagtgctgcagttcttaagggagatgtaaaagcaatattatt |

TABLE 38 -continued pLogic031-nsrR-norB-butyrate construct (SEQ ID NO: 79)

| Description | Nucleotide sequences of pLogic031-nsrR-norB-butyrate construct (SEQ ID NO: 79) |
|---|---|
| | aactggtggaatcgcatattcaaaaatgtttacagaaatgattg |
| | cagatagagttaaatttatagcagatgtaaaagtttatccaggt |
| | gaagatgaaatgattgcattagctcaaggtggacttagagtttt |
| | aactggtgaagaagaggctcaagtttatgataactaataa |

TABLE 39

Nucleotide sequences of pLogic046-nsrR-norB-butyrate construct

| Description | Nucleotide sequences of pLogic046-nsrR-norB-butyrate construct (SEQ ID NO: 80) |
|---|---|
| Nucleic acid sequence of an exemplary RNS-regulated construct comprising a gene encoding nsrR, a regulatory region of norB, and a butyrogenic gene cassette pLogic046-nsrR-norB-butyrate construct; SEQ ID NO: 80). | ttattatcgcaccgcaatcgggattttcgattcataaagcaggtcgta |
| | ggtcggcttgttgagcaggtcttgcagcgtgaaaccgtccagatacgt |
| | gaaaaacgacttcattgcaccgccgagtatgcccgtcagccggcagga |
| | cggcgtaatcaggcattcgttgttcgggcccatacactcgaccagctg |
| | catcggttcgaggtggcggacgaccgcgccgatattgatgcgttcggg |
| | cggcgcggccagcctcagcccgccgcctttcccgcgtacgctgtgcaa |
| | gaacccgcctttgaccagcgcgggtaaccactttcatcaaatggctttt |
| | ggaaatgccgtaggtcgaggcgatggtggcgatattgaccagcgcgtc |
| | gtcgttgacggcggtgtagatgaggacgcgcagcccgtagtcggtatg |
| | ttgggtcagatacatacaacctccttagtacatgcaaaattatttcta |
| | gagcaacatacgagccggaagcataaagtgtaaagcctggggtgccta |
| | atgagttgagttgaggaattataacaggaagaaatattcctcatacgc |
| | ttgtaattcctctatggttgttgacaattaatcatcggctcgtataat |
| | g|tataacattcatattttgtgaattttaaa|ctctagaaataattttgt |
| | ttaactttaagaaggagatatacatatgatcgtaaaacctatggtacg |
| | caacaatatctgcctgaacgcccatcctcagggctgcaagaagggagt |
| | ggaagatcagattgaatataccaagaaacgcattaccgcagaagtcaa |
| | agctggcgcaaaagctccaaaaaacgttctggtgcttggctgctcaaa |
| | tggttacggcctggcgagccgcattactgctgcgttcggatacggggc |
| | tgcgaccatcggcgtgtcctttgaaaaagcgggttcagaaaccaaata |
| | tggtacaccgggatggtacaataatttggcatttgatgaagcggcaaa |
| | acgcgagggtctttatagcgtgacgatcgacggcgatgcgttttcaga |
| | cgagatcaaggcccaggtaattgaggaagccaaaaaaaaaggtatcaa |
| | atttgatctgatcgtatacagcttggccagcccagtacgtactgatcc |
| | tgatacaggtatcatgcacaaaagcgttttgaaacccttggaaaaac |
| | gttcacaggcaaaacagtagatccgtttactggcgagctgaaggaaat |
| | ctccgcggaaccagcaaatgacgaggaagcagccgccactgttaaagt |
| | tatggggggtgaagattgggaacgttggattaagcagctgtcgaagga |

TABLE 39 -continued

Nucleotide sequences of pLogic046-nsrR-norB-butyrate construct

| Description | Nucleotide sequences of pLogic046-nsrR-norB-butyrate construct (SEQ ID NO: 80) |
|---|---|
| | aggcctcttagaagaaggctgtattaccttggcctatagttatattgg |
| | ccctgaagctacccaagctttgtaccgtaaaggcacaatcggcaaggc |
| | caaagaacacctggaggccacagcacaccgtctcaacaaagagaaccc |
| | gtcaatccgtgccttcgtgagcgtgaataaaggcctggtaacccgcgc |
| | aagcgccgtaatcccggtaatccctctgtatctcgccagcttgttcaa |
| | agtaatgaaagagaagggcaatcatgaaggttgtattgaacagatcac |
| | gcgtctgtacgccgagcgcctgtaccgtaaagatggtacaattccagt |
| | tgatgaggaaaatcgcattcgcattgatgattgggagttagaagaaga |
| | cgtccagaaagcggtatccgcgttgatggagaaagtcacgggtgaaaa |
| | cgcagaatctctcactgacttagcggggtaccgccatgatttcttagc |
| | tagtaacggctttgatgtagaaggtattaattatgaagcggaagttga |
| | acgcttcgaccgtatctgataagaaggagatatacatatgagagaagt |
| | agtaattgccagtgcagctagaacagcagtaggaagttttggaggagc |
| | atttaaatcagtttcagcggtagagttaggggtaacagcagctaaaga |
| | agctataaaaagagctaacataactccagatatgatagatgaatctct |
| | tttaggggagtacttacagcaggtcttggacaaaatatagcaagaca |
| | aatagcattaggagcaggaataccagtagaaaaaccagctatgactat |
| | aaatatagtttgtggttctggattaagatctgtttcaatggcatctca |
| | acttatagcattaggtgatgctgatataatgttagttggtggagctga |
| | aaacatgagtatgtctccttatttagtaccaagtgcgagatatggtgc |
| | aagaatgggtgatgctgcttttgttgattcaatgataaaagatggatt |
| | atcagacatatttaataactatcacatgggtattactgctgaaaacat |
| | agcagagcaatggaatataactagagaagaacaagatgaattagctct |
| | tgcaagtcaaaataaagctgaaaaagctcaagctgaaggaaaatttga |
| | tgaagaaatagttcctgttgttataaaaggaagaaaaggtgacactgt |
| | agtagataaagatgaatatattaagcctggcactacaatggagaaact |
| | tgctaagttaagacctgcatttaaaaaagatggaacagttactgctgg |
| | taatgcatcaggaataaatgatggtgctgctatgttagtagtaatggc |
| | taaagaaaaagctgaagaactaggaatagagcctcttgcaactatagt |
| | ttcttatggaacagctggtgttgaccctaaaataatgggatatggacc |
| | agttccagcaactaaaaaagctttagaagctgctaatatgactattga |
| | agatatagatttagttgaagctaatgaggcatttgctgcccaatctgt |
| | agctgtaataagagacttaaatatagatatgaataaagttaatgttaa |
| | tggtggagcaatagctataggacatccaataggatgctcaggagcaag |
| | aatacttactacactttatatgaaatgaagagaagagatgctaaaac |
| | tggtcttgctacactttgtataggcggtggaatgggaactactttaat |
| | agttaagagatagtaagaaggagatatacatatgaaattagctgtaat |
| | aggtagtggaactatgggaagtggtattgtacaaacttttgcaagttg |

TABLE 39 -continued

Nucleotide sequences of pLogic046-nsrR-norB-butyrate construct

| Description | Nucleotide sequences of pLogic046-nsrR-norB-butyrate construct (SEQ ID NO: 80) |
|---|---|
| | tggacatgatgtatgtttaaagagtagaactcaaggtgctatagataa |
| | atgtttagctttattagataaaaatttaactaagttagttactaaggg |
| | aaaaatggatgaagctacaaaagcagaaatattaagtcatgttagttc |
| | aactactaattatgaagatttaaaagatatggatttaataatagaagc |
| | atctgtagaagacatgaatataaagaaagatgttttcaagttactaga |
| | tgaattatgtaaagaagatactatcttggcaacaaatacttcatcatt |
| | atctataacagaaatagcttcttctactaagcgcccagataaagttat |
| | aggaatgcatttctttaatccagttcctatgatgaaattagttgaagt |
| | tataagtggtcagttaacatcaaaagttacttttgatacagtatttga |
| | attatctaagagtatcaataaagtaccagtagatgtatctgaatctcc |
| | tggatttgtagtaaatagaatacttatacctatgataaatgaagctgt |
| | tggtatatatgcagatggtgttgcaagtaaagaagaaatagatgaagc |
| | tatgaaattaggagcaaaccatccaatgggaccactagcattaggtga |
| | tttaatcggattagatgttgttttagctataatgaacgttttatatac |
| | tgaatttggagatactaaatatagacctcatccacttttagctaaaat |
| | ggttagagctaatcaattaggaagaaaaactaagataggattctatga |
| | ttataaataataagaaggagatatacatatgagtacaagtgatgt |
| | taaagtttatgagaatgtagctgttgaagtagatggaaatatatgtac |
| | agtgaaaatgaatagacctaaagcccttaatgcaataaattcaaagac |
| | tttagaagaactttatgaagtatttgtagatattaataatgatgaaac |
| | tattgatgttgtaatattgacaggggaaggaaaggcatttgtagctgg |
| | agcagatattgcatacatgaaagatttagatgctgtagctgctaaaga |
| | ttttagtatcttaggagcaaaagcttttggagaaatagaaaatagtaa |
| | aaaagtagtgatagctgctgtaaacggatttgctttaggtggaggatg |
| | tgaacttgcaatggcatgtgatataagaattgcatctgctaaagctaa |
| | atttggtcagccagaagtaactcttggaataactccaggatatggagg |
| | aactcaaaggcttacaagattggttggaatggcaaaagcaaaagaatt |
| | aatctttacaggtcaagttataaaagctgatgaagctgaaaaaatagg |
| | gctagtaaatagagtcgttgagccagacatttaatagaagaagttga |
| | gaaattagctaagataatagctaaaaatgctcagcttgcagttagata |
| | ctctaaagaagcaatacaacttggtgctcaaactgatataaatactgg |
| | aatagatatagaatctaatttatttggtctttgtttttcaactaaaga |
| | ccaaaaagaaggaatgtcagctttcgttgaaaagagagaagctaactt |
| | tataaagggtaataagaaggagatatacatatgagaagttttgaaga |
| | agtaattaagtttgcaaaagaaagaggacctaaaactatatcagtagc |
| | atgttgccaagataaagaagttttaatggcagttgaaatggctagaaa |
| | agaaaaaatagcaaatgccattttagtaggagatatagaaaagactaa |

TABLE 39 -continued

Nucleotide sequences of pLogic046-nsrR-norB-butyrate construct

| Description | Nucleotide sequences of pLogic046-nsrR-norB-butyrate construct (SEQ ID NO: 80) |
|---|---|
| | agaaattgcaaaaagcatagacatggatatcgaaaattatgaactgat |
| | agatataaaagatttagcagaagcatctctaaaatctgttgaattagt |
| | ttcacaaggaaaagccgacatggtaatgaaaggcttagtagacacatc |
| | aataatactaaaagcagttttaaataaagaagtaggtcttagaactgg |
| | aaatgtattaagtcacgtagcagtatttgatgtagagggatatgatag |
| | attattttcgtaactgacgcagctatgaacttagctcctgatacaaa |
| | tactaaaaagcaaatcatagaaaatgcttgcacagtagcacattcatt |
| | agatataagtgaaccaaaagttgctgcaatatgcgcaaaagaaaaagt |
| | aaatccaaaaatgaaagatacagttgaagctaaagaactagaagaaat |
| | gtatgaagaggagaaatcaaaggttgtatggttggtgggccttttgc |
| | aattgataatgcagtatctttagaagcagctaaacataaaggtataaa |
| | tcatcctgtagcaggacgagctgatatattattagccccagatattga |
| | aggtggtaacatattatataaagctttggtattcttctcaaaatcaaa |
| | aaatgcaggagttatagttggggctaaagcaccaataatattaacttc |
| | tagagcagacagtgaagaaactaaactaaactcaatagctttaggtgt |
| | tttaatggcagcaaaggcataataagaaggagatatacatatgagcaa |
| | aatatttaaaatcttaacaataaatcctggttcgacatcaactaaaat |
| | agctgtatttgataatgaggatttagtatttgaaaaaactttaagaca |
| | ttcttcagaagaaataggaaaatatgagaaggtgtctgaccaatttga |
| | atttcgtaaacaagtaatagaagaagctctaaaagaaggtggagtaaa |
| | aacatctgaattagatgctgtagtaggtagaggaggacttcttaaacc |
| | tataaaaggtggtacttattcagtaagtgctgctatgattgaagattt |
| | aaaagtgggagttttaggagaacacgcttcaaacctaggtggaataat |
| | agcaaaacaaataggtgaagaagtaaatgttccttcatacatagtaga |
| | ccctgttgttgtagatgaattagaagatgttgctagaatttctggtat |
| | gcctgaaataagtagagcaagtgtagtacatgctttaaatcaaaaggc |
| | aatagcaagaagatatgctagagaaataaacaagaaatatgaagatat |
| | aaatcttatagttgcacacatgggtggaggagtttctgttggagctca |
| | taaaaatggtaaaatagtagatgttgcaaacgcattagatggagaagg |
| | acctttctctccagaaagaagtggtggactaccagtaggtgcattagt |
| | aaaaatgtgctttagtggaaaatatactcaagatgaaattaaaaagaa |
| | aataaaaggtaatggcggactagttgcatacttaaacactaatgatgc |
| | tagagaagttgaagaaagaattgaagctggtgatgaaaaagctaaatt |
| | agtatatgaagctatggcatatcaaatctctaaagaaataggagctag |
| | tgctgcagttcttaagggagatgtaaaagcaatattattaactggtgg |

TABLE 39 -continued

Nucleotide sequences of pLogic046-nsrR-norB-butyrate construct

| Description | Nucleotide sequences of pLogic046-nsrR-norB-butyrate construct (SEQ ID NO: 80) |
|---|---|
| | aatcgcatattcaaaaatgtttacagaaatgattgcagatagagttaa |
| | atttatagcagatgtaaaagtttatccaggtgaagatgaaatgattgc |
| | attagctcaaggtggacttagagttttaactggtgaagaagaggctca |
| | agtttatgataactaataa |

The gene products of the bcd2-etfA3-etfB3 genes form a complex that converts crotonyl-CoA to butyryl-CoA and may exhibit dependence on oxygen as a co-oxidant. Because the recombinant bacteria of the invention are designed to produce butyrate in an oxygen-limited environment (e.g. the mammalian gut), that dependence on oxygen could have a negative effect of butyrate production in the gut. It has been shown that a single gene from *Treponema denticola*, trans-2-enoynl-CoA reductase (ter), can functionally replace this three gene complex in an oxygen-independent manner. Therefore, a second butyrate gene cassette in which the ter gene replaces the bcd2-etfA3-etfB3 genes of the first butyrate cassette is synthesized (Genewiz, Cambridge, Mass.). The ter gene is codon-optimized for *E. coli* codon usage using Integrated DNA Technologies online codon optimization tool (https://www.idtdna.com/CodonOpt). The second butyrate gene cassette, as well as transcriptional and translational elements, is synthesized (Gen9, Cambridge, Mass.) and cloned into vector pBR322. The second butyrate gene cassette is placed under control of a FNR regulatory region as described above. In certain constructs, the butyrate gene cassette is placed under the control of an RNS-responsive regulatory region, e.g., norB, and the bacteria further comprises a gene encoding a corresponding RNS-responsive transcription factor, e.g., nsrR (see, e.g., Table 38 and Table 39). In certain constructs, the butyrate gene cassette is placed under the control of an ROS-responsive regulatory region, e.g., oxyS, and the bacteria further comprises a gene encoding a corresponding ROS-responsive transcription factor, e.g., oxyR (see, e.g., Table C and Table 40).

TABLE 40

ROS regulated constructs, OxyR construct, Tet-regulated constructs

| Description | Sequence |
|---|---|
| Nucleotide sequences of pLogic031-oxyS-butyrate construct (SEQ ID NO: 81) | ctcgagttcattatccatcctccatcgccacgatagttcatggcgataggtagaatagc |
| | aatgaacgattatccctatcaagcattctgactgataattgctcacacgaattcattaa |
| | agaggagaaaggtaccatggatttaaattctaaaaaatatcagatgcttaaagagctat |
| | atgtaagcttcgctgaaaatgaagttaaacctttagcaacagaacttgatgaagaagaa |
| | agatttccttatgaaacagtggaaaaaatggcaaaagcaggaatgatgggtataccata |
| | tccaaaagaatatggtggagaaggtggagacactgtaggatatataatggcagttgaag |
| | aattgtctagagtttgtggtactacaggagttatattatcagctcatacatctcttggc |
| | tcatggcctatatatcaatatggtaatgaagaacaaaaacaaaaattcttaagaccact |
| | agcaagtggagaaaaattaggagcatttggtcttactgagcctaatgctggtacagatg |
| | cgtctggccaacaaacaactgctgttttagacggggatgaatacatacttaatggctca |
| | aaaatatttataacaaacgcaatagctggtgacatatatgtagtaatggcaatgactga |
| | taaatctaaggggaacaaaggaatatcagcatttatagttgaaaaaggaactcctgggt |
| | ttagctttggagttaaagaaaagaaatgggtataagaggttcagctacgagtgaatta |
| | atatttgaggattgcagaatacctaaagaaaatttacttggaaaagaaggtcaaggatt |
| | taagatagcaatgtctactcttgatggtggtagaattggtatagctgcacaagctttag |
| | gtttagcacaaggtgctcttgatgaaactgttaaatatgtaaaagaaagagtacaattt |
| | ggtagaccattatcaaaattccaaaatacacaattccaattagctgatatggaagttaa |
| | ggtacaagcggctagacaccttgtatatcaagcagctataaataaagacttaggaaaac |
| | cttatggagtagaagcagcaatggcaaaattatttgcagctgaaacagctatggaagtt |

TABLE 40 -continued

ROS regulated constructs, OxyR construct, Tet-regulated constructs

| Description | Sequence |
|---|---|
| | actacaaaagctgtacaacttcatggaggatatggatacactcgtgactatccagtaga |
| | aagaatgatgagagatgctaagataactgaaatatatgaaggaactagtgaagttcaaa |
| | gaatggttatttcaggaaaactattaaaatagtaagaaggagatatacatatggaggaa |
| | ggatttatgaatatagtcgtttgtataaaacaagttccagatacaacagaagttaaact |
| | agatcctaatacaggtactttaattagagatggagtaccaagtataataaaccctgatg |
| | ataaagcaggtttagaagaagctataaaattaaaagaagaaatgggtgctcatgtaact |
| | gttataacaatgggacctcctcaagcagatatggctttaaaagaagctttagcaatggg |
| | tgcagatagaggtatattattaacagatagagcatttgcgggtgctgatacttgggcaa |
| | cttcatcagcattagcaggagcattaaaaaatatagattttgatattataatagctgga |
| | agacaggcgatagatggagatactgcacaagttggacctcaaatagctgaacatttaaa |
| | tcttccatcaataacatatgctgaagaaataaaaactgaaggtgaatatgtattagtaa |
| | aaagacaatttgaagattgttgccatgacttaaaagttaaaatgccatgccttataaca |
| | actcttaaagatatgaacacaccaagatacatgaaagttggaagaatatatgatgcttt |
| | cgaaaatgatgtagtagaaacatggactgtaaaagatatagaagttgacccttctaatt |
| | taggtcttaaaggttctccaactagtgtatttaaatcatttacaaaatcagttaaacca |
| | gctggtacaatatacaatgaagatgcgaaaacatcagctggaattatcatagataaatt |
| | aaaagagaagtatatcatataataagaaggagatatacatatgggtaacgttttagtag |
| | taatagaacaaagagaaaatgtaattcaaactgtttctttagaattactaggaaaggct |
| | acagaaatagcaaaagattatgatacaaaagtttctgcattacttttaggtagtaaggt |
| | agaaggtttaatagatacattagcacactatggtgcagatgaggtaatagtagtagatg |
| | atgaagctttagcagtgtatacaactgaaccatatacaaaagcagcttatgaagcaata |
| | aaagcagctgaccctatagttgtattatttggtgcaacttcaataggtagagatttagc |
| | gcctagagtttctgctagaatacatacaggtcttactgctgactgtacaggtcttgcag |
| | tagctgaagatacaaaattattattaatgacaagacctgcctttggtggaaatataatg |
| | gcaacaatagtttgtaaagatttcagacctcaaatgtctacagttagaccaggggttat |
| | gaagaaaaatgaacctgatgaaactaaagaagctgtaattaaccgtttcaaggtagaat |
| | ttaatgatgctgataaattagttcaagttgtacaagtaataaaagaagctaaaaaacaa |
| | gttaaaatagaagatgctaagatattagtttctgctggacgtggaatgggtggaaaaga |
| | aaacttagacatactttatgaattagctgaaattataggtggagaagtttctggttctc |
| | gtgccactatagatgcaggttggttagataaagcaagacaagttggtcaaactggtaaa |
| | actgtaagaccagacctttatatagcatgtggtatatctggagcaatacaacatatagc |
| | tggtatggaagatgctgagtttatagttgctataaataaaaatccagaagctccaatat |
| | ttaaatatgctgatgttggtatagttggagatgttcataaagtgcttccagaacttatc |
| | agtcagttaagtgttgcaaaagaaaaggtgaagttttagctaactaataagaaggaga |
| | tatacatatgagagaagtagtaattgccagtgcagctagaacagcagtaggaagttttg |
| | gaggagcatttaaatcagtttcagcggtagagttaggggtaacagcagctaaagaagct |
| | ataaaaagagctaacataactccagatatgatagatgaatctcttttaggggagtact |
| | tacagcaggtcttggacaaaatatagcaagacaaatagcattaggagcaggaataccag |

TABLE 40 -continued

ROS regulated constructs, OxyR construct, Tet-regulated constructs

| Description | Sequence |
|---|---|
| | tagaaaaaccagctatgactataaatatagtttgtggttctggattaagatctgtttca |
| | atggcatctcaacttatagcattaggtgatgctgatataatgttagttggtggagctga |
| | aaacatgagtatgtctccttatttagtaccaagtgcgagatatggtgcaagaatgggtg |
| | atgctgcttttgttgattcaatgataaaagatggattatcagacatatttaataactat |
| | cacatgggtattactgctgaaaacatagcagagcaatggaatataactagagaagaaca |
| | agatgaattagctcttgcaagtcaaaataaagctgaaaaagctcaagctgaaggaaaat |
| | ttgatgaagaaatagttcctgttgttataaaaggaagaaaaggtgacactgtagtagat |
| | aaagatgaatatattaagcctggcactacaatggagaaacttgctaagttaagacctgc |
| | atttaaaaaagatggaacagttactgctggtaatgcatcaggaataaatgatggtgctg |
| | ctatgttagtagtaatggctaaagaaaaagctgaagaactaggaatagagcctcttgca |
| | actatagtttcttatggaacagctggtgttgaccctaaaataatgggatatggaccagt |
| | tccagcaactaaaaaagctttagaagctgctaatatgactattgaagatatagatttag |
| | ttgaagctaatgaggcatttgctgcccaatctgtagctgtaataagagacttaaatata |
| | gatatgaataaagttaatgttaatggtggagcaatagctataggacatccaataggatg |
| | ctcaggagcaagaatacttactacacttttatatgaaatgaagagaagagatgctaaaa |
| | ctggtcttgctacactttgtataggcggtggaatgggaactactttaatagttaagaga |
| | tagtaagaaggagatatacatatgaaattagctgtaataggtagtggaactatgggaag |
| | tggtattgtacaaacttttgcaagttgtggacatgatgtatgtttaaagagtagaactc |
| | aaggtgctatagataaatgtttagctttattagataaaaatttaactaagttagttact |
| | aagggaaaaatggatgaagctacaaaagcagaaatattaagtcatgttagttcaactac |
| | taattatgaagatttaaaagatatggatttaataatagaagcatctgtagaagacatga |
| | atataaagaaagatgttttcaagttactagatgaattatgtaaagaagatactatcttg |
| | gcaacaaatacttcatcattatctataacagaaatagcttcttctactaagcgcccaga |
| | taaagttataggaatgcatttctttaatccagttcctatgatgaaattagttgaagtta |
| | taagtggtcagttaacatcaaaagttacttttgatacagtatttgaattatctaagagt |
| | atcaataaagtaccagtagatgtatctgaatctcctggatttgtagtaaatagaatact |
| | tatacctatgataaatgaagctgttggtatatatgcagatggtgttgcaagtaaagaag |
| | aaatagatgaagctatgaaattaggagcaaaccatccaatgggaccactagcattaggt |
| | gatttaatcggattagatgttgttttagctataatgaacgttttatatactgaatttgg |
| | agatactaaatatagacctcatccacttttagctaaaatggttagagctaatcaattag |
| | gaagaaaaactaagataggattctatgattataataataataagaaggagatatacat |
| | atgagtacaagtgatgttaaagtttatgagaatgtagctgttgaagtagatggaaatat |
| | atgtacagtgaaaatgaatagacctaaagcccttaatgcaataaattcaaagactttag |
| | aagaactttatgaagtatttgtagatattaataatgatgaaactattgatgttgtaata |
| | ttgacaggggaaggaaaggcatttgtagctggagcagatattgcatacatgaaagattt |
| | agatgctgtagctgctaaagattttagtatcttaggagcaaaagcttttggagaaatag |
| | aaaatagtaaaaaagtagtgatagctgctgtaaacggatttgctttaggtggaggatgt |
| | gaacttgcaatggcatgtgatataagaattgcatctgctaaagctaaatttggtcagcc |

TABLE 40 -continued

ROS regulated constructs, OxyR construct, Tet-regulated constructs

| Description | Sequence |
|---|---|
| | agaagtaactcttggaataactccaggatatggaggaactcaaaggcttacaagattgg |
| | ttggaatggcaaaagcaaaagaattaatctttacaggtcaagttataaaagctgatgaa |
| | gctgaaaaaatagggctagtaaatagagtcgttgagccagacattttaatagaagaagt |
| | tgagaaattagctaagataatagctaaaaatgctcagcttgcagttagatactctaaag |
| | aagcaatacaacttggtgctcaaactgatataaatactggaatagatatagaatctaat |
| | ttatttggtctttgttttcaactaaagaccaaaaagaaggaatgtcagctttcgttga |
| | aaagagagaagctaactttataaaagggtaataagaaggagatatacatatgagaagtt |
| | ttgaagaagtaattaagtttgcaaaagaaagaggacctaaaactatatcagtagcatgt |
| | tgccaagataaagaagttttaatggcagttgaaatggctagaaaagaaaaaatagcaaa |
| | tgccattttagtaggagatatagaaaagactaaagaaattgcaaaaagcatagacatgg |
| | atatcgaaaattatgaactgatagatataaaagatttagcagaagcatctctaaaatct |
| | gttgaattagtttcacaaggaaaagccgacatggtaatgaaaggcttagtagacacatc |
| | aataatactaaaagcagttttaaataaagaagtaggtcttagaactggaaatgtattaa |
| | gtcacgtagcagtatttgatgtagagggatatgatagattattttttcgtaactgacgca |
| | gctatgaacttagctcctgatacaaatactaaaaagcaaatcatagaaaatgcttgcac |
| | agtagcacattcattagatataagtgaaccaaaagttgctgcaatatgcgcaaaagaaa |
| | aagtaaatccaaaaatgaaagatacagttgaagctaaagaactagaagaaatgtatgaa |
| | agaggagaaatcaaaggttgtatggttggtgggccttttgcaattgataatgcagtatc |
| | tttagaagcagctaaacataaaggtataaatcatcctgtagcaggacgagctgatatat |
| | tattagccccagatattgaaggtggtaacatattatataaagctttggtattcttctca |
| | aaatcaaaaaatgcaggagttatagttggggctaaagcaccaataatattaacttctag |
| | agcagacagtgaagaaactaaactaaactcaatagctttaggtgttttaatggcagcaa |
| | aggcataataagaaggagatatacatatgagcaaaatatttaaaatcttaacaataaat |
| | cctggttcgacatcaactaaaatagctgtatttgataatgaggatttagtatttgaaaa |
| | aactttaagacattcttcagaagaaataggaaaatatgagaaggtgtctgaccaatttg |
| | aatttcgtaaacaagtaatagaagaagctctaaaagaaggtggagtaaaaacatctgaa |
| | ttagatgctgtagtaggtagaggaggacttcttaaacctataaaaggtggtacttattc |
| | agtaagtgctgctatgattgaagatttaaaagtgggagttttaggagaacacgcttcaa |
| | acctaggtggaataatagcaaaacaaatagg tgaagaagtaaatgttccttcatacata |
| | gtagaccctgttgttgtagatgaattagaagatgttgctagaatttctggtatgcctga |
| | aataagtagagcaagtgtagtacatgctttaaatcaaaaggcaatagcaagaagatatg |
| | ctagagaaataaacaagaaatatgaagatataaatcttatagttgcacacatgggtgga |
| | ggagtttctgttggagctcataaaaatggtaaaatagtagatgttgcaaacgcattaga |
| | tggagaaggacctttctctccagaaagaagtggtggactaccagtaggtgcattagtaa |
| | aaatgtgctttagtggaaaatatactcaagatgaaattaaaaagaaaataaaaggtaat |
| | ggcggactagttgcatacttaaacactaatgatgctagagaagttgaagaaagaattga |
| | agctggtgatgaaaaagctaaattagtatatgaagctatggcatatcaaatctctaaag |
| | aaataggagctagtgctgcagttcttaagggagatgtaaaagcaatattattaactggt |

TABLE 40 -continued

ROS regulated constructs, OxyR construct, Tet-regulated constructs

| Description | Sequence |
|---|---|
| | ggaatcgcatattcaaaaatgtttacagaaatgattgcagatagagttaaatttatagc |
| | agatgtaaaagtttatccaggtgaagatgaaatgattgcattagctcaaggtggactta |
| | gagttttaactggtgaagaagaggctcaagtttatgataactaataa |
| Nucleotide sequences of pLogic046-oxyS-butyrate construct (SEQ ID NO: 82) | ctcgagttcattatccatcctccatcgccacgatagttcatggcgataggtagaatagc |
| | aatgaacgattatccctatcaagcattctgactgataattgctcacacgaattcattaa |
| | agaggagaaaggtaccatgatcgtaaaacctatggtacgcaacaatatctgcctgaacg |
| | cccatcctcagggctgcaagaagggagtggaagatcagattgaatataccaagaaacgc |
| | attaccgcagaagtcaaagctggcgcaaaagctccaaaaaacgttctggtgcttggctg |
| | ctcaaatggttacggcctggcgagccgcattactgctgcgttcggatacggggctgcga |
| | ccatcggcgtgtcctttgaaaaagcgggttcagaaaccaaatatggtacaccgggatgg |
| | tacaataatttggcatttgatgaagcggcaaaacgcgagggtctttatagcgtgacgat |
| | cgacggcgatgcgttttcagacgagatcaaggcccaggtaattgaggaagccaaaaaaa |
| | aaggtatcaaatttgatctgatcgtatacagcttggccagcccagtacgtactgatcct |
| | gatacaggtatcatgcacaaaagcgttttgaaacccttcggaaaaacgttcacaggcaa |
| | aacagtagatccgtttactggcgagctgaaggaaatctccgcggaaccagcaaatgacg |
| | aggaagcagccgccactgttaaagttatgggggtgaagattgggaacgttggattaag |
| | cagctgtcgaaggaaggcctcttagaagaaggctgtattaccttggcctatagttatat |
| | tggccctgaagctacccaagctttgtaccgtaaaggcacaatcggcaaggccaaagaac |
| | acctggaggccacagcacaccgtctcaacaaagagaacccgtcaatccgtgccttcgtg |
| | agcgtgaataaaggcctggtaacccgcgcaagcgccgtaatcccggtaatccctctgta |
| | tctcgccagcttgttcaaagtaatgaaagagaagggcaatcatgaaggttgtattgaac |
| | agatcacgcgtctgtacgccgagcgcctgtaccgtaaagatggtacaattccagttgat |
| | gaggaaaatcgcattcgcattgatgattgggagttagaagaagacgtccagaaagcggt |
| | atccgcgttgatggagaaagtcacgggtgaaaacgcagaatctctcactgacttagcgg |
| | ggtaccgccatgatttcttagctagtaacggctttgatgtagaaggtattaattatgaa |
| | gcggaagttgaacgcttcgaccgtatctgataagaaggagatatacatatgagagaagt |
| | agtaattgccagtgcagctagaacagcagtaggaagttttggaggagcatttaaatcag |
| | tttcagcggtagagttaggggtaacagcagctaaagaagctataaaaagagctaacata |
| | actccagatatgatagatgaatctcttttaggggagtacttacagcaggtcttggaca |
| | aaatatagcaagacaaatagcattaggagcaggaataccagtagaaaaaccagctatga |
| | ctataaatatagtttgtggttctggattaagatctgtttcaatggcatctcaacttata |
| | gcattaggtgatgctgatataatgttagttggtggagctgaaaacatgagtatgtctcc |
| | ttatttagtaccaagtgcgagatatggtgcaagaatgggtgatgctgcttttgttgatt |
| | caatgataaaagatggattatcagacatatttaataactatcacatgggtattactgct |
| | gaaaacatagcagagcaatggaatataactagagaagaacaagatgaattagctcttgc |
| | aagtcaaaataaagctgaaaaagctcaagctgaaggaaaatttgatgaagaaatagttc |
| | ctgttgttataaaaggaagaaaaggtgacactgtagtagataaagatgaatatattaag |
| | cctggcactacaatggagaaacttgctaagttaagacctgcatttaaaaaagatggaac |

TABLE 40 -continued

ROS regulated constructs, OxyR construct, Tet-regulated constructs

| Description | Sequence |
|---|---|
| | agttactgctggtaatgcatcaggaataaatgatggtgctgctatgttagtagtaatgg |
| | ctaaagaaaaagctgaagaactaggaatagagcctcttgcaactatagtttcttatgga |
| | acagctggtgttgaccctaaaataatgggatatggaccagttccagcaactaaaaaagc |
| | tttagaagctgctaatatgactattgaagatatagatttagttgaagctaatgaggcat |
| | ttgctgcccaatctgtagctgtaataagagacttaaatatagatatgaataaagttaat |
| | gttaatggtggagcaatagctataggacatccaataggatgctcaggagcaagaatact |
| | tactacactttatatgaaatgaagagaagagatgctaaaactggtcttgctacacttt |
| | gtataggcggtggaatgggaactactttaatagttaagagatagtaagaaggagatata |
| | catatgaaattagctgtaataggtagtggaactatgggaagtggtattgtacaaacttt |
| | tgcaagttgtggacatgatgtatgtttaaagagtagaactcaaggtgctatagataaat |
| | gtttagctttattagataaaaatttaactaagttagttactaagggaaaaatggatgaa |
| | gctacaaaagcagaaatattaagtcatgttagttcaactactaattatgaagatttaaa |
| | agatatggatttaataatagaagcatctgtagaagacatgaatataaagaaagatgttt |
| | tcaagttactagatgaattatgtaaagaagatactatcttggcaacaaatacttcatca |
| | ttatctataacagaaatagcttcttctactaagcgcccagataaagttataggaatgca |
| | tttctttaatccagttcctatgatgaaattagttgaagtttataagtggtcagttaacat |
| | caaaagttacttttgatacagtatttgaattatctaagagtatcaataaagtaccagta |
| | gatgtatctgaatctcctggatttgtagtaaatagaatacttatacctatgataaatga |
| | agctgttggtatatatgcagatggtgttgcaagtaaagaagaaatagatgaagctatga |
| | attaggagcaaaccatccaatgggaccactagcattaggtgatttaatcggattagat |
| | gttgttttagctataatgaacgttttatatactgaatttggagatactaaatatagacc |
| | tcatccacttttagctaaaatggttagagctaatcaattaggaagaaaaactaagatag |
| | gattctatgattataataataataagaaggagatatacatatgagtacaagtgatgtt |
| | aaagtttatgagaatgtagctgttgaagtagatggaaatatatgtacagtgaaaatgaa |
| | tagacctaaagcccttaatgcaataaattcaaagactttagaagaactttatgaagtat |
| | ttgtagatattaataatgatgaaactattgatgttgtaatattgacaggggaaggaaag |
| | gcatttgtagctggagcagatattgcatacatgaaagatttagatgctgtagctgctaa |
| | agattttagtatcttaggagcaaaagcttttggagaaatagaaaatagtaaaaaagtag |
| | tgatagctgctgtaaacggatttgctttaggtggaggatgtgaacttgcaatggcatgt |
| | gatataagaattgcatctgctaaagctaaatttggtcagccagaagtaactcttggaat |
| | aactccaggatatggaggaactcaaaggcttacaagattggttggaatggcaaaagcaa |
| | aagaattaatctttacaggtcaagttataaaagctgatgaagctgaaaaaatagggcta |
| | gtaaatagagtcgttgagccagacatttttaatagaagaagttgagaaattagctaagat |
| | aatagctaaaaatgctcagcttgcagttagatactctaaagaagcaatacaacttggtg |
| | ctcaaactgatatatactggaatagatatagaatctaatttatttggtctttgtttt |
| | tcaactaaagaccaaaaagaaggaatgtcagctttcgttgaaaagagagaagctaactt |
| | tataaagggtaataagaaggagatatacatatgagaagttttgaagaagtaattaagt |
| | ttgcaaaagaaagaggacctaaaactatatcagtagcatgttgccaagataaagaagtt |

TABLE 40 -continued

ROS regulated constructs, OxyR construct, Tet-regulated constructs

| Description | Sequence |
|---|---|
| | ttaatggcagttgaaatggctagaaaagaaaaaatagcaaatgccattttagtaggaga |
| | tatagaaaagactaaagaaattgcaaaaagcatagacatggatatcgaaaattatgaac |
| | tgatagatataaaagatttagcagaagcatctctaaaatctgttgaattagtttcacaa |
| | ggaaaagccgacatggtaatgaaaggcttagtagacacatcaataatactaaaagcagt |
| | tttaaataaagaagtaggtcttagaactggaaatgtattaagtcacgtagcagtatttg |
| | atgtagagggatatgatagattatttttcgtaactgacgcagctatgaacttagctcct |
| | gatacaaatactaaaaagcaaatcatagaaaatgcttgcacagtagcacattcattaga |
| | tataagtgaaccaaaagttgctgcaatatgcgcaaaagaaaaagtaaatccaaaaatga |
| | aagatacagttgaagctaaagaactagaagaaatgtatgaaagaggagaaatcaaaggt |
| | tgtatggttggtgggccttttgcaattgataatgcagtatctttagaagcagctaaaca |
| | taaaggtataaatcatcctgtagcaggacgagctgatatattattagcccagatattg |
| | aaggtggtaacatattatataaagctttggtattcttctcaaaatcaaaaaatgcagga |
| | gttatagttggggctaaagcaccaataatattaacttctagagcagacagtgaagaaac |
| | taaactaaactcaatagctttaggtgttttaatggcagcaaaggcataataagaaggag |
| | atatacatatgagcaaaatatttaaaatcttaacaataaatcctggttcgacatcaact |
| | aaaatagctgtatttgataatgaggatttagtatttgaaaaaactttaagacattcttc |
| | agaagaaataggaaaatatgagaaggtgtctgaccaatttgaatttcgtaaacaagtaa |
| | tagaagaagctctaaaagaaggtggagtaaaaacatctgaattagatgctgtagtaggt |
| | agaggaggacttcttaaacctataaaaggtggtacttattcagtaagtgctgctatgat |
| | tgaagatttaaaagtgggagttttaggagaacacgcttcaaacctaggtggaataatag |
| | caaaacaaataggtgaagaagtaaatgttccttcatacatagtagaccctgttgttgta |
| | gatgaattagaagatgttgctagaatttctggtatgcctgaaataagtagagcaagtgt |
| | agtacatgctttaaatcaaaaggcaatagcaagaagatatgctagagaaataaacaaga |
| | aatatgaagatataaatcttatagttgcacacatgggtggaggagtttctgttggagct |
| | TCTGTACCGTCCCAATCATGGCTCGCTGGAAAAAGTTGGTCTTATGGCAGAAGACCCCT |
| | GTACACAACACCCGT |
| | neered bacteria comprise the nucleic acid |
| | ttaaacactaatgatgctagagaagttgaagaaagaattgaagctggtgatgaaaaagc |
| | taaattagtatatgaagctatggcatatcaaatctctaaagaaataggagctagtgctg |
| | cagttcttaagggagatgtaaaagcaatattattaactggtggaatcgcatattcaaaa |
| | atgttacagaaatgattgcagatagagttaaatttatagcagatgtaaaagtttatcc |
| | aggtgaagatgaaatgattgcattagctcaaggtggacttagagttttaactggtgaag |
| | aagaggctcaagtttatgataactaataa |
| Nucleotide sequences of pZA22-oxyR construct (SEQ ID NO: 83) | ctcgagatgctagcaattgtgagcggataacaattgacattgtgagcggataacaagat |
| | actgagcacatcagcaggacgcactgacccttaattaaaagaattcattaaagaggagaa |
| | aggtaccatgaatattcgtgatcttgagtacctggtggcattggctgaacaccgccatt |
| | ttcggcgtgcggcagattcctgccacgttagccagccgacgcttagcgggcaaattcgt |
| | aagctggaagatgagctgggcgtgatgttgctggagcggaccagccgtaaagtgttgtt |

TABLE 40 -continued

ROS regulated constructs, OxyR construct, Tet-regulated constructs

| Description | Sequence |
|---|---|
| | cacccaggcgggaatgctgctggtggatcaggcgcgtaccgtgctgcgtgaggtgaaag |
| | tccttaaagagatggcaagccagcagggcgagacgatgtccggaccgctgcacattggt |
| | ttgattcccacagttggaccgtacctgctaccgcatattatccctatgctgcaccagac |
| | ctttccaaagctggaaatgtatctgcatgaagcacagacccaccagttactggcgcaac |
| | tggacagcggcaaactcgattgcgtgatcctcgcgctggtgaaagagagcgaagcattc |
| | attgaagtgccgttgtttgatgagccaatgttgctggctatctatgaagatcacccgtg |
| | ggcgaaccgcgaatgcgtaccgatggccgatctggcaggggaaaaactgctgatgctgg |
| | aagatggtcactgtttgcgcgatcaggcaatgggtttctgttttgaagccggggcggat |
| | gaagatacacacttccgcgcgaccagcctggaaactctgcgcaacatggtggcggcagg |
| | tagcgggatcactttactgccagcgctggctgtgccgccggagcgcaaacgcgatgggg |
| | ttgtttatctgccgtgcattaagccggaaccacgccgcactattggcctggtttatcgt |
| | cctggctcaccgctgcgcagccgctatgagcagctggcagaggccatccgcgcaagaat |
| | ggatggccatttcgataaagttttaaaacaggcggtttaaggatcccatggtacgcgtg |
| | ctagaggcatcaaataaaacgaaaggctcagtcgaaagactgggcctttcgttttatct |
| | gttgtttgtcggtgaacgctctcctgagtaggacaaatccgccgccctagacctagggg |
| | atatattccgcttcctcgctcactgactcgctacgctcggtcgttcgactgcggcgagc |
| | ggaaatggcttacgaacggggcggagatttcctggaagatgccaggaagatacttaaca |
| | gggaagtgagagggccgcggcaaagccgttttccataggctccgcccccctgacaagc |
| | atcacgaaatctgacgctcaaatcagtggtggcgaaacccgacaggactataaagatac |
| | caggcgtttccccctggcggctccctcgtgcgctctcctgttcctgcctttcggtttac |
| | cggtgtcattccgctgttatggccgcgtttgtctcattccacgcctgacactcagttcc |
| | gggtaggcagttcgctccaagctggactgtatgcacgaaccccccgttcagtccgaccg |
| | ctgcgccttatccggtaactatcgtcttgagtccaacccggaaagacatgcaaaagcac |
| | cactggcagcagccactggtaattgatttagaggagttagtcttgaagtcatgcgccgg |
| | ttaaggctaaactgaaaggacaagttttggtgactgcgctcctccaagccagttacctc |
| | ggttcaaagagttggtagctcagagaaccttcgaaaaaccgccctgcaaggcggttttt |
| | tcgttttcagagcaagagattacgcgcagaccaaaacgatctcaagaagatcatcttat |
| | taatcagataaaatatttctagatttcagtgcaatttatctcttcaaatgtagcacctg |
| | aagtcagccccatacgatataagttgttactagtgcttggattctcaccaataaaaaac |
| | gcccggcggcaaccgagcgttctgaacaaatccagatggagttctgaggtcattactgg |
| | atctatcaacaggagtccaagcgagctctcgaacccagagtcccgctcagaagaactc |
| | gtcaagaaggcgatagaaggcgatgcgctgcgaatcgggagcggcgataccgtaaagca |
| | cgaggaagcggtcagcccattcgccgccaagctcttcagcaatatcacgggtagccaac |
| | gctatgtcctgatagcggtccgccacacccagccggccacagtcgatgaatccagaaaa |
| | gcggccattttccaccatgatattcggcaagcaggcatcgccatgggtcacgacgagat |
| | cctcgccgtcgggcatgcgcgccttgagcctggcgaacagttcggctggcgcgagcccc |
| | tgatgctcttcgtccagatcatcctgatcgacaagaccggcttccatccgagtacgtgc |
| | tcgctcgatgcgatgtttcgcttggtggtcgaatgggcaggtagccggatcaagcgtat |

TABLE 40 -continued

ROS regulated constructs, OxyR construct, Tet-regulated constructs

| Description | Sequence |
|---|---|
| | gcagccgccgcattgcatcagccatgatggatactttctcggcaggagcaaggtgagat |
| | gacaggagatcctgccccggcacttcgcccaatagcagccagtcccttcccgcttcagt |
| | gacaacgtcgagcacagctgcgcaaggaacgcccgtcgtggccagccacgatagccgcg |
| | ctgcctcgtcctgcagttcattcagggcaccggacaggtcggtcttgacaaaaagaacc |
| | gggcgccctgcgctgacagccggaacacggcggcatcagagcagccgattgtctgttg |
| | tgcccagtcatagccgaatagcctctccacccaagcggccggagaacctgcgtgcaatc |
| | catcttgttcaatcatgcgaaacgatcctcatcctgtctcttgatcagatcttgatccc |
| | ctgcgccatcagatccttggcggcaagaaagccatccagtttactttgcagggcttccc |
| | aaccttaccagagggcgccccagctggcaattccgacgtctaagaaaccattattatca |
| | tgacattaacctataaaaataggcgtatcacgaggccctttcgtcttcac |
| Nucleotide sequences of pLogic031-tet-butyrate construct (SEQ ID NO: 84) The sequence encoding TetR is underlined, and the overlapping tetR/tetA promoters are boxed. | gtaaaacgacggccagtgaattcg<u>ttaagacccactttcacatttaagttgttttcta</u> <u>atccgcatatgatcaattcaaggccgaataagaaggctggctctgcaccttggtgatca</u> <u>aataattcgatagcttgtcgtaataatggcggcatactatcagtagtaggtgtttccct</u> <u>ttcttctttagcgacttgatgctcttgatcttccaatacgcaacctaaagtaaaatgcc</u> <u>ccacagcgctgagtgcatataatgcattctctagtgaaaaaccttgttggcataaaaag</u> <u>gctaattgattttcgagagtttcatactgttttctgtaggccgtgtacctaaatgtac</u> <u>ttttgctccatcgcgatgacttagtaaagcacatctaaaacttttagcgttattacgta</u> <u>aaaaatcttgccagctttcccttctaaagggcaaaagtgagtatggtgcctatctaac</u> <u>atctcaatggctaaggcgtcgagcaaagcccgcttattttttacatgccaatacaatgt</u> <u>aggctgctctacacctagcttctgggcgagtttacgggttgttaaaccttcgattccga</u> <u>cctcattaagcagctctaatgcgctgttaatcactttacttttatctaatctagacatc</u> attaattcctaattttt[gttgacactctatcattgatagagttatttaccactcccta] [tcagtgatagagaa]aagtgaactctagaaataattttgtttaactttaagaaggagata tacatatggatttaaattctaaaaaatatcagatgcttaaagagctatatgtaagcttc gctgaaaatgaagttaaacctttagcaacagaacttgatgaagaagaaagatttcctta tgaaacagtggaaaaaatggcaaaagcaggaatgatgggtataccatatccaaaagaat atggtggagaaggtggagacactgtaggatatataatggcagttgaagaattgtctaga gtttgtggtactacaggagttatattatcagctcatacatctcttggctcatggcctat atatcaatatggtaatgaagaacaaaaacaaaaattcttaagaccactagcaagtggag aaaaattaggagcatttggtcttactgagcctaatgctggtacagatgcgtctggccaa caaacaactgctgttttagacggggatgaatacatacttaatggctcaaaaatatttat aacaaacgcaatagctggtgacatatatgtagtaatggcaatgactgataaatctaagg ggaacaaaggaatatcagcatttatagttgaaaaaggaactcctgggtttagctttgga gttaaagaaagaaatgggtataagaggttcagctacgagtgaattaatatttgagga ttgcagaatacctaaagaaaatttacttggaaaagaaggtcaaggatttaagatagcaa tgtctactcttgatggtggtagaattggtatagctgcacaagctttaggtttagcacaa ggtgctcttgatgaaactgttaaatatgtaaaagaaagagtacaatttggtagaccatt |

TABLE 40 -continued

ROS regulated constructs, OxyR construct, Tet-regulated constructs

| Description | Sequence |
|---|---|
| | atcaaaattccaaaatacacaattccaattagctgatatggaagttaaggtacaagcgg |
| | ctagacaccttgtatatcaagcagctataaataaagacttaggaaaaccttatggagta |
| | gaagcagcaatggcaaaattatttgcagctgaaacagctatggaagttactacaaaagc |
| | tgtacaacttcatggaggatatggatacactcgtgactatccagtagaaagaatgatga |
| | gagatgctaagataactgaaatatatgaaggaactagtgaagttcaaagaatggttatt |
| | tcaggaaaactattaaaatagtaagaaggagatatacatatggaggaaggatttatgaa |
| | tatagtcgtttgtataaaacaagttccagatacaacagaagttaaactagatcctaata |
| | caggtactttaattagagatggagtaccaagtataataaaccctgatgataaagcaggt |
| | ttagaagaagctataaaattaaaagaagaaatgggtgctcatgtaactgttataacaat |
| | gggacctcctcaagcagatatggctttaaaagaagctttagcaatgggtgcagatagag |
| | gtatattattaacagatagagcatttgcgggtgctgatacttgggcaacttcatcagca |
| | ttagcaggagcattaaaaaatatagattttgatattataatagctggaagacaggcgat |
| | agatggagatactgcacaagttggaccctcaaatagctgaacatttaaatcttccatcaa |
| | taacatatgctgaagaaataaaaactgaaggtgaatatgtattagtaaaaagacaattt |
| | gaagattgttgccatgacttaaaagttaaaatgccatgccttataacaactcttaaaga |
| | tatgaacacaccaagatacatgaaagttggaagaatatatgatgctttcgaaaatgatg |
| | tagtagaaacatggactgtaaaagatatagaagttgacccttctaatttaggtcttaaa |
| | ggttctccaactagtgtatttaaatcatttacaaaatcagttaaaccagctggtacaat |
| | atacaatgaagatgcgaaaacatcagctggaattatcatagataaattaaaagagaagt |
| | atatcatataataagaaggagatatacatatgggtaacgttttagtagtaatagaacaa |
| | agagaaaatgtaattcaaactgtttctttagaattactaggaaaggctacagaaatagc |
| | aaaagattatgatacaaaagtttctgcattacttttaggtagtaaggtagaaggtttaa |
| | tagatacattagcacactatggtgcagatgaggtaatagtagtagatgatgaagcttta |
| | gcagtgtatacaactgaaccatatacaaaagcagcttatgaagcaataaaagcagctga |
| | ccctatagttgtattatttggtgcaacttcaataggtagagatttagcgcctagagttt |
| | ctgctagaatacatacaggtcttactgctgactgtacaggtcttgcagtagctgaagat |
| | acaaaattattattaatgacaagacctgcctttggtggaaatataatggcaacaatagt |
| | ttgtaaagatttcagacctcaaatgtctacagttagaccaggggttatgaagaaaaatg |
| | aacctgatgaaactaaagaagctgtaattaaccgtttcaaggtagaatttaatgatgct |
| | gataaattagttcaagttgtacaagtaataaaagaagctaaaaaacaagttaaaataga |
| | agatgctaagatattagtttctgctggacgtggaatgggtggaaaagaaaacttagaca |
| | tactttatgaattagctgaaattataggtggagaagtttctggttctcgtgccactata |
| | gatgcaggttggttagataaagcaagacaagttggtcaaactggtaaaactgtaagacc |
| | agacctttatatagcatgtggtatatctggagcaatacaacatatagctggtatggaag |
| | atgctgagtttatagttgctataaataaaaatccagaagctccaatatttaaatatgct |
| | gatgttggtatagttggagatgttcataaagtgcttccagaacttatcagtcagttaag |
| | tgttgcaaaagaaaaaggtgaagttttagctaactaataagaaggagatatacatatga |
| | gagaagtagtaattgccagtgcagctagaacagcagtaggaagttttggaggagcattt |

TABLE 40 -continued

ROS regulated constructs, OxyR construct, Tet-regulated constructs

| Description | Sequence |
|---|---|
| | aaatcagtttcagcggtagagttaggggtaacagcagctaaagaagctataaaagagc |
| | taacataactccagatatgatagatgaatctcttttaggggagtacttacagcaggtc |
| | ttggacaaaatatagcaagacaaatagcattaggagcaggaataccagtagaaaaacca |
| | gctatgactataaatatagtttgtggttctggattaagatctgtttcaatggcatctca |
| | acttatagcattaggtgatgctgatataatgttagttggtggagctgaaaacatgagta |
| | tgtctccttatttagtaccaagtgcgagatatggtgcaagaatgggtgatgctgctttt |
| | gttgattcaatgataaaagatggattatcagacatatttaataactatcacatgggtat |
| | tactgctgaaaacatagcagagcaatggaatataactagagaagaacaagatgaattag |
| | ctcttgcaagtcaaaataaagctgaaaaagctcaagctgaaggaaaatttgatgaagaa |
| | atagttcctgttgttataaaaggaagaaaaggtgacactgtagtagataaagatgaata |
| | tattaagcctggcactacaatggagaaacttgctaagttaagacctgcatttaaaaaag |
| | atggaacagttactgctggtaatgcatcaggaataaatgatggtgctgctatgttagta |
| | gtaatggctaaagaaaaagctgaagaactaggaatagagcctcttgcaactatagtttc |
| | ttatggaacagctggtgttgaccctaaaataatgggatatggaccagttccagcaacta |
| | aaaaagctttagaagctgctaatatgactattgaagatatagatttagttgaagctaat |
| | gaggcatttgctgcccaatctgtagctgtaataagagacttaaatatagatatgaataa |
| | agttaatgttaatggtggagcaatagctataggacatccaataggatgctcaggagcaa |
| | gaatacttactacactttatatgaaatgaagagaagagatgctaaaactggtcttgct |
| | acactttgtataggcggtggaatgggaactactttaatagttaagagatagtaagaagg |
| | agatatacatatgaaattagctgtaataggtagtggaactatgggaagtggtattgtac |
| | aaacttttgcaagttgtggacatgatgtatgtttaaagagtagaactcaaggtgctata |
| | gataaatgtttagctttattagataaaaatttaactaagttagttactaagggaaaaat |
| | ggatgaagctacaaaagcagaaatattaagtcatgttagttcaactactaattatgaag |
| | atttaaaagatatggatttaataatagaagcatctgtagaagacatgaatataaagaaa |
| | gatgttttcaagttactagatgaattatgtaaagaagatactatcttggcaacaaatac |
| | ttcatcattatctataacagaaatagcttcttctactaagcgcccagataaagttatag |
| | gaatgcatttctttaatccagttcctatgatgaaattagttgaagttataagtggtcag |
| | ttaacatcaaaagttacttttgatacagtatttgaattatctaagagtatcaataaagt |
| | accagtagatgtatctgaatctcctggatttgtagtaaatagaatacttatacctatga |
| | taaatgaagctgttggtatatatgcagatggtgttgcaagtaaagaagaaatagatgaa |
| | gctatgaaattaggagcaaaccatccaatgggaccactagcattaggtgatttaatcgg |
| | attagatgttgttttagctataatgaacgttttatatactgaatttggagatactaaat |
| | atagacctcatccacttttagctaaaatggttagagctaatcaattaggaagaaaaact |
| | aagataggattctatgattataataaataataagaaggagatatacatatgagtacaag |
| | tgatgttaaagtttatgagaatgtagctgttgaagtagatggaaatatatgtacagtga |
| | aaatgaatagacctaaagcccttaatgcaataaattcaaagactttagaagaactttat |
| | gaagtatttgtagatattaataatgatgaaactattgatgttgtaatattgacaggga |
| | aggaaaggcatttgtagctggagcagatattgcatacatgaaagatttagatgctgtag |

TABLE 40 -continued

ROS regulated constructs, OxyR construct, Tet-regulated constructs

| Description | Sequence |
|---|---|
| | ctgctaaagattttagtatcttaggagcaaaagcttttggagaaatagaaaatagtaaa |
| | aaagtagtgatagctgctgtaaacggatttgctttaggtggaggatgtgaacttgcaat |
| | ggcatgtgatataagaattgcatctgctaaagctaaatttggtcagccagaagtaactc |
| | ttggaataactccaggatatggaggaactcaaaggcttacaagattggttggaatggca |
| | aaagcaaaagaattaatctttacaggtcaagttataaaagctgatgaagctgaaaaaat |
| | agggctagtaaatagagtcgttgagccagacatttaatagaagaagttgagaaattag |
| | ctaagataatagctaaaaatgctcagcttgcagttagatactctaaagaagcaatacaa |
| | cttggtgctcaaactgatataaatactggaatagatatagaatctaatttatttggtct |
| | ttgttttcaactaaagaccaaaaagaaggaatgtcagctttcgttgaaaagagagaag |
| | ctaactttataaaagggtaataagaaggagatacatatgagaagttttgaagaagta |
| | attaagtttgcaaaagaagaggacctaaaactatatcagtagcatgttgccaagataa |
| | agaagttttaatggcagttgaaatggctagaaaagaaaaaatagcaaatgccattttag |
| | taggagatatagaaaagactaaagaaattgcaaaaagcatagacatggatatcgaaaat |
| | tatgaactgatagatataaaagatttagcagaagcatctctaaaatctgttgaattagt |
| | ttcacaaggaaaagccgacatggtaatgaaaggcttagtagacacatcaataatactaa |
| | aagcagttttaaataaagaagtaggtcttagaactggaaatgtattaagtcacgtagca |
| | gtatttgatgtagagggatatgatagattatttttcgtaactgacgcagctatgaactt |
| | agctcctgatacaaatactaaaaagcaaatcatagaaaatgcttgcacagtagcacatt |
| | cattagatataagtgaaccaaaagttgctgcaatatgcgcaaaagaaaaagtaaatcca |
| | aaaatgaaagatacagttgaagctaaagaactagaagaaatgtatgaaagaggagaaat |
| | caaaggttgtatggttggtgggccttttgcaattgataatgcagtatctttagaagcag |
| | ctaaacataaaggtataaatcatcctgtagcaggacgagctgatatattattagcccca |
| | gatattgaaggtggtaacatattatataaagctttggtattcttctcaaaatcaaaaaa |
| | tgcaggagttatagttggggctaaagcaccaataatattaacttctagagcagacagtg |
| | aagaaactaaactaaactcaatagctttaggtgttttaatggcagcaaaggcataataa |
| | gaaggagatatacatatgagcaaaatatttaaaatcttaacaataaatcctggttcgac |
| | atcaactaaaatagctgtatttgataatgaggatttagtatttgaaaaaacttaagac |
| | attcttcagaagaaataggaaaatatgagaaggtgtctgaccaatttgaatttcgtaaa |
| | caagtaatagaagaagctctaaaagaaggtggagtaaaaacatctgaattagatgctgt |
| | agtaggtagaggaggacttcttaaacctataaaaggtggtacttattcagtaagtgctg |
| | ctatgattgaagatttaaaagtgggagttttaggagaacacgcttcaaacctaggtgga |
| | ataatagcaaaacaataggtgaagaagtaaatgttccttcatacatagtagaccctgt |
| | tgttgtagatgaattagaagatgttgctagaatttctggtatgcctgaaataagtagag |
| | caagtgtagtacatgcttaaatcaaaaggcaatagcaagaagatatgctagagaaata |
| | aacaagaaatatgaagatataaatcttatagttgcacacatgggtggaggagtttctgt |
| | tggagctcataaaaatggtaaaatagtagatgttgcaaacgcattagatggagaaggac |
| | ctttctctccagaaagaagtggtggactaccagtaggtgcattagtaaaaatgtgctt |
| | agtggaaaatatactcaagatgaaattaaaaagaaaataaaaggtaatggcggactagt |

TABLE 40 -continued

ROS regulated constructs, OxyR construct, Tet-regulated constructs

| Description | Sequence |
|---|---|
| | tgcatacttaaacactaatgatgctagagaagttgaagaaagaattgaagctggtgatg |
| | aaaaagctaaattagtatatgaagctatggcatatcaaatctctaaagaaataggagct |
| | agtgctgcagttcttaagggagatgtaaaagcaatattattaactggtggaatcgcata |
| | ttcaaaaatgtttacagaaatgattgcagatagagttaaatttatagcagatgtaaaag |
| | tttatccaggtgaagatgaaatgattgcattagctcaaggtggacttagagttttaact |
| | ggtgaagaagaggctcaagtttatgataactaataa |
| Nucleotide sequences of pLogic046-tet-butyrate construct (SEQ ID NO: 85) The sequence encoding TetR is underlined, and the overlapping tetR/tetA promoters are boxed. | gtaaaacgacggccagtgaattcg<u>ttaagacccactttcacatttaagttgtttttcta</u> |
| | <u>atccgcatatgatcaattcaaggccgaataagaaggctggctctgcaccttggtgatca</u> |
| | <u>aataattcgatagcttgtcgtaataatggcggcatactatcagtagtaggtgtttccct</u> |
| | <u>ttcttctttagcgacttgatgctcttgatcttccaatacgcaacctaaagtaaaatgcc</u> |
| | <u>ccacagcgctgagtgcatataatgcattctctagtgaaaaaccttgttggcataaaaag</u> |
| | <u>gctaattgattttcgagagtttcatactgtttttctgtaggccgtgtacctaaatgtac</u> |
| | <u>ttttgctccatcgcgatgacttagtaaagcacatctaaaacttttagcgttattacgta</u> |
| | <u>aaaaatcttgccagctttcccttctaaagggcaaaagtgagtatggtgcctatctaac</u> |
| | <u>atctcaatggctaaggcgtcgagcaaagcccgcttattttttacatgccaatacaatgt</u> |
| | aggctgctctacacctagcttctgggcgagtttacgggttgttaaaccttcgattccga |
| | cctcattaagcagctctaatgcgctgttaatcacttttacttttatctaatctagacatc |
| | attaattcctaattttt<span style="border:1px solid">gttgacactctatcattgatagagttatttaccactcccta</span> |
| | <span style="border:1px solid">tcagtgatagagaa</span>aagtgaactctagaaataattttgtttaactttaagaaggagata |
| | tacatatgatcgtaaaacctatggtacgcaacaatatctgcctgaacgccatcctcag |
| | ggctgcaagaagggagtggaagatcagattgaatataccaagaaacgcattaccgcaga |
| | agtcaaagctggcgcaaaagctccaaaaaacgttctggtgcttggctgctcaaatggtt |
| | acggcctggcgagccgcattactgctgcgttcggatacggggctgcgaccatcggcgtg |
| | tcctttgaaaaagcgggttcagaaaccaaatatggtacaccgggatggtacaataattt |
| | ggcatttgatgaagcggcaaaacgcgagggtcttatagcgtgacgatcgacggcgatg |
| | cgttttcagacagagatcaaggcccaggtaattgaggaagccaaaaaaaaggtatcaaa |
| | tttgatctgatcgtatacagcttggccagcccagtacgtactgatcctgatacaggtat |
| | catgcacaaaagcgttttgaaaccctttggaaaaacgttcacaggcaaaacagtagatc |
| | cgttactggcgagctgaaggaaatctccgcggaaccagcaaatgacgaggaagcagcc |
| | gccactgttaaagttatggggggtgaagattgggaacgttggattaagcagctgtcgaa |
| | ggaaggcctcttagaagaaggctgtattaccttggcctatagttatattggccctgaag |
| | ctacccaagctttgtaccgtaaaggcacaatcggcaaggccaaagaacacctggaggcc |
| | acagcacaccgtctcaacaaagagaacccgtcaatccgtgccttcgtgagcgtgaataa |
| | aggcctggtaacccgcgcaagcgccgtaatcccggtaatccctctgtatctcgccagct |
| | tgttcaaagtaatgaaagagaagggcaatcatgaaggttgtattgaacagatcacgcgt |
| | ctgtacgccgagcgcctgtaccgtaaagatggtacaattccagttgatgaggaaatcg |
| | cattcgcattgatgattgggagttagaagaagacgtccagaaagcggtatccgcgttga |

TABLE 40 -continued

ROS regulated constructs, OxyR construct, Tet-regulated constructs

| Description | Sequence |
|---|---| tggagaaagtcacgggtgaaaacgcagaatctctcactgacttagcggggtaccgccat gatttcttagctagtaacggctttgatgtagaaggtattaattatgaagcggaagttga acgcttcgaccgtatctgataagaaggagatatacatatgagagaagtagtaattgcca gtgcagctagaacagcagtaggaagttttggaggagcatttaaatcagtttcagcggta gagttaggggtaacagcagctaaagaagctataaaaagagctaacataactccagatat gatagatgaatctcttttaggggggagtacttacagcaggtcttggacaaaatatagcaa gacaaatagcattaggagcaggaataccagtagaaaaaccagctatgactataaatata gtttgtggttctggattaagatctgtttcaatggcatctcaacttatagcattaggtga tgctgatataatgttagttggtggagctgaaaacatgagtatgtctccttatttagtac caagtgcgagatatggtgcaagaatgggtgatgctgcttttgttgattcaatgataaaa gatggattatcagacatatttaataactatcacatgggtattactgctgaaaacatagc agagcaatggaatataactagagaagaacaagatgaattagctcttgcaagtcaaaata aagctgaaaaagctcaagctgaaggaaaatttgatgaagaaatagttcctgttgttata aaaggaagaaaaggtgacactgtagtagataaagatgaatatattaagcctggcactac aatggagaaacttgctaagttaagacctgcatttaaaaaagatggaacagttactgctg gtaatgcatcaggaataaatgatggtgctgctatgttagtagtaatggctaaagaaaaa gctgaagaactaggaatagagcctcttgcaactatagtttcttatggaacagctggtgt tgaccctaaaataatgggatatggaccagttccagcaactaaaaaagctttagaagctg ctaatatgactattgaagatatagatttagttgaagctaatgaggcatttgctgcccaa tctgtagctgtaataagagacttaaatatagatatgaataaagttaatgttaatggtgg agcaatagctataggacatccaataggatgctcaggagcaagaatacttactacactt tatatgaaatgaagagaagagatgctaaaactggtcttgctacactttgtataggcggt ggaatgggaactactttaatagttaagagatagtaagaaggagatatacatatgaaatt agctgtaataggtagtggaactatgggaagtggtattgtacaaacttttgcaagttgtg gacatgatgtatgtttaaagagtagaactcaaggtgctatagataaatgtttagcttta ttagataaaaatttaactaagttagttactaagggaaaaatggatgaagctacaaaagc agaaatattaagtcatgttagttcaactactaattatgaagatttaaaagatatggatt taataatagaagcatctgtagaagacatgaatataaagaaagatgttttcaagttacta gatgaattatgtaaagaagatactatcttggcaacaaatacttcatcattatctataac agaaatagcttcttctactaagcgcccagataaagttataggaatgcatttctttaatc cagttcctatgatgaaattagttgaagttataagtggtcagttaacatcaaaagttact tttgatacagtatttgaattatctaagagtatcaataaagtaccagtagatgtatctga atctcctggatttgtagtaaatagaatacttatacctatgataaatgaagctgttggta tatatgcagatggtgttgcaagtaaagaagaaatagatgaagctatgaaattaggagca aaccatccaatgggaccactagcattaggtgatttaatcggattagatgttgttttagc tataatgaacgttttatatactgaatttggagatactaaatatagacctcatccacttt tagctaaaatggttagagctaatcaattaggaagaaaaactaagataggattctatgat tataataaataataagaaggagatatacatatgagtacaagtgatgttaaagtttatga TABLE 40 -continued ROS regulated constructs, OxyR construct, Tet-regulated constructs

| Description | Sequence |
|---|---|
| | gaatgtagctgttgaagtagatggaaatatatgtacagtgaaaatgaatagacctaaag |
| | cccttaatgcaataaattcaaagactttagaagaactttatgaagtatttgtagatatt |
| | aataatgatgaaactattgatgttgtaatattgacaggggaaggaaaggcatttgtagc |
| | tggagcagatattgcatacatgaaagatttagatgctgtagctgctaaagattttagta |
| | tcttaggagcaaaagcttttggagaaatagaaaatagtaaaaaagtagtgatagctgct |
| | gtaaacggatttgctttaggtggaggatgtgaacttgcaatggcatgtgatataagaat |
| | tgcatctgctaaagctaaatttggtcagccagaagtaactcttggaataactccaggat |
| | atggaggaactcaaaggcttacaagattggttggaatggcaaaagcaaaagaattaatc |
| | tttacaggtcaagttataaaagctgatgaagctgaaaaaatagggctagtaaatagagt |
| | cgttgagccagacattttaatagaagaagttgagaaattagctaagataatagctaaaa |
| | atgctcagcttgcagttagatactctaaagaagcaatacaacttggtgctcaaactgat |
| | ataaatactggaatagatatagaatctaatttatttggtctttgttttcaactaaaga |
| | ccaaaaagaaggaatgtcagctttcgttgaaaagagagaagctaactttataaaagggt |
| | aataagaaggagatatacatatgagaagttttgaagaagtaattaagtttgcaaaagaa |
| | agaggacctaaaactatatcagtagcatgttgccaagataaagaagttttaatggcagt |
| | tgaaatggctagaaaagaaaaaatagcaaatgccattttagtaggagatatagaaaaga |
| | ctaaagaaattgcaaaaagcatagacatggatatcgaaaattatgaactgatagatata |
| | aaagatttagcagaagcatctctaaaatctgttgaattagtttcacaaggaaaagccga |
| | catggtaatgaaaggcttagtagacacatcaataatactaaaagcagttttaaataaag |
| | aagtaggtcttagaactggaaatgtattaagtcacgtagcagtatttgatgtagaggga |
| | tatgatagattatttttcgtaactgacgcagctatgaacttagctcctgatacaaatac |
| | taaaaagcaaatcatagaaaatgcttgcacagtagcacattcattagatataagtgaac |
| | caaaagttgctgcaatatgcgcaaaagaaaaagtaaatccaaaaatgaaagatacagtt |
| | gaagctaaagaactagaagaaatgtatgaaagaggagaaatcaaaggttgtatggttgg |
| | tgggccttttgcaattgataatgcagtatctttagaagcagctaaacataaaggtataa |
| | atcatcctgtagcaggacgagctgatatattattagccccagatattgaaggtggtaac |
| | atattatataaagctttggtattcttctcaaaatcaaaaaatgcaggagttatagttgg |
| | ggctaaagcaccaataatattaacttctagagcagacagtgaagaaactaaactaaact |
| | caatagctttaggtgttttaatggcagcaaaggcataataagaaggagatatacatatg |
| | agcaaaatatttaaaatcttaacaataaatcctggttcgacatcaactaaaatagctgt |
| | atttgataatgaggatttagtatttgaaaaaactttaagacattcttcagaagaaatag |
| | gaaaatatgagaaggtgtctgaccaatttgaatttcgtaaacaagtaatagaagaagct |
| | ctaaaagaaggtggagtaaaaacatctgaattagatgctgtagtaggtagaggaggact |
| | tcttaaacctataaaaggtggtacttattcagtaagtgctgctatgattgaagatttaa |
| | aagtgggagttttaggagaacacgcttcaaacctaggtggaataatagcaaaacaaata |
| | ggtgaagaagtaaatgttccttcatacatagtagaccctgttgttgtagatgaattaga |
| | agatgttgctagaatttctggtatgcctgaaataagtagagcaagtgtagtacatgctt |
| | taaatcaaaaggcaatagcaagaagatatgctagagaaataaacaagaaatatgaagat |

TABLE 40 -continued

ROS regulated constructs, OxyR construct, Tet-regulated constructs

| Description | Sequence |
|---|---|
| | ataaatcttatagttgcacacatgggtggaggagtttctgttggagctcataaaaatgg |
| | taaaatagtagatgttgcaaacgcattagatggagaaggacctttctctccagaaagaa |
| | gtggtggactaccagtaggtgcattagtaaaaatgtgctttagtggaaaatatactcaa |
| | gatgaaattaaaaagaaaataaaaggtaatggcggactagttgcatacttaaacactaa |
| | tgatgctagagaagttgaagaaagaattgaagctggtgatgaaaaagctaaattagtat |
| | atgaagctatggcatatcaaatctctaaagaaataggagctagtgctgcagttcttaag |
| | ggagatgtaaaagcaatattattaactggtggaatcgcatattcaaaaatgtttacaga |
| | aatgattgcagatagagttaaatttatagcagatgtaaaagtttatccaggtgaagatg |
| | aaatgattgcattagctcaaggtggacttagagttttaactggtgaagaagaggctcaa |
| | gtttatgataactaataa |

In certain constructs, the butyrate gene cassette is placed under the control of a tetracycline-inducible or constitutive promoter.

In a third butyrate gene cassette, the pbt and buk genes are replaced with tesB. TesB is a thioesterase found in *E. Coli* that cleaves off the butyrate from butyryl-coA, thus obviating the need for pbt-buk.

In one embodiment, tesB is placed under the control of a FNR regulatory region selected from any of the sequences in Table 6. In an alternate embodiment, tesB is placed under the control of an RNS-responsive regulatory region, e.g., norB, and the bacteria further comprises a gene encoding a corresponding RNS-responsive transcription factor, e.g., nsrR. In yet another embodiment, tesB is placed under the control of an ROS-responsive regulatory region, e.g., oxyS, and the bacteria further comprises a gene encoding a corresponding ROS-responsive transcription factor, e.g., oxyR. In certain constructs, the different described butyrate gene cassettes are each placed under the control of a tetracycline-inducible or constitutive promoter. For example, genetically engineered Nissle are generated comprising a butyrate gene cassette in which the pbt and buk genes are replaced with tesB expressed under the control of a nitric oxide-responsive regulatory element. SEQ ID NO: 86 comprises a reverse complement of the nsrR repressor gene from *Neisseria gonorrhoeae* (underlined), intergenic region containing divergent promoters controlling nsrR and the butyrogenic gene cassette and their respective RBS (bold), and the butyrate genes (ter-thiA-hbd-crt-tesB) separated by RBS.

TABLE 41

SEQ ID NO: 86

SEQ ID NO: 86
ttatta<u>tcgcaccgcaatcgggattttcgattcataaagcaggtcgtagg
tcggcttgttgagcaggtcttgcagcgtgaaaccgtccagatacgtgaaa
aacgacttcattgcaccgccgagtatgcccgtcagccggcaggacggcgt
aatcaggcattcgttgttcgggcccatacactcgaccagctgcatcggtt
cgaggtggcggacgaccgcgccgatattgatgcgttcgggcggcgcggcc
agcctcagcccgccgcctttcccgcgtcacgctgtgcaagaaccccgcctt
gaccagcgcggtaaccacttttcatcaaatggcttttggaaatgccgtagg
tcgaggcgatggtggcgatattgaccagcgcgtcgtcgttgacggcggtg
tagatgaggacgcgcagcccgtagtcggtatgttgggtcagatacat</u>**aca
acctccttagtacatgcaaaattatttctagagcaacatacgagccggaa**

TABLE 41-continued

SEQ ID NO: 86

**gcataaagtgtaaagcctggggtgcctaatgagttgagttgaggaattat
aacaggaagaaatattcctcatacgcttgtaattcctctatggttgttga
caattaatcatcggctcgtataatgtataacattcatattttgtgaattt
taaactctagaaataattttgtttaactttaagaaggagatatacat**atg
atcgtaaaacctatggtacgcaacaatatctgcctgaacgccatcctca
gggctgcaagaagggagtggaagatcagattgaatataccaagaaacgca
ttaccgcagaagtcaaagctggcgcaaaagctccaaaaaacgttctggtg
cttggctgctcaaatggttacggcctggcgagccgcattactgctgcgtt
cggatacggggctgcgaccatcggcgtgtcctttgaaaaagcgggttcag
aaaccaaatatggtacaccgggatggtacaataatttggcatttgatgaa
gcggcaaaacgcgagggtctttatagcgtgacgatcgacggcgatgcgtt
tccagacgagatcaaggcccaggtaattgaggaagccaaaaaaaaaggta
tcaaatttgatctgatcgtatacagcttggccagcccagtacgtactgat
cctgatacaggtatcatgcacaaaagcgttttgaaacccttttggaaaaac
gttcacaggcaaaacagtagatccgtttactggcgagctgaaggaaatct
ccgcggaaccagcaaatgacgaggaagcagccgccactgttaaagttatg
ggggtgaagattgggaacgttggattaagcagctgtcgaaggaaggcct
cttagaagaaggctgtattaccttggcctatagttatattggccctgaag
ctacccaagctttgtaccgtaaaggcacaatcggcaaggccaaagaacac
ctggaggccacagcacaccgtctcaacaaagagaacccgtcaatccgtgc
cttcgtgagcgtgaataaaggcctggtaacccgcgcaagcgccgtaatcc
cggtaatccctctgtatctcgccagcttgttcaaagtaatgaaagagaag
ggcaatcatgaaggttgtattgaacagatcacgcgtctgtacgccgagcg
cctgtaccgtaaagatggtacaattccagttgatgaggaaaatcgcattc
gcattgatgattgggagttagaagaagacgtccagaaagcggtatccgcg
ttgatggagaaagtcacgggtgaaaacgcagaatctctcactgacttagc
ggggtaccgccatgatttcttagctagtaacggctttgatgtagaaggta
ttaattatgaagcggaagttgaacgcttcgaccgtatctgataagaagga
gatatacatatgagagaagtagtaattgccagtgcagctagaacagcagt
aggaagttttggaggagcatttaaatcagtttcagcggtagagttagggg
taacagcagctaaagaagctataaaaagagctaacataactccagatatg
atagatgaatctcttttaggggagtacttcacagcaggtcttggacaaaa
tatagcaagcaaatagcattaggagcaggaatacccagtagaaaaaccag
ctatgactataaatatagtttgtggttctggattaagatctgtttcaatg
gcatctcaacttatagcattaggtgatgctgatataatgttagttggtgg
agctgaaaacatgagtatgtctccttatttagtaccaagtgcgagatatg
gtgcaagaatgggtgatgctgcttttgttgattcaatgataaaagatgga
ttatcagacatatttaataactatcacatgggtattactgctgaaaacat
agcagagcaatggaatataactagagaagaacaagatgaattagctcttg
caagtcaaaatataaagctgaaaaagctcaagctgaaggaaaatttgatgaa
gaaatagttcctgttgttataaaaggaagaaaaggtgacactgtagtaga
taaagatgaatatattaagcctggcactacaatggagaaacttgctaagt
taagacctgcatttaaaaaagatggaacagttactgctggtaatgcatca
ggaataaatgatgtgctgctatgttagtagtaatggctaaagaaaaagc
tgaagaactaggaatagagcctcttgcaactatagtttcttatggaacag
ctggtgttgaccctaaaataatgggatatggaccagttccagcaactaaa
aagctttagaagctgctaatatgactattgaagatatagatttagttga
agctaatgaggcatttgctgcccaatctgtagctgtaataagagacttaa**

TABLE 41-continued

SEQ ID NO: 86

```
atatagatatgaataaagttaatgttaatggtggagcaatagctatagga
catccaataggatgctcaggagcaagaatacttactacactttatatga
aatgaagagaagagatgctaaaactggtcttgctacactttgtataggcg
gtggaatgggaactactttaatagttaagagatagtaagaaggagatata
catatgaaattagctgtaataggtagtggaactatgggaagtggtattgt
acaaacttttgcaagttgtggacatgatgtatgtttaaagagtagaactc
aaggtgctatagataaatgtttagctttattagataaaaatttaactaag
ttagttactaagggaaaaatggatgaagctacaaaagcagaaatattaag
tcatgttagttcaactactaattatgaagatttaaaagatatggatttaa
taatagaagcatctgtagaagacatgaatataaagaaagatgttttcaag
ttactagatgaattatgtaaagaagatactatcttggcaacaaatacttc
atcattatctataacagaaatagcttcttctactaagcgcccagataaag
ttataggaatgcatttctttaatccagttcctatgatgaaattagttgaa
gttataagtggtcagttaacatcaaaagttacttttgatacagtatttga
attatctaagagtatcaataaagtaccagtagatgtatctgaatctcctg
gatttgtagtaaatagaatacttatacctatgataaatgaagctgttggt
atatatgcagatggtgttgcaagtaaagaagaaatagatgaagctatgaa
attaggagcaaaccatccaatgggaccactagcattaggtgatttaatcg
gattagatgttgttttagctataatgaacgttttatatactgaatttgga
gatactaaatatagacctcatccacttttagctaaaatggttagagctaa
tcaattaggaagaaaaactaagataggattctatgattataataaataat
aagaaggagatatacatatgagtacaagtgatgttaaagtttatgagaat
gtagctgttgaagtagatggaaatatatgtacagtgaaaatgaatagacc
taaagcccttaatgcaataaattcaaagactttagaagaacttttatgaag
tatttgtagatattaataatgatgaaactattgatgttgtaatattgaca
ggggaaggaaaggcatttgtagctggagcagatattgcatacatgaaaga
tttagatgctgtagctgctaaagattttagtatcttaggagcaaaagctt
ttggagaaatagaaaatagtaaaaaagtagtgatagctgctgtaaacgga
tttgctttaggtggaggatgtgaacttgcaatggcatgtgatataagaat
tgcatctgctaaagctaaatttggtcagccagaagtaactcttggaataa
ctccaggatatggaggaactcaaaggcttacaagattggttggaatggca
aaagcaaaagaattaatctttacaggtcaagttataaaagctgagagc
tgaaaaaatagggctagtaaatagagtcgttgagccagacattttaatag
aagaagttgagaaattagctaagataatagctaaaaatgctcagcttgca
gttagatactctaaagaagcaatacaacttggtgctcaaactgatataaa
tactggaatagatatagaatctaatttatttggtcttttgtttttcaacta
aagaccaaaagaaggaatgtcagctttcgttgaaaagagagaagctaac
tttataaaagggtaataagaaggagatatacatatgAGTCAGGCGCTAAA
AAATTTACTGACATTGTTAAATCTGGAAAAAATTGAGGAAGGACTCTTTC
GCGGCCAGAGTGAAGATTTAGGTTTACGCCAGGTGTTTGGCGGCCAGGTC
GTGGGTCAGGCCTTGTATGCTGCAAAAGAGACCGTCCCTGAAGAGCGGCT
GGTACATTCGTTTCACAGCTACTTTCTTCGCCCTGGCGATAGTAAGAAGC
CGATTATTTATGATGTCGAAACGCTGCGTGACGGTAACAGCTTCAGCGCC
CGCCGGGTTGCTGCTATTCAAAACGGCAAACCGATTTTTTATATGACTGC
CTCTTTCCAGGCACCAGAAGCGGGTTTCGAACATCAAAAAACAATGCCGT
CCGCGCCAGCGCCTGATGGCCTCCCTTCGGAAACGCAAATCGCCCAATCG
CTGGCGCACCTGCTGCCGCCAGTGCTGAAAGATAAATTCATCTGCGATCG
TCCGCTGGAAGTCCGTCCGGTGGAGTTTCATAACCCACTGAAAGGTCAG
TCGCAGAACCACATCGTCAGGTGTGGATCCGCGCAAATGGTAGCGTGCCG
GATGACCTGCGCGTTCATCAGTATCTGCTCGGTTACGCTTCTGATCTTAA
CTTCCTGCCGGTAGCTCTACAGCCGCACGGCATCGGTTTTCTCGAACCGG
GGATTCAGATTGCCACCATTGACCATTCCATGTGGTTCCATCGCCCGTTT
AATTTGAATGAATGGCTGCTGTATAGCGTGGAGAGCACCTCGGCGTCCAG
CGCACGTGGCTTTGTGCGCGGTGAGTTTTATACCCAAGACGGCGTACTGG
TTGCCTCGACCGTTCAGGAAGGGGTGATGCGTAATCACAATtaa
```

Example 33

Construction of Vectors for Overproducing Butyrate Using a Tet-Inducible Promoter To facilitate inducible production of butyrate in *Escherichia coli* Nissle, the eight genes of the butyrate production pathway from *Peptoclostridium difficile* (bcd, etfB, etfA, thiA, hbd, crt, bpt, and buk; NCBI), as well as transcriptional and translational elements, were synthesized (Gen, Cambridge, Mass.) and cloned into vector pBR to create pLogic. As synthesized, the genes were placed under control of a tetracycline-inducible promoter, with the tet repressor (tetR) expressed constitutively, divergent from the tet-inducible synthetic butyrate operon. For efficient translation of butyrate genes, each synthetic gene in the operon was separated by a base pair ribosome binding site derived from the T promoter.

The gene products of bcd-etfA-etfB form a complex that convert crotonyl-CoA to butyryl-CoA, and may show some dependence on oxygen as a co-oxidant. Because an effective probiotic should be able to function in an oxygen-limited environment (e.g. the mammalian gut), and because it has been shown that a single gene from *Treponema denticola* can functionally replace this three gene complex in an oxygen-independent manner (trans-enoynl-CoA reductase; ter), we created a second plasmid capable of butyrate production in *E. coli*. Inverse PCR was used to amplify the entire sequence of pLogic outside of the bcd-etfA-etfB region. The ter gene was codon optimized for *E. coli* codon usage using Integrated DNA technologies online codon optimization tool (https://www.idtdna.com/CodonOpt), synthesized (Genewiz, Cambridge, Mass.), and cloned into this inverse PCR fragment using Gibson assembly to create pLogic.

Example 34

Transforming *E. coli*

Each plasmid is transformed into *E. coli* Nissle or *E. coli* DH5a. All tubes, solutions, and cuvettes are pre-chilled to 4° C. An overnight culture of *E. coli* Nissle or *E. coli* DH5a is diluted 1:100 in 5 mL of lysogeny broth (LB) and grown until it reached an OD600 of 0.4-0.6. The cell culture medium contains a selection marker, e.g., ampicillin, that is suitable for the plasmid. The *E. coli* cells are then centrifuged at 2,000 rpm for 5 min. at 4° C., the supernatant is removed, and the cells are resuspended in 1 mL of 4° C. water. The *E. coli* are again centrifuged at 2,000 rpm for 5 min. at 4° C., the supernatant is removed, and the cells are resuspended in 0.5 mL of 4° C. water. The *E. coli* are again centrifuged at 2,000 rpm for 5 min. at 4° C., the supernatant is removed, and the cells are finally resuspended in 0.1 mL of 4° C. water. The electroporator is set to 2.5 kV. 0.5 µg of one of the above plasmids is added to the cells, mixed by pipetting, and pipetted into a sterile, chilled cuvette. The dry cuvette is placed into the sample chamber, and the electric pulse is applied. One mL of room-temperature SOC media is immediately added, and the mixture is transferred to a culture tube and incubated at 37° C. for 1 hr. The cells are spread out on an LB plate containing ampicillin and incubated overnight.

In alternate embodiments, the butyrate cassette can be inserted into the Nissle genome through homologous recombination (Genewiz, Cambridge, Mass.). Organization of the constructs and nucleotide sequences are provided herein. To create a vector capable of integrating the synthesized butyrate cassette construct into the chromosome, Gibson assembly was first used to add 1000 bp sequences of DNA homologous to the Nissle lacZ locus into the R6K origin plasmid pKD3. This targets DNA cloned between these homology arms to be integrated into the lacZ locus in the Nissle genome. Gibson assembly was used to clone the fragment between these arms. PCR was used to amplify the region from this plasmid containing the entire sequence of the homology arms, as well as the butyrate cassette between them. This PCR fragment was used to transform electrocompetent Nissle-pKD46, a strain that contains a temperature-sensitive plasmid encoding the lambda red recombinase genes. After transformation, cells were grown out for 2 hours before plating on chloramphenicol at 20 ug/mL at 37 degrees C. Growth at 37 degrees C. also cures the pKD46 plasmid. Transformants containing cassette were chloramphenicol resistant and lac-minus (lac−).

Example 35

Production of Butyrate in Recombinant E. coli

Production of butyrate is assessed in *E. coli* Nissle strains containing the butyrate cassettes described above in order to determine the effect of oxygen on butyrate production. All incubations are performed at 37° C. Cultures of *E. coli* strains DH5a and Nissle transformed with the butyrate cassettes are grown overnight in LB and then diluted 1:200 into 4 mL of M9 minimal medium containing 0.5% glucose. The cells are grown with shaking (250 rpm) for 4-6 h and incubated aerobically or anaerobically in a Coy anaerobic chamber (supplying 90% N2, 5% CO2, 5% H2). One mL culture aliquots are prepared in 1.5 mL capped tubes and incubated in a stationary incubator to limit culture aeration. One tube is removed at each time point (0, 1, 2, 4, and 20 hrs) and analyzed for butyrate concentration by LC-MS to confirm that butyrate production in these recombinant strains can be achieved in a low-oxygen environment.

Example 36

Production of Butyrate in Recombinant E. coli

Production of butyrate is assessed in *E. coli* Nissle strains containing the butyrate cassettes described above in order to determine the effect of oxygen on butyrate production. All incubations are performed at 37° C. Cultures of *E. coli* strains DH5a and Nissle transformed with the butyrate cassettes are grown overnight in LB and then diluted 1:200 into 4 mL of M9 minimal medium containing 0.5% glucose. The cells are grown with shaking (250 rpm) for 4-6 h and incubated aerobically or anaerobically in a Coy anaerobic chamber (supplying 90% N2, 5% CO2, 5% H2). One mL culture aliquots are prepared in 1.5 mL capped tubes and incubated in a stationary incubator to limit culture aeration. One tube is removed at each time point (0, 1, 2, 4, and 20 hrs) and analyzed for butyrate concentration by LC-MS to confirm that butyrate production in these recombinant strains can be achieved in a low-oxygen environment.

Example 37

Production of Butyrate in Recombinant E. coli Using Tet-Inducible Promoter

Figure 51A:
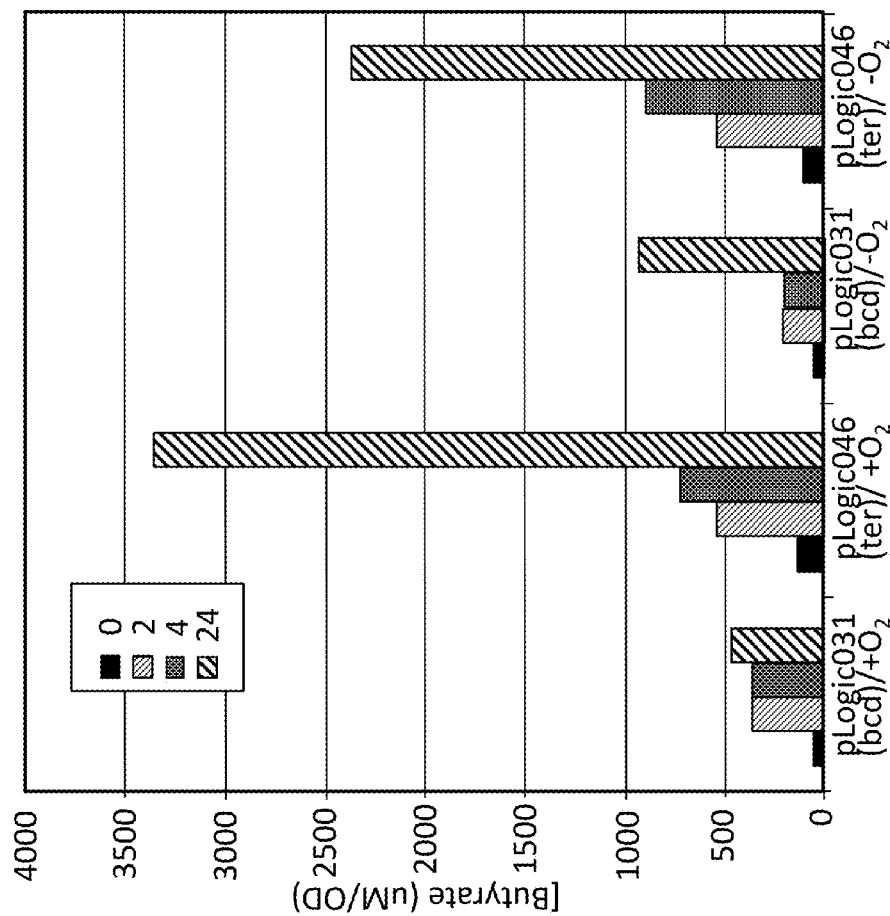
FIGS. 51A and 51B depict a graph of butyrate production using the circuits (SYN-UCD-503, SYN-UCD-504, SYN-UCD-505) shown in FIGS. 48B-D. Cells were grown in M9 minimal media containing 0.2% glucose and induced with ATC at early log phase.

FIG. 48 shows butyrate cassettes described above under the control of a tet-inducible promoter. Production of butyrate is assessed using the methods described below in Example 40. The tet-inducible cassettes tested include (1) tet-butyrate cassette comprising all eight genes (pLOGIC031); (2) tet-butyrate cassette in which the ter is substituted (pLOGIC046) and (3) tet-butyarte cassette in which tesB is substituted in place of pbt and buk genes. FIG. 51A shows butyrate production in strains pLOGIC031 and pLOGIC046 in the presence and absence of oxygen, in which there is no significant difference in butyrate production. Enhanced butyrate production was shown in Nissle in low copy plasmid expressing pLOGIC046 which contain a deletion of the final two genes (ptb-buk) and their replacement with the endogenous *E. Coli* tesB gene (a thioesterase that cleaves off the butyrate portion from butyryl CoA).

Figure 51B:
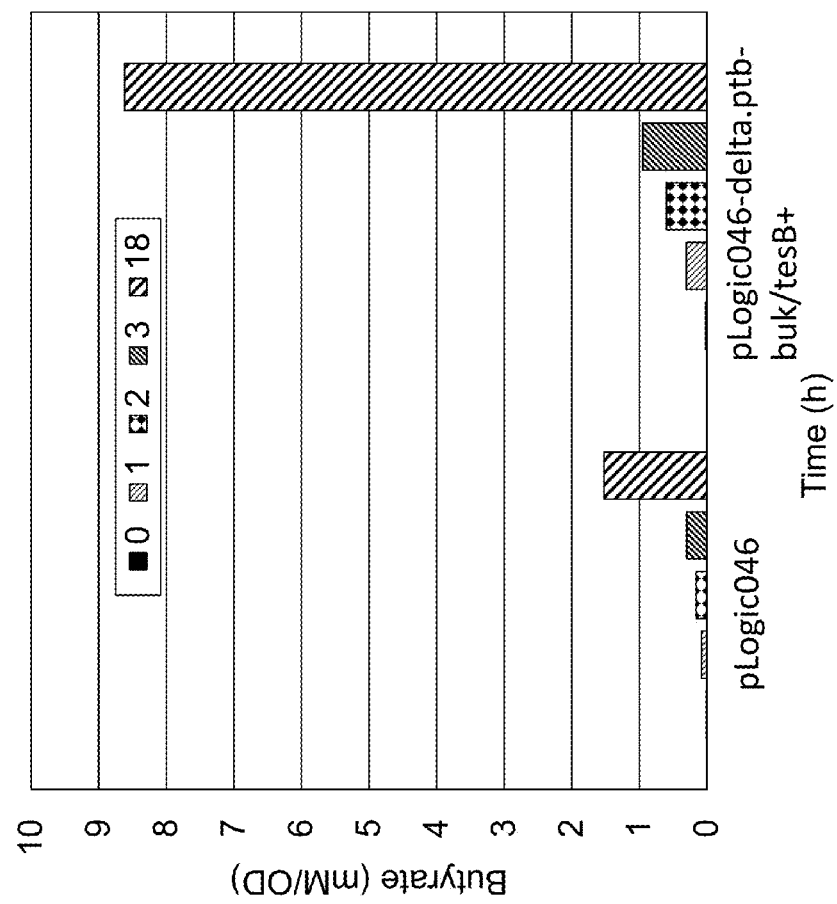

Overnight cultures of cells were diluted 1:100 in Lb and grown for 1.5 hours until early log phase was reached at which point anhydrous tet was added at a final concentration of 100 ng/ml to induce plasmid expression. After 2 hours induction, cells were washed and resuspended in M9 minimal media containing 0.5% glucose at OD600=0.5. Samples were removed at indicated times and cells spun down. The supernatant was tested for butyrate production using LC-MS. FIG. 51B shows butyrate production in strains comprising a tet-butyrate cassette having ter substitution (pLOGIC046) or the tesB substitution (ptb-buk deletion), demonstrating that the tesB substituted strain has greater butyrate production.

Figure 52:
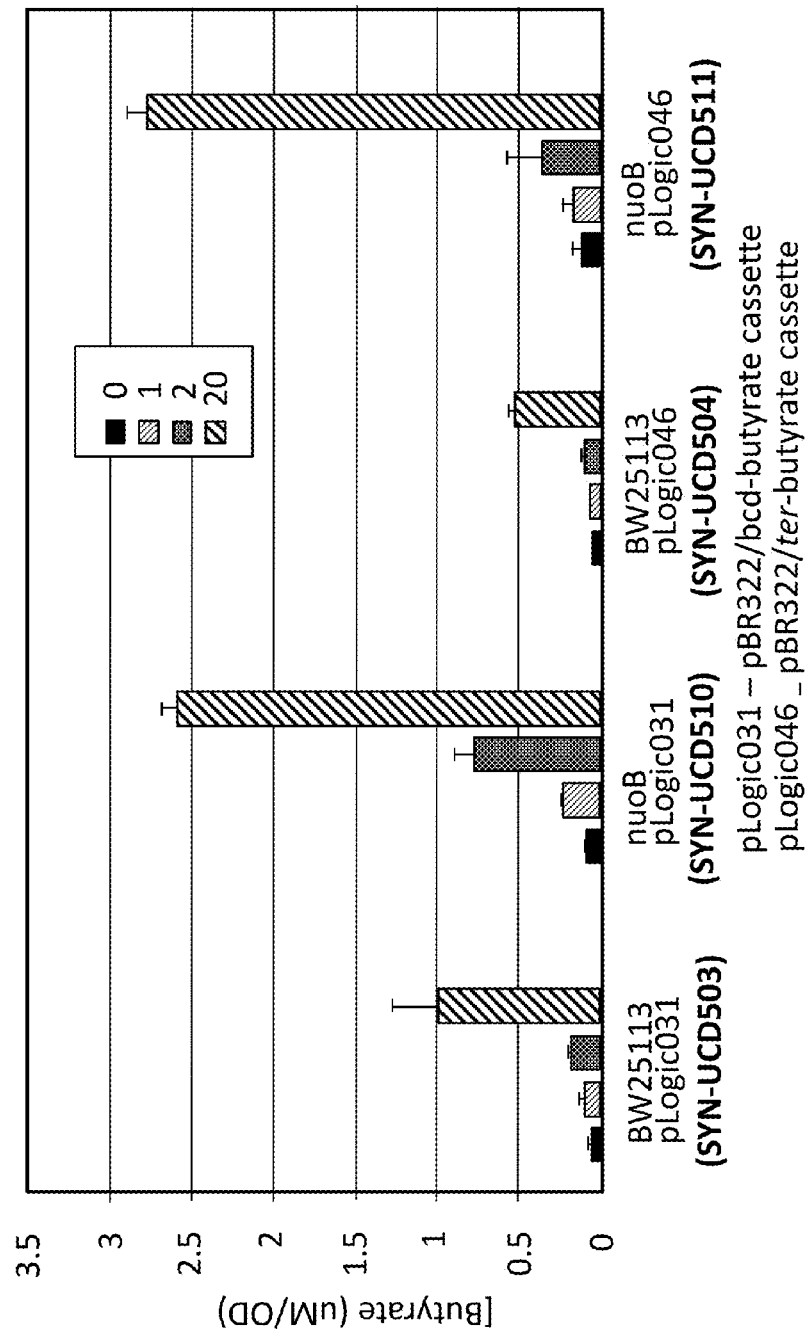
FIG. 52 depicts a graph of butyrate production using different butyrate-producing circuits comprising a nuoB gene deletion. Strains depicted are SYN-UCD503, SYN-UCD504, SYN-UCD510 (SYN-UCD510 is the same as SYN-UCD503 except that it further comprises a nuoB deletion), and SYN-UCD511 (SYN-UCD511 is the same as SYN-UCD504 except that it further comprises a nuoB deletion). The NuoB gene deletion results in greater levels of butyrate production as compared to a wild-type parent control in butyrate producing strains. NuoB is a main protein complex involved in the oxidation of NADH during respiratory growth. In some embodiments, preventing the coupling of NADH oxidation to electron transport increases the amount of NADH being used to support butyrate production.

FIG. 52 shows the BW25113 strain of *E. Coli*, which is a common cloning strain and the background of the KEIO collection of *E. Coli* mutants. NuoB mutants having NuoB deletion were obtained. NuoB is a protein complex involved in the oxidation of NADH during respiratory growth (form of growth requiring electron transport). Preventing the coupling of NADH oxidation to electron transport allows an increase in the amount of NADH being used to support butyrate production. FIG. 52 shows that compared with wild-type Nissle, deletion of NuoB results in grater production of butyrate.

TABLE 42 pLOGIC046-tesB-butyrate pLOGIC046-tesB-butyrate:

SEQ ID NO: 87

```
gtaaaacgacggccagtgaattcgttaagacccactttcacatttaagtt
gtttttctaatccgcatatgatcaattcaaggccgaataagaaggctggc
tctgcaccttggtgatcaaataattcgatagcttgtcgtaataatggcgg
catactatcagtagtaggtgtttccctttcttctttagcgacttgatgct
cttgatcttccaatacgcaacctaaagtaaaatgcccacagcgctgagt
gcatataatgcattctctagtgaaaaaccttgttggcataaaaaggctaa
ttgattttcgagagtttcatactgtttttctgtaggccgtgtacctaaat
gtacttttgctccatcgcgatgacttagtaaagcacatctaaaactttta
gcgttattacgtaaaaaatcttgccagctttccccttctaaagggcaaaa
gtgagtatggtgcctatctaacatctcaatggctaaggcgtcgagcaaag
cccgcttattttttacatgccaatacaatgtaggctgctctacacctagc
ttctgggcgagtttacgggttgttaaaccttcgattccgacctcattaag
cagctctaatgcgctgttaatcacttttacttttatctaatctagacatca
ttaattcctaattttgttgacactctatcattgatagagttattttacc
actccctatcagtgatagagaaaagtgaactctagaaataattttgttta
actttaagaaggagatatacatatgatcgtaaaacctatggtacgcaaca
atatctgcctgaacgcccatcctcagggcgtgcaagaagggagtggaagat
cagattgaatataccaagaaacgcattaccgcagaagtcaaagctggcgc
aaaagctccaaaaaacgttctggtgcttggctgctcaaatggttacggcc
tggcgagccgcattactgctgcgttcggatacggggctgcgaccatcggc
gtgtcctttgaaaaagcgggttcagaaaccaaatatggtacaccgggatg
gtacaataattttggcatttgatgaagcggcaaaacgcgagggtctttata
gcgtgacgatcgacggcgatgcgttttcagacgagatcaaggcccaggta
attgaggaagccaaaaaaaaaggtatcaaatttgatctgatcgtatacag
cttggccagcccagtacgtactgatcctgatacaggtatcatgcacaaaa
gcgttttgaaaccctttggaaaaacgttcacaggcaaaacagtagatccg
tttactggcgagctgaaggaaatctccgcggaaccagcaaatgacgagga
agcagccgccactgttaaagttatgggggtgaagattgggaacgttgga
ttaagcagctgtcgaaggaaggcctcttagaagaaggctgtattaccttg
gcctatagttatattggccctgaagctacccaagctttgtaccgtaaagg
cacaatcggcaaggccaaagaacacctggaggccacagcacaccgtctca
acaaagagaacccgtcaatccgtgccttcgtgagcgtgaataaaggcctg
gtaacccgcgcaagcgccgtaatcccggtaatccctctgtatctcgccag
cttgttcaaagtaatgaaagagaagggcaatcatgaaggttgtattgaac
agatcacgcgtctgtacgccgagcgcctgtaccgtaaagatggtacaatt
ccagttgatgaggaaaatcgcattcgcattgatgattgggagttagaaga
agacgtccagaaaagcggtatccgcgttgatggagaaagtcacgggtgaaa
acgcagaatctctcactgacttagcggggtaccgccatgatttcttagct
agtaacggctttgatgtagaaggtattaattatgaagcggaagttgaacg
cttcgaccgtatctgataagaaggagatatacatatgagagaagtagtaa
ttgccagtgcagctagaaacagcagtaggaagtttggaggagcatttaaa
tcagtttcagcggtagagttaggggtaacagcagctaaagaagctataaa
aagagctaacataactccagatatgatagatgaatctctttaggggag
tacttacagcaggtcttggacaaaatatagcaagacaaatagcattagga
gcaggaataccagtagaaaaaccagctatgactataaatatagtttgtgg
```

TABLE 42-continued pLOGIC046-tesB-butyrate

```
ttctggattaagatctgtttcaatggcatctcaacttatagcattaggtg
atgctgatataatgttagttggtggagctgaaaacatgagtatgtctcct
tatttagtaccaagtgcgagatatggtgcaagaatgggtgatgctgcttt
tgttgattcaatgataaaagatggattatcagacatatttaataactatc
acatgggtattactgctgaaaacatagcagagcaatggaatataactaga
gaagaacaagatgaattagctcttgcaagtcaaaataaagctgaaaaagc
tcaagctgaaggaaaatttgatgaagaaatagttcctgttgttataaaag
gaagaaaagtgacactgtagtagataaagatgaatatattaagcctggc
actacaatggagaaacttgctaagttaagacctgcatttaaaaaagatgg
aacagttactgctggtaatgcatcaggaataaatgatggtgctgctatgt
tagtagtaatggctaaagaaaaagctgaagaactaggaatagagcctctt
gcaactatagtttcttatggaacagctggtgttgaccctaaaataatggg
atatggaccagttccagcaactaaaaaagctttagaagctgctaatatga
ctattgaagatatagatttagttgaagctaatgaggcatttgctgcccaa
tctgtagctgtaatagagacttaaatatagatatgaataaagttaatgt
taatggtggagcaatagctataggacatccaataggatgctcaggagcaa
gaatacttactacacttttatatgaaatgaagagaagagatgctaaaact
ggtcttgctacactttgtataggcggtggaatgggaactactttaatagt
taagagatagtaagaaggagatatacatatgaaattagctgtaataggta
gtggaactatgggaagtggtattgtacaaacttttgcaagttgtggacat
gatgtatgtttaaagagtagaactcaaggtgctatagataaatgtttagc
tttattagataaaaatttaactaagttagttactaagggaaaaatggatg
aagctacaaaagcagaaatattaagtcatgttagttcaactactaattat
gaagatttaaaagatatggatttaataatagaagcatctgtagaagacat
gaatataaagaaagatgttttcaagttactagatgaattatgtaaagaag
atactatcttggcaacaaatacttcatcattatctataacagaaatagct
tcttctactaagcgcccagataaagttataggaatgcatttctttaatcc
agttcctatgatgaaattagttgaagttataagtggtcagttaacatcaa
aagttacttttgatacagtatttgaattatctaagagtatcaataaagta
ccagtagatgtatctgaatctcctggatttgtagtaaatagaatacttat
acctatgataaatgaagctgttggtatatatgcagatggtgttgcaagta
aagaagaaatagatgaagctatgaaattaggagcaaaccatccaatggga
ccactagcattaggtgatttaatcggattagatgttgttttagctataat
gaacgttttatatactgaatttggagatactaaatatagacctcatccac
ttttagctaaaatggttagagctaatcaattaggaagaaaaactaagata
ggattctatgattataataaataatgaaggagatatacatatgagtac
aagtgatgttaaagtttatgagaatgtagctgttgaagtagatggaaata
tatgtacagtgaaaatgaatagacctaaagcccttaatgcaataaattca
aagactttagaagaactttatgaagtatttgtagatattaataatgatga
aactattgatgttgtaatattgacaggggaaggaaaggcatttgtagctg
gagcagatattgcatacatgaaagatttagatgctgtagctgctaaagat
tttagtatcttaggagcaaaagcttttggagaaatagaaaatagtaaaaa
agtagtgatagctgctgtaaacggatttgctttaggtggaggatgtgaac
ttgcaatggcatgtgatataagaagttgcatctgctaaagctaaatttggt
cagccagaagtaactcttggaataactccaggatatggaggaactcaaag
gcttacaagattggttggaatggcaaaagcaaaagaattaatctttacag
gtcaagttataaaagctgatgaagctgaaaaaataggggctagtaaataga
gtcgttgagccagacattttaatagaagaagttgagaaattagctaagat
aatagctaaaaatgctcagcttgcagttagatactctaaagaagcaatac
aacttggtgctcaaactgatataaatactggaatagatatagaatctaat
ttatttggtctttgttttcaactaaagaccaaaaagaaggaatgtcagc
tttcgttgaaaagagagaagctaactttataaaagggtaataagaaggag
atatacatatgAGTCAGGCGCTAAAAAATTTACTGACATTGTTAAATCTG
GAAAAAATTGAGGAAGGACTCTTTCGCGGCCAGAGTGAAGATTTAGGTTT
ACGCCAGGTGTTTGGCGGCCAGGTCGTGGGTCAGGCCTTGTATGCTGCAA
AAGAGACCGTCCCTGAAGAGCGGCTGGTACATTCGTTTCACAGCTACTTT
CTTCGCCCTGGCGATAGTAAGAAGCCGATTATTTATGATGTCGAAACGCT
GCGTGACGGTAACAGCTTCAGCGCCCGCCGGGTTGCTGCTATTCAAAACG
GCAAACCGATTTTTTATATGACTGCCTCTTTCCAGGCACCAGAAGCGGGT
TTCGAACATCAAAAACAATGCCGTCCGCGCCAGCGCCTGATGGCCTCCC
TTCGGAAACGCAAATCGCCCAATCGCTGGCGCACCTGCTGCCGCCAGTGC
TGAAAGATAAATTCATCTGCGATCGTCCGCTGGAAGTCCGTCCGGTGGAG
TTTCATAACCCACTGAAAGGTCACGTCGCAGAACCACATCGTCAGGTGTG
GATCCGCGCAAATGGTAGCGTGCCGGATGACCTGCGCGTTCATCAGTATC
TGCTCGGTTACGCTTCGATCTTAACTTCCTGCCGGTAGCTCTACAGCCG
CACGGCATCGGTTTTCTCGAACCGGGGATTCAGATTGCCACCATTGACCA
TTCCATGTGGTTCCATCGCCCGTTTAATTTGAATGATGGCTGCTGTATA
GCGTGGAGAGCACCTCGGCGTCCAGCGCACGTGGCTTTGTGCGCGGTGAG
TTTTATACCCAAGACGGCGTACTGGTTGCCCTCGACCGTTCAGGAAGGGGT
GATGCGTAATCACAATtaa
```

Example 38

Production of Butyrate in Recombinant E. coli

Production of butyrate is assessed in *E. coli* Nissle strains containing the butyrate cassettes described above in order to determine the effect of oxygen on butyrate production. All incubations are performed at 37° C. Cultures of *E. coli* strains DH5α and Nissle transformed with the butyrate cassettes are grown overnight in LB and then diluted 1:200 into 4 mL of M9 minimal medium containing 0.5% glucose. The cells are grown with shaking (250 rpm) for 4-6 h and incubated aerobically or anaerobically in a Coy anaerobic chamber (supplying 90% N2, 5% CO2, 5% H2). One mL culture aliquots are prepared in 1.5 mL capped tubes and incubated in a stationary incubator to limit culture aeration. One tube is removed at each time point (0, 1, 2, 4, and 20 hours) and analyzed for butyrate concentration by LC-MS to confirm that butyrate production in these recombinant strains can be achieved in a low-oxygen environment.

In an alternate embodiment, overnight bacterial cultures were diluted 1:100 into fresh LB and grown for 1.5 hrs to allow entry into early log phase. At this point, long half-life nitric oxide donor (DETA-NO; diethylenetriamine-nitric oxide adduct) was added to cultures at a final concentration of 0.3 mM to induce expression from plasmid. After 2 hours of induction, cells were spun down, supernatant was discarded, and the cells were resuspended in M9 minimal media containing 0.5% glucose. Culture supernatant was then analyzed at indicated time points to assess levels of butyrate production. Genetically engineered Nissle comprising pLogic031-nsrR-norB-butyrate operon construct; SYN-UCD507) or (pLogic046-nsrR-norB-butyrate operon construct; SYN-UCD508) produce significantly more butyrate as compared to wild-type Nissle.

Genetically engineered Nissle were generated comprising a butyrate gene cassette in which the pbt and buk genes are replaced with tesB (SEQ ID NO: 48) expressed under the control of a tetracycline promoter (pLOGIC046-tesB-butyrate; SEQ ID NO: 88). SEQ ID NO: 88 comprises a reverse complement of the tetR repressor (underlined), an intergenic region containing divergent promoters controlling tetR and the butyrate operon and their respective RBS (bold), and the butyrate genes (ter-thiA1-hbd-crt2-tesB) separated by RBS.

TABLE 43 pLOGIC046-tesB-butyrate sequence

SEQ ID NO: 88

```
gtaaaacgacggccagtgaattcgttaagacccactttcacatttaagtt
gtttttctaatccgcatatgatcaattcaaggccgaataagaaggctggc
tctgcaccttggtgatcaaataattcgatagcttgtcgtaataatggcgg
catactatcagtagtaggtgtttcccttcttctttagcgacttgatgct
cttgatcttccaatacgcaacctaaagtaaaatgccccacagcgctgagt
gcatataatgcattctctagtgaaaaaccttgttggcataaaaaggctaa
ttgattttcgagagtttcatactgttttctgtaggccgtgtacctaaat
gtacttttgctccatcgcgatgacttagtaaagcacatctaaaacttta
gcgttattacgtaaaaaatcttgccagctttcccttctaaagggcaaaa
gtgagtatggtgcctatctaacatctcaatggctaaggcgtcgagcaaag
cccgcttattttttacatgccaatacaatgtaggctgctctacacctagc
ttctgggcgagtttacgggttgttaaacccttcgattccgacctcattaag
cagctctaatgcgctgttaatcactttactttatctaatctagacatca
ttaattcctaattttttgttgacactctatcattgatagagttattttacc
actccctatcagtgatagagaaaagtgaactctagaaataattttgttta
actttaagaaggagatatacatatgatcgtaaaacctatggtacgcaaca
atatctgcctgaacgccatcctcagggctgcaagaagggagtggaagat
cagattgaatataccaagaaacgcattaccgcagaagtcaaagctggcgc
aaaagctccaaaaaacgttctggtgcttggctgctcaaatggttacggcc
```

TABLE 43-continued pLOGIC046-tesB-butyrate sequence

```
tggcgagccgcattactgctgcgttcggatacggggctgcgaccatcggc
gtgtcctttgaaaaagcgggttcagaaaccaaatatggtacaccgggatg
gtacaataatttggcatttgatgaagcggcaaaacgcgagggtctttata
gcgtgacgatcgacggcgatgcgttttcagacgagatcaaggcccaggta
attgaggaagccaaaaaaaaggtatcaaatttgatctgatcgtatacag
cttggccagcccagtacgtactgatcctgatacaggtatcatgcacaaaa
gcgttttgaaaccctttggaaaaacgttcacaggcaaaacagtagatccg
tttactggcgagctgaaggaaatctccgcggaaccagcaaatgacgagga
agcagccgccactgttaaagttatgggggggtgaagattgggaacgttgga
ttaagcagctgtcgaaggaaggcctcttagaagaaggctgtattaccttg
gcctatagttatattggccctgaagctacccaagctttgtaccgtaaagg
cacaatcggcaaggccaaagaacacctggaggccacagcacaccgtctca
acaaagagaacccgtcaatccgtgccttcgtgagcgtgaataaaggcctg
gtaacccgcgcaagcgccgtaatcccggtaatccctctgtatctcgccag
cttgttcaaagtaatgaaaagagaagggcaatcatgaaggttgtattgaac
agatcacgcgtctgtacgccgagcgcctgtaccgtaaagatggtacaatt
ccagttgatgaggaaaatcgcattcgcattgatgattgggagttagaaga
agacgtccagaaagcggtatccgcgttgatggagaaagtcacgggtgaaa
acgcagaatctctcactgacttagcggggtaccgccatgatttcttagct
agtaacggctttgatgtagaaggtattaattatgaagcggaagttgaacg
cttcgaccgtatctgataagaaggagatatacatatgagagaagtagtaa
ttgccagtgcagctagaacagcagtaggaagttttggaggagcatttaaa
tcagtttcagcggtagagttaggggtaacagcgctaaagaagctataaa
aagagctaacataactccagatatgatagatgaatctcttttaggggag
tacttacagcaggtcttggacaaaatatagcaagacaaatagcattagga
gcaggaataccagtagaaaaaccagctatgactataaatatagtttgtgg
ttctggattaagatctgtttcaatggcatctcaacttatagcattaggtg
atgctgatataatgttagttggtggagctgaaaacatgagtatgtctcct
tatttagtaccaagtgcagatatggtgcaagaatgggtgatgctgcttt
tgttgattcaatgataaaagatggattatcagacatatttaataactatc
acatgggtattactgctgaaaacatagcagagcaatggaatataactaga
gaagaacaagatgaattagctcttgcaagtcaaaataaagctgaaaaagc
tcaagctgaaggaaaatttgatgaagaaatagttcctgttgttataaaag
gaagaaaaggtgacactgtagtagataaagatgaatatattaagcctggc
actacaatggagaaacttgctaagttaagacctgcatttaaaaaagatgg
aacagttactgctggtaatgcatcaggaataaatgatggtgctgctatgt
tagtagtaatggctaaagaaaaagctgaagaactaggaatagagcctctt
gcaactatagtttcttatggaacagctggtgttgaccctaaaataatggg
atatggaccagttccagcaactaaaaaagctttagaagctgctaatatga
ctattgaagatatagatttagttgaagctaatgaggcatttgctgcccaa
tctgtagctgtaataagagactttaaatatagatatgaataaagttaatgt
taatggtggagcaatagctataggacatccaataggatgctcaggagcaa
gaatacttactacactttatatgaaatgaagagaagagatgctaaaact
ggtcttgctcacttttgtataggcggtggaatgggaactactttaatagt
taagagatagtaaggaagagatatacatatgaaattagctgtaataggta
gtggaactatgggaagtggtattgtacaaacttttgcaagttgtggacat
gatgtatgtttaaagagtagaactcaaggtgctatagatatgtttagc
tttattagataaaaatttaactaagttagttactaagggaaaaatggagtg
aagctacaaaagcagaaatattaagtcatgttagttcaactactaattat
gaagatttaaaagatatggatttaataatagaagcatctgtagaagacat
gaatataaagaaagatgttttcaagttactagatgaattatgtaaagaag
atactatcttggcaacaaatacttcatcattatctataacagaaatagct
tcttctactaagcgcccagataaagttataggaatgcatttctttaatcc
agttcctatgatgaaattagttgaagttataagtggtcagttaacatcaa
aagttactttgatacagtattgaattatctaagagtatcaataaagta
ccagtagatgtatctgaatctcctggatttgtagtaaatagaatacttat
acctatgataaatgaagctgttggtatatatgcagatggtgttgcaagta
aagaagaaatagatgaagctatgaaattaggagcaaaccatccaatggga
ccactagcattaggtgatttaatcggattagatgttgtttagctataat
gaacgtttatatactgaatttggagatactaaatatagacctcatccac
ttttagctaaaatggttagagctaatcaattaggaagaaaaactaagata
ggattctatgattataataaataataagaaggagatatacatatgagtac
aagtgatgttaaagtttatgagaatgtagctgttgaagtagatggaaata
tatgtacagtgaaatgaatagacctaaagcccttaatgcaataaattca
aagactttagaagaacttatgaagtatttgtagatattaataatgatga
aactattgatgttgtaatattgacagggagaaggaaacggcatttgtagctg
gagcagatattgcatacatgaaagatttagatgctgtagctgctaaagat
tttagtatcttaggagcaaaagcttttggagaaatagaaatagtaaaaa
agtagtgatagctgctgtaaacggattttgctttaggtggaggatgtgaac
ttgcaatggcatgtgatataagaatttgcatctgctaaagctaaatttggt
cagccagaagtaactcttggaataactccaggatattggaggaactcaaag
gcttacaagattggttggaatggcaaaagcaaaagaattaatctttacag
gtcaagttataaaagctgatgaagctgaaaaaatagggctagtaaataga
gtcgttgagccagacatttaatagaagaagttgagaaattagctaagat
aatagctaaaaatgctcagcttgcagttagatactctaaagaagcaatac
aacttggtgctcaaactgatataaatactggaatagatatagaatctaat
ttatttggtctttgtttttcaactaaagaccaaaaagaaggaatgtcagc
tttcgttgaaaagagagaagctaacttttataaagggtaataagaaggag
```

TABLE 43-continued pLOGIC046-tesB-butyrate sequence

```
atatacatatgAGTCAGGCGCTAAAAAATTTACTGACATTGTTAAATCTG
GAAAAAATTGAGGAAGGACTCTTTCGCGGCCAGAGTGAAGATTTAGGTTT
ACGCCAGGTGTTTGGCGGCCAGGTCGTGGGTCAGGCCTTGTATGCTGCAA
AAGAGACCGTCCCTGAAGAGCGGCTGGTACATTCGTTTCACAGCTACTTT
CTTCGCCCTGGCGATAGTAAGAAGCCGATTATTTATGATGTCGAAACGCT
GCGTGACGGTAACAGCTTCAGCGCCCGCCGGGTTGCTGCTATTCAAAACG
GCAAACCGATTTTTTATATGACTGCCTCTTTCCAGGCACCAGAAGCGGGT
TTCGAACATCAAAAAACAATGCCGTCCGCGCCAGCGCCTGATGGCCTCCC
TTCGGAAACGCAAATCGCCCAATCGCTGGCGCACCTGCTGCCGCCAGTGC
TGAAAGATAAATTCATCTGCGATCGTCCGCTGGAAGTCCGTCCGGTGGAG
TTTCATAACCCACTGAAAGGTCACGTCGCAGAACCACATCGTCAGGTGTG
GATCCGCGCAAATGGTAGCGTGCCGGATGACCTGCGCGTTCATCAGTATC
TGCTCGGTTACGCTTCTGATCTTAACTTCCTGCCGGTAGCTCTACAGCCG
CACGGCATCGGTTTTCTCGAACCGGGGATTCAGATTGCCACCATTGACCA
TTCCATGTGGTTCCATCGCCCGTTTAATTTGAATGAATGGCTGCTGTATA
GCGTGGAGAGCACCTCGGCGTCCAGCGCACGTGGCTTTGTGCGCGGTGAG
TTTTATACCCAAGACGGCGTACTGGTTGCCTCGACCGTTCAGGAAGGGGT
GATGCGTAATCACAATtaa
```

Overnight bacterial cultures were diluted 1:100 into fresh LB and grown for 1.5 hrs to allow entry into early log phase. At this point, anhydrous tetracycline (ATC) was added to cultures at a final concentration of 100 ng/mL to induce expression of butyrate genes from plasmid. After 2 hours of induction, cells were spun down, supernatant was discarded, and the cells were resuspended in M9 minimal media containing 0.5% glucose. Culture supernatant was then analyzed at indicated time points to assess levels of butyrate production. Replacement of pbt and buk with tesB leads to greater levels of butyrate production.

Figure 53A:
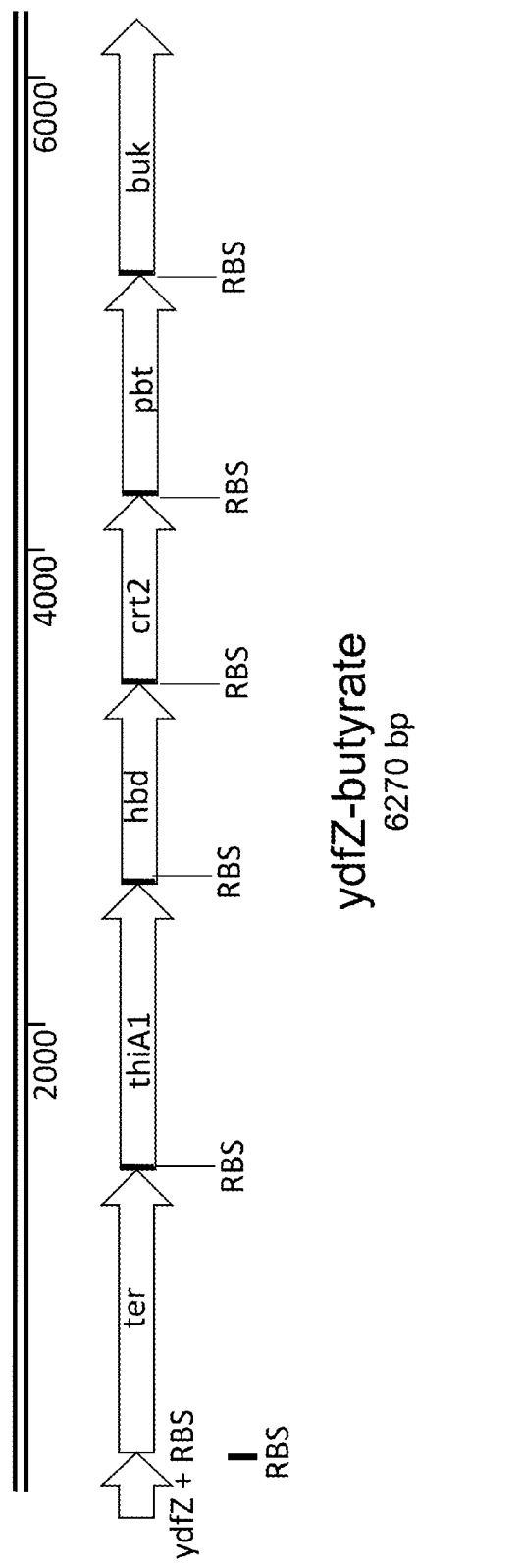
FIG. 53A depicts a schematic of a butyrate producing circuit under the control of an FNR promoter.
Figure 53B:
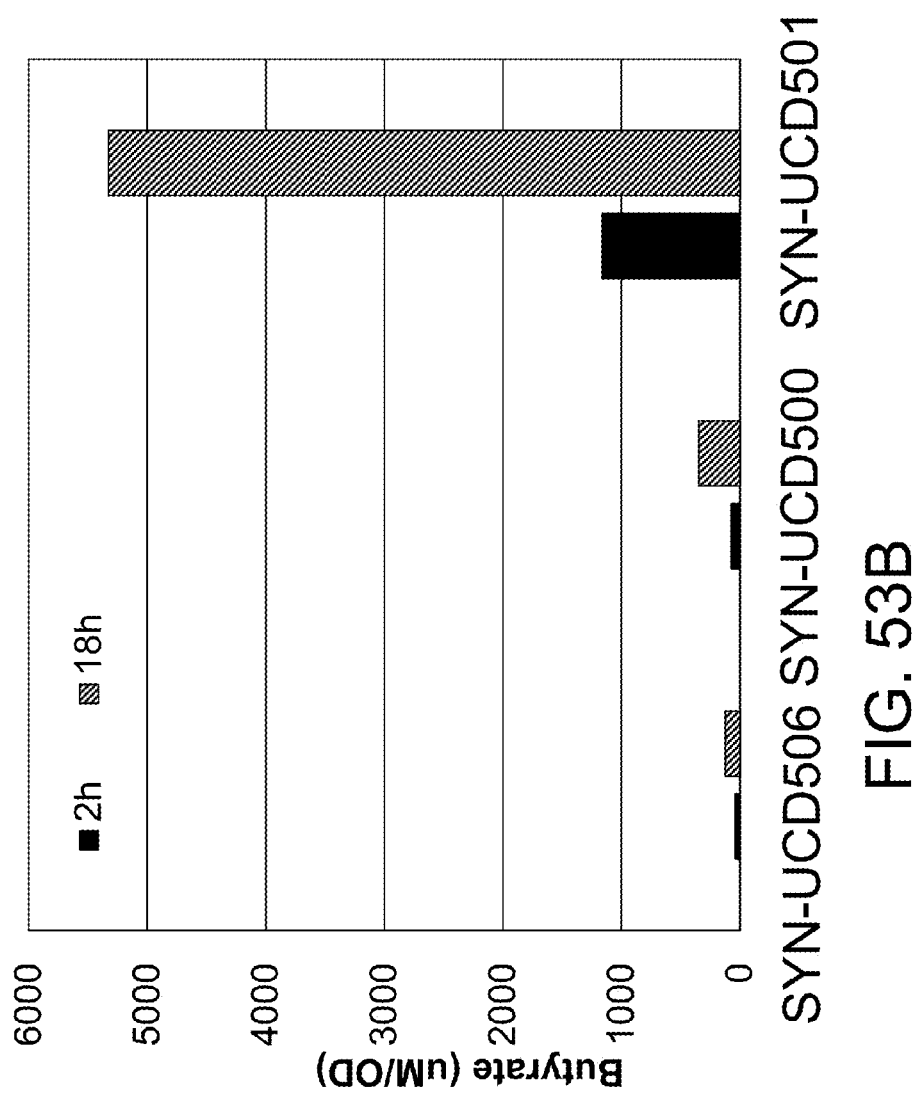
FIG. 53B depicts a bar graph of anaerobic induction of butyrate production. FNR-responsive promoters were fused to butyrate cassettes containing either the bcd or ter circuits. Transformed cells were grown in LB to early log and placed in anaerobic chamber for 4 hours to induce expression of butyrate genes. Cells were washed and resuspended in minimal media w/ 0.5% glucose and incubated microaerobically to monitor butyrate production over time. SYN-UCD501 led to significant butyrate production under anaerobic conditions.
Figure 53C:
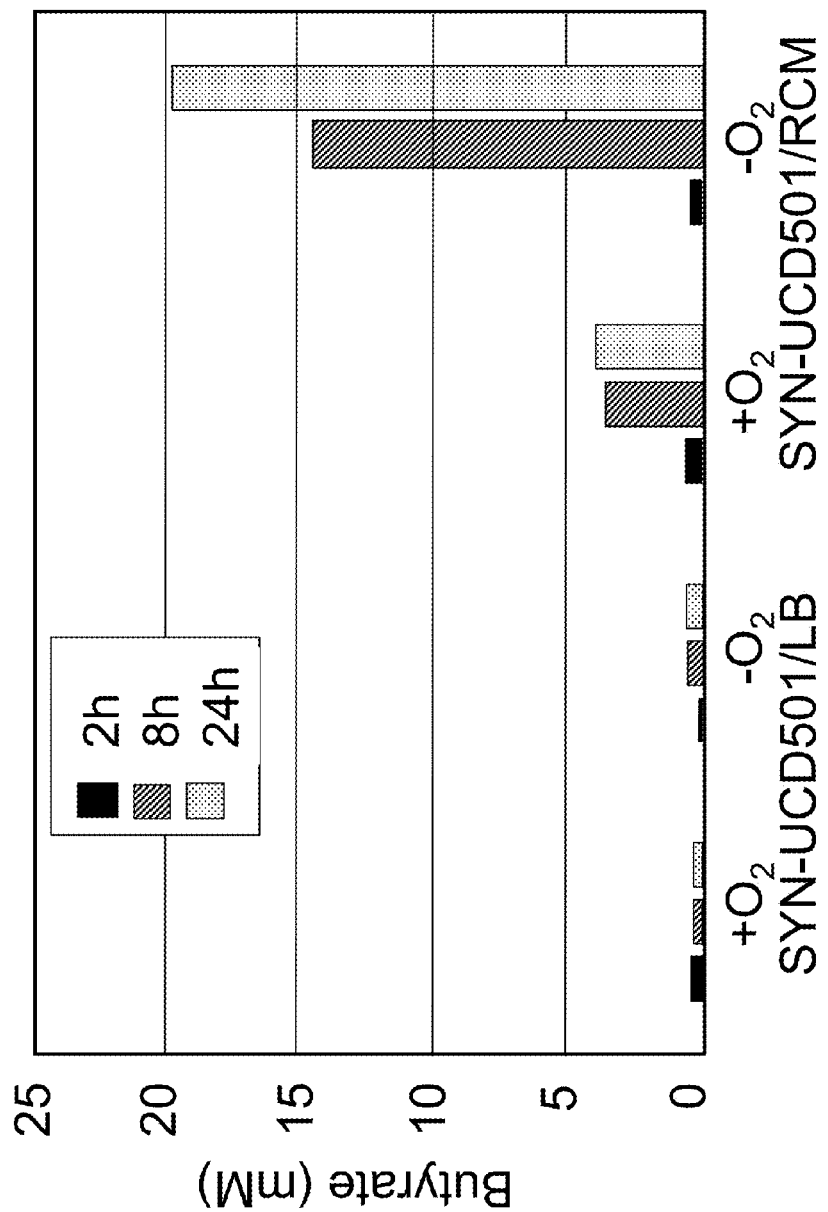
FIG. 53C depicts SYN-UCD501 in the presence and absence of glucose and oxygen in vitro. SYN-UCD501 comprises pSC101 PydfZ-ter butyrate plasmid; SYN-UCD500 comprises pSC101 PydfZ-bcd butyrate plasmid; SYN-UCD506 comprises pSC101 nirB-bcd butyrate plasmid.

FIG. 53C shows butyrate production in strains comprising an FNR-butyrate cassette syn 363 (having the ter substitution) in the presence/absence of glucose and oxygen. FIG. 53C shows that bacteria need both glucose and anaerobic conditions for butyrate production from the FNR promoter. Cells were grown aerobically or anaerobically in media containg no glucose (LB) or in media containing glucose at 0.5% (RMC). Culture samples were taken at indicaed time pints and supernatant fractions were assessed for butyrate concentration using LC-MS. These data show that SYN 363 requires glucose for butyrate production and that in the presence of glucose butyrate production can be enhanced under anaerobic conditions when under the control of the anaerobic FNR-regulated ydfZ promoter.

Example 39

In Vitro Activity of Bacterial Strain Comprising Ammonia-Metabolizing and Butyrate Producing Circuits Do determine whether ammonia uptake and conversion to arginine and production of butyrate could be accomplished in one strain, a plasmid (Logic156) comprising a butyrate production cassette construct, was used for initial proof-of-concept experiments. The following strains were generated using the plasmid: SYN-UCD501 (comprising Logic156 (pSC101 PydfZ-ter butyrate plasmid; amp resistance); and SYN-UCD601, which is SYN-UCD-305, additionally comprising Logic156 (i.e., SYN-UCD601 comprises ΔArgR, PfnrS-ArgAfbr integrated into the chromosome at the malEK locus, ΔThyA, and Logic156 (pSC101 PydfZ-ter butyrate plasmid; amp resistance)). Arginine and butyrate production was the compared between the butyrate only producer SYN-UCD 501, the arginine only producer SYN- UCD305, and the combined butyrate/arginine producer SYN-UCD-601. Sequences for the butyrate cassette used are shown in Table 38.

Briefly, 3 ml LB (containing selective antibiotics (Amp for SYN-UCD501 and SYN-UCD601) and 3 mM thymidine for SYN-UCD-305 and SYN-UCD601) with bacteria from frozen glycerol stocks. Bacteria were grown overnight at 37 C with shaking. Overnight cultures were diluted 1:100 dilution into 10 ml LB (containing antibiotics and thymidine where necessary as above) in a 125 ml baffled flask. Cultures were grown aerobically at 37 C with shaking for about 1.5 h, and then transferred to the anaerobic chamber at 37 C for 4 h. Bacteria (2×108 CFU) were added to 1 ml M9 media containing 50 mM MOPS with 0.5% glucose in microcentrifuge tubes. Cells were plated to determine cell counts. The assay tubes were placed in the anaerobic chamber at 37 C. At indicated times (1, 2, 24 h), 120 ul cells were removed and pelleted at 14,000 rpm for 1 min, and 100 ul of the supernatant was transferred to a 96-well assay plate and sealed with aluminum foil, and stored at −80 C until analysis by LC-MS for arginine and butyrate concentrations (as described in Example 13 and Example 40).

Results are depicted in FIG. 53A and FIG. 53B, and show that SYN-UCD601 is able to produce similar levels of arginine as SYN-UCD305 and similar levels of butyrate as SYN-UCD501 in vitro.

TABLE 44

Butyrate cassette sequences

| Description | Sequence | SEQ ID NO |
|---|---|---|
| ydfZ + RBS (RBS is bolded) | CATTTCCTCTCATCCCATCCGGGGTGAGAGTCTTTTC CCCCGACTTATGGCTCATGCATGCATCAAAAAAGATG TGAGCTTGATCAAAAACAAAAAATATTTCACTCGACA GGAGTATTTATATTGCGCCCGGATCCCTCTAGAAATA ATTTTGTTTAACTTTAAGAAGGAGATATACAT | SEQ ID NO: 89 |
| Ter (polynucleotide sequence) | atgatcgtaaaacctatggtacgcaacaatatctgcctgaacgccatcctca gggctgcaagaagggagtggaagatcagattgaatataccaagaaacgca ttaccgcagaagtcaaagctggcgcaaaagctccaaaaaacgttctggtgctt ggctgctcaaatggttacggcctggcgagccgcattactgctgcgttcggatac ggggctgcgaccatcggcgtgtcctttgaaaaagcgggttcagaaaccaaat atggtacaccgggatggtacaataatttggcatttgatgaagcggcaaaacgc gagggtctttatagcgtgacgatcgacggcgatgcgttttcagacgagatcaa ggcccaggtaattgaggaagcaaaaaaaaaggtatcaaatttgatctgatc gtatacagcttggccagcccagtacgtactgatcctgatacaggtatcatgcac aaaagcgttttgaaacccctttggaaaaacgttcacaggcaaaacagtagatc cgtttactggcgagctgaaggaaatctccgcggaaccagcaaatgacgagg aagcagccgccactgttaaagttatgggggtgaagattgggaacgttggatt aagcagctgtcgaaggaaggcctcttagaagaaggctgtattaccttggccta tagttatattggccctgaagctacccaagctttgtaccgtaaaggcacaatcgg caaggccaaagaacacctggaggccacagcacaccgtctcaacaaagag aacccgtcaatccgtgccttcgtgagcgtgaataaaggcctggtaacccgcg caagcgccgtaatcccggtaatccctctgtatctcgccagcttgttcaaagtaat gaaagagaagggcaatcatgaaggttgtattgaacagatcacgcgtctgtac gccgagcgcctgtaccgtaaagatggtacaattccagttgatgaggaaaatc gcattcgcattgatgattgggagttagaagaagacgtccagaaagcgggtatcc gcgttgatggagaaagtcacgggtgaaaacgcagaatctctcactgacttag cggggtaccgccatgatttcttagctagtaacggctttgatgtagaaggtattaat tatgaagcggaagttgaacgcttcgaccgtatctga | SEQ ID NO: 90 |
| Ter (polypeptide sequence) | MIVKPMVRNNICLNAHPQGCKKGVEDQIEYTKKRITAEV KAGAKAPKNVLVLGCSNGYGLASRITAAFGYGAATIGV SFEKAGSETKYGTPGWYNNLAFDEAAKREGLYSVTIDG DAFSDEIKAQVIEEAKKKGIKFDLIVYSLASPVRTDPDTGI MHKSVLKPFGKTFTGKTVDPFTGELKEISAEPANDEEA AATVKVMGGEDWERWIKQLSKEGLLEEGCITLAYSYIG PEATQALYRKGTIGKAKEHLEATAHRLNKENPSIRAFVS VNKGLVTRASAVIPVIPLYLASLFKVMKEKGNHEGCIEQI TRLYAERLYRKDGTIPVDEENRIRIDDWELEEDVQKAVS ALMEKVTGENAESLTDLAGYRHDFLASNGFDVEGINYE AEVERFDRI | SEQ ID NO: 91 |
| ThiA (polynucleotide sequence) | atgagagaagtagtaattgccagtgcagctagaacagcagtaggaagttttg gaggagcatttaaatcagtttcagcggtagagttaggggtaacagcagctaa agaagctataaaaagagctaacataactccagatatgatagatgaatctcttt agggggagtacttacagcaggtcttggacaaaatatagcaagacaaatagc attaggagcaggaataccagtagaaaaaccagctatgactataaatatagttt gtggttctggattaagatctgtttcaatggcatctcaacttatagcattaggtgatg ctgatataatgttagttggtgagctgaaaacatgagtatgtctccttatttagtac caagtgcgagatatggtgcaagaatgggtgatgctgctttttgttgattcaatgat aaaagatggattatcagacatatttaataactatcacatgggtattactgctgaa aacatagcagagcaatggaatataactagagaagaacaagatgaattagct cttgcaagtcaaaataaagctgaaaaagctcaagctgaaggaaaaatttgatg aagaaatagttcctgttgttataaaaggaagaaaaggtgacactgtagtagat aaagatgaatatattaagcctggcactacaatggagaaacttgctaagttaag acctgcatttaaaaaagatggaacagttactgctggtaatgcatcaggaataa atgatggtgctgctatgttagtagtaatggctaaagaaaaagctgaagaacta ggaatagagcctcttgcaactatagtttcttatggaacagctggtgttgaccta | SEQ ID NO: 92 |

TABLE 44-continued

Butyrate cassette sequences

| Description | Sequence | SEQ ID NO |
|---|---|---|
| | aaataatgggatatggaccagttccagcaactaaaaaagctttagaagctgct<br>aatatgactattgaagatatagatttagttgaagctaatgaggcatttgctgccc<br>aatctgtagctgtaataagagacttaaatatagatatgaataaagttaatgttaat<br>ggtggagcaatagctataggacatccaataggatgctcaggagcaagaata<br>cttactacacttttatatgaaatgaagagaagagatgctaaaactggtcttgcta<br>cactttgtataggcggtggaatgggaactacttttaatagttaagagatag | |
| ThiA (polypeptide sequence) | MREVVIASAARTAVGSFGGAFKSVSAVELGVTAAKEAIK<br>RANITPDMIDESLLGGVLTAGLGQNIARQIALGAGIPVEK<br>PAMTINIVCGSGLRSVSMASQLIALGDADIMLVGGAENM<br>SMSPYLVPSARYGARMGDAAFVDSMIKDGLSDIFNNYH<br>MGITAENIAEQWNITREEQDELALASQNKAEKAQAEGK<br>FDEEIVPVVIKGRKGDTVVDKDEYIKPGTTMEKLAKLRP<br>AFKKDGTVTAGNASGINDGAAMLWMAKEKAEELGIEP<br>LATIVSYGTAGVDPKIMGYGPVPATKKALEAANMTIEDID<br>LVEANEAFAAQSVAVIRDLNIDMNKVNVNGGAIAIGHPIG<br>CSGARILTTLLYEMKRRDAKTGLATLCIGGGMGTTLIVKR | SEQ ID NO: 93 |
| Hbd (polynucleotide sequence) | atgaaattagctgtaataggtagtggaactatgggaagtggtattgtacaactt<br>ttgcaagttgtggacatgatgtatgtttaaagagtagaactcaaggtgctataga<br>taaatgtttagctttattagataaaaatttaactaagttagttactaagggaaaaat<br>ggatgaagctacaaaagcagaaatattaagtcatgttagttcaactactaatta<br>tgaagatttaaaagatatggatttaataatagaagcatctgtagaagacatgaa<br>tataaagaaagatgttttcaagttactagatgaattatgtgtaaagaagatactatct<br>tggcaacaaatacttcatcattatctataacagaaatagcttcttctactaagcgc<br>ccagataaagttataggaatgcatttctttaatccagttcctatgatgaaattagtt<br>gaagttataagtggtcagttaacatcaaaagttactttttgatacagtatttgaatta<br>tctaagagtatcaataaagtaccagtagatgtatctgaatctcctggatttgtagt<br>aaatagaatacttataccctatgataaatgaagctgttggtatatatgcagatggt<br>gttgcaagtaaagaagaaatagatgaagctatgaaattaggagcaaaccat<br>ccaatgggaccactagcattaggtgatttaatcggattagatgttgttttagctata<br>atgaacgttttatatactgaatttggagatactaaatatagacctcatccacttttta<br>gctaaaatggttagagctaatcaattaggaagaaaaactaagataggattcta<br>tgattataataaataa | SEQ ID NO: 94 |
| Hbd (polypeptide sequence) | MKLAVIGSGTMGSGIVQTFASCGHDVCLKSRTQGAIDK<br>CLALLDKNLTKLVTKGKMDEATKAEILSHVSSTTNYEDL<br>KDMDLIIEASVEDMNIKKDVFKLLDELCKEDTILATNTSS<br>LSITEIASSTKRPDKVIGMHFFNPVPMMKLVEVISGQLTS<br>KVTFDTVFELSKSINKVPVDVSESPGFVVNRILIPMINEA<br>VGIYADGVASKEEIDEAMKLGANHPMGPLALGDLIGLDV<br>VLAIMNVLYTEFGDTKYRPHPLLAKMVRANQLGRKTKIG<br>FYDYNK | SEQ ID NO: 95 |
| Crt2 (polynucleotide sequence) | atgagtacaagtgatgttaaagtttatgagaatgtagctgttgaagtagatgga<br>aatatatgtacagtgaaaatgaatagacctaaagcccttaatgcaataaattca<br>aagactttagaagaactttatgaagtatttgtagatattaataatgatgaaactatt<br>gatgttgtaatattgacaggggaaggaaaggcatttgtagctggagcagatatt<br>gcatacatgaaagatttagatgctgtagctgctaaagattttagtatcttaggag<br>caaaagcttttggagaaatagaaaatagtaaaaaagtagtgatagctgctgta<br>aacggatttgctttaggtggaggatgtgaacttgcaatggcatgtgatataaga<br>attgcatctgctaaagctaaatttggtcagccagaagtaactcttggaataactc<br>caggatatggaggaactcaaaggcttacaagattggttggaatggcaaaag<br>caaaagaattaatcttttacaggtcaagttataaaagctgatgaagctgaaaaa<br>atagggctagtaaatagagtcgttgagccagacatttttaatagaagaagttga<br>gaaattagctaagataatagctaaaaatgctcagcttgcagttagatactctaa<br>agaagcaatacaacttggtgctcaaactgatataaatactggaatagatatag<br>aatctaattttatttggtctttgtttttcaactaaagaccaaaaagaaggaatgtca<br>gctttcgttgaaaagagagaagctaactttataaaagggtaa | SEQ ID NO: 96 |
| Crt2 (polypeptide sequence) | MSTSDVKVYENVAVEVDGNICTVKMNRPKALNAINSKT<br>LEELYEVFVDINNDETIDWILTGEGKAFVAGADIAYMKD<br>LDAVAAKDFSILGAKAFGEIENSKKVVIAAVNGFALGGG<br>CELAMACDIRIASAKAKFGQPEVTLGITPGYGGTQRLTR<br>LVGMAKAKELIFTGQVIKADEAEKIGLVNRWEPDILIEEV<br>EKLAKIIAKNAQLAVRYSKEAIQLGAQTDINTGIDIESNLF<br>GLCFSTKDQKEGMSAFVEKREANFIKG | SEQ ID NO: 97 |
| Pbt (polynucleotide sequence) | atgagaagttttgaagaagtaattaagtttgcaaaagaaagaggacctaaaa<br>ctatatcagtagcatgttgccaagataaagaagtttttaatggcagttgaaatgg<br>ctagaaaagaaaaaatagcaaatgccattttagtaggagatatagaaaaga<br>ctaaagaaattgcaaaaagcatagacatggatatcgaaaattatgaactgat<br>agatataaaagatttagcagaagcatctctaaaatctgttgaattagttttcacaa<br>ggaaaagccgacatggtaatgaaaggcttagtagacacatcaataatactaa<br>aagcagttttaaataagaagtaggtcttagaactggaaatgtattaagtcacg | SEQ ID NO: 98 |

TABLE 44-continued

Butyrate cassette sequences

| Description | Sequence | SEQ ID NO |
|---|---|---|
| | tagcagtatttgatgtagagggatatgatagattattttttcgtaactgacgcagct<br>atgaacttagctcctgatacaaatactaaaaagcaaatcatagaaaatgcttg<br>cacagtagcacattcattagatataagtgaaccaaaagttgctgcaatatgcg<br>caaaagaaaaagtaaatccaaaaatgaaagatacagttgaagctaaagaa<br>ctagaagaaatgtatgaaagaggagaaatcaaaggttgtatggttggtgggc<br>cttttgcaattgataatgcagtatctttagaagcagctaaacataaaggtataaa<br>tcatcctgtagcaggacgagctgatatattattagccccagatattgaaggtggt<br>aacatatttatataaagctttggtattcttctcaaaatcaaaaaatgcaggagttat<br>agttggggctaaagcaccaataatattaacttctagagcagacagtgaagaa<br>actaaactaaactcaatagctttaggtgttttaatggcagcaaaggcataa | |
| Pbt (polypeptide sequence) | MRSFEEVIKFAKERGPKTISVACCQDKEVLMAVEMARK<br>EKIANAILVGDIEKTKEIAKSIDMDIENYELIDIKDLAEASL<br>KSVELVSQGKADMVMKGLVDTSIILKAVLNKEVGLRTG<br>NVLSHVAVFDVEGYDRLFFVTDAAMNLAPDTNTKKQIIE<br>NACTVAHSLDISEPKVAAICAKEKVNPKMKDTVEAKELE<br>EMYERGEIKGCMVGGPFAIDNAVSLEAAKHKGINHPVA<br>GRADILLAPDIEGGNILYKALVFFSKSKNAGVIVGAKAPII<br>LTSRADSEETKLNSIALGVLMAAKA | SEQ ID NO: 99 |
| Buk (polynucleotide sequence) | atgagcaaaatatttaaaatcttaacaataaatcctggttcgacatcaactaaa<br>atagctgtatttgataatgaggatttagtatttgaaaaaactttaagacattcttca<br>gaagaaataggaaaatatgagaaggtgtctgaccaatttgaatttcgtaaaca<br>gtaatagaagaagctctaaaagaaggtggagtaaaaacatctgaattagat<br>gctgtagtaggtagaggaggacttcttaaacctataaaaggtggtacttattca<br>gtaagtgctgctatgattgaagatttaaaagtgggagtttttaggagaacacgctt<br>caaacctaggtggaataatagcaaaacaaataggtgaagaagtaaatgttc<br>cttcatacatagtagaccctgttgttgtagatgaattagaagatgttgctagaattt<br>ctggtatgcctgaaataagtagagcaagtgtagtacatgctttaaatcaaaag<br>gcaatagcaagaagatatgctagagaaataaacaagaaatatgaagatata<br>aatcttatagttgcacacatgggtggaggagtttctgttggagctcataaaaatg<br>gtaaaatagtagatgttgcaaacgcattagatggagaaggacctttctctccag<br>aaagaagtggtggactaccagtaggtgcattagtaaaaatgtgctttagtgga<br>aaatatactcaagatgaaatttaaaaagaaaataaaaggtaatggcggacta<br>gttgcatacttaaacactaatgatgctagagaagttgaagaaagaattgaagc<br>tggtgatgaaaaagctaaattagtatatgaagctatggcatatcaaatctctaa<br>agaaataggagctagtgctgcagttcttaagggagatgtaaaagcaatattatt<br>aactggtggaatcgcatattcaaaaatgtttacagaaatgattgcagatagagt<br>taaatttatagcagatgtaaaagtttatccaggtgaagatgaaatgattgcatta<br>gctcaaggtggacttagagttttaactggtgaagaagaggctcaagtttatgat<br>aactaa | SEQ ID NO: 100 |
| Buk (polypeptide sequence) | MSKIFKILTINPGSTSTKIAVFDNEDLVFEKTLRHSSEEIG<br>KYEKVSDQFEFRKQVIEEALKEGGVKTSELDAVVGRGG<br>LLKPIKGGTYSVSAAMIEDLKVGVLGEHASNLGGIIAKQI<br>GEEVNVPSYIVDPVVVDELEDVARISGMPEISRASVVHA<br>LNQKAIARRYAREINKKYEDINLIVAHMGGGVSVGAHKN<br>GKIVDVANALDGEGPFSPERSGGLPVGALVKMCFSGK<br>YTQDEIKKKIKGNGGLVAYLNTNDAREVEERIEAGDEKA<br>KLVYEAMAYQISKEIGASAAVLKGDVKAILLTGGIAYSKM<br>FTEMIADRVKFIADVKVYPGEDEMIALAQGGLRVLTGEE<br>EAQVYDN | SEQ ID NO: 101 |
| First RBS (in ydfZ = RBS) | TTTGTTTAACTTTAAGAAGGAGA | SEQ ID NO: 102 |
| Internal RBS between genes | taagaaggagatatacat | SEQ ID NO: 103 |
| Butryate cassette under the control of the ydfZ promoter (uppercase: ydfZ promoter, with RBS in bold; lower case: coding regions in the following order: ter, thiA, hbd, crt2, pbt, buk, | CATTTCCTCTCATCCCATCCGGGGTGAGAGTCTTTTC<br>CCCCGACTTATGGCTCATGCATGCATCAAAAAGATG<br>TGAGCTTGATCAAAAACAAAAAATATTTCACTCGACA<br>GGAGTATTTATATTGCGCCCGGATCCCTCTAGAAATA<br>ATTTTGTTTAACTTTAAGAAGGAGATATACATatgatcgt<br>aaaacctatggtacgcaacaatatctgcctgaacgcccatcctcagggctgc<br>aagaagggagtggaagatcagattgaatataccaagaaacgcattaccgca<br>gaagtcaaagctggcgcaaaagctccaaaaaacgttctggtgcttggctgctc<br>aaatggttacggcctggcgagccgcattactgctgcgttcggatacgggctg<br>cgaccatcggcgtgtcctttgaaaaagcgggttcagaaaccaaatatggtac<br>accgggatggtacaataatttggcatttgatgaagcggcaaaacgcgagggt<br>ctttatagcgtgacgatcgacggcgatgcgttttcagacgagatcaaggccca<br>ggtaattgaggaagcaaaaaaaaggtatcaaatttgatctgatcgtataca<br>gcttggccagcccagtacgtactgatcctgatacaggtatcatgcacaaaagc | SEQ ID NO: 104 |

TABLE 44-continued

Butyrate cassette sequences

| Description | Sequence | SEQ ID NO |
|---|---|---|
| separated by internal RBS (uppercase and underlined) | gttttgaaacccttttggaaaaaacgttcacaggcaaaacagtagatccgtttact<br>ggcgagctgaaggaaatctccgcggaaccagcaaatgacgaggaagcag<br>ccgccactgttaaagttatgggggtgaagattgggaacgttggattaagcag<br>ctgtcgaaggaaggcctcttagaagaaggctgtattaccttggcctatagttata<br>ttggccctgaagctacccaagctttgtaccgtaaaggcacaatcggcaaggc<br>caaagaacacctggaggccacagcacaccgtctcaacaaagagaacccg<br>tcaatccgtgccttcgtgagcgtgaataaaggcctggtaacccgcgcaagcg<br>ccgtaatcccggtaatccctctgtatctcgccagcttgttcaaagtaatgaaaga<br>gaagggcaatcatgaaggttgtattgaacagatcacgcgtctgtacgccgag<br>cgcctgtaccgtaaagatggtacaattccagttgatgaggaaaatcgcattcg<br>cattgatgattgggagttagaagaagacgtccagaaagcggtatccgcgttga<br>tggagaaagtcacgggtgaaaacgcagaatctctcactgacttagcggggta<br>ccgccatgatttcttagctagtaacggctttgatgtagaaggtattaattatgaag<br>cggaagttgaacgcttcgaccgtatctga<u>TAAGAAGGAGATATACA<br>T</u>atgagagaagtagtaattgccagtgcagctagaacagcagtaggaagtttt<br>ggaggagcatttaaatcagtttcagcggtagagttaggggtaacagcagcta<br>aagaagctataaaaagagctaacataactccagatatgatagatgaatctcttt<br>tagggggagtacttacagcaggtcttggacaaaatatagcaagacaaatagc<br>attaggagcaggaataccagtagaaaaaccagctatgactataaatatagttt<br>gtggttctggattaagatctgtttcaatggcatctcaacttatagcattaggtgatg<br>ctgatataatgttagttggtggagctgaaaacatgagtatgtctccttatttagtac<br>caagtgcgagatatggtgcaagaatgggtgatgctgcttttgttgattcaatgat<br>aaaagatggattatcagacatatttaataactatcacatgggtattactgctgaa<br>aacatagcagagcaatgaatataactagagaagaacaagatgaattagct<br>cttgcaagtcaaaataaagctgaaaaagctcaagctgaaggaaaatttgatg<br>aagaaatagttcctgttgttataaaaggaagaaaaggtgacactgtagtagat<br>aaagatgaatatattaagcctggcactacaatggagaaacttgctaagttaag<br>acctgcatttaaaaaagatggaacagttactgctggtaatgcatcaggaataa<br>atgatggtgctgctatgttagtagtaatggctaaagaaaaagctgaagaacta<br>ggaatagagcctcttgcaactatagtttcttatggaacagctggtgttgacccta<br>aaataatgggatatggaccagttccagcaactaaaaaagctttagaagctgct<br>aatatgactattgaagatatagatttagttgaagctaatgaggcatttgctgccc<br>aatctgtagctgtaataagagacttaaatatagatatgaataagttaatgttaat<br>ggtggagcaatagctataggacatccaataggatgctcaggagcaagaata<br>cttactacacttttatatgaaatgaagagaagagatgctaaaactggtcttgcta<br>cactttgtataggcggtggaatgggaactactttaatagttaagagatag<u>TAA<br>GAAGGAGATATACAT</u>atgaaaattagctgtaataggtagtggaactat<br>gggaagtggtattgtacaaacttttgcaagttgtggacatgatgtatgtttaaaga<br>gtagaactcaaggtgctatagataaatgtttagctttattagataaaaatttaact<br>aagttagttactaagggaaaaatggatgaagctacaaaagcagaaatattaa<br>gtcatgttagttcaactactaattatgaagatttaaaagatatggatttaataatag<br>aagcatctgtagaagacatgaatataaagaaagatgttttcaagttactagatg<br>aattatgtaaagaagatactatcttggcaacaaatacttcatcattatctataaca<br>gaaatagcttcttctactaagcgcccagataaagttataggaatgcatttctttaa<br>tccagttcctatgatgaaattagttgaagttataagtggtcagttaacatcaaaa<br>gttacttttgatacagtatttgaattatctaagagtatcaataaaagtaccagtagat<br>gtatctgaatctcctggatttgtagtaaatagaatacttatacctatgataaatga<br>agctgttggtatatatgcagatggtgttgcaagtaaagaagaaatagatgaag<br>ctatgaaattaggagcaaaccatccaatgggaccactagcattaggtgattta<br>atcggattagatgttgttttagctataatgaacgttttatatactgaatttggagata<br>ctaaatatagacctcatccacttttagctaaaatggttagagctaatcaattagg<br>aagaaaaactaagataggattctatgattataataaat<u>TAAGAAGGA<br>GATATACAT</u>atgagtacaagtgatgttaaagtttatgagaatgtagctgttg<br>aagtagatggaaatatatgtacagtgaaaatgaatagacctaaagcccttaat<br>gcaataaattcaaagactttagaagaacttatgaagtatttgtagatattaataa<br>tgatgaaactattgatgttgtaatattgacaggggaaggaaaggcatttgtagct<br>ggagcagatattgcatacatgaaagatttagatgctgtagctgctaaagatttta<br>gtatcttaggagcaaaagcttttggagaaatagaaaatagtaaaaaagtagtg<br>atagctgctgtaaacggatttgcttaggtggaggatgtgaacttgcaatggcat<br>gtgatataagaattgcatctgctaaagctaaatttggtcagccagaagtaactct<br>tggaataactccaggatatggaggaactcaaaggcttacaagattggttgga<br>atggcaaaagcaaaagaattaatcttacaggtcaagttataaaagctgatga<br>agctgaaaaaatagggctagtaaatagagtcgttgagccagacattttaatag<br>aagaagttgagaaattagctaagataatagctaaaaatgctcagcttgcagtt<br>agatactctaaagaagcaatacaacttggtgctcaaactgatataaatactgg<br>aatagatatagaatctaatttatttggtctttgttttttcaactaaagaccaaaaaga<br>aggaatgtcagctttcgttgaaaagagagaagctaactttataaaagggtaa<u>T<br>AAGAAGGAGATATACAT</u>atgagaagttttgaagaagtaattaagttt<br>gcaaaagaaagaggacctaaaactatatcagtagcatgttgccaagataaa<br>gaagtttaatggcagttgaaatggctagaaaagaaaaaatagcaaatgcca<br>tttagtaggagatatagaaaagactaaagaaattgcaaaaagcatagacat<br>ggatatcgaaaattgaactgatagatataaaagatttagcagaagcatctct<br>aaaatctgttgaattagtttcacaaggaaaagccgacatggtaatgaaaggct<br>tagtagacacatcaataatactaaaagcagtttttaaataaagaagtaggtctta<br>gaactggaaatgtattaagtcacgtagcagtatttgatgtagagggatatgata | |

TABLE 44-continued

Butyrate cassette sequences

| Description | Sequence | SEQ ID NO |
|---|---|---|
| | gattattttcgtaactgacgcagctatgaacttagctcctgatacaaatactaaa<br>aagcaaatcatagaaaatgcttgcacagtagcacattcattagatataagtga<br>accaaaagttgctgcaatatgcgcaaaagaaaaagtaaatccaaaaatgaa<br>agatacagttgaagctaaagaactagaagaaatgtatgaaagaggagaaat<br>caaaggttgtatggttggtgggcctttttgcaattgataatgcagtatctttagaag<br>cagctaaacataaaggtataaatcatcctgtagcaggacgagctgatatattat<br>tagccccagatattgaaggtggtaacatattatataaagctttggtattcttctcaa<br>aatcaaaaaatgcaggagttatagttggggctaaagcaccaataatattaact<br>tctagagcagacagtgaagaaactaaactaaactcaatagctttaggtgttta<br>atggcagcaaaggcataa<u>TAAGAAGGAGATATACAT</u>atgagcaa<br>aatatttaaaatcttaacaataaatcctggttcgacatcaactaaaatagctgtat<br>ttgataatgaggatttagtatttgaaaaaactttaagacattcttcagaagaaata<br>ggaaaatatgagaaggtgtctgaccaatttgaatttcgtaaacaagtaataga<br>agaagctctaaaagaaggtggagtaaaaacatctgaattagatgctgtagta<br>ggtagaggaggacttcttaaacctataaaaggtggtacttattcagtaagtgct<br>gctatgattgaagatttaaaagtgggagttttaggagaacacgcttcaaaccta<br>ggtggaataatagcaaaacaaataggtgaagaagtaaatgttccttcatacat<br>agtagaccctgttgttgtagatgaattagaagatgttgctagaatttctggtatgc<br>ctgaaataagtagagcaagtgtagtacatgctttaaatcaaaggcaatagc<br>aagaagatatgctagagaaataaacaagaaatatgaagatataaatcttata<br>gttgcacacatgggtggaggagtttctgttggagctcataaaaatggtaaaata<br>gtagatgttgcaaacgcattagatggagaaggacctttctctccagaaagaag<br>tggtggactaccagtaggtgcattagtaaaaatgtgctttagtggaaaatatact<br>caagatgaaattaaaaagaaaataaaaggtaatggcggactagttgcatact<br>taaacactaatgatgctagagaagttgaagaaagaattgaagctggtgatga<br>aaaagctaaattagtatatgaagctatggcatatcaaatctctaaagaaatag<br>gagctagtgctgcagttcttaagggagatgtaaaagcaatattattaactggtg<br>gaatcgcatattcaaaaatgtttacagaaatgattgcagatagagttaaatttat<br>agcagatgtaaaagtttatccaggtgaagatgaaatgattgcattagctcaag<br>gtggacttagagttttaactggtgaagaagaggctcaagtttatgataactaataa | |

In some embodiments, the genetically engineered bacteria comprise the nucleic acid sequence of SEQ ID NO: 90 or a functional fragment thereof. In some embodiments, the genetically engineered bacteria comprise a nucleic acid sequence that, but for the redundancy of the genetic code, encodes the same polypeptide as SEQ ID NO: 90 or a functional fragment thereof. In some embodiments, genetically engineered bacteria comprise a nucleic acid sequence that is at least about 80%, at least about 85%, at least about 90%, at least about 95%, or at least about 99% homologous to the DNA sequence of SEQ ID NO: 90 or a functional fragment thereof, or a nucleic acid sequence that, but for the redundancy of the genetic code, encodes the same polypeptide as SEQ ID NO: 90 or a functional fragment thereof.

In some embodiments, the genetically engineered bacteria comprise the nucleic acid sequence of SEQ ID NO: 92 or a functional fragment thereof. In some embodiments, the genetically engineered bacteria comprise a nucleic acid sequence that, but for the redundancy of the genetic code, encodes the same polypeptide as SEQ ID NO: 92 or a functional fragment thereof. In some embodiments, genetically engineered bacteria comprise a nucleic acid sequence that is at least about 80%, at least about 85%, at least about 90%, at least about 95%, or at least about 99% homologous to the DNA sequence of SEQ ID NO: 92 or a functional fragment thereof, or a nucleic acid sequence that, but for the redundancy of the genetic code, encodes the same polypeptide as SEQ ID NO: 92 or a functional fragment thereof.

In some embodiments, the genetically engineered bacteria comprise the nucleic acid sequence of SEQ ID NO: 94 or a functional fragment thereof. In some embodiments, the genetically engineered bacteria comprise a nucleic acid sequence that, but for the redundancy of the genetic code, encodes the same polypeptide as SEQ ID NO: 94 or a functional fragment thereof. In some embodiments, genetically engineered bacteria comprise a nucleic acid sequence that is at least about 80%, at least about 85%, at least about 90%, at least about 95%, or at least about 99% homologous to the DNA sequence of SEQ ID NO: 94 or a functional fragment thereof, or a nucleic acid sequence that, but for the redundancy of the genetic code, encodes the same polypeptide as SEQ ID NO: 94 or a functional fragment thereof.

In some embodiments, the genetically engineered bacteria comprise the nucleic acid sequence of SEQ ID NO: 96 or a functional fragment thereof. In some embodiments, the genetically engineered bacteria comprise a nucleic acid sequence that, but for the redundancy of the genetic code, encodes the same polypeptide as SEQ ID NO: 96 or a functional fragment thereof. In some embodiments, genetically engineered bacteria comprise a nucleic acid sequence that is at least about 80%, at least about 85%, at least about 90%, at least about 95%, or at least about 99% homologous to the DNA sequence of SEQ ID NO: 96 or a functional fragment thereof, or a nucleic acid sequence that, but for the redundancy of the genetic code, encodes the same polypeptide as SEQ ID NO: 96 or a functional fragment thereof.

In some embodiments, the genetically engineered bacteria comprise the nucleic acid sequence of SEQ ID NO: 98 or a functional fragment thereof. In some embodiments, the genetically engineered bacteria comprise a nucleic acid sequence that, but for the redundancy of the genetic code, encodes the same polypeptide as SEQ ID NO: 98 or a functional fragment thereof. In some embodiments, genetically engineered bacteria comprise a nucleic acid sequence that is at least about 80%, at least about 85%, at least about 90%, at least about 95%, or at least about 99% homologous to the DNA sequence of SEQ ID NO: 98 or a functional fragment thereof, or a nucleic acid sequence that, but for the redundancy of the genetic code, encodes the same polypeptide as SEQ ID NO: 98 or a functional fragment thereof.

In some embodiments, the genetically engineered bacteria comprise the nucleic acid sequence of SEQ ID NO: 100 or a functional fragment thereof. In some embodiments, the genetically engineered bacteria comprise a nucleic acid sequence that, but for the redundancy of the genetic code, encodes the same polypeptide as SEQ ID NO: 100 or a functional fragment thereof. In some embodiments, genetically engineered bacteria comprise a nucleic acid sequence that is at least about 80%, at least about 85%, at least about 90%, at least about 95%, or at least about 99% homologous to the DNA sequence of SEQ ID NO: 100 or a functional fragment thereof, or a nucleic acid sequence that, but for the redundancy of the genetic code, encodes the same polypeptide as SEQ ID NO: 100 or a functional fragment thereof.

In some embodiments, the genetically engineered bacteria comprise the nucleic acid sequence of SEQ ID NO: 104 or a functional fragment thereof. In some embodiments, the genetically engineered bacteria comprise a nucleic acid sequence that, but for the redundancy of the genetic code, encodes the same polypeptide as SEQ ID NO: 104 or a functional fragment thereof. In some embodiments, genetically engineered bacteria comprise a nucleic acid sequence that is at least about 80%, at least about 85%, at least about 90%, at least about 95%, or at least about 99% homologous to the DNA sequence of SEQ ID NO: 104 or a functional fragment thereof, or a nucleic acid sequence that, but for the redundancy of the genetic code, encodes the same polypeptide as SEQ ID NO: 104 or a functional fragment thereof.

In some embodiments, the genetically engineered bacteria comprise the nucleic acid sequence of SEQ ID NO: 48 or a functional fragment thereof. In some embodiments, the genetically engineered bacteria comprise a nucleic acid sequence that, but for the redundancy of the genetic code, encodes the same polypeptide as SEQ ID NO: 48 or a functional fragment thereof. In some embodiments, genetically engineered bacteria comprise a nucleic acid sequence that is at least about 80%, at least about 85%, at least about 90%, at least about 95%, or at least about 99% homologous to the DNA sequence of SEQ ID NO: 48 or a functional fragment thereof, or a nucleic acid sequence that, but for the redundancy of the genetic code, encodes the same polypeptide as SEQ ID NO: 48 or a functional fragment thereof.

In alternate embodiments, pbt and buk are replaced with TesB (SEQ ID NO: 48)

In some embodiments, the butyrate cassette is driven by an inducible promoter. For example, other FNR promotors can be used in lieu of ydfZ, e.g., in SEQ ID NO:.

Non-limiting FNR promoter sequences are provided herein. In some embodiments, the genetically engineered bacteria of the invention comprise a butyrate cassette under the control of one or more of promoter sequences found in Table 6, e.g., nirB promoter, ydfZ promoter, nirB promoter fused to a strong ribosome binding site, ydfZ promoter fused to a strong ribosome binding site, fnrS, an anaerobically induced small RNA gene (fnrS promoter), nirB promoter fused to a crp binding site, and fnrS fused to a crp binding site.

In some embodiments, the butyrate cassetted is under the control of a promoter which is inducible by metabolites present in the gut. In some embodiments the butyrate cassette is induced by HE-specific molecules or metabolites indicative of liver damage, e.g., bilirubin. In some embodiments, the butyrate cassette is placed under the control of promoter, which is inducible by inflammation or an inflammatory response (e.g., RNS or ROS promoter).

In some embodiments, the genetically engineered bacteria comprise a butyrate cassette driven by a promoter induced by a molecule or metabolite, e.g., bilirubin, aspartate aminotransferase, alanine aminotransferase, blood coagulation factors II, VII, IX, and X, alkaline phosphatase, gamma glutamyl transferase, hepatitis antigens and antibodies, alpha fetoprotein, anti-mitochondrial, smooth muscle, and anti-nuclear antibodies, iron, transferrin, ferritin, copper, ceruloplasmin, ammonia, and manganese in their blood and intestines. Promoters that respond to one of these molecules or their metabolites may be used in the genetically engineered bacteria provided herein.

In some embodiments, the butyrate cassette is inducible by arabinose and is driven by the AraBAD promoter.

Example 40

Quantification of Butyrate by LC-MS/MS

To obtain the butyrate measurements in Example 37 a LC-MS/MS protocol for butyrate quantification was used.

Sample Preparation

First, fresh sodium butyrate stock solution (10 mg/m), and 1000, 500, 250, 100, 20, 4 and 0.8 µg/mL of sodium butyrate standards were prepared in water. Then, 10 µL of sample (bacterial supernatants and standards) were pipetted into a V-bottom polypropylene 96-well plate, and 90 µL of 67% ACN (60 uL ACN+30 uL water per reaction) with 4 ug/mL of butyrate-d7 (CDN isotope) internal standard in final solution were added to each sample. The plate was heat-sealed, mixed well, and centrifuged at 4000 rpm for 5 minutes. In a round-bottom 96-well polypropylene plate, 20 µL of diluted samples were added to 180 µL of a buffer containing 10 mM MES pH4.5, 20 mM EDC (N-(3-Dimethylaminopropyl)-N'-ethylcarbodiimide), and 20 mM TFEA (2,2,2-trifluroethylamine). The plate was again heat-sealed and mixed well, and samples were incubated at room temperature for 1 hour.

LC-MS/MS Method

Butyrate was measured by liquid chromatography coupled to tandem mass spectrometry (LC-MS/MS) using a Thermo TSQ Quantum Max triple quadrupole mass spectrometer. HPLC Details are listed in Table 45 and Table 46. Tandem Mass Spectrometry details are found in Table 47.

TABLE 45

| HPLC Details | |
|---|---|
| Column | Thermo Aquasil C18 column, 5 µm (50 × 2.1 mm) |
| Mobile Phase A | 100% H2O, 0.1% Formic Acid |
| Mobile Phase B | 100% ACN, 0.1% Formic Acid |
| Injection volume | 10 uL |

TABLE 46

| HPLC Method | | | |
|---|---|---|---|
| Total Time (min) | Flow Rate (µL/min) | A % | B % |
| 0 | 0.5 | 100 | 0 |
| 1 | 0.5 | 100 | 0 |

TABLE 46-continued

HPLC Method

| Total Time (min) | Flow Rate (μL/min) | A % | B % |
|---|---|---|---|
| 2 | 0.5 | 10 | 90 |
| 4 | 0.5 | 10 | 90 |
| 4.01 | 0.5 | 100 | 0 |
| 4.25 | 0.5 | 100 | 0 |

TABLE 47

Tandem Mass Spectrometry Details

| | |
|---|---|
| Ion Source | HESI-II |
| Polarity | Positive |
| SRM transitions | Butyrate 170.0/71.1, Butyrate d7 177.1/78.3 |

Example 41

Efficacy of Genetically Engineered Bacteria Producing Arginine and/or Butyrate in a Bile Duct Ligation Model Ligation of the common bile duct in rodents has used as an experimental procedure in research for many years to induce liver cholestasis and fibrosis (see e.g., Tag et a., Bile Duct Ligation in Mice: Induction of Inflammatory Liver Injury and Fibrosis by Obstructive Cholestasis, Journal of Visualized Experiments, February 2015; 96; e52438, and references therein).

To determine the efficacy of a strain comprising an arginine and butyrate producing circuit in reducing symptoms of liver inflammation and fibrosis, a bile duct ligation model is used. A Nissle control (SYN-UCD107, kanamycin resistant Nissle), an arginine producing strain (SYN-UCD305), a butyrate producing strain (SYN-UCD502), and a strain producing both butyrate and arginine (SYN-UCD605) are compared in the study. ALT/AST levels, fibrosis (portal, perisinusoidal and total) and hepatic inflammation are the primary endpoints of the study; overall animal health is the secondary endpoint of the study.

Animals (C57BL6, 8 weeks) are treated by oral gavage with either H2O control (n=12), or SYN-UCD107 (n=12; kanamycin resistant Nissle), or arginine producing SYN-UCD305 (n=12; comprising ΔArgR, PfnrS-ArgAfbr integrated into the chromosome at the malEK locus, ΔThyA, and no antibiotic resistance), or butyrate producing SYN-UCD502 (n=12; comprising a PydfZ-ter butyrate cassette integrated on the chromosome) or SYN-UCD605 (n=12; comprising ΔArgR, PfnrS-ArgAfbr integrated into the chromosome at the malEK locus, ΔThyA, and PydfZ-ter butyrate cassette integrated on the chromosome, and no antibiotic resistance). Bacteria are administered at a dose of >10e10 cells/ml.

In some embodiments, SYN-UCD501 (comprising wild type ArgR, no FNR-ArgAfbr, wild type ThyA, and Logic156 (pSC101 PydfZ-ter butyrate plasmid; amp resistance) and SYN-UCD602 (comprising ΔArgR, PfnrS-ArgAfbr integrated into the chromosome at the malEK locus, ΔThyA, and Logic156 (pSC101 PydfZ-ter butyrate plasmid; amp resistance)) are used instead of SYN-UCD502 and SYN-UCD605.

On Day 0, bile duct ligation surgery is performed as described in Example 40. On day 1, mice are weighed and randomized. Mice are gavaged with 100 ul H2O, SYN-UCD107, SYN-UCD305, SYN-UCD502 or SYN-UCD605 in the AM and PM. On day two, mice are gavaged with 100 ul H2O, SYN798 and SYN993-in the AM and PM. On day three, mice are gavaged with 100 ul H2O, SYN-UCD107, SYN-UCD305, SYN-UCD502 or SYN-UCD605 in the AM and PM. At 4 h post AM dose, blood is collected for ALT/AST analysis. On days 4-6, mice are gavaged with 100 ul H2O, SYN-UCD107, SYN-UCD305, SYN-UCD502 or SYN-UCD605 in the AM and PM. On day 7, mice are gavaged with 100 ul H2O, SYN-UCD107, SYN-UCD305, SYN-UCD502 or SYN-UCD605 in the AM and PM. At 4 h post AM dose, blood is collected for ALT/AST analysis. On days 8-9, mice are gavaged with 100 ul H2O, SYN-UCD107, SYN-UCD305, SYN-UCD502 or SYN-UCD605 in the AM and PM. On day 10, mice are gavaged with 100 ul H2O, SYN-UCD107, SYN-UCD305, SYN-UCD502 or SYN-UCD605 in the AM and PM. At 4 h post AM dose, blood is collected for ALT/AST analysis. On days 11-13, mice are gavaged with 100 ul H2O, SYN-UCD107, SYN-UCD305, SYN-UCD502 or SYN-UCD605 in the AM and PM. On day 14, animals are gavaged with 100 ul H2O, SYN-UCD107, SYN-UCD305, SYN-UCD502 or SYN-UCD605 in the AM. Then, 4 h post dose animals are euthanized, and blood is collected by cardiac bleed for ALT/AST analysis. The liver tissue is harvested for fibrosis analysis by histological assessment.

Example 42

Bile Duct Ligation Procedure

Bile Duct Ligation
Pre-Surgical Preparation:

During the complete experimentation, the animal is kept on a warming plate at a temperature of 37° C., permanently connected to an anesthesia system, and the operational area is covered overall with fluid-impermeable, self-adhesive drapes.

The mouse is anaesthetized with inhalation of 4 vol % isoflurane in 100% oxygen at a flow rate of 4 L/min for the induction of the anesthesia. The depth of anesthetization is sufficient when the following vital criteria are reached: regular spontaneous breathing, no reflex after setting of pain stimuli between toes, and no response to pain. The abdominal fur of the mouse is shaved with an electric fur shaver and the eyes are protected from drying out by usage of eye and nose ointment. The mouse is placed on a 37° C. heated hot plate, the mouse snout is inserted in the Fluovac mask of a Fluovac anesthesia system, and the legs of the animal are fixed with stripes of silk tape. Anesthesia of the mouse is maintained by inhalation of 1.5-3 vol % isoflurane in 100% oxygen at a flow rate of 1 L/min and induct perioperative analgesia via intraperitoneal injection of buprenorphine solution (0.1 mg/kg BW dissolved in 0.9% NaCl solution).

The shaved abdominal skin is sterilized with a gauze swab that is moistened with a standard antiseptic, ready to use alcoholic solution for preoperative treatment of the skin.
Surgical Procedures:

The abdomen is opened with a midline laparotomy of a length of approximately 2 cm by cutting the cutis plus fascia at the same time with an 11.5 cm surgical scissor. The connective tissue on top of the peritoneum is dissected by using the scissor as a spreader. The peritoneum is cut along the linea alba to open the peritoneal cavity. The cavity is enlarged by inserting a holding suture in the sternum, raising the filament of the suture, and fixing it on top of the Fluovac mask. The operation area is spread by inserting a Colibri retractor in the peritoneal cavity. The liver is lifted with a moisturized (0.9% NaCl solution) cotton swab so that the ventral side of it sticks to the diaphragm and the hilum is clearly visible. The bile duct is expoed by caudal movement of the gut. The bile duct is separated carefully from the flanking portal vein and hepatic artery using a microserrations forceps. The 5-0 suture is placed around the bile duct and secured with two surgical knots. When tying the knots the tractive force is increased continuously to ensure effective obstruction without severing the bile duct. A second cranial ligation is added in the same manner without dissecting the bile duct in between. The ends of the sutures are cut, the sternum lowered, and the retractor removed. The peritoneal cavity is rinsed with 0.9% NaCl solution and the abdominal organs replaced to the physiological positions. Both abdominal layers (peritoneum and cutis plus facia) are closed with separate running sutures with 6-0 Mersilk. The ends of the sutures are cut and the operation area is sterilized with a gauze swab moistened with antiseptic solution.

Postoperative Treatment and Follow-Up:

The mouse is allowed to recover in a cage warmed up by an infrared lamp until the mouse is fully awake and active. Afterwards, the mouse is moved to a normal cage and provided ad libitum access to water and food. After the surgery, the animals are monitored at regular intervals and follow-up postoperative treatments are carried out with suitable analgesia (e.g., buprenorphine solution) following the local recommendation of the internal animal care and use committees. Animals are kept with free access to food and water ad libitum until the end of the experiment.

Example 43

TAA Model of Hepatic Encephalopathy

TAA treatment of mice has previously been employed in the literature to model increased blood ammonia levels associated with UCDs, acute and chronic liver disease and HE (Wallace M C, et al., Lab Anim. 2015 April; 49(1 Suppl):21-9. Standard operating procedures in experimental liver research: thioacetamide model in mice and rat)s. In some embodiments, a TAA-induced mouse model of hyperammonemia is employed to investigate the duration of activity of the genetically engineered bacteria and to generate additional data to support this approach to the treatment of hepatic encephalopathy.

To determine the efficacy of a strain comprising an arginine and butyrate producing circuit in alleviating symptoms of liver inflammation and fibrosis, Nissle control (SYN-UCD107, kanamycin resistant Nissle), an arginine producing strain (SYN-UCD305), a butyrate producing strain (SYN-UCD502), and a strain producing both butyrate and arginine (SYN-UCD605) are compared in a TAA model study. ALT/AST levels, fibrosis (portal, perisinusoidal and total) and hepatic inflammation are the primary endpoints of the study. Overall animal health is the secondary endpoint of the study.

To investigate the effects of engineered bacteria on prolonged elevations of blood ammonia, the bacteria are administered to C57BL6 mice that are also administered a dose of 300 mpk thioacetamide (TAA).

C57BL6 (10 weeks old) are administered one daily dose of SYN-UCD107, or SYN-UCD305 (n=12), SYN-UCD502 (n=12), or SYN-UCD605 (n=12) (100 ul of >1×10$^{10}$ cells/ml) or vehicle control. Alternatively, mice are administered 2 daily doses of bacteria (100 ul of >1×10$^{10}$ cells/ml) (n=5 for each treatment group), once in the AM and once in the PM. After three days of pre-dosing with the bacteria, the mice are treated intraperitoneally with thioacetamide (TAA) at 300 mpk or with H2O as control. Alternatively, the mice are treated twice daily, once in the AM and once in the PM with 250 mpk. The duration of the study is five days. Ammonium levels are measured and overall health survival, body weight change is monitored.

In brief, animals are acclimated for 7 days. On day 1 of the time course, animals are weighed, bled to measure baseline ALT/AST and collect fecal pellets (per cage), and are randomized based on ALT/AST levels. Animals are dosed by oral gavage either once or twice (AM and PM) with H2O, SYN-UCD107, SYN-UCD305, SYN-UCD502, or SYN-UCD605 (100 ul/dose/animal). Water is changed to H2O (+)20 mg/ml ATC. On day 2, animals are dosed by oral gavage either once or twice (AM and PM) with H2O, SYN-UCD107, SYN-UCD305, SYN-UCD502, or SYN-UCD605 (100 ul/dose/animal). On day 3, animals are weighed and dosed by oral gavage either once or twice (AM and PM) with H2O, SYN-UCD107, SYN-UCD305, SYN-UCD502, or SYN-UCD605 (100 ul/dose/animal). Additionally, animals are dosed intraperitoneally with 300 mpk TAA (or saline control). Alternatively, animals are dosed with 250 mpk TAA (or saline control) once in the AM and once in the PM. On day 4, animals are weighed and blood is collected for ALT/AST analysis. Fecal pellets are collected per cage. Animals are dosed per oral gavage either once or twice (AM and PM) with H2O, SYN-UCD107, SYN-UCD305, SYN-UCD502, or SYN-UCD605 (100 ul/dose/animal). Animals may also be dosed with 250 mpk TAA (or saline control). On day 5, animals are weighed and blood is collected for ALT/AST analysis. Fecal pellets are collected (per cage). Animals are dosed by oral gavage either once or twice (AM and PM) with H2O, SYN-UCD107, SYN-UCD305, SYN-UCD502, or SYN-UCD605 (100 ul/dose/animal). ALT/AST levels, bacterial load in the fecal pellets, and overall health survival, and body weight changes are monitored. The liver tissue is harvested for fibrosis analysis by histological assessment.

Example 44

Carbontetrachloride (CCl4) Model of Hepatic Encephalopathy

CCl4 is often used to induce hepaticfibrosis and cirrhosis in animals because the underlying iochemical mechanisms and histological characteristics are similar to those observed in human liver cirrhosis (Nhung et al., Establishment of a standardized mouse model of hepatic fibrosis for biomedical research; Biomedical Research and Therapy 2014, 1(2):43-49).

CYP2E1 is an enzyme which is expressed in perivenular hepatocytes, and which converts CCl4 into a CCl3+ radical. The accumulation of the CCl3+ radical causes centrilobular necrosis and changes the permeability of the hepatocyte plasma and mitochondrial membranes. As a result, an increase in inflammation and fibrogenesis, and extracellular matrix deposition is observed. Chronic CCl4 exposure causes the formation of nodules and fibrosis, products of the wound healing process. CCl4 treatment has been shown to cause fibrosis after 2-4 weeks, significant bridging fibrosis after 5-7 weeks, cirrhosis after 9-11 weeks, and micronodular cirrhosis after 10-20 weeks (Nhung et al., Establishment of a standardized mouse model of hepatic fibrosis for biomedical research; Biomedical Research and Therapy 2014, 1(2):43-49, and references therein).

To determine the efficacy of a strain comprising an arginine and butyrate producing circuit in alleviating symptoms of liver inflammation and fibrosis, a CCl4 mouse model of liver cirrhosis is used. A Nissle control (SYN-UCD107, kanamycin resistant Nissle), an arginine producing strain (SYN-UCD305), a butyrate producing strain (SYN-UCD502), and a strain producing both butyrate and arginine (SYN-UCD605) are compared in the study. ALT/AST levels, fibrosis (portal, perisinusoidal and total) and hepatic inflammation are the primary endpoints of the study. Overall animal health is the secondary endpoint of the study. Study duration is 8 weeks.

Animals (C57BL6, 8 weeks) are treated by oral gavage with either H2O control (n=12), or SYN-UCD107 (n=12; kanamycin resistant Nissle), or arginine producing SYN-UCD305 (n=12; comprising ΔArgR, PfnrS-ArgAfbr integrated into the chromosome at the malEK locus, ΔThyA, and no antibiotic resistance), or butyrate producing SYN-UCD502 (n=12; comprising wild type ArgR, no FNR-ArgAfbr, wild type ThyA, and a PydfZ-ter butyrate cassette integrated on the chromosome) or SYN-UCD605 (n=12; comprising ΔArgR, PfnrS-ArgAfbr integrated into the chromosome at the malEK locus, ΔThyA, PydfZ-ter butyrate cassette integrated on the chromosome, and no antibiotic resistance. Bacteria are administered at a dose of >10e10 cells/ml in 100 ul.

In some embodiments, SYN-UCD501 (comprising Wild type ArgR, no FNR-ArgAfbr, wild type ThyA, and Logic156 (pSC101 PydfZ-ter butyrate plasmid; amp resistance) and SYN-UCD602 (comprising ΔArgR, PfnrS-ArgAfbr integrated into the chromosome at the malEK locus, ΔThyA, and Logic156 (pSC101 PydfZ-ter butyrate plasmid; amp resistance)) are used instead of SYN-UCD502 and SYN-UCD605.

On Day 1, mice are weighed and randomized. Animals are gavaged with 100 ul H2O, SYN-UCD107, SYN-UCD305, SYN-UCD502, or SYN-UCD605 in the AM. Additionally animals are gavaged with olive oil (sham control) or 1 ml/kg CCL4 in olive oil (all other treatment groups). Animals are gavaged with 100 ul H2O, SYN-UCD107, SYN-UCD305, SYN-UCD502, or SYN-UCD605 in the PM.

Through Week 1-8, animals are gavaged BID with 100 ul H2O, SYN-UCD107, SYN-UCD305, SYN-UCD502, or SYN-UCD605. Additionally, animals are gavaged 3×/week with olive oil (sham control) or 1 ml/kg CCL4 in olive oil (all other treatment groups). Animals are weighed 3×/week, and blood for ALT/AST analysis is collected 1×/week.

At the end of Week 8 animals are gavaged with 100 ul with 100 ul H2O, SYN-UCD107, SYN-UCD305, SYN-UCD502, or SYN-UCD605 in the AM. At 4 h post dose, animals are weighed, euthanized and blood is collected by cardiac bleed for ALT/AST analysis. The liver is harvested for fibrosis analysis by histological assessment.

Example 45

Efficacy of Butyrate-Expressing Bacteria in a DSS Mouse Model

Bacteria harboring the butyrate cassettes described above are grown overnight in LB. Bacteria are then diluted 1:100 into LB containing a suitable selection marker, e.g., ampicillin, and grown to an optical density of 0.4-0.5 and then pelleted by centrifugation. Bacteria are resuspended in phosphate buffered saline and 100 microliters is administered by oral gavage to mice. Damage to the gut is induced in mice by supplementing drinking water with 3% dextran sodium sulfate for 7 days prior to bacterial gavage. Mice are treated daily for 1 week and bacteria in stool samples are detected by plating stool homogenate on agar plates supplemented with a suitable selection marker, e.g., ampicillin. After 5 days of bacterial treatment, gut damage is scored in live mice using endoscopy. Endoscopic damage score is determined by assessing colon translucency, fibrin attachment, mucosal and vascular pathology, and/or stool characteristics. Mice are sacrificed and colonic tissues are isolated. Distal colonic sections are fixed and scored for inflammation and ulceration. Colonic tissue is homogenized and measurements are made for myeloperoxidase activity using an enzymatic assay kit and for cytokine levels (IL-1β, TNF-α, IL-6, IFN-γ and IL-10).

Example 46

Generating a DSS-Induced Mouse Model of HE

The genetically engineered bacteria described can be tested in the dextran sodium sulfate (DSS)-induced mouse model. The administration of DSS to animals results in chemical injury to the intestinal epithelium, allowing proinflammatory intestinal contents (e.g., luminal antigens, enteric bacteria, bacterial products) to disseminate and trigger inflammation (Low et al., 2013). To prepare mice for DSS treatment, mice are labeled using ear punch, or any other suitable labeling method. Labeling individual mice allows the investigator to track disease progression in each mouse, since mice show differential susceptibilities and responsiveness to DSS induction. Mice are then weighed, and if required, the average group weight is equilibrated to eliminate any significant weight differences between groups. Stool is also collected prior to DSS administration, as a control for subsequent assays. Exemplary assays for fecal markers of inflammation (e.g., cytokine levels or myeloperoxidase activity) are described below.

For DSS administration, a 3% solution of DSS (MP Biomedicals, Santa Ana, Calif.; Cat. No. 160110) in autoclaved water is prepared. Cage water bottles are then filled with 100 mL of DSS water, and control mice are given the same amount of water without DSS supplementation. This amount is generally sufficient for 5 mice for 2-3 days. Although DSS is stable at room temperature, both types of water are changed every 2 days, or when turbidity in the bottles is observed.

Acute, chronic, and resolving models of intestinal inflammation are achieved by modifying the dosage of DSS (usually 1-5%) and the duration of DSS administration (Chassaing et al., 2014). For example, acute and resolving gut damage may be achieved after a single continuous exposure to DSS over one week or less, whereas chronic gut damage is typically induced by cyclical administration of DSS punctuated with recovery periods (e.g., four cycles of DSS treatment for 7 days, followed by 7-10 days of water).

Figure 53D:
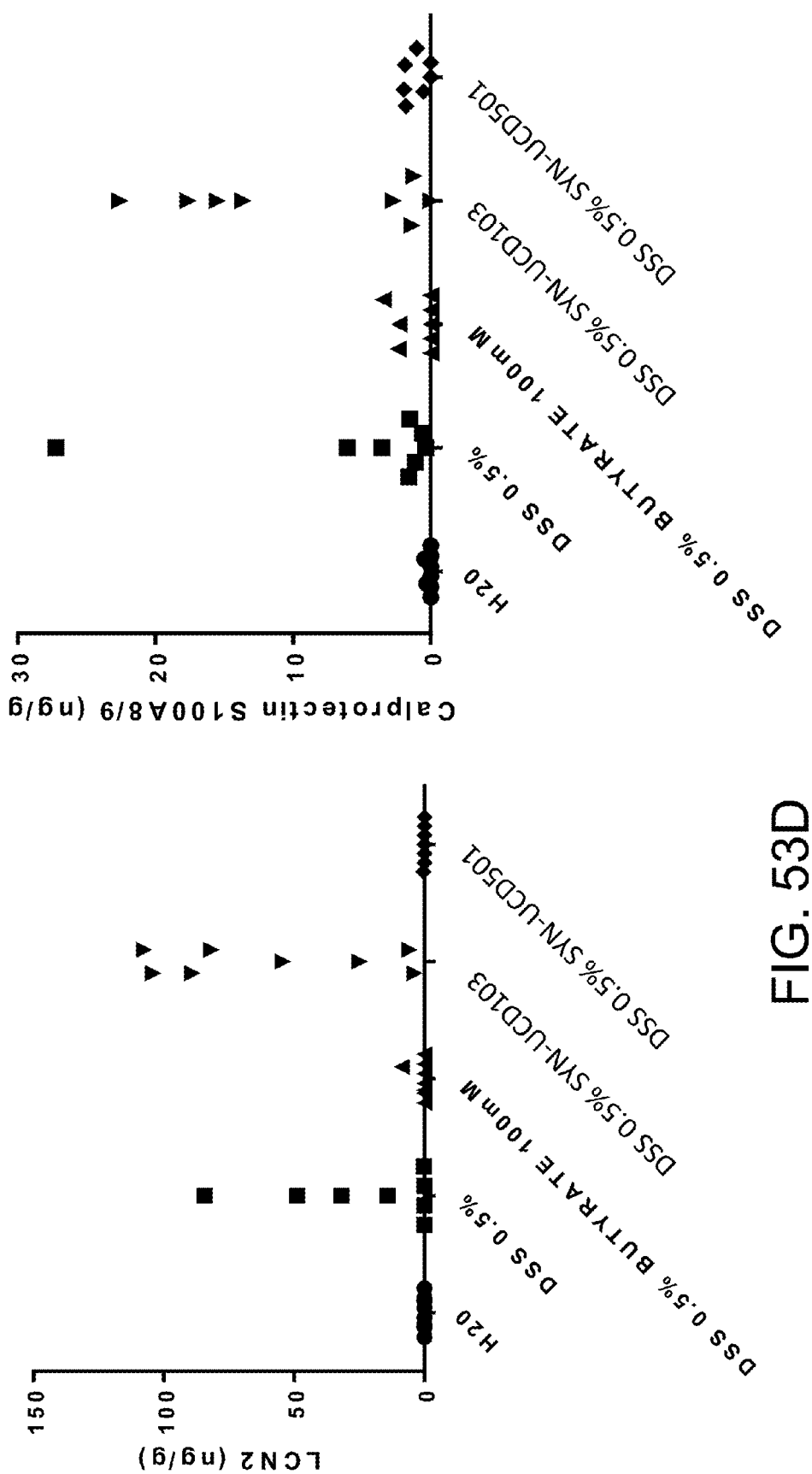
FIG. 53D depicts levels of mouse lipocalin 2 and calprotectin quantified by ELISA using the fecal samples in an in vivo model of HE. SYN-UCD501 reduces inflammation and/or protects gut barrier function as compared to control SYN-UCD103.
Figure 54A:
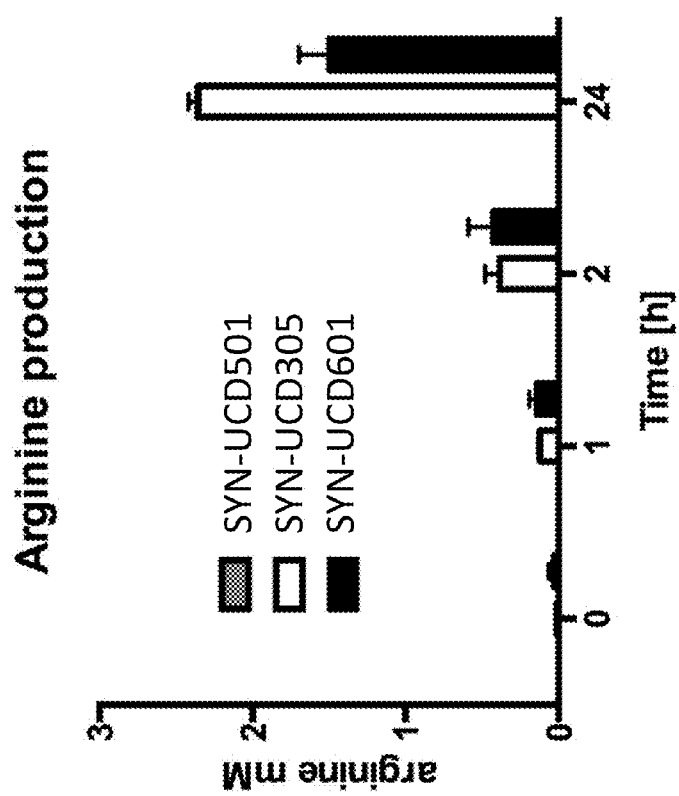
FIGS. 54A and 54B depict bar graphs showing in vitro arginine (FIG. 54A) and butyrate (FIG. 54B) production for (1) butyrate producing strain; (2) arginine producing strain (ammonia consuming strain), and (3) strain that produces butyrate and also consumes ammonia. SYN-UCD501 (butyrate producing strain comprising Logic156 (pSC101 PydfZ-ter butyrate plasmid; amp resistance)), and SYN-UCD305 (arginine producing/ammonia consuming strain comprising ΔArgR, PfnrS-ArgAfbr integrated into the chromosome at the malEK locus, and ΔThyA, with no antibiotic resistance), and SYN-UCD601 (butyrate producing and arginine producing/ammonia consuming strain comprising ΔArgR, PfnrS-ArgAfbr integrated into the chromosome at the malEK locus, ΔThyA, and Logic156 (pSC101 PydfZ-ter butyrate plasmid; amp resistance)). The data show that SYN-UCD601 is able to produce similar levels of arginine as SYN-UCD305 and similar levels of butyrate as SYN-UCD501 in vitro.
Figure 54B:
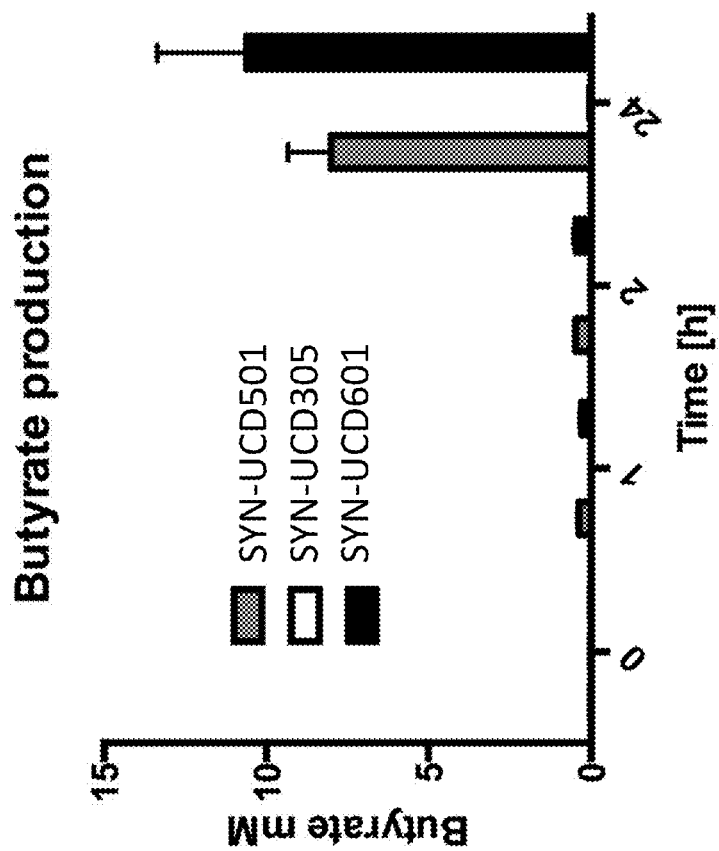
Figure 56:
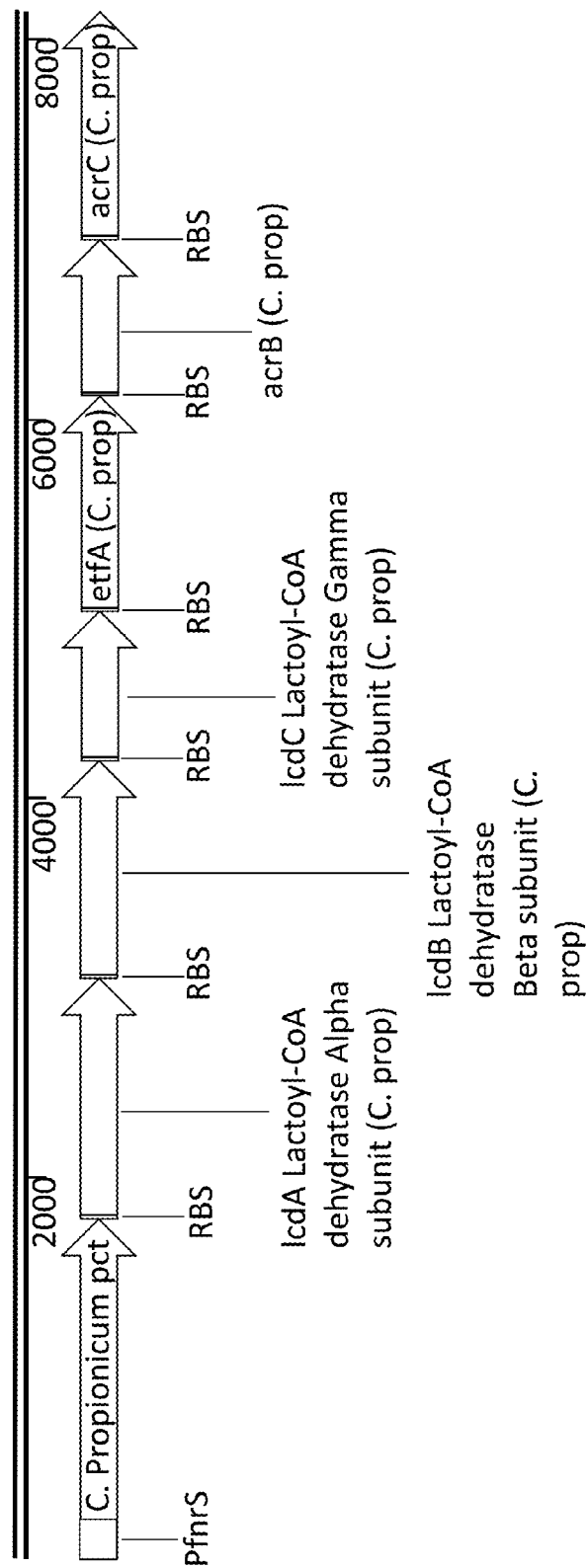
FIG. 56 depicts an exemplary propionate biosynthesis gene cassette.
Figure 57C:
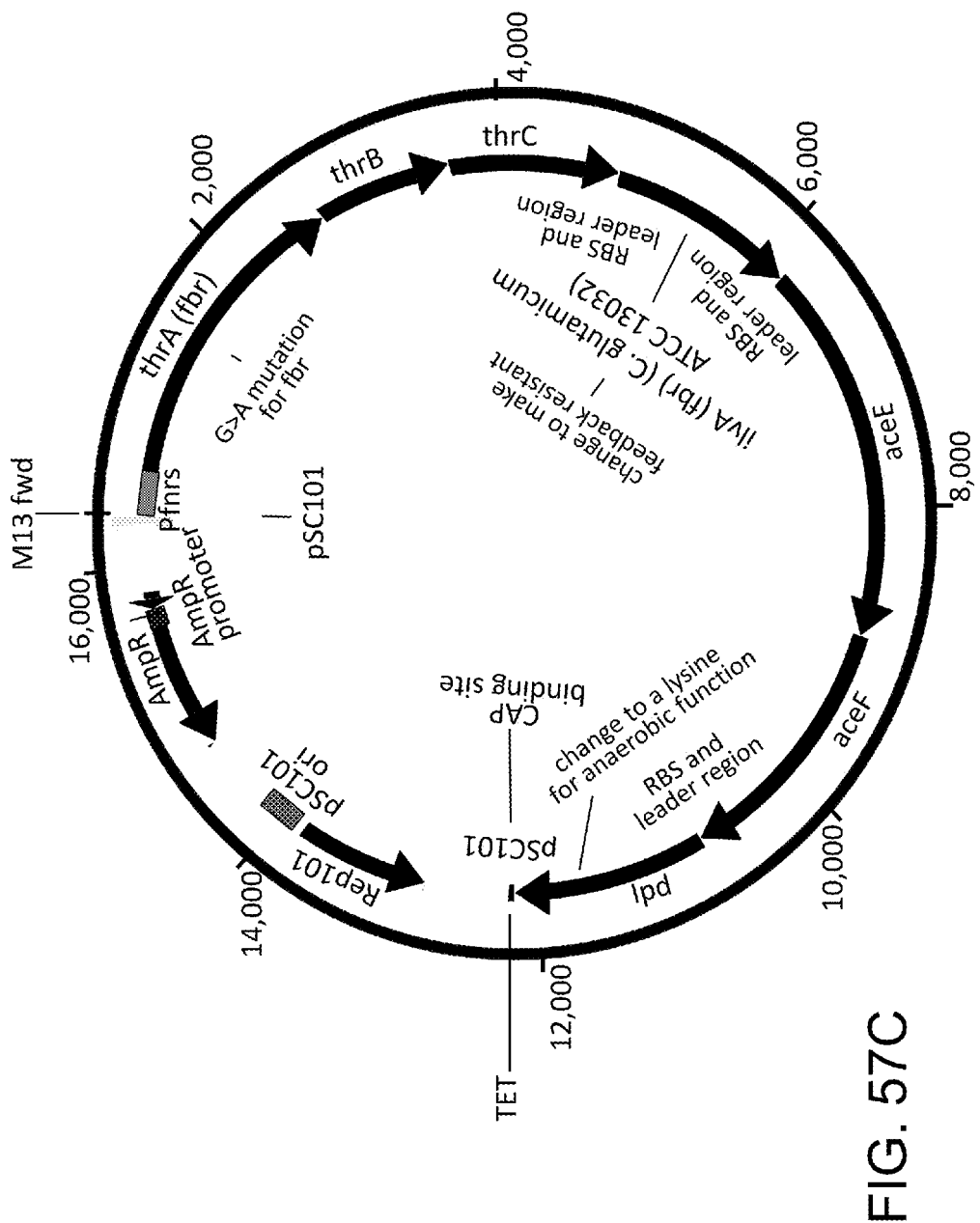
Figure 59:
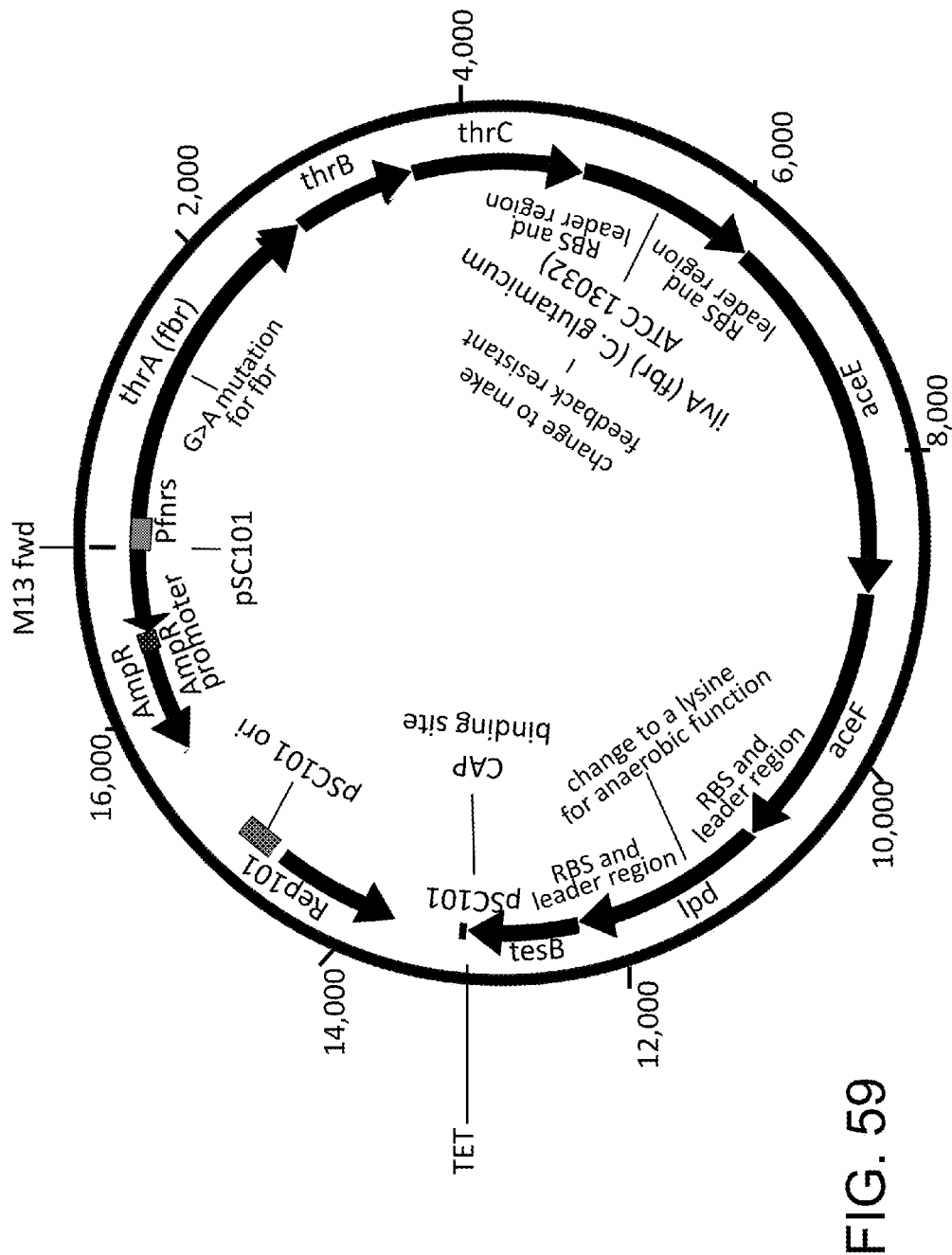
FIG. 59 depicts an exemplary propionate biosynthesis gene cassette.

FIG. 53D shows that butyrate produced in vivo in DSS mouse models under the control of an FNR promoter can be gut protective. LCN2 and calprotectin are both a measure of gut barrier disruption (measure by ELISA in this assay). FIG. 53D shows that Syn 363 (ter substitution) reduces inflammation and/or protects gut barrier as compared to Syn 94 (wildtype Nissle).

Example 47

Monitoring Disease Progression In Vivo

Following initial administration of DSS, stool is collected from each animal daily, by placing a single mouse in an empty cage (without bedding material) for 15-30 min. However, as DSS administration progresses and inflammation becomes more robust, the time period required for collection increases. Stool samples are collected using sterile forceps, and placed in a microfuge tube. A single pellet is used to monitor occult blood according to the following scoring system: 0, normal stool consistency with negative hemoccult; 1, soft stools with positive hemoccult; 2, very soft stools with traces of blood; and 3, watery stools with visible rectal bleeding. This scale is used for comparative analysis of intestinal bleeding. All remaining stool is reserved for the measurement of inflammatory markers, and frozen at −20° C.

The body weight of each animal is also measured daily. Body weights may increase slightly during the first three days following initial DSS administration, and then begin to decrease gradually upon initiation of bleeding. For mouse models of acute colitis, DSS is typically administered for 7 days. However, this length of time may be modified at the discretion of the investigator.

Example 48

In Vivo Efficacy of Genetically Engineered Bacteria Following DSS Induction The genetically engineered bacteria described herein can be tested in DSS-induced animal models of HE. Bacteria are grown overnight in LB supplemented with the appropriate antibiotic. Bacteria are then diluted 1:100 in fresh LB containing selective antibiotic, grown to an optical density of 0.4-0.5, and pelleted by centrifugation. Bacteria are then resuspended in phosphate buffered saline (PBS). Gut damage is induced in mice by supplementing drinking water with 3% DSS for 7 days prior to bacterial gavage. On day 7 of DSS treatment, 100 µL of bacteria (or vehicle) is administered to mice by oral gavage. Bacterial treatment is repeated once daily for 1 week, and bacteria in stool samples are detected by plating stool homogenate on selective agar plates.

After 5 days of bacterial treatment, gut damage is scored in live mice using the Coloview system (Karl Storz Veterinary Endoscopy, Goleta, Calif.). In mice under 1.5-2.0% isoflurane anesthesia, colons are inflated with air and approximately 3 cm of the proximal colon can be visualized (Chassaing et al., 2014). Endoscopic damage is scored by assessing colon translucency (score 0-3), fibrin attachment to the bowel wall (score 0-3), mucosal granularity (score 0-3), vascular pathology (score 0-3), stool characteristics (normal to diarrhea; score 0-3), and the presence of blood in the lumen (score 0-3), to generate a maximum score of 18. Mice are sacrificed and colonic tissues are isolated using protocols described in Examples 8 and 9. Distal colonic sections are fixed and scored for inflammation and ulceration. Remaining colonic tissue is homogenized and cytokine levels (e.g., IL-1β, TNF-α, IL-6, IFN-γ, and IL-10), as well as myeloperoxidase activity, are measured using methods described below.

Example 49

Euthanasia Procedures for Rodent Models of HE

Four and 24 hours prior to sacrifice, 5-bromo-2'-deooxyuridine (BrdU) (Invitrogen, Waltham, Mass.; Cat. No. B23151) may be intraperitoneally administered to mice, as recommended by the supplier. BrdU is used to monitor intestinal epithelial cell proliferation and/or migration via immunohistochemistry with standard anti-BrdU antibodies (Abcam, Cambridge, Mass.).

On the day of sacrifice, mice are deprived of food for 4 hours, and then gavaged with FITC-dextran tracer (4 kDa, 0.6 mg/g body weight). Fecal pellets are collected, and mice are euthanized 3 hours following FITC-dextran administration. Animals are then cardiac bled to collect hemolysis-free serum. Intestinal permeability correlates with fluorescence intensity of appropriately diluted serum (excitation, 488 nm; emission, 520 nm), and is measured using spectrophotometry. Serial dilutions of a known amount of FITC-dextran in mouse serum are used to prepare a standard curve.

Alternatively, intestinal inflammation is quantified according to levels of serum keratinocyte-derived chemokine (KC), lipocalin 2, calprotectin, and/or CRP-1. These proteins are reliable biomarkers of inflammatory disease activity, and are measured using DuoSet ELISA kits (R&D Systems, Minneapolis, Minn.) according to manufacturer's instructions. For these assays, control serum samples are diluted 1:2 or 1:4 for KC, and 1:200 for lipocalin 2. Samples from DSS-treated mice require a significantly higher dilution.

Example 42

Non-Obese Diabetes (NOD) Model of Hepatic Encephalopathy

NOD mice can be used as an in vivo model for testing the efficacy of bacteria comprising a gut-barrier enhancing circuit, e.g., a butyrate biosynthetic cassette, as these mice exhibit a pronounced "leaky gut" phenotype, which is evidenced by a decrease in the level of tight junction proteins (e.g., occludin, zonula occludin, mucin, E-cadherin).

To determine the efficacy of a strain comprising an arginine and butyrate producing circuit in alleviating symptoms associated with "leaky gut", a NOD mouse model is used. NOD mice result from the autoimmune destruction of pancreatic islet β cells. A Nissle control (SYN-UCD107, kanamycin resistant Nissle), an arginine producing strain (SYN-UCD305), a butyrate producing strain (SYN-UCD502), and a strain producing both butyrate and arginine (SYN-UCD605) are compared in the study. Epithelial gut integrity (occludin and other tight junction markers) and gut inflammation (inflammatory biomarkers, e.g., IL-1A, IL-6, TNFa, IL-21) are the primary endpoints of the study. Overall animal health is the secondary endpoint of the study. Study duration is 8 weeks.

Animals (C57BL6, 8 weeks) are treated by oral gavage with either H2O control (n=12), or 100 mM butyrate (n=12), or arginine producing SYN-UCD305 (n=12; comprising ΔArgR, PfnrS-ArgAfbr integrated into the chromosome at the malEK locus, ΔThyA, and no antibiotic resistance), or butyrate producing SYN-UCD502 (n=12; comprising wild type ArgR, no FNR-ArgAfbr, wild type ThyA, and a PydfZ-ter butyrate cassette integrated on the chromosome) or SYN-UCD605 (n=12; comprising ΔArgR, PfnrS-ArgAfbr integrated into the chromosome at the malEK locus, ΔThyA, PydfZ-ter butyrate cassette integrated on the chromosome, and no antibiotic resistance. Bacteria are administered at a dose of >10e10 cells/ml in 100 ul.

In some embodiments, SYN-UCD501 (comprising Wild type ArgR, no FNR-ArgAfbr, wild type ThyA, and Logic156 (pSC101 PydfZ-ter butyrate plasmid; amp resistance) and SYN-UCD602 (comprising ΔArgR, PfnrS-ArgAfbr integrated into the chromosome at the malEK locus, ΔThyA, and Logic156 (pSC101 PydfZ-ter butyrate plasmid; amp resistance)) are used instead of SYN-UCD502 and SYN-UCD605.

On Day 1, mice are weighed and randomized. Animals are gavaged with 100 ul H2O, 100 mM butyrate, SYN-UCD305, SYN-UCD502, or SYN-UCD605 in the AM. Animals are gavaged with 100 ul H2O, 100 mM butyrate, SYN-UCD305, SYN-UCD502, or SYN-UCD605 in the PM. Animals are gavaged BID with 100 ul H2O, 100 mM butyrate, SYN-UCD305, SYN-UCD502, or SYN-UCD605. Animals are weighed daily.

On day 5, mice are fasted for 4 h and then gavaged with 0.6 mg/g FITC-dextran (40 kD). 3 h post FITC-dex administration mice are weighed, and blood is collected by cardiac bleed and colons and fecal pellets are harvested.

Haptoglobin/zonulin and Lcn2 are measured. RNA levels of TJP1, OCLN, CLDN25, and EPCAM are measured in colon samples (increased levels of these markers indicate therapeutic effect). RNA levels of inflammatory biomarkers are measured in the blood samples (decreased levels of these biomarkers indicate therapeutic effect).

Example 51

GABA Transport and Metabolic Circuits

In addition to the ammonia conversion circuit described above, the *E. coli* Nissle bacteria further comprise one or more GABA transport and/or one or more GABA metabolic circuits. Genetically engineered strains comprising at least one GABA transport circuit comprising a gene encoding an exemplary GABA transport protein, such as GabP (SEQ ID NO: 105, Table 48; SEQ ID NO: 106, Table 49), and are constructed using methods described above. Genetically engineered strains comprising at least one GABA metabolic circuit comprise genes encoding enzymes required for GABA catabolism, including, but not limited to GSST and SSDH, and are constructed using methods described above. The genes encoding GabP, GSST, and SSDH are expressed under the control of a tetracycline-inducible promoter, a FNR promoter selected from SEQ ID NOs: 18-29, or a promoter induced by HE-related molecules or metabolites. The genes encoding GabP, GSST, and SSDH may be expressed under the control of the same or different promoters. As discussed herein, other promoters may be used. The genes encoding GabP, GSST, and SSDH are expressed on a high-copy plasmid, a low-copy plasmid, or a chromosome. The genes encoding GabP, GSST, and SSDH are inserted into the bacterial genome at one or more of the following insertion sites in *E. coli* Nissle: malE/K, araC/BAD, lacZ, thyA, malP/T. Any suitable insertion site may be used, see, e.g., FIG. 18.

TABLE 48

Amino acid sequence of GabP transporter (SEQ ID NO: 105)

MGQSSQPHELGGGLKSRHVTMLSIAGVIGASLFVGSSVAIAEAGPAVLLA
YLFAGLLVVMIMRMLAEMAVATPDTGSFSTYADKAIGRWAGYTIGWLYWW

TABLE 48-continued

Amino acid sequence of GabP transporter (SEQ ID NO: 105)

FWVLVIPLEANIAAMILHSWVPGIPIWLFSLVITLALTGSNLLSVKNYGE
FEFWLALCKVIAILAFIFLGAVAISGFYPYAEVSGISRLWDSGGFMPNGF
GAVLSAMLITMFSFMGAEIVTIAAAESDTPEKHIVRATNSVIWRISIFYL
CSIFVVVALIPWNMPGLKAVGSYRSVLELLNIPHAKLIMDCVILLSVTSC
LNSALYTASRMLYSLSRRGDAPAVMGKINRSKTPYVAVLLSTGAAFLTVV
VNYYAPAKVFKFLIDSSGAIALLVYLVIAVSQLRMRKILRAEGSEIRLRM
WLYPWLTWLVIGFITFVLVVMLFRPAQQLEVISTGLLAIGIICTVPIMAR
WKKLVLWQKTPVHNTR

TABLE 49

Codon optimized polynucleotide sequence of GabP transporter (SEQ ID NO: 106)

ATGGGACAGTCTTCACAACCACACGAACTTGGGGGTGGATTGAAATCGCG
CCATGTGACCATGTTAAGTATCGCAGGCGTGATTGGCGCCTCCTTATTTG
TGGGGTCCTCCGTGGCGATTGCAGAGGCGGGTCCGGCTGTACTTTTGGCA
TATCTTTTTGCGGGTTTACTGGTTGTGATGATCATGCGCATGCTTGCCGA
AATGGCTGTGGCCACGCCGGACACGGGGTCATTTTCCACTTATGCGGACA
AGGCGATTGGCCGCTGGGCCGGGTACACAATCGGGTGGCTGTATTGGTGG
TTCTGGGTGTTAGTTATCCCCTTGGAGGCCAACATCGCCGCAATGATTCT
GCACTCCTGGGTTCCGGGTATCCCGATCTGGCTGTTCAGCTTGGTGATCA
CCCTGGCACTGACGGGCAGCAACTTATTGAGTGTGAAAAACTATGGAGAG
TTTGAATTTTGGCTGGCCCTGTGTAAAGTCATTGCTATCTTGGCATTCAT
TTTTTTAGGAGCGGTAGCAATCAGTGGCTTCTACCCTTATGCAGAAGTTT
CGGGGATTTCCCGTCTTTGGGATAGTGGCGGATTCATGCCAAACGGGTTT
GGAGCTGTACTGTCAGCCATGTTGATTACCATGTTTAGCTTTATGGGTGC
CGAGATCGTGACAATCGCCGCAGCCGAGAGTGATACCCCGGAAAAGCACA
TTGTTCGTGCGACGAATTCGGTAATTTGGCGTATTTCGATTTTTTACTTA
TGCTCCATTTTCGTTGTGGTCGCCCTTATCCCCTGGAACATGCCAGGCTT
AAAAGCAGTAGGCAGCTACCGCTCAGTCCTGGAATTACTGAACATTCCTC
ACGCGAAGTTAATTATGGATTGCGTAATCCTGTTATCGGTAACGAGCTGC
CTTAACAGTGCTCTGTACACGGCTTCACGTATGCTGTACTCTTTAAGTCG
CCGTGGCGATGCACCTGCCGTTATGGGCAAGATTAACCGCAGTAAGACGC
CGTATGTAGCTGTTTTGCTGTCGACTGGAGCTGCGTTTCTTACAGTCGTA
GTAAACTATTACGCACCAGCTAAAGTTTTCAAATTCCTTATTGATTCGTC
TGGGGCAATCGCACTTCTGGTGTACCTGGTCATCGCGGTGTCACAACTTC
GCATGCGCAAGATCTTGCGTGCGGAGGCAGTGAGATTCGTTTGCGTATG
TGGCTGTATCCGTGGCTGACGTGGCTTGTTATTGGTTTCATTACTTTTGT
GTTGGTAGTGATGCTGTTTCGTCCAGCGCAACAGCTGGAGGTGATTTCTA
CCGGACTGTTGGCAATCGGCATCATCTGTACCGTCCCAATCATGGCTCGC
TGGAAAAAGTTGGTCTTATGGCAGAAGACCCCTGTACACAACACCCGT

In some embodiments, the genetically engineered bacteria comprise the nucleic acid sequence of SEQ ID NO: 106 or a functional fragment thereof. In some embodiments, the genetically engineered bacteria comprise a nucleic acid sequence that, but for the redundancy of the genetic code, encodes the same polypeptide as SEQ ID NO: 106 or a functional fragment thereof. In some embodiments, genetically engineered bacteria comprise a nucleic acid sequence that is at least about 80%, at least about 85%, at least about 90%, at least about 95%, or at least about 99% homologous to the DNA sequence of SEQ ID NO: 106 or a functional fragment thereof, or a nucleic acid sequence that, but for the redundancy of the genetic code, encodes the same polypeptide as SEQ ID NO: 106 or a functional fragment thereof.

Example 52

Manganese Transport Circuit

In addition to the circuits described above, the *E. coli* Nissle bacteria further comprise one or more manganese transport circuits. Genetically engineered strains comprising at least one manganese transport circuit comprise a gene encoding an exemplary manganese transport protein, such as MntH (SEQ ID NO: 107, Table 50, SEQ ID NO: 108, Table 51), and are constructed using methods described above.

The gene encoding MntH is expressed under the control of a tetracycline-inducible promoter, a FNR promoter selected from SEQ ID NOs: 18-29, or a promoter induced by HE-related molecules or metabolites. As discussed herein, other promoters may be used. The gene encoding MntH is expressed on a high-copy plasmid, a low-copy plasmid, or a chromosome. The gene encoding MntH is inserted into the bacterial genome at one or more of the following insertion sites in *E. coli* Nissle: malE/K, araC/BAD, lacZ, thyA, malP/T. Any suitable insertion site may be used, see, e.g., FIG. 18.

TABLE 50

Amino acid sequence of MntH transporter
(SEQ ID NO: 107)

MTNYRVESSSGRAARKMRLALMGPAFIAAIGYIDPGNFATNIQAGASFGY
QLLWVVVWANLMAMLIQILSAKLGIATGKNLAEQIRDHYPRPVVWFYWVQ
AEIIAMATDLAEFIGAAIGFKLILGVSLLQGAVLTGIATFLILMLQRRGQ
KPLEKVIGGLLLFVAAAYIVELIFSQPNLAQLGKGMVIPSLPTSEAVFLA
AGVLGATIMPHVIYLHSSLTQHLHGGSRQQRYSATKWDVAIAMTIAGFVN
LAMMATAAAAFHFSGHTGVADLDEAYLTLQPLLSHAAATVFGLSLVAAGL
SSTVVGTLAGQVVMQGFIRFHIPLWVRRTVTMLPSFIVILMGLDPTRILV
MSQVLLSFGIALALVPLLIFTSDSKLMGDLVNSKRVKQTGWVIVVLVVAL
NIWLLVGTALGL

TABLE 51

Polynucleotide sequence of MntH transporter
(SEQ ID NO: 108)

ATGACCAATTATCGTGTTGAAAGTAGTAGTGGCCGCGCGGCTCGTAAAAT
GCGTCTGGCCTTAATGGGCCCGGCGTTTATTGCTGCGATTGGATACATTG
ATCCGGGCAATTTCGCTACAAACATCCAAGCAGGTGCATCCTTCGGTTAC
CAGCTTCTGTGGGTAGTGGTATGGGCTAACCTGATGGCCATGCTTATTCA
AATTCTTTCAGCTAAGCTTGGTATTGCCACAGGAAAGAATTTAGCCGAGC
AGATTCGTGACCACTATCCCCGCCCCGTGGTCTGGTTCTATTGGGTCCAG
GCAGAGATTATCGCGATGGCGACTGATTTAGCCGAATTTATTGGGGCAGC
TATTGGATTTAAGCTGATCCTTGGCGTATCTCTGTTGCAAGGCGCGGTAT
TGACCGGAATTGCAACCTTTTTGATTCTTATGTTGCAACGTCGTGGGCAG
AAGCCTCTGGAAAAAGTCATCGGCGGGTTATTGCTTTTTGTTGCCGCGGC

TABLE 51-continued

Polynucleotide sequence of MntH transporter
(SEQ ID NO: 108)

CTACATTGTGGAACTGATCTTTTCTCAACCTAACCTGGCGCAGCTTGGTA
AAGGCATGGTAATCCCGTCACTTCCTACATCTGAGGCAGTATTCTTAGCA
GCCGGCGTCTTGGGCGCAACTATCATGCCCCATGTCATCTACTTACACAG
TTCTCTGACTCAGCACTTACACGGTGGGTCGCGCCAACAGCGTTACTCCG
CAACAAAGTGGGACGTTGCAATTGCCATGACCATTGCCGGTTTTGTTAAC
CTGGCGATGATGGCCACGGCTGCTGCCGCCTTTCATTTCAGTGGCCACAC
TGGTGTAGCCGATCTGGATGAGGCATACCTGACCTTGCAGCCTCTGTTGT
CTCATGCAGCCGCCACCGTTTTTGGTTTAAGCTTAGTAGCCGCCGGCTTG
AGTAGCACGGTGGTAGGCACATTGGCTGGACAGGTCGTGATGCAAGGTTT
CATTCGTTTCCATATTCCGTTATGGGTACGTCGCACGGTAACGATGCTGC
CGTCATTTATCGTCATCCTGATGGGATTAGACCCGACGCGCATCCTGGTA
ATGTCGCAAGTTTTACTGAGCTTTGGAATCGCGTTGGCCCTGGTGCCATT
ACTTATCTTCACTAGCGATAGTAAGTTGATGGGTGATCTTGTCAATAGCA
AACGTGTGAAGCAAACAGGCTGGGTCATTGTGGTACTGGTTGTGGCCTTA
AACATTTGGTTGTTAGTGGGCACGGCCCTTGGCTTG

Example 53

Circuit Comprising TesB

The nucleic acid sequence of TesB is translated as follows.

TABLE 52

TesB sequences

| tesB<br>SEQ ID NO:<br>48 | ATGAGTCAGGCGCTAAAAAATTTACTGACATTGTTAAATCTGGAAAAAAT<br>TGAGGAAGGACTCTTTCGCGGCCAGAGTGAAGATTTAGGTTTACGCCAGG<br>TGTTTGGCGGCCAGGTCGTGGGTCAGGCCTTGTATGCTGCAAAAGAGACC<br>GTCCCTGAAGAGCGGCTGGTACATTCGTTTCACAGCTACTTTCTTCGCCC<br>TGGCGATAGTAAGAAGCCGATTATTTATGATGTCGAAACGCTGCGTGACG<br>GTAACAGCTTCAGCGCCCGCCGGGTTGCTGCTATTCAAAACGGCAAACCG<br>ATTTTTTATATGACTGCCTCTTTCCAGGCACCAGAAGCGGGTTTCGAACA<br>TCAAAAAACAATGCCGTCCGCGCCAGCGCCTGATGGCCTCCCTTCGGAAA<br>CGCAAATCGCCCAATCGCTGGCGCACCTGCTGCCGCCAGTGCTGAAAGAT<br>AAATTCATCTGCGATCGTCCGCTGGAAGTCCGTCCGGTGGAGTTTCATAA<br>CCCACTGAAAGGTCACGTCGCAGAACCACATCGTCAGGTGTGGATCCGCG<br>CAAATGGTAGCGTGCCGGATGACCTGCGCGTTCATCAGTATCTGCTCGGT<br>TACGCTTCTGATCTTAACTTCCTGCCGGTAGCTCTACAGCCGCACGGCAT<br>CGGTTTTCTCGAACCGGGGATTCAGATTGCCACCATTGACCATTCCATGT<br>GGTTCCATCGCCCGTTTAATTTGAATGAATGGCTGCTGTATAGCGTGGAG<br>AGCACCTCGGCGTCCAGCGCACGTGGCTTTGTGCGCGGTGAGTTTTATAC<br>CCAAGACGGCGTACTGGTTGCCTCGACCGTTCAGGAAGGGGTGATGCGTA<br>ATCACAATTAA |
|---|---|
| tesB: SEQ<br>ID NO: 109 | MSQALKNLLTLLNLEKIEEGLFRGQSEDLGLRQVFGGQVVGQALYAAKET<br>VPEERLVHSFHSYFLRPGDSKKPIIYDVETLRDGNSFSARRVAAIQNGKP<br>IFYMTASFQAPEAGFEHQKTMPSAPAPDGLPSETQIAQSLAHLLPPVLKD<br>KFICDRPLEVRPVEFHNPLKGHVAEPHRQVWIRANGSVPDDLRVHQYLLG<br>YASDLNFLPVALQPHGIGFLEPGIQIATIDHSMWFHRPFNLNEWLLYSVE<br>STSASSARGFVRGEFYTQDGVLVASTVQEGVMRNHN |

In some embodiments, the genetically engineered bacteria comprise the amino acid sequence of SEQ ID NO: 109 or a functional fragment thereof. In some embodiments, genetically engineered bacteria comprise an amino acid sequence that is at least about 80%, at least about 85%, at least about 90%, at least about 95%, or at least about 99% homologous to the amino acid sequence of SEQ ID NO: 109 or a functional fragment thereof, or a nucleic acid sequence that, but for the redundancy of the genetic code, encodes the same polypeptide as SEQ ID NO: 109 or a functional fragment thereof.

In some embodiments, the genetically engineered bacteria comprise the amino acid sequence of SEQ ID NO: 91 or a functional fragment thereof. In some embodiments, genetically engineered bacteria comprise an amino acid sequence that is at least about 80%, at least about 85%, at least about 90%, at least about 95%, or at least about 99% homologous to the amino acid sequence of SEQ ID NO: 91 or a functional fragment thereof, or a nucleic acid sequence that, but for the redundancy of the genetic code, encodes the same polypeptide as SEQ ID NO: 91 or a functional fragment thereof.

In some embodiments, the genetically engineered bacteria comprise the amino acid sequence of SEQ ID NO: 93 or a functional fragment thereof. In some embodiments, genetically engineered bacteria comprise an amino acid sequence that is at least about 80%, at least about 85%, at least about 90%, at least about 95%, or at least about 99% homologous to the amino acid sequence of SEQ ID NO: 93 or a functional fragment thereof, or a nucleic acid sequence that, but for the redundancy of the genetic code, encodes the same polypeptide as SEQ ID NO: 93 or a functional fragment thereof.

In some embodiments, the genetically engineered bacteria comprise the amino acid sequence of SEQ ID NO: 95 or a functional fragment thereof. In some embodiments, genetically engineered bacteria comprise an amino acid sequence that is at least about 80%, at least about 85%, at least about 90%, at least about 95%, or at least about 99% homologous to the amino acid sequence of SEQ ID NO: 95 or a functional fragment thereof, or a nucleic acid sequence that, but for the redundancy of the genetic code, encodes the same polypeptide as SEQ ID NO: 95 or a functional fragment thereof.

In some embodiments, the genetically engineered bacteria comprise the amino acid sequence of SEQ ID NO: 97 or a functional fragment thereof. In some embodiments, genetically engineered bacteria comprise an amino acid sequence that is at least about 80%, at least about 85%, at least about 90%, at least about 95%, or at least about 99% homologous to the amino acid sequence of SEQ ID NO: 97 or a functional fragment thereof, or a nucleic acid sequence that, but for the redundancy of the genetic code, encodes the same polypeptide as SEQ ID NO: 97 or a functional fragment thereof.

In some embodiments, the genetically engineered bacteria comprise the amino acid sequence of SEQ ID NO: 99 or a functional fragment thereof. In some embodiments, genetically engineered bacteria comprise an amino acid sequence that is at least about 80%, at least about 85%, at least about 90%, at least about 95%, or at least about 99% homologous to the amino acid sequence of SEQ ID NO: 99 or a functional fragment thereof, or a nucleic acid sequence that, but for the redundancy of the genetic code, encodes the same polypeptide as SEQ ID NO: 99 or a functional fragment thereof.

TABLE 53

FNRS-fbrArgA and no antibiotic resistance

| Description | Sequence | SEQ ID |
|---|---|---|
| Terminator sequence | CAAATAAAATGAAAGGCTCAGTCGAAAGACTGGGCC TTTCGTTTTATCTGTTGTTTGTCGGTGAACGCTCTC CTGAGTAGGACAAAT | SEQ ID NO: 110 |
| Terminator | AGAAGGCCATCCTGACGGATGGCCTTTT | SEQ ID NO: 111 |
| FRT site | GAAGTTCCTA*TACTTTCTAGAGAATAGGAACTTCGG AATAGGAACTA* | SEQ ID NO: 112 |
| FNRS promoter | GTACCAGTTGTTCTTATTGGTGGTGTTGCTTTATGG TTGCATCGTAGTAAATGGTTGTAACAAAAGCAATTT TTCCGGCTGTCTGTATACAAAAACGCCGTAAAGTTT GAGCGAAGTCAATAAACTCTCTACCCATTCAGGGCA ATATCTCTCTTGGATCC | SEQ ID NO: 113 |
| ArgAfbr | ATGGTAAAGGAACGTAAAACCGAGTTGGTCGAGGGA TTCCGCCATTCGGTTCCCTGTATCAATACCCACCGG GGAAAAACGTTTGTCATCATGCTCGGCGGTGAAGCC ATTGAGCATGAGAATTTCTCCAGTATCGTTAATGAT ATCGGGTTGTTGCACAGCCTCGGCATCCGTCTGGTG GTGGTCTATGGCGCACGTCCGCAGATCGACGCAAAT CTGGCTGCGCATCACCACGAACCGCTGTATCACAAG AATATACGTGTGACCGACGCCAAAACACTGGAACTG GTGAAGCAGGCTGCGGGAACATTGCAACTGGATATT ACTGCTCGCCTGTCGATGAGTCTCAATAACACGCCG CTGCAGGGCGCGCATATCAACGTCGTCAGTGGCAAT TTTATTATTGCCCAGCCGCTGGGCGTCGATGACGGC GTGGATTACTGCCATAGCGGGCGTATCCGGCGGATT GATGAAGACGCGATCCATCGTCAACTGGACAGCGGT GCAATAGTGCTAATGGGGCCGGTCGCTGTTTCAGTC ACTGGCGAGAGCTTTAACCTGACCTCGGAAGAGATT GCCACTCAACTGGCCATCAAACTGAAAGCTGAAAAG ATGATTGGTTTTTGCTCTTCCCAGGGCGTCACTAAT GACGACGGTGATATTGTCTCCGAACTTTTCCCTAAC GAAGCGCAAGCGCGGGTAGAAGCCCAGGAAGAGAAA GGCGATTACAACTCCGGTACGGTGCGCTTTTTGCGT GGCGCAGTGAAAGCCTGCCGCAGCGGCGTGCGTCGC TGTCATTTAATCAGTTATCAGGAAGATGGCGCGCTG TTGCAAGAGTTGTTCTCACGCGACGGTATCGGTACG CAGATTGTGATGGAAAGCGCCGAGCAGATTCGTCGC GCAACAATCAACGATATTGGCGGTATTCTGGAGTTG ATTCGCCCACTGGAGCAGCAAGGTATTCTGGTACGC |

TABLE 53-continued

FNRS-fbrArgA and no antibiotic resistance

| Description | Sequence | SEQ ID |
|---|---|---|
| | CGTTCTCGCGAGCAGCTGGAGATGGAAATCGACAAA<br>TTCACCATTATTCAGCGCGATAACACGACTATTGCC<br>TGCGCCGCGCTCTATCCGTTCCCGGAAGAGAAGATT<br>GGGGAAATGGCCTGTGTGGCAGTTCACCCGGATTAC<br>CGCAGTTCATCAAGGGGTGAAGTTCTGCTGGAACGC<br>ATTGCCGCTCAGGCTAAGCAGAGCGGCTTAAGCAAA<br>TTGTTTGTGCTGACCACGCGCAGTATTCACTGGTTC<br>CAGGAACGTGGATTTACCCCAGTGGATATTGATTTA<br>CTGCCCGAGAGCAAAAAGCAGTTGTACAACTACCAG<br>CGTAAATCCAAAGTGTTGATGGCGGATTTAGGGTAA<br><br>*GAAGTTCCTATACTTTCTAGAGAATAGGAACTTCGG*<br>*AATAGGAACTTC* | SEQ ID<br>NO: 115 |
| KanR gene | atgattgaacaagatggattgcacgcaggttctccg<br>gccgcttgggtggagaggctattcggctatgactgg<br>gcacaacagacaatcggctgctctgatgccgccgtg<br>ttccggctgtcagcgcaggggcgcccggttctttt<br>gtcaagaccgacctgtccggtgccctgaatgaactg<br>caggacgaggcagcgcggctatcgtggctggccacg<br>acgggcgttccttgcgcagctgtgctcgacgttgtc<br>actgaagcgggaagggactggctgctattgggcgaa<br>gtgccggggcaggatctcctgtcatctcaccttgct<br>cctgccgagaaagtatccatcatggctgatgcaatg<br>cggcggctgcatacgcttgatccggctacctgccca<br>ttcgaccaccaagcgaaacatcgcatcgagcgagca<br>cgtactcggatggaagccggtcttgtcgatcaggat<br>gatctggacgaagagcatcaggggctcgcgccagcc<br>gaactgttcgccaggctcaaggcgcgcatgcccgac<br>ggcgaggatctcgtcgtgacccatggcgatgcctgc<br>ttgccgaatatcatggtggaaaatggccgcttttct<br>ggattcatcgactgtggccggctgggtgtggcggac<br>cgctatcaggacatagcgttggctacccgtgatatt<br>gctgaagagcttggcggcgaatgggctgaccgcttc<br>ctcgtgctttacggtatcgccgctcccgattcgcag<br>cgcatcgccttctatcgccttcttgacgagttcttc<br>tgagcgggactctggggttcgaaatgaccgaccaag<br>cgacgcccaacctgccatcacgagatttcgattcca<br>ccgccgccttctatgaaaggttgggcttcggaatcg<br>ttttccgggacgccggctggatgatcctccagcgcg<br>gggatctcatgctggagttcttcgcccaccccagct<br>tcaaaagcgctct | SEQ ID NO: 116 |
| KanR<br>promoter | ggttgggaagccctgcaaagtaaactggatggcttt<br>cttgccgccaaggatctgatggcgcaggggatcaag<br>atctgatcaagagacaggatgaggatcgtttcgc | SEQ ID NO: 117 |
| CamR gene | TCATCGCAGTACTGTTGTATTCATTAAGCATCTGCC<br>GACATGGAAGCCATCACAAACGGCATGATGAACCTG<br>AATCGCCAGCGGCATCAGCACCTTGTCGCCTTGCGT<br>ATAATATTTGCCCATGGTGAAAACGGGGGCGAAGAA<br>GTTGTCCATATTGGCCACGTTTAAATCAAAACTGGT<br>GAAACTCACCCAGGGATTGGCTGAGACGAAAAACAT<br>ATTCTCAATAAACCCTTTAGGGAAATAGGCCAGGTT<br>TTCACCGTAACACGCCACATCTTGCGAATATATGTG<br>TAGAAACTGCCGGAAATCGTCGTGGTATTCACTCCA<br>GAGCGATGAAAACGTTTCAGTTTGCTCATGGAAAAC<br>GGTGTAACAAGGGTGAACACTATCCCATATCACCAG<br>CTCACCGTCTTTCATTGCCATACGTAATTCCGGATG<br>AGCATTCATCAGGCGGGCAAGAATGTGAATAAAGGC<br>CGGATAAAACTTGTGCTTATTTTTCTTTACGGTCTT<br>TAAAAAGGCCGTAATATCCAGCTGAACGGTCTGGTT<br>ATAGGTACATTGAGCAACTGACTGAAATGCCTCAAA<br>ATGTTCTTTACGATGCCATTGGGATATATCAACGGT<br>GGTATATCCAGTGATTTTTTCTCCAT | SEQ ID NO: 118 |
| CamR<br>promoter | *TTTAGCTTCCTTAGCTCCTGAAAATCTCGACAACTC*<br>*AAAAAATACGCCCGGTAGTGATCTTATTTCATTATG*<br>*GTGAAAGTTGGAACCTCTTACGTGCCGATCAACGTC*<br>TCATTTTCGCCAAAAGTTGGCCCAGGGCTTCCCGGT<br>ATCAACAGGGACACCAGGATTTATTTATTCTGCGAA<br>GTGATCTTCCGTCACAGGTAGGCGCGCC*G* | SEQ ID NO: 119 |

In some embodiments, the genetically engineered bacteria comprise the amino acid sequence of SEQ ID NO: 101 or a functional fragment thereof. In some embodiments, genetically engineered bacteria comprise an amino acid sequence that is at least about 80%, at least about 85%, at least about 90%, at least about 95%, or at least about 99% homologous to the amino acid sequence of SEQ ID NO: 101 or a functional fragment thereof, or a nucleic acid sequence that, but for the redundancy of the genetic code, encodes the same polypeptide as SEQ ID NO: 101 or a functional fragment thereof.

The invention claimed is:

1. A bacterium comprising a gene sequence encoding an arginine feedback resistant N-acetylglutamate synthetase (ArgA$^{fbr}$), wherein the ArgA$^{fbr}$ has reduced arginine feedback inhibition as compared to a wild-type N-acetylglutamate synthetase from the same bacterial subtype under the same conditions,
    wherein the gene sequence encoding the ArgA$^{fbr}$ is present in the bacterial chromosome and is operably linked in the chromosome to a promoter that is induced by low-oxygen or anaerobic conditions;
    wherein the bacterium has been modified to lack a functional ArgR; and
    wherein the bacterium is an auxotroph in a gene that is complemented when the bacterium is present in a mammalian gut.

2. The bacterium of claim 1, wherein the bacterium is a thyA or dapB auxotroph.

3. The bacterium of claim 1, wherein the bacterium comprises an antibiotic resistance gene.

4. The bacterium of claim 3, wherein the antibiotic resistance gene is selected from a kanamycin resistance gene, a chloramphenicol resistance gene, and a rifaximin resistance gene.

5. The bacterium of claim 1, wherein the bacterium contains a DNA sequence having at least 90% homology to SEQ ID NO: 38.

6. The bacterium of claim 5, wherein the bacterium contains a DNA sequence comprising SEQ ID NO: 38.

7. The bacterium of claim 1, wherein the promoter that is induced by low-oxygen or anaerobic conditions is an FNR promoter selected from nirB1, nirB2, nirB3, ydfZ, fnrS1, and fnrS2.

8. The bacterium of claim 7, wherein the FNR promoter is fnrS1.

9. The bacterium of claim 8, wherein the fnrS1 promoter comprises SEQ ID NO: 113.

10. The bacterium of claim 1, wherein the arginine feedback resistant N-acetylglutamate synthetase gene has a DNA sequence selected from:
    a) SEQ ID NO: 30,
    b) a DNA sequence that, but for the redundancy of the genetic code, encodes the same polypeptide as encoded by SEQ ID NO: 30,
    c) a DNA sequence that encodes the polypeptide of SEQ ID NO: 31, and
    d) a DNA sequence that encodes a polypeptide having 95% homology with the polypeptide of SEQ ID NO: 31.

11. The bacterium of claim 1, wherein the bacterium is *Escherichia coil* strain Nissle.

12. A pharmaceutical composition comprising the bacterium of claim 1 and a pharmaceutically acceptable carrier.

13. The pharmaceutical composition of claim 12, wherein the pharmaceutical composition is formulated for oral administration.

14. The bacterium of claim 1, wherein the bacterium comprises a gene sequence encoding a biosynthetic pathway for producing butyrate.

15. The bacterium of claim 14, wherein the gene sequence encoding the biosynthetic pathway for producing butyrate is operably linked to a promoter that is induced by low-oxygen or anaerobic conditions.

16. The bacterium of claim 15, wherein the promoter that is operably linked to the gene sequence encoding ArgA$^{fbr}$ and the promoter that is operably linked to the gene sequence encoding the biosynthetic pathway for producing butyrate is an FNR promoter.

17. A bacterium comprising a gene sequence encoding an arginine feedback resistant N-acetylglutamate synthetase (ArgA$^{fbr}$), wherein the ArgA$^{fbr}$ has reduced arginine feedback inhibition as compared to a wild-type N-acetylglutamate synthetase from the same bacterial subtype under the same conditions,
wherein the gene sequence encoding the ArgA$^{fbr}$ is operably linked to a promoter that is induced by low-oxygen or anaerobic conditions;
wherein the bacterium has been modified to lack a functional ArgR; and
wherein the bacterium comprises a gene sequence encoding a biosynthetic pathway for producing butyrate.

18. The bacterium of claim 17, wherein the bacterium is an auxotroph in a gene that is complemented when the bacterium is present in a mammalian gut.

19. The bacterium of claim 18, wherein the gene sequence encoding the biosynthetic pathway for producing butyrate is operably linked to a promoter that is induced by low-oxygen or anaerobic conditions.

20. The bacterium of claim 17, wherein the bacterium is selected from the group consisting of *Bacteroides, Bifidobacterium, Clostridium, Escherichia, Lactobacillus*, and *Lactococcus*.

* * * * *

```
                              SEQUENCE LISTING

<160> NUMBER OF SEQ ID NOS: 125

<210> SEQ ID NO 1
<211> LENGTH: 60
<212> TYPE: DNA
<213> ORGANISM: Escherichia coli

<400> SEQUENCE: 1
gcaaaaaaac agaataaaaa tacaataatt tcgaataatc atgcaaagag gtgtaccgtg      60

<210> SEQ ID NO 2
<211> LENGTH: 60
<212> TYPE: DNA
<213> ORGANISM: Escherichia coli

<400> SEQUENCE: 2
gcaaaaaaac actttaaaaa cttaataatt tcctttaatc acttaaagag gtgtaccgtg      60

<210> SEQ ID NO 3
<211> LENGTH: 76
<212> TYPE: DNA
<213> ORGANISM: Escherichia coli

<400> SEQUENCE: 3
agacttgcaa atgaataatc atccatatag attgaattt aattcattaa ggcgttagcc       60
acaggaggga tctatg                                                     76

<210> SEQ ID NO 4
<211> LENGTH: 76
<212> TYPE: DNA
<213> ORGANISM: Escherichia coli

<400> SEQUENCE: 4
agacttgcaa acttatactt atccatatag attttgtttt aatttgttaa ggcgttagcc      60
acaggaggga tctatg                                                     76

<210> SEQ ID NO 5
<211> LENGTH: 160
<212> TYPE: DNA
<213> ORGANISM: Escherichia coli

<400> SEQUENCE: 5
tcattgttga cacacctctg gtcatgatag tatcaatatt catgcagtat ttatgaataa      60
aaatacacta acgttgagcg taataaaacc caccagccgt aaggtgaatg ttttacgttt     120
aacctggcaa ccagacataa gaaggtgaat agccccgatg                           160

<210> SEQ ID NO 6
<211> LENGTH: 160
<212> TYPE: DNA
<213> ORGANISM: Escherichia coli

<400> SEQUENCE: 6
tcattgttga cacacctctg gtcatgatag tatcaaactt catgggatat ttatctttaa      60
aaatacttga acgttgagcg taataaaacc caccagccgt aaggtgaatg ttttacgttt     120
```

```
aacctggcaa ccagacataa gaaggtgaat agccccgatg                                  160

<210> SEQ ID NO 7
<211> LENGTH: 160
<212> TYPE: DNA
<213> ORGANISM: Escherichia coli

<400> SEQUENCE: 7
catcggggct attcaccttc ttatgtctgg ttgccaggtt aaacgtaaaa cattcacctt            60
acggctggtg ggttttatta cgctcaacgt tagtgtattt ttattcataa atactgcatg           120
aatattgata ctatcatgac cagaggtgtg tcaacaatga                                 160

<210> SEQ ID NO 8
<211> LENGTH: 160
<212> TYPE: DNA
<213> ORGANISM: Escherichia coli

<400> SEQUENCE: 8
catcggggct attcaccttc ttatgtctgg ttgccaggtt aaacgtaaaa cattcacctt            60
acggctggtg ggttttatta cgctcaacgt tcaagtattt ttaaagataa atatcccatg           120
aagtttgata ctatcatgac cagaggtgtg tcaacaatga                                 160

<210> SEQ ID NO 9
<211> LENGTH: 81
<212> TYPE: DNA
<213> ORGANISM: Escherichia coli

<400> SEQUENCE: 9
agcagatttg cattgattta cgtcatcatt gtgaattaat atgcaaataa agtgagtgaa            60
tattctctgg agggtgtttt g                                                     81

<210> SEQ ID NO 10
<211> LENGTH: 81
<212> TYPE: DNA
<213> ORGANISM: Escherichia coli

<400> SEQUENCE: 10
agcagatttg cattgattta cgtcatcatt gtcttttaat atcttaataa ctggagtgac            60
gtttctctgg agggtgtttt g                                                     81

<210> SEQ ID NO 11
<211> LENGTH: 88
<212> TYPE: DNA
<213> ORGANISM: Escherichia coli

<400> SEQUENCE: 11
tttctgattg ccattcagtg atttttttatg catattttgt gattataatt tcatatttat          60
ttatgcgtaa cagggtgatc atgagatg                                              88

<210> SEQ ID NO 12
<211> LENGTH: 88
<212> TYPE: DNA
<213> ORGANISM: Escherichia coli

<400> SEQUENCE: 12
tttctgattg ccattcagtc tttttttact tatattttgt ctttataatc ttatatttat           60
ttatgcgtaa cagggtgatc atgagatg                                              88
```

<210> SEQ ID NO 13
<211> LENGTH: 219
<212> TYPE: DNA
<213> ORGANISM: Escherichia coli

<400> SEQUENCE: 13

| | | | | | |
|---|---|---|---|---|---|
| ctaatcacgt | gaatgaatat | ccagttcact | ttcatttgtt | gaatactttt | accttctcct | 60 |
| gctttccctt | aagcgcatta | ttttacaaaa | aacacactaa | actcttcctg | tctccgataa | 120 |
| aagatgatta | aatgaaaact | catttatttt | gcataaaaat | tcagtgaaag | cagaaatcca | 180 |
| ggctcatcat | cagttaatta | agcagggtgt | tattttatg | | | 219 |

<210> SEQ ID NO 14
<211> LENGTH: 219
<212> TYPE: DNA
<213> ORGANISM: Escherichia coli

<400> SEQUENCE: 14

| | | | | | |
|---|---|---|---|---|---|
| ctaatcacct | taatgaatct | tcagttcact | ttcatttgtt | gaatactttt | accttctcct | 60 |
| gctttccctt | aagcgcatta | ttttacaaaa | aacacactaa | actcttcctg | tctccgataa | 120 |
| aagatgatct | tatgaaaacc | ttttattc | ttataaaaat | cttgtgaaag | cagaaatcca | 180 |
| ggctcatcat | cagttaatta | agcagggtgt | tattttatg | | | 219 |

<210> SEQ ID NO 15
<211> LENGTH: 233
<212> TYPE: DNA
<213> ORGANISM: Escherichia coli

<400> SEQUENCE: 15

| | | | | | |
|---|---|---|---|---|---|
| cctgaaacgt | ggcaaattct | actcgttttg | ggtaaaaaat | gcaaatactg | ctgggatttg | 60 |
| gtgtaccgag | acgggacgta | aaatctgcag | gcattatagt | gatccacgcc | acattttgtc | 120 |
| aacgttatt | gctaatcatt | gacggctagc | tcagtcctag | gtacagtgct | agcacccgtt | 180 |
| tttttgggct | agaaataatt | ttgtttaact | ttaagaagga | gatatacata | ccc | 233 |

<210> SEQ ID NO 16
<211> LENGTH: 1053
<212> TYPE: DNA
<213> ORGANISM: Escherichia coli

<400> SEQUENCE: 16

| | | | | | |
|---|---|---|---|---|---|
| gtgatccacg | ccacattttg | tcaacgttta | ttgctaatca | cgtgaatgaa | tatccagttc | 60 |
| actttcattt | gttgaatact | tttaccttct | cctgctttcc | cttaagcgca | ttattttaca | 120 |
| aaaacacac | taactcttc | ctgtctccga | taaagatga | ttaaatgaaa | actcatttat | 180 |
| tttgcataaa | aattcagtga | aagcagaaat | ccaggctcat | catcagttaa | ttaagcaggg | 240 |
| tgttattta | tgacgacgat | tctcaagcat | ctcccggtag | gtcaacgtat | tggtatcgct | 300 |
| ttttccggcg | gtctggacac | cagtgccgca | ctgctgtgga | tgcgacaaaa | gggagcggtt | 360 |
| ccttatgcat | atactgcaaa | cctgggccag | ccagacgaag | aggattatga | tgcgatccct | 420 |
| cgtcgtgcca | tggaatacgg | cgcggagaac | gcacgtctga | tcgactgccg | caaacaactg | 480 |
| gtggccgaag | gtattgccgc | tattcagtgt | ggcgcatttc | ataacaccac | tggtggactg | 540 |
| acctatttca | acacgacgcc | gctgggccgc | gccgtgaccg | gcaccatgct | ggttgctgct | 600 |
| atgaaagaag | atggcgtgaa | tatctggggt | gacggcagca | cctataaagg | aaacgatatc | 660 |
| gaacgttct | accgttacgg | tctgctgacc | aatgctgaac | tgcagattta | caaaccgtgg | 720 |

```
cttgatactg actttattga tgaactgggt ggccgtcatg agatgtctga atttatgatt    780
gcctgcggtt tcgactacaa aatgtctgtc gaaaaagctt actccacgga ctccaacatg    840
cttggtgcaa cgcatgaagc gaaggatctg gaatacctca actccagcgt caaaatcgtc    900
aacccaatta tgggcgtgaa gttttgggat gagagcgtga aaatcccggc agaagaagtc    960
acagtacgct ttgagcaagg tcatccggtg gcgctgaacg gtaaaaccttt agcgacgac   1020
gtagaaatga tgctggaagc taaccgcatc ggc                                1053
```

<210> SEQ ID NO 17
<211> LENGTH: 734
<212> TYPE: DNA
<213> ORGANISM: Escherichia coli

<400> SEQUENCE: 17

```
ttgacggcta gctcagtcct aggtacagtg ctagcacccg ttttttttggg ctagaaataa    60
ttttgtttaa ctttaagaag gagatataca tacccatgac gacgattctc aagcatctcc   120
cggtaggtca acgtattggt atcgcttttt ccggcggtct ggacaccagt gccgcactgc   180
tgtggatgcg acaaaaggga gcggttcctt atgcatatac tgcaaacctg gccagccag   240
acgaagagga ttatgatgcg atccctcgtc gtgccatgga atacggcgcg gagaacgcac   300
gtctgatcga ctgccgcaaa caactggtgg ccgaaggtat tgccgctatt cagtgtggcg   360
catttcataa caccactggt ggactgacct atttcaacac gacgccgctg ggccgcgccg   420
tgaccggcac catgctggtt gctgctatga agaagatgg cgtgaatatc tggggtgacg   480
gcagcaccta taaggaaac gatatcgaac gtttctaccg ttacggtctg ctgaccaatg   540
ctgaactgca gatttacaaa ccgtggcttg tatactgactt tattgatgaa ctgggtggcc   600
gtcatgagat gtctgaattt atgattgcct gcggtttcga ctacaaaatg tctgtcgaaa   660
aagcttactc cacggactcc aacatgcttg gtgcaacgca tgaagcgaag gatctggaat   720
acctcaactc cagc                                                     734
```

<210> SEQ ID NO 18
<211> LENGTH: 117
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 18

```
atccccatca ctcttgatgg agatcaattc cccaagctgc tagagcgtta ccttgcccttt    60
aaacattagc aatgtcgatt tatcagaggg ccgacaggct cccacaggag aaaaccg       117
```

<210> SEQ ID NO 19
<211> LENGTH: 108
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 19

```
ctcttgatcg ttatcaattc ccacgctgtt tcagagcgtt accttgcccct taaacattag    60
caatgtcgat ttatcagagg gccgacaggc tcccacagga gaaaaccg                 108
```

<210> SEQ ID NO 20

```
<211> LENGTH: 290
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 20
gtcagcataa caccctgacc tctcattaat tgttcatgcc gggcggcact atcgtcgtcc    60
ggccttttcc tctcttactc tgctacgtac atctatttct ataaatccgt tcaatttgtc   120
tgttttttgc acaaacatga aatatcagac aattccgtga cttaagaaaa tttatacaaa   180
tcagcaatat accccttaag gagtatataa aggtgaattt gatttacatc aataagcggg   240
gttgctgaat cgttaaggta ggcggtaata gaaaagaaat cgaggcaaaa               290

<210> SEQ ID NO 21
<211> LENGTH: 433
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 21
cggcccgatc gttgaacata gcggtccgca ggcggcactg cttacagcaa acggtctgta    60
cgctgtcgtc tttgtgatgt gcttcctgtt aggtttcgtc agccgtcacc gtcagcataa   120
caccctgacc tctcattaat tgctcatgcc ggacggcact atcgtcgtcc ggccttttcc   180
tctcttcccc cgctacgtgc atctatttct ataaacccgc tcattttgtc tattttttgc   240
acaaacatga aatatcagac aattccgtga cttaagaaaa tttatacaaa tcagcaatat   300
acccattaag gagtatataa aggtgaattt gatttacatc aataagcggg gttgctgaat   360
cgttaaggta ggcggtaata gaaaagaaat cgaggcaaaa atgtttgttt aactttaaga   420
aggagatata cat                                                      433

<210> SEQ ID NO 22
<211> LENGTH: 290
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 22
gtcagcataa caccctgacc tctcattaat tgctcatgcc ggacggcact atcgtcgtcc    60
ggccttttcc tctcttcccc cgctacgtgc atctatttct ataaacccgc tcattttgtc   120
tattttttgc acaaacatga aatatcagac aattccgtga cttaagaaaa tttatacaaa   180
tcagcaatat acccattaag gagtatataa aggtgaattt gatttacatc aataagcggg   240
gttgctgaat cgttaaggta ggcggtaata gaaaagaaat cgaggcaaaa               290

<210> SEQ ID NO 23
<211> LENGTH: 173
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 23
atttcctctc atcccatccg gggtgagagt cttttccccc gacttatggc tcatgcatgc    60
```

```
atcaaaaaag atgtgagctt gatcaaaaac aaaaaatatt tcactcgaca ggagtattta      120
tattgcgccc gttacgtggg cttcgactgt aaatcagaaa ggagaaaaca cct             173
```

<210> SEQ ID NO 24
<211> LENGTH: 305
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 24

```
gtcagcataa caccctgacc tctcattaat tgttcatgcc gggcggcact atcgtcgtcc       60
ggccttttcc tctcttactc tgctacgtac atctatttct ataaatccgt tcaatttgtc      120
tgttttttgc acaaacatga aatatcagac aattccgtga cttaagaaaa tttatacaaa      180
tcagcaatat acccttaag gagtatataa aggtgaattt gatttacatc aataagcggg       240
gttgctgaat cgttaaggat ccctctagaa ataattttgt ttaactttaa gaaggagata      300
tacat                                                                  305
```

<210> SEQ ID NO 25
<211> LENGTH: 180
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 25

```
catttcctct catcccatcc ggggtgagag tcttttcccc cgacttatgg ctcatgcatg       60
catcaaaaaa gatgtgagct tgatcaaaaa caaaaaatat ttcactcgac aggagtattt      120
atattgcgcc cggatccctc tagaaataat tttgtttaac tttaagaagg agatatacat      180
```

<210> SEQ ID NO 26
<211> LENGTH: 199
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 26

```
agttgttctt attggtggtg ttgctttatg gttgcatcgt agtaaatggt tgtaacaaaa       60 gcaattttc cggctgtctg tatacaaaaa cgccgtaaag tttgagcgaa gtcaataaac       120
tctctaccca ttcagggcaa tatctctctt ggatccctct agaaataatt ttgtttaact      180
ttaagaagga gatatacat                                                   199
```

<210> SEQ ID NO 27
<211> LENGTH: 207
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 27

```
agttgttctt attggtggtg ttgctttatg gttgcatcgt agtaaatggt tgtaacaaaa       60 gcaattttc cggctgtctg tatacaaaaa cgccgcaaag tttgagcgaa gtcaataaac       120
```
tctctaccca ttcagggcaa tatctctctt ggatccaaag tgaactctag aaataatttt    180
gtttaacttt aagaaggaga tatacat                                        207

<210> SEQ ID NO 28
<211> LENGTH: 390
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 28
tcgtctttgt gatgtgcttc ctgttaggtt tcgtcagccg tcaccgtcag cataacaccc    60
tgacctctca ttaattgctc atgccggacg gcactatcgt cgtccggcct tttcctctct   120
tcccccgcta cgtgcatcta tttctataaa cccgctcatt ttgtctattt tttgcacaaa   180
catgaaatat cagacaattc cgtgacttaa gaaaatttat acaaatcagc aatatatccca  240 ttaaggagta tataaggtg aatttgattt acatcaataa gcggggttgc tgaatcgtta    300
aggtagaaat gtgatctagt tcacatttgc ggtaatagaa aagaaatcga ggcaaaaatg   360
tttgtttaac tttaagaagg agatatacat                                    390

<210> SEQ ID NO 29
<211> LENGTH: 200
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 29
agttgttctt attggtggtg ttgctttatg gttgcatcgt agtaaatggt tgtaacaaaa    60
gcaatttttc cggctgtctg tatacaaaaa cgccgcaaag tttgagcgaa gtcaataaac   120
tctctaccca ttcagggcaa tatctctcaa atgtgatcta gttcacattt tttgtttaac   180
tttaagaagg agatatacat                                               200

<210> SEQ ID NO 30
<211> LENGTH: 1332
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 30
atggtaaagg aacgtaaaac cgagttggtc gagggattcc gccattcggt tccctgtatc    60
aatacccacc ggggaaaaac gtttgtcatc atgctcggcg gtgaagccat tgagcatgag   120
aatttctcca gtatcgttaa tgatatcggg ttgttgcaca gcctcggcat ccgtctggtg   180
gtggtctatg gcgcacgtcc gcagatcgac gcaaatctgg ctgcgcatca ccacgaaccg   240
ctgtatcaca agaatatacg tgtgaccgac gccaaaacac tggaactggt gaagcaggct   300
gcgggaacat tgcaactgga tattactgct cgcctgtcga tgagtctcaa taacacgccg   360
ctgcagggcg cgcatatcaa cgtcgtcagt ggcaattttt tattgcccca gccgctgggc   420
gtcgatgacg gcgtggatta ctgccatagc gggcgtatcc ggcggattga tgaagacgcg   480
atccatcgtc aactgacag cggtgcaata gtgctaatgg ggcgtgtcgc tgtttcagtc   540
actggcgaga gctttaacct gacctcggaa gagattgcca ctcaactggc catcaaactg   600

```
aaagctgaaa agatgattgg tttttgctct tcccagggcg tcactaatga cgacggtgat    660
attgtctccg aacttttccc taacgaagcg caagcgcggg tagaagccca ggaagagaaa    720
ggcgattaca actccggtac ggtgcgcttt ttgcgtggcg cagtgaaagc ctgccgcagc    780
ggcgtgcgtc gctgtcattt aatcagttat caggaagatg gcgcgctgtt gcaagagttg    840
ttctcacgcg acggtatcgg tacgcagatt gtgatggaaa gcgccgagca gattcgtcgc    900
gcaacaatca acgatattgg cggtattctg gagttgattc gcccactgga gcagcaaggt    960
attctggtac gccgttctcg cgagcagctg gagatggaaa tcgacaaatt caccattatt   1020
cagcgcgata acacgactat tgcctgcgcc gcgctctatc cgttcccgga agagaagatt   1080
ggggaaatgg cctgtgtggc agttcacccg gattaccgca gttcatcaag gggtgaagtt   1140
ctgctggaac gcattgccgc tcaggctaag cagagcggct taagcaaatt gtttgtgctg   1200
accacgcgca gtattcactg gttccaggaa cgtggattta ccccagtgga tattgattta   1260
ctgcccgaga gcaaaaagca gttgtacaac taccagcgta atccaaagt gttgatggcg    1320 gatttagggt aa                                                       1332
```

```
<210> SEQ ID NO 31
<211> LENGTH: 443
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Met Val Lys Glu Arg Lys Thr Glu Leu Val Glu Gly Phe Arg His Ser
1               5                   10                  15

Val Pro Cys Ile Asn Thr His Arg Gly Lys Thr Phe Val Ile Met Leu
            20                  25                  30

Gly Gly Glu Ala Ile Glu His Glu Asn Phe Ser Ser Ile Val Asn Asp
        35                  40                  45

Ile Gly Leu Leu His Ser Leu Gly Ile Arg Leu Val Val Val Tyr Gly
    50                  55                  60

Ala Arg Pro Gln Ile Asp Ala Asn Leu Ala Ala His His Glu Pro
65                  70                  75                  80

Leu Tyr His Lys Asn Ile Arg Val Thr Asp Ala Lys Thr Leu Glu Leu
                85                  90                  95

Val Lys Gln Ala Ala Gly Thr Leu Gln Leu Asp Ile Thr Ala Arg Leu
            100                 105                 110

Ser Met Ser Leu Asn Asn Thr Pro Leu Gln Gly Ala His Ile Asn Val
        115                 120                 125

Val Ser Gly Asn Phe Ile Ile Ala Gln Pro Leu Gly Val Asp Asp Gly
    130                 135                 140

Val Asp Tyr Cys His Ser Gly Arg Ile Arg Arg Ile Asp Glu Asp Ala
145                 150                 155                 160

Ile His Arg Gln Leu Asp Ser Gly Ala Ile Val Leu Met Gly Pro Val
                165                 170                 175

Ala Val Ser Val Thr Gly Glu Ser Phe Asn Leu Thr Ser Glu Glu Ile
            180                 185                 190

Ala Thr Gln Leu Ala Ile Lys Leu Lys Ala Glu Lys Met Ile Gly Phe
        195                 200                 205

Cys Ser Ser Gln Gly Val Thr Asn Asp Asp Gly Asp Ile Val Ser Glu
    210                 215                 220
```

```
Leu Phe Pro Asn Glu Ala Gln Ala Arg Val Glu Ala Gln Glu Glu Lys
225                 230                 235                 240

Gly Asp Tyr Asn Ser Gly Thr Val Arg Phe Leu Arg Gly Ala Val Lys
            245                 250                 255

Ala Cys Arg Ser Gly Val Arg Arg Cys His Leu Ile Ser Tyr Gln Glu
        260                 265                 270

Asp Gly Ala Leu Leu Gln Glu Leu Phe Ser Arg Asp Gly Ile Gly Thr
    275                 280                 285

Gln Ile Val Met Glu Ser Ala Glu Gln Ile Arg Arg Ala Thr Ile Asn
290                 295                 300

Asp Ile Gly Gly Ile Leu Glu Leu Ile Arg Pro Leu Glu Gln Gln Gly
305                 310                 315                 320

Ile Leu Val Arg Arg Ser Arg Glu Gln Leu Glu Met Glu Ile Asp Lys
                325                 330                 335

Phe Thr Ile Ile Gln Arg Asp Asn Thr Thr Ile Ala Cys Ala Ala Leu
            340                 345                 350

Tyr Pro Phe Pro Glu Glu Lys Ile Gly Glu Met Ala Cys Val Ala Val
        355                 360                 365

His Pro Asp Tyr Arg Ser Ser Ser Arg Gly Glu Val Leu Leu Glu Arg
    370                 375                 380

Ile Ala Ala Gln Ala Lys Gln Ser Gly Leu Ser Lys Leu Phe Val Leu
385                 390                 395                 400

Thr Thr Arg Ser Ile His Trp Phe Gln Glu Arg Gly Phe Thr Pro Val
                405                 410                 415

Asp Ile Asp Leu Leu Pro Glu Ser Lys Lys Gln Leu Tyr Asn Tyr Gln
            420                 425                 430

Arg Lys Ser Lys Val Leu Met Ala Asp Leu Gly
        435                 440

<210> SEQ ID NO 32
<211> LENGTH: 1539
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 32
agttgttctt attggtggtg ttgctttatg gttgcatcgt agtaaatggt tgtaacaaaa        60 gcaattttc  cggctgtctg tatacaaaaa cgccgcaaag tttgagcgaa gtcaataaac       120
tctctaccca ttcagggcaa tatctctctt ggatccaaag tgaactctag aaataattt        180 gtttaacttt aagaaggaga tatacatatg gtaaaggaac gtaaaaccga gttggtcgag       240
ggattccgcc attcggttcc ctgtatcaat acccaccggg gaaaaacgtt tgtcatcatg       300
ctcggcggtg aagccattga gcatgagaat ttctccagta tcgttaatga tatcgggttg       360
ttgcacagcc tcggcatccg tctggtggtg gtctatggcg cacgtccgca gatcgacgca       420
aatctggctg cgcatcacca cgaaccgctg tatcacaaga atatacgtgt gaccgacgcc       480
aaaacactgg aactggtgaa gcaggctgcg ggaacattgc aactggatat tactgctcgc       540
ctgtcgatga gtctcaataa cacgccgctg cagggcgcgc atatcaacgt cgtcagtggc       600
aattttatta ttgcccagcc gctgggcgtc gatgacggcg tggattactg ccatagcggg       660
cgtatccggc ggattgatga agacgcgatc catcgtcaac tggacagcgg tgcaatagtg       720
ctaatgggcc cggtcgctgt ttcagtcact ggcgagagct taaccctgac ctcggaagag       780
```

```
attgccactc aactggccat caaactgaaa gctgaaaaga tgattggttt ttgctcttcc      840
cagggcgtca ctaatgacga cggtgatatt gtctccgaac ttttccctaa cgaagcgcaa      900
gcgcgggtag aagcccagga agagaaaggc gattacaact ccggtacggt gcgcttttg      960 cgtggcgcag tgaaagcctg ccgcagcggc gtgcgtcgct gtcatttaat cagttatcag     1020
gaagatggcg cgctgttgca agagttgttc tcacgcgacg gtatcggtac gcagattgtg     1080
atggaaagcg ccgagcagat tcgtcgcgca caatcaacg atattggcgg tattctggag     1140
ttgattcgcc cactggagca gcaaggtatt ctggtacgcc gttctcgcga gcagctggag     1200
atggaaatcg acaaattcac cattattcag cgcgataaca cgactattgc ctgcgccgcg     1260
ctctatccgt tcccggaaga aagattggg gaaatggcct gtgtggcagt tcacccggat     1320
taccgcagtt catcaagggg tgaagttctg ctggaacgca ttgccgctca ggctaagcag     1380
agcggcttaa gcaaattgtt tgtgctgacc acgcgcagta ttcactggtt ccaggaacgt     1440
ggatttaccc cagtggatat tgatttactg cccgagagca aaaagcagtt gtacaactac     1500
cagcgtaaat ccaaagtgtt gatggcggat ttagggtaa                            1539

<210> SEQ ID NO 33
<211> LENGTH: 5417
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 33
gtaaaacgac ggccagtgaa ttcgagctcg gtaccatccc catcactctt gatggagatc       60
aattccccaa gctgctagag cgttaccttg cccttaaaca ttagcaatgt cgatttatca      120
gagggccgac aggctcccac aggagaaaac cgatggtaaa ggaacgtaaa accgagttgg      180
tcgagggatt ccgccattcg gttccctgta tcaatacccca ccggggaaaa acgtttgtca     240
tcatgctcgg cggtgaagcc attgagcatg agaatttctc cagtatcgtt aatgatatcg      300
ggttgttgca cagcctcggc atccgtctgg tggtggtcta tggcgcacgt ccgcagatcg      360
acgcaaatct ggctgcgcat caccacgaac cgctgtatca caagaatata cgtgtgaccg      420
acgccaaaac actggaactg gtgaagcagg ctgcgggaac attgcaactg gatattactg      480
ctcgcctgtc gatgagtctc aataacacgc cgctgcaggg cgcgcatatc aacgtcgtca      540
gtggcaattt tattattgcc cagccgctgg gcgtcgatga cggcgtggat tactgccata      600
gcgggcgtat ccggcggatt gatgaagacg cgatccatcg tcaactggac agcggtgcaa      660
tagtgctaat ggggccggtc gctgtttcag tcactggcga gagctttaac ctgacctcgg      720
aagagattgc cactcaactg ccatcaaac tgaaagctga aaagatgatt ggttttgct       780 cttcccaggg cgtcactaat gacgacggtg atattgtctc cgaacttttc cctaacgaag      840
cgcaagcgcg ggtagaagcc caggaagaga aggcgattac aactccggt acggtgcgct      900 ttttgcgtgg cgcagtgaaa gcctgccgca gcggcgtgcg tcgctgtcat taatcagtt      960 atcaggaaga tggcgcgctg ttgcaagagt tgttctcacg cgacggtatc ggtacgcaga     1020
ttgtgatgga aagcgccgag cagattcgtc gcgcaacaat caacgatatt ggcggtattc     1080
tggagttgat tcgcccactg gagcagcaag gtattctggt acgccgttct cgcgagcagc     1140
tggagatgga aatcgacaaa ttcaccatta ttcagcgcga taacacgact attgcctgcg     1200
ccgcgctcta tccgttcccg gaagagaaga ttggggaaat ggcctgtgtg gcagttcacc     1260
```

```
cggattaccg cagttcatca aggggtgaag ttctgctgga acgcattgcc gctcaggcta    1320
agcagagcgg cttaagcaaa ttgtttgtgc tgaccacgcg cagtattcac tggttccagg    1380
aacgtggatt taccccagtg atattgatt tactgcccga gagcaaaaag cagttgtaca    1440
actaccagcg taaatccaaa gtgttgatgg cggatttagg gtaaacagaa taaaaataca    1500
ataatttcga ataatcatgc aaagcttggc gtaatcatgg tcatagctgt ttcctgtgtg    1560
aaattgttat ccgctcacaa ttccacacaa catacgagcc ggaagcatgt acgggttttg    1620
ctgcccgcaa acgggctgtt ctggtgttgc tagtttgtta tcagaatcgc agatccggct    1680
tcaggtttgc cggctgaaag cgctatttct tccagaattg ccatgatttt ttccccacgg    1740
gaggcgtcac tggctcccgt gttgtcggca gctttgattc gataagcagc atcgcctgtt    1800
tcaggctgtc tatgtgtgac tgttgagctg taacaagttg tctcaggtgt tcaatttcat    1860
gttctagttg ctttgtttta ctggtttcac ctgttctatt aggtgttaca tgctgttcat    1920
ctgttacatt gtcgatctgt tcatggtgaa cagcttaaaa tgcaccaaaa actcgtaaaa    1980
gctctgatgt atctatcttt tttacaccgt tttcatctgt gcatatggac agttttccct    2040
ttgatatcta acggtgaaca gttgttctac ttttgtttgt tagtcttgat gcttcactga    2100
tagatacaag agccataaga acctcagatc cttccgtatt tagccagtat gttctctagt    2160
gtggttcgtt gttttgcgt gagccatgag aacgaaccat tgagatcatg cttactttgc    2220
atgtcactca aaattttgc ctcaaaactg gtgagctgaa ttttgcagt aaagcatcg    2280 tgtagtgttt ttcttagtcc gttacgtagg taggaatctg atgtaatggt tgttggtatt    2340
ttgtcaccat tcattttat ctggttgttc tcaagttcgg ttacgagatc catttgtcta    2400
tctagttcaa cttggaaaat caacgtatca gtcgggcggc ctcgcttatc aaccaccaat    2460
ttcatattgc tgtaagtgtt taaatcttta cttattggtt tcaaaaccca ttggttaagc    2520
ctttaaaact catggtagtt attttcaagc attaacatga acttaaattc atcaaggcta    2580
atctctatat ttgccttgtg agttttcttt tgtgttagtt cttttaataa ccactcataa    2640
atcctcatag agtatttgtt ttcaaaagac ttaacatgtt ccagattata ttttatgaat    2700
ttttttaact ggaaaagata aggcaatatc tcttcactaa aaactaattc taattttcg    2760 cttgagaact tggcatagtt tgtccactgg aaaatctcaa agcctttaac caaaggattc    2820
ctgatttcca cagttctcgt catcagctct ctggttgctt tagctaatac accataagca    2880
ttttccctac tgatgttcat catctgagcg tattggttat aagtgaacga taccgtccgt    2940
tctttccttg tagggttttc aatcgtgggg ttgagtagtg ccacacagca taaaattagc    3000
ttggtttcat gctccgttaa gtcatagcga ctaatcgcta gttcatttgc tttgaaaaca    3060
actaattcag acatacatct caattggtct aggtgatttt aatcactata ccaattgaga    3120
tgggctagtc aatgataatt actagtcctt ttcctttgag ttgtgggtat ctgtaaattc    3180
tgctagacct ttgctggaaa acttgtaaat tctgctagac cctctgtaaa ttccgctaga    3240
cctttgtgtg ttttttttgt ttatattcaa gtggttataa tttatagaat aaagaaagaa    3300 taaaaaaga taaaaagaat agatcccagc cctgtgtata actcactact ttagtcagtt    3360
ccgcagtatt acaaaaggat gtcgcaaacg ctgtttgctc ctctacaaaa cagaccttaa    3420
aaccctaaag gcttaagtag caccctcgca agctcgggca aatcgctgaa tattccttt    3480 gtctccgacc atcaggcacc tgagtcgctg tcttttcgt gacattcagt tcgctgcgct    3540
cacggctctg gcagtgaatg ggggtaaatg gcactacagg cgcctttat ggattcatgc    3600 aaggaaacta cccataatac aagaaaagcc cgtcacgggc ttctcagggc gttttatggc    3660
```

-continued

```
gggtctgcta tgtggtgcta tctgactttt tgctgttcag cagttcctgc cctctgattt      3720
tccagtctga ccacttcgga ttatcccgtg acaggtcatt cagactggct aatgcaccca      3780
gtaaggcagc ggtatcatca acaggcttac ccgtcttact gtcttttcta cggggtctga      3840
cgctcagtgg aacgaaaact cacgttaagg gattttggtc atgagattat caaaaaggat      3900
cttcacctag atccttttaa attaaaaatg aagttttaaa tcaatctaaa gtatatatga      3960
gtaaacttgg tctgacagtt accaatgctt aatcagtgag gcacctatct cagcgatctg      4020
tctatttcgt tcatccatag ttgcctgact ccccgtcgtg tagataacta cgatacggga      4080
gggcttacca tctggcccca gtgctgcaat gataccgcga acccacgct caccggctcc       4140 agatttatca gcaataaacc agccagccgg aagggccgag cgcagaagtg gtcctgcaac      4200
tttatccgcc tccatccagt ctattaattg ttgccgggaa gctagagtaa gtagttcgcc      4260
agttaatagt ttgcgcaacg ttgttgccat tgctacaggc atcgtggtgt cacgctcgtc      4320
gtttggtatg gcttcattca gctccggttc ccaacgatca aggcgagtta catgatcccc      4380
catgttgtgc aaaaaagcgg ttagctcctt cggtcctccg atcgttgtca gaagtaagtt      4440
ggccgcagtg ttatcactca tggttatggc agcactgcat aattctctta ctgtcatgcc      4500
atccgtaaga tgcttttctg tgactggtga gtactcaacc aagtcattct gagaatagtg      4560
tatgcggcga ccgagttgct cttgcccggc gtcaatacgg gataataccg cgccacatag      4620
cagaacttta aaagtgctca tcattggaaa acgttcttcg gggcgaaaac tctcaaggat      4680
cttaccgctg ttgagatcca gttcgatgta acccactcgt gcacccaact gatcttcagc      4740
atcttttact ttcaccagcg tttctgggtg agcaaaaaca ggaaggcaaa atgccgcaaa      4800
aaagggaata agggcgacac ggaaatgttg aatactcata ctcttccttt ttcaatatta     4860
ttgaagcatt tatcagggtt attgtctcat gagcggatac atatttgaat gtatttagaa      4920
aaataaacaa ataggggttc cgcgcacatt tccccgaaaa gtgccacctg acgtctaaga     4980
aaccattatt atcatgacat taacctataa aaataggcgt atcacgaggc cctttcgtct     5040
cgcgcgtttc ggtgatgacg gtgaaaacct ctgacacatg cagctcccgg agacggtcac     5100
agcttgtctg taagcggatg ccgggagcag acaagcccgt cagggcgcgt cagcgggtgt      5160
tggcgggtgt cggggctggc ttaactatgc ggcatcagag cagattgtac tgagagtgca      5220
ccatatgcgg tgtgaaatac cgcacagatg cgtaaggaga aaataccgca tcaggcgcca     5280
ttcgccattc aggctgcgca actgttggga agggcgatcg gtgcgggcct cttcgctatt     5340
acgccagctg gcgaaagggg gatgtgctgc aaggcgatta agttgggtaa cgccagggtt     5400
ttcccagtca cgacgtt                                                   5417
```

<210> SEQ ID NO 34
<211> LENGTH: 3995
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 34

```
attaagttgg gtaacgccag ggttttccca gtcacgacgt tattgcgttg cgctcactgc        60 ccgcttttcca gtcgggaaac ctgtcgtgcc agctgcatta atgaatcggc caacgcgcgg     120
ggagaggcgg tttgcgtatt gggcgctctt ccgcttcctc gctcactgac tcgctgcgct      180
cggtcgttcg gctgcggcga gcggtatcag ctcactcaaa ggcggtagta cgggttttgc      240
```

```
tgcccgcaaa cgggctgttc tggtgttgct agtttgttat cagaatcgca gatccggctt    300
caggtttgcc ggctgaaagc gctatttctt ccagaattgc catgatttt tccccacggg     360 aggcgtcact ggctcccgtg ttgtcggcag ctttgattcg ataagcagca tcgcctgttt    420
caggctgtct atgtgtgact gttgagctgt aacaagttgt ctcaggtgtt caatttcatg    480
ttctagttgc tttgttttac tggtttcacc tgttctatta ggtgttacat gctgttcatc    540
tgttacattg tcgatctgtt catggtgaac agctttaaat gcaccaaaaa ctcgtaaaag    600
ctctgatgta tctatctttt ttacaccgtt ttcatctgtg catatggaca gttttcccctt   660 tgatatctaa cggtgaacag ttgttctact tttgtttgtt agtcttgatg cttcactgat    720
agatacaaga gccataagaa cctcagatcc ttccgtatt agccagtatg ttctctagtg     780
tggttcgttg ttttttgcgtg agccatgaga acgaaccatt gagatcatgc ttactttgca   840
tgtcactcaa aaattttgcc tcaaaactgg tgagctgaat ttttgcagtt aaagcatcgt    900
gtagtgtttt tcttagtccg ttacgtaggt aggaatctga tgtaatggtt gttggtatt    960 tgtcaccatt catttttatc tggttgttct caagttcggt tacgagatcc atttgtctat    1020
ctagttcaac ttggaaaatc aacgtatcag tcgggcggcc tcgcttatca accaccaatt   1080
tcatattgct gtaagtgttt aaatctttac ttattggttt caaaacccat tggttaagcc   1140
ttttaaactc atggtagtta ttttcaagca ttaacatgaa cttaaattca tcaaggctaa    1200
tctctatatt tgccttgtga gttttctttt gtgttagttc ttttaataac cactcataaa   1260
tcctcataga gtatttgttt tcaaaagact taacatgttc cagattatat tttatgaatt   1320 ttttttaactg gaaaagataa ggcaatatct cttcactaaa aactaattct aatttttcgc   1380
ttgagaactt ggcatagttt gtccactgga aaatctcaaa gcctttaacc aaaggattcc    1440
tgatttccac agttctcgtc atcagctctc tggttgcttt agctaataca ccataagcat    1500
tttccctact gatgttcatc atctgagcgt attggttata agtgaacgat accgtccgtt   1560
ctttccttgt agggttttca atcgtggggt tgagtagtgc cacacagcat aaaattagct    1620
tggtttcatg ctccgttaag tcatagcgac taatcgctag ttcatttgct ttgaaaacaa    1680
ctaattcaga catacatctc aattggtcta ggtgatttta atcactatac caattgagat    1740
gggctagtca atgataatta ctagtccttt tcctttgagt tgtgggtatc tgtaaattct   1800
gctagacctt tgctggaaaa cttgtaaatt ctgctagacc ctctgtaaat tccgctagac   1860
ctttgtgtgt tttttttgtt tatattcaag tggttataat ttatagaata aagaaagaat    1920
aaaaaaagat aaaaagaata gatcccagcc ctgtgtataa ctcactactt tagtcagttc    1980
cgcagtatta caaaggatg tcgcaaacgc tgtttgctcc tctacaaaac agaccttaaa    2040
accctaaagg cttaagtagc accctcgcaa gctcgggcaa atcgctgaat attccttttg   2100
tctccgacca tcaggcacct gagtcgctgt ctttttcgtg acattcagtt cgctgcgctc   2160
acggctctgg cagtgaatgg gggtaaatgg cactacaggc gccttttatg gattcatgca   2220
aggaaactac ccataataca agaaaagccc gtcacgggct tctcagggcg ttttatggcg   2280
ggtctgctat gtggtgctat ctgacttttt gctgttcagc agttcctgcc ctctgatttt    2340
ccagtctgac cacttcggat tatcccgtga caggtcatta agactggcta atgcacccag    2400
taaggcagcg gtatcatcaa caggcttacc cgtcttactg tcttttctac ggggtctgac   2460
gctcagtgga acgaaaactc acgttaaggg attttggtca tgagattatc aaaaaggatc   2520
ttcacctaga tcctttaaa ttaaaaatga agtttaaat caatctaaag tatatatgag     2580
```

| | | | | |
|---|---|---|---|---|
| taaacttggt | ctgacagtta | ccaatgctta | atcagtgagg | cacctatctc | agcgatctgt | 2640 |
| ctatttcgtt | catccatagt | tgcctgactc | cccgtcgtgt | agataactac | gatacgggag | 2700 |
| ggcttaccat | ctggccccag | tgctgcaatg | ataccgcgag | acccacgctc | accggctcca | 2760 |
| gatttatcag | caataaacca | gccagccgga | agggccgagc | gcagaagtgg | tcctgcaact | 2820 |
| ttatccgcct | ccatccagtc | tattaattgt | tgccgggaag | ctagagtaag | tagttcgcca | 2880 |
| gttaatagtt | tgcgcaacgt | tgttgccatt | gctacaggca | tcgtggtgtc | acgctcgtcg | 2940 |
| tttggtatgg | cttcattcag | ctccggttcc | caacgatcaa | ggcgagttac | atgatccccc | 3000 |
| atgttgtgca | aaaaagcggt | tagctccttc | ggtcctccga | tcgttgtcag | aagtaagttg | 3060 |
| gccgcagtgt | tatcactcat | ggttatggca | gcactgcata | attctcttac | tgtcatgcca | 3120 |
| tccgtaagat | gcttttctgt | gactggtgag | tactcaacca | agtcattctg | agaatagtgt | 3180 |
| atgcggcgac | cgagttgctc | ttgcccggcg | tcaatacggg | ataataccgc | gccacatagc | 3240 |
| agaactttaa | aagtgctcat | cattggaaaa | cgttcttcgg | ggcgaaaact | ctcaaggatc | 3300 |
| ttaccgctgt | tgagatccag | ttcgatgtaa | cccactcgtg | cacccaactg | atcttcagca | 3360 |
| tcttttactt | tcaccagcgt | ttctgggtga | gcaaaaacag | gaaggcaaaa | tgccgcaaaa | 3420 |
| aagggaataa | gggcgacacg | gaaatgttga | atactcatac | tcttcctttt | tcaatattat | 3480 |
| tgaagcattt | atcagggtta | ttgtctcatg | agcggataca | tatttgaatg | tatttagaaa | 3540 |
| aataaacaaa | taggggttcc | gcgcacattt | ccccgaaaag | tgccacctga | cgtctaagaa | 3600 |
| accattatta | tcatgacatt | aacctataaa | aataggcgta | tcacgaggcc | ctttcgtctc | 3660 |
| gcgcgtttcg | gtgatgacgg | tgaaaacctc | tgacacatgc | agctcccgga | gacggtcaca | 3720 |
| gcttgtctgt | aagcggatgc | cgggagcaga | caagcccgtc | agggcgcgtc | agcgggtgtt | 3780 |
| ggcgggtgtc | ggggctggct | taactatgcg | gcatcagagc | agattgtact | gagagtgcac | 3840 |
| catatgcggt | gtgaaatacc | gcacagatgc | gtaaggagaa | aataccgcat | caggcgccat | 3900 |
| tcgccattca | ggctgcgcaa | ctgttgggaa | gggcgatcgg | tgcgggcctc | ttcgctatta | 3960 |
| cgccagctgg | cgaaaggggg | atgtgctgca | aggcg | | | 3995 |

<210> SEQ ID NO 35
<211> LENGTH: 5660
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 35

| | | | | |
|---|---|---|---|---|
| ggtaccagtt | gttcttattg | gtggtgttgc | tttatggttg | catcgtagta | aatggttgta | 60 |
| acaaaagcaa | ttttccggc | tgtctgtata | caaaaacgcc | gcaaagtttg | agcgaagtca | 120 |
| ataaactctc | tacccattca | gggcaatatc | tctcttggat | ccaaagtgaa | ctctagaaat | 180 |
| aattttgttt | aactttaaga | aggagatata | catatggtaa | aggaacgtaa | aaccgagttg | 240 |
| gtcgagggat | tccgccattc | ggttccctgt | atcaataccc | accggggaaa | aacgtttgtc | 300 |
| atcatgctcg | gcggtgaagc | cattgagcat | gagaatttct | ccagtatcgt | taatgatatc | 360 |
| gggttgttgc | acagcctcgg | catccgtctg | gtggtggtc | atggcgcacg | tccgcagatc | 420 |
| gacgcaaatc | tggctgcgca | tcaccacgaa | ccgctgtatc | acaagaatat | acgtgtgacc | 480 |
| gacgccaaaa | cactggaact | ggtgaagcag | gctgcgggaa | cattgcaact | ggatattact | 540 |
| gctcgcctgt | cgatgagtct | caataacacg | ccgctgcagg | gcgcgcatat | caacgtcgtc | 600 |

```
agtggcaatt ttattattgc ccagccgctg ggcgtcgatg acggcgtgga ttactgccat      660
agcgggcgta tccggcggat tgatgaagac gcgatccatc gtcaactgga cagcggtgca      720
atagtgctaa tggggccggt cgctgtttca gtcactggcg agagctttaa cctgacctcg      780
gaagagattg ccactcaact ggccatcaaa ctgaaagctg aaaagatgat tggttttgc       840 tcttcccagg gcgtcactaa tgacgacggt gatattgtct ccgaactttt ccctaacgaa      900
gcgcaagcgc gggtagaagc ccaggaagag aaaggcgatt acaactccgg tacggtgcgc      960
tttttgcgtg gcgcagtgaa agcctgccgc agcggcgtgc gtcgctgtca tttaatcagt     1020
tatcaggaag atggcgcgct gttgcaagag ttgttctcac gcgacggtat cggtacgcag     1080
attgtgatgg aaagcgccga gcagattcgt cgcgcaacaa tcaacgatat tggcggtatt     1140
ctggagttga ttcgcccact ggagcagcaa ggtattctgg tacgccgttc tcgcgagcag     1200
ctggagatgg aaatcgacaa attcaccatt attcagcgcg ataacacgac tattgcctgc     1260
gccgcgctct atccgttccc ggaagagaag attggggaaa tggcctgtgt ggcagttcac     1320
ccggattacc gcagttcatc aagggtgaa gttctgctgg aacgcattgc cgctcaggct      1380
aagcagagcg gcttaagcaa attgtttgtg ctgaccacgc gcagtattca ctggttccag     1440
gaacgtggat ttaccccagt ggatattgat ttactgcccg agagcaaaaa gcagttgtac     1500
aactaccagc gtaaatccaa agtgttgatg gcggatttag ggtaaggaag tttgtctaga     1560
tctcaggcgt ggatggcttg gcgtaatcat ggtcatagct gtttcctgtg tgaaattgtt     1620
atccgctcac aattccacac aacatacgag ccggaagcat aaagtgtaaa gcctggggtg     1680
cctaatgagt gagctaactc acattaattg cgttgcgctc actgcccgct ttccagtcgg     1740
gaaacctgtc gtgccagctg cattaatgaa tcggccaacg cgcggggaga gcggtttgc      1800 gtattgggcg ctcttccgct tcctcgctca ctgactcgct gcgctcggtc gttcggctgc     1860
ggcgagcggt atcagctcac tcaaaggcgg tagtacgggt tttgctgccc gcaaacgggc     1920
tgttctggtt ttgctagttt gttatcagaa tcgcagatcc ggcttcaggt ttgccggctg     1980
aaagcgctat tcttccaga attgccatga ttttttcccc acgggaggcg tcactggctc      2040
ccgtgttgtc ggcagctttg attcgataag cagcatcgcc tgtttcaggc tgtctatgtg     2100
tgactgttga gctgtaacaa gttgtctcag gtgttcaatt tcatgttcta gttgctttgt     2160
tttactggtt tcacctgttc tattaggtgt tacatgctgt tcatctgtta cattgtcgat     2220
ctgttcatgg tgaacagctt taaatgcacc aaaaactcgt aaaagctctg atgtatctat     2280
cttttttaca ccgttttcat ctgtgcatat ggacagtttt ccctttgata tctaacggtg     2340
aacagttgtt ctacttttgt ttgttagtct tgatgcttca ctgatagata caagagccat     2400
aagaacctca gatccttccg tatttagcca gtatgttctc tagtgtggtt cgttgttttt     2460
gcgtgagcca tgagaacgaa ccattgagat catgcttact ttgcatgtca ctcaaaaatt     2520
ttgcctcaaa actggtgagc tgaattttg cagttaaagc atcgtgtagt gttttcttta     2580
gtccgttacg taggtaggaa tctgatgtaa tggttgttgg tattttgtca ccattcattt     2640
ttatctggtt gttctcaagt tcggttacga gatccatttg tctatctagt tcaacttgga     2700
aaatcaacgt atcagtcggg cggcctcgct tatcaaccac caatttcata ttgctgtaag     2760
tgtttaaatc tttacttatt ggtttcaaaa cccattggtt aagccttta aactcatggt      2820 agttattttc aagcattaac atgaacttaa attcatcaag gctaatctct atatttgcct     2880
tgtgagtttt cttttgtgtt agttctttta ataaccactc ataaatcctc atagagtatt     2940
tgttttcaaa agacttaaca tgttccagat tatatttat gaattttttt aactggaaaa      3000
```

```
gataaggcaa tatctcttca ctaaaaacta attctaattt ttcgcttgag aacttggcat    3060
agtttgtcca ctggaaaatc tcaaagcctt taaccaaagg attcctgatt tccacagttc    3120
tcgtcatcag ctctctggtt gctttagcta atacaccata agcattttcc ctactgatgt    3180
tcatcatctg agcgtattgg ttataagtga acgataccgt ccgttctttc cttgtagggt    3240
tttcaatcgt ggggttgagt agtgccacac agcataaaat tagcttggtt tcatgctccg    3300
ttaagtcata gcgactaatc gctagttcat ttgctttgaa aacaactaat tcagacatac    3360
atctcaattg gtctaggtga ttttaatcac tataccaatt gagatgggct agtcaatgat    3420
aattactagt cctttttcctt tgagttgtgg gtatctgtaa attctgctag acctttgctg    3480
gaaaacttgt aaattctgct agaccctctg taaattccgc tagacctttg tgtgtttttt    3540
ttgtttatat tcaagtggtt ataatttata gaataaagaa agaataaaaa aagataaaaa    3600
gaatagatcc cagccctgtg tataactcac tactttagtc agttccgcag tattacaaaa    3660
ggatgtcgca aacgctgttt gctcctctac aaaacagacc ttaaaaccct aaaggcttaa    3720
gtagcaccct cgcaagctcg ggcaaatcgc tgaatattcc ttttgtctcc gaccatcagg    3780
cacctgagtc gctgtctttt tcgtgacatt cagttcgctg cgctcacggc tctggcagtg    3840
aatgggggta aatggcacta caggcgcctt ttatggattc atgcaaggaa actacccata    3900
atacaagaaa agcccgtcac gggcttctca gggcgtttta tggcgggtct gctatgtggt    3960
gctatctgac ttttttgctgt tcagcagttc ctgccctctg atttttccagt ctgaccactt    4020 cggattatcc cgtgacaggt cattcagact ggctaatgca cccagtaagg cagcggtatc    4080
atcaacaggc ttacccgtct tactgtctttt tctacggggt ctgacgctca gtggaacgaa    4140
aactcacgtt aagggatttt ggtcatgaga ttatcaaaaa ggatcttcac ctagatcctt    4200
ttaaattaaa aatgaagttt taaatcaatc taaagtatat atgagtaaac ttggtctgac    4260
agttaccaat gcttaatcag tgaggcacct atctcagcga tctgtctatt tcgttcatcc    4320
atagttgcct gactccccgt cgtgtagata actacgatac gggagggctt accatctggc    4380
cccagtgctg caatgatacc gcgagaccca cgctcaccgg ctccagattt atcagcaata    4440
aaccagccag ccggaagggc cgagcgcaga agtggtcctg caactttatc cgcctccatc    4500
cagtctatta attgttgccg ggaagctaga gtaagtagtt cgccagttaa tagtttgcgc    4560
aacgttgttg ccattgctac aggcatcgtg gtgtcacgct cgtcgtttgg tatggcttca    4620
ttcagctccg gttcccaacg atcaaggcga gttacatgat cccccatgtt gtgcaaaaaa    4680
gcggttagct ccttcggtcc tccgatcgtt gtcagaagta agttggccgc agtgttatca    4740
ctcatggtta tggcagcact gcataattct cttactgtca tgccatccgt aagatgcttt    4800
tctgtgactg gtgagtactc aaccaagtca ttctgagaat agtgtatgcg gcgaccgagt    4860
tgctcttgcc cggcgtcaat acgggataat accgcgccac atagcagaac tttaaaagtg    4920
ctcatcattg gaaaacgttc ttcggggcga aaactctcaa ggatcttacc gctgttgaga    4980
tccagttcga tgtaacccac tcgtgcaccc aactgatctt cagcatcttt tactttcacc    5040
agcgtttctg ggtgagcaaa aacaggaagg caaaatgccg caaaaaaggg aataagggcg    5100
acacggaaat gttgaatact catactcttc cttttcaat attattgaag catttatcag    5160
ggttattgtc tcatgagcgg atacatattt gaatgtattt agaaaaataa acaaataggg    5220
gttccgcgca catttccccg aaaagtgcca cctgacgtct aagaaaccat tattatcatg    5280
acattaacct ataaaaatag gcgtatcacg aggccctttc gtctcgcgcg tttcggtgat    5340
```

```
gacggtgaaa acctctgaca catgcagctc ccggagacgg tcacagcttg tctgtaagcg    5400
gatgccggga gcagacaagc ccgtcagggc gcgtcagcgg gtgttggcgg gtgtcggggc    5460
tggcttaact atgcggcatc agagcagatt gtactgagag tgcaccatat gcggtgtgaa    5520
ataccgcaca gatgcgtaag gagaaaatac cgcatcaggc gccattcgcc attcaggctg    5580
cgcaactgtt gggaagggcg atcggtgcgg gcctcttcgc tattacgcca gctggcgaaa    5640
gggggatgtg ctgcaaggcg                                                5660
```

<210> SEQ ID NO 36
<211> LENGTH: 3115
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 36

```
ctacgcccca tcgttgcttt gtgtgatctc tgttacagaa ttggcggtaa tgtggagatg      60
cgcacataaa atcgccatga ttttgcaag caacatcacg aaattcctta catgacctcg     120
gtttagttca caggacgtcc catggctcga gcatgcgaga gtagggaact gccaggcatc     180
aaataaaatg aaaggctcag tcgaaagact gggccttcg ttttatctgt tgtttgtcgg     240
tgaacgctct cctgagtagg acaaatccgc cgggagcgga tttgaacgtt gcgaagcaac     300
ggcccggagg gtggcgggca ggacgcccgc cataaactgc caggcatcaa attaagcaga     360
aggccatcct gacggatggc cttttttgcgt ggccagtgcc aagcttgcat gcagattgca     420
gcattacacg tcttgagcga ttgtgtaggc tggagctgct tcgaagttcc tatactttct     480
agagaatagg aacttcggaa taggaacttc atttaaatgg cgcgccttac gccccgccct     540
gccactcatc gcagtactgt tgtattcatt aagcatctgc cgacatggaa gccatcacaa     600
acggcatgat gaacctgaat cgccagcggc atcagcacct gtcgccttg cgtataatat     660 ttgcccatgg tgaaaacggg ggcgaagaag ttgtccatat tggccacgtt taaatcaaaa     720
ctggtgaaac tcacccaggg attggctgag acgaaaaaca tattctcaat aaacccttta     780
gggaaatagg ccaggtttc accgtaacac gccacatctt gcgaatatat gtgtagaaac     840
tgccggaaat cgtcgtggta ttcactccag agcgatgaaa acgtttcagt ttgctcatgg     900
aaaacggtgt aacaagggtg aacactatcc catatccacca gctcaccgtc tttcattgcc     960
atacgtaatt ccggatgagc attcatcagg cgggcaagaa tgtgaataaa ggccggataa    1020
aacttgtgct tatttttctt tacggtcttt aaaaaggccg taatatccag ctgaacggtc    1080
tggttatagg tacattgagc aactgactga atgcctcaa atgttcttt acgatgccat    1140 tgggatatat caacggtggt atatccagtg atttttttct ccattttagc ttccttagct    1200
cctgaaaatc tcgacaactc aaaaaatacg cccggtagtg atcttatttc attatggtga    1260
aagttggaac ctcttacgtg ccgatcaacg tctcatttc gccaaaagtt ggcccagggc    1320
ttcccggtat caacagggac accaggattt atttattctg cgaagtgatc ttccgtcaca    1380
ggtaggcgcg ccgaagttcc tatactttct agagaatagg aacttcggaa taggaactaa    1440
ggaggatatt catatggacc atggctaatt cccaggtacc agttgttctt attggtggtg    1500
ttgctttatg gttgcatcgt agtaaatggt tgtaacaaaa gcaattttc cggctgtctg    1560 tatacaaaaa cgccgtaaag tttgagcgaa gtcaataaac tctctaccca ttcagggcaa    1620
tatctctctt ggatccaaag tgaactctag aaataatttt gtttaacttt aagaaggaga    1680
```

| | |
|---|---|
| tatacatatg gtaaaggaac gtaaaaccga gttggtcgag ggattccgcc attcggttcc | 1740 |
| ctgtatcaat acccaccggg gaaaaacgtt tgtcatcatg ctcggcggtg aagccattga | 1800 |
| gcatgagaat ttctccagta tcgttaatga tatcggggttg ttgcacagcc tcggcatccg | 1860 |
| tctggtggtg gtctatggcg cacgtccgca gatcgacgca aatctggctg cgcatcacca | 1920 |
| cgaaccgctg tatcacaaga atatacgtgt gaccgacgcc aaaacactgg aactggtgaa | 1980 |
| gcaggctgcg ggaacattgc aactggatat tactgctcgc ctgtcgatga gtctcaataa | 2040 |
| cacgccgctg cagggcgcgc atatcaacgt cgtcagtggc aatttttatta ttgcccagcc | 2100 |
| gctgggcgtc gatgacggcg tggattactg ccatagcggg cgtatccggc ggattgatga | 2160 |
| agacgcgatc catcgtcaac tggacagcgg tgcaatagtg ctaatggggc cggtcgctgt | 2220 |
| ttcagtcact ggcgagagct taacctgac ctcggaagag attgccactc aactggccat | 2280 |
| caaactgaaa gctgaaaaga tgattggttt ttgctcttcc cagggcgtca ctaatgacga | 2340 |
| cggtgatatt gtctccgaac ttttccctaa cgaagcgcaa gcgcgggtag aagcccagga | 2400 |
| agagaaaggc gattacaact ccggtacggt gcgcttttttg cgtggcgcag tgaaagcctg | 2460 |
| ccgcagcggc gtgcgtcgct gtcatttaat cagttatcag gaagatggcg cgctgttgca | 2520 |
| agagttgttc tcacgcgacg gtatcggtac gcagattgtg atggaaagcg ccgagcagat | 2580 |
| tcgtcgcgca acaatcaacg atattggcgg tattctggag ttgattcgcc cactggagca | 2640 |
| gcaaggtatt ctggtacgcc gttctcgcga gcagctggga atggaaatcg acaaattcac | 2700 |
| cattattcag cgcgataaca cgactattgc ctgcgccgcg ctctatccgt tcccggaaga | 2760 |
| gaagattggg gaaatggcct gtgtggcagt tcacccggat taccgcagtt catcaagggg | 2820 |
| tgaagttctg ctggaacgca ttgccgctca ggctaagcag agcggcttaa gcaaattgtt | 2880 |
| tgtgctgacc acgcgcagta ttcactggtt ccaggaacgt ggatttaccc cagtggatat | 2940 |
| tgatttactg cccgagagca aaaagcagtt gtacaactac cagcgtaaat ccaaagtgtt | 3000 |
| gatggcggat ttagggtaag tcgacgcatg catcgataag ccgcgttctc atcctcccgc | 3060 |
| ctcctccccc ataaaaaagc cagggggtgg aggatttaag ccatctcctg atgac | 3115 |

<210> SEQ ID NO 37
<211> LENGTH: 3583
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 37

| | |
|---|---|
| ctacgcccca tcgttgcttt gtgtgatctc tgttacagaa ttggcggtaa tgtggagatg | 60 |
| cgcacataaa atcgccatga tttttgcaag caacatcacg aaattcctta catgacctcg | 120 |
| gtttagttca caggacgtcc catggctcga gcatgcgaga gtagggaact gccaggcatc | 180 |
| aaataaaatg aaaggctcag tcgaaagact gggccttttcg ttttatctgt tgtttgtcgg | 240 |
| tgaacgctct cctgagtagg acaaatccgc cgggagcgga tttgaacgtt gcgaagcaac | 300 |
| ggcccggagg gtggcgggca ggacgcccgc cataaactgc caggcatcaa attaagcaga | 360 |
| aggccatcct gacggatggc cttttttgcgt ggccagtgcc aagcttgcat gcagattgca | 420 |
| gcattacacg tcttgagcga ttgtgtaggc tggagctgct tcgaagttcc tatactttct | 480 |
| agagaatagg aacttcggaa taggaacttc aagatcccct cacgctgccg caagcactca | 540 |
| gggcgcaagg gctgctaaag gaagcggaac acgtagaaag ccagtccgca gaaacggtgc | 600 |

-continued

```
tgaccccgga tgaatgtcag ctactgggct atctggacaa gggaaaacgc aagcgcaaag      660
agaaagcagg tagcttgcag tgggcttaca tggcgatagc tagactgggc ggttttatgg      720
acagcaagcg aaccggaatt gccagctggg gcgccctctg gtaaggttgg gaagccctgc      780
aaagtaaact ggatggcttt cttgccgcca aggatctgat ggcgcagggg atcaagatct      840
gatcaagaga caggatgagg atcgtttcgc atgattgaac aagatggatt gcacgcaggt      900
tctccggccg cttgggtgga gaggctattc ggctatgact gggcacaaca dacaatcggc      960
tgctctgatg ccgccgtgtt ccggctgtca gcgcagggggc gcccggttct ttttgtcaag     1020
accgacctgt ccggtgccct gaatgaactg caggacgagg cagcgcggct atcgtggctg     1080
gccacgacgg gcgttccttg cgcagctgtg ctcgacgttg tcactgaagc gggaagggac     1140
tggctgctat tgggcgaagt gccggggcag gatctcctgt catctcacct tgctcctgcc     1200
gagaaagtat ccatcatggc tgatgcaatg cggcggctgc atacgcttga tccggctacc     1260
tgcccattcg accaccaagc gaaacatcgc atcgagcgag cacgtactcg gatggaagcc     1320
ggtcttgtcg atcaggatga tctggacgaa gagcatcagg ggctcgcgcc agccgaactg     1380
ttcgccaggc tcaaggcgcg catgcccgac ggcgaggatc tcgtcgtgac ccatggcgat     1440
gcctgcttgc cgaatatcat ggtggaaaat ggccgctttt ctggattcat cgactgtggc     1500
cggctgggtg tggcggaccg ctatcaggac atagcgttgg ctacccgtga tattgctgaa     1560
gagcttggcg gcgaatgggc tgaccgcttc ctcgtgcttt acggtatcgc cgctcccgat     1620
tcgcagcgca tcgccttcta tcgccttctt gacgagttct tctgagcggg actctggggt     1680
tcgaaatgac cgaccaagcg acgcccaacc tgccatcacg agatttcgat tccaccgccg     1740
ccttctatga aggttgggc ttcggaatcg ttttccggga cgccggctgg atgatcctcc     1800
agcgcgggga tctcatgctg gagttcttcg cccaccccag cttcaaaagc gctctgaagt     1860
tcctatactt tctagagaat aggaacttcg gaataggaac taaggaggat attcatatgg     1920
accatggcta attcccagat atggtaccag ttgttcttat tggtggtgtt gctttatggt     1980
tgcatcgtag taaatggttg taacaaaagc aattttttccg gctgtctgta tacaaaaacg     2040
ccgtaaagtt tgagcgaagt caataaactc tctacccatt cagggcaata tctctcttgg     2100
atccaaagtg aactctagaa ataattttgt ttaactttaa gaaggagata tacatatggt     2160 aaaggaacg aaaaccgagt tggtcgaggg attccgccat tcggttccct gtatcaatac     2220
ccaccgggga aaaacgtttg tcatcatgct cggcggtgaa gccattgagc atgagaattt     2280
ctccagtatc gttaatgata tcgggttgtt gcacagcctc ggcatccgtc tggtggtggt     2340
ctatggcgca cgtccgcaga tcgacgcaaa tctggctgcg catcaccacg aaccgctgta     2400
tcacaagaat atacgtgtga ccgacgccaa acactggaa ctggtgaagc aggctgcggg     2460
aacattgcaa ctggatatta ctgctcgcct gtcgatgagt ctcaataaca cgccgctgca     2520
gggcgcgcat atcaacgtcg tcagtggcaa ttttattatt gcccagccgc tgggcgtcga     2580
tgacggcgtg gattactgcc atagcgggcg tatccgcgg attgatgaag acgcgatcca     2640
tcgtcaactg gacagcggtg caatagtgct aatgggccg gtcgctgttt cagtcactgg     2700
cgagagcttt aacctgacct cggaagagat tgccactcaa ctggccatca aactgaaagc     2760
tgaaaagatg attggttttt gctcttccca gggcgtcact aatgacgacg gtgatattgt     2820
ctccgaactt ttccctaacg aagcgcaagc gcgggtagaa gcccaggaag agaaaggcga     2880
ttacaactcc ggtacggtgc gctttttgcg tggcgcagtg aaagcctgcc gcagcggcgt     2940
gcgtcgctgt catttaatca gttatcagga agatggcgcg ctgttgcaag agttgttctc     3000
```

-continued

```
acgcgacggt atcggtacgc agattgtgat ggaaagcgcc gagcagattc gtcgcgcaac    3060
aatcaacgat attggcggta ttctggagtt gattcgccca ctggagcagc aaggtattct    3120
ggtacgccgt tctcgcgagc agctggagat ggaaatcgac aaattcacca ttattcagcg    3180
cgataacacg actattgcct cgccgcgct ctatccgttc ccggaagaga agattgggga    3240
aatggcctgt gtggcagttc acccggatta ccgcagttca tcaagggtg aagttctgct    3300 ggaacgcatt gccgctcagg ctaagcagag cggcttaagc aaattgtttg tgctgaccac    3360
gcgcagtatt cactggttcc aggaacgtgg atttacccca gtggatattg atttactgcc    3420
cgagagcaaa aagcagttgt acaactacca gcgtaaatcc aaagtgttga tggcggattt    3480
agggtaagtc gacgcatgca tcgataagcc gcgttctcat cctcccgcct cctcccccat    3540
aaaaaagcca gggggtggag gatttaagcc atctcctgat gac                     3583
```

<210> SEQ ID NO 38
<211> LENGTH: 2185
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 38

```
ctacgcccca tcgttgcttt gtgtgatctc tgttacagaa ttggcggtaa tgtggagatg      60
cgcacataaa atcgccatga tttttgcaag caacatcacg aaattcctta catgacctcg     120
gtttagttca caggacgtcc catggctcga gcatgcgaga gtagggaact gccaggcatc     180
aaataaaatg aaaggctcag tcgaaagact gggcctttcg ttttatctgt tgtttgtcgg     240
tgaacgctct cctgagtagg acaaatccgc cgggagcgga tttgaacgtt gcgaagcaac     300
ggcccggagg gtggcgggca ggacgcccgc cataaactgc caggcatcaa attaagcaga     360
aggccatcct gacggatggc cttttttgcgt ggccagtgcc aagcttgcat gcagattgca     420
gcattacacg tcttgagcga ttgtgtaggc tggagctgct tcgaagttcc tatactttct     480
agagaatagg aacttcggaa taggaactaa ggaggatatt catatggacc atggctaatt     540
cccaggtacc agttgttctt attggtggtg ttgctttatg gttgcatcgt agtaaatggt     600
tgtaacaaaa gcaattttc cggctgtctg tatacaaaaa cgccgtaaag tttgagcgaa     660
gtcaataaac tctctaccca ttcagggcaa tatctctctt ggatccaaag tgaactctag     720
aaataatttt gtttaacttt aagaaggaga tatacatatg gtaaaggaac gtaaaaccga     780
gttggtcgag ggattccgcc attcggttcc ctgtatcaat acccaccggg gaaaaacgtt     840
tgtcatcatg ctcggcggtg aagccattga gcatgagaat ttctccagta tcgttaatga     900
tatcgggttg ttgcacagcc tcggcatccg tctggtggtg gtctatggcg cacgtccgca     960
gatcgacgca aatctggctg cgcatcacca cgaaccgctg tatcacaaga atatacgtgt    1020
gaccgacgcc aaaacactgg aactggtgaa gcaggctgcg ggaacattgc aactggatat    1080
tactgctcgc ctgtcgatga gtctcaataa cacgccgctg cagggcgcgc atatcaacgt    1140
cgtcagtggc aattttatta ttgcccagcc gctgggcgtc gatgacgcg tggattactg    1200 ccatagcggg cgtatccggc ggattgatga agacgcgatc catcgtcaac tggacagcgg    1260
tgcaatagtg ctaatggggc cggtcgctgt ttcagtcact ggcgagagct taacctgac    1320 ctcggaagag attgccactc aactggccat caaactgaaa gctgaaaga tgattggttt    1380 ttgctcttcc cagggcgtca ctaatgacga cggtgatatt gtctccgaac ttttccctaa    1440
```

| | | | | |
|---|---|---|---|---|
| cgaagcgcaa | gcgcgggtag | aagcccagga | agagaaaggc | gattacaact ccggtacggt | 1500 |
| gcgcttttg | cgtggcgcag | tgaaagcctg | ccgcagcggc | gtgcgtcgct gtcatttaat | 1560 |
| cagttatcag | gaagatggcg | cgctgttgca | agagttgttc | tcacgcgacg gtatcggtac | 1620 |
| gcagattgtg | atggaaagcg | ccgagcagat | tcgtcgcgca | acaatcaacg atattggcgg | 1680 |
| tattctggag | ttgattcgcc | cactggagca | gcaaggtatt | ctggtacgcc gttctcgcga | 1740 |
| gcagctggag | atggaaatcg | acaaattcac | cattattcag | cgcgataaca cgactattgc | 1800 |
| ctgcgccgcg | ctctatccgt | tcccggaaga | gaagattggg | gaaatggcct gtgtggcagt | 1860 |
| tcacccggat | taccgcagtt | catcaagggg | tgaagttctg | ctggaacgca ttgccgctca | 1920 |
| ggctaagcag | agcggcttaa | gcaaattgtt | tgtgctgacc | acgcgcagta ttcactggtt | 1980 |
| ccaggaacgt | ggatttaccc | cagtggatat | tgatttactg | cccgagagca aaaagcagtt | 2040 |
| gtacaactac | cagcgtaaat | ccaaagtgtt | gatggcggat | ttagggtaag tcgacgcatg | 2100 |
| catcgataag | ccgcgttctc | atcctcccgc | ctcctccccc | ataaaaaagc caggggtgg | 2160 |
| aggatttaag | ccatctcctg | atgac | | | 2185 |

<210> SEQ ID NO 39
<211> LENGTH: 1137
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 39

| | | | | |
|---|---|---|---|---|
| atggatttaa | attctaaaaa | atatcagatg | cttaaagagc | tatatgtaag cttcgctgaa | 60 |
| aatgaagtta | aaccttttagc | aacagaactt | gatgaagaag | aaagatttcc ttatgaaaca | 120 |
| gtggaaaaaa | tggcaaaagc | aggaatgatg | ggtataccat | atccaaaaga atatggtgga | 180 |
| gaaggtggag | acactgtagg | atatataatg | gcagttgaag | aattgtctag agtttgtggt | 240 |
| actacaggag | ttatattatc | agctcataca | tctcttggct | catggcctat atatcaatat | 300 |
| ggtaatgaag | aacaaaaaca | aaattctta | agaccactag | caagtggaga aaaattagga | 360 |
| gcatttggtc | ttactgagcc | taatgctggt | acagatgcgt | ctggccaaca aacaactgct | 420 |
| gttttagacg | gggatgaata | catacttaat | ggctcaaaaa | tatttataac aaacgcaata | 480 |
| gctggtgaca | tatatgtagt | aatggcaatg | actgataaat | ctaaggggaa caaaggaata | 540 |
| tcagcattta | tagttgaaaa | aggaactcct | gggtttagct | ttggagttaa agaaaagaaa | 600 |
| atgggtataa | gaggttcagc | tacgagtgaa | ttaatatttg | aggattgcag aatacctaaa | 660 |
| gaaaatttac | ttggaaaaga | aggtcaagga | tttaagatag | caatgtctac tcttgatggt | 720 |
| ggtagaattg | gtatagctgc | acaagcttta | ggtttagcac | aaggtgctct tgatgaaact | 780 |
| gttaaatatg | taaagaaag | agtacaattt | ggtagaccat | atcaaaaatt ccaaatacaa | 840 |
| caattccaat | tagctgatat | ggaagttaag | gtacaagcgg | ctagcacct tgtatatcaa | 900 |
| gcagctataa | ataaagactt | aggaaaacct | tatggagtag | aagcagcaat ggcaaaatta | 960 |
| tttgcagctg | aaacagctat | ggaagttact | acaaaagctg | tacaacttca tggaggatat | 1020 |
| ggatacactc | gtgactatcc | agtagaaaga | atgatgagag | atgctaagat aactgaaata | 1080 |
| tatgaaggaa | ctagtgaagt | tcaaagaatg | gttatttcag | gaaaactatt aaaatag | 1137 |

<210> SEQ ID NO 40
<211> LENGTH: 783

```
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 40
atgaatatag tcgtttgtat aaaacaagtt ccagatacaa cagaagttaa actagatcct    60
aatacaggta cttaattag agatggagta ccaagtataa taaaccctga tgataaagca    120
ggtttagaag aagctataaa attaaaagaa gaaatgggtg ctcatgtaac tgttataaca    180
atgggacctc ctcaagcaga tatggcttta aagaagctt tagcaatggg tgcagataga    240
ggtatattat taacagatag agcatttgcg ggtgctgata cttgggcaac ttcatcagca    300
ttagcaggag cattaaaaaa tatagatttt gatattataa tagctggaag acaggcgata    360
gatggagata ctgcacaagt tggacctcaa atagctgaac atttaaatct tccatcaata    420
acatatgctg aagaaataaa aactgaaggt gaatatgtat tagtaaaaag acaatttgaa    480
gattgttgcc atgacttaaa agttaaaatg ccatgcctta acaactct taaagatatg    540 aacacaccaa gatacatgaa agttggaaga atatatgatg ctttcgaaaa tgatgtagta    600
gaaacatgga ctgtaaaaga tatagaagtt gacccttcta atttaggtct taaaggttct    660
ccaactagtg tatttaaatc atttacaaaa tcagttaaac cagctggtac aatatacaat    720
gaagatgcga aacatcagc tggaattatc atagataaat taaaagagaa gtatatcata    780
taa                                                                 783

<210> SEQ ID NO 41
<211> LENGTH: 1011
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 41
atgggtaacg ttttagtagt aatagaacaa agagaaaatg taattcaaac tgtttctta    60 gaattactag gaaaggctac agaaatagca aaagattatg atacaaaagt ttctgcatta    120
cttttaggta gtaaggtaga aggttaata gatacattag cacactatgg tgcagatgag    180
gtaatagtag tagatgatga agctttagca gtgtatacaa ctgaaccata caaaaagca    240 gcttatgaag caataaaagc agctgaccct atagttgtat tatttggtgc aacttcaata    300
ggtagagatt tagcgcctag agtttctgct agaatacata caggtcttac tgctgactgt    360
acaggtcttg cagtagctga agatacaaaa ttattattaa tgacaagacc tgcctttggt    420
ggaaatataa tggcaacaat agtttgtaaa gatttcagac ctcaaatgtc tacagttaga    480 ccagggggtta tgaagaaaaa tgaacctgat gaaactaaag aagctgtaat taaccgtttc    540
aaggtagaat taatgatgc tgataaatta gttcaagttg tacaagtaat aaaagaagct    600
aaaaaacaag ttaaaataga agatgctaag atattagttt ctgctggacg tggaatgggt    660 ggaaagaaa acttagacat acttatgaa ttagctgaaa ttataggtgg agaagtttct    720
ggttctcgtg ccactataga tgcaggttgg ttagataaag caagacaagt tggtcaaact    780
ggtaaaactg taagaccaga cctttatata gcatgtggta tatctggagc aatacaacat    840
atagctggta tggaagatgc tgagtttata gttgctataa ataaaaatcc agaagctcca    900
atatttaaat atgctgatgt tggtatagtt ggagatgttc ataaagtgct tccagaactt    960
```
atcagtcagt taagtgttgc aaaagaaaaa ggtgaagttt tagctaacta a        1011

<210> SEQ ID NO 42
<211> LENGTH: 1176
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 42

| | | | | |
|---|---|---|---|---|
| atgagagaag | tagtaattgc | cagtgcagct | agaacagcag | taggaagttt tggaggagca | 60 |
| tttaaatcag | tttcagcggt | agagttaggg | gtaacagcag | ctaaagaagc tataaaaga | 120 |
| gctaacataa | ctccagatat | gatagatgaa | tctcttttag | ggggagtact tacagcaggt | 180 |
| cttggacaaa | atatagcaag | acaaatagca | ttaggagcag | gaataccagt agaaaaacca | 240 |
| gctatgacta | taaatatagt | ttgtggttct | ggattaagat | ctgtttcaat ggcatctcaa | 300 |
| cttatagcat | taggtgatgc | tgatataatg | ttagttggtg | gagctgaaaa catgagtatg | 360 |
| tctccttatt | tagtaccaag | tgcgagatat | ggtgcaagaa | tgggtgatgc tgcttttgtt | 420 |
| gattcaatga | taaagatgg | attatcagac | atatttaata | actatcacat gggtattact | 480 |
| gctgaaaaca | tagcagagca | atggaatata | actagagaag | aacaagatga attagctctt | 540 |
| gcaagtcaaa | ataaagctga | aaaagctcaa | gctgaaggaa | aatttgatga gaaatagtt | 600 |
| cctgttgtta | taaaaggaag | aaaaggtgac | actgtagtag | ataaagatga atatattaag | 660 |
| cctggcacta | caatggagaa | acttgctaag | ttaagacctg | catttaaaaa agatggaaca | 720 |
| gttactgctg | gtaatgcatc | aggaataaat | gatggtgctg | ctatgttagt agtaatggct | 780 |
| aaagaaaaag | ctgaagaact | aggaatagag | cctcttgcaa | ctatagtttc ttatggaaca | 840 |
| gctggtgttg | accctaaaat | aatgggatat | ggaccagttc | cagcaactaa aaaagcttta | 900 |
| gaagctgcta | atatgactat | tgaagatata | gatttagttg | aagctaatga ggcatttgct | 960 |
| gcccaatctg | tagctgtaat | aagagactta | aatatagata | tgaataaagt taatgttaat | 1020 |
| ggtggagcaa | tagctatagg | acatccaata | ggatgctcag | gagcaagaat acttactaca | 1080 |
| ctttatatg | aaatgaagag | aagagatgct | aaaactggtc | ttgctacact ttgtataggc | 1140 |
| ggtggaatgg | gaactacttt | aatagttaag | agatag | | 1176 |

<210> SEQ ID NO 43
<211> LENGTH: 846
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 43

| | | | | |
|---|---|---|---|---|
| atgaaattag | ctgtaatagg | tagtggaact | atgggaagtg | gtattgtaca aactttgca | 60 |
| agttgtggac | atgatgtatg | tttaaagagt | agaactcaag | gtgctataga taatgttta | 120 |
| gcttattag | ataaaaattt | aactaagtta | gttactaagg | gaaaaatgga tgaagctaca | 180 |
| aaagcagaaa | tattaagtca | tgttagttca | actactaatt | atgaagattt aaagatatg | 240 |
| gatttaataa | tagaagcatc | tgtagaagac | atgaatataa | agaaagatgt ttcaagtta | 300 |
| ctagatgaat | tatgtaaaga | agatactatc | ttggcaacaa | atacttcatc attatctata | 360 |
| acagaaatag | cttcttctac | taagcgccca | gataaagtta | taggaatgca tttctttaat | 420 |
| ccagttccta | tgatgaaatt | agttgaagtt | ataagtggtc | agttaacatc aaaagttact | 480 |

```
tttgatacag tatttgaatt atctaagagt atcaataaag taccagtaga tgtatctgaa    540
tctcctggat tgtagtaaa tagaatactt atacctatga taaatgaagc tgttggtata    600
tatgcagatg gtgttgcaag taaagaagaa atagatgaag ctatgaaatt aggagcaaac    660
catccaatgg gaccactagc attaggtgat ttaatcggat tagatgttgt tttagctata    720
atgaacgttt tatatactga atttggagat actaaatata gacctcatcc acttttagct    780
aaaatggtta gagctaatca attaggaaga aaaactaaga taggattcta tgattataat    840
aaataa                                                              846

<210> SEQ ID NO 44
<211> LENGTH: 798
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 44
atgagtacaa gtgatgttaa agtttatgag aatgtagctg ttgaagtaga tggaaatata     60
tgtacagtga aaatgaatag acctaaagcc cttaatgcaa taaattcaaa gactttagaa    120
gaactttatg aagtatttgt agatattaat aatgatgaaa ctattgatgt tgtaatattg    180
acaggggaag gaaaggcatt tgtagctgga gcagatattg catacatgaa agatttagat    240
gctgtagctg ctaaagattt tagtatctta ggagcaaaag cttttggaga aatagaaaat    300
agtaaaaaag tagtgatagc tgctgtaaac ggatttgctt taggtggagg atgtgaactt    360
gcaatggcat gtgatataag aattgcatct gctaaagcta aatttggtca gccagaagta    420
actcttggaa taactccagg atatggagga actcaaaggc ttacaagatt ggttggaatg    480
gcaaaagcaa aagaattaat cttttacaggt caagttataa aagctgatga agctgaaaaa    540
atagggctag taaatagagt cgttgagcca gacattttaa tagaagaagt tgagaaatta    600
gctaagataa tagctaaaaa tgctcagctt gcagttagat actctaaaga agcaatacaa    660
cttggtgctc aaactgatat aaatactgga atagatatag aatctaattt atttggtctt    720 tgttttttcaa ctaaagacca aaaagaagga atgtcagctt tcgttgaaaa gagagaagct    780
aactttataa aagggtaa                                                 798

<210> SEQ ID NO 45
<211> LENGTH: 903
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 45
atgagaagtt ttgaagaagt aattaagttt gcaaaagaaa gaggacctaa aactatatca     60
gtagcatgtt gccaagataa agaagtttta atggcagttg aaatggctag aaaagaaaaa    120
atagcaaatg ccattttagt aggagatata gaaaagacta agaaattgc aaaaagcata    180 gacatggata tcgaaaatta tgaactgata gatataaaag atttagcaga agcatctcta    240
aaatctgttg aattagtttc acaaggaaaa gccgacatgg taatgaaagg cttagtagac    300
acatcaataa tactaaaagc agttttaaat aaagaagtag gtcttagaac tggaaatgta    360
ttaagtcacg tagcagtatt tgatgtagag ggatatgata gattattttt cgtaactgac    420
```

```
gcagctatga acttagctcc tgatacaaat actaaaaagc aaatcataga aaatgcttgc    480
acagtagcac attcattaga tataagtgaa ccaaaagttg ctgcaatatg cgcaaaagaa    540
aaagtaaatc caaaaatgaa agatacagtt gaagctaaag aactagaaga aatgtatgaa    600
agaggagaaa tcaaaggttg tatggttggt gggccttttg caattgataa tgcagtatct    660
ttagaagcag ctaaacataa aggtataaat catcctgtag caggacgagc tgatatatta    720
ttagccccag atattgaagg tggtaacata ttatataaag ctttggtatt cttctcaaaa    780
tcaaaaaatg caggagttat agttggggct aaagcaccaa taatattaac ttctagagca    840
gacagtgaag aaactaaact aaactcaata gctttaggtg ttttaatggc agcaaaggca    900
taa                                                                 903
```

<210> SEQ ID NO 46
<211> LENGTH: 1080
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 46

```
atgagcaaaa tatttaaaat cttaacaata aatcctggtt cgacatcaac taaaatagct     60
gtatttgata tgaggatttt agtatttgaa aaaactttaa gacattcttc agaagaaata    120
ggaaaatatg agaaggtgtc tgaccaattt gaatttcgta acaagtaat agaagaagct    180 ctaaaagaag gtggagtaaa aacatctgaa ttagatgctg tagtaggtag aggaggactt    240
cttaaaccta taaaggtgg tacttattca gtaagtgctg ctatgattga agatttaaaa    300
gtgggagttt taggagaaca cgcttcaaac ctaggtggaa taatagcaaa acaaataggt    360
gaagaagtaa atgttccttc atacatagta gaccctgttg ttgtagatga attagaagat    420
gttgctagaa tttctggtat gcctgaaata agtagagcaa gtgtagtaca tgctttaaat    480
caaaaggcaa tagcaagaag atatgctaga gaaataaaca agaaatatga agatataaat    540
cttatagttg cacacatggg tggaggagtt tctgttggag ctcataaaaa tggtaaaata    600
gtagatgttg caaacgcatt agatggagaa ggaccttct ctccagaaag aagtggtgga    660
ctaccagtag gtgcattagt aaaaatgtgc tttagtggaa aatatactca agatgaaatt    720 aaaagaaaa taaaggtaa tggcggacta gttgcatact aaacactaa tgatgctaga    780 gaagttgaag aaagaattga agctggtgat gaaaagcta aattagtata tgaagctatg    840
gcatatcaaa tctctaaaga aataggagct agtgctgcag ttcttaaggg agatgtaaaa    900
gcaatattat taactggtgg aatcgcatat tcaaaaatgt ttacagaaat gattgcagat    960
agagttaaat ttatagcaga tgtaaaagtt tatccaggtg aagatgaaat gattgcatta   1020
gctcaaggtg gacttagagt tttaactggt gaagaagagg ctcaagttta tgataactaa   1080
```

<210> SEQ ID NO 47
<211> LENGTH: 1194
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 47

```
atgatcgtaa aacctatggt acgcaacaat atctgcctga cgcccatcc tcagggctgc     60 aagaagggag tggaagatca gattgaatat accaagaaac gcattaccgc agaagtcaaa    120
```

```
gctggcgcaa aagctccaaa aaacgttctg gtgcttggct gctcaaatgg ttacggcctg      180
gcgagccgca ttactgctgc gttcggatac ggggctgcga ccatcggcgt gtcctttgaa      240
aaagcgggtt cagaaaccaa atatggtaca ccgggatggt acaataattt ggcatttgat      300
gaagcggcaa aacgcgaggg tctttatagc gtgacgatcg acggcgatgc gttttcagac      360
gagatcaagg cccaggtaat tgaggaagcc aaaaaaaaag gtatcaaatt tgatctgatc      420
gtatacagct tggccagccc agtacgtact gatcctgata caggtatcat gcacaaaagc      480
gttttgaaac cctttggaaa aacgttcaca ggcaaaacag tagatccgtt tactggcgag      540
ctgaaggaaa tctccgcgga accagcaaat gacgaggaag cagccgccac tgttaaagtt      600 atgggggtg aagattggga acgttggatt aagcagctgt cgaaggaagg cctcttagaa       660
gaaggctgta ttaccttggc ctatagttat attggccctg aagctaccca agctttgtac      720
cgtaaaggca caatcggcaa ggccaaagaa cacctggagg ccacagcaca ccgtctcaac      780
aaagagaacc cgtcaatccg tgccttcgtg agcgtgaata aaggcctggt aacccgcgca      840
agcgccgtaa tcccggtaat ccctctgtat ctcgccagct tgttcaaagt aatgaaagag      900
aagggcaatc atgaaggttg tattgaacag atcacgcgtc tgtacgccga gcgcctgtac      960
cgtaaagatg gtacaattcc agttgatgag gaaaatcgca ttcgcattga tgattgggag     1020
ttagaagaag acgtccagaa agcggtatcc gcgttgatgg agaaagtcac gggtgaaaac     1080
gcagaatctc tcactgactt agcggggtac cgccatgatt tcttagctag taacggcttt     1140
gatgtagaag gtattaatta tgaagcggaa gttgaacgct tcgaccgtat ctga           1194
```

<210> SEQ ID NO 48
<211> LENGTH: 861
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 48

```
atgagtcagg cgctaaaaaa tttactgaca ttgttaaatc tggaaaaaat tgaggaagga       60
ctctttcgcg gccagagtga agatttaggt ttacgccagg tgtttggcgg ccaggtcgtg      120
ggtcaggcct tgtatgctgc aaaagagacc gtccctgaag agcggctggt acattcgttt      180
cacagctact ttcttcgccc tggcgatagt aagaagccga ttatttatga tgtcgaaacg      240
ctgcgtgacg gtaacagctt cagcgcccgc cgggttgctg ctattcaaaa cggcaaaccg      300
atttttatta tgactgcctc tttccaggca ccagaagcgg gtttcgaaca tcaaaaaaca      360
atgccgtccg cgccagcgcc tgatggcctc ccttcggaaa cgcaaatcgc caatcgctg      420 gcgcacctgc tgccgccagt gctgaaagat aaattcatct gcgatcgtcc gctggaagtc      480
cgtccggtgg agtttcataa cccactgaaa ggtcacgtcg cagaaccaca tcgtcaggtg      540
tggatccgcg caaatggtag cgtgccggat gacctgcgcg ttcatcagta tctgctcggt      600
tacgcttctg atcttaactt cctgccggta gctctacagc cgcacggcat cggttttctc      660
gaaccgggga ttcagattgc caccattgac cattccatgt ggttccatcg cccgtttaat      720
ttgaatgaat ggctgctgta tagcgtggag agcacctcgg cgtccagcgc acgtggcttt      780
gtgcgcggtg agttttatac ccaagacggc gtactggttg cctcgaccgt tcaggaaggg      840
gtgatgcgta atcacaatta a                                                861
```

-continued

<210> SEQ ID NO 49
<211> LENGTH: 1575
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 49

| | | | | | |
|---|---|---|---|---|---|
| atgcgcaaag | tgccgattat | cacggctgac | gaggccgcaa | aactgatcaa | ggacggcgac | 60 |
| accgtgacaa | ctagcggctt | tgtgggtaac | gcgatccctg | aggcccttga | ccgtgcagtc | 120 |
| gaaaagcgtt | tcctggaaac | gggcgaaccg | aagaacatta | cttatgtata | ttgcggcagt | 180 |
| cagggcaatc | gcgacggtcg | tggcgcagaa | catttcgcgc | atgaaggcct | gctgaaacgt | 240 |
| tatatcgctg | gccattgggc | gaccgtcccg | gcgttaggga | aaatggccat | ggagaataaa | 300 |
| atggaggcct | acaatgtctc | tcagggcgcc | ttgtgtcatc | tctttcgcga | tattgcgagc | 360 |
| cataaaccgg | gtgtgttcac | gaaagtagga | atcggcacct | tcattgatcc | acgtaacggt | 420 |
| ggtgggaagg | tcaacgatat | taccaaggaa | gatatcgtag | aactggtgga | aattaaaggg | 480 |
| caggaatacc | tgttttatcc | ggcgttcccg | atccatgtcg | cgctgattcg | tggcacctat | 540 |
| gcggacgaga | gtggtaacat | cacctttgaa | aagaggtag | cgcctttgga | agggacttct | 600 |
| gtctgtcaag | cggtgaagaa | ctcgggtggc | attgtcgtgg | ttcaggttga | gcgtgtcgtc | 660 |
| aaagcaggca | cgctggatcc | gcgccatgtg | aaagttccgg | gtatctatgt | agattacgta | 720 |
| gtcgtcgcgg | atccggagga | ccatcaacag | tcccttgact | gcgaatatga | tcctgccctt | 780 |
| agtggagagc | accgtcgtcc | ggaggtggtg | ggtgaaccac | tgcctttatc | cgcgaagaaa | 840 |
| gtcatcggcc | gccgtggcgc | gattgagctc | gagaaagacg | ttgcagtgaa | ccttggggta | 900 |
| ggtgcacctg | agtatgtggc | ctccgtggcc | gatgaagaag | gcattgtgga | ttttatgact | 960 |
| ctcacagcgg | agtccggcgc | tatcggtggc | gttccagccg | gcggtgttcg | ctttggggcg | 1020 |
| agctacaatg | ctgacgcctt | gatcgaccag | ggctaccaat | ttgattatta | cgacggtggg | 1080 |
| ggtctggatc | tttgttacct | gggtttagct | gaatgcgacg | aaaagggtaa | tatcaatgtt | 1140 |
| agccgcttcg | gtcctcgtat | cgctgggtgc | ggcggattca | ttaacattac | caaaacacg | 1200 |
| ccgaaagtct | tcttttgtgg | gacctttaca | gccggggggc | tgaaagtgaa | aattgaagat | 1260 |
| ggtaaggtga | ttatcgttca | ggaagggaaa | cagaagaaat | tccttaaggc | agtggagcaa | 1320 |
| atcacccttta | atggagacgt | ggccttagcg | aacaagcaac | aagttaccta | catcacggag | 1380 |
| cgttgcgtct | tcctcctcaa | agaagacggt | ttacaccttt | cggaaatcgc | gccaggcatc | 1440 |
| gatctgcaga | cccagatttt | ggatgttatg | gactttgccc | cgatcattga | tcgtgacgca | 1500 |
| aacgggcaga | ttaaactgat | ggacgcggcg | ttattcgcag | aagggctgat | gggcttgaaa | 1560 |
| gaaatgaagt | cttaa | | | | | 1575 |

<210> SEQ ID NO 50
<211> LENGTH: 1269
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 50

| | | | | | |
|---|---|---|---|---|---|
| atgagcttaa | cccaaggcat | gaaagctaaa | caactgttag | catactttca | gggtaaagcc | 60 |
| gatcaggatg | cacgtgaagc | gaaagcccgc | ggtgagctgg | tctgctggtc | ggcgtcagtc | 120 |

| | |
|---|---|
| gcgccgccgg aattttgcgt aacaatgggc attgccatga tctacccgga gactcatgca | 180 |
| gcgggcatcg gtgcccgcaa aggtgcgatg gacatgctgg aagttgcgga ccgcaaaggc | 240 |
| tacaacgtgg attgttgttc ctacggccgt gtaaatatgg gttacatgga atgtttaaaa | 300 |
| gaagccgcca tcacgggcgt caagccggaa gttttggtta attccctgc tgctgacgtt | 360 |
| ccgcttcccg atttggtgat tacgtgtaat aatatctgta acacgctgct gaaatggtac | 420 |
| gaaaacttag cagcagaact cgatattcct tgcatcgtga tcgacgtacc gtttaatcat | 480 |
| accatgccga ttccggaata tgccaaggcc tacatcgcgg accagttccg caatgcaatt | 540 |
| tctcagctgg aagttatttg tggccgtccg ttcgattgga agaaatttaa ggaggtcaaa | 600 |
| gatcagaccc agcgtagcgt ataccactgg aaccgcattg ccgagatggc gaaatacaag | 660 |
| cctagcccgc tgaacggctt cgatctgttc aattacatgg cgttaatcgt ggcgtgccgc | 720 |
| agcctggatt atgcagaaat tacctttaaa gcgttcgcgg acgaattaga agagaatttg | 780 |
| aaggcgggta tctacgcctt taaaggtgcg gaaaaaacgc gctttcaatg ggaaggtatc | 840 |
| gcggtgtggc cacatttagg tcacacgttt aaatctatga agaatctgaa ttcgattatg | 900 |
| accggtacgg catacccgc cctttgggac ctgcactatg acgctaacga cgaatctatg | 960 |
| cactctatgg ctgaagcgta cacccgtatt tatattaata cttgtctgca gaacaaagta | 1020 |
| gaggtcctgc ttgggatcat ggaaaaaggc caggtggatg gtaccgtata tcatctgaat | 1080 |
| cgcagctgca aactgatgag tttcctgaac gtggaaacgg ctgaaattat aaagagaag | 1140 |
| aacggtcttc cttacgtctc cattgatggc gatcagaccg atcctcgcgt ttttctccg | 1200 |
| gcccagtttg atacccgtgt tcaggccctg gttgagatga tggaggccaa tatggcggca | 1260 |
| gcggaataa | 1269 |

<210> SEQ ID NO 51
<211> LENGTH: 1125
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 51

| | |
|---|---|
| atgtcacgcg tggaggcaat cctgtcgcag ctgaaagatg tcgccgcgaa tccgaaaaaa | 60 |
| gccatggatg actataaagc tgaaacaggt aagggcgcgg ttggtatcat gccgatctac | 120 |
| agccccgaag aaatggtaca cgccgctggc tatttgccga tgggaatctg ggcgcccag | 180 |
| ggcaaaacga ttagtaaagc gcgcacctat ctgcctgctt ttgcctgcag cgtaatgcag | 240 |
| caggttatgg aattacagtg cgagggcgcg tatgatgacc tgtccgcagt tatttttagc | 300 |
| gtaccgtgcg acactctcaa atgtcttagc cagaaatgga aagtacgtc cccagtgatt | 360 |
| gtatttacgc atccgcagaa ccgcggatta gaagcggcga accaattctt ggttaccgag | 420 |
| tatgaactgc taaaagcaca actggaatca gttctgggtg tgaaaatttc aaacgccgcc | 480 |
| ctggaaaatt cgattgcaat ttataacgag atcgtgccg tgatgcgtga ttcgtgaaa | 540 |
| gtggcagcgg actatcctca agtcattgac gcagtgagcc gccacgcggt ttttaaagcg | 600 |
| cgccagttta tgcttaagga aaaacatacc gcacttgtga agaactgat cgctgagatt | 660 |
| aaagcaacgc cagtccagcc gtgggacgga aaaaaggttg tagtgacggg cattctgttg | 720 |
| gaaccgaatg agttattaga tatctttaat gagtttaaga tcgcgattgt tgatgatgat | 780 |
| ttagcgcagg aaagccgtca gatccgtgtt gacgttctgg acggagaagg cggaccgctc | 840 |

-continued

| | |
|---|---|
| taccgtatgg ctaaagcgtg gcagcaaatg tatggctgct cgctggcaac cgacaccaag | 900 |
| aagggtcgcg gccgtatgtt aattaacaaa acgattcaga ccggtgcgga cgctatcgta | 960 |
| gttgcaatga tgaagttttg cgacccagaa gaatgggatt atccggtaat gtaccgtgaa | 1020 |
| tttgaagaaa aagggggtcaa atcacttatg attgaggtgg atcaggaagt atcgtctttc | 1080 |
| gaacagatta aaacccgtct gcagtcattc gtcgaaatgc tttaa | 1125 |

<210> SEQ ID NO 52
<211> LENGTH: 779
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 52

| | |
|---|---|
| atgtatacct tggggattga tgtcggttct gcctctagta aagcggtgat tctgaaagat | 60 |
| ggaaaagata ttgtcgctgc cgaggttgtc caagtcggta ccggctcctc gggtccccaa | 120 |
| cgcgcactgg acaaagcctt tgaagtctct ggcttaaaaa aggaagacat cagctacaca | 180 |
| gtagctacgg gctatgggcg cttcaatttt agcgacgcgg ataaacagat tcggaaatt | 240 |
| agctgtcatg ccaaaggcat ttatttctta gtaccaactg cgcgcactat tattgacatt | 300 |
| ggcggccaag atgcgaaagc catccgcctg gacgacaagg ggggtattaa gcaattcttc | 360 |
| atgaatgata aatgcgcggc gggcacgggg cgtttcctgg aagtcatggc tcgcgtactt | 420 |
| gaaaccaccc tggatgaaat ggctgaactg atgaacagg cgactgacac cgctcccatt | 480 |
| tcaagcacct gcacggtttt cgccgaaagc gaagtaatta gccaattgag caatggtgtc | 540 |
| tcacgcaaca acatcattaa aggtgtccat ctgagcgttg cgtcacgtgc gtgtggtctg | 600 |
| gcgtatcgcg gcggtttgga gaaagatgtt gttatgacag gtggcgtggc aaaaaatgca | 660 |
| ggggtggtgc gcgcggtggc gggcgttctg aagaccgatg ttatcgttgc tccgaatcct | 720 |
| cagacgaccg gtgcactggg ggcagcgctg tatgcttatg aggccgccca gaagaagta | 779 |

<210> SEQ ID NO 53
<211> LENGTH: 1104
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 53

| | |
|---|---|
| atggccttca atagcgcaga tattaattct ttccgcgata tttgggtgtt ttgtgaacag | 60 |
| cgtgagggca aactgattaa caccgatttc gaattaatta gcgaaggtcg taaactggct | 120 |
| gacgaacgcg gaagcaaact ggttggaatt ttgctggggc acgaagttga agaaatcgca | 180 |
| aaagaattag gcggctatgg tgcggacaag gtaattgtgt gcgatcatcc ggaacttaaa | 240 |
| ttttacacta cggatgctta tgccaaagtt ttatgtgacg tcgtgatgga agagaaaccg | 300 |
| gaggtaattt tgatcggtgc caccaacatt ggccgtgatc tcggaccgcg ttgtgctgca | 360 |
| cgcttgcaca cggggctgac ggctgattgc acgcacctgg atattgatat gaataaatat | 420 |
| gtggactttc ttagcaccag tagcaccttg gatatctcgt cgatgacttt ccctatggaa | 480 |
| gatacaaacc ttaaaatgac gcgccctgca tttggcggac atctgatggc aacgatcatt | 540 |
| tgtccacgct tccgtccctg tatgagcaca gtgcgccccg gagtgatgaa gaaagcggag | 600 |
| ttctcgcagg agatggcgca agcatgtcaa gtagtgaccc gtcacgtaaa tttgtcggat | 660 |

```
gaagacctta aaactaaagt aattaatatc gtgaaggaaa cgaaaaagat tgtggatctg    720
atcggcgcag aaattattgt gtcagttggt cgtggtatct cgaaagatgt ccaaggtgga    780
attgcactgg ctgaaaaact tgcggacgca tttggtaacg gtgtcgtggg cggctcgcgc    840
gcagtgattg attccggctg gttacctgcg gatcatcagg ttggacaaac cggtaagacc    900
gtgcacccga agtctacgt ggcgctgggt attagtgggg ctatccagca taaggctggg    960
atgcaagact ctgaactgat cattgccgtc aacaaagacg aaacggcgcc tatcttcgac    1020
tgcgccgatt atggcatcac cggtgattta tttaaaatcg taccgatgat gatcgacgcg    1080
atcaaagagg gtaaaaacgc atga                                           1104
```

<210> SEQ ID NO 54
<211> LENGTH: 804
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 54

```
atgcgcatct atgtgtgtgt gaaacaagtc ccagatacga gcggcaaggt ggccgttaac     60
cctgatggga cccttaaccg tgcctcaatg gcagcgatta ttaacccgga cgatatgtcc    120
gcgatcgaac aggcattaaa actgaaagat gaaaccggat gccaggttac ggcgcttacg    180
atgggtcctc ctcctgccga gggcatgttg cgcgaaatta ttgcaatggg ggccgacgat    240
ggtgtgctga tttcggcccg tgaatttggg ggtccgata ccttcgcaac cagtcaaatt     300
attagcgcgg caatccataa attaggctta agcaatgaag acatgatctt tgcggtcgt    360 caggccattg acgtgatac ggcccaagtc ggccctcaaa ttgccgaaaa actgagcatc    420
ccacaggtaa cctatggcgc aggaatcaaa aaatctggtg atttagtgct ggtgaagcgt    480
atgttggagg atggttatat gatgatcgaa gtcgaaactc catgtctgat tacctgcatt    540
caggataaag cggtaaaacc acgttacatg actctcaacg gtattatgga atgctactcc    600
aagccgctcc tcgttctcga ttacgaagca ctgaaagatg aaccgctgat cgaacttgat    660
accattgggc ttaaaggctc cccgacgaat atctttaaat cgtttacgcc gcctcagaaa    720
ggcgttggtg tcatgctcca aggcaccgat aaggaaaaag tcgaggatct ggtggataag    780
ctgatgcaga acatgtcat ctaa                                            804
```

<210> SEQ ID NO 55
<211> LENGTH: 1185
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 55

```
atgttcttac tgaagattaa aaaagaacgt atgaaacgca tggactttag tttaacgcgt     60
gaacaggaga tgttaaaaaa actggcgcgt cagtttgctg agatcgagct ggaaccggtg    120
gccgaagaga ttgatcgtga gcacgttttt cctgcagaaa actttaagaa gatgcggaa    180 attggcttaa ccggcattgg tatcccgaaa gaatttggtg gctccggtgg aggcaccctg    240
gagaaggtca ttgccgtgtc agaattcggc aaaaagtgta tggcctcagc ttccatttta    300
agcattcatc ttatcgcgcc gcaggcaatc tacaaatatg gaccaaaga acagaaagag    360
```

| | |
|---|---|
| acgtacctgc cgcgtcttac caaaggtggt gaactgggcg cctttgcgct gacagaacca | 420 |
| aacgccggaa gcgatgccgg cgcggtaaaa acgaccgcga ttctggacag ccagacaaac | 480 |
| gagtacgtgc tgaatggcac caaatgcttt atcagcgggg cgggcgcgc gggtgttctt | 540 |
| gtaatttttg cgcttactga accgaaaaaa ggtctgaaag ggatgagcgc gattatcgtg | 600 |
| gagaaaggga ccccgggctt cagcatcggc aaggtggaga gcaagatggg gatcgcaggt | 660 |
| tcggaaaccg cggaacttat cttcgaagat tgtcgcgttc cggctgccaa ccttttaggt | 720 |
| aaagaaggca aaggctttaa aattgctatg gaagccctgg atggcgcccg tattggcgtg | 780 |
| ggcgctcaag caatcggaat tgccgagggg gcgatcgacc tgagtgtgaa gtacgttcac | 840 |
| gagcgcattc aatttggtaa accgatcgcg aatctgcagg gaattcaatg gtatatcgcg | 900 |
| gatatggcga ccaaaaccgc gcggcacgc gcacttgttg agtttgcagc gtatcttgaa | 960 |
| gacgcgggta accgttcac aaaggaatct gctatgtgca agctgaacgc ctccgaaaac | 1020 |
| gcgcgttttg tgacaaattt agctctgcag attcacgggg gttacggtta tatgaaagat | 1080 |
| tatccgttag agcgtatgta tcgcgatgct aagattacga aaatttacga ggggacatca | 1140 |
| gaaatccata aggtggtgat tgcgcgtgaa gtaatgaaac gctaa | 1185 |

<210> SEQ ID NO 56
<211> LENGTH: 2463
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 56

| | |
|---|---|
| atgcgagtgt tgaagttcgg cggtacatca gtggcaaatg cagaacgttt tctgcgtgtt | 60 |
| gccgatattc tggaaagcaa tgccaggcag gggcaggtgg ccaccgtcct ctctgccccc | 120 |
| gccaaaatca ccaaccacct ggtggcgatg attgaaaaaa ccattagcgg ccaggatgct | 180 |
| ttacccaata tcagcgatgc cgaacgtatt ttttgccgaac ttttgacggg actcgccgcc | 240 |
| gcccagccgg ggttcccgct ggcgcaattg aaaactttcg tcgatcagga atttgcccaa | 300 |
| ataaaacatg tcctgcatgg cattagtttg ttggggcagt gcccggatag catcaacgct | 360 |
| gcgctgattt gccgtggcga gaaaatgtcg atcgccatta tggccggcgt attagaagcg | 420 |
| cgcggtcaca acgttactgt tatcgatccg gtcgaaaaac tgctggcagt ggggcattac | 480 |
| ctcgaatcta ccgtcgatat tgctgagtcc acccgccgta ttgcggcaag ccgcattccg | 540 |
| gctgatcaca tggtgctgat ggcaggtttc accgccggta tgaaaaagg cgaactggtg | 600 |
| gtgcttggac gcaacggttc cgactactct gctgcggtgc tggctgcctg tttacgcgcc | 660 |
| gattgttgcg agatttggac ggacgttgac ggggtctata cctgcgaccc gcgtcaggtg | 720 |
| cccgatgcga ggttgttgaa gtcgatgtcc taccaggaag cgatggagct ttcctacttc | 780 |
| ggcgctaaag ttcttcaccc ccgcaccatt accccatcg cccagttcca gatcccttgc | 840 |
| ctgattaaaa ataccggaaa tcctcaagca ccaggtacgc tcattggtgc cagccgtgat | 900 |
| gaagacgaat taccggtcaa gggcatttcc aatctgaata acatggcaat gttcagcgtt | 960 |
| tctggtccgg ggatgaaagg gatggtcggc atggcggcgc gcgtctttgc agcgatgtca | 1020 |
| cgcgcccgta tttccgtggt gctgattacg caatcatctt ccgaatacag catcagtttc | 1080 |
| tgcgttccac aaagcgactg tgtgcgagct gaacgggcaa tgcaggaaga gttctacctg | 1140 |
| gaactgaaag aaggcttact ggagccgctg cagtgacgg aacggctggc cattatctcg | 1200 |

-continued

```
gtggtaggtg atggtatgcg caccttgcgt gggatctcgg cgaaattctt tgccgcactg    1260
gcccgcgcca atatcaacat tgtcgccatt gctcagagat cttctgaacg ctcaatctct    1320
gtcgtggtaa ataacgatga tgcgaccact ggcgtgcgcg ttactcatca gatgctgttc    1380
aataccgatc aggttatcga agtgtttgtg attggcgtcg gtggcgttgg cggtgcgctg    1440
ctggagcaac tgaagcgtca gcaaagctgg ctgaagaata acatatcga cttacgtgtc    1500 tgcggtgttg ccaactcgaa ggctctgctc accaatgtac atggccttaa tctggaaaac    1560
tggcaggaag aactggcgca agccaaagag ccgtttaatc tcgggcgctt aattcgcctc    1620
gtgaaagaat atcatctgct gaacccggtc attgttgact gcacttccag ccaggcagtg    1680
gcggatcaat atgccgactt cctgcgcgaa ggtttccacg ttgtcacgcc gaacaaaaag    1740
gccaacacct cgtcgatgga ttactaccat cagttgcgtt atgcggcgga aaaatcgcgg    1800
cgtaaattcc tctatgacac caacgttggg gctggattac cggttattga aacctgcaa     1860 aatctgctca atgcaggtga tgaattgatg aagttctccg gcattctttc tggttcgctt    1920
tcttatatct tcggcaagtt agacgaaggc atgagtttct ccgaggcgac cacgctggcg    1980
cgggaaatgg gttataccga accggacccg cgagatgatc tttctggtat ggatgtggcg    2040
cgtaaactat tgattctcgc tcgtgaaacg ggacgtgaac tggagctggc ggatattgaa    2100
attgaacctg tgctgcccgc agagtttaac gccgagggtg atgttgccgc ttttatggcg    2160
aatctgtcac aactcgacga tctctttgcc gcgcgcgtgg cgaaggcccg tgatgaagga    2220
aaagttttgc gctatgttgg caatattgat gaagatggcg tctgccgcgt gaagattgcc    2280
gaagtggatg gtaatgatcc gctgttcaaa gtgaaaaatg cgaaaacgc cctggccttc     2340 tatagccact attatcagcc gctgccgttg gtactgcgcg gatatggtgc gggcaatgac    2400
gttacagctg ccggtgtctt tgctgatctg ctacgtaccc ctcatggaa gttaggagtc     2460 tga                                                                  2463
```

<210> SEQ ID NO 57
<211> LENGTH: 933
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 57

```
atggttaaag tttatgcccc ggcttccagt gccaatatga gcgtcgggtt tgatgtgctc      60
ggggcggcgg tgacacctgt tgatggtgca ttgctcggag atgtagtcac ggttgaggcg     120
gcagagacat tcagtctcaa caacctcgga cgctttgccg ataagctgcc gtcagaacca     180
cgggaaaata tcgtttatca gtgctggag cgttttttgcc aggaactggg taagcaaatt     240
ccagtggcga tgaccctgga aaagaatatg ccgatcggtt cgggcttagg ctccagtgcc     300
tgttcggtgg tcgcggcgct gatggcgatg aatgaacact gcggcaagcc gcttaatgac    360
actcgtttgc tggctttgat gggcgagctg gaaggccgta tctccggcag cattcattac    420
gacaacgtgg caccgtgttt tctcggtggt atgcagttga tgatcgaaga aaacgacatc    480
atcagccagc aagtgccagg gtttgatgag tggctgtggg tgctggcgta tccgggatt     540 aaagtctcga cggcagaagc cagggctatt ttaccggcgc agtatcgccg ccaggattgc    600
attgcgcacg gcgacatct ggcaggcttc attcacgcct gctattcccg tcagcctgag     660
cttgccgcga agctgatgaa agatgttatc gctgaaccct accgtgaacg gttactgcca    720
```

```
ggcttccggc aggcgcggca ggcggtcgcg gaaatcggcg cggtagcgag cggtatctcc    780
ggctccggcc cgaccttgtt cgctctgtgt gacaagccgg aaaccgccca gcgcgttgcc    840
gactggttgg gtaagaacta cctgcaaaat caggaaggtt ttgttcatat ttgccggctg    900
gatacggcgg gcgcacgagt actggaaaac taa                                 933
```

<210> SEQ ID NO 58
<211> LENGTH: 1287
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 58

```
atgaaactct acaatctgaa agatcacaac gagcaggtca gctttgcgca agccgtaacc     60
caggggttgg gcaaaaatca ggggctgttt tttccgcacg acctgccgga attcagcctg    120
actgaaattg atgagatgct gaagctggat tttgtcaccc gcagtgcgaa gatcctctcg    180
gcgtttattg gtgatgaaat cccacaggaa atcctggaag agcgcgtgcg cgcggcgttt    240
gccttcccgg ctccggtcgc caatgttgaa agcgatgtcg gttgtctgga attgttccac    300
gggccaacgc tggcatttaa agatttcggc ggtcgcttta tggcacaaat gctgacccat    360
attgcgggtg ataagccagt gaccattctg accgcgacct ccggtgatac cggagcggca    420
gtggctcatg ctttctacgg tttaccgaat gtgaaagtgg ttatcctcta tccacgaggc    480
aaaatcagtc cactgcaaga aaaactgttc tgtacattgg gcggcaatat cgaaactgtt    540
gccatcgacg gcgatttcga tgcctgtcag gcgctggtga agcaggcgtt tgatgatgaa    600
gaactgaaag tggcgctagg gttaaactcg gctaactcga ttaacatcag ccgtttgctg    660
gcgcagattt gctactactt tgaagctgtt gcgcagctgc cgcaggagac gcgcaaccag    720
ctggttgtct cggtgccaag cggaaacttc ggcgatttga cggcgggtct gctggcgaag    780
tcactcggtc tgccggtgaa acgttttatt gctgcgacca acgtgaacga taccgtgcca    840
cgtttcctgc acgacggtca gtggtcaccc aaagcgactc aggcgacgtt atccaacgcg    900
atggacgtga gtcagccgaa caactggccg cgtgtggaag agttgttccg ccgcaaaatc    960
tggcaactga agagctgggt tatgcagcc gtggatgatg aaaccacgca acagacaatg   1020
cgtgagttaa agaactgggc tacacttcg gagccgcacg ctgccgtagc ttatcgtgcg   1080
ctgcgtgatc agttgaatcc aggcgaatat ggcttgttcc tcggcaccgc gcatccggcg   1140
aaatttaaag agagcgtgga agcgattctc ggtgaaacgt tggatctgcc aaaagagctg   1200
gcagaacgtg ctgatttacc cttgctttca cataatctgc ccgccgattt tgctgcgttg   1260
cgtaaattga tgatgaatca tcagtaa                                      1287
```

<210> SEQ ID NO 59
<211> LENGTH: 1311
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 59

```
atgagtgaaa catacgtgtc tgagaaaagt ccaggagtga tggctagcgg agcggagctg     60
attcgtgccg ccgacattca aacggcgcag gcacgaattt cctccgtcat tgcaccaact    120
ccattgcagt attgccctcg tctttctgag gaaaccggag cggaaatcta ccttaagcgt    180
```

```
gaggatctgc aggatgttcg ttcctacaag atccgcggtg cgctgaactc tggagcgcag    240
ctcacccaag agcagcgcga tgcaggtatc gttgccgcat ctgcaggtaa ccatgcccag    300
ggcgtggcct atgtgtgcaa gtccttgggc gttcagggac gcatctatgt tcctgtgcag    360
actccaaagc aaaagcgtga ccgcatcatg gttcacggcg agagtttgt ctccttggtg     420 gtcactggca ataacttcga cgaagcatcg gctgcagcgc atgaagatgc agagcgcacc    480
ggcgcaacgc tgatcgagcc tttcgatgct cgcaacaccg tcatcggtca gggcaccgtg    540
gctgctgaga tcttgtcgca gctgacttcc atgggcaaga gtgcagatca cgtgatggtt    600
ccagtcggcg gtggcggact tcttgcaggt gtggtcagct acatggctga tatggcacct    660
cgcactgcga tcgttggtat cgaaccagcg ggagcagcat ccatgcaggc tgcattgcac    720
aatggtggac caatcacttt ggagactgtt gatcccttg tggacggcgc agcagtcaaa     780
cgtgtcggag atctcaacta caccatcgtg gagaagaacc agggtcgcgt gcacatgatg    840
agcgcgaccg agggcgctgt gtgtactgag atgctcgatc tttaccaaaa cgaaggcatc    900
atcgcggagc ctgctggcgc gctgtctatc gctgggttga aggaaatgtc ctttgcacct    960
ggttctgcag tggtgtgcat catctctggt ggcaacaacg atgtgctgcg ttatgcggaa   1020
atcgctgagc gctccttggt gcaccgcggt ttgaagcact acttcttggt gaacttcccg   1080
caaaagcctg gtcagttgcg tcacttcctg gaagatatcc tgggaccgga tgatgacatc   1140
acgctgtttg agtacctcaa cgcaacaac cgtgagaccg gtactgcgtt ggtgggtatt    1200
cacttgagtg aagcatcagg attggattct ttgctggaac gtatggagga atcggcaatt   1260
gattcccgtc gcctcgagcc gggcacccct gagtacgaat acttgaccta a            1311
```

<210> SEQ ID NO 60
<211> LENGTH: 2664
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 60

```
atgtcagaac gtttcccaaa tgacgtggat ccgatcgaaa ctcgcgactg gctccaggcg     60
atcgaatcgg tcatccgtga agaaggtgtt gagcgtgctc agtatctgat cgaccaactg    120
cttgctgaag cccgcaaagg cggtgtaaac gtagccgcag gcacaggtat cagcaactac    180
atcaacacca tccccgttga agaacaaccg gagtatccgg gtaatctgga actggaacgc    240
cgtattcgtt cagctatccg ctggaacgcc atcatgacgg tgctgcgtgc gtcgaaaaaa    300
gacctcgaac tgggcggcca tatggcgtcc ttccagtctt ccgcaaccat ttatgatgtg    360
tgctttaacc acttcttccg tgcacgcaac gagcaggatg gcggcgacct ggtttacttc    420
cagggccaca tctcccccggg cgtgtacgct cgtgcttttcc tggaaggtcg tctgactcag    480
gagcagctgg ataacttccg tcaggaagtt cacggcaatg gcctctcttc ctatccgcac    540
ccgaaactga tgccggaatt ctggcagttc ccgaccgtat ctatgggtct gggtccgatt    600
ggtgctattt accaggctaa attcctgaaa tatctggaac accgtggcct gaaagatacc    660
tctaaacaaa ccgtttacgc gttcctcggt gacggtgaaa tggacgaacc ggaatccaaa    720
ggtgcgatca ccatcgctac ccgtgaaaaa ctggataacc tggtcttcgt tatcaactgt    780
aacctgcagc gtcttgacgg cccggtcacc ggtaacggca agatcatcaa cgaactggaa    840
ggcatcttcg aaggtgctgg ctggaacgtg atcaaagtga tgtggggtag ccgttgggat    900
```

```
gaactgctgc gtaaggatac cagcggtaaa ctgatccagc tgatgaacga aaccgttgac    960
ggcgactacc agaccttcaa atcgaaagat ggtgcgtacg ttcgtgaaca cttcttcggt   1020
aaatatcctg aaaccgcagc actggttgca gactggactg acgagcagat ctgggcactg   1080
aaccgtggtg gtcacgatcc gaagaaaatc tacgctgcat tcaagaaagc gcaggaaacc   1140
aaaggcaaag cgacagtaat ccttgctcat accattaaag gttacggcat gggcgacgcg   1200
gctgaaggta aaacatcgc gcaccaggtt aagaaaatga acatggacgg tgtgcgtcat   1260
atccgcgacc gtttcaatgt gccggtgtct gatgcagata tcgaaaaact gccgtacatc   1320
accttcccgg aaggttctga agagcatacc tatctgcacg ctcagcgtca gaaactgcac   1380
ggttatctgc aagccgtca gccgaacttc accgagaagc ttgagctgcc gagcctgcaa   1440
gacttcggcg cgctgttgga agagcagagc aaagagatct ctaccactat cgctttcgtt   1500
cgtgctctga acgtgatgct gaagaacaag tcgatcaaag atcgtctggt accgatcatc   1560
gccgacgaag cgcgtacttt cggtatggaa ggtctgttcc gtcagattgg tatttacagc   1620
ccgaacggtc agcagtacac cccgcaggac cgcgagcagg ttgcttacta taagaagac   1680 gagaaaggtc agattctgca ggaagggatc aacgagctgg gcgcaggttg ttcctggctg   1740
gcagcggcga cctcttacag caccaacaat ctgccgatga tcccgttcta catctattac   1800
tcgatgttcg gcttccagcg tattggcgat ctgtgctggg cggctggcga ccagcaagcg   1860
cgtggcttcc tgatcggcgg tacttccggt cgtaccaccc tgaacggcga aggtctgcag   1920
cacgaagatg gtcacagcca cattcagtcg ctgactatcc cgaactgtat ctcttacgac   1980
ccggcttacg cttacgaagt tgctgtcatc atgcatgacg gtctggagcg tatgtacggt   2040
gaaaaacaag agaacgttta ctactacatc actacgctga acgaaaacta ccacatgccg   2100
gcaatgccgg aaggtgctga ggaaggtatc cgtaaaggta tctacaaact cgaaactatt   2160
gaaggtagca aaggtaaagt tcagctgctc ggctccggtt ctatcctgcg tcacgtccgt   2220
gaagcagctg agatcctggc gaaagattac ggcgtaggtt ctgacgttta tagcgtgacc   2280
tccttcaccg agctggcgcg tgatggtcag gattgtgaac gctggaacat gctgcacccg   2340
ctggaaactc cgcgcgttcc gtatatcgct caggtgatga cgacgctcc ggcagtggca   2400 tctaccgact atatgaaact gttcgctgag caggtccgta cttacgtacc ggctgacgac   2460
taccgcgtac tgggtactga tggcttcggt cgttccgaca gccgtgagaa cctgcgtcac   2520
cacttcgaag ttgatgcttc ttatgtcgtg gttgcggcgc tgggcgaact ggctaaacgt   2580
ggcgaaatcg ataagaaagt ggttgctgac gcaatcgcca aattcaacat cgatgcagat   2640
aaagttaacc cgcgtctggc gtaa                                         2664
```

<210> SEQ ID NO 61
<211> LENGTH: 1893
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 61

```
atggctatcg aaatcaaagt accggacatc ggggctgatg aagttgaaat caccgagatc     60
ctggtcaaag tgggcgacaa agttgaagcc gaacagtcgc tgatcaccgt agaaggcgac   120
aaagcctcta tggaagttcc gtctccgcag gcgggtatcg ttaaagagat caaagtctct   180
gttggcgata aaacccagac cggcgcactg attatgattt tcgattccgc cgacggtgca   240
```

```
gcagacgctg cacctgctca ggcagaagag aagaaagaag cagctccggc agcagcacca      300
gcggctgcgg cggcaaaaga cgttaacgtt ccgatatcg gcagcgacga agttgaagtg       360
accgaaatcc tggtgaaagt tggcgataaa gttgaagctg aacagtcgct gatcaccgta     420
gaaggcgaca aggcttctat ggaagttccg gctccgtttg ctggcaccgt gaaagagatc     480
aaagtgaacg tgggtgacaa agtgtctacc ggctcgctga ttatggtctt cgaagtcgcg     540
ggtgaagcag cgcgggcagc tccggccgct aaacaggaag cagctccggc agcggcccct    600
gcaccagcgg ctggcgtgaa agaagttaac gttccggata tcggcggtga cgaagttgaa    660
gtgactgaag tgatggtgaa agtgggcgac aaagttgccg ctgaacagtc actgatcacc    720
gtagaaggcg acaaagcttc tatggaagtt ccggcgccgt ttgcaggcgt cgtgaaggaa    780
ctgaaagtca cgttggcga taaagtgaaa actggctcgc tgattatgat cttcgaagtt     840
gaaggcgcag cgcctgcggc agctcctgcg aaacaggaag cggcagcgcc ggcaccggca    900
gcaaaagctg aagccccggc agcagcacca gctgcgaaag cggaaggcaa atctgaattt    960
gctgaaaacg acgcttatgt tcacgcgact ccgctgatcc gccgtctggc acgcgagttt    1020
ggtgttaacc ttgcgaaagt gaagggcact ggccgtaaag gtcgtatcct gcgcgaagac    1080
gttcaggctt acgtgaaaga agctatcaaa cgtgcagaag cagctccggc agcgactggc    1140
ggtggtatcc ctggcatgct gccgtggccg aaggtggact tcagcaagtt tggtgaaatc    1200
gaagaagtgg aactgggccg catccagaaa atctctggtg cgaacctgag ccgtaactgg    1260
gtaatgatcc cgcatgttac tcacttcgac aaaaccgata tcaccgagtt ggaagcgttc    1320
cgtaaacagc agaacgaaga agcggcgaaa cgtaagctgg atgtgaagat cacccccggtt  1380 gtcttcatca tgaaagccgt tgctgcagct cttgagcaga tgcctcgctt caatagttcg    1440
ctgtcggaag acggtcagcg tctgaccctg aagaaataca tcaacatcgg tgtggcggtg    1500
gataccccga acggtctggt tgttccggta ttcaaagacg tcaacaagaa aggcatcatc    1560
gagctgtctc gcgagctgat gactatttct aagaaagcgc gtgacggtaa gctgactgcg   1620
ggcgaaatgc agggcggttg cttcaccatc tccagcatcg gcggcctggg tactaccccac   1680 ttcgcgccga ttgtgaacgc gccggaagtg gctatcctcg gcgtttccaa gtccgcgatg   1740
gagccggtgt ggaatggtaa agagttcgtg ccgcgtctga tgctgccgat ttctctctcc    1800
ttcgaccacc gcgtgatcga cggtgctgat ggtgcccgtt tcattaccat cattaacaac   1860
acgctgtctg acattcgccg tctggtgatg taa                                1893
```

<210> SEQ ID NO 62
<211> LENGTH: 1425
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 62

```
atgagtactg aaatcaaaac tcaggtcgtg gtacttgggg caggccccgc aggttactcc      60
gctgccttcc gttgcgctga tttaggtctg gaaaccgtaa tcgtagaacg ttacaacacc    120
cttggcggtg tttgcctgaa cgtcggctgt atcccttcta agcactgct gcacgtagca     180 aaagttatcg aagaagccaa agcgctggct gaacacggta tcgtcttcgg cgaaccgaaa    240
accgatatcg acaagattcg tacctggaaa gagaaagtga tcaatcagct gaccggtggt    300
ctggctggta tggcgaaagg ccgcaaagtc aaagtggtca acggtctggg taaattcacc    360
```

```
ggggctaaca ccctggaagt tgaaggtgag aacggcaaaa ccgtgatcaa cttcgacaac      420
gcgatcattg cagcgggttc tcgcccgatc caactgccgt ttattccgca tgaagatccg      480
cgtatctggg actccactga cgcgctggaa ctgaaagaag taccagaacg cctgctggta      540
atgggtggcg gtatcatcgg tctggaaatg ggcaccgttt accacgcgct gggttcacag      600
attgacgtgg ttgaaatgtt cgaccaggtt atcccggcag ctgacaaaga catcgttaaa      660
gtcttcacca gcgtatcag caagaaattc aacctgatgc tggaaaccaa agttaccgcc      720
gttgaagcga agaagacgg catttatgtg acgatggaag gcaaaaaagc acccgctgaa      780
ccgcagcgtt acgacgccgt gctggtagcg attggtcgtg tgccgaacgg taaaaacctc      840
gacgcaggca agcaggcgt ggaagttgac gaccgtggtt tcatccgcgt tgacaaacag      900
ctgcgtacca acgtaccgca catctttgct atcggcgata tcgtcggtca accgatgctg      960
gcacacaaag gtgttcacga aggtcacgtt gccgctgaag ttatcgccgg taagaaacac     1020
tacttcgatc cgaaagttat cccgtccatc gcctatacca accagaagt tgcatgggtg     1080 ggtctgactg agaaagaagc gaaagagaaa ggcatcagct atgaaaccgc caccttcccg     1140
tgggctgctt ctggtcgtgc tatcgcttcc gactgcgcag acggtatgac caagctgatt     1200
ttcgacaaag aatctcaccg tgtgatcggt ggtgcgattg tcggtactaa cggcggcgag     1260
ctgctgggtg aaatcggcct ggcaatcgaa atgggttgtg atgctgaaga catcgcactg     1320
accatccacg cgcacccgac tctgcacgag tctgtgggcc tggcggcaga agtgttcgaa     1380
ggtagcatta ccgacctgcc gaacccgaaa gcgaagaaga agtaa                    1425
```

<210> SEQ ID NO 63
<211> LENGTH: 355
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 63

```
tgtggctttt atgaaaatca cacagtgatc acaaattta aacagagcac aaaatgctgc       60
ctcgaaatga gggcgggaaa ataaggttat cagccttgtt ttctccctca ttacttgaag      120
gatatgaagc taaacccctt ttttataaag catttgtccg aattcggaca taatcaaaaa      180
agcttaatta agatcaattt gatctacatc tctttaacca acaatatgta agatctcaac      240
tatcgcatcc gtggattaat tcaattataa cttctctcta acgctgtgta tcgtaacggt      300
aacactgtag aggggagcac attgatgcga attcattaaa gaggagaaag gtacc          355
```

<210> SEQ ID NO 64
<211> LENGTH: 228
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 64

```
ttccgaaaat tcctggcgag cagataaata agaattgttc ttatcaatat atctaactca       60
ttgaatcttt attagttttg tttttcacgc ttgttaccac tattagtgtg ataggaacag      120
ccagaatagc ggaacacata gccggtgcta tacttaatct cgttaattac tgggacataa      180
catcaagagg atatgaaatt cgaattcatt aaagaggaga aaggtacc                  228
```

<210> SEQ ID NO 65
<211> LENGTH: 334
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 65

```
gcttagatca ggtgattgcc ctttgtttat gagggtgttg taatccatgt cgttgttgca      60
tttgtaaggg caacacctca gcctgcaggc aggcactgaa gataccaaag ggtagttcag     120
attacacggt cacctggaaa gggggccatt ttacttttta tcgccgctgg cggtgcaaag     180
ttcacaaagt tgtcttacga aggttgtaag gtaaaactta tcgatttgat aatggaaacg     240
cattagccga atcggcaaaa attggttacc ttacatctca tcgaaaacac ggaggaagta     300
tagatgcgaa ttcattaaag aggagaaagg tacc                                 334
```

<210> SEQ ID NO 66
<211> LENGTH: 134
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 66

```
ctcgagttca ttatccatcc tccatcgcca cgatagttca tggcgatagg tagaatagca      60
atgaacgatt atccctatca agcattctga ctgataattg ctcacacgaa ttcattaaag     120
aggagaaagg tacc                                                       134
```

<210> SEQ ID NO 67
<211> LENGTH: 3518
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 67

```
cgacggtggc gataggcatc cgggtggtgc tcaaaagcag cttcgcctga ctgatgcgct      60
ggtcctcgcg ccagcttaat acgctaatcc ctaactgctg gcggaacaaa tgcgacagac     120
gcgacggcga caggcagaca tgctgtgcga cgctggcgat atcaaaatta ctgtctgcca     180
ggtgatcgct gatgtactga caagcctcgc gtacccgatt atccatcggt ggatggagcg     240
actcgttaat cgcttccatg cgccgcagta acaattgctc aagcagattt atcgccagca     300
attccgaata gcgcccttcc ccttgtccgg cattaatgat ttgcccaaac aggtcgctga     360
aatgcggctg gtgcgcttca tccgggcgaa agaaaccggt attggcaaat atcgacggcc     420
agttaagcca ttcatgccag taggcgcgcg gacgaaagta aacccactgg tgataccatt     480
cgtgagcctc cggatgacga ccgtagtgat gaatctctcc aggcgggaac agcaaaatat     540
cacccggtcg gcagacaaat tctcgtccct gattttttcac cacccctga ccgcgaatgg     600 tgagattgag aatataacct ttcattccca gcggtcggtc gataaaaaaa tcgagataac     660
cgttggcctc aatcggcgtt aaacccgcca ccagatgggc gttaaacgag tatcccggca     720 gcagggatc attttgcgct tcagccatac ttttcatact cccgccattc agagaagaaa     780
ccaattgtcc atattgcatc agacattgcc gtcactgcgt cttttactgg ctcttctcgc     840
```

```
taacccaacc ggtaaccccg cttattaaaa gcattctgta acaaagcggg accaaagcca    900
tgacaaaaac gcgtaacaaa agtgtctata atcacggcag aaaagtccac attgattatt    960
tgcacggcgt cacactttgc tatgccatag cattttttatc cataagatta gcggatccag   1020
cctgacgctt tttttcgcaa ctctctactg tttctccata cccgtttttt tggatggagt   1080
gaaacgatgg taaggaacg taaaaccgag ttggtcgagg gattccgcca ttcggttccc    1140
tgtatcaata cccaccgggg aaaaacgttt gtcatcatgc tcggcggtga agccattgag   1200
catgagaatt tctccagtat cgttaatgat atcgggttgt tgcacagcct cggcatccgt   1260
ctggtggtgg tctatggcgc acgtccgcag atcgacgcaa atctggctgc gcatcaccac   1320
gaaccgctgt atcacaagaa tatacgtgtg accgacgcca aaacactgga actggtgaag   1380
caggctgcgg gaacattgca actggatatt actgctcgcc tgtcgatgag tctcaataac   1440
acgccgctgc agggcgcgca tatcaacgtc gtcagtggca attttattat tgcccagccg   1500
ctgggcgtcg atgacggcgt ggattactgc catagcgggc gtatccggcg gattgatgaa   1560
gacgcgatcc atcgtcaact ggacagcggt gcaatagtgc taatggggcc ggtcgctgtt   1620
tcagtcactg gcgagagctt taacctgacc tcggaagaga ttgccactca actggccatc   1680
aaactgaaag ctgaaaagat gattggtttt tgctcttccc agggcgtcac taatgacgac   1740
ggtgatattg tctccgaact tttccctaac gaagcgcaag cgcgggtaga agcccaggaa   1800
gagaaaggcg attacaactc cggtacggtg cgcttttttgc gtggcgcagt gaaagcctgc   1860
cgcagcggcg tgcgtcgctg tcatttaatc agttatcagg aagatggcgc gctgttgcaa   1920
gagttgttct cacgcgacgg tatcggtacg cagattgtga tggaaagcgc cgagcagatt   1980
cgtcgcgcaa caatcaacga tattggcggt attctggagt tgattcgccc actggagcag   2040
caaggtattc tggtacgccg ttctcgcgag cagctggaga tggaaatcga caaattcacc   2100
attattcagc gcgataacac gactattgcc tgcgccgcgc tctatccgtt cccggaagag   2160
aagattgggg aaatggcctg tgtggcagtt cacccggatt accgcagttc atcaaggggt   2220
gaagttctgc tggaacgcat tgccgctcag gctaagcaga gcggcttaag caaattgttt   2280
gtgctgacca cgcgcagtat tcactggttc caggaacgtg gatttacccc agtggatatt   2340
gatttactgc ccgagagcaa aaagcagttg tacaactacc agcgtaaatc caaagtgttg   2400
atggcggatt tagggtaatg ggaattagcc atggtccata tgaatatcct ccttagttcc   2460
tattccgaag ttcctattcc gaagttccta ttctctagaa agtataggaa cttcgaagca   2520
gctccagcct acacaatcgc tcaagacgtg taatgctgca atctgcatgc aagcttggca   2580
ctggccacgc aaaaaggcca tccgtcagga tggccttctg cttaatttga tgcctggcag   2640
tttatgcggg gcgtcctgcc cgccaccctc cgggccgttg cttcgcaacg ttcaaatccg   2700
ctcccggcgg atttgtccta ctcaggagag cgttcaccga caaacaacag ataaaacgaa   2760
aggcccagtc tttcgactga cctttcgtt ttatttgatg cctggcagtt ccctactctc    2820
gcatgctcga gccatgggac gtccaggtat tagaagccaa cctggcgctg ccaaaacaca   2880
acctggtcac gctcacctgg ggcaatgtca gcgccgttga tcgcgggcgc ggcgtcctgg   2940
tgatcaaacc ttccggcgtc gactacagca tcatgaccgc tgacgatatg gtcgtggtca   3000
gcatcgaaac cggtgaagtg gttgaaggta cgaaaaagcc ctcctccgac acgccaactc   3060
accggctgct ctatcaggca ttcccgtcta ttggcggcat tgtgcacaca cactcgcgcc   3120
acgccaccat ctgggcgcag gcgggccagt cgattccagc agccggcacc acccacgccg   3180
actatttcta cggcaccatt ccctgcaccc gcaaaatgac cgacgcagaa atcaacggtg   3240
```

```
aatatgagtg ggaaaccggt aacgtcatcg tagaaacctt cgaaaaacag ggtatcaatg    3300
cagcgcaaat gcccggcgtg ctggtccatt ctcacggccc atttgcatgg ggaaaaaacg    3360
ccgaagatgc ggtgcataac gccatcgtgc tggaagaagt cgcttatatg gggatattct    3420
gccgtcagtt agcgccgcag ttaccggata tgcagcaaac gctgctggat aaacactatc    3480
tgcgtaagca tggcgcgaag gcatattacg ggcagtaa                            3518
```

<210> SEQ ID NO 68
<211> LENGTH: 60
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 68

```
tagaactgat gcaaaaagtg ctcgacgaag gcacacagat gtgtaggctg agctgcttc     60
```

<210> SEQ ID NO 69
<211> LENGTH: 471
<212> TYPE: DNA
<213> ORGANISM: Escherichia coli

<400> SEQUENCE: 69

```
atgcgaagct cggctaagca agaagaacta gttaaagcat ttaaagcatt acttaaagaa    60
gagaaattta gctcccaggg cgaaatcgtc gccgcgttgc aggagcaagg ctttgacaat   120
attaatcagt ctaaagtctc gcggatgttg accaagtttg gtgctgtacg tacacgcaat   180
gccaaaatgg aaatggttta ctgcctgcca gctgaactgg gtgtaccaac cacctccagt   240
ccattgaaga atctggtact ggatatcgac tacaacgatg cagttgtcgt gattcatacc   300
agccctggtg cggcgcagtt aattgctcgc ctgctggact cactgggcaa agcagaaggt   360
attctgggca ccatcgctgg cgatgacacc atctttacta cccctgctaa cggtttcacc   420
gtcaaagagc tgtacgaagc gattttagag ctgttcgacc aggagcttta a             471
```

<210> SEQ ID NO 70
<211> LENGTH: 52
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 70

```
caacacgttt cctgaggaac catgaaacag tatttagaac tgatgcaaaa ag            52
```

<210> SEQ ID NO 71
<211> LENGTH: 46
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 71

```
cgcacactgg cgtcggctct ggcaggatgt ttcgtaatta gatagc                   46
```

<210> SEQ ID NO 72
<211> LENGTH: 36
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 72
atatcgtcgc agcccacagc aacacgtttc ctgagg                              36

<210> SEQ ID NO 73
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
aagaatttaa cggagggcaa aaaaaaccga cgcacactgg cgtcggc                  47

<210> SEQ ID NO 74
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
gcaactggcc cgtaattatc c                                              21

<210> SEQ ID NO 75
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
acgcatcgca cgtaggttt                                                 19

<210> SEQ ID NO 76
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
ggcaggccta acacatgcaa g                                              21

<210> SEQ ID NO 77
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
gtcgcctagg tgagccttta cc                                             22

<210> SEQ ID NO 78
<211> LENGTH: 191
<212> TYPE: DNA
<213> ORGANISM: Artificial Sequence
<220> FEATURE:
```

<223> OTHER INFORMATION: Description of Artificial Sequence: Synthetic
polynucleotide

<400> SEQUENCE: 78

| gcaactggcc cgtaattatc catagctgta gtgatcactc ggtccgaatt aaacgcaatg | 60 |
| atggcgagct gagaacgatt agcatcaaac gctttaacga agattttgaa cgagtggagc | 120 |
| atgatgagta tcgcaaaata tgtgccgaaa tagagcagga acaaacctg aaaaacctac | 180 |
| gtgcgatgcg t | 191 |

<210> SEQ ID NO 79
<211> LENGTH: 8575
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 79

| ttattatcgc accgcaatcg ggattttcga ttcataaagc aggtcgtagg tcggcttgtt | 60 |
| gagcaggtct tgcagcgtga aaccgtccag atacgtgaaa aacgacttca ttgcaccgcc | 120 |
| gagtatgccc gtcagccggc aggacggcgt aatcaggcat tcgttgttcg ggcccataca | 180 |
| ctcgaccagc tgcatcggtt cgaggtggcg gacgaccgcg ccgatattga tgcgttcggg | 240 |
| cggcgcggc agcctcagcc cgccgccttt cccgcgtacg ctgtgcaaga acccgccttt | 300 |
| gaccagcgcg gtaaccactt tcatcaaatg gcttttggaa atgccgtagg tcgaggcgat | 360 |
| ggtggcgata ttgaccagcg cgtcgtcgtt gacggcggtg tagatgagga cgcgcagccc | 420 |
| gtagtcggta tgttgggtca gatacataca acctccttag tacatgcaaa attatttcta | 480 |
| gagcaacata cgagccggaa gcataaagtg taaagcctgg ggtgcctaat gagttgagtt | 540 |
| gaggaattat aacaggaaga atattcctc atacgcttgt aattcctcta tggttgttga | 600 |
| caattaatca tcggctcgta taatgtataa cattcatatt ttgtgaattt taaactctag | 660 |
| aaataatttt gtttaacttt aagaaggaga tatacatatg gatttaaatt ctaaaaaata | 720 |
| tcagatgctt aaagagctat atgtaagctt cgctgaaaat gaagttaaac ctttagcaac | 780 |
| agaacttgat gaagaagaaa gatttcctta tgaaacagtg gaaaaaatgg caaaagcagg | 840 |
| aatgatgggt ataccatatc caaaagaata tggtggagaa ggtggagaca ctgtaggata | 900 |
| tataatggca gttgaagaat tgtctagagt ttgtggtact acaggagtta tattatcagc | 960 |
| tcatacatct cttggctcat ggcctatata tcaatatggt aatgaagaac aaaaacaaaa | 1020 |
| attcttaaga ccactagcaa gtggagaaaa attaggagca tttggtctta ctgagcctaa | 1080 |
| tgctggtaca gatgcgtctg gccaacaaac aactgctgtt ttagacgggg atgaatacat | 1140 |
| acttaatggc tcaaaaatat ttataacaaa cgcaatagct ggtgacatat atgtagtaat | 1200 |
| ggcaatgact gataaatcta agggaacaa aggaatatca gcatttatag ttgaaaaagg | 1260 |
| aactcctggg tttagctttg gagttaaaga aaagaaaatg ggtataagag gttcagctac | 1320 |
| gagtgaatta atatttgagg attgcagaat acctaaagaa aatttacttg gaaaagaagg | 1380 |
| tcaaggattt aagatagcaa tgtctactct tgatggtggt agaattggta tagctgcaca | 1440 |
| agctttaggt ttagcacaag gtgctcttga tgaaactgtt aaatatgtaa agaaaagagt | 1500 |
| acaatttggt agaccattat caaaattcca aatacacaa ttccaattag ctgatatgga | 1560 |
| agttaaggta caagcggcta gacacctgt atatcaagca gctataaata agacttagg | 1620 |
| aaaaccttat ggagtagaag cagcaatggc aaaattattt gcagctgaaa cagctatgga | 1680 |

```
agttactaca aaagctgtac aacttcatgg aggatatgga tacactcgtg actatccagt    1740
agaaagaatg atgagagatg ctaagataac tgaaatatat gaaggaacta gtgaagttca    1800
aagaatggtt atttcaggaa aactattaaa atagtaagaa ggagatatac atatggagga    1860
aggatttatg aatatagtcg tttgtataaa acaagttcca gatacaacag aagttaaact    1920
agatcctaat acaggtactt taattagaga tggagtacca agtataataa accctgatga    1980
taaagcaggt ttagaagaag ctataaaatt aaaagaagaa atgggtgctc atgtaactgt    2040
tataacaatg ggacctcctc aagcagatat ggctttaaaa gaagctttag caatgggtgc    2100
agatagaggt atattattaa cagatagagc atttgcgggt gctgatactt gggcaacttc    2160
atcagcatta gcaggagcat taaaaaatat agattttgat attataatag ctggaagaca    2220
ggcgatagat ggagatactg cacaagttgg acctcaaata gctgaacatt taaatcttcc    2280
atcaataaca tatgctgaag aaataaaaac tgaaggtgaa tatgtattag taaaaagaca    2340
atttgaagat tgttgccatg acttaaaagt taaaatgcca tgccttataa caactcttaa    2400
agatatgaac acaccaagat acatgaaagt tggaagaata tatgatgctt cgaaaatga    2460 tgtagtagaa acatggactg taaaagatat agaagttgac ccttctaatt taggtcttaa    2520
aggttctcca actagtgtat ttaaatcatt tacaaaatca gttaaaccag ctggtacaat    2580
atacaatgaa gatgcgaaaa catcagctgg aattatcata gataaattaa agagaagta    2640 tatcatataa taagaaggag atatacatat gggtaacgtt ttagtagtaa tagaacaaag    2700
agaaaatgta attcaaactg tttctttaga attactagga aaggctacag aaatagcaaa    2760
agattatgat acaaaagttt ctgcattact tttaggtagt aaggtagaag gtttaataga    2820
tacattagca cactatggtg cagatgaggt aatagtagta gatgatgaag ctttagcagt    2880
gtatacaact gaaccatata caaaagcagc ttatgaagca ataaaagcag ctgaccctat    2940
agttgtatta tttggtgcaa cttcaatagg tagagattta gcgcctagag tttctgctag    3000
aatacataca ggtcttactg ctgactgtac aggtcttgca gtagctgaag atacaaaatt    3060
attattaatg acaagacctg cctttggtgg aaatataatg gcaacaatag tttgtaaaga    3120
tttcagacct caaatgtcta cagttagacc aggggttatg aagaaaaatg aacctgatga    3180
aactaaagaa gctgtaatta accgtttcaa ggtagaattt aatgatgctg ataaattagt    3240
tcaagttgta caagtaataa aagaagctaa aaaacaagtt aaaatagaag atgctaagat    3300
attagtttct gctggacgtg gaatgggtgg aaaagaaaac ttagacatac tttatgaatt    3360
agctgaaatt ataggtggag aagtttctgg ttctcgtgcc actatagatg caggttggtt    3420
agataaagca agacaagttg gtcaaactgg taaaactgta agaccagacc tttatatagc    3480
atgtggtata tctggagcaa tacaacatat agctggtatg gaagatgctg agtttatagt    3540
tgctataaat aaaaatccag aagctccaat atttaaatat gctgatgttg gtatagttgg    3600
agatgttcat aaaagtgcttc cagaacttat cagtcagtta agtgttgcaa agaaaaagg    3660 tgaagtttta gctaactaat aagaaggaga tatacatatg agagaagtag taattgccag    3720
tgcagctaga acagcagtag gaagttttgg aggagcattt aaatcagttt cagcggtaga    3780
gttaggggta acagcagcta aagaagctat aaaaagagct aacataactc cagatatgat    3840
agatgaatct ctttttaggg gagtacttac agcaggtctt ggacaaaata tagcaagaca    3900
aatagcatta ggagcaggaa taccagtaga aaaaccagct atgactataa atatagtttg    3960
tggttctgga ttaagatctg tttcaatggc atctcaactt atagcattag gtgatgctga    4020
```

```
tataatgtta gttggtggag ctgaaaacat gagtatgtct ccttatttag taccaagtgc    4080
gagatatggt gcaagaatgg gtgatgctgc ttttgttgat tcaatgataa aagatggatt    4140
atcagacata tttaataact atcacatggg tattactgct gaaaacatag cagagcaatg    4200
gaatataact agagaagaac aagatgaatt agctcttgca agtcaaaata aagctgaaaa    4260
agctcaagct gaaggaaaat tgatgaaga aatagttcct gttgttataa aaggaagaaa    4320
aggtgacact gtagtagata aagatgaata tattaagcct ggcactacaa tggagaaact    4380
tgctaagtta agacctgcat ttaaaaaaga tggaacagtt actgctggta atgcatcagg    4440
aataaatgat ggtgctgcta tgttagtagt aatggctaaa gaaaaagctg aagaactagg    4500
aatagagcct cttgcaacta tagtttctta tggaacagct ggtgttgacc ctaaaataat    4560
gggatatgga ccagttccag caactaaaaa agctttagaa gctgctaata tgactattga    4620
agatatagat ttagttgaag ctaatgaggc atttgctgcc caatctgtag ctgtaataag    4680
agacttaaat atagatatga ataaagttaa tgttaatggt ggagcaatag ctataggaca    4740
tccaatagga tgctcaggag caagaatact tactacactt ttatatgaaa tgaagagaag    4800
agatgctaaa actggtcttg ctacactttg tataggcggt ggaatgggaa ctactttaat    4860
agttaagaga tagtaagaag gagatataca tatgaaatta gctgtaatag gtagtggaac    4920
tatgggaagt ggtattgtac aaacttttgc aagttgtgga catgatgtat gtttaaagag    4980
tagaactcaa ggtgctatag ataaatgttt agctttatta gataaaaatt taactaagtt    5040
agttactaag ggaaaaatgg atgaagctac aaaagcagaa atattaagtc atgttagttc    5100
aactactaat tatgaagatt taaaagatat ggatttaata atagaagcat ctgtagaaga    5160
catgaatata taagaaagatg tttttcaagtt actagatgaa ttatgtaaag aagatactat    5220
cttggcaaca aatacttcat cattatctat aacagaaata gcttcttcta ctaagcgccc    5280
agataaagtt ataggaatgc atttctttaa tccagttcct atgatgaaat tagttgaagt    5340
tataagtggt cagttaacat caaaagttac ttttgataca gtatttgaat tatctaagag    5400
tatcaataaa gtaccagtag atgtatctga atctcctgga tttgtagtaa atagaatact    5460
tatacctatg ataaatgaag ctgttggtat atatgcagat ggtgttgcaa gtaaagaaga    5520
aatagatgaa gctatgaaat taggagcaaa ccatccaatg ggaccactag cattaggtga    5580
tttaatcgga ttagatgttg ttttagctat aatgaacgtt ttatatactg aatttggaga    5640
tactaaatat agacctcatc cacttttagc taaaatggtt agagctaatc aattaggaag    5700
aaaaactaag ataggattct atgattataa taaataataa gaaggagata tacatatgag    5760
tacaagtgat gttaaagttt atgagaatgt agctgttgaa gtagatggaa atatatgtac    5820
agtgaaaatg aatagaccta aagcccttaa tgcaataaat tcaaagactt tagaagaact    5880
ttatgaagta tttgtagata ttaataatga tgaaactatt gatgttgtaa tattgacagg    5940
ggaaggaaag gcatttgtag ctggagcaga tattgcatac atgaaagatt tagatgctgt    6000
agctgctaaa gattttagta tcttaggagc aaaagctttt ggagaaatag aaaatagtaa    6060
aaaagtagtg atagctgctg taaacggatt tgctttaggt ggaggatgtg aacttgcaat    6120
ggcatgtgat ataagaattg catctgctaa agctaaattt ggtcagccag aagtaactct    6180
tggaataact ccaggatatg gaggaactca aaggcttaca agattggttg gaatggcaaa    6240
agcaaaagaa ttaatcttta caggtcaagt tataaaagct gatgaagctg aaaaaatagg    6300
gctagtaaat agagtcgttg agccagacat tttaatagaa gaagttgaga attagctaa    6360 gataatagct aaaaatgctc agcttgcagt tagatactct aaagaagcaa tacaacttgg    6420
```

```
tgctcaaact gatataaata ctggaataga tatagaatct aatttatttg gtctttgttt    6480
ttcaactaaa gaccaaaaag aaggaatgtc agctttcgtt gaaaagagag aagctaactt    6540
tataaagggg taataagaag gagatataca tatgagaagt tttgaagaag taattaagtt    6600
tgcaaaagaa agaggaccta aaactatatc agtagcatgt tgccaagata aagaagtttt    6660
aatggcagtt gaaatggcta gaaaagaaaa aatagcaaat gccattttag taggagatat    6720
agaaaagact aaagaaattg caaaaagcat agacatggat atcgaaaatt atgaactgat    6780
agatataaaa gatttagcag aagcatctct aaaatctgtt gaattagttt cacaaggaaa    6840
agccgacatg gtaatgaaag cttagtagaa cacatcaata atactaaaag cagttttaaa    6900
taaagaagta ggtcttagaa ctggaaatgt attaagtcac gtagcagtat ttgatgtaga    6960
gggatatgat agattatttt tcgtaactga cgcagctatg aacttagctc ctgatacaaa    7020
tactaaaaag caaatcatag aaaatgcttg cacagtagca cattcattag atataagtga    7080
accaaaagtt gctgcaatat gcgcaaaaga aaaagtaaat ccaaaaatga agatacagt    7140 tgaagctaaa gaactagaag aaatgtatga agaggagaa atcaaaggtt gtatggttgg    7200
tgggcctttt gcaattgata atgcagtatc tttagaagca gctaaacata aaggtataaa    7260
tcatcctgta gcaggacgag ctgatatatt attagcccca gatattgaag gtggtaacat    7320
attatataaa gctttggtat tcttctcaaa atcaaaaaat gcaggagtta tagttggggc    7380
taaagcacca ataatattaa cttctagagc agacagtgaa gaaactaaac taaactcaat    7440
agctttaggt gttttaatgg cagcaaaggc ataataagaa ggagatatac atatgagcaa    7500
aatatttaaa atcttaacaa taaatcctgg ttcgacatca actaaaatag ctgtatttga    7560
taatgaggat ttagtatttg aaaaaactttt aagacattct tcagaagaaa taggaaaata    7620
tgagaaggtg tctgaccaat ttgaatttcg taaacaagta atagaagaag ctctaaaaga    7680
aggtggagta aaaacatctg aattagatgc tgtagtaggt agaggaggac ttcttaaacc    7740
tataaaaggt ggtacttatt cagtaagtgc tgctatgatt gaagatttaa agtgggagt    7800 tttaggagaa cacgcttcaa acctaggtgg aataatagca aaacaaatag gtgaagaagt    7860
aaatgttcct tcatacatag tagaccctgt tgttgtagat gaattagaag atgttgctag    7920
aatttctggt atgcctgaaa taagtagagc aagtgtagta catgctttaa atcaaaaggc    7980
aatagcaaga agatatgcta gagaaataaa caagaaatat gaagatataa atcttatagt    8040
tgcacacatg ggtggaggag tttctgttgg agctcataaa aatggtaaaa tagtagatgt    8100
tgcaaacgca ttagatggag aaggacctttt ctctccagaa agaagtggtg gactaccagt    8160
aggtgcatta gtaaaaatgt gctttagtgg aaaatatact caagatgaaa ttaaaaagaa    8220
aataaaaggt aatggcggac tagttgcata cttaaacact aatgatgcta gagaagttga    8280
agaaagaatt gaagctggtg atgaaaaagc taaattagta tatgaagcta tggcatatca    8340
aatctctaaa gaaataggag ctagtgctgc agttcttaag ggagatgtaa aagcaatatt    8400
attaactggt ggaatcgcat attcaaaaat gtttacagaa atgattgcag atagagttaa    8460
atttatagca gatgtaaaag tttatccagg tgaagatgaa atgattgcat agctcaagg    8520 tggacttaga gttttaactg gtgaagaaga ggctcaagtt tatgataact aataa         8575
```

<210> SEQ ID NO 80
<211> LENGTH: 6787
<212> TYPE: DNA
<213> ORGANISM: Artificial Sequence
<220> FEATURE:

<223> OTHER INFORMATION: Description of Artificial Sequence: Synthetic polynucleotide

<400> SEQUENCE: 80

```
ttattatcgc accgcaatcg ggattttcga ttcataaagc aggtcgtagg tcggcttgtt      60
gagcaggtct tgcagcgtga aaccgtccag atacgtgaaa aacgacttca ttgcaccgcc     120
gagtatgccc gtcagccggc aggacggcgt aatcaggcat tcgttgttcg ggcccataca     180
ctcgaccagc tgcatcggtt cgaggtggcg gacgaccgcg ccgatattga tgcgttcggg     240
cggcgcggcc agcctcagcc cgccgccttt cccgcgtacg ctgtgcaaga acccgccttt     300
gaccagcgcg gtaaccactt tcatcaaatg gcttttggaa atgccgtagg tcgaggcgat     360
ggtggcgata ttgaccagcg cgtcgtcgtt gacggcggtg tagatgagga cgcgcagccc     420
gtagtcggta tgttgggtca gatacataca acctccttag tacatgcaaa attatttcta     480
gagcaacata cgagccggaa gcataaagtg taaagcctgg ggtgcctaat gagttgagtt     540
gaggaattat aacaggaaga aatattcctc atacgcttgt aattcctcta tggttgttga     600
caattaatca tcggctcgta taatgtataa cattcatatt ttgtgaattt taaactctag     660
aaataatttt gtttaacttt aagaaggaga tatacatatg atcgtaaaac ctatggtacg     720
caacaatatc tgcctgaacg cccatcctca gggctgcaag aagggagtgg aagatcagat     780
tgaatatacc aagaaacgca ttaccgcaga agtcaaagct ggcgcaaaag ctccaaaaaa     840
cgttctggtg cttggctgct caaatggtta cggcctggcg agccgcatta ctgctgcgtt     900
cggatacggg gctgcgacca tcggcgtgtc ctttgaaaaa gcgggttcag aaaccaaata     960
tggtacaccg ggatggtaca ataatttggc atttgatgaa gcggcaaaac gcgagggtct    1020
ttatagcgtg acgatcgacg gcgatgcgtt ttcagacgag atcaaggccc aggtaattga    1080
ggaagccaaa aaaaaggta tcaaatttga tctgatcgta tacagcttgg ccagcccagt    1140
acgtactgat cctgatacag gtatcatgca caaaagcgtt ttgaaaccct ttggaaaaac    1200
gttcacaggc aaaacagtag atccgtttac tggcgagctg aaggaaatct ccgcggaacc    1260
agcaaatgac gaggaagcag ccgccactgt taaagttatg ggggtgaag attgggaacg    1320
ttggattaag cagctgtcga aggaaggcct cttagaagaa ggctgtatta ccttggccta    1380
tagttatatt ggccctgaag ctacccaagc tttgtaccgt aaaggcacaa tcggcaaggc    1440
caaagaacac ctggaggcca cagcacaccg tctcaacaaa gagaacccgt caatccgtgc    1500
cttcgtgagc gtgaataaag gcctggtaac ccgcgcaagc gccgtaatcc cggtaatccc    1560
tctgtatctc gccagcttgt tcaaagtaat gaaagagaag gcaatcatg aaggttgtat    1620
tgaacagatc acgcgtctgt acgccgagcg cctgtaccgt aaagatggta caattccagt    1680
tgatgaggaa aatcgcattc gcattgatga ttgggagtta aagaagacg tccagaaagc    1740
ggtatccgcg ttgatggaga aagtcacggg tgaaaacgca gaatctctca ctgacttagc    1800
ggggtaccgc catgatttct tagctagtaa cggctttgat gtagaaggta ttaattatga    1860
agcggaagtt gaacgcttcg accgtatctg ataagaagga gatatacata tgagagaagt    1920
agtaattgcc agtgcagcta gaacagcagt aggaagtttt ggaggagcat ttaaatcagt    1980
ttcagcggta gagttagggg taacagcagc taaagaagct ataaaaagag ctaacataac    2040
tccagatatg atagatgaat ctcttttagg gggagtactt acagcaggtc ttggacaaaa    2100
tatagcaaga caaatagcat taggagcagg aataccagta gaaaaccag ctatgactat    2160
aaatatagtt tgtggttctg gattaagatc tgtttcaatg gcatctcaac ttatagcatt    2220
```

```
aggtgatgct gatataatgt tagttggtgg agctgaaaac atgagtatgt ctccttattt    2280
agtaccaagt gcgagatatg gtgcaagaat gggtgatgct gcttttgttg attcaatgat    2340
aaaagatgga ttatcagaca tatttaataa ctatcacatg ggtattactg ctgaaaacat    2400
agcagagcaa tggaatataa ctagagaaga acaagatgaa ttagctcttg caagtcaaaa    2460
taaagctgaa aaagctcaag ctgaaggaaa atttgatgaa gaaatagttc ctgttgttat    2520
aaaaggaaga aaaggtgaca ctgtagtaga taaagatgaa tatattaagc ctggcactac    2580
aatggagaaa cttgctaagt taagacctgc atttaaaaaa gatggaacag ttactgctgg    2640
taatgcatca ggaataaatg atggtgctgc tatgttagta gtaatggcta agaaaaagc    2700
tgaagaacta ggaatagagc ctcttgcaac tatagtttct tatggaacag ctggtgttga    2760
ccctaaaata atgggatatg gaccagttcc agcaactaaa aaagctttag aagctgctaa    2820
tatgactatt gaagatatag atttagttga agctaatgag gcatttgctg cccaatctgt    2880
agctgtaata agagacttaa atatagatat gaataaagtt aatgttaatg gtggagcaat    2940
agctatagga catccaatag gatgctcagg agcaagaata cttactacac ttttatatga    3000
aatgaagaga agagatgcta aaactggtct tgctacactt tgtataggcg gtggaatggg    3060
aactactttta atagttaaga gatagtaaga aggagatata catgaaaat tagctgtaat    3120
aggtagtgga actatgggaa gtggtattgt acaaactttt gcaagttgtg gacatgatgt    3180
atgtttaaag agtagaactc aaggtgctat agataaatgt ttagctttat tagataaaaa    3240
tttaactaag ttagttacta agggaaaaat ggatgaagct acaaaagcag aaatattaag    3300
tcatgttagt tcaactacta attatgaaga tttaaagat atggatttaa taatagaagc    3360
atctgtagaa gacatgaata taaagaaga tgttttcaag ttactagatg aattatgtaa    3420
agaagatact atcttggcaa caaatacttc atcattatct ataacagaaa tagcttcttc    3480
tactaagcgc ccagataaag ttataggaat gcatttcttt aatccagttc ctatgatgaa    3540
attagttgaa gttataagtg gtcagttaac atcaaaagtt acttttgata cagtatttga    3600
attatctaag agtatcaata aagtaccagt agatgtatct gaatctcctg gatttgtagt    3660
aaatagaata cttataccta tgataaatga agctgttggt atatatgcag atggtgttgc    3720
aagtaaagaa gaaatagatg aagctatgaa attaggagca aaccatccaa tgggaccact    3780
agcattaggt gatttaatcg gattagatgt tgtttttagct ataatgaacg ttttatatac    3840
tgaatttgga gatactaaat atagacctca tccactttta gctaaaatgg ttagagctaa    3900
tcaattagga agaaaaacta agataggatt ctatgattat aataaataat aagaaggaga    3960
tatacatatg agtacaagtg atgttaaagt ttatgagaat gtagctgttg aagtagatgg    4020
aaatatatgt acagtgaaaa tgaatagacc taaagcccctt aatgcaataa attcaaagac    4080
tttagaagaa ctttatgaag tatttgtaga tattaataat gatgaaacta ttgatgttgt    4140
aatattgaca ggggaaggaa aggcatttgt agctggagca gatattgcat acatgaaaga    4200
tttagatgct gtagctgcta agatttttag tatcttagga gcaaaagctt ttggagaaat    4260
agaaaatagt aaaaagtag tgatagctgc tgtaaacgga tttgctttag gtggaggatg    4320
tgaacttgca atggcatgtg atataagaat tgcatctgct aaagctaaat ttggtcagcc    4380
agaagtaact cttggaataa ctccaggata tggaggaact caaaggctta caagattggt    4440
tggaatggca aaagcaaaag aattaatctt tacaggtcaa gttataaaag ctgatgaagc    4500
tgaaaaaata gggctagtaa atagagtcgt tgagccagac atttttaatag aagaagttga    4560
gaaattagct aagataatag ctaaaaatgc tcagcttgca gttagatact ctaaagaagc    4620
```

```
aatacaactt ggtgctcaaa ctgatataaa tactggaata gatatagaat ctaatttatt    4680
tggtctttgt ttttcaacta aagaccaaaa agaaggaatg tcagctttcg ttgaaaagag    4740
agaagctaac tttataaaag ggtaataaga aggagatata catatgagaa gttttgaaga    4800
agtaattaag tttgcaaaag aaagaggacc taaaactata tcagtagcat gttgccaaga    4860
taaagaagtt ttaatggcag ttgaaatggc tagaaaagaa aaaatagcaa atgccatttt    4920
agtaggagat atagaaaaga ctaaagaaat tgcaaaaagc atagacatgg atatcgaaaa    4980
ttatgaactg atagatataa aagatttagc agaagcatct ctaaaatctg ttgaattagt    5040
ttcacaagga aaagccgaca tggtaatgaa aggcttagta gacacatcaa taatactaaa    5100
agcagtttta aataaagaag taggtcttag aactggaaat gtattaagtc acgtagcagt    5160
atttgatgta gagggatatg atagattatt tttcgtaact gacgcagcta tgaacttagc    5220
tcctgataca aatactaaaa agcaaatcat agaaaatgct tgcacagtag cacattcatt    5280
agatataagt gaaccaaaag ttgctgcaat atgcgcaaaa gaaaaagtaa atccaaaaat    5340
gaaagataca gttgaagcta agaactaga agaaatgtat gaaagaggag aaatcaaagg    5400
ttgtatggtt ggtgggcctt ttgcaattga taatgcagta tctttagaag cagctaaaca    5460
taaaggtata aatcatcctg tagcaggacg agctgatata ttattagccc cagatattga    5520
aggtggtaac atattatata aagctttggt attcttctca aaatcaaaaa atgcaggagt    5580
tatagttggg gctaaagcac caataatatt aacttctaga gcagacagtg aagaaactaa    5640
actaaactca atagctttag gtgttttaat ggcagcaaag gcataataag aaggagatat    5700
acatatgagc aaaatattta aaatcttaac aataaatcct ggttcgacat caactaaaat    5760
agctgtattt gataatgagg atttagtatt tgaaaaaact ttaagacatt cttcagaaga    5820
aataggaaaa tatgagaagg tgtctgacca atttgaattt cgtaaacaag taatagaaga    5880
agctctaaaa gaaggtggag taaaaacatc tgaattagat gctgtagtag gtagaggagg    5940
acttcttaaa cctataaaag gtggtactta ttcagtaagt gctgctatga ttgaagattt    6000
aaaagtggga gttttaggag aacacgcttc aaacctaggt ggaataatag caaaacaaat    6060
aggtgaagaa gtaaatgttc cttcatacat agtagaccct gttgttgtag atgaattaga    6120
agatgttgct agaatttctg gtatgcctga aataagtaga gcaagtgtag tacatgcttt    6180
aaatcaaaag gcaatagcaa gaagatatgc tagagaaata aacaagaaat atgaagatat    6240
aaatcttata gttgcacaca tgggtggagg agtttctgtt ggagctcata aaaatggtaa    6300
aatagtagat gttgcaaacg cattagatgg agaaggacct ttctctccag aaagaagtgg    6360
tggactacca gtaggtgcat tagtaaaaat gtgctttagt ggaaaatata ctcaagatga    6420
aattaaaaag aaaataaaag gtaatggcgg actagttgca tacttaaaca ctaatgatgc    6480
tagagaagtt gaagaaagaa ttgaagctgg tgatgaaaaa gctaaattag tatatgaagc    6540
tatggcatat caaatctcta agaaatagg agctagtgct gcagttctta agggagatgt    6600
aaaagcaata ttattaactg gtggaatcgc atattcaaaa atgtttacag aaatgattgc    6660
agatagagtt aaatttatag cagatgtaaa agtttatcca ggtgaagatg aaatgattgc    6720
attagctcaa ggtggactta gagttttaac tggtgaagaa gaggctcaag tttatgataa    6780
ctaataa                                                             6787
```

<210> SEQ ID NO 81
<211> LENGTH: 8012
<212> TYPE: DNA

<213> ORGANISM: Artificial Sequence
<220> FEATURE:
<223> OTHER INFORMATION: Description of Artificial Sequence: Synthetic polynucleotide

<400> SEQUENCE: 81

```
ctcgagttca ttatccatcc tccatcgcca cgatagttca tggcgatagg tagaatagca      60
atgaacgatt atccctatca agcattctga ctgataattg ctcacacgaa ttcattaaag     120
aggagaaagg taccatggat ttaaattcta aaaatatca gatgcttaaa gagctatatg      180
taagcttcgc tgaaaatgaa gttaaacctt tagcaacaga acttgatgaa gaagaaagat    240
ttccttatga acagtggaa aaaatggcaa agcaggaat gatgggtata ccatatccaa      300
aagaatatgg tggagaaggt ggagacactg taggatatat aatggcagtt gaagaattgt    360
ctagagtttg tggtactaca ggagttatat tatcagctca tacatctctt ggctcatggc   420
ctatatatca atatggtaat gaagaacaaa acaaaaatt cttaagacca ctagcaagtg    480
gagaaaaatt aggagcattt ggtcttactg agcctaatgc tggtacagat gcgtctggcc   540
aacaaacaac tgctgtttta gacggggatg aatacatact taatggctca aaaatattta   600
taacaaacgc aatagctggt gacatatatg tagtaatggc aatgactgat aaatctaagg   660
ggaacaaagg aatatcagca tttatagttg aaaaaggaac tcctgggttt agctttggag   720
ttaaagaaaa gaaatggggt ataagaggtt cagctacgag tgaattaata tttgaggatt    780
gcagaatacc taaagaaaat ttacttggaa aagaaggtca aggatttaag atagcaatgt   840
ctactcttga tggtggtaga attggtatag ctgcacaagc tttaggttta gcacaaggtg    900
ctcttgatga aactgttaaa tatgtaaaag aaagagtaca atttggtaga ccattatcaa   960
aattccaaaa tacacaattc caattagctg atatggaagt taaggtacaa gcggctagac  1020
accttgtata tcaagcagct ataaataaag acttaggaaa accttatgga gtagaagcag  1080
caatggcaaa attatttgca gctgaaacag ctatggaagt tactacaaaa gctgtacaac  1140
ttcatggagg atatggatac actcgtgact atccagtaga aagaatgatg agagatgcta  1200
agataactga aatatatgaa ggaactagtg aagttcaaag aatggttatt tcaggaaaac  1260
tattaaaata gtaagaagga gatatacata tggaggaagg atttatgaat atagtcgttt  1320
gtataaaaca agttccagat acaacagaag ttaaactaga tcctaataca ggtactttaa  1380
ttagagatgg agtaccaagt ataataaacc ctgatgataa agcaggttta gaagaagcta  1440
taaaattaaa agaagaaatg ggtgctcatg taactgttat aacaatggga cctcctcaag  1500
cagatatggc tttaaaagaa gctttagcaa tgggtgcaga tagaggtata ttattaacag  1560
atagagcatt tgcgggtgct gatacttggg caacttcatc agcattagca ggagcattaa  1620
aaatataga tttgatatt ataatagctg aagacaggc gatagatgga gatactgcac     1680
aagttggacc tcaaatagct gaacatttaa atcttccatc aataacatat gctgaagaaa  1740
taaaaactga aggtgaatat gtattagtaa aagacaatt tgaagattgt tgccatgact   1800
taaaagttaa aatgccatgc cttataacaa ctcttaaaga tatgaacaca ccaagataca  1860
tgaaagttgg aagaatatat gatgctttcg aaaatgatgt agtagaaaca tggactgtaa  1920
aagatataga agttgacccct tctaatttag gtcttaaagg ttctccaact agtgtattta  1980
aatcatttac aaaatcagtt aaaccagctg gtacaatata caatgaagat gcgaaaacat  2040
cagctggaat tatcatagat aaattaaaag agaagtatat catataataa gaaggagata  2100
tacatatggg taacgtttta gtagtaatag aacaaagaga aaatgtaatt caaactgttt  2160
```

```
ctttagaatt actaggaaag gctacagaaa tagcaaaaga ttatgataca aaagtttctg    2220
cattactttt aggtagtaag gtagaaggtt aatagatac attagcacac tatggtgcag     2280
atgaggtaat agtagtagat gatgaagctt tagcagtgta tacaactgaa ccatatacaa    2340
aagcagctta tgaagcaata aaagcagctg accctatagt tgtattattt ggtgcaactt    2400
caataggtag agatttagcg cctagagttt ctgctagaat acatacaggt cttactgctg    2460
actgtacagg tcttgcagta gctgaagata caaaattatt attaatgaca agacctgcct    2520
ttggtggaaa tataatggca acaatagttt gtaaagattt cagacctcaa atgtctacag    2580
ttagaccagg ggttatgaag aaaaatgaac ctgatgaaac taagaagct gtaattaacc      2640 gtttcaaggt agaatttaat gatgctgata aattagttca agttgtacaa gtaataaaag    2700
aagctaaaaa acaagttaaa atagaagatg ctaagatatt agtttctgct ggacgtggaa    2760
tgggtggaaa agaaaactta gacatacttt atgaattagc tgaaattata ggtggagaag    2820
tttctggttc tcgtgccact atagatgcag gttggttaga taaagcaaga caagttggtc    2880
aaactggtaa aactgtaaga ccagacctt atatagcatg tggtatatct ggagcaatac       2940
aacatatagc tggtatggaa gatgctgagt ttatagttgc tataaataaa atccagaaag    3000
ctccaatatt taaatatgct gatgttggta tagttggaga tgttcataaa gtgcttccag    3060
aacttatcag tcagttaagt gttgcaaaag aaaaggtga agttttagct aactaataag        3120
aaggagatat acatatgaga gaagtagtaa ttgccagtgc agctagaaca gcagtaggaa    3180
gttttggagg agcatttaaa tcagtttcag cggtagagtt aggggtaaca gcagctaaag    3240
aagctataaa aagagctaac ataactccag atatgataga tgaatctctt ttaggggag     3300 tacttacagc aggtcttgga caaaatatag caagacaaat agcattagga gcaggaatac    3360
cagtagaaaa accagctatg actataaata tagtttgtgg ttctggatta agatctgttt    3420
caatggcatc tcaacttata gcattaggtg atgctgatat aatgttagtt ggtggagctg    3480
aaaacatgag tatgtctcct tatttagtac caagtgcgag atatggtgca agaatgggtg    3540
atgctgcttt tgttgattca atgataaaag atggattatc agacatattt aataactatc    3600
acatgggtat tactgctgaa acatagcag agcaatggaa tataactaga gaagaacaag      3660
atgaattagc tcttgcaagt caaaataaag ctgaaaagc tcaagctgaa ggaaaatttg      3720
atgaagaaat agttcctgtt gttataaaag gaagaaaagg tgacactgta gtagataaag    3780
atgaatatat taagcctggc actacaatgg agaaacttgc taagttaaga cctgcattta    3840
aaaaagatgg aacagttact gctggtaatg catcaggaat aaatgatggt gctgctatgt    3900
tagtagtaat ggctaaagaa aaagctgaag aactaggaat agagcctctt gcaactatag    3960
tttcttatgg aacagctggt gttgacccta aataatggg atatggacca gttccagcaa     4020
ctaaaaaagc tttagaagct gctaatatga ctattgaaga tatagattta gttgaagcta    4080
atgaggcatt tgctgcccaa tctgtagctg taataagaga cttaaatata gatatgaata    4140
aagttaatgt taatggtgga gcaatagcta taggacatcc aataggatgc tcaggagcaa    4200
gaatacttac tacactttta tatgaaatga gagaagaga tgctaaaact ggtcttgcta      4260
cactttgtat aggcggtgga atgggaacta ctttaatagt taagagatag taagaaggag    4320
atatacatat gaaattagct gtaataggta gtggaactat gggaagtggt attgtacaaa    4380
cttttgcaag ttgtggacat gatgtatgtt taagagtag aactcaaggt gctatagata    4440
aatgtttagc tttattagat aaaaatttaa ctaagttagt tactaaggga aaaatggatg    4500
aagctacaaa agcagaaata ttaagtcatg ttagttcaac tactaattat gaagatttaa    4560
```

```
aagatatgga tttaataata gaagcatctg tagaagacat gaatataaag aaagatgttt    4620
tcaagttact agatgaatta tgtaaagaag atactatctt ggcaacaaat acttcatcat    4680
tatctataac agaaatagct tcttctacta agcgcccaga taaagttata ggaatgcatt    4740
tctttaatcc agttcctatg atgaaattag ttgaagttat aagtggtcag ttaacatcaa    4800
aagttacttt tgatacagta tttgaattat ctaagagtat caataaagta ccagtagatg    4860
tatctgaatc tcctggattt gtagtaaata gaatacttat acctatgata aatgaagctg    4920
ttggtatata tgcagatggt gttgcaagta aagaagaaat agatgaagct atgaaattag    4980
gagcaaacca tccaatggga ccactagcat taggtgattt aatcggatta gatgttgttt    5040
tagctataat gaacgtttta tatactgaat ttggagatac taaatataga cctcatccac    5100
ttttagctaa aatggttaga gctaatcaat taggaagaaa aactaagata ggattctatg    5160
attataataa ataataagaa ggagatatac atatgagtac aagtgatgtt aaagtttatg    5220
agaatgtagc tgttgaagta gatggaaata tatgtacagt gaaatgaat agacctaaag     5280
cccttaatgc aataaattca aagactttag aagaacttta tgaagtattt gtagatatta    5340
ataatgatga aactattgat gttgtaatat tgacagggga aggaaaggca tttgtagctg    5400
gagcagatat tgcatacatg aaagatttag atgctgtagc tgctaaagat tttagtatct    5460
taggagcaaa agcttttgga gaaatagaaa atagtaaaaa agtagtgata gctgctgtaa    5520
acggatttgc tttaggtgga ggatgtgaac ttgcaatggc atgtgatata agaattgcat    5580
ctgctaaagc taaatttggt cagccagaag taactcttgg aataactcca ggatatggag    5640
gaactcaaag gcttacaaga ttggttggaa tggcaaaagc aaaagaatta atctttacag    5700
gtcaagttat aaaagctgat gaagctgaaa aaatagggct agtaaataga gtcgttgagc    5760
cagacatttt aatagaagaa gttgagaaat tagctaagat aatagctaaa aatgctcagc    5820
ttgcagttag atactctaaa gaagcaatac aacttggtgc tcaaactgat ataaatactg    5880
gaatagatat agaatctaat ttatttggtc tttgttttc aactaaagac caaaagaag     5940
gaatgtcagc tttcgttgaa agagagaag ctaactttat aaaagggtaa taagaaggag     6000
atatacatat gagaagtttt gaagaagtaa ttaagtttgc aaaagaaaga ggacctaaaa    6060
ctatatcagt agcatgttgc caagataaag aagttttaat ggcagttgaa atggctagaa    6120
aagaaaaaat agcaaatgcc attttagtag gagatataga aaagactaaa gaattgcaa     6180
aaagcataga catggatatc gaaaattatg aactgataga tataaaagat ttagcagaag    6240
catctctaaa atctgttgaa ttagtttcac aaggaaaagc cgacatggta atgaaaggct    6300
tagtagacac atcaataata ctaaaagcag ttttaaataa agaagtaggt cttagaactg    6360
gaaatgtatt aagtcacgta gcagtatttg atgtagaggg atatgataga ttattttcg     6420
taactgacgc agctatgaac ttagctcctg atacaaatac taaaagcaa atcatagaaa     6480
atgcttgcac agtagcacat tcattagata taagtgaacc aaaagttgct gcaatatgcg    6540
caaaagaaaa agtaaatcca aaaatgaaag atacagttga agctaaagaa ctagaagaaa    6600
tgtatgaaag aggagaaatc aaaggttgta tggttggtgg gccttttgca attgataatg    6660
cagtatcttt agaagcagct aaacataaag gtataaatca tcctgtagca ggacgagctg    6720
atatattatt agcccagat attgaaggtg gtaacatat atataaagct ttggtattct      6780
tctcaaaatc aaaaaatgca ggagttatag ttggggctaa agcaccaata atattaactt    6840
ctagagcaga cagtgaagaa actaaactaa actcaatagc tttaggtgtt ttaatggcag    6900
```

| | |
|---|---|
| caaaggcata ataagaagga gatatacata tgagcaaaat atttaaaatc ttaacaataa | 6960 |
| atcctggttc gacatcaact aaaatagctg tatttgataa tgaggattta gtatttgaaa | 7020 |
| aaactttaag acattcttca gaagaaatag gaaaatatga gaaggtgtct gaccaatttg | 7080 |
| aatttcgtaa acaagtaata gaagaagctc taaaagaagg tggagtaaaa acatctgaat | 7140 |
| tagatgctgt agtaggtaga ggaggacttc ttaaacctat aaaaggtggt acttattcag | 7200 |
| taagtgctgc tatgattgaa gatttaaaag tgggagtttt aggagaacac gcttcaaacc | 7260 |
| taggtggaat aatagcaaaa caaataggtg aagaagtaaa tgttccttca tacatagtag | 7320 |
| accctgttgt tgtagatgaa ttagaagatg ttgctagaat ttctggtatg cctgaaataa | 7380 |
| gtagagcaag tgtagtacat gctttaaatc aaaaggcaat agcaagaaga tatgctagag | 7440 |
| aaataaacaa gaaatatgaa gatataaatc ttatagttgc acacatgggt ggaggagttt | 7500 |
| ctgttggagc tcataaaaat ggtaaaatag tagatgttgc aaacgcatta gatggagaag | 7560 |
| gacctttctc tccagaaaga agtggtggac taccagtagg tgcattagta aaaatgtgct | 7620 |
| ttagtggaaa atatactcaa gatgaaatta aaagaaaat aaaaggtaat ggcggactag | 7680 |
| ttgcatactt aaacactaat gatgctagag aagttgaaga agaattgaa gctggtgatg | 7740 |
| aaaaagctaa attagtatat gaagctatgg catatcaaat ctctaaagaa ataggagcta | 7800 |
| gtgctgcagt tcttaaggga gatgtaaaag caatattatt aactggtgga atcgcatatt | 7860 |
| caaaaatgtt tacagaaatg attgcagata gagttaaatt tatagcagat gtaaaagttt | 7920 |
| atccaggtga agatgaaatg attgcattag ctcaaggtgg acttagagtt ttaactggtg | 7980 |
| aagaagaggc tcaagtttat gataactaat aa | 8012 |

<210> SEQ ID NO 82
<211> LENGTH: 6224
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 82

| | |
|---|---|
| ctcgagttca ttatccatcc tccatcgcca cgatagttca tggcgatagg tagaatagca | 60 |
| atgaacgatt atccctatca agcattctga ctgataattg ctcacacgaa ttcattaaag | 120 |
| aggagaaagg taccatgatc gtaaaaccta tggtacgcaa caatatctgc ctgaacgccc | 180 |
| atcctcaggg ctgcaagaag ggagtggaag atcagattga atataccaag aaacgcatta | 240 |
| ccgcagaagt caaagctggc gcaaaagctc caaaaaacgt tctggtgctt ggctgctcaa | 300 |
| atggttacgg cctggcgagc cgcattactg ctgcgttcgg atacggggct gcgaccatcg | 360 |
| gcgtgtcctt tgaaaaagcg ggttcagaaa ccaaatatgg tacaccggga tggtacaata | 420 |
| atttggcatt tgatgaagcg gcaaaacgcg agggtctttt agcgtgacg atcgacggcg | 480 |
| atgcgttttc agacgagatc aaggcccagg taattgagga agccaaaaaa aaaggtatca | 540 |
| aatttgatct gatcgtatac agcttggcca gcccagtacg tactgatcct gatacaggta | 600 |
| tcatgcacaa aagcgttttg aaacccttg gaaaaacgtt cacaggcaaa acagtagatc | 660 |
| cgtttactgg cgagctgaag gaaatctccg cggaaccagc aaatgacgag gaagcagccg | 720 |
| ccactgttaa agttatgggg ggtgaagatt gggaacgttg gattaagcag ctgtcgaagg | 780 |
| aaggcctctt agaagaaggc tgtattacct tggcctatag ttatattggc cctgaagcta | 840 |
| cccaagcttt gtaccgtaaa ggcacaatcg gcaaggccaa agaacacctg gaggccacag | 900 |

-continued

```
cacaccgtct caacaaagag aacccgtcaa tccgtgcctt cgtgagcgtg aataaaggcc    960
tggtaacccg cgcaagcgcc gtaatcccgg taatccctct gtatctcgcc agcttgttca   1020
aagtaatgaa agagaagggc aatcatgaag gttgtattga acagatcacg cgtctgtacg   1080
ccgagcgcct gtaccgtaaa gatggtacaa ttccagttga tgaggaaaat cgcattcgca   1140
ttgatgattg ggagttagaa gaagacgtcc agaaagcggt atccgcgttg atggagaaag   1200
tcacgggtga aaacgcagaa tctctcactg acttagcggg gtaccgccat gatttcttag   1260
ctagtaacgg ctttgatgta gaaggtatta attatgaagc ggaagttgaa cgcttcgacc   1320
gtatctgata agaaggagat atacatatga gagaagtagt aattgccagt gcagctagaa   1380
cagcagtagg aagttttgga ggagcattta atcagtttc agcggtagag ttagggtaa   1440 cagcagctaa agaagctata aaagagcta acataactcc agatatgata gatgaatctc   1500
ttttaggggg agtacttaca gcaggtcttg acaaaatat agcaagacaa atagcattag   1560
gagcaggaat accagtagaa aaaccagcta tgactataaa tatagtttgt ggttctggat   1620
taagatctgt ttcaatggca tctcaactta tagcattagg tgatgctgat ataatgttag   1680
ttggtggagc tgaaaacatg agtatgtctc cttatttagt accaagtgcg agatatggtg   1740
caagaatggg tgatgctgct tttgttgatt caatgataaa agatggatta tcagacatat   1800
ttaataacta tcacatgggt attactgctg aaaacatagc agagcaatgg aatataacta   1860
gagaagaaca agatgaatta gctcttgcaa gtcaaaataa agctgaaaaa gctcaagctg   1920
aaggaaaatt tgatgaagaa atagttcctg ttgttataaa aggaagaaaa ggtgacactg   1980
tagtagataa agatgaatat attaagcctg gcactacaat ggagaaactt gctaagttaa   2040
gacctgcatt taaaaagat ggaacagtta ctgctggtaa tgcatcagga ataaatgatg   2100
gtgctgctat gttagtagta atggctaaag aaaaagctga agaactagga atagagcctc   2160
ttgcaactat agtttcttat ggaacagctg gtgttgaccc taaaataatg ggatatggac   2220
cagttccagc aactaaaaaa gctttagaag ctgctaatat gactattgaa gatatagatt   2280
tagttgaagc taatgaggca tttgctgccc aatctgtagc tgtaataaga gacttaaata   2340
tagatatgaa taaagttaat gttaatggtg gagcaatagc tataggacat ccaataggat   2400
gctcaggagc aagaatactt actacacttt tatatgaaat gaagagaaga gatgctaaaa   2460
ctggtcttgc tacactttgt ataggcggtg gaatgggaac tactttaata gttaagagat   2520
agtaagaagg agatatacat atgaaattag ctgtaatagg tagtggaact atgggaagtg   2580
gtattgtaca aacttttgca agttgtggac atgatgtatg tttaaagagt agaactcaag   2640
gtgctataga taaatgttta gctttattag ataaaaattt aactaagtta gttactaagg   2700
gaaaaatgga tgaagctaca aaagcagaaa tattaagtca tgttagttca actactaatt   2760
atgaagattt aaaagatatg gatttaataa tagaagcatc tgtagaagac atgaatataa   2820
agaaagatgt tttcaagtta ctagatgaat tatgtaaaga agatactatc ttggcaacaa   2880
atacttcatc attatctata acagaaatag cttcttctac taagcgccca gataaagtta   2940
taggaatgca tttctttaat ccagttccta tgatgaaatt agttgaagtt ataagtggtc   3000
agttaacatc aaaagttact tttgatacag tatttgaatt atctaagagt atcaataaag   3060
taccagtaga tgtatctgaa tctcctggat tgtagtaaaa tagaatactt ataccgatga   3120
taaatgaagc tgttggtata tatgcagatg gtgttgcaag taagaagaa atagatgaag   3180 ctatgaaatt aggagcaaac catccaatgg gaccactagc attaggtgat ttaatcggat   3240
tagatgttgt tttagctata atgaacgttt tatatactga atttggagat actaaatata   3300
```

```
gacctcatcc acttttagct aaaatggtta gagctaatca attaggaaga aaaactaaga    3360
taggattcta tgattataat aaataataag aaggagatat acatatgagt acaagtgatg    3420
ttaaagttta tgagaatgta gctgttgaag tagatggaaa tatatgtaca gtgaaaatga    3480
atagacctaa agcccttaat gcaataaatt caaagacttt agaagaactt tatgaagtat    3540
ttgtagatat taataatgat gaaactattg atgttgtaat attgacaggg gaaggaaagg    3600
catttgtagc tggagcagat attgcataca tgaaagattt agatgctgta gctgctaaag    3660
attttagtat cttaggagca aaagcttttg gagaaataga aaatagtaaa aaagtagtga    3720
tagctgctgt aaacggattt gctttaggtg gaggatgtga acttgcaatg gcatgtgata    3780
taagaattgc atctgctaaa gctaaatttg gtcagccaga agtaactctt ggaataactc    3840
caggatatgg aggaactcaa aggcttacaa gattggttgg aatggcaaaa gcaaaagaat    3900
taatctttac aggtcaagtt ataaaagctg atgaagctga aaaaataggg ctagtaaata    3960
gagtcgttga gccagacatt ttaatagaag aagttgagaa attagctaag ataatagcta    4020
aaaatgctca gcttgcagtt agatactcta agaagcaat acaacttggt gctcaaactg    4080
atataaatac tggaatagat atagaatcta atttatttgg tctttgtttt tcaactaaag    4140
accaaaaaga aggaatgtca gctttcgttg aaaagagaga agctaacttt ataaaagggt    4200
aataagaagg agatatacat atgagaagtt ttgaagaagt aattaagttt gcaaaagaaa    4260
gaggacctaa aactatatca gtagcatgtt gccaagataa agaagtttta atggcagttg    4320 aaaatggctag aaaagaaaaa atagcaaatg ccatttttagt aggagatata gaaaagacta    4380
aagaaattgc aaaaagcata gacatggata tcgaaaatta tgaactgata gatataaaag    4440
atttagcaga agcatctcta aaatctgttg aattagtttc acaaggaaaa gccgacatgg    4500
taatgaaagg cttagtagac acatcaataa tactaaaagc agtttttaaat aaagaagtag    4560 gtcttagaac tggaaatgta ttaagtcacg tagcagtatt tgatgtagag ggatatgata    4620 gattatttt cgtaactgac gcagctatga acttagctcc tgatacaaat actaaaaagc    4680
aaatcataga aaatgcttgc acagtagcac attcattaga tataagtgaa ccaaaagttg    4740
ctgcaatatg cgcaaaagaa aaagtaaatc caaaaatgaa agatacagtt gaagctaaag    4800
aactagaaga aatgtatgaa agaggagaaa tcaaaggttg tatggttggt gggcctttttg    4860 caattgataa tgcagtatct ttagaagcag ctaaacataa aggtataaat catcctgtag    4920
caggacgagc tgatatatta ttagccccag atattgaagg tggtaacata ttatataaag    4980
ctttggtatt cttctcaaaa tcaaaaaatg caggagttat agttggggct aaagcaccaa    5040
taatattaac ttctagagca gacagtgaag aaactaaact aaactcaata gctttaggtg    5100
ttttaatggc agcaaaggca taataagaag gagatataca tatgagcaaa atatttaaaa    5160
tcttaacaat aaatcctggt tcgacatcaa ctaaaatagc tgtatttgat aatgaggatt    5220
tagtatttga aaaaacttta agacattctt cagaagaaat aggaaaatat gagaaggtgt    5280
ctgaccaatt tgaatttcgt aaacaagtaa tagaagaagc tctaaaagaa ggtggagtaa    5340
aaacatctga attagatgct gtagtaggta gaggaggact tcttaaacct ataaaaggtg    5400
gtacttattc agtaagtgct gctatgattg aagattaa agtgggagtt ttaggagaac    5460
acgcttcaaa cctaggtgga ataatagcaa acaaatagg tgaagaagta atgttccttt    5520
catacatagt agaccctgtt gttgtagatg aattagaaga tgttgctaga atttctggta    5580
tgcctgaaat aagtagagca agtgtagtac atgctttaaa tcaaaaggca atagcaagaa    5640
```

| | |
|---|---|
| gatatgctag agaaataaac aagaaatatg aagatataaa tcttatagtt gcacacatgg | 5700 |
| gtggaggagt ttctgttgga gctcataaaa atggtaaaat agtagatgtt gcaaacgcat | 5760 |
| tagatggaga aggacctttc tctccagaaa gaagtggtgg actaccagta ggtgcattag | 5820 |
| taaaaatgtg ctttagtgga aaatatactc aagatgaaat taaaagaaa ataaaaggta | 5880 |
| atggcggact agttgcatac ttaaacacta atgatgctag agaagttgaa gaaagaattg | 5940 |
| aagctggtga tgaaaaagct aaattagtat atgaagctat ggcatatcaa atctctaaag | 6000 |
| aaataggagc tagtgctgca gttcttaagg gagatgtaaa agcaatatta ttaactggtg | 6060 |
| gaatcgcata ttcaaaaatg tttacagaaa tgattgcaga tagagttaaa tttatagcag | 6120 |
| atgtaaaagt ttatccaggt gaagatgaaa tgattgcatt agctcaaggt ggacttagag | 6180 |
| ttttaactgg tgaagaagag gctcaagttt atgataacta taa | 6224 |

<210> SEQ ID NO 83
<211> LENGTH: 3118
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 83

| | |
|---|---|
| ctcgagatgc tagcaattgt gagcggataa caattgacat tgtgagcgga taacaagata | 60 |
| ctgagcacat cagcaggacg cactgacctt aattaaaaga attcattaaa gaggagaaag | 120 |
| gtaccatgaa tattcgtgat cttgagtacc tggtggcatt ggctgaacac cgccattttc | 180 |
| ggcgtgcggc agattcctgc cacgttagcc agccgacgct tagcgggcaa attcgtaagc | 240 |
| tggaagatga gctgggcgtg atgttgctgg agcggaccag ccgtaaagtg ttgttcaccc | 300 |
| aggcgggaat gctgctggtg gatcaggcgc gtaccgtgct gcgtgaggtg aaagtcctta | 360 |
| aagagatggc aagccagcag ggcgagacga tgtccggacc gctgcacatt ggtttgattc | 420 |
| ccacagttgg accgtacctg ctaccgcata ttatccctat gctgcaccag accttccaa | 480 |
| agctggaaat gtatctgcat gaagcacaga cccaccagtt actggcgcaa ctggacagcg | 540 |
| gcaaactcga ttgcgtgatc ctcgcgctgg tgaaagagag cgaagcattc attgaagtgc | 600 |
| cgttgtttga tgagccaatg ttgctggcta tctatgaaga tcacccgtgg gcgaaccgcg | 660 |
| aatgcgtacc gatggccgat ctggcagggg aaaaactgct gatgctggaa gatggtcact | 720 |
| gtttgcgcga tcaggcaatg ggtttctgtt ttgaagccgg ggcggatgaa gatacacact | 780 |
| tccgcgcgac cagcctggaa actctgcgca acatggtggc ggcaggtagc gggatcactt | 840 |
| tactgccagc gctggctgtg ccgccggagc gcaaacgcga tggggttgtt tatctgccgt | 900 |
| gcattaagcc ggaaccacgc cgcactattg gcctggttta tcgtcctggc tcaccgctgc | 960 |
| gcagccgcta tgagcagctg gcagaggcca tccgcgcaag aatggatggc catttcgata | 1020 |
| aagttttaaa acaggcggtt taaggatccc atggtacgcg tgctagaggc atcaaataaa | 1080 |
| acgaaaggct cagtcgaaag actgggcctt tcgttttatc tgttgtttgt cggtgaacgc | 1140 |
| tctcctgagt aggacaaatc cgccgcccta gacctagggg atatattccg cttcctcgct | 1200 |
| cactgactcg ctacgctcgg tcgttcgact gcggcgagcg gaaatggctt acgaacgggg | 1260 |
| cggagatttc ctggaagatg ccaggaagat acttaacagg gaagtgagag gccgcggca | 1320 |
| aagccgtttt tccataggct ccgcccccct gacaagcatc acgaaatctg acgctcaaat | 1380 |
| cagtggtggc gaaacccgac aggactataa agataccagg cgtttccccc tggcggctcc | 1440 |

| | |
|---|---|
| ctcgtgcgct ctcctgttcc tgcctttcgg tttaccggtg tcattccgct gttatggccg | 1500 |
| cgtttgtctc attccacgcc tgacactcag ttccgggtag gcagttcgct ccaagctgga | 1560 |
| ctgtatgcac gaaccccccg ttcagtccga ccgctgcgcc ttatccggta actatcgtct | 1620 |
| tgagtccaac ccggaaagac atgcaaaagc accactggca gcagccactg gtaattgatt | 1680 |
| tagaggagtt agtcttgaag tcatgcgccg gttaaggcta aactgaaagg acaagttttg | 1740 |
| gtgactgcgc tcctccaagc cagttacctc ggttcaaaga gttggtagct cagagaacct | 1800 |
| tcgaaaaacc gccctgcaag gcggttttt cgttttcaga gcaagagatt acgcgcagac | 1860 |
| caaaacgatc tcaagaagat catcttatta atcagataaa atatttctag atttcagtgc | 1920 |
| aatttatctc ttcaaatgta gcacctgaag tcagccccat acgatataag ttgttactag | 1980 |
| tgcttggatt ctcaccaata aaaaacgccc ggcggcaacc gagcgttctg aacaaatcca | 2040 |
| gatggagttc tgaggtcatt actggatcta tcaacaggag tccaagcgag ctctcgaacc | 2100 |
| ccagagtccc gctcagaaga actcgtcaag aaggcgatag aaggcgatgc gctgcgaatc | 2160 |
| gggagcggcg ataccgtaaa gcacgaggaa gcggtcagcc cattcgccgc caagctcttc | 2220 |
| agcaatatca cgggtagcca acgctatgtc ctgatagcgg tccgccacac ccagccggcc | 2280 |
| acagtcgatg aatccagaaa agcggccatt ttccaccatg atattcggca agcaggcatc | 2340 |
| gccatgggtc acgacgagat cctcgccgtc gggcatgcgc gccttgagcc tggcgaacag | 2400 |
| ttcggctggc gcgagcccct gatgctcttc gtccagatca tcctgatcga caagaccggc | 2460 |
| ttccatccga gtacgtgctc gctcgatgcg atgtttcgct tggtggtcga atgggcaggt | 2520 |
| agccggatca agcgtatgca gccgccgcat tgcatcagcc atgatggata ctttctcggc | 2580 |
| aggagcaagg tgagatgaca ggagatcctg ccccggcact cgcccaata gcagccagtc | 2640 |
| ccttcccgct tcagtgacaa cgtcgagcac agctgcgcaa ggaacgcccg tcgtggccag | 2700 |
| ccacgatagc cgcgctgcct cgtcctgcag ttcattcagg gcaccggaca ggtcggtctt | 2760 |
| gacaaaaaga accgggcgcc cctgcgctga cagccggaac acggcggcat cagagcagcc | 2820 |
| gattgtctgt tgtgcccagt catagccgaa tagcctctcc acccaagcgg ccggagaacc | 2880 |
| tgcgtgcaat ccatcttgtt caatcatgcg aaacgatcct catcctgtct cttgatcaga | 2940 |
| tcttgatccc ctgcgccatc agatccttgg cggcaagaaa gccatccagt ttactttgca | 3000 |
| gggcttccca accttaccag agggcgcccc agctggcaat tccgacgtct aagaaaccat | 3060 |
| tattatcatg acattaacct ataaaaatag gcgtatcacg aggccctttc gtcttcac | 3118 |

<210> SEQ ID NO 84
<211> LENGTH: 8650
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 84

| | |
|---|---|
| gtaaaacgac ggccagtgaa ttcgttaaga cccactttca catttaagtt gttttttctaa | 60 |
| tccgcatatg atcaattcaa ggccgaataa gaaggctggc tctgcacctt ggtgatcaaa | 120 |
| taattcgata gcttgtcgta ataatggcgg catactatca gtagtaggtg tttccctttc | 180 |
| ttctttagcg acttgatgct cttgatcttc caatacgcaa cctaaagtaa aatgccccac | 240 |
| agcgctgagt gcatataatg cattctctag tgaaaaacct tgttggcata aaaggctaa | 300 |
| ttgatttttcg agagtttcat actgtttttc tgtaggccgt gtacctaaat gtacttttgc | 360 |

```
tccatcgcga tgacttagta aagcacatct aaaactttta gcgttattac gtaaaaaatc      420
ttgccagctt tccccttcta aagggcaaaa gtgagtatgg tgcctatcta acatctcaat      480
ggctaaggcg tcgagcaaag cccgcttatt ttttacatgc aatacaatg  taggctgctc      540 tacacctagc ttctgggcga gtttacgggt tgttaaacct tcgattccga cctcattaag      600
cagctctaat gcgctgttaa tcactttact tttatctaat ctagacatca ttaattccta      660 attttttgttg acactctatc attgatagag ttattttacc actccctatc agtgatagag     720
aaaagtgaac tctagaaata attttgttta actttaagaa ggagatatac atatggattt      780
aaattctaaa aaatatcaga tgcttaaaga gctatatgta agcttcgctg aaaatgaagt      840
taaaccttta gcaacagaac ttgatgaaga agaaagattt ccttatgaaa cagtggaaaa      900
aatggcaaaa gcaggaatga tgggtatacc atatccaaaa gaatatggtg agaaggtgg      960 agacactgta ggatatataa tggcagttga agaattgtct agagtttgtg gtactacagg      1020
agttatatta tcagctcata catctcttgg ctcatggcct atatatcaat atggtaatga     1080
agaacaaaaa caaaaattct aagaccact  agcaagtgga gaaaaattag gagcatttgg     1140
tcttactgag cctaatgctg gtacagatgc gtctggccaa caaacaactg ctgttttaga     1200
cggggatgaa tacatactta atggctcaaa aatatttata acaaacgcaa tagctggtga     1260
catatatgta gtaatggcaa tgactgataa atctaagggg aacaaaggaa tatcagcatt     1320
tatagttgaa aaaggaactc ctgggtttag cttttggagtt aaagaaaaga aaatgggtat    1380
aagaggttca gctacgagtg aattaatatt tgaggattgc agaataccta agaaaatttt     1440
acttggaaaa gaaggtcaag gatttaagat agcaatgtct actcttgatg gtggtagaat     1500
tggtatagct gcacaagctt taggtttagc acaaggtgct cttgatgaaa ctgttaaata     1560
tgtaaaagaa agagtacaat ttggtagacc attatcaaaa ttccaaaata cacaattcca     1620
attagctgat atggaagtta aggtacaagc ggctagacac cttgtatatc aagcagctat     1680
aaataaagac ttaggaaaac cttatggagt agaagcagca atggcaaaat tatttgcagc     1740
tgaaacagct atggaagtta ctacaaaagc tgtacaactt catggaggat atggatacac     1800
tcgtgactat ccagtagaaa gaatgatgag agatgctaag ataactgaaa tatatgaagg     1860
aactagtgaa gttcaaagaa tggttatttc aggaaaacta ttaaaatagt aagaaggaga    1920
tatacatatg gaggaaggat ttatgaatat agtcgtttgt ataaaacaag ttccagatac     1980
aacagaagtt aaactagatc ctaatacagg tactttaatt agagatggag taccaagtat    2040
aataaaccct gatgataaag caggtttaga agaagctata aaattaaaag aagaaatggg    2100
tgctcatgta actgttataa caatgggacc tcctcaagca gatatggctt taaaagaagc    2160
tttagcaatg ggtgcagata gaggtatatt attaacagat agagcatttg cgggtgctga    2220
tacttgggca acttcatcag cattagcagg agcattaaaa aatatagatt ttgatattat    2280
aatagctgga agacaggcga tagatggaga tactgcacaa gttggacctc aaatagctga    2340
acatttaaat cttccatcaa taacatatgc tgaagaaata aaaactgaag gtgaatatgt    2400
attagtaaaa agacaatttg aagattgttg ccatgactta aaagttaaaa tgccatgcct    2460
tataacaact cttaaagata tgaacacacc aagatacatg aaagttggaa gaatatatga    2520
tgctttcgaa aatgatgtag tagaaacatg gactgtaaaa gatatagaag ttgacccttc    2580
taatttaggt cttaaaggtt ctccaactag tgtatttaaa tcatttacaa atcagttaa     2640 accagctggt acaatataca atgaagatgc gaaaacatca gctggaatta tcatagataa    2700
attaaaagag aagtatatca tataataaga aggagatata catatgggta acgttttagt    2760
```

```
agtaatagaa caaagagaaa atgtaattca aactgtttct ttagaattac taggaaaggc    2820
tacagaaata gcaaaagatt atgatacaaa agtttctgca ttacttttag gtagtaaggt    2880
agaaggttta atagatacat tagcacacta tggtgcagat gaggtaatag tagtagatga    2940
tgaagcttta gcagtgtata caactgaacc atatacaaaa gcagcttatg aagcaataaa    3000
agcagctgac cctatagttg tattatttgg tgcaacttca ataggtagag atttagcgcc    3060
tagagtttct gctagaatac atacaggtct tactgctgac tgtacaggtc ttgcagtagc    3120
tgaagataca aaattattat taatgacaag acctgccttt ggtggaaata taatggcaac    3180
aatagtttgt aaagatttca gacctcaaat gtctacagtt agaccagggg ttatgaagaa    3240
aaatgaacct gatgaaacta agaagctgt aattaaccgt ttcaaggtag aatttaatga    3300
tgctgataaa ttagttcaag ttgtacaagt aataaaagaa gctaaaaaac aagttaaaat    3360
agaagatgct aagatattag tttctgctgg acgtggaatg ggtggaaaag aaaacttaga    3420
catactttat gaattagctg aaattatagg tggagaagtt tctggttctc gtgccactat    3480
agatgcaggt tggttagata agcaagaca agttggtcaa actggtaaaa ctgtaagacc    3540
agacctttat atagcatgtg gtatatctgg agcaatacaa catatagctg gtatggaaga    3600
tgctgagttt atagttgcta taaataaaaa tccagaagct ccaatattta aatatgctga    3660
tgttggtata gttggagatg ttcataaagt gcttccagaa cttatcagtc agttaagtgt    3720
tgcaaaagaa aaaggtgaag ttttagctaa ctaataagaa ggagatatac atatgagaga    3780
agtagtaatt gccagtgcag ctagaacagc agtaggaagt tttggaggag catttaaatc    3840
agtttcagcg gtagagttag gggtaacagc agctaaagaa gctataaaaa gagctaacat    3900
aactccagat atgatagatg aatctctttt agggggagta cttacagcag gtcttggaca    3960
aaatatagca agacaaatag cattaggagc aggaatacca gtagaaaaac cagctatgac    4020
tataaatata gtttgtggt ctggattaag atctgtttca atggcatctc aacttatagc    4080
attaggtgat gctgatataa tgttagttgg tggagctgaa acatgagta tgtctcctta    4140 tttagtacca agtgcgagat atggtgcaag aatgggtgat gctgcttttg ttgattcaat    4200
gataaaagat ggattatcag acatatttaa taactatcac atgggtatta ctgctgaaaa    4260
catagcagag caatggaata taactagaga agaacaagat gaattagctc ttgcaagtca    4320
aaataaagct gaaaaagctc aagctgaagg aaaatttgat gaagaaatag ttcctgttgt    4380
tataaaagga agaaaaggtg acactgtagt agataaagat gaatatatta gcctggcac    4440 tacaatggag aaacttgcta agttaagacc tgcatttaaa aaagatggaa cagttactgc    4500
tggtaatgca tcaggaataa atgatggtgc tgctatgtta gtagtaatgg ctaaagaaaa    4560
agctgaagaa ctaggaatag agcctcttgc aactatagtt tcttatggaa cagctggtgt    4620
tgaccctaaa ataatgggat atggaccagt tccagcaact aaaaaagctt tagaagctgc    4680
taatatgact attgaagata tagatttagt tgaagctaat gaggcatttg ctgcccaatc    4740
tgtagctgta ataagagact aaatatagaa tatgaataaa gttaatgtta atggtggagc    4800
aatagctata ggacatccaa taggatgctc aggagcaaga atacttacta cacttttata    4860
tgaaatgaag agaagagatg ctaaaactgg tcttgctaca ctttgtatag gcggtggaat    4920
gggaactact ttaatagtta agagatagta agaaggagat atacatatga aattagctgt    4980
aataggtagt ggaactatgg gaagtggtat tgtacaaact tttgcaagtt gtggacatga    5040
tgtatgttta aagagtagaa ctcaaggtgc tatagataaa tgtttagctt tattagataa    5100
```

```
aaatttaact aagttagtta ctaagggaaa aatggatgaa gctacaaaag cagaaatatt    5160
aagtcatgtt agttcaacta ctaattatga agatttaaaa gatatggatt taataataga    5220
agcatctgta gaagacatga atataaagaa agatgttttc aagttactag atgaattatg    5280
taaagaagat actatcttgg caacaaatac ttcatcatta tctataacag aaatagcttc    5340
ttctactaag cgcccagata aagttatagg aatgcatttc tttaatccag ttcctatgat    5400
gaaattagtt gaagttataa gtggtcagtt aacatcaaaa gttacttttg atacagtatt    5460
tgaattatct aagagtatca ataaagtacc agtagatgta tctgaatctc ctggatttgt    5520
agtaaataga atacttatac ctatgataaa tgaagctgtt ggtatatatg cagatggtgt    5580
tgcaagtaaa gaagaaatag atgaagctat gaaattagga gcaaaccatc caatgggacc    5640
actagcatta ggtgatttaa tcggattaga tgttgtttta gctataatga acgttttata    5700
tactgaattt ggagatacta atatagacc tcatccactt ttagctaaaa tggttagagc    5760
taatcaatta ggaagaaaaa ctaagatagg attctatgat tataataaat aataagaagg    5820
agatatacat atgagtacaa gtgatgttaa agtttatgag aatgtagctg ttgaagtaga    5880
tggaaatata tgtacagtga aaatgaatag acctaaagcc cttaatgcaa taaattcaaa    5940
gactttagaa gaacttatg aagtatttgt agatattaat aatgatgaaa ctattgatgt    6000
tgtaatattg acaggggaag gaaaggcatt tgtagctgga gcagatattg catacatgaa    6060
agatttagat gctgtagctg ctaaagattt tagtatctta ggagcaaaag cttttggaga    6120
aatagaaaat agtaaaaaag tagtgatagc tgctgtaaac ggatttgctt taggtggagg    6180
atgtgaactt gcaatggcat gtgatataag aattgcatct gctaaagcta aatttggtca    6240
gccagaagta actcttggaa taactccagg atatggagga actcaaaggc ttacaagatt    6300
ggttggaatg caaaagcaa aagaattaat ctttacaggt caagttataa aagctgatga    6360
agctgaaaaa atagggctag taaatagagt cgttgagcca gacatttaa tagaagaagt    6420 tgagaaatta gctaagataa tagctaaaaa tgctcagctt gcagttagat actctaaaga    6480
agcaatacaa cttggtgctc aaactgatat aaatactgga atagatatag aatctaattt    6540
atttggtctt tgttttcaa ctaaagacca aaaagaagga atgtcagctt tcgttgaaaa    6600
gagagaagct aactttataa aagggtaata agaaggagat atacatatga aagttttga    6660 agaagtaatt aagtttgcaa aagaaagagg acctaaaact atatcagtag catgttgcca    6720
agataaagaa gttttaatgg cagttgaaat ggctagaaaa gaaaaaatag caaatgccat    6780
tttagtagga gatatagaaa agactaaaga aattgcaaaa agcatagaca tggatatcga    6840
aaattatgaa ctgatagata taaagatttt agcagaagca tctctaaaat ctgttgaatt    6900
agtttcacaa ggaaaagccg acatggtaat gaaaggctta gtagacacat caataatact    6960
aaaagcagtt ttaaataaag aagtaggtct tagaactgga aatgtattaa gtcacgtagc    7020
agtatttgat gtagagggat atgatagatt atttttcgta actgacgcag ctatgaactt    7080
agctcctgat acaaatacta aaagcaaat catagaaaat gcttgcacag tagcacattc    7140
attagatata agtgaaccaa aagttgctgc aatatgcgca aaagaaaaag taaatccaaa    7200
aatgaaagat acagttgaag ctaaagaact agaagaaatg tatgaaagag gagaaatcaa    7260
aggttgtatg gttggtgggc ttttgcaat tgataatgca gtatctttag aagcagctaa    7320
acataaaggt ataaatcatc ctgtagcagg acgagctgat atattattag ccccagatat    7380
tgaaggtggt aacatattat ataaagcttt ggtattcttc tcaaaatcaa aaatgcagg    7440 agttatagtt ggggctaaag caccaataat attaacttct agagcagaca gtgaagaaac    7500
```

```
taaactaaac tcaatagctt taggtgtttt aatggcagca aaggcataat aagaaggaga    7560
tatacatatg agcaaaatat ttaaaatctt aacaataaat cctggttcga catcaactaa    7620
aatagctgta tttgataatg aggatttagt atttgaaaaa actttaagac attcttcaga    7680
agaaatagga aaatatgaga aggtgtctga ccaatttgaa tttcgtaaac aagtaataga    7740
agaagctcta aaagaaggtg gagtaaaaac atctgaatta gatgctgtag taggtagagg    7800
aggacttctt aaacctataa aaggtggtac ttattcagta agtgctgcta tgattgaaga    7860
tttaaaagtg ggagttttag gagaacacgc ttcaaaccta ggtggaataa tagcaaaaca    7920
aataggtgaa gaagtaaatg ttccttcata catagtagac cctgttgttg tagatgaatt    7980
agaagatgtt gctagaattt ctggtatgcc tgaaataagt agagcaagtg tagtacatgc    8040
tttaaatcaa aaggcaatag caagaagata tgctagagaa ataaacaaga aatatgaaga    8100
tataaatctt atagttgcac acatgggtgg aggagtttct gttggagctc ataaaaatgg    8160
taaaatagta gatgttgcaa acgcattaga tggagaagga cctttctctc cagaaagaag    8220
tggtggacta ccagtaggtg cattagtaaa aatgtgcttt agtggaaaat atactcaaga    8280
tgaaattaaa aagaaaataa aaggtaatgg cggactagtt gcatacttaa acactaatga    8340
tgctagagaa gttgaagaaa gaattgaagc tggtgatgaa aaagctaaat tagtatatga    8400
agctatggca tatcaaatct ctaaagaaat aggagctagt gctgcagttc ttaagggaga    8460
tgtaaaagca atattattaa ctggtggaat cgcatattca aaaatgttta cagaaatgat    8520
tgcagataga gttaaatttta tagcagatgt aaaagtttat ccaggtgaag atgaaatgat    8580
tgcattagct caaggtggac ttagagtttt aactggtgaa gaagaggctc aagtttatga    8640
taactaataa                                                          8650
```

<210> SEQ ID NO 85
<211> LENGTH: 6862
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 85

```
gtaaaacgac ggccagtgaa ttcgttaaga cccactttca catttaagtt gttttctaa      60 tccgcatatg atcaattcaa ggccgaataa gaaggctggc tctgcacctt ggtgatcaaa    120
taattcgata gcttgtcgta ataatggcgg catactatca gtagtaggtg tttcccttcc    180
ttctttagcg acttgatgct cttgatcttc caatacgcaa cctaaagtaa aatgccccac    240
agcgctgagt gcatataatg cattctctag tgaaaaacct tgttggcata aaaaggctaa    300
ttgattttcg agagtttcat actgtttttc tgtaggccgt gtacctaaat gtacttttgc    360
tccatcgcga tgacttagta aagcacatct aaaactttta gcgttattac gtaaaaaatc    420
ttgccagctt tccccttcta aagggcaaaa gtgagtatgg tgcctatcta acatctcaat    480
ggctaaggcg tcgagcaaag cccgcttatt ttttacatgc aatacaatg taggctgctc    540 tacacctagc ttctgggcga gtttacgggt tgttaaacct tcgattccga cctcattaag    600
cagctctaat gcgctgttaa tcactttact tttatctaat ctagacatca ttaattccta    660 attttttgttg acactctatc attgatagag ttattttacc actccctatc agtgatagag    720
aaaagtgaac tctagaaata attttgttta actttaagaa ggagatatac atatgatcgt    780
aaaacctatg gtacgcaaca atatctgcct gaacgcccat cctcagggct gcaagaaggg    840
```

```
agtggaagat cagattgaat ataccaagaa acgcattacc gcagaagtca aagctggcgc    900
aaaagctcca aaaaacgttc tggtgcttgg ctgctcaaat ggttacgcc tggcgagccg      960 cattactgct gcgttcggat acggggctgc gaccatcggc gtgtcctttg aaaaagcggg   1020
ttcagaaacc aaatatggta caccgggatg gtacaataat ttggcatttg atgaagcggc   1080
aaaacgcgag ggtctttata gcgtgacgat cgacggcgat gcgttttcag acgagatcaa   1140
ggcccaggta attgaggaag ccaaaaaaaa aggtatcaaa tttgatctga tcgtatacag   1200
cttggccagc ccagtacgta ctgatcctga tacaggtatc atgcacaaaa gcgttttgaa   1260
acccttTgga aaaacgttca caggcaaaac agtagatccg tttactggcg agctgaagga   1320
aatctccgcg gaaccagcaa atgacgagga agcagccgcc actgttaaag ttatgggggg   1380
tgaagattgg gaacgttgga ttaagcagct gtcgaaggaa ggcctcttag aagaaggctg   1440
tattaccttg gcctatagtt atattggccc tgaagctacc caagctttgt accgtaaagg   1500
cacaatcggc aaggccaaag aacacctgga ggccacagca caccgtctca acaaagagaa   1560
cccgtcaatc cgtgccttcg tgagcgtgaa taaaggcctg gtaacccgcg caagcgccgt   1620
aatcccggta atccctctgt atctcgccag cttgttcaaa gtaatgaaag agaagggcaa   1680
tcatgaaggt tgtattgaac agatcacgcg tctgtacgcc gagcgcctgt accgtaaaga   1740
tggtacaatt ccagttgatg aggaaaatcg cattcgcatt gatgattggg agttagaaga   1800
agacgtccag aaagcggtat ccgcgttgat ggagaaagtc acgggtgaaa acgcagaatc   1860
tctcactgac ttagcggggt accgccatga tttcttagct agtaacggct ttgatgtaga   1920
aggtattaat tatgaagcgg aagttgaacg cttcgaccgt atctgataag aaggagatat   1980
acatatgaga gaagtagtaa ttgccagtgc agctagaaca gcagtaggaa gttttggagg   2040
agcatttaaa tcagtttcag cggtagagtt aggggtaaca gcagctaaag aagctataaa   2100
aagagctaac ataactccag atatgataga tgaatctctt ttaggggag tacttacagc   2160 aggtcttgga caaaatatag caagacaaat agcattagga gcaggaatac cagtagaaaa   2220
accagctatg actataaata tagttttgtg ttctggatta agatctgttt caatggcatc   2280
tcaacttata gcattaggtg atgctgatat aatgttagtt ggtggagctg aaaacatgag   2340
tatgtctcct tatttagtac caagtgcgag atatggtgca agaatgggtg atgctgcttt   2400
tgttgattca atgataaaag atggattatc agacatattt aataactatc acatgggtat   2460
tactgctgaa acatagcag agcaatggaa tataactaga gaagaacaag atgaattagc   2520
tcttgcaagt caaaataaag ctgaaaaagc tcaagctgaa ggaaaatttg atgaagaaat   2580
agttcctgtt gttataaaag gaagaaaagg tgacactgta gtagataaag atgaatatat   2640
taagcctggc actacaatgg agaaacttgc taagttaaga cctgcattta aaaaagatgg   2700
aacagttact gctggtaatg catcaggaat aaatgatggt gctgctatgt tagtagtaat   2760
ggctaaagaa aaagctgaag aactaggaat agagcctctt gcaactatag tttcttatgg   2820
aacagctggt gttgacccta aaataatggg atatggacca gttccagcaa ctaaaaaagc   2880
tttagaagct gctaatatga ctattgaaga tatagattta gttgaagcta atgaggcatt   2940
tgctgcccaa tctgtagctg taataagaga cttaaatata gatatgaata agttaatgt   3000 taatggtgga gcaatagcta taggacatcc aataggatgc tcaggagcaa gaatacttac   3060
tacactttta tatgaaatga agagaagaga tgctaaaact ggtcttgcta cactttgtat   3120
aggcggtgga atgggaacta ctttaatagt taagagatag taagaaggag atatacatat   3180
```

```
gaaattagct gtaataggta gtggaactat gggaagtggt attgtacaaa cttttgcaag      3240
ttgtggacat gatgtatgtt taaagagtag aactcaaggt gctatagata aatgtttagc      3300
tttattagat aaaaatttaa ctaagttagt tactaaggga aaaatggatg aagctacaaa      3360
agcagaaata ttaagtcatg ttagttcaac tactaattat gaagatttaa agatatggaa      3420
tttaataata gaagcatctg tagaagacat gaatataaag aaagatgttt tcaagttact      3480
agatgaatta tgtaaagaag atactatctt ggcaacaaat acttcatcat tatctataac      3540
agaaatagct tcttctacta agcgcccaga taaagttata ggaatgcatt tctttaatcc      3600
agttcctatg atgaaattag ttgaagttat aagtggtcag ttaacatcaa aagttacttt      3660
tgatacagta tttgaattat ctaagagtat caataaagta ccagtagatg tatctgaatc      3720
tcctggattt gtagtaaata gaatacttat acctatgata aatgaagctg ttggtatata      3780
tgcagatggt gttgcaagta aagaagaaat agatgaagct atgaaattag gagcaaacca      3840
tccaatggga ccactagcat taggtgattt aatcggatta gatgttgttt tagctataat      3900
gaacgtttta tatactgaat ttggagatac taaaatataga cctcatccac ttttagctaa      3960
aatggttaga gctaatcaat taggaagaaa aactaagata ggattctatg attataataa      4020
ataataagaa ggagatatac atatgagtac aagtgatgtt aaagtttatg agaatgtagc      4080
tgttgaagta gatggaaata tatgtacagt gaaaatgaat agacctaaag cccttaatgc      4140
aataaattca aagactttag aagaacttta tgaagtattt gtagatatta ataatgatga      4200
aactattgat gttgtaatat tgacagggga aggaaaggca tttgtagctg gagcagatat      4260
tgcatacatg aaagatttag atgctgtagc tgctaaagat tttagtatct taggagcaaa      4320
agcttttgga gaaatagaaa atagtaaaaa agtagtgata gctgctgtaa acggatttgc      4380
tttaggtgga ggatgtgaac ttgcaatggc atgtgatata agaattgcat ctgctaaagc      4440
taaatttggt cagccagaag taactcttgg aataactcca ggatatggag gaactcaaag      4500
gcttacaaga ttggttggaa tggcaaaagc aaaagaatta atctttacag gtcaagttat      4560
aaaagctgat gaagctgaaa aaatagggct agtaaataga gtcgttgagc cagacatttt      4620
aatagaagaa gttgagaaat tagctaagat aaatagctaaa aatgctcagc ttgcagttag      4680
atactctaaa gaagcaatac aacttggtgc tcaaactgat ataaatactg aatagatat      4740 agaatctaat ttatttggtc tttgtttttc aactaaagac caaaagaag gaatgtcagc      4800 tttcgttgaa aagagagaag ctaactttat aaaagggtaa taagaaggag atatacatat      4860
gagaagtttt gaagaagtaa ttaagtttgc aaaagaaaga ggacctaaaa ctatatcagt      4920
agcatgttgc caagataaag aagtttaaat ggcagttgaa atggctagaa agaaaaaat      4980 agcaaatgcc attttagtag gagatataga aaagactaaa gaaattgcaa aaagcataga      5040
catggatatc gaaaattatg aactgataga tataaaagat ttagcagaag catctctaaa      5100
atctgttgaa ttagttttcac aaggaaaagc cgacatggta atgaaaggct tagtagacac      5160
atcaataata ctaaaagcag tttttaaataa agaagtaggt cttagaactg gaaatgtatt      5220
aagtcacgta gcagtatttg atgtagaggg atatgataga ttatttttcg taactgacgc      5280
agctatgaac ttagctcctg atacaaatac taaaagcaa atcatagaaa atgcttgcac      5340
agtagcacat tcattagata taagtgaacc aaaagttgct gcaatatgcg caaaagaaaa      5400
agtaaatcca aaaatgaaag atacagttga agctaaagaa ctagaagaaa tgtatgaaag      5460
aggagaaatc aaaggttgta tggttggtgg gccttttgca attgataatg cagtatcttt      5520
agaagcagct aaacataaag gtataaatca tcctgtagca ggacgagctg atatattatt      5580
```

```
agccccagat attgaaggtg gtaacatatt atataaagct ttggtattct tctcaaaatc    5640
aaaaaatgca ggagttatag ttggggctaa agcaccaata atattaactt ctagagcaga    5700
cagtgaagaa actaaactaa actcaatagc tttaggtgtt ttaatggcag caaaggcata    5760
ataagaagga gatatacata tgagcaaaat atttaaaatc ttaacaataa atcctggttc    5820
gacatcaact aaaatagctg tatttgataa tgaggattta gtatttgaaa aaactttaag    5880
acattcttca gaagaaatag gaaaatatga gaaggtgtct gaccaatttg aatttcgtaa    5940
acaagtaata gaagaagctc taaaagaagg tggagtaaaa acatctgaat tagatgctgt    6000
agtaggtaga ggaggacttc ttaaacctat aaaaggtggt acttattcag taagtgctgc    6060
tatgattgaa gatttaaaag tgggagtttt aggagaacac gcttcaaacc taggtggaat    6120
aatagcaaaa caataggtg aagaagtaaa tgttccttca tacatagtag accctgttgt    6180
tgtagatgaa ttagaagatg ttgctagaat ttctggtatg cctgaaataa gtagagcaag    6240
tgtagtacat gctttaaatc aaaaggcaat agcaagaaga tatgctagag aaataaacaa    6300
gaaatatgaa gatataaatc ttatagttgc acacatgggt ggaggagttt ctgttggagc    6360
tcataaaaat ggtaaaatag tagatgttgc aaacgcatta gatggagaag gacctttctc    6420
tccagaaaga agtggtggac taccagtagg tgcattagta aaaatgtgct ttagtggaaa    6480
atatactcaa gatgaaatta aaagaaaat aaaggtaat ggcggactag ttgcatactt    6540
aaacactaat gatgctagag aagttgaaga agaattgaa gctggtgatg aaaaagctaa    6600
attagtatat gaagctatgg catatcaaat ctctaaagaa ataggagcta gtgctgcagt    6660
tcttaaggga gatgtaaaag caatattatt aactggtgga atcgcatatt caaaaatgtt    6720
tacagaaatg attgcagata gagttaaatt tatagcagat gtaaaagttt atccaggtga    6780
agatgaaatg attgcattag ctcaaggtgg acttagagtt ttaactggtg aagaagaggc    6840
tcaagtttat gataactaat aa                                             6862
```

<210> SEQ ID NO 86
<211> LENGTH: 5644
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 86

```
ttattatcgc accgcaatcg ggattttcga ttcataaagc aggtcgtagg tcggcttgtt      60
gagcaggtct tgcagcgtga aaccgtccag atacgtgaaa aacgacttca ttgcaccgcc     120
gagtatgccc gtcagccggc aggacggcgt aatcaggcat tcgttgttcg ggcccataca     180
ctcgaccagc tgcatcggtt cgaggtggcg gacgaccgcg ccgatattga tgcgttcggg     240
cggcgcggcc agcctcagcc cgccgccttt cccgcgtacg ctgtgcaaga acccgccttt     300
gaccagcgcg gtaaccactt tcatcaaatg gcttttggaa atgccgtagg tcgaggcgat     360
ggtggcgata ttgaccagcg cgtcgtcgtt gacggcggtg tagatgagga cgcgcagccc     420
gtagtcggta tgttgggtca gatacataca acctccttag tacatgcaaa attatttcta     480
gagcaacata cgagccggaa gcataaagtg taaagcctgg ggtgcctaat gagttgagtt     540
gaggaattat aacaggaaga atattcctc atacgcttgt aattcctcta tggttgttga     600
caattaatca tcggctcgta taatgtataa cattcatatt ttgtgaattt taaactctag     660
aaataatttt gtttaacttt aagaaggaga tatacatatg atcgtaaaac ctatggtacg     720
```

```
caacaatatc tgcctgaacg cccatcctca gggctgcaag aagggagtgg aagatcagat      780
tgaatatacc aagaaacgca ttaccgcaga agtcaaagct ggcgcaaaag ctccaaaaaa      840
cgttctggtg cttggctgct caaatggtta cggcctggcg agccgcatta ctgctgcgtt      900
cggatacggg gctgcgacca tcggcgtgtc ctttgaaaaa gcgggttcag aaaccaaata      960
tggtacaccg ggatggtaca ataatttggc atttgatgaa gcggcaaaac gcgagggtct     1020
ttatagcgtg acgatcgacg gcgatgcgtt ttcagacgag atcaaggccc aggtaattga     1080
ggaagccaaa aaaaaggta tcaaatttga tctgatcgta tacagcttgg ccagcccagt     1140
acgtactgat cctgatacag gtatcatgca caaaagcgtt ttgaaaccct ttggaaaaac     1200
gttcacaggc aaaacagtag atccgtttac tggcgagctg aaggaaatct ccgcggaacc     1260
agcaaatgac gaggaagcag ccgccactgt taaagttatg gggggtgaag attgggaacg     1320
ttggattaag cagctgtcga aggaaggcct cttagaagaa ggctgtatta ccttggccta     1380
tagttatatt ggccctgaag ctacccaagc tttgtaccgt aaaggcacaa tcggcaaggc     1440
caaagaacac ctggaggcca gcacaccgt ctcaacaaaa gagaacccgt caatccgtgc     1500
cttcgtgagc gtgaataaag gcctggtaac ccgcgcaagc gccgtaatcc cggtaatccc     1560
tctgtatctc gccagcttgt tcaaagtaat gaaagagaag ggcaatcatg aaggttgtat     1620
tgaacagatc acgcgtctgt acgccgagcg cctgtaccgt aaagatggta caattccagt     1680
tgatgaggaa aatcgcattc gcattgatga ttgggagtta aagaagacg tccagaaagc     1740 ggtatccgcg ttgatggaga aagtcacggg tgaaaacgca gaatctctca ctgacttagc     1800
ggggtaccgc catgatttct tagctagtaa cggctttgat gtagaaggta ttaattatga     1860
agcggaagtt gaacgcttcg accgtatctg ataagaagga gatatacata tgagagaagt     1920
agtaattgcc agtgcagcta gaacagcagt aggaagtttt ggaggagcat ttaaatcagt     1980
ttcagcggta gagttagggg taacagcagc taaagaagct ataaaagag ctaacataac     2040 tccagatatg atagatgaat ctcttttagg gggagtactt acagcaggtc ttggacaaaa     2100
tatagcaaga caaatagcat taggagcagg aataccagta gaaaaaccag ctatgactat     2160
aaatatagtt tgtggttctg gattaagatc tgtttcaatg gcatctcaac ttatagcatt     2220
aggtgatgct gatataatgt tagttggtgg agctgaaaac atgagtatgt ctccttattt     2280
agtaccaagt gcgagatatg gtgcaagaat gggtgatgct gcttttgttg attcaatgat     2340 aaagatgga ttatcagaca tatttaataa ctatcacatg ggtattactg ctgaaaacat     2400
agcagagcaa tggaatataa ctagagaaga acaagatgaa ttagctcttg caagtcaaaa     2460
taaagctgaa aaagctcaag ctgaaggaaa atttgatgaa gaaatagttc ctgttgttat     2520
aaaaggaaga aaaggtgaca ctgtagtaga taaagatgaa tatattaagc ctggcactac     2580
aatggagaaa cttgctaagt taagacctgc atttaaaaaa gatggaacag ttactgctgg     2640
taatgcatca ggaataaatg atggtgctgc tatgttagta gtaatggcta agaaaaagc     2700 tgaagaacta ggaatagagc ctcttgcaac tatagtttct tatggaacag ctggtgttga     2760
ccctaaaata atgggatatg gaccagttcc agcaactaaa aaagctttag aagctgctaa     2820
tatgactatt gaagatatag atttagttga agctaatgag gcatttgctg cccaatctgt     2880
agctgtaata agagacttaa atatagatat gaataaagtt aatgttaatg gtggagcaat     2940 agctataggacatccaatag gatgctcagg agcaagaata cttactacac tttatatga     3000 aatgaagaga agagatgcta aaactggtct tgctacactt tgtataggcg gtggaatggg     3060
```

```
aactacttta atagttaaga gatagtaaga aggagatata catatgaaat tagctgtaat    3120
aggtagtgga actatgggaa gtggtattgt acaaactttt gcaagttgtg gacatgatgt    3180
atgtttaaag agtagaactc aaggtgctat agataaatgt ttagctttat tagataaaaa    3240
tttaactaag ttagttacta agggaaaaat ggatgaagct acaaaagcag aaatattaag    3300
tcatgttagt tcaactacta attatgaaga tttaaaagat atggatttaa aatagaagc     3360 atctgtagaa gacatgaata taagaaaga tgttttcaag ttactagatg aattatgtaa    3420
agaagatact atcttggcaa caaatacttc atcattatct ataacagaaa tagcttcttc    3480
tactaagcgc ccagataaag ttataggaat gcatttcttt aatccagttc ctatgatgaa    3540
attagttgaa gttataagtg gtcagttaac atcaaaagtt acttttgata cagtatttga    3600
attatctaag agtatcaata aagtaccagt agatgtatct gaatctcctg gatttgtagt    3660
aaatagaata cttatacctc tgataaatga agctgttggt atatatgcag atggtgttgc    3720
aagtaaagaa gaaatagatg aagctatgaa attaggagca aaccatccaa tgggaccact    3780
agcattaggt gatttaatcg gattagatgt tgttttagct ataatgaacg ttttatatac    3840
tgaatttgga gatactaaat atagacctca tccactttta gctaaaatgg ttagagctaa    3900
tcaattagga agaaaaacta agataggatt ctatgattat aataaataat aagaaggaga    3960
tatacatatg agtacaagtg atgttaaagt ttatgagaat gtagctgttg aagtagatgg    4020
aaatatatgt acagtgaaaa tgaatagacc taaagccctt aatgcaataa attcaaagac    4080
tttagaagaa cttatgaag tatttgtaga tattaataat gatgaaacta ttgatgttgt    4140
aatattgaca ggggaaggaa aggcatttgt agctggagca gatattgcat acatgaaaga    4200
tttagatgct gtagctgcta aagatttag tatcttagga gcaaaagctt ttggagaaat    4260
agaaaatagt aaaaaagtag tgatagctgc tgtaaacgga tttgctttag gtggaggatg    4320
tgaacttgca atggcatgtg atataagaat tgcatctgct aaagctaaat ttggtcagcc    4380
agaagtaact cttggaataa ctccaggata tggaggaact caaaggctta caagattggt    4440
tggaatggca aaagcaaaag aattaatctt tacaggtcaa gttataaaag ctgatgaagc    4500
tgaaaaaata gggctagtaa atagagtcgt tgagccagac attttaatag aagaagttga    4560
gaaattagct aagataatag ctaaaaatgc tcagcttgca gttagatact ctaaagaagc    4620
aatcaaactt ggtgctcaaa ctgatataaa tactggaata gatatagaat ctaatttatt    4680
tggtctttgt ttttcaacta agaccaaaa agaaggaatg tcagctttcg ttgaaaagag    4740
agaagctaac tttataaaag ggtaataaga aggagatata catatgagtc aggcgctaaa    4800
aaatttactg acattgttaa atctggaaaa aattgaggaa ggactctttc gcggccagag    4860
tgaagattta ggtttacgcc aggtgtttgg cggccaggtc gtgggtcagg ccttgtatgc    4920
tgcaaaagag accgtccctg aagagcggct ggtacattcg tttcacagct actttcttcg    4980
ccctggcgat agtaagaagc cgattattta tgatgtcgaa acgctgcgtg acggtaacag    5040
cttcagcgcc cgccgggttg ctgctattca aaacggcaaa ccgattttt atatgactgc    5100 ctctttccag gcaccagaag cgggtttcga acatcaaaaa acaatgccgt ccgcgccagc    5160
gcctgatggc ctcccttcgg aaacgcaaat cgcccaatcg ctggcgcacc tgctgccgcc    5220
agtgctgaaa gataaattca tctgcgatcg tccgctggaa gtccgtccgg tggagtttca    5280
taacccactg aaaggtcacg tcgcagaacc acatcgtcag gtgtggatcc gcgcaaatgg    5340
tagcgtgccg gatgacctgc gcgttcatca gtatctgctc ggttacgctt ctgatcttaa    5400
cttcctgccg gtagctctac agccgcacgg catcggtttt ctcgaaccgg ggattcagat    5460
```

```
tgccaccatt gaccattcca tgtggttcca tcgcccgttt aatttgaatg aatggctgct    5520
gtatagcgtg gagagcacct cggcgtccag cgcacgtggc tttgtgcgcg gtgagtttta    5580
tacccaagac ggcgtactgg ttgcctcgac cgttcaggaa ggggtgatgc gtaatcacaa    5640
ttaa                                                                 5644
```

<210> SEQ ID NO 87
<211> LENGTH: 5719
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 87

```
gtaaaacgac ggccagtgaa ttcgttaaga cccactttca catttaagtt gttttctaa      60 tccgcatatg atcaattcaa ggccgaataa gaaggctggc tctgcacctt ggtgatcaaa    120
taattcgata gcttgtcgta ataatggcgg catactatca gtagtaggtg tttcccttc     180 ttctttagcg acttgatgct cttgatcttc aatacgcaa cctaaagtaa aatgccccac     240
agcgctgagt gcatataatg cattctctag tgaaaaacct tgttggcata aaaggctaa     300 ttgattttcg agagtttcat actgtttttc tgtaggccgt gtacctaaat gtacttttgc    360
tccatcgcga tgacttagta aagcacatct aaaactttta gcgttattac gtaaaaaatc    420
ttgccagctt tccccttcta aagggcaaaa gtgagtatgg tgcctatcta acatctcaat    480
ggctaaggcg tcgagcaaag cccgcttatt ttttacatgc caatacaatg taggctgctc    540
tacacctagc ttctgggcga gtttacgggt tgttaaacct tcgattccga cctcattaag    600
cagctctaat gcgctgttaa tcactttact tttatctaat ctagacatca ttaattccta    660 attttttgttg acactctatc attgatagag ttattttacc actccctatc agtgatagag    720
aaaagtgaac tctagaaaata attttgttta actttaagaa ggagatatac atatgatcgt    780
aaaacctatg gtacgcaaca atatctgcct gaacgcccat cctcagggct gcaagaaggg    840
agtggaagat cagattgaat ataccaagaa acgcattacc gcagaagtca aagctggcgc    900
aaaagctcca aaaaacgttc tggtgcttgg ctgctcaaat ggttacggcc tggcgagccg    960
cattactgct gcgttcggat acggggctgc gaccatcggc gtgtcctttg aaaaagcggg   1020
ttcagaaacc aaatatggta caccgggatg gtacaataat ttggcatttg atgaagcggc   1080
aaaacgcgag ggtctttata gcgtgacgat cgacggcgat gcgttttcag acgagatcaa   1140
ggcccaggta attgaggaag ccaaaaaaaa aggtatcaaa tttgatctga tcgtatacag   1200
cttggccagc ccagtacgta ctgatcctga tacaggtatc atgcacaaaa gcgttttgaa   1260 acccttttgga aaaacgttca caggcaaaaac agtagatccg tttactggcg agctgaagga   1320
aatctccgcg gaaccagcaa atgacgagga agcagccgcc actgttaaag ttatgggggg   1380
tgaagattgg gaacgttgga ttaagcagct gtcgaaggaa ggcctcttag aagaaggctg   1440
tattaccttg gcctatagtt atattggccc tgaagctacc caagctttgt accgtaaagg   1500
cacaatcggc aaggccaaag aacacctgga ggccacagca caccgtctca acaaagagaa   1560
cccgtcaatc cgtgccttcg tgagcgtgaa taaaggcctg gtaacccgcg caagcgccgt   1620
aatcccggta atccctctgt atctcgccag cttgttcaaa gtaatgaaag agaagggcaa   1680
tcatgaaggt tgtattgaac agatcacgcg tctgtacgcc gagcgcctgt accgtaaaga   1740
tggtacaatt ccagttgatg aggaaaatcg cattcgcatt gatgattggg agttagaaga   1800
```

```
agacgtccag aaagcggtat ccgcgttgat ggagaaagtc acgggtgaaa acgcagaatc    1860
tctcactgac ttagcggggt accgccatga tttcttagct agtaacggct ttgatgtaga    1920
aggtattaat tatgaagcgg aagttgaacg cttcgaccgt atctgataag aaggagatat    1980
acatatgaga gaagtagtaa ttgccagtgc agctagaaca gcagtaggaa gttttggagg    2040
agcatttaaa tcagtttcag cggtagagtt aggggtaaca gcagctaaag aagctataaa    2100
aagagctaac ataactccag atatgataga tgaatctctt ttaggggag tacttacagc     2160 aggtcttgga caaaatatag caagacaaat agcattagga gcaggaatac cagtagaaaa    2220
accagctatg actataaata tagttttgtgg ttctggatta agatctgttt caatggcatc   2280
tcaacttata gcattaggtg atgctgatat aatgttagtt ggtggagctg aaaacatgag    2340
tatgtctcct tatttagtac caagtgcgag atatggtgca agaatgggtg atgctgcttt    2400
tgttgattca atgataaaag atggattatc agacatattt aataactatc acatgggtat    2460
tactgctgaa aacatagcag agcaatggaa tataactaga gaagaacaag atgaattagc    2520
tcttgcaagt caaaataaag ctgaaaaagc tcaagctgaa ggaaaatttg atgaagaaat    2580
agttcctgtt gttataaaag gaagaaaagg tgacactgta gtagataaag atgaatatat    2640
taagcctggc actacaatgg agaaacttgc taagttaaga cctgcattta aaaagatgg    2700 aacagttact gctggtaatg catcaggaat aaatgatggt gctgctatgt tagtagtaat    2760
ggctaaagaa aaagctgaag aactaggaat agagcctctt gcaactatag tttcttatgg    2820
aacagctggt gttgacccta aaataatggg atatggacca gttccagcaa ctaaaaaagc    2880
tttagaagct gctaatatga ctattgaaga tatagattta gttgaagcta atgaggcatt    2940
tgctgcccaa tctgtagctg taataagaga cttaaatata gatatgaata agttaatgt    3000 taatggtgga gcaatagcta taggacatcc aataggatgc tcaggagcaa gaatacttac    3060 tacacttttta tatgaaatga agagaagaga tgctaaaact ggtcttgcta cactttgtat    3120
aggcggtgga atgggaacta ctttaatagt taagagatag taagaaggag atatacatat    3180
gaaattagct gtaataggta gtggaactat gggaagtggt attgtacaaa cttttgcaag    3240
ttgtggacat gatgtatgtt taagagtag aactcaaggt gctatagata aatgtttagc     3300
tttattagat aaaaatttaa ctaagttagt tactaaggga aaaatggatg aagctacaaa    3360
agcagaaata ttaagtcatg ttagttcaac tactaattat gaagatttaa agatatgga    3420 tttaataata gaagcatctg tagaagacat gaatataaag aaagatgttt tcaagttact    3480
agatgaatta tgtaaagaag atactatctt ggcaacaaat acttcatcat tatctataac    3540
agaaatagct tcttctacta gcgcccaga taaagttata ggaatgcatt tctttaatcc    3600
agttcctatg atgaaattag ttgaagttat aagtggtcag ttaacatcaa aagttacttt    3660
tgatacagta tttgaattat ctaagagtat caataaagta ccagtagatg tatctgaatc    3720
tcctggattt gtagtaaata gaatacttat acctatgata aatgaagctg ttggtatata    3780
tgcagatggt gttgcaagta aagaagaaat agatgaagct atgaaattag agcaaaccaa    3840
tccaatggga ccactagcat taggtgatt aatcggatta gatgttgttt tagctataat     3900
gaacgtttta tatactgaat ttggagatac taaatataga cctcatccac ttttagctaa    3960
aatggttaga gctaatcaat taggaagaaa aactaagata ggattctatg attataataa    4020
ataataagaa ggagatatac atatgagtac aagtgatgtt aaagtttatg agaatgtagc    4080
tgttgaagta gatggaaata tatgtacagt gaaaatgaat agacctaaag cccttaatgc    4140
```

| | | | |
|---|---|---|---|
| aataaattca | aagactttag | aagaacttta tgaagtattt gtagatatta ataatgatga | 4200 |
| aactattgat | gttgtaatat | tgacagggga aggaaaggca tttgtagctg agcagatat | 4260 |
| tgcatacatg | aaagatttag | atgctgtagc tgctaaagat tttagtatct taggagcaaa | 4320 |
| agcttttgga | gaaatagaaa | atagtaaaaa agtagtgata gctgctgtaa acggatttgc | 4380 |
| tttaggtgga | ggatgtgaac | ttgcaatggc atgtgatata agaattgcat ctgctaaagc | 4440 |
| taaatttggt | cagccagaag | taactcttgg aataactcca ggatatggag gaactcaaag | 4500 |
| gcttacaaga | ttggttggaa | tggcaaaagc aaaagaatta atctttacag gtcaagttat | 4560 |
| aaaagctgat | gaagctgaaa | aaatagggct agtaaataga gtcgttgagc cagacatttt | 4620 |
| aatagaagaa | gttgagaaat | tagctaagat aatagctaaa aatgctcagc ttgcagttag | 4680 |
| atactctaaa | gaagcaatac | aacttggtgc tcaaactgat ataaatactg aatagatat | 4740 |
| agaatctaat | ttatttggtc | tttgttttc aactaaagac caaaagaag gaatgtcagc | 4800 |
| tttcgttgaa | aagagagaag | ctaactttat aaaagggtaa taagaaggag atatacatat | 4860 |
| gagtcaggcg | ctaaaaaatt | tactgacatt gttaaatctg gaaaaaattg aggaaggact | 4920 |
| cttcgcggc | cagagtgaag | atttaggttt acgccaggtg tttggcggcc aggtcgtggg | 4980 |
| tcaggccttg | tatgctgcaa | aagagaccgt ccctgaagag cggctggtac attcgtttca | 5040 |
| cagctacttt | cttcgccctg | gcgatagtaa gaagccgatt atttatgatg tcgaaacgct | 5100 |
| gcgtgacggt | aacagcttca | cgccccgccg ggttgctgct attcaaaacg gcaaaccgat | 5160 |
| ttttatatg | actgcctctt | tccaggcacc agaagcgggt ttcgaacatc aaaaaacaat | 5220 |
| gccgtccgcg | ccagcgcctg | atggcctccc ttcggaaacg caaatcgccc aatcgctggc | 5280 |
| gcacctgctg | ccgccagtgc | tgaaagataa attcatctgc gatcgtccgc tggaagtccg | 5340 |
| tccggtggag | tttcataacc | cactgaaagg tcacgtcgca gaaccacatc gtcaggtgtg | 5400 |
| gatccgcgca | aatggtagcg | tgccggatga cctgcgcgtt catcagtatc tgctcggtta | 5460 |
| cgcttctgat | cttaacttcc | tgccggtagc tctacagccg cacggcatcg ttttctcga | 5520 |
| accggggatt | cagattgcca | ccattgacca ttccatgtgg ttccatcgcc cgtttaattt | 5580 |
| gaatgaatgg | ctgctgtata | gcgtggagag cacctcggcg tccagcgcac gtggctttgt | 5640 |
| gcgcggtgag | ttttataccc | aagacggcgt actggttgcc tcgaccgttc aggaaggggt | 5700 |
| gatgcgtaat | cacaattaa | | 5719 |

<210> SEQ ID NO 88
<211> LENGTH: 5719
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 88

| | | | |
|---|---|---|---|
| gtaaaacgac | ggccagtgaa | ttcgttaaga cccactttca catttaagtt gttttctaa | 60 |
| tccgcatatg | atcaattcaa | ggccgaataa gaaggctggc tctgcaccct ggtgatcaaa | 120 |
| taattcgata | gcttgtcgta | ataatggcgg catactatca gtagtaggtg tttccctttc | 180 |
| ttctttagcg | acttgatgct | cttgatcttc caatacgcaa cctaaagtaa aatgccccac | 240 |
| agcgctgagt | gcatataatg | cattctctag tgaaaaacct tgttggcata aaaaggctaa | 300 |
| ttgattttcg | agagtttcat | actgtttttc tgtaggccgt gtacctaaat gtacttttgc | 360 |
| tccatcgcga | tgacttagta | aagcacatct aaaacttta gcgttattac gtaaaaaatc | 420 |

```
ttgccagctt tccccttcta aagggcaaaa gtgagtatgg tgcctatcta acatctcaat    480
ggctaaggcg tcgagcaaag cccgcttatt ttttacatgc caatacaatg taggctgctc    540
tacacctagc ttctgggcga gtttacgggt tgttaaacct tcgattccga cctcattaag    600
cagctctaat gcgctgttaa tcactttact tttatctaat ctagacatca ttaattccta    660
atttttgttg acactctatc attgatagag ttattttacc actccctatc agtgatagag    720
aaaagtgaac tctagaaata attttgttta actttaagaa ggagatatac atatgatcgt    780
aaaacctatg gtacgcaaca atatctgcct gaacgcccat cctcagggct gcaagaaggg    840
agtggaagat cagattgaat ataccaagaa acgcattacc gcagaagtca agctggcgc    900 aaaagctcca aaaacgttc tggtgcttgg ctgctcaaat ggttacggcc tggcgagccg    960
cattactgct gcgttcggat acggggctgc gaccatcggc gtgtcctttg aaaaagcggg   1020
ttcagaaacc aaatatggta caccgggatg gtacaataat ttggcatttg atgaagcggc   1080
aaaacgcgag ggtctttata gcgtgacgat cgacggcgat gcgttttcag acagagatcaa  1140 ggcccaggta attgaggaag ccaaaaaaaa aggtatcaaa tttgatctga tcgtatacag   1200
cttggccagc ccagtacgta ctgatcctga tacaggtatc atgcacaaaa gcgttttgaa   1260
acccttggga aaaacgttca caggcaaaac agtagatccg tttactggcg agctgaagga   1320
aatctccgcg gaaccagcaa atgacgagga agcagccgcc actgttaaag ttatgggggg   1380
tgaagattgg gaacgttgga ttaagcagct gtcgaaggaa ggcctcttag aagaaggctg   1440
tattaccttg gcctatagtt atattggccc tgaagctacc caagctttgt accgtaaagg   1500
cacaatcggc aaggccaaag aacacctgga ggccacagca caccgtctca acaaagagaa   1560
cccgtcaatc cgtgccttcg tgagcgtgaa taaaggcctg gtaacccgcg caagcgccgt   1620
aatcccggta atccctctgt atctcgccag cttgttcaaa gtaatgaaag agaagggcaa   1680
tcatgaaggt tgtattgaac agatcacgcg tctgtacgcc gagcgcctgt accgtaaaga   1740
tggtacaatt ccagttgatg aggaaaatcg cattcgcatt gatgattggg agttagaaga   1800
agacgtccag aaagcggtat ccgcgttgat ggagaaagtc acgggtgaaa acgcagaatc   1860
tctcactgac ttagcggggt accgccatga tttcttagct agtaacggct ttgatgtaga   1920
aggtattaat tatgaagcgg aagttgaacg cttcgaccgt atctgataag aaggagatat   1980
acatatgaga gaagtagtaa ttgccagtgc agctagaaca gcagtaggaa gttttggagg   2040
agcatttaaa tcagtttcag cggtagagtt aggggtaaca gcagctaaag aagctataaa   2100
aagagctaac ataactccag atatgataga tgaatctctt ttaggggag tacttacagc   2160 aggtcttgga caaaatatag caagacaaat agcattagga gcaggaatac cagtagaaaa   2220
accagctatg actataaata tagtttgtgg ttctggatta agatctgttt caatggcatc   2280
tcaacttata gcattaggtg atgctgatat aatgttagtt ggtggagctg aaaacatgag   2340
tatgtctcct tatttagtac caagtgcgag atatggtgca agaatgggtg atgctgcttt   2400
tgttgattca atgataaaag atggattatc agacatattt aataactatc acatgggtat   2460
tactgctgaa acatagcag agcaatggaa tataactaga gaagaacaag atgaattagc   2520
tcttgcaagt caaaataaag ctgaaaaagc tcaagctgaa ggaaaatttg atgaagaaat   2580
agttcctgtt gttataaaag gaagaaaagg tgacactgta gtagataaag atgaatatat   2640
taagcctggc actacaatgg agaaacttgc taagttaaga cctgcattta aaaaagatgg   2700
aacagttact gctggtaatg catcaggaat aaatgatggt gctgctatgt tagtagtaat   2760
ggctaaagaa aaagctgaag aactaggaat agagcctctt gcaactatag tttcttatgg   2820
```

```
aacagctggt gttgacccta aaataatggg atatggacca gttccagcaa ctaaaaaagc    2880
tttagaagct gctaatatga ctattgaaga tatagattta gttgaagcta atgaggcatt    2940
tgctgcccaa tctgtagctg taataagaga cttaaatata gatatgaata aagttaatgt    3000
taatggtgga gcaatagcta taggacatcc aataggatgc tcaggagcaa gaatacttac    3060
tacactttta tatgaaatga agagaagaga tgctaaaact ggtcttgcta cactttgtat    3120
aggcggtgga atgggaacta ctttaatagt taagagatag taagaaggag atatacatat    3180
gaaattagct gtaataggta gtggaactat gggaagtggt attgtacaaa cttttgcaag    3240
ttgtggacat gatgtatgtt taagagtag aactcaaggt gctatagata atgtttagc     3300 tttattagat aaaaatttaa ctaagttagt tactaaggga aaaatggatg aagctacaaa    3360
agcagaaata ttaagtcatg ttagttcaac tactaattat gaagatttaa agatatgga    3420 tttaataata gaagcatctg tagaagacat gaatataaag aaagatgttt tcaagttact    3480
agatgaatta tgtaaagaag atactatctt ggcaacaaat acttcatcat tatctataac    3540
agaaatagct tcttctacta agcgcccaga taaagttata ggaatgcatt tctttaatcc    3600
agttcctatg atgaaattag ttgaagttat aagtggtcag ttaacatcaa aagttacttt    3660
tgatacagta tttgaattat ctaagagtat caataaagta ccagtagatg tatctgaatc    3720
tcctggattt gtagtaaata gaatacttat acctatgata aatgaagctg ttggtatata    3780
tgcagatggt gttgcaagta aagaagaaat agatgaagct atgaaattag gagcaaacca    3840
tccaatggga ccactagcat taggtgattt aatcggatta gatgttgttt tagctataat    3900
gaacgtttta tatactgaat ttggagatac taaatataga cctcatccac ttttagctaa    3960
aatggttaga gctaatcaat taggaagaaa aactaagata ggattctatg attataataa    4020
ataataagaa ggagatatac atatgagtac aagtgatgtt aaagtttatg agaatgtagc    4080
tgttgaagta gatggaaata tatgtacagt gaaaatgaat agacctaaag ccccttaatgc   4140 aataaattca aagactttag aagaactta tgaagtattt gtagatatta ataatgatga    4200
aactattgat gttgtaatat tgacagggga aggaaaggca tttgtagctg gagcagatat    4260
tgcatacatg aaagatttag atgctgtagc tgctaaagat tttagtatct taggagcaaa    4320
agcttttgga gaaatagaaa atagtaaaaa agtagtgata gctgctgtaa acggatttgc    4380
tttaggtgga ggatgtgaac ttgcaatggc atgtgatata agaattgcat ctgctaaagc    4440
taaatttggt cagccagaag taactcttgg aataactcca ggatatggag gaactcaaag    4500
gcttacaaga ttggttggaa tggcaaaagc aaaagaatta atctttacag gtcaagttat    4560
aaaagctgat gaagctgaaa aaatagggct agtaaataga gtcgttgagc cagacatttt    4620
aatagaagaa gttgagaaat tagctaagat aatagctaaa aatgctcagc ttgcagttag    4680
atactctaaa gaagcaatac aacttggtgc tcaaactgat ataaatactg aatagatat    4740 agaatctaat ttatttggtc tttgtttttc aactaaagac caaaagaag gaatgtcagc    4800 tttcgttgaa aagagagaag ctaactttat aaaagggtaa taagaaggag atatacatat    4860
gagtcaggcg ctaaaaaatt tactgacatt gttaaatctg gaaaaaattg aggaaggact    4920
ctttcgcggc cagagtgaag atttaggttt acgccaggtg tttggcggcc aggtcgtggg    4980
tcaggccttg tatgctgcaa agagaccgt ccctgaagag cggctggtac attcgtttca    5040
cagctacttt cttcgccctg gcgatagtaa gaagccgatt atttatgatg tcgaaacgct    5100
gcgtgacggt aacagcttca gcgcccgccg ggttgctgct attcaaaacg gcaaaccgat    5160
```

| | |
|---|---|
| tttttatatg actgcctctt tccaggcacc agaagcgggt ttcgaacatc aaaaaacaat | 5220 |
| gccgtccgcg ccagcgcctg atggcctccc ttcggaaacg caaatcgccc aatcgctggc | 5280 |
| gcacctgctg ccgccagtgc tgaaagataa attcatctgc gatcgtccgc tggaagtccg | 5340 |
| tccggtggag tttcataacc cactgaaagg tcacgtcgca gaaccacatc gtcaggtgtg | 5400 |
| gatccgcgca aatggtagcg tgccggatga cctgcgcgtt catcagtatc tgctcggtta | 5460 |
| cgcttctgat cttaacttcc tgccggtagc tctacagccg cacggcatcg gttttctcga | 5520 |
| accggggatt cagattgcca ccattgacca ttccatgtgg ttccatcgcc cgtttaattt | 5580 |
| gaatgaatgg ctgctgtata gcgtggagag cacctcggcg tccagcgcac gtggctttgt | 5640 |
| gcgcggtgag ttttataccc aagacggcgt actggttgcc tcgaccgttc aggaaggggt | 5700 |
| gatgcgtaat cacaattaa | 5719 |

<210> SEQ ID NO 89
<211> LENGTH: 180
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 89

| | |
|---|---|
| catttcctct catcccatcc ggggtgagag tcttttcccc cgacttatgg ctcatgcatg | 60 |
| catcaaaaaa gatgtgagct tgatcaaaaa caaaaaatat ttcactcgac aggagtattt | 120 |
| atattgcgcc cggatccctc tagaaataat tttgtttaac tttaagaagg agatatacat | 180 |

<210> SEQ ID NO 90
<211> LENGTH: 1194
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 90

| | |
|---|---|
| atgatcgtaa aacctatggt acgcaacaat atctgcctga cgcccatccc tcagggctgc | 60 |
| aagaagggag tggaagatca gattgaatat accaagaaac gcattaccgc agaagtcaaa | 120 |
| gctggcgcaa aagctccaaa aaacgttctg gtgcttggct gctcaaatgg ttacggcctg | 180 |
| gcgagccgca ttactgctgc gttcggatac ggggctgcga ccatcggcgt gtccttgaa | 240 |
| aaagcgggtt cagaaaccaa atatggtaca ccgggatggt acaataattt ggcatttgat | 300 |
| gaagcggcaa acgcgaggg tctttatagc gtgacgatcg acggcgatgc gttttcagac | 360 |
| gagatcaagg cccaggtaat tgaggaagcc aaaaaaaaag gtatcaaatt tgatctgatc | 420 |
| gtatacagct tggccagccc agtacgtact gatcctgata caggtatcat gcacaaaagc | 480 |
| gttttgaaac cctttggaaa aacgttcaca ggcaaaacag tagatccgtt tactggcgag | 540 |
| ctgaaggaaa tctccgcgga accagcaaat gacgaggaag cagccgccac tgttaaagtt | 600 |
| atgggggtg aagattggga acgttggatt aagcagctgt cgaaggaagg cctcttagaa | 660 |
| gaaggctgta ttaccttggc ctatagttat attggccctg aagctaccca agctttgtac | 720 |
| cgtaaaggca caatcggcaa ggccaaagaa cacctggagg ccacagcaca ccgtctcaac | 780 |
| aaagagaacc cgtcaatccg tgccttcgtg agcgtgaata aaggcctggt aacccgcgca | 840 |
| agcgccgtaa tcccgtaat ccctctgtat ctcgccagct tgttcaaagt aatgaaagag | 900 |
| aagggcaatc atgaaggttg tattgaacag atcacgcgtc tgtacgccga gcgcctgtac | 960 |

```
cgtaaagatg gtacaattcc agttgatgag gaaaatcgca ttcgcattga tgattgggag    1020
ttagaagaag acgtccagaa agcggtatcc gcgttgatgg agaaagtcac gggtgaaaac    1080
gcagaatctc tcactgactt agcggggtac cgccatgatt tcttagctag taacggcttt    1140
gatgtagaag gtattaatta tgaagcggaa gttgaacgct tcgaccgtat ctga          1194
```

<210> SEQ ID NO 91
<211> LENGTH: 397
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 91

```
Met Ile Val Lys Pro Met Val Arg Asn Asn Ile Cys Leu Asn Ala His
1               5                   10                  15

Pro Gln Gly Cys Lys Lys Gly Val Glu Asp Gln Ile Glu Tyr Thr Lys
            20                  25                  30

Lys Arg Ile Thr Ala Glu Val Lys Ala Gly Ala Lys Ala Pro Lys Asn
        35                  40                  45

Val Leu Val Leu Gly Cys Ser Asn Gly Tyr Gly Leu Ala Ser Arg Ile
    50                  55                  60

Thr Ala Ala Phe Gly Tyr Gly Ala Ala Thr Ile Gly Val Ser Phe Glu
65                  70                  75                  80

Lys Ala Gly Ser Glu Thr Lys Tyr Gly Thr Pro Gly Trp Tyr Asn Asn
                85                  90                  95

Leu Ala Phe Asp Glu Ala Ala Lys Arg Glu Gly Leu Tyr Ser Val Thr
            100                 105                 110

Ile Asp Gly Asp Ala Phe Ser Asp Glu Ile Lys Ala Gln Val Ile Glu
        115                 120                 125

Glu Ala Lys Lys Lys Gly Ile Lys Phe Asp Leu Ile Val Tyr Ser Leu
    130                 135                 140

Ala Ser Pro Val Arg Thr Asp Pro Asp Thr Gly Ile Met His Lys Ser
145                 150                 155                 160

Val Leu Lys Pro Phe Gly Lys Thr Phe Thr Gly Lys Thr Val Asp Pro
                165                 170                 175

Phe Thr Gly Glu Leu Lys Glu Ile Ser Ala Glu Pro Ala Asn Asp Glu
            180                 185                 190

Glu Ala Ala Ala Thr Val Lys Val Met Gly Gly Glu Asp Trp Glu Arg
        195                 200                 205

Trp Ile Lys Gln Leu Ser Lys Glu Gly Leu Leu Glu Glu Gly Cys Ile
    210                 215                 220

Thr Leu Ala Tyr Ser Tyr Ile Gly Pro Glu Ala Thr Gln Ala Leu Tyr
225                 230                 235                 240

Arg Lys Gly Thr Ile Gly Lys Ala Lys Glu His Leu Glu Ala Thr Ala
                245                 250                 255

His Arg Leu Asn Lys Glu Asn Pro Ser Ile Arg Ala Phe Val Ser Val
            260                 265                 270

Asn Lys Gly Leu Val Thr Arg Ala Ser Ala Val Ile Pro Val Ile Pro
        275                 280                 285

Leu Tyr Leu Ala Ser Leu Phe Lys Val Met Lys Glu Lys Gly Asn His
    290                 295                 300

Glu Gly Cys Ile Glu Gln Ile Thr Arg Leu Tyr Ala Glu Arg Leu Tyr
305                 310                 315                 320
```

```
Arg Lys Asp Gly Thr Ile Pro Val Asp Glu Glu Asn Arg Ile Arg Ile
            325                 330                 335

Asp Asp Trp Glu Leu Glu Glu Asp Val Gln Lys Ala Val Ser Ala Leu
            340                 345                 350

Met Glu Lys Val Thr Gly Glu Asn Ala Glu Ser Leu Thr Asp Leu Ala
            355                 360                 365

Gly Tyr Arg His Asp Phe Leu Ala Ser Asn Gly Phe Asp Val Glu Gly
            370                 375                 380

Ile Asn Tyr Glu Ala Glu Val Glu Arg Phe Asp Arg Ile
385                 390                 395

<210> SEQ ID NO 92
<211> LENGTH: 1176
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 92
atgagagaag tagtaattgc cagtgcagct agaacagcag taggaagttt tggaggagca       60
tttaaatcag tttcagcggt agagttaggg gtaacagcag ctaaagaagc tataaaaaga      120
gctaacataa ctccagatat gatagatgaa tctcttttag ggggagtact tacagcaggt      180
cttggacaaa atatagcaag acaaatagca ttaggagcag gaataccagt agaaaaacca      240
gctatgacta taaatatagt ttgtggttct ggattaagat ctgtttcaat ggcatctcaa      300
cttatagcat taggtgatgc tgatataatg ttagttggtg gagctgaaaa catgagtatg      360
tctccttatt tagtaccaag tgcgagatat ggtgcaagaa tgggtgatgc tgcttttgtt      420
gattcaatga taaagatgg attatcagac atatttaata actatcacat gggtattact      480
gctgaaaaca tagcagagca atggaatata actagagaag aacaagatga attagctctt      540
gcaagtcaaa ataaagctga aaaagctcaa gctgaaggaa atttgatga agaaatagtt      600 cctgttgtta taaaggaag aaaaggtgac actgtagtag ataaagatga atatattaag      660
cctggcacta caatggagaa acttgctaag ttaagacctg catttaaaaa agatggaaca      720
gttactgctg gtaatgcatc aggaataaat gatggtgctg ctatgttagt agtaatggct      780
aaagaaaaag ctgaagaact aggaatagag cctcttgcaa ctatagtttc ttatggaaca      840
gctggtgttg accctaaaat aatgggatat ggaccagttc cagcaactaa aaaagctta      900 gaagctgcta atatgactat tgaagatata gatttagttg aagctaatga ggcatttgct      960
gcccaatctg tagctgtaat aagagactta aatatagata tgaataaagt taatgttaat     1020
ggtggagcaa tagctatagg acatccaata ggatgctcag gagcaagaat acttactaca     1080
cttttatatg aaatgaagag aagagatgct aaaactggtc ttgctacact tgtataggc      1140 ggtggaatgg gaactacttt aatagttaag agatag                              1176

<210> SEQ ID NO 93
<211> LENGTH: 391
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 93

Met Arg Glu Val Val Ile Ala Ser Ala Ala Arg Thr Ala Val Gly Ser
```

-continued

```
  1               5                  10                 15
Phe Gly Gly Ala Phe Lys Ser Val Ser Ala Val Glu Leu Gly Val Thr
                 20                 25                 30
Ala Ala Lys Glu Ala Ile Lys Arg Ala Asn Ile Thr Pro Asp Met Ile
                 35                 40                 45
Asp Glu Ser Leu Leu Gly Val Leu Thr Ala Gly Leu Gly Gln Asn
     50                 55                 60
Ile Ala Arg Gln Ile Ala Leu Gly Ala Gly Ile Pro Val Glu Lys Pro
 65              70                 75                 80
Ala Met Thr Ile Asn Ile Val Cys Gly Ser Gly Leu Arg Ser Val Ser
                 85                 90                 95
Met Ala Ser Gln Leu Ile Ala Leu Gly Asp Ala Asp Ile Met Leu Val
                100                105                110
Gly Gly Ala Glu Asn Met Ser Met Ser Pro Tyr Leu Val Pro Ser Ala
                115                120                125
Arg Tyr Gly Ala Arg Met Gly Asp Ala Ala Phe Val Asp Ser Met Ile
                130                135                140
Lys Asp Gly Leu Ser Asp Ile Phe Asn Asn Tyr His Met Gly Ile Thr
145                150                155                160
Ala Glu Asn Ile Ala Glu Gln Trp Asn Ile Thr Arg Glu Glu Gln Asp
                165                170                175
Glu Leu Ala Leu Ala Ser Gln Asn Lys Ala Glu Lys Ala Gln Ala Glu
                180                185                190
Gly Lys Phe Asp Glu Glu Ile Val Pro Val Val Ile Lys Gly Arg Lys
                195                200                205
Gly Asp Thr Val Val Asp Lys Asp Glu Tyr Ile Lys Pro Gly Thr Thr
                210                215                220
Met Glu Lys Leu Ala Lys Leu Arg Pro Ala Phe Lys Lys Asp Gly Thr
225                230                235                240
Val Thr Ala Gly Asn Ala Ser Gly Ile Asn Asp Gly Ala Ala Met Leu
                245                250                255
Val Val Met Ala Lys Glu Lys Ala Glu Glu Leu Gly Ile Glu Pro Leu
                260                265                270
Ala Thr Ile Val Ser Tyr Gly Thr Ala Gly Val Asp Pro Lys Ile Met
                275                280                285
Gly Tyr Gly Pro Val Pro Ala Thr Lys Lys Ala Leu Glu Ala Ala Asn
                290                295                300
Met Thr Ile Glu Asp Ile Asp Leu Val Glu Ala Asn Glu Ala Phe Ala
305                310                315                320
Ala Gln Ser Val Ala Val Ile Arg Asp Leu Asn Ile Asp Met Asn Lys
                325                330                335
Val Asn Val Asn Gly Gly Ala Ile Ala Ile Gly His Pro Ile Gly Cys
                340                345                350
Ser Gly Ala Arg Ile Leu Thr Thr Leu Leu Tyr Glu Met Lys Arg Arg
                355                360                365
Asp Ala Lys Thr Gly Leu Ala Thr Leu Cys Ile Gly Gly Gly Met Gly
                370                375                380
Thr Thr Leu Ile Val Lys Arg
385                390
```

<210> SEQ ID NO 94
<211> LENGTH: 846
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 94

```
atgaaattag ctgtaatagg tagtggaact atgggaagtg gtattgtaca aacttttgca    60
agttgtggac atgatgtatg tttaaagagt agaactcaag gtgctataga taaatgttta   120
gctttattag ataaaaattt aactaagtta gttactaagg gaaaaatgga tgaagctaca   180
aaagcagaaa tattaagtca tgttagttca actactaatt atgaagattt aaaagatatg   240
gatttaataa tagaagcatc tgtagaagac atgaatataa agaaagatgt tttcaagtta   300
ctagatgaat tatgtaaaga agatactatc ttggcaacaa atacttcatc attatctata   360
acagaaatag cttcttctac taagcgccca gataaagtta taggaatgca tttctttaat   420
ccagttccta tgatgaaatt agttgaagtt ataagtggtc agttaacatc aaaagttact   480
tttgatacag tatttgaatt atctaagagt atcaataaag taccagtaga tgtatctgaa   540
tctcctggat ttgtagtaaa tagaatactt atacctatga taaatgaagc tgttggtata   600
tatgcagatg gtgttgcaag taaagaagaa atagatgaag ctatgaaatt aggagcaaac   660
catccaatgg gaccactagc attaggtgat ttaatcggat tagatgttgt tttagctata   720
atgaacgttt tatatactga atttggagat actaaatata gacctcatcc acttttagct   780
aaaatggtta gagctaatca attaggaaga aaaactaaga taggattcta tgattataat   840
aaataa                                                              846
```

<210> SEQ ID NO 95
<211> LENGTH: 281
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 95

```
Met Lys Leu Ala Val Ile Gly Ser Gly Thr Met Gly Ser Gly Ile Val
1               5                   10                  15

Gln Thr Phe Ala Ser Cys Gly His Asp Val Cys Leu Lys Ser Arg Thr
                20                  25                  30

Gln Gly Ala Ile Asp Lys Cys Leu Ala Leu Leu Asp Lys Asn Leu Thr
            35                  40                  45

Lys Leu Val Thr Lys Gly Lys Met Asp Glu Ala Thr Lys Ala Glu Ile
        50                  55                  60

Leu Ser His Val Ser Ser Thr Thr Asn Tyr Glu Asp Leu Lys Asp Met
65                  70                  75                  80

Asp Leu Ile Ile Glu Ala Ser Val Glu Asp Met Asn Ile Lys Lys Asp
                85                  90                  95

Val Phe Lys Leu Leu Asp Glu Leu Cys Lys Glu Asp Thr Ile Leu Ala
                100                 105                 110

Thr Asn Thr Ser Ser Leu Ser Ile Thr Glu Ile Ala Ser Ser Thr Lys
            115                 120                 125

Arg Pro Asp Lys Val Ile Gly Met His Phe Phe Asn Pro Val Pro Met
        130                 135                 140

Met Lys Leu Val Glu Val Ile Ser Gly Gln Leu Thr Ser Lys Val Thr
145                 150                 155                 160

Phe Asp Thr Val Phe Glu Leu Ser Lys Ser Ile Asn Lys Val Pro Val
                165                 170                 175
```

Asp Val Ser Glu Ser Pro Gly Phe Val Val Asn Arg Ile Leu Ile Pro
                180                 185                 190

Met Ile Asn Glu Ala Val Gly Ile Tyr Ala Asp Gly Val Ala Ser Lys
            195                 200                 205

Glu Glu Ile Asp Glu Ala Met Lys Leu Gly Ala Asn His Pro Met Gly
210                 215                 220

Pro Leu Ala Leu Gly Asp Leu Ile Gly Leu Asp Val Val Leu Ala Ile
225                 230                 235                 240

Met Asn Val Leu Tyr Thr Glu Phe Gly Asp Thr Lys Tyr Arg Pro His
                245                 250                 255

Pro Leu Leu Ala Lys Met Val Arg Ala Asn Gln Leu Gly Arg Lys Thr
            260                 265                 270

Lys Ile Gly Phe Tyr Asp Tyr Asn Lys
            275                 280

<210> SEQ ID NO 96
<211> LENGTH: 798
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 96
atgagtacaa gtgatgttaa agtttatgag aatgtagctg ttgaagtaga tggaaatata      60
tgtacagtga aaatgaatag acctaaagcc cttaatgcaa taaattcaaa gactttagaa     120
gaactttatg aagtatttgt agatattaat aatgatgaaa ctattgatgt tgtaatattg     180
acaggggaag gaaaggcatt tgtagctgga gcagatattg catacatgaa agatttagat     240
gctgtagctg ctaaagattt tagtatctta ggagcaaaag cttttggaga aatagaaaat     300
agtaaaaaag tagtgatagc tgctgtaaac ggatttgctt taggtggagg atgtgaactt     360
gcaatggcat gtgatataag aattgcatct gctaaagcta aatttggtca gccagaagta     420
actcttggaa taactccagg atatggagga actcaaaggc ttacaagatt ggttggaatg     480
gcaaaagcaa agaattaat ctttacaggt caagttataa aagctgatga agctgaaaaa     540
atagggctag taaatagagt cgttgagcca gacattttaa tagaagaagt tgagaaatta     600
gctaagataa tagctaaaaa tgctcagctt gcagttagat actctaaaga agcaatacaa     660
cttggtgctc aaactgatat aaatactgga atagatatag aatctaattt atttggtctt     720
tgtttttcaa ctaaagacca aaaagaagga atgtcagctt tcgttgaaaa gagagaagct     780
aactttataa aagggtaa                                                    798

<210> SEQ ID NO 97
<211> LENGTH: 265
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 97

Met Ser Thr Ser Asp Val Lys Val Tyr Glu Asn Val Ala Val Glu Val
1               5                   10                  15

Asp Gly Asn Ile Cys Thr Val Lys Met Asn Arg Pro Lys Ala Leu Asn
            20                  25                  30

Ala Ile Asn Ser Lys Thr Leu Glu Glu Leu Tyr Glu Val Phe Val Asp

```
                35                  40                  45
Ile Asn Asn Asp Glu Thr Ile Asp Val Val Ile Leu Thr Gly Glu Gly
 50                  55                  60

Lys Ala Phe Val Ala Gly Ala Asp Ile Ala Tyr Met Lys Asp Leu Asp
 65                  70                  75                  80

Ala Val Ala Ala Lys Asp Phe Ser Ile Leu Gly Ala Lys Ala Phe Gly
                 85                  90                  95

Glu Ile Glu Asn Ser Lys Lys Val Val Ile Ala Ala Val Asn Gly Phe
                100                 105                 110

Ala Leu Gly Gly Gly Cys Glu Leu Ala Met Ala Cys Asp Ile Arg Ile
                115                 120                 125

Ala Ser Ala Lys Ala Lys Phe Gly Gln Pro Glu Val Thr Leu Gly Ile
            130                 135                 140

Thr Pro Gly Tyr Gly Gly Thr Gln Arg Leu Thr Arg Leu Val Gly Met
145                 150                 155                 160

Ala Lys Ala Lys Glu Leu Ile Phe Thr Gly Gln Val Ile Lys Ala Asp
                165                 170                 175

Glu Ala Glu Lys Ile Gly Leu Val Asn Arg Val Val Glu Pro Asp Ile
                180                 185                 190

Leu Ile Glu Glu Val Glu Lys Leu Ala Lys Ile Ile Ala Lys Asn Ala
            195                 200                 205

Gln Leu Ala Val Arg Tyr Ser Lys Glu Ala Ile Gln Leu Gly Ala Gln
        210                 215                 220

Thr Asp Ile Asn Thr Gly Ile Asp Ile Glu Ser Asn Leu Phe Gly Leu
225                 230                 235                 240

Cys Phe Ser Thr Lys Asp Gln Lys Gly Met Ser Ala Phe Val Glu
                245                 250                 255

Lys Arg Glu Ala Asn Phe Ile Lys Gly
            260                 265

<210> SEQ ID NO 98
<211> LENGTH: 903
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 98
atgagaagtt ttgaagaagt aattaagttt gcaaaagaaa gaggacctaa aactatatca      60
gtagcatgtt gccaagataa agaagtttta atggcagttg aaatggctag aaagaaaaa     120 atagcaaatg ccattttagt aggagatata gaaaagacta agaaattgc aaaaagcata     180 gacatggata tcgaaaatta tgaactgata gatataaaag atttagcaga agcatctcta     240
aaatctgttg aattagtttc acaaggaaaa gccgacatgg taatgaaagg cttagtagac     300
acatcaataa tactaaaagc agttttaaat aaagaagtag tcttagaac tggaaatgta     360 ttaagtcacg tagcagtatt tgatgtagag ggatatgata gattattttt cgtaactgac     420
gcagctatga acttagctcc tgatacaaat actaaaaagc aaatcataga aaatgcttgc     480
acagtagcac attcattaga tataagtgaa ccaaaagttg ctgcaatatg cgcaaaagaa     540
aaagtaaatc caaaatgaa agatacagtt gaagctaaag aactagaaga atgtatgaa     600 agaggagaaa tcaaaggttg tatggttggt gggccttttg caattgataa tgcagtatct     660
ttagaagcag ctaaacataa aggtataaat catcctgtag caggacgagc tgatatatta     720
```

```
ttagccccag atattgaagg tggtaacata ttatataaag ctttggtatt cttctcaaaa      780
tcaaaaaatg caggagttat agttggggct aaagcaccaa taatattaac ttctagagca      840
gacagtgaag aaactaaact aaactcaata gctttaggtg ttttaatggc agcaaaggca      900
taa                                                                   903
```

<210> SEQ ID NO 99
<211> LENGTH: 300
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 99

```
Met Arg Ser Phe Glu Glu Val Ile Lys Phe Ala Lys Glu Arg Gly Pro
1               5                   10                  15

Lys Thr Ile Ser Val Ala Cys Cys Gln Asp Lys Glu Val Leu Met Ala
            20                  25                  30

Val Glu Met Ala Arg Lys Glu Lys Ile Ala Asn Ala Ile Leu Val Gly
        35                  40                  45

Asp Ile Glu Lys Thr Lys Glu Ile Ala Lys Ser Ile Asp Met Asp Ile
    50                  55                  60

Glu Asn Tyr Glu Leu Ile Asp Ile Lys Asp Leu Ala Glu Ala Ser Leu
65                  70                  75                  80

Lys Ser Val Glu Leu Val Ser Gln Gly Lys Ala Asp Met Val Met Lys
                85                  90                  95

Gly Leu Val Asp Thr Ser Ile Ile Leu Lys Ala Val Leu Asn Lys Glu
            100                 105                 110

Val Gly Leu Arg Thr Gly Asn Val Leu Ser His Val Ala Val Phe Asp
        115                 120                 125

Val Glu Gly Tyr Asp Arg Leu Phe Phe Val Thr Asp Ala Ala Met Asn
    130                 135                 140

Leu Ala Pro Asp Thr Asn Thr Lys Lys Gln Ile Ile Glu Asn Ala Cys
145                 150                 155                 160

Thr Val Ala His Ser Leu Asp Ile Ser Glu Pro Lys Val Ala Ala Ile
                165                 170                 175

Cys Ala Lys Glu Lys Val Asn Pro Lys Met Lys Asp Thr Val Glu Ala
            180                 185                 190

Lys Glu Leu Glu Glu Met Tyr Glu Arg Gly Glu Ile Lys Gly Cys Met
        195                 200                 205

Val Gly Gly Pro Phe Ala Ile Asp Asn Ala Val Ser Leu Glu Ala Ala
    210                 215                 220

Lys His Lys Gly Ile Asn His Pro Val Ala Gly Arg Ala Asp Ile Leu
225                 230                 235                 240

Leu Ala Pro Asp Ile Glu Gly Gly Asn Ile Leu Tyr Lys Ala Leu Val
                245                 250                 255

Phe Phe Ser Lys Ser Lys Asn Ala Gly Val Ile Val Gly Ala Lys Ala
            260                 265                 270

Pro Ile Ile Leu Thr Ser Arg Ala Asp Ser Glu Glu Thr Lys Leu Asn
        275                 280                 285

Ser Ile Ala Leu Gly Val Leu Met Ala Ala Lys Ala
    290                 295                 300
```

<210> SEQ ID NO 100
<211> LENGTH: 1080

```
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 100
atgagcaaaa tatttaaaat cttaacaata aatcctggtt cgacatcaac taaaatagct      60
gtatttgata atgaggattt agtatttgaa aaactttaa gacattcttc agaagaaata     120
ggaaaatatg agaaggtgtc tgaccaattt gaatttcgta acaagtaat agaagaagct     180
ctaaaagaag gtggagtaaa aacatctgaa ttagatgctg tagtaggtag aggaggactt     240
cttaaaccta taaaaggtgg tacttattca gtaagtgctg ctatgattga agatttaaaa     300
gtgggagttt aggagaaaca cgcttcaaac ctaggtggaa taatagcaaa acaaataggt     360
gaagaagtaa atgttccttc atacatagta gaccctgttg ttgtagatga attagaagat     420
gttgctagaa tttctggtat gcctgaaata agtagagcaa gtgtagtaca tgctttaaat     480
caaaaggcaa tagcaagaag atatgctaga gaaataaaca agaaatatga agatataaat     540
cttatagttg cacacatggg tggaggagtt tctgttggag ctcataaaaa tggtaaaata     600
gtagatgttg caaacgcatt agatggagaa ggacctttct ctccagaaag aagtggtgga     660
ctaccagtag gtgcattagt aaaaatgtgc tttagtggaa atatactca agatgaaatt     720
aaaaagaaaa taaaggtaa tggcggacta gttgcatact aaacactaa tgatgctaga     780
gaagttgaag aaagaattga agctggtgat gaaaaagcta aattagtata tgaagctatg     840
gcatatcaaa tctctaaaga aataggagct agtgctgcag ttcttaaggg agatgtaaaa     900
gcaatattat taactggtgg aatcgcatat tcaaaaatgt ttacagaaat gattgcagat     960
agagttaaat ttatagcaga tgtaaaagtt tatccaggtg aagatgaaat gattgcatta    1020
gctcaaggtg gacttagagt tttaactggt gaagaagagg ctcaagttta tgataactaa    1080

<210> SEQ ID NO 101
<211> LENGTH: 359
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 101

Met Ser Lys Ile Phe Lys Ile Leu Thr Ile Asn Pro Gly Ser Thr Ser
1               5                   10                  15

Thr Lys Ile Ala Val Phe Asp Asn Glu Asp Leu Val Phe Glu Lys Thr
            20                  25                  30

Leu Arg His Ser Ser Glu Glu Ile Gly Lys Tyr Glu Lys Val Ser Asp
        35                  40                  45

Gln Phe Glu Phe Arg Lys Gln Val Ile Glu Glu Ala Leu Lys Glu Gly
    50                  55                  60

Gly Val Lys Thr Ser Glu Leu Asp Ala Val Val Gly Arg Gly Gly Leu
65                  70                  75                  80

Leu Lys Pro Ile Lys Gly Gly Thr Tyr Ser Val Ser Ala Ala Met Ile
                85                  90                  95

Glu Asp Leu Lys Val Gly Val Leu Gly Glu His Ala Ser Asn Leu Gly
            100                 105                 110

Gly Ile Ile Ala Lys Gln Ile Gly Glu Glu Val Asn Val Pro Ser Tyr
        115                 120                 125
```

Ile Val Asp Pro Val Val Val Asp Glu Leu Glu Asp Val Ala Arg Ile
130                 135                 140

Ser Gly Met Pro Glu Ile Ser Arg Ala Ser Val Val His Ala Leu Asn
145                 150                 155                 160

Gln Lys Ala Ile Ala Arg Arg Tyr Ala Arg Glu Ile Asn Lys Lys Tyr
            165                 170                 175

Glu Asp Ile Asn Leu Ile Val Ala His Met Gly Gly Val Ser Val
            180                 185                 190

Gly Ala His Lys Asn Gly Lys Ile Val Asp Val Ala Asn Ala Leu Asp
            195                 200                 205

Gly Glu Gly Pro Phe Ser Pro Glu Arg Ser Gly Leu Pro Val Gly
210                 215                 220

Ala Leu Val Lys Met Cys Phe Ser Gly Lys Tyr Thr Gln Asp Glu Ile
225                 230                 235                 240

Lys Lys Lys Ile Lys Gly Asn Gly Gly Leu Val Ala Tyr Leu Asn Thr
                245                 250                 255

Asn Asp Ala Arg Glu Val Glu Glu Arg Ile Glu Ala Gly Asp Glu Lys
            260                 265                 270

Ala Lys Leu Val Tyr Glu Ala Met Ala Tyr Gln Ile Ser Lys Glu Ile
        275                 280                 285

Gly Ala Ser Ala Ala Val Leu Lys Gly Asp Val Lys Ala Ile Leu Leu
290                 295                 300

Thr Gly Gly Ile Ala Tyr Ser Lys Met Phe Thr Glu Met Ile Ala Asp
305                 310                 315                 320

Arg Val Lys Phe Ile Ala Asp Val Lys Val Tyr Pro Gly Glu Asp Glu
                325                 330                 335

Met Ile Ala Leu Ala Gln Gly Gly Leu Arg Val Leu Thr Gly Glu Glu
            340                 345                 350

Glu Ala Gln Val Tyr Asp Asn
            355

<210> SEQ ID NO 102
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 102
tttgtttaac tttaagaagg aga                                          23

<210> SEQ ID NO 103
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 103
taagaaggag atatacat                                                18

<210> SEQ ID NO 104
<211> LENGTH: 6270
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 104

```
catttcctct catcccatcc ggggtgagag tcttttcccc cgacttatgg ctcatgcatg    60
catcaaaaaa gatgtgagct tgatcaaaaa caaaaaatat ttcactcgac aggagtattt   120
atattgcgcc cggatccctc tagaaataat tttgtttaac tttaagaagg agatatacat   180
atgatcgtaa aacctatggt acgcaacaat atctgcctga acgcccatcc tcagggctgc   240
aagaagggag tggaagatca gattgaatat accaagaaac gcattaccgc agaagtcaaa   300
gctggcgcaa aagctccaaa aaacgttctg gtgcttggct gctcaaatgg ttacggcctg   360
gcgagccgca ttactgctgc gttcggatac ggggctgcga ccatcggcgt gtcctttgaa   420
aaagcgggtt cagaaaccaa atatggtaca ccgggatggt acaataattt ggcatttgat   480
gaagcggcaa aacgcgaggg tctttatagc gtgacgatcg acggcgatgc gttttcagac   540
gagatcaagg cccaggtaat tgaggaagcc aaaaaaaaag gtatcaaatt tgatctgatc   600
gtatacagct tggccagccc agtacgtact gatcctgata caggtatcat gcacaaaagc   660
gttttgaaac cctttggaaa aacgttcaca ggcaaaacag tagatccgtt tactggcgag   720
ctgaaggaaa tctccgcgga accagcaaat gacgaggaag cagccgccac tgttaaagtt   780
atgggggggtg aagattggga acgttggatt aagcagctgt cgaaggaagg cctcttagaa   840
gaaggctgta ttaccttggc ctatagttat attggccctg aagctaccca agctttgtac   900
cgtaaaggca aatcggcaa ggccaaagaa cacctggagg ccacagcaca ccgtctcaac   960
aaagagaacc cgtcaatccg tgccttcgtg agcgtaata aaggcctggt aacccgcgca  1020
agcgccgtaa tcccggtaat ccctctgtat ctcgccagct tgttcaaagt aatgaaagag  1080
aagggcaatc atgaaggttg tattgaacag atcacgcgtc tgtacgccga gcgcctgtac  1140
cgtaaagatg gtacaattcc agttgatgag gaaaatcgca ttcgcattga tgattgggag  1200
ttagaagaag acgtccagaa agcggtatcc gcgttgatgg agaaagtcac gggtgaaaac  1260
gcagaatctc tcactgactt agcggggtac cgccatgatt tcttagctag taacggcttt  1320
gatgtagaag gtattaatta tgaagcggaa gttgaacgct tcgaccgtat ctgataagaa  1380
ggagatatac atatgagaga agtagtaatt gccagtgcag ctagaacagc agtaggaagt  1440
tttggaggag catttaaatc agtttcagcg gtagagttag gggtaacagc agctaaagaa  1500
gctataaaaa gagctaacat aactccagat atgatagatg aatctctttt aggggagta  1560
cttacagcag gtcttggaca aaatatagca agacaaatag cattaggagc aggaatacca  1620
gtagaaaaac cagctatgac tataaatata gtttgtggt ctggattaag atctgtttca  1680
atggcatctc aacttatagc attaggtgat gctgatataa tgttagttgg tggagctgaa  1740
aacatgagta tgtctcctta tttagtacca agtgcgagat atggtgcaag aatgggtgat  1800
gctgcttttg ttgattcaat gataaaagat ggattatcag acatatttaa taactatcac  1860
atgggtatta ctgctgaaaa catagcagag caatggaata taactagaga agaacaagat  1920
gaattagctc ttgcaagtca aaataaagct gaaaaagctc aagctgaagg aaaatttgat  1980
gaagaaatag ttcctgttgt tataaaagga gaaaaaggtg acactgtagt agataaagat  2040
gaatatatta agcctggcac tacaatggag aaacttgcta agttaagacc tgcatttaaa  2100
aaagatggaa cagttactgc tggtaatgca tcaggaataa atgatggtgc tgctatgtta  2160
gtagtaatgg ctaaagaaaa agctgaagaa ctaggaatag agcctcttgc aactatagtt  2220
tcttatggaa cagctggtgt tgaccctaaa ataatgggat atggaccagt tccagcaact  2280
```

```
aaaaaagctt tagaagctgc taatatgact attgaagata tagatttagt tgaagctaat    2340
gaggcatttg ctgcccaatc tgtagctgta ataagagact taaatataga tatgaataaa    2400
gttaatgtta atggtggagc aatagctata ggacatccaa taggatgctc aggagcaaga    2460
atacttacta cacttttata tgaaatgaag agaagagatg ctaaaactgg tcttgctaca    2520 cttttgtatag gcggtggaat gggaactact ttaatagtta agagatagta agaaggagat    2580
atacatatga aattagctgt aataggtagt ggaactatgg gaagtggtat tgtacaaact    2640
tttgcaagtt gtggacatga tgtatgttta aagagtagaa ctcaaggtgc tatagataaa    2700
tgtttagctt tattagataa aaatttaact aagttagtta ctaagggaaa aatggatgaa    2760
gctacaaaag cagaaatatt aagtcatgtt agttcaacta ctaattatga agatttaaaa    2820
gatatggatt taataataga agcatctgta gaagacatga atataaagaa agatgttttc    2880
aagttactag atgaattatg taagaagat actatcttgg caacaaatac ttcatcatta    2940
tctataacag aaatagcttc ttctactaag cgcccagata agttatagg aatgcatttc    3000 tttaatccag ttcctatgat gaaattagtt gaagttataa gtggtcagtt aacatcaaaa    3060
gttacttttg atacagtatt tgaattatct aagagtatca ataaagtacc agtgagatgta    3120 tctgaatctc ctggatttgt agtaaataga atacttatac ctatgataaa tgaagctgtt    3180
ggtatatatg cagatggtgt tgcaagtaaa aagaaaatag atgaagctat gaaattagga    3240
gcaaaccatc caatgggacc actagcatta ggtgatttaa tcggattaga tgttgtttta    3300
gctataatga acgttttata tactgaattt ggagatacta aatatagacc tcatccactt    3360
ttagctaaaa tggttagagc taatcaatta ggaagaaaaa ctaagatagg attctatgat    3420
tataataaat aataagaagg agatatacat atgagtacaa gtgatgttaa agtttatgag    3480
aatgtagctg ttgaagtaga tggaaatata tgtacagtga aatgaatag acctaaagcc    3540 cttaatgcaa taaattcaaa gactttagaa gaactttatg aagtatttgt agatattaat    3600
aatgatgaaa ctattgatgt tgtaatattg acaggggaag gaaaggcatt tgtagctgga    3660
gcagatattg catacatgaa agatttagat gctgtagctg ctaaagattt tagtatctta    3720
ggagcaaaag cttttggaga aatagaaaat agtaaaaaag tagtgatagc tgctgtaaac    3780
ggatttgctt taggtggagg atgtgaactt gcaatggcat gtgatataag aattgcatct    3840
gctaaagcta aatttggtca gccagaagta actcttggaa taactccagg atatggagga    3900
actcaaaggc ttacaagatt ggttggaatg gcaaaagcaa agaattaat ctttacaggt    3960 caagttataa aagctgatga agctgaaaaa atagggctag taaatagagt cgttgagcca    4020 gacatttta tagaagaagt tgagaaatta gctaagataa tagctaaaaa tgctcagctt    4080
gcagttagat actctaaaga agcaatacaa cttggtgctc aaactgatat aaatactgga    4140
atagatatag aatctaattt atttggtctt tgtttttcaa ctaaagacca aaagaagga    4200 atgtcagctt tcgttgaaaa agagagaagct aactttataa aagggtaata agaaggagat    4260
atacatatga aagttttga agaagtaatt aagtttgcaa agaaagagg acctaaaact    4320 atatcagtag catgttgcca agataaagaa gttttaatgg cagttgaaat ggctagaaaa    4380
gaaaaaatag caaatgccat tttagtagga gatatagaaa agactaaaga aattgcaaaa    4440
agcatagaca tggatatcga aaattatgaa ctgatagata taaaagattt agcagaagca    4500
tctctaaaat ctgttgaatt agtttcacaa ggaaaagccg acatggtaat gaaaggctta    4560
gtagacacat caataaatact aaaagcagtt ttaaataaag aagtaggtct tagaactgga    4620
aatgtattaa gtcacgtagc agtatttgat gtagagggat atgatagatt attttttcgta    4680
```

```
actgacgcag ctatgaactt agctcctgat acaaatacta aaaagcaaat catagaaaat    4740
gcttgcacag tagcacattc attagatata agtgaaccaa agttgctgc aatatgcgca    4800 aaagaaaaag taaatccaaa aatgaaagat acagttgaag ctaagaact agaagaaatg    4860 tatgaaagag gagaaatcaa aggttgtatg gttggtgggc cttttgcaat tgataatgca    4920
gtatctttag aagcagctaa acataaaggt ataaatcatc ctgtagcagg acgagctgat    4980
atattattag ccccagatat tgaaggtggt aacatattat ataaagcttt ggtattcttc    5040
tcaaaatcaa aaatgcagg agttatagtt ggggctaaag caccaataat attaacttct    5100
agagcagaca gtgaagaaac taaactaaac tcaatagctt taggtgtttt aatggcagca    5160
aaggcataat aagaaggaga tatacatatg agcaaaatat ttaaaatctt aacaataaat    5220
cctggttcga catcaactaa aatagctgta tttgataatg aggatttagt atttgaaaaa    5280
actttaagac attcttcaga agaaatagga aaatatgaga aggtgtctga ccaatttgaa    5340
tttcgtaaac aagtaataga agaagctcta aagaaggtg gagtaaaaac atctgaatta    5400
gatgctgtag taggtagagg aggacttctt aaacctataa aaggtggtac ttattcagta    5460
agtgctgcta tgattgaaga tttaaaagtg ggagttttag gagaacacgc ttcaaaccta    5520
ggtggaataa tagcaaaaca aataggtgaa gaagtaaatg ttccttcata catagtagac    5580
cctgttgttg tagatgaatt agaagatgtt gctagaattt ctggtatgcc tgaaataagt    5640
agagcaagtg tagtacatgc tttaaatcaa aaggcaatag caagaagata tgctagagaa    5700
ataaacaaga aatatgaaga tataaatctt atagttgcac acatgggtgg aggagttttct    5760 gttggagctc ataaaaatgg taaaatagta gatgttgcaa acgcattaga tggagaagga    5820
cctttctctc cagaaagaag tggtggacta ccagtaggtg cattagtaaa aatgtgcttt    5880
agtggaaaat atactcaaga tgaaattaaa agaaaataa aaggtaatgg cggactagtt    5940
gcatacttaa acactaatga tgctagagaa gttgaagaaa gaattgaagc tggtgatgaa    6000
aaagctaaat tagtatatga agctatggca tatcaaatct ctaaagaaat aggagctagt    6060
gctgcagttc ttaagggaga tgtaaaagca atattattaa ctggtggaat cgcatattca    6120
aaaatgttta cagaaatgat tgcagataga gttaaattta tagcagatgt aaaagtttat    6180
ccaggtgaag atgaaatgat tgcattagct caaggtggac ttagagtttt aactggtgaa    6240
gaagaggctc aagtttatga taactaataa                                    6270
```

<210> SEQ ID NO 105
<211> LENGTH: 466
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 105

```
Met Gly Gln Ser Ser Gln Pro His Glu Leu Gly Gly Gly Leu Lys Ser
1               5                   10                  15

Arg His Val Thr Met Leu Ser Ile Ala Gly Val Ile Gly Ala Ser Leu
            20                  25                  30

Phe Val Gly Ser Ser Val Ala Ile Ala Glu Ala Gly Pro Ala Val Leu
        35                  40                  45

Leu Ala Tyr Leu Phe Ala Gly Leu Leu Val Val Met Ile Met Arg Met
    50                  55                  60

Leu Ala Glu Met Ala Val Ala Thr Pro Asp Thr Gly Ser Phe Ser Thr
```

```
                65                  70                  75                  80
Tyr Ala Asp Lys Ala Ile Gly Arg Trp Ala Gly Tyr Thr Ile Gly Trp
                    85                  90                  95
Leu Tyr Trp Trp Phe Trp Val Leu Val Ile Pro Leu Glu Ala Asn Ile
                    100                 105                 110
Ala Ala Met Ile Leu His Ser Trp Val Pro Gly Ile Pro Ile Trp Leu
                    115                 120                 125
Phe Ser Leu Val Ile Thr Leu Ala Leu Thr Gly Ser Asn Leu Leu Ser
                    130                 135                 140
Val Lys Asn Tyr Gly Glu Phe Glu Phe Trp Leu Ala Leu Cys Lys Val
145                 150                 155                 160
Ile Ala Ile Leu Ala Phe Ile Phe Leu Gly Ala Val Ala Ile Ser Gly
                    165                 170                 175
Phe Tyr Pro Tyr Ala Glu Val Ser Gly Ile Ser Arg Leu Trp Asp Ser
                    180                 185                 190
Gly Gly Phe Met Pro Asn Gly Phe Gly Ala Val Leu Ser Ala Met Leu
                    195                 200                 205
Ile Thr Met Phe Ser Phe Met Gly Ala Glu Ile Val Thr Ile Ala Ala
                    210                 215                 220
Ala Glu Ser Asp Thr Pro Glu Lys His Ile Val Arg Ala Thr Asn Ser
225                 230                 235                 240
Val Ile Trp Arg Ile Ser Ile Phe Tyr Leu Cys Ser Ile Phe Val Val
                    245                 250                 255
Val Ala Leu Ile Pro Trp Asn Met Pro Gly Leu Lys Ala Val Gly Ser
                    260                 265                 270
Tyr Arg Ser Val Leu Glu Leu Leu Asn Ile Pro His Ala Lys Leu Ile
                    275                 280                 285
Met Asp Cys Val Ile Leu Leu Ser Val Thr Ser Cys Leu Asn Ser Ala
                    290                 295                 300
Leu Tyr Thr Ala Ser Arg Met Leu Tyr Ser Leu Ser Arg Arg Gly Asp
305                 310                 315                 320
Ala Pro Ala Val Met Gly Lys Ile Asn Arg Ser Lys Thr Pro Tyr Val
                    325                 330                 335
Ala Val Leu Leu Ser Thr Gly Ala Ala Phe Leu Thr Val Val Val Asn
                    340                 345                 350
Tyr Tyr Ala Pro Ala Lys Val Phe Lys Phe Leu Ile Asp Ser Ser Gly
                    355                 360                 365
Ala Ile Ala Leu Leu Val Tyr Leu Val Ile Ala Val Ser Gln Leu Arg
                    370                 375                 380
Met Arg Lys Ile Leu Arg Ala Glu Gly Ser Glu Ile Arg Leu Arg Met
385                 390                 395                 400
Trp Leu Tyr Pro Trp Leu Thr Trp Leu Val Ile Gly Phe Ile Thr Phe
                    405                 410                 415
Val Leu Val Val Met Leu Phe Arg Pro Ala Gln Gln Leu Glu Val Ile
                    420                 425                 430
Ser Thr Gly Leu Leu Ala Ile Gly Ile Ile Cys Thr Val Pro Ile Met
                    435                 440                 445
Ala Arg Trp Lys Lys Leu Val Leu Trp Gln Lys Thr Pro Val His Asn
                    450                 455                 460
Thr Arg
465

<210> SEQ ID NO 106
```

<211> LENGTH: 1398
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 106

```
atgggacagt cttcacaacc acacgaactt ggggtggat tgaaatcgcg ccatgtgacc      60
atgttaagta tcgcaggcgt gattggcgcc tccttatttg tggggtcctc cgtggcgatt    120
gcagaggcgg gtccggctgt acttttggca tatctttttg cgggtttact ggttgtgatg    180
atcatgcgca tgcttgccga atggctgtg gccacgccgg acacgggtc attttccact     240
tatgcggaca aggcgattgg ccgctgggcc gggtacacaa tcgggtggct gtattggtgg    300
ttctgggtgt tagttatccc cttggaggcc aacatcgccg caatgattct gcactcctgg    360
gttccgggta tcccgatctg gctgttcagc ttggtgatca ccctggcact gacgggcagc    420
aacttattga gtgtgaaaaa ctatggagag tttgaatttt ggctggccct gtgtaaagtc    480
attgctatct tggcattcat ttttttagga gcggtagcaa tcagtggctt ctacccttat    540
gcagaagttt cggggatttc ccgtctttgg gatagtggcg gattcatgcc aaacgggttt    600
ggagctgtac tgtcagccat gttgattacc atgtttagct tatgggtgc cgagatcgtg    660
acaatcgccg cagccgagag tgatacccg gaaaagcaca ttgttcgtgc gacgaattcg    720
gtaatttggc gtatttcgat ttttttactta tgctccattt tcgttgtggt cgcccttatc    780
ccctggaaca tgccaggctt aaaagcagta ggcagctacc gctcagtcct ggaattactg    840
aacattcctc acgcgaagtt aattatggat tgcgtaatcc tgttatcggt aacgagctgc    900
cttaacagtg ctctgtacac ggcttcacgt atgctgtact cttaagtcg ccgtggcgat     960
gcacctgccg ttatgggcaa gattaaccgc agtaagacgc cgtatgtagc tgttttgctg   1020
tcgactggag ctgcgtttct tacagtcgta gtaaactatt acgcaccagc taaagttttc   1080
aaattcctta ttgattcgtc tggggcaatc gcacttctgg tgtacctggt catcgcggtg   1140
tcacaacttc gcatgcgcaa gatcttgcgt gcggagggca gtgagattcg tttgcgtatg   1200
tggctgtatc cgtggctgac gtggcttgtt attggtttca ttacttttgt gttggtagtg   1260
atgctgtttc gtccagcgca acagctggag gtgatttcta ccggactgtt ggcaatcggc   1320
atcatctgta ccgtcccaat catggctcgc tggaaaaagt tggtcttatg gcagaagacc   1380
cctgtacaca acacccgt                                                 1398
```

<210> SEQ ID NO 107
<211> LENGTH: 412
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 107

```
Met Thr Asn Tyr Arg Val Glu Ser Ser Gly Arg Ala Ala Arg Lys
1               5                   10                  15

Met Arg Leu Ala Leu Met Gly Pro Ala Phe Ile Ala Ile Gly Tyr
            20                  25                  30

Ile Asp Pro Gly Asn Phe Ala Thr Asn Ile Gln Ala Gly Ala Ser Phe
        35                  40                  45

Gly Tyr Gln Leu Leu Trp Val Val Val Trp Ala Asn Leu Met Ala Met
    50                  55                  60
```

| | | | | | | | | | | | | | | |
|---|---|---|---|---|---|---|---|---|---|---|---|---|---|---|

Leu Ile Gln Ile Leu Ser Ala Lys Leu Gly Ile Ala Thr Gly Lys Asn
65                        70                       75                       80

Leu Ala Glu Gln Ile Arg Asp His Tyr Pro Arg Pro Val Val Trp Phe
                       85                       90                       95

Tyr Trp Val Gln Ala Glu Ile Ala Met Ala Thr Asp Leu Ala Glu
           100                   105                   110

Phe Ile Gly Ala Ala Ile Gly Phe Lys Leu Ile Leu Gly Val Ser Leu
             115                   120                   125

Leu Gln Gly Ala Val Leu Thr Gly Ile Ala Thr Phe Leu Ile Leu Met
130                     135                   140

Leu Gln Arg Arg Gly Gln Lys Pro Leu Glu Lys Val Ile Gly Gly Leu
145                     150                   155                   160

Leu Leu Phe Val Ala Ala Tyr Ile Val Glu Leu Ile Phe Ser Gln
             165                   170                   175

Pro Asn Leu Ala Gln Leu Gly Lys Gly Met Val Ile Pro Ser Leu Pro
             180                   185                   190

Thr Ser Glu Ala Val Phe Leu Ala Ala Gly Val Leu Gly Ala Thr Ile
             195                   200                   205

Met Pro His Val Ile Tyr Leu His Ser Ser Leu Thr Gln His Leu His
    210                   215                   220

Gly Gly Ser Arg Gln Gln Arg Tyr Ser Ala Thr Lys Trp Asp Val Ala
225                     230                   235                   240

Ile Ala Met Thr Ile Ala Gly Phe Val Asn Leu Ala Met Met Ala Thr
             245                   250                   255

Ala Ala Ala Ala Phe His Phe Ser Gly His Thr Gly Val Ala Asp Leu
             260                   265                   270

Asp Glu Ala Tyr Leu Thr Leu Gln Pro Leu Leu Ser His Ala Ala Ala
             275                   280                   285

Thr Val Phe Gly Leu Ser Leu Val Ala Ala Gly Leu Ser Ser Thr Val
    290                   295                   300

Val Gly Thr Leu Ala Gly Gln Val Val Met Gln Gly Phe Ile Arg Phe
305                     310                   315                   320

His Ile Pro Leu Trp Val Arg Arg Thr Val Thr Met Leu Pro Ser Phe
             325                   330                   335

Ile Val Ile Leu Met Gly Leu Asp Pro Thr Arg Ile Leu Val Met Ser
             340                   345                   350

Gln Val Leu Leu Ser Phe Gly Ile Ala Leu Ala Leu Val Pro Leu Leu
             355                   360                   365

Ile Phe Thr Ser Asp Ser Lys Leu Met Gly Asp Leu Val Asn Ser Lys
             370                   375                   380

Arg Val Lys Gln Thr Gly Trp Val Ile Val Leu Val Ala Leu
385                     390                   395                   400

Asn Ile Trp Leu Leu Val Gly Thr Ala Leu Gly Leu
             405                   410

<210> SEQ ID NO 108
<211> LENGTH: 1236
<212> TYPE: DNA
<213> ORGANISM: Artificial Sequence
<220> FEATURE:
<223> OTHER INFORMATION: Description of Artificial Sequence: Synthetic
     polynucleotide

<400> SEQUENCE: 108
atgaccaatt atcgtgttga aagtagtagt ggccgcgcgg ctcgtaaaat gcgtctggcc    60

-continued

```
ttaatgggcc cggcgtttat tgctgcgatt ggatacattg atccgggcaa tttcgctaca      120
aacatccaag caggtgcatc cttcggttac cagcttctgt gggtagtggt atgggctaac      180
ctgatggcca tgcttattca aattctttca gctaagcttg gtattgccac aggaaagaat      240
ttagccgagc agattcgtga ccactatccc cgccccgtgg tctggttcta tgggtccag       300 gcagagatta tcgcgatggc gactgattta gccgaattta ttggggcagc tattggattt      360
aagctgatcc ttggcgtatc tctgttgcaa ggcgcgtat tgaccggaat tgcaaccttt       420
ttgattctta tgttgcaacg tcgtgggcag aagcctctgg aaaaagtcat cggcgggtta      480
ttgctttttg ttgccgcggc ctacattgtg aactgatct tttctcaacc taacctggcg       540
cagcttggta aaggcatggt aatcccgtca cttcctacat ctgaggcagt attcttagca      600
gccggcgtct tgggcgcaac tatcatgccc catgtcatct acttacacag ttctctgact      660
cagcacttac acggtgggtc gcgccaacag cgttactccg caacaaagtg ggacgttgca      720
attgccatga ccattgccgg ttttgttaac ctggcgatga tggccacggc tgctgccgcc      780
tttcatttca gtggccacac tggtgtagcc gatctggatg aggcatacct gaccttgcag      840
cctctgttgt ctcatgcagc cgccaccgtt tttggtttaa gcttagtagc cgccggcttg      900
agtagcacgg tggtaggcac attggctgga caggtcgtga tgcaaggttt cattcgtttc      960
catattccgt tatgggtacg tcgcacggta acgatgctgc cgtcatttat cgtcatcctg     1020
atgggattag acccgacgcg catcctggta atgtcgcaag ttttactgag ctttggaatc     1080
gcgttggccc tggtgccatt acttatcttc actagcgata gtaagttgat gggtgatctt     1140
gtcaatagca aacgtgtgaa gcaaacaggc tgggtcattg tggtactggt tgtggcctta     1200
aacatttggt tgttagtggg cacggcccctt ggcttg                              1236
```

<210> SEQ ID NO 109
<211> LENGTH: 286
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 109

```
Met Ser Gln Ala Leu Lys Asn Leu Leu Thr Leu Leu Asn Leu Glu Lys
1               5                   10                  15

Ile Glu Glu Gly Leu Phe Arg Gly Gln Ser Glu Asp Leu Gly Leu Arg
            20                  25                  30

Gln Val Phe Gly Gly Gln Val Gly Gln Ala Leu Tyr Ala Ala Lys
        35                  40                  45

Glu Thr Val Pro Glu Glu Arg Leu Val His Ser Phe His Ser Tyr Phe
    50                  55                  60

Leu Arg Pro Gly Asp Ser Lys Lys Pro Ile Ile Tyr Asp Val Glu Thr
65                  70                  75                  80

Leu Arg Asp Gly Asn Ser Phe Ser Ala Arg Arg Val Ala Ala Ile Gln
                85                  90                  95

Asn Gly Lys Pro Ile Phe Tyr Met Thr Ala Ser Phe Gln Ala Pro Glu
            100                 105                 110

Ala Gly Phe Glu His Gln Lys Thr Met Pro Ser Ala Pro Ala Pro Asp
        115                 120                 125

Gly Leu Pro Ser Glu Thr Gln Ile Ala Gln Ser Leu Ala His Leu Leu
    130                 135                 140
```

Pro Pro Val Leu Lys Asp Lys Phe Ile Cys Asp Arg Pro Leu Glu Val
145                 150                 155                 160

Arg Pro Val Glu Phe His Asn Pro Leu Lys Gly His Val Ala Glu Pro
                165                 170                 175

His Arg Gln Val Trp Ile Arg Ala Asn Gly Ser Val Pro Asp Asp Leu
            180                 185                 190

Arg Val His Gln Tyr Leu Leu Gly Tyr Ala Ser Asp Leu Asn Phe Leu
        195                 200                 205

Pro Val Ala Leu Gln Pro His Gly Ile Gly Phe Leu Glu Pro Gly Ile
    210                 215                 220

Gln Ile Ala Thr Ile Asp His Ser Met Trp Phe His Arg Pro Phe Asn
225                 230                 235                 240

Leu Asn Glu Trp Leu Leu Tyr Ser Val Glu Ser Thr Ser Ala Ser Ser
                245                 250                 255

Ala Arg Gly Phe Val Arg Gly Glu Phe Tyr Thr Gln Asp Gly Val Leu
            260                 265                 270

Val Ala Ser Thr Val Gln Glu Gly Val Met Arg Asn His Asn
        275                 280                 285

<210> SEQ ID NO 110
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 110
caaataaaat gaaaggctca gtcgaaagac tgggcctttc gttttatctg ttgtttgtcg    60
gtgaacgctc tcctgagtag gacaaat                                        87

<210> SEQ ID NO 111
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 111
agaaggccat cctgacggat ggcctttt                                       28

<210> SEQ ID NO 112
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 112
gaagttccta tactttctag agaataggaa cttcggaata ggaacta                  47

<210> SEQ ID NO 113
<211> LENGTH: 161
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 113

```
gtaccagttg ttcttattgg tggtgttgct ttatggttgc atcgtagtaa atggttgtaa    60
caaaagcaat ttttccggct gtctgtatac aaaaacgccg taaagtttga gcgaagtcaa   120
taaactctct acccattcag ggcaatatct ctcttggatc c                       161
```

<210> SEQ ID NO 114
<211> LENGTH: 1332
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 114

```
atggtaaagg aacgtaaaac cgagttggtc gagggattcc gccattcggt tccctgtatc    60
aatacccacc ggggaaaaac gtttgtcatc atgctcggcg gtgaagccat tgagcatgag   120
aatttctcca gtatcgttaa tgatatcggg ttgttgcaca gcctcggcat ccgtctggtg   180
gtggtctatg gcgcacgtcc gcagatcgac gcaaatctgg ctgcgcatca ccacgaaccg   240
ctgtatcaca agaatatacg tgtgaccgac gccaaaacac tggaactggt gaagcaggct   300
gcgggaacat tgcaactgga tattactgct cgcctgtcga tgagtctcaa taacacgccg   360
ctgcagggcg cgcatatcaa cgtcgtcagt ggcaatttta ttattgccca gccgctgggc   420
gtcgatgacg gcgtggatta ctgccatagc gggcgtatcc ggcggattga tgaagacgcg   480
atccatcgtc aactggacag cggtgcaata gtgctaatgg ggccggtcgc tgtttcagtc   540
actggcgaga gctttaacct gacctcggaa gagattgcca ctcaactggc catcaaactg   600
aaagctgaaa agatgattgg tttttgctct tcccagggcg tcactaatga cgacggtgat   660
attgtctccg aacttttccc taacgaagcg caagcgcggg tagaagccca ggaagagaaa   720
ggcgattaca actccggtac ggtgcgcttt ttgcgtggcg cagtgaaagc ctgccgcagc   780
ggcgtgcgtc gctgtcattt aatcagttat caggaagatg gcgcgctgtt gcaagagttg   840
ttctcacgcg acggtatcgg tacgcagatt gtgatggaaa gcgccgagca gattcgtcgc   900
gcaacaatca cgatattggg cggtattctg gagttgattc gcccactgga gcagcaaggt   960
attctggtac gccgttctcg cgagcagctg agatgaaaa tcgacaaatt caccattatt  1020
cagcgcgata acacgactat tgcctgcgcc gcgctctatc cgttcccgga agagaagatt  1080
ggggaaatgg cctgtgtggc agttcacccg gattaccgca gttcatcaag gggtgaagtt  1140
ctgctggaac gcattgccgc tcaggctaag cagagcggct taagcaaatt gtttgtgctg  1200
accacgcgca gtattcactg gttccaggaa cgtggattta ccccagtgga tattgattta  1260
ctgcccgaga gcaaaaagca gttgtacaac taccagcgta atccaaagtg ttgatggcg   1320 gatttagggt aa                                                       1332
```

<210> SEQ ID NO 115
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 115

```
gaagttccta tactttctag agaataggaa cttcggaata ggaacttc                 48
```

<210> SEQ ID NO 116
<211> LENGTH: 985

```
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 116
atgattgaac aagatggatt gcacgcaggt tctccggccg cttgggtgga gaggctattc      60
ggctatgact gggcacaaca gacaatcggc tgctctgatg ccgccgtgtt ccggctgtca     120
gcgcaggggc gcccggttct ttttgtcaag accgacctgt ccggtgccct gaatgaactg     180
caggacgagg cagcgcggct atcgtggctg gccacgacgg gcgttccttg cgcagctgtg     240
ctcgacgttg tcactgaagc gggaagggac tggctgctat tgggcgaagt gccggggcag     300
gatctcctgt catctcacct tgctcctgcc gagaaagtat ccatcatggc tgatgcaatg     360
cggcggctgc atacgcttga tccggctacc tgcccattcg accaccaagc gaaacatcgc     420
atcgagcgag cacgtactcg gatggaagcc ggtcttgtcg atcaggatga tctggacgaa     480
gagcatcagg ggctcgcgcc agccgaactg ttcgccaggc tcaaggcgcg catgcccgac     540
ggcgaggatc tcgtcgtgac ccatggcgat gcctgcttgc cgaatatcat ggtggaaaat     600
ggccgctttt ctggattcat cgactgtggc cggctgggtg tggcggaccg ctatcaggac     660
atagcgttgg ctacccgtga tattgctgaa gagcttggcg gcgaatgggc tgaccgcttc     720
ctcgtgcttt acggtatcgc cgctcccgat tcgcagcgca tcgccttcta tcgccttctt     780
gacgagttct tctgagcggg actctggggt tcgaaatgac cgaccaagcg acgcccaacc     840
tgccatcacg agatttcgat tccaccgccg ccttctatga aaggttgggc ttcggaatcg     900
ttttccggga cgccggctgg atgatcctcc agcgcgggga tctcatgctg agttcttcg     960 cccaccccag cttcaaaagc gctct                                           985

<210> SEQ ID NO 117
<211> LENGTH: 106
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 117
ggttgggaag ccctgcaaag taaactggat ggctttcttg ccgccaagga tctgatggcg      60
caggggatca agatctgatc aagagacagg atgaggatcg tttcgc                    106

<210> SEQ ID NO 118
<211> LENGTH: 639
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 118
tcatcgcagt actgttgtat tcattaagca tctgccgaca tggaagccat cacaaacggc      60
atgatgaacc tgaatcgcca gcggcatcag caccttgtcg ccttgcgtat aatatttgcc     120
catggtgaaa acgggggcga agaagttgtc catattggcc acgtttaaat caaaactggt     180
gaaactcacc cagggattgg ctgagacgaa aaacatattc tcaataaacc ctttagggaa     240
ataggccagg ttttcaccgt aacacgccac atcttgcgaa tatatgtgta gaaactgccg     300
gaaatcgtcg tggtattcac tccagagcga tgaaaacgtt tcagtttgct catggaaaac     360
```

```
ggtgtaacaa gggtgaacac tatcccatat caccagctca ccgtctttca ttgccatacg    420
taattccgga tgagcattca tcaggcgggc aagaatgtga ataaaggccg gataaaactt    480
gtgcttattt ttctttacgg tctttaaaaa ggccgtaata tccagctgaa cggtctggtt    540
ataggtacat tgagcaactg actgaaatgc ctcaaaatgt tctttacgat gccattggga    600
tatatcaacg gtggtatatc cagtgatttt tttctccat                          639
```

```
<210> SEQ ID NO 119
<211> LENGTH: 209
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 119
```

```
tttagcttcc ttagctcctg aaaatctcga caactcaaaa aatacgcccg gtagtgatct    60
tatttcatta tggtgaaagt tggaacctct tacgtgccga tcaacgtctc attttcgcca    120
aaagttggcc cagggcttcc cggtatcaac agggacacca ggatttattt attctgcgaa    180
gtgatcttcc gtcacaggta ggcgcgccg                                     209
```

```
<210> SEQ ID NO 120
<211> LENGTH: 18
<212> TYPE: DNA
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: modified_base
<222> LOCATION: (2)..(2)
<223> OTHER INFORMATION: a, c, t, g, unknown or other
<220> FEATURE:
<221> NAME/KEY: modified_base
<222> LOCATION: (17)..(17)
<223> OTHER INFORMATION: a, c, t, g, unknown or other

<400> SEQUENCE: 120
wntgaatwww wattcanw                                                 18
```

```
<210> SEQ ID NO 121
<211> LENGTH: 14
<212> TYPE: DNA
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: modified_base
<222> LOCATION: (6)..(9)
<223> OTHER INFORMATION: a, c, t, g, unknown or other

<400> SEQUENCE: 121
ttgatnnnna tcaa                                                     14
```

```
<210> SEQ ID NO 122
<211> LENGTH: 18
<212> TYPE: DNA
<213> ORGANISM: Artificial Sequence
<220> FEATURE:
<223> OTHER INFORMATION: Description of Artificial Sequence: Synthetic
      consensus sequence

<400> SEQUENCE: 122
```

```
ttgttgayry rtcaacwa                                                    18

<210> SEQ ID NO 123
<211> LENGTH: 15
<212> TYPE: DNA
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: modified_base
<222> LOCATION: (8)..(8)
<223> OTHER INFORMATION: a, c, t, g, unknown or other

<400> SEQUENCE: 123
ttataatnat tataa                                                       15

<210> SEQ ID NO 124
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 124
atgcgaagct cggctaagca agaagagagc tgttcgacca ggagctttaa                 50

<210> SEQ ID NO 125
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 125
gtttcgtaat tagatagcca ccggcgcttt aatgcccgga catatgaata tcctccttag      60
```

UNITED STATES PATENT AND TRADEMARK OFFICE
CERTIFICATE OF CORRECTION

PATENT NO.        : 9,688,967 B2
APPLICATION NO.   : 15/164828
DATED             : June 27, 2017
INVENTOR(S)       : Dean Falb et al.

It is certified that error appears in the above-identified patent and that said Letters Patent is hereby corrected as shown below:

In the Claims

Claim 11, Column 488, Line 65, "Coilstrain" should read -- coli strain --.

Signed and Sealed this
Fifth Day of September, 2017

Joseph Matal
*Performing the Functions and Duties of the*
*Under Secretary of Commerce for Intellectual Property and*
*Director of the United States Patent and Trademark Office*